(12) United States Patent
Swayze

(10) Patent No.: US 12,215,321 B2
(45) Date of Patent: Feb. 4, 2025

(54) MODULATORS OF DIACYGLYCEROL ACYLTRANSFERASE 2 (DGAT2)

(71) Applicant: Ionis Pharmaceuticals, Inc., Carlsbad, CA (US)

(72) Inventor: Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 125 days.

(21) Appl. No.: 17/677,875

(22) Filed: Feb. 22, 2022

(65) Prior Publication Data
US 2023/0047452 A1 Feb. 16, 2023

Related U.S. Application Data

(63) Continuation of application No. 16/456,432, filed on Jun. 28, 2019, now Pat. No. 11,312,962, which is a continuation of application No. 15/741,996, filed as application No. PCT/US2016/041410 on Jul. 8, 2016, now abandoned.

(60) Provisional application No. 62/191,231, filed on Jul. 10, 2015.

(51) Int. Cl.
| | | |
|---|---|---|
| C12N 15/113 | (2010.01) | |
| A61P 1/16 | (2006.01) | |
| C07H 21/00 | (2006.01) | |

(52) U.S. Cl.
CPC ............ *C12N 15/1137* (2013.01); *A61P 1/16* (2018.01); *C07H 21/00* (2013.01); *C12Y 203/0102* (2013.01); *C12N 2310/11* (2013.01); *C12N 2310/315* (2013.01); *C12N 2310/3341* (2013.01); *C12N 2310/341* (2013.01); *C12N 2310/346* (2013.01); *C12N 2320/35* (2013.01)

(58) Field of Classification Search
CPC ............ C12N 15/1137; C12N 2310/11; C12N 2310/315; C12N 2310/3341; C12N 2310/341; C12N 2310/346; C12N 15/113; C12N 2310/321; C12N 2310/3525
USPC .................... 435/6.1, 91.1, 91.31, 455, 458; 514/44 A; 536/23.1, 24.5
See application file for complete search history.

(56) References Cited

U.S. PATENT DOCUMENTS

| | | |
|---|---|---|
| 4,035,504 A | 7/1977 | Hidy et al. |
| 5,801,154 A | 9/1998 | Baracchini et al. |
| 5,837,542 A | 11/1998 | Grimm et al. |
| 5,998,148 A | 12/1999 | Bennett et al. |
| 6,083,695 A | 7/2000 | Hardin et al. |
| 6,100,077 A | 8/2000 | Sturley et al. |
| 6,127,533 A | 10/2000 | Cook et al. |
| 6,284,538 B1 | 9/2001 | Monia et al. |
| 6,344,548 B1 | 2/2002 | Farese, Jr. et al. |
| 6,444,427 B1 | 9/2002 | Ludwig et al. |
| 6,512,099 B2 | 1/2003 | Omura et al. |
| 6,582,908 B2 | 6/2003 | Fodor et al. |
| 6,605,451 B1 | 8/2003 | Marmaro et al. |
| 6,607,893 B2 | 8/2003 | Ramharack et al. |
| 6,673,661 B1 | 1/2004 | Liu et al. |
| 6,822,141 B2 | 11/2004 | Lardizabal et al. |
| 7,250,289 B2 | 7/2007 | Zhou |
| 7,250,496 B2 | 7/2007 | Bentwich |
| 7,691,997 B2 | 4/2010 | Khvorova et al. |
| 8,258,289 B2 | 9/2012 | Bhanot et al. |
| 11,312,962 B2 | 4/2022 | Bhanot et al. |
| 2001/0053519 A1 | 12/2001 | Fodor et al. |
| 2002/0119138 A1 | 8/2002 | Cases et al. |
| 2002/0127627 A1 | 9/2002 | Ramharack et al. |
| 2002/0193315 A1 | 12/2002 | Omura et al. |
| 2003/0028923 A1 | 2/2003 | Lardizabal et al. |
| 2003/0073103 A1 | 4/2003 | Ludwig et al. |
| 2003/0100480 A1 | 5/2003 | Smith et al. |
| 2003/0104414 A1 | 6/2003 | Attersand |
| 2003/0115632 A1 | 6/2003 | Lardizabal et al. |
| 2003/0124126 A1 | 7/2003 | Cases et al. |
| 2003/0152574 A1 | 8/2003 | Logan et al. |
| 2003/0161831 A1 | 8/2003 | Cases et al. |
| 2003/0170691 A1 | 9/2003 | Gimeno et al. |
| 2003/0200563 A1 | 10/2003 | Butler et al. |
| 2003/0202968 A1 | 10/2003 | Cases et al. |
| 2003/0228597 A1 | 12/2003 | Cowsert et al. |
| 2004/0054177 A1 | 3/2004 | Otake et al. |
| 2004/0058820 A1 | 3/2004 | Hagmann et al. |
| 2004/0097459 A1 | 5/2004 | Dobie et al. |
| 2004/0122033 A1 | 6/2004 | Nargund et al. |
| 2004/0259247 A1 | 12/2004 | Tuschl et al. |
| 2005/0043524 A1 | 2/2005 | Bhanot et al. |
| 2005/0048531 A1 | 3/2005 | Mittman et al. |
| 2005/0272680 A1 | 12/2005 | Bhanot et al. |
| 2007/0031844 A1 | 2/2007 | Khvorova et al. |
| 2013/0123331 A1 | 5/2013 | Bhanot et al. |
| 2016/0251655 A1 | 9/2016 | Freier et al. |

FOREIGN PATENT DOCUMENTS

| | | |
|---|---|---|
| EP | 1071826 B1 | 1/2001 |
| EP | 1308459 A2 | 5/2003 |
| EP | 2363481 B1 | 9/2011 |
| WO | WO 00/62774 | 10/2000 |
| WO | WO 00/78961 | 12/2000 |
| WO | WO 2001/051659 A2 | 7/2001 |
| WO | WO 01/068848 | 9/2001 |
| WO | WO 01/077389 | 10/2001 |
| WO | WO 01/092512 | 12/2001 |

(Continued)

OTHER PUBLICATIONS

Azrak et al., "upQMPSF, a Method for the Detection of BRCA1 Exon Copy Number Variants" Biochem Genet (2015) 53: 141-157.

(Continued)

*Primary Examiner* — Jane J Zara
(74) *Attorney, Agent, or Firm* — Knobbe, Martens, Olson & Bear, LLP

(57) ABSTRACT

The present embodiments provide methods, compounds, and compositions useful for inhibiting DGAT2 expression, which may be useful for treating, preventing, or ameliorating a disease associated with DGAT2.

13 Claims, No Drawings

Specification includes a Sequence Listing.

(56) References Cited

FOREIGN PATENT DOCUMENTS

| WO | WO 02/008260 | 1/2002 |
|---|---|---|
| WO | WO 02/22635 | 3/2002 |
| WO | WO 02/068595 | 9/2002 |
| WO | WO 03/053363 | 7/2003 |
| WO | WO 2004/044123 A2 | 5/2004 |
| WO | WO 2004/094636 | 11/2004 |
| WO | WO 2005/019418 | 3/2005 |
| WO | WO 2006/034348 A2 | 3/2006 |
| WO | WO 2007/143315 A2 | 12/2007 |
| WO | WO 2008/150729 | 12/2008 |
| WO | WO 2008/154401 | 12/2008 |
| WO | WO 2009/006478 | 1/2009 |
| WO | WO 2012/135736 | 10/2012 |
| WO | WO 2013/173789 A2 | 11/2013 |
| WO | WO 2013/192233 | 12/2013 |
| WO | WO 2014/179627 | 11/2014 |
| WO | WO 2015/054676 | 4/2015 |

OTHER PUBLICATIONS

Girard et al., "A germline-specific class of small RNAs binds mammalian Piwi proteins" Nature (2006) 442: 199-202.
Slingsby et al., "Sequence-specific 2'-O-methoxyethyl antisense oligonucleotides activate human platelets through glycoprotein VI, triggering formation of platelet-leukocyte aggregates" Haematologica (2022) 107: 519-531.
Extended European Search Report dated Feb. 17, 2023, for European Patent Application No. 22167853.5.
Partial European Search Report dated Oct. 25, 2022, for European Patent Application No. 22167853.5.
Branch et al., "A good antisense molecule is hard to find" TIBS (1998) 23:45-50.
Buhman et al., "DGAT1 is not essential for intestinal triacylglycerol absorption or chylomicron synthesis" J. Biol. Chem. (2002) 277:25474-25479.
Byrne et al., "NAFLD: a multisystem disease" J Hepatol (2015): S47-S64.
Cao et al., "Catalytic properties of MGAT3, a putative triacylgycerol synthase" J Lipid Res (2007) 48(3): 583-591.
Cases et al., "Identification of a gene encoding an acyl CoA: diacylglycerol acyltransferase, a key enzyme in triacylglycerol synthesis" Proc. Natl. Acad. Sci. (1998) 95:13018-13023.
Cases et al., "Cloning of DGAT2, a second mammalian diacylglycerol acyltransferase, and related family members" J. Biol. Chem. (2001) 276:38870-38876.
Chan et al., "Clinical classification and treatment of congenital and acquired lipodystrophy" Endocr Pract (2010) 16(2): 310-323.
Charlton et al., "Frequency and outcomes of liver transplantation for nonalcoholic steatohepatitis in the United States" Gastroenterology (2011) 141(4): 1249-1253.
Chen et al., "Increased insulin and leptin sensitivity in mice lacking acyl CoA:diacylglycerol acyltransferase 1" J. Clin. Invest. (2002) 109:1049-1055.
Chen et al., "Leptin modulates the effects of acyl CoA: diacylglycerol acyltransferase deficiency on murine fur and sebaceuous glands" J. Clin. Invest. (2002) 109:175-181.
Cheng et al., "Human acyl-CoA: diacylglycerol acyltransferase is a tetrameric protein" Biochem. J. (2001) 359:707-714.
Cheng et al., "Acylation of acylglycerols by acyl coenzyme A:diacylglycerol acyltransferase 1 (DGAT1). Functional importance of DGAT1 in the intestinal fat absorption" J Biol Chem (2008) 283(44): 29802-29811.
Chin, "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Cohen et al., "Human fatty liver disease: old questions and new insights" Science (2011) 332(6037): 1519-1523.
Crooke et al., "Basic Principles of Antisense Therapeutics" Antisense Research and Application (1998) Chapter 1:1-50.
Desai et al., "Phenotypic Correction of Diabetic Mice by Adenovirus-Mediated Glucokinase Expression" Diabetes (2001) 50:2287-2295.
Egli et al., "Synthesis, improved antisense activity and structural rationale for the divergent RNA affinities of 3'-fluoro hexitol nucleic acid (FHNA and Ara-FHNA) modified oligonucleotides" J Am Chem Soc (2011) 133(41): 16642-16649.
Farese et al., "Triglyceride synthesis: insights from the cloning of diacylglycerol acyltransferase" Curr. Opin. Lipidol. (2000) 11:229-234.
Farrell et al., "Nonalcoholic fatty liver disease: from steatosis to cirrhosis" Hepatology (2006) 43(2): S99-S112.
Garg "Clinical review#: Lipodystrophies: genetic and acquired body fat disorders" J Clin Endocrinol Metlab (2011) 96(11): 3313-3325.
Garg "Acquired and inherited lipodystrophies" N Engl J Med (2004) 350(12): 1220-1234.
Gautschi et al., "Activity of a novel bcl-2/bcl-xL-bispecific antisense oligonucleotide against tumors of diverse histologic origins" J Natl Cancer Inst (2001) 93(6): 463-471.
Guo et al., "par-1, a Gene Required for Establishing Polarity in C. elegans Embryos, Encodes a Putative Ser/Thr Kinase that is Asymmetrically Distributed" Cell (1995) 81:611-620.
Handelsman et al., "The clinical approach to the detection of lipodystrophy—an AACE consensus statement" Endocr Pract (2013) 19(1): 107-116.
Huang-Doran et al., "Lipodystrophy: metabolic insights from a rare disorder" J Endocrinol (2010) 207(3): 245-255.
Lardizabal et al., "DGAT2 is a new diacylglycerol acyltransferase gene family: purification, cloning, and expression in insect cells of two polypeptides from Mortierella ramanniana with diacylglycerol acyltransferase activity" J. Biol. Chem. (2001) 276:38862-38869.
Ludwig et al., "DGAT1 promotor polymorphism associated with alterations in body mass index, high density lipoprotein levels and blood pressure in Turkish women" Clin. Genet. (2002) 62:68-73.
Maher et al., "Comparative hybrid arrest by tandem antisense oligodeoxyribonucleotides or oligodeoxyribonucleoside methylphosphonates in a cell-free system" Nucleic Acids Res (1988) 16(8): 3341-3358.
Maier et al., "Synthesis of antisense oligonucleotides conjugated to a multivalent carbohydrate cluster for cellular targeting" Bioconjug Chem (2003) 14(1): 18-29.
Marchesini et al., "Nonalcoholic fatty liver, steatohepatitis, and the metabolic syndrome" Hepatology (2003) 37(4): 917-923.
Martin, "Ein Neuer Zugang Zu 2'-O-Alkylribonucleosiden Und Eigenschaften Deren Oligonucleotide" Helvetica Chimica Acta (1995) 78:486-504.
McCullough "Pathophysiology of nonalcoholic steatohepatitis" J Clin Gastroenterol (2006) 40(1): S17-S29.
Meegalla et al., "Concerted elevation of acyl-coenzyme A:diacylglycerol acyltransferase (DGAT) activity through independent stimulation of mRNA expression of DGAT1 and DGAT2 by carbohydrate and insulin" Biochem. Biophys. Res. Comm. (2002) 298:317-323.
Melo et al., "Genetic therapies for cardiovascular diseases." Trends in Molecular Medicine, 2005, 11:240-250.
Montgomery et al., "RNA as a target of double-stranded RNA-mediated genetic interference in Caenorhabditis elegans" Proc. Natl Acad. Sci. (1998) 95:15502-15507.
New England Biolabs 1998/1999 Catalog, cover page, pp. 121 and 284.
Oelkers et al., "Characterization of two human genes encoding acyl coenzyme A: cholesterol acyltransferase-related enzymes" J. Biol. Chem. (1998) 273:26765-26771.
Rensen et al., "Design and synthesis of novel N-acetylgalactosamine-terminated glycolipids for targeting of lipoproteins to the hepatic asialoglycoprotein receptor" J Med Chem (2004) 47(23): 5798-5808.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.

(56) References Cited

OTHER PUBLICATIONS

Seth et al., "Short antisense oligonucleotides with novel 2'-4' conformationaly restricted nucleoside analogues show improved potency without increased toxicity in animals" J Med Chem (2009) 52(1): 10-13.
Shulman "Ectopic fat in insulin resistance, dyslipidemia, and cardiometabolic disease" N Engl J Med (2014) 371(12): 1131-1141.
Smith et al., "Obesity resistance and multiple mechanisms of triglyceride synthesis in mice lacking Dgat" Nat. Genet. (2000) 25:87-90.
Stone et al., "Lipopenia and Skin Barrier Abnormalities in DGAT2-deficient Mice" J. Biol. Chem. (2004) 279(12):11767-11776.
Tabata et al., "Xanthohumols, diacylglycerol acyltransferase inhibitors, from Humulus lupulus" Phytochemistry (1997) 46:683-687.
Tijsterman et al., "RNA Helicase MUT-14-Dependent Gene Silencing Triggered in C. elegans by Short Antisense RNAs" Science (2002) 295:694-697.
Tomoda et al., "Roselipins, inhibitors of diacylglycerol acyltransferase, produced by Gliocladium roseum KF-1040" J. Antibiot. Tokyo (1999) 52:689-694.
Vaughan et al., "Tumors and the heart: molecular genetic advances." Current Opinions in Cardiology, 2001, 16:195-200.
Waterman et al., "Distinct ontogenic patterns of overt and latent DGAT activities of rat liver microsomes" J. Lipid Res. (2002) 43:1555-1562.
Williams et al., "Prevalence of nonalcoholic fatty liver disease and nonalcoholic steatohepatitis among a largely middle-aged population utilizing ultrasound and liver biopsy: a prospective study" Gastroenterology (2011) 140(1): 124-131.
Woolf et al., "Specificity of antisense oligonucleotides in vivo" Proc Natl Acad Sci USA (1992) 89(16): 7305-7309.
Yamaguchi et al., "Inhibiting Triglyceride Synthesis Improves Hepatic Steatosis but Exacerbates Liver Damage and Fibrosis in Obese Mice with Nonalcoholic Steatohepatitis" Hepatology (2007) 45:1366-1374.
Yu et al., "Posttranscriptional control of the expression and function of diacylglycerol acyltransferase-1 in mouse adipocytes" J. Biol. Chem. (2002) 277:50876-50884.
Yu et al., "Antisense Oligonucleotide Inhibition of DGAT2 Expression Reduced Hepatic Steatosis and Hyperlipidemia in Diet-Induced Obese Mice" Obesity Res. (2003) NAASO's 2003 Annual Meeting, Oct. 11-15, 11:A48.
Yu et al., "Antisense Oligonucleotide Reduction of DGAT2 Expression Improves Hepatic Steatosis and Hyperlipidemia in Obese Mice" Hepatology (2005) 42:362-371.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J Org. Chem. (2009) 74: 118-134.
European Supplementary Search Report for Application No. EP 04779444.1 dated Jul. 4, 2008.
European Search Report for application EP 10175722.7 dated Mar. 23, 2011.
Partial Search Report for EP 16824926.6 dated Dec. 3, 2018.
International Search Report for Int. Application No. PCT/US04/24384 dated Mar. 23, 2006.
International Search Report for Int. Application No. PCT/US16/41410 dated Dec. 15, 2016.
Extended EP Search Report for 16824926.6 dated Mar. 13, 2019.

MODULATORS OF DIACYGLYCEROL ACYLTRANSFERASE 2 (DGAT2)

SEQUENCE LISTING

The present application is being filed along with a Sequence Listing in electronic format. The Sequence Listing is provided as a file entitled BIOL0178USC2SEQ_ST25.txt created Feb. 18, 2022, which is 1 mb in size. The information in the electronic format of the sequence listing is incorporated herein by reference in its entirety.

FIELD

The present embodiments provide methods, compounds, and compositions for treating, preventing, or ameliorating a disease associated with nonalcoholic fatty liver disease, including non-alcoholic steatohepatitis (NASH) and hepatic steatosis, by administering a diacylglycerol acyltransferase 2 (DGAT2) specific inhibitor to an individual.

BACKGROUND

Nonalcoholic fatty liver diseases (NAFLDs) including NASH (nonalcoholic steatohepatitis) are considered to be hepatic manifestations of the metabolic syndrome (Marchesini G, et al. Hepatology 2003; 37: 917-923) and are characterized by the accumulation of triglycerides in the liver of patients without a history of excessive alcohol consumption. The majority of patients with NAFLD are obese or morbidly obese and have accompanying insulin resistance (Byrne C D and Targher G. J Hepatol 2015 April; 62(1S): S47-S64). The incidence of NAFLD/NASH has been rapidly increasing worldwide consistent with the increased prevalence of obesity, and is currently the most common chronic liver disease. Recently, the incidence of NAFLD and NASH was reported to be 46% and 12%, respectively, in a largely middle-aged population (Williams C D, et al. Gastroenterology 2011; 140: 124-131).

NAFLD is classified into simple steatosis, in which only hepatic steatosis is observed, and NASH, in which intralobular inflammation and ballooning degeneration of hepatocytes is observed along with hepatic steatosis. The proportion of patients with NAFLD who have NASH is still not clear but might range from 20-40%. NASH is a progressive disease and may lead to liver cirrhosis and hepatocellular carcinoma (Farrell G C and Larter C Z. Hepatology 2006; 43: S99-S112; Cohen J C, et al. Science 2011; 332: 1519-1523). Twenty percent of NASH patients are reported to develop cirrhosis, and 30-40% of patients with NASH cirrhosis experience liver-related death (McCullough A J. J Clin Gastroenterol 2006; 40 Suppl 1: S17-S29). Recently, NASH has become the third most common indication for liver transplantation in the United States (Charlton M R, et al. Gastroenterology 2011; 141: 1249-1253).

Currently, the principal treatment for NAFLD/NASH is lifestyle modification by diet and exercise. However, pharmacological therapy is indispensable because obese patients with NAFLD often have difficulty maintaining improved lifestyles.

Lipodystrophy syndromes are a group of rare metabolic diseases characterized by selective loss of adipose tissue that leads to ectopic fat deposition in liver and muscle and the development of insulin resistance, diabetes, dyslipidemia and fatty liver disease (Shulman G I. N Engl J Med 2014; 371: 1131-1141; Garg A. J Clin Endocrinol Metab 2011; 96: 3313-3325; Chan J L and Oral E A. Endocr Pract 2010; 16: 310-323; Garg A. N Engl J Med 2004; 350: 1220-1234). These syndromes constitute a significant medical unmet need as these patients are refractory to current therapies, mainly used to treat diabetes and elevated TG levels, in an attempt to reduce the risk of serious associated complications (coronary artery disease, diabetic nephropathy, cirrhosis and pancreatitis).

Partial Lipodystrophy has a higher prevalence (estimated ~2-3 in one (1) million) than generalized lipodystrophy, but the extent of the prevalence is unknown because these patients are greatly under-diagnosed (Chan J L and Oral E A. Endocr Pract 2010; 16: 310-323; Garg A. J Clin Endocrinol Metab 2011; 96: 3313-3325). Partial lipodystrophy is further divided into acquired partial lipdystrophy (APL) or Familial partial lipodystrophy (FPL). The diagnosis of PL is mainly clinical and needs to be considered in patients presenting with the triad of insulin resistance (with or without overt diabetes), significant dyslipidemia in the form of hypertriglyceridemia, and fatty liver (Huang-Doran I, et al. J Endocrinol 2010; 207: 245-255). Patients often present with diabetes and severe insulin resistance requiring high doses of insulin.

Current treatment includes lifestyle modification such as reducing caloric intake and increasing energy expenditure via exercise. Conventional therapies used to treat severe insulin resistance (metformin, thiazolidinediones, GLP-1s, insulin), and/or high TGs (dietary fat restriction, fibrates, fish oils) are not very efficacious in these patients (Chan J L and Oral E A. Endocr Pract 2010; 16: 310-323; Garg A. J Clin Endocrinol Metab 2011). Partial Lipodystrophy is an ultra-orphan indication for which there is a significant unmet medical need. Diabetes, NASH, and/or hypertriglyceridemia associated with this condition can lead to serious complications (Handelsman Y, et al. Endocr Pract 2013; 19: 107-116).

Diacylglycerol O-acyltransferase (DGAT) catalyzes the final step in triglyceride (TG) synthesis by facilitating the linkage of sn-1,2-diacylglycerol (DAG) with an acyl-CoA. There are two isoforms of DGATs (DGAT1 and DGAT2), and studies indicate that both DGAT1 and DGAT2 play important roles in TG synthesis. DGAT1 is most highly expressed in small intestine and white adipose tissue (WAT), whereas DGAT2 is primarily expressed in liver and WAT (Cases S, et al. Proc Natl Acad Sci USA 1998; 95, 13018-13023; Cases S, et al. J Biol Chem 2001; 276, 38870-38876). Although both DGAT1 and DGAT2 catalyze the same reactions in TG synthesis with DAG or monoacylglycerol (MAG) and acyl-CoA as substrates, they are functionally distinguished not only by their tissue expression, but by their differences in catalytic properties (Cao J, et al. J Lipid Res 2007; 48: 583-591; Cheng D, et al. J Biol Chem 2008; 283: 29802-29811), subcellular localization (Stone S J, et al. J Biol Chem 2004; 279: 11767-11776), and physiological regulation (Meegalla R L, et al. Biochem Biophys Res Commun 2002, 298, 317-323). For example, suppression of DGAT2, but not of DGAT1, by antisense oligonucleotide treatment improved hepatic steatosis and blood lipid levels independent of adiposity in rodent models of obesity and the data indicated that these effects were related to decreased hepatic lipid synthesis (Yu X X, et al. Hepatology 2005; 42: 362-371).

These studies demonstrate that DGAT2 inhibition may improve NAFLD/NASH, as well as the metabolic profile of patients with lipodystrophy syndromes by reducing triglycerides, improving insulin sensitivity, and decreasing hepatic steatosis.

SUMMARY

The present embodiments provided herein are directed to potent and/or tolerable compounds and compositions useful for treating, preventing, ameliorating, or slowing progression of NAFLD, such as NASH, as well as lipodystrophy syndromes, such as partial lipodystrophy.

Several embodiments provided herein are directed to several antisense compounds that are more potent and efficacious than antisense oligonucleotides from an earlier published application, WO 2005/019418. Several embodiments provided herein are directed to compounds and compositions that are potent and tolerable.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by ISIS number (ISIS #) indicate a combination of nucleobase sequence, chemical modification, and motif.

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (e.g., uracil).

"2'-O-methoxyethyl" (also 2'-MOE and 2'-O(CH$_2$)$_2$—OCH$_3$) refers to an O-methoxy-ethyl modification at the 2' position of a sugar ring, e.g. a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a furanosyl sugar moiety comprising a 2'-substituent group other than H or OH.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase.

"About" means within +10% of a value. For example, if it is stated, "the compounds affected at least about 70% inhibition of DGAT2", it is implied that DGAT2 levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both agents be administered in a single pharmaceutical composition, in the same dosage form, by the same route of administration, or at the same time. The effects of both agents need not manifest themselves at the same time. The effects need only be overlapping for a period of time and need not be coextensive. Concomitant administration or co-administration encompasses administration in parallel or sequentially.

"Amelioration" refers to a lessening of at least one indicator, sign, or symptom of an associated disease, disorder, or condition. In certain embodiments, amelioration includes a delay or slowing in the progression of one or more indicators of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an antisense oligonucleotide and optionally one or more additional features, such as a conjugate group or terminal group. Examples of antisense compounds include single-stranded and double-stranded compounds. Examples are antisense oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or a region or segment thereof. In certain embodiments, an antisense oligonucleotide is specifically hybridizable to a target nucleic acid or a region or segment thereof.

"Bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"Cleavable moiety" means a bond or group of atoms that is cleaved under physiological conditions, for example, inside a cell, an animal, or a human.

"cEt" or "constrained ethyl" means a bicyclic sugar moiety comprising a bridge connecting the 4'-carbon and the 2'-carbon, wherein the bridge has the formula: 4'-CH($CH_3$)—O-2'.

"Chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Conjugate group" means a group of atoms that is directly or indirectly attached to a parent compound, e.g., an oligonucleotide.

"Conjugate linker" means a group of atoms that connects a conjugate group to a parent compound, e.g., an oligonucleotide.

"Constrained ethyl nucleoside" (also cEt nucleoside) means a nucleoside comprising a bicyclic sugar moiety comprising a 4'-CH($CH_3$)—O-2' bridge.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other.

"Designing" or "Designed to" refer to the process of designing an oligomeric compound that specifically hybridizes with a selected nucleic acid molecule.

"DGAT2" means any nucleic acid or protein of DGAT2. "DGAT2 nucleic acid" means any nucleic acid encoding DGAT2. For example, in certain embodiments, a DGAT2 nucleic acid includes a DNA sequence encoding DGAT2, an RNA sequence transcribed from DNA encoding DGAT2 (including genomic DNA comprising introns and exons), including a non-protein encoding (i.e. non-coding) RNA sequence, and an mRNA sequence encoding DGAT2. "DGAT2 mRNA" means an mRNA encoding a DGAT2 protein.

"DGAT2 specific inhibitor" refers to any agent capable of specifically inhibiting DGAT2 RNA and/or DGAT2 protein expression or activity at the molecular level. For example, DGAT2 specific inhibitors include nucleic acids (including antisense compounds), peptides, antibodies, small molecules, and other agents capable of inhibiting the expression of DGAT2 RNA and/or DGAT2 protein.

"Dose" means a specified quantity of a pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in an individual. In other embodiments, the pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double-stranded antisense compound" means an antisense compound comprising two oligomeric compounds that are complementary to each other and form a duplex, and wherein one of the two said oligomeric compounds comprises an antisense oligonucleotide.

"Effective amount" means the amount of compound sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully modified" in reference to an oligonucleotide means a modified oligonucleotide in which each nucleoside is modified. "Uniformly modified" in reference to an oligonucleotide means a fully modified oligonucleotide in which at least one modification of each nucleoside is the same. For example, the nucleosides of a uniformly modified oligonucleotide can each have a 2'-MOE modification but different nucleobase modifications, and the internucleoside linkages may be different.

"Gapmer" means a chimeric antisense compound in which an internal region having a plurality of nucleosides that is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." In certain embodiments, the structure of a gapmer may support RNase H cleavage.

"Hybridization" means the pairing or annealing of complementary oligonucleotides and/or nucleic acid molecules. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Identifying an animal having, or at risk for having, a disease, disorder and/or condition" means identifying an animal having been diagnosed with the disease, disorder and/or condition or identifying an animal predisposed to develop the disease, disorder and/or condition. Such identification may be accomplished by any method including evaluating an individual's medical history and standard clinical tests or assessments.

"Immediately adjacent" means there are no intervening elements between the immediately adjacent elements of the same kind (e.g. no intervening nucleobases between adjacent nucleobases).

"Individual" means a human or non-human animal selected for treatment or therapy.

"Inhibiting the expression or activity" refers to a reduction, blockade of the expression or activity relative to the expression or activity in an untreated or control sample, and does not necessarily indicate a total elimination of expression or activity.

"Internucleoside linkage" means a group or bond that forms a covalent linkage between adjacent nucleosides in an oligonucleotide. As used herein "modified internucleoside linkage" means any internucleoside linkage other than a naturally occurring, phosphate internucleoside linkage. Naturally occurring, non-phosphate linkages are referred to herein as modified internucleoside linkages.

"Phosphorothioate linkage" means a linkage between nucleosides wherein the phosphodiester bond of a phosphate linkage is modified by replacing one of the non-bridging oxygen atoms with a sulfur atom. A phosphorothioate linkage is a modified internucleoside linkage.

"Lengthened" antisense oligonucleotides are those that have one or more additional nucleosides relative to an antisense oligonucleotide disclosed herein; e.g. a parent oligonucleotide.

"Linearly modified sugar" or "linearly modified sugar moiety" means a modified sugar moiety that comprises an acyclic or non-bridging modification. Such linear modifications are distinct from bicyclic sugar modifications.

"Linked deoxynucleoside" means a nucleic acid base (A, G, C, T, U) substituted by deoxyribose linked by a phosphate ester to form a nucleotide.

"Linked nucleosides" are nucleosides that are connected in a continuous sequence (i.e. no additional nucleosides are present between those that are linked).

As used herein, "mismatch" or "non-complementary" means a nucleobase of a first oligonucleotide that is not complementary to the corresponding nucleobase of a second oligonucleotide or target nucleic acid when the first and second oligonucleotides are aligned. For example, a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U). A "universal base" is a nucleobase that can pair with any one of the five unmodified nucleobases.

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modulating" refers to changing or adjusting a feature in a cell, tissue, organ or organism. For example, modulating DGAT2 RNA can mean to increase or decrease the level of DGAT2 RNA and/or DGAT2 protein in a cell, tissue, organ or organism. A "modulator" effects the change in the cell, tissue, organ or organism. For example, a DGAT2 antisense compound can be a modulator that decreases the amount of DGAT2 RNA and/or DGAT2 protein in a cell, tissue, organ or organism.

"Monomer" refers to a single unit of an oligomer. Monomers include, but are not limited to, nucleosides and nucleotides, whether naturally occurring or modified.

"Motif" means the pattern of unmodified and/or modified sugar moieties, nucleobases, and/or internucleoside linkages, in an oligonucleotide.

"Natural" or "Naturally occurring" means found in nature. "Naturally occurring internucleoside linkage" means a 3' to 5' phosphodiester linkage. "Natural sugar moiety" means a sugar moiety found in DNA (2'-H) or RNA (2'-OH). "Naturally occurring nucleobase" means the purine bases adenine (A) and guanine (G), and the pyrimidine bases thymine (T), cytosine (C) and uracil (U). "Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid.

"Nucleobase sequence" means the order of contiguous nucleobases independent of any sugar, linkage, and/or nucleobase modification.

"Nucleoside" means a compound comprising a nucleobase and a sugar moiety. The nucleobase and sugar moiety are each, independently, unmodified or modified.

"Nucleotide" means a nucleoside having a phosphate group covalently linked to the sugar portion of the nucleoside.

"Oligomeric compound" means a compound comprising an oligonucleotide and optionally one or more additional features, such as a conjugate group or terminal group. Examples of oligomeric compounds include single-stranded and double-stranded compounds, such as, antisense compounds, antisense oligonucleotides, ribozymes, siRNAs, shRNAs, ssRNAs, and occupancy-based compounds.

"Oligonucleoside" means an oligonucleotide in which the internucleoside linkages do not contain a phosphorus atom.

"Oligonucleotide" means a polymer of linked nucleosides each of which can be modified or unmodified, independent one from another.

"Parent oligonucleotide" means an oligonucleotide whose sequence is used as the basis of design for more oligonucleotides of similar sequence but with different lengths, motifs, and chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means a medium or diluent suitable for use in administering to an animal. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or antisense compounds, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of compounds suitable for administering to an individual. For example, a pharmaceutical composition may comprise one or more compounds or salts thereof and a sterile aqueous solution.

"Phosphorothioate linkage" means a modified internucleoside linkage between nucleosides where the phosphodiester bond is modified by replacing one of the non-bridging oxygen atoms with a sulfur atom.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound "Prevent" refers to delaying or forestalling the onset, development or progression of a disease, disorder, or condition for a period of time from minutes to indefinitely. Prevent may also mean reducing the risk of developing a disease, disorder, or condition.

"Prodrug" means a form of a compound which, when administered to an individual, is metabolized to another form. In certain embodiments, the metabolized form is the active, or more active, form of the compound (e.g., drug).

"Prophylactically effective amount" refers to an amount of a pharmaceutical agent that provides a prophylactic or preventative benefit to an animal.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"Ribonucleotide" means a nucleotide having a hydroxy at the 2' position of the sugar portion of the nucleotide.

"RNAi compound" means an oligomeric compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. The term RNAi compound excludes antisense oligonucleotides that act through RNase H.

"Segment" is defined as a smaller or sub-portion of region within an antisense compound, an oligonucleotide, or a target nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to an antisense compound or oligomeric compound means there is one oligonucleotide in the compound. "Self-complementary" in reference to an antisense compound or oligomeric compound means a compound that at least partially hybridizes to itself. A compound consisting of one antisense or oligomeric compound, wherein the oligonucleotide of the compound is self-complementary, is a single-stranded compound. A single-stranded antisense or oligomeric compound may be capable of binding to a complementary compound to form a duplex.

"Sites," as used herein, are defined as unique nucleobase positions within a target nucleic acid.

"Slows progression" means decrease in the development of the said disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids.

"Specifically inhibit" a target nucleic acid means to reduce or block expression of the target nucleic acid while exhibiting fewer, minimal, or no effects on non-target nucleic acids reduction and does not necessarily indicate a total elimination of the target nucleic acid's expression.

"Sugar moiety" means a group of atoms that can link a nucleobase to another group, such as an internucleoside linkage, conjugate group, or terminal group. In certain embodiments, a sugar moiety is attached to a nucleobase to form a nucleoside. As used herein, "unmodified sugar moiety" or "unmodified sugar" means a 2'-OH(H) furanosyl moiety, as found in RNA, or a 2'-H(H) moiety, as found in DNA. Unmodified sugar moieties have one hydrogen at each of the 1', 3', and 4' positions, an oxygen at the 3' position, and two hydrogens at the 5' position. As used herein, "modified sugar moiety" or "modified sugar" means a furanosyl moiety comprising a non-hydrogen substituent in place of at least one hydrogen of an unmodified sugar moiety, or a sugar surrogate. In certain embodiments, a modified sugar moiety is a 2'-substituted sugar moiety. Such modified sugar moieties include bicyclic sugars and linearly modified sugars.

"Sugar surrogate" means a modified sugar moiety having other than a furanosyl moiety that can link a nucleobase to another group, such as an internucleoside linkage, conjugate group, or terminal group. Modified nucleosides comprising sugar surrogates can be incorporated into one or more positions within an oligonucleotide. In certain embodiments, such oligonucleotides are capable of hybridizing to complementary oligomeric compounds or nucleic acids.

"Synergy" or "synergize" refers to an effect of a combination that is greater than additive of the effects of each component alone.

"Target gene" refers to a gene encoding a target.

"Target nucleic acid," "target RNA," "target RNA transcript" and "nucleic acid target" mean a nucleic acid capable of being targeted by antisense compounds.

"Targeting" means the process of design and selection of an antisense compound that will specifically hybridize to a target nucleic acid and induce a desired effect.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Treat" refers to administering a compound or pharmaceutical composition to an animal in order to effect an alteration or improvement of a disease, disorder, or condition in the animal.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleotides) or a DNA nucleotide (i.e. β-D-deoxyribonucleotide).

CERTAIN EMBODIMENTS

Certain embodiments provide methods, compounds and compositions for inhibiting DGAT2 (DGAT2) expression.

Certain embodiments provide antisense compounds targeted to a DGAT2 nucleic acid. In certain embodiments, the DGAT2 nucleic acid has the sequence set forth in RefSeq No. NM_032564.3 (incorporated by reference, disclosed herein as SEQ ID NO: 1) or nucleotides 5669186 to 5712008 of RefSeq No. NT_033927.5 (incorporated by reference, disclosed herein as SEQ ID NO: 2). In certain embodiments, the antisense compound is a single-stranded oligonucleotide.

Certain embodiments provide an antisense compound comprising a modified oligonucleotide consisting of 10 to 30 linked nucleosides and having a nucleobase sequence comprising at least 8 contiguous nucleobases of any of the nucleobase sequences of SEQ ID NOs: 16-4679. In certain embodiments, the antisense compound is a single-stranded oligonucleotide.

Certain embodiments provide an antisense compound comprising a modified oligonucleotide consisting of 10 to 30 linked nucleosides and having a nucleobase sequence comprising at least 9, at least 10, at least 11, or at least 12 contiguous nucleobases of any of the nucleobase sequences of SEQ ID NOs: 16-4679. In certain embodiments, the antisense compound is a single-stranded oligonucleotide.

Certain embodiments provide an antisense compound comprising a modified oligonucleotide consisting of 10 to 30 linked nucleosides and having a nucleobase sequence comprising the nucleobase sequence of any one of SEQ ID NOs: 16-4679. In certain embodiments, the antisense compound is a single-stranded oligonucleotide.

Certain embodiments provide an antisense compound comprising a modified oligonucleotide consisting of the nucleobase sequence of any one of SEQ ID NOs: 16-4679. In certain embodiments, the antisense compound is a single-stranded oligonucleotide.

In certain embodiments, antisense compounds or antisense oligonucleotides target the 26711-26802 of a DGAT2 nucleic acid. In certain aspects, antisense compounds or antisense oligonucleotides target within nucleotides 26711-26802 of a DGAT2 nucleic acid having the nucleobase sequence of SEQ ID NO: 2 (nucleotides 5669186 to 5712008 of RefSeq No. NT_033927.5). In certain aspects, antisense compounds or antisense oligonucleotides have at least an 8, 9, 10, 11, 12, 13, 14, 15, or 16 contiguous nucleobase portion complementary to an equal length portion within nucleotides 26711-26802 of a DGAT2 nucleic acid having the nucleobase sequence of SEQ ID NO: 2 (nucleotides 5669186 to 5712008 of RefSeq No. NT_033927.5).

In certain embodiments, antisense compounds or antisense oligonucleotides target a region of a DGAT2 nucleic acid having the nucleobase sequence of SEQ ID NO: 2 within nucleobases 26711-26799, 26711-26730, 26721-26740, 26755-26744, 26778-26797, 26779-26798, 26755-26798, and 26780-26799. In certain aspects, antisense compounds or antisense oligonucleotides target at least an 8, 9, 10, 11, 12, 13, 14, 15, or 16 contiguous nucleobases within the aforementioned nucleobase regions.

In certain embodiments, the following nucleotide regions of SEQ ID NO: 2, when targeted by antisense compounds or oligonucleotides, display at least 60% inhibition: 9930-9949, 9953-9973, 9959-9978, 9961-9981, 9970-9992, 9975-9994, 9984-10003, 10040-10059, 10043-10063, 10045-10064, 10046-10065, 10049-10068, 10054-10073, 10160-10179, 10209-10229, 10212-10231, 10214-10235, 10217-10236, 10218-10238, 10327-10346, 10389-10413, 10490-10511, 10522-10548, 10530-10549, 10531-10551, 10533-10553, 10645-10669, 10651-10670, 10653-10673, 10655-10674, 10656-10675, 10657-10676, 10658-10680, 10662-10681, 10663-10684, 10666-10685, 10667-10684, 10670-10689, 10702-10721, 10727-10747, 10729-10748, 10730-10750, 10733-10755, 10737-10756, 10742-10761, 10763-10782, 10814-10835, 10817-10836, 10818-10837, 10940-10964, 11008-11027, 11074-11097, 11123-11150, 11158-11182, 11168-11187, 11170-11190, 11171-11197, 11199-11218, 11200-11220, 11209-11228, 11318-11342, 11413-11432, 11559-11578, 11594-11618, 11707-11731, 11872-11891, 11920-11939, 12247-12266, 12285-12304, 12549-12573, 12671-12695, 12806-12826, 12839-12863, 12890-12909, 12927-12961, 13098-13117, 13212-13231, 13239-13258, 13441-13461, 13921-13945, 13962-13996, 14177-14201, 14194-14218, 14239-14258, 14385-14404, 14457-14522, 14504-14527, 14537-14556, 14648-14697, 14715-14790, 14715-14739, 14735-14764, 14746-14765, 14749-14774, 14756-14779, 14765-14789, 14771-14790, 14807-14831, 14852-14871, 14882-14901, 14953-15015, 14997-15065, 15041-15107, 15041-15092, 15083-15107, 15178-15197, 15214-15243, 15219-15243, 15248-15276, 15255-15276, 15292-15311, 15318-15338, 15321-15342, 15353-15372, 15368-15392, 15514-15533, 15573-15665, 15573-15597, 15729-15753, 15804-15828, 15814-15833, 15876-15900, 15876-15896, 15933-15962, 15933-15954, 15991-16010, 16046-16073, 16082-16124, 16237-16256, 16288-16314, 16288-16478, 16308-16329, 16428-16478, 16510-16529, 16808-16855, 16808-16828, 16811-16855, 16898-16921, 17007-17031, 17038-17057, 17207-17229, 17269-17298, 17273-17294, 17328-17357, 17420-17444, 17450-17471, 17530-17559, 17328-17559, 17960-17989, 18078-18097, 18155-18176, 18155-18198, 18177-18200, 18225-18305, 18306-18327, 18309-18330, 18312-18330, 18312-18332, 18315-18344, 18329-18355, 18379-18398, 18417-18446, 18430-18451, 1818450-18473, 18470-18494, 18581-18601, 18583-18605, 18581-18611, 18588-18611, 18821-18850, 18821-18847, 18836-18899, 18890-18914, 18898-18919, 19013-19037, 19013-19040, 19360-19411, 19363-19383, 19804-19823, 19909-19932, 19987-20009, 20232-20256, 20296-20325, 20462-20481, 20541-20560, 20668-20692, 20775-20797, 20779-20797, 20817-20841, 20828-20863, 20878-20897, 20956-20979, 21046-21120, 21091-21120, 21164-21203, 21164-21188, 21374-21403, 21659-21678, 21708-21727, 21765-21784, 21933-21955, 22153-22191, 22153-22175, 22158-22179, 22167-22191, 22439-22463, 22547-22567, 22770-22790, 22770-22795, 22775-22795, 22835-22870, 22841-22865, 22881-22901, 22885-22905, 22889-22910, 23095-23115, 23098-23119, 23099-23119, 23128-23157, 23179-23251, 23238-23258, 23240-23260, 23242-23262, 23429-23449, 23480-23566, 23547-23581, 23553-23573, 23555-23576, 23562-23586, 23597-23616, 23641-23670, 24123-24144, 24123-24147, 24202-24223, 24202-24241, 24799-25039, 24799-24847, 25018-2509, 25023-25053, 25026-25053, 25069-25092, 25069-25114, 25077-25104, 25088-25114, 25183-25205, 25183-25217, 25198-25217, 25226-25250, 25226-25265, 25236-25260, 25244-25291, 25312-25394, 25380-25400, 25717-25736, 25782-25860, 25845-25866, 25866-25935, 25919-25939, 25950-25971, 25954-25973, 25981-26030, 26102-26126, 26162-26220, 26300-26324, 26331-26372, 26363-26405, 26389-26409, 26396-26420, 26479-26504, 26516-26550, 26534-26555, 26534-26560, 26540-26560, 26610-26634, 26620-26640, 26626-26648, 26620-26664, 26633-26655, 26640-26664, 26716-26740, 26716-26799, 26755-26799, 26786-26807, 26789-26809, 26786-26809, 26811-26831, 26849-26869, 26869-26898, 26883-26903, 26926-26943, 27046-27075, 27106-27130, 27174-27230, 27221-27241, 27226-27258, 27241-27265, 27249-27269, 27367-27406, 27367-27402, 27386-27406, 27638-27664, 27769-27791, 27775-27810, 27852-27877, 28026-28049, 28128-28154, 28462-28492, 28475-28508, 28516-28542, 28584-28605, 28804-28826, 29010-29035, 29143-29167, 29151-29180, 29196-29218, 29244-29268, 29253-29282, 29361-29383, 29369-29391, 29450-29495, 29480-29504, 29538-29654, 29673-29697, 29681-29702, 29781-29801, 29804-29828, 29827-29847, 29832-29852, 29838-29858, 29844-29878, 30484-30504, 30524-30548, 30554-30588, 30669-30731, 30972-30997, 30984-31005, 31551-31571, 31554-31584, 31794-31818, 31932-31952, 31936-31956, 31939-31963, 31946-31971, 32115-32136, 32119-32140, 32130-32159, 32175-32201, 32428-32454, 32436-32467, 32459-32479, 32463-32489, 32474-32495, 32480-32529, 32586-32638, 32621-32641, 32756-32776, 32801-32825, 32816-32840, 33070-33180, 33176-33199, 33182-33202, 33411-33433, 33572-33601, 33729-33759, 33846-33876, 33860-33882, 33866-33886, 34063-34117, 34211-34232, 34686-34710, 34739-34887, 34901-34950, 35263-35292, 35277-35302, 35322-35346, 35408-35433, 35421-35441, 35436-35457, 35665-35685, 36246-36267, 36250-36270, 36253-36274, 36258-36281, 36268-36531, 36516-36537, 36573-36597, 36581-36603, 36632-36666, 36677-36698, 36682-36702, 36689-36757, 36742-36772, 36841-36874, 36846-36874, 36865-37041, 37054-37073, 37838-37858, 39668-39694, 39684-39705, 39820-39840, 39830-39852, and 40909-40933.

In certain embodiments, the following nucleotide regions of SEQ ID NO: 2, when targeted by antisense compounds or oligonucleotides, display at least 70% inhibition: 9971-9991, 9975-9994, 9984-10003, 10040-10059, 10044-10063, 10045-10064, 10049-10068, 10054-10179, 10210-10229, 10214-10234, 10216-10235, 10217-10236, 10218-10237, 10327-10346, 10490-10509, 10491-10511, 10522-10541, 10528-10548, 10530-10549, 10531-10550, 10532-10551, 10533-10553, 10536-10555, 10537-10556, 10645-10664, 10647-10666, 10649-10669, 10653-10673, 10655-10674, 10656-10675, 10657-10676, 10658-10677, 10659-10679, 10661-10680, 10662-10681, 10663-10683, 10665-10684, 10666-10685, 10667-10686, 10668-10687, 10670-10689, 10672-10691, 10702-10721, 10727-10747, 10729-10748, 10730-10750, 10732-10751, 10733-10752, 10734-10753, 10735-10754, 10737-10756, 10742-10756, 10742-10761, 10763-10782, 10815-10835, 10817-10836, 10818-10837, 10819-10840, 10940-10959, 10941-10960, 10942-10961, 10944-10963, 11008-11027, 11074-11093, 11075-11094, 11076-11095, 11078-11097, 11124-11146, 11128-11147, 11129-11148, 11130-11149, 11131-11177, 11159-11178, 11160-11179, 11161-11180, 11168-11187, 11170-11190, 11172-11191, 11173-11192, 11174-11196, 11180-11218, 11200-11219, 11201-11221, 11203-11222, 11204-11220, 11209-11228, 11323-11342, 11413-11432, 11559-11578, 11599-11618, 11872-11891, 112285-12304, 12549-12568, 12806-12826, 12809-12828, 12927-12946, 12942-12961, 13441-13461, 13926-13945, 14182-14201, 14194-14213, 14196-14216, 14239-14258, 14385-14404, 14462-14522, 14504-14523, 14505-14524, 14506-14527, 14537-14556, 14648-14667, 14649-14668, 14650-14669, 14651-14670, 14658-14682, 14664-14683, 14665-14684, 14666-14686, 14668-14687, 14673-14739, 14741-14764, 14746-14765, 14749-14774, 14756-14775, 14757-14779, 14765-14784, 14767-14786, 14769-14789, 14771-14790, 14772-14793, 14807-14831, 14852-15005, 14992-15012, 14995-15015, 14997-15016, 14998-15017, 14999-15020, 15011-15040, 15073-15092, 15214-15233, 15219-15243, 15248-15269, 15248-15276, 15251-15270, 15252-15272, 15254-15273, 15255-15274, 15256-15276, 15321-15342, 15573-15595, 15578-15665, 15729-15748, 15809-15828, 15876-15895, 15881-15952, 15991-16066, 16051-16070, 16053-16102, 16289-16309, 16292-16312, 16310-16329, 16248-16448, 16432-16451, 16438-16457, 16808-16828, 16811-16830, 16813-16832, 16815-16835, 16828-16852, 16836-16855, 16898-16917, 16900-16921, 17007-17027, 17207-17227, 17210-17229, 17274-17294, 17328-17347, 17330-17352, 17450-17549, 17960-17979, 18155-18175, 18157-18176, 18160-15180, 18162-18181, 18163-18182, 18164-18183, 18165-18184, 18166-18185, 18172-18193, 18175-18194, 18176-18194, 18176-18195, 18178-18199, 18181-18200, 18225-18244, 18235-18305, 18307-18327, 18309-18328, 18310-18330, 18312-18332, 18315-18337, 18320-18340, 18322-18341, 18323-18342, 18324-18343, 18325-18347, 18330-18355, 18379-18436, 18418-18437, 18419-18438, 18420-18439, 18422-18441, 18431-18451, 18450-18469, 18451-18470, 18452-18471, 18470-18489, 18581-18600, 18582-18601, 18583-18602, 18584-18604, 18588-18610, 18828-18847, 18829-18848, 18831-18850, 18869-18888, 18870-18889, 18899-18919, 19013-19032, 19016-19035, 19018-19037, 19020-19039, 19360-19380, 19364-19383, 19911-19932, 19987-20008, 20232-20251, 20298-20317, 20300-20325, 20668-20689, 20672-20692, 20775-20796, 20780-20800, 20822-20841, 20829-20851, 20837-20857, 20840-20862, 20958-20979, 21164-21183, 21384-21403, 21933-21952, 22155-22175, 22439-22463, 22548-22567, 22549-22568, 22771-22790, 22772-22791, 22773-22792, 22846-22865, 22886-22905, 22888-22907, 22889-22908, 23095-23115, 23098-23117, 23099-23119, 23128-23147, 23138-23157, 23184-23251, 23238-23258, 23242-23261, 23243-23262, 23244-23263, 23245-23264, 23246-23262, 23305-23324, 23426-23446, 23430-23449, 23551-23570, 23552-23571, 23553-23572, 23554-23573, 23557-23576, 23562-23586, 23641-23665, 24123-24142, 24799-24897, 25019-25038, 25023-25042, 25026-25045, 25028-25092, 25075-25094, 25077-25101, 25085-25104, 25088-25202, 25186-25205, 25193-25212, 25198-25250, 25236-25255, 25245-25291, 25312-25394, 25380-25399, 25429-25448, 25717-25808, 25841-25860, 25846-25865, 25900-25928, 25911-25930, 25913-25935, 25920-25971, 25981-26026, 26010-26030, 26102-26121, 26165-26186, 26169-26219, 26300-26324, 26353-26372, 26358-26377, 26363-26404, 26389-26409, 26397-26416, 26479-26498, 26482-26503, 26516-26535, 26517-26536, 26518-26537, 26519-26538, 26520-26540, 26526-26550, 26535-26555, 26537-26556, 26538-26557, 26539-26558, 26615-26634, 26620-26640, 26626-26646, 26628-26647, 26629-26648, 26630-26649, 26631-26650, 26632-26651, 26633-26652, 26635-26654, 26640-26659, 26711-26730, 26721-26799, 26786-26807, 26811-26830, 26852-26871, 26854-26873, 26869-26898, 26883-26903, 26927-26946, 27050-27075, 27106-27125, 27221-27240, 27228-27247, 27231-27250, 27235-27257, 27241-27265, 27249-27268, 27367-27386, 27377-27396, 27379-27398, 27381-27401, 27383-27402, 27387-27406, 27438-27457, 27639-27658, 27642-27661, 27644-27664, 27769-27790, 27775-27799, 27782-27809, 27853-27877, 28026-28048, 28128-28154, 28463-28484, 28468-28489, 28475-28500, 28516-28542, 28806-28826, 29010-28033, 29140-29159, 29143-29165, 29148-29167, 29154-29177, 29160-29180, 29193-29212, 29196-29218, 29201-29220, 29245-29265, 29253-29272, 29255-29274, 29257-29278, 29262-29282, 26361-29382, 29369-29388, 29371-29390, 29485-29504, 29538-29557, 29548-29594, 29635-29654, 29673-29692, 29675-29695, 29678-29697, 29682-29702, 29781-29801, 29809-29828, 29827-59847, 29829-29848, 29830-29849, 29831-29850, 29832-29852, 29838-29858, 29840-29859, 29842-29861, 29843-29862, 29844-29873, 30483-30502, 30484-30503, 30514-30533, 30529-30548, 30559-30578, 30669-30693, 30972-30992, 30977-30996, 30982-31001, 30986-31005, 31554-31573, 31768-31787, 31797-31817, 31933-31952, 31936-31956, 31942-31961, 32116-32135, 32120-32140, 32131-32151, 32135-32158, 32177-32198, 32182-32201, 32336-32355, 32428-32447, 32429-32448, 32430-32449, 32431-32450, 32432-32451, 32433-32452, 32434-32450, 32435-32454, 32436-32455, 32446-32466, 32449-32468, 32450-32469, 32451-32470, 32452-32471, 32453-32472, 32454-32473, 32455-32474, 32456-32475, 32457-32476, 32459-32479, 32461-32480, 32462-32481, 32463-32483, 32465-32486, 32468-32489, 32475-32495, 32477-32496, 32478-32497, 32480-32500, 32510-32529, 32619-32638, 32621-32640, 32622-32641, 32623-32642, 32645-32664, 32670-32689, 32711-32730, 32752-32771, 32753-32772, 32755-32774, 32756-32776, 32816-32840, 33096-33125, 33161-33180, 33179-33199, 33181-33200, 33182-33201, 33412-33433, 33729-33750, 33861-33881, 33866-33885, 33918-33937, 34017-34036, 34211-34231, 34216-34235, 34350-34369, 34460-34479, 34739-34887, 34901-34950, 35278-35298, 35322-35346, 35362-35381, 35410-35430, 35414-35433, 35421-35440, 35436-35457, 35665-36685, 36246-36267, 36249-36268, 36250-36269, 36251-36270, 36252-36271, 36253-36272, 36258-36277, 36262-36281, 36268-36287, 36354-36428, 36512-36531, 36517-36536, 36573-36597, 36582-36602, 36617-36636, 36677-36698, 36680-36699, 36681-36700, 36682-36702, 36691-36754, 36738-36757, 36743-36772, 36758-36777, 36841-36860, 36846-36865, 36865-36942, 37054-37138, 37389-37408, 37497-37516, 37499-37518, 37501-37520, 37745-37764, 39670-39689, 39685-39704, 39820-39839, 39830-39849, 39832-39852, and 40333-40352.

In certain embodiments, the following nucleotide regions of SEQ ID NO: 2, when targeted by antisense compounds or oligonucleotides, display at least 80% inhibition: 10040-10059, 10044-10063, 10045-10064, 10054-10073, 10210-10229, 10214-10234, 10217-10236, 10490-10509, 10531-10550, 10532-10551, 10533-10552, 10645-10664, 10650-10669, 10655-10674, 10656-10675, 10657-10676, 10659-10678, 10660-10679, 10661-10680, 10663-10682, 10664-10683, 10665-10684, 10666-10685, 10667-10686, 10670-10689, 10727-10746, 10730-10749, 10731-10750, 10732-10751, 10734-10753, 10735-10754, 10737-10756, 10816-10835, 10817-10836, 10818-10837, 10819-10838, 10820-10840, 10940-10959, 10941-10960, 10942-10961, 10944-10963, 11074-11093, 11075-11094, 11127-11146, 11128-11147, 11129-11148, 11130-11149, 11131-11177, 11159-11178, 11160-11179, 11170-11190, 11172-11191, 11173-11192, 11174-11193, 11175-11196, 11178-11197, 11199-

11218, 11200-11219, 11201-11220, 11202-11221, 11203-11222, 11559-11578, 11599-11618, 12285-12304, 13442-13461, 14462-14481, 14503-14522, 14504-14523, 14505-14524, 14506-14527, 14648-14667, 14649-14668, 14650-14669, 14651-14670, 14658-14682, 14664-14683, 14666-14686, 14673-14697, 14741-14760, 14743-14764, 14746-14765, 14750-04769, 14752-14774, 14756-14775, 14757-14775, 14758-14777, 14759-14778, 14769-14789, 14771-14790, 14772-14791, 14773-14792, 14774-14793, 14807-14826, 14882-14901, 14986-15005, 14993-15012, 14995-15015, 14997-15016, 14998-15017, 14999-15018, 15000-15019, 15001-15020, 15016-15035, 15248-15268, 15250-15269, 15251-15270, 15252-15272, 15254-15273, 15319-15338, 15321-15342, 15574-15593, 15646-15665, 15881-15952, 16310-16329, 16813-16832, 16830-16852, 16900-16921, 17007-17026, 17208-17227, 17450-17470, 18156-18175, 18157-18176, 18161-18180, 18164-18183, 18166-18185, 18173-18193, 18175-18194, 18176-18195, 18180-18199, 18308-18327, 18310-18329, 18311-18330, 18312-18331, 18321-18340, 18323-18342, 18324-18343, 18325-18344, 18326-18345, 18327-18346, 18328-18347, 18331-18350, 18379-18436, 18432-18451, 18450-18469, 18581-18600, 18585-18604, 18828-18847, 18829-18848, 18900-18919, 19911-19930, 20300-20321, 20668-20687, 20830-20849, 20837-20857, 20958-20977, 22444-22463, 22548-22567, 22771-22790, 22772-22791, 22773-22792, 22886-22905, 23096-23115, 23100-23119, 23239-23258, 23242-23261, 23243-23262, 23244-23263, 23245-23264, 23246-23262, 23427-23446, 23551-23570, 23552-23571, 23557-23576, 24123-24142, 24878-24897, 25023-25042, 25028-25047, 25033-25088, 25073-25092, 25075-25094, 25078-25101, 25085-25104, 25183-25202, 25193-25212, 25246-25291, 25375-25394, 25380-25399, 25782-25804, 25787-25806, 25841-25860, 25846-25865, 25900-25919, 25905-25928, 25911-25930, 25915-25934, 25950-25970, 26005-26025, 26010-26029, 26162-26185, 26169-26191, 26174-26194, 26179-26219, 26300-26319, 26302-26321, 26304-26324, 26353-26372, 26358-26377, 26482-26501, 26517-26536, 26519-26538, 26520-26539, 26521-26540, 26536-26550, 26537-26556, 26538-26557, 26615-26634, 26620-26639, 26627-26646, 26629-26648, 26630-26649, 26631-26650, 26632-26651, 26635-26654, 26640-26659, 26711-26730, 26778-26798, 26788-26807, 26811-26830, 26884-26903, 27050-27070, 27053-27072, 27055-27075, 27221-27240, 27231-27250, 27236-27256, 27241-27260, 27382-27401, 27383-27402, 27387-27406, 27770-27789, 27775-27794, 27777-27796, 27779-27799, 27782-27804, 27787-27809, 27853-27877, 28026-28046, 28029-28048, 28128-28149, 28133-28152, 28463-28482, 28468-28488, 28476-28497, 28480-28500, 29011-29030, 29143-29163, 29160-29179, 29193-29212, 29245-29265, 26253-26272, 29369-29388, 29548-29589, 29678-29697, 29683-29702, 29782-29801, 29827-29847, 29829-29848, 29830-29849, 29838-29858, 29840-29859, 29841-29860, 29842-29861, 29844-29863, 29854-29873, 30483-30502, 30484-30503, 30529-30548, 30674-30693, 30982-31001, 31554-31573, 32131-32151, 32135-32154, 32182-32201, 32431-32450, 32432-32451, 32433-32452, 32434-32453, 32446-32466, 32448-32467, 32449-32468, 32450-32469, 32451-32470, 32452-32471, 32453-32472, 32454-32473, 32455-32474, 32456-32475, 32459-32479, 32461-32480, 32462-32481, 32463-32482, 32464-32483, 32465-32484, 32466-32485, 32467-32486, 32468-32487, 32469-32488, 32470-32489, 32476-32495, 32477-32496, 32480-32499, 32619-32638, 32620-32639, 32621-32640, 32623-32642, 32645-32664, 32752-32771, 32753-32772, 32757-32776, 32816-32835, 33179-33199, 33181-33200, 33182-33201, 33412-33433, 33729-33749, 33866-33885, 34211-34231, 34739-34758, 34931-34950, 35436-35456, 35666-35685, 36247-36266, 36249-36268, 36250-36269, 36251-36270, 36252-36271, 36253-36272, 36258-36277, 36354-36373, 36409-36428, 36512-36531, 36517-36536, 36583-36602, 36680-36699, 36681-36700, 36841-36860, 36846-36865, 39670-39689, and 39832-39851.

In certain embodiments, the following nucleotide regions of SEQ ID NO: 2, when targeted by antisense compounds or oligonucleotides, display at least 90% inhibition: 32447-32466, 32452-32471, 32460-32479, 32462-32481, 32464-32483, 32465-32484, 32466-32485, 32467-32486, 32468-32487, 32619-32638, 32620-32639, 32753-32772, 36250-36269, 36517-36536, 32432-32451, 32431-32450, 30483-30502, 29828-29847, 29011-29030, 28026-28045, 29011-29030, 29828-29847, 30483-30502, 32431-32450, 32432-32451, 32447-32466, 32452-32471, 32460-32479, 32462-32481, 32464-32483, 32465-32484, 32466-32485, 32467-32486, 32468-32487, 32619-32638, 32620-32639, 32753-32772, 36250-36269, 36252-36271, 36409-36428, and 36517-36536.

In certain embodiments, the following antisense compounds or antisense oligonucleotides target a region of a DGAT2 nucleic acid and effect at least a 60% inhibition of a DGAT2 mRNA, ISIS NOs: 413236, 413284, 413391, 413399, 413413, 413422, 413433, 413433, 413441, 413446, 423460-423466, 423520-423527, 423601-423604, 472182, 472188, 472189, 472194-472196, 472203-472206, 472208, 472347, 472349-472352, 472398, 483803, 483811-483814, 483816-483818, 483821-483823, 483825-483835, 483838-483842, 483846-483848, 483852, 483853, 483862, 483866, 483868-483875, 483879, 483886-483890, 483892, 483895, 483897-483903, 483906-483913, 483916-483929, 483932-483934, 483936, 483942, 483948-483950, 483952, 483954, 483956, 483961, 483968-483973, 483975-483979, 483981, 483983-483989, 483992-483997, 484001, 484002, 484004-484006, 484008-484013, 484015-484017, 484019, 484020, 484028, 484030, 484031, 484041, 484049, 484050, 484054-484057, 484063-484065, 484069-484073, 484081-484083, 484085, 484089, 484094, 484097-484107, 484110, 484111, 484114-484119, 484123, 484125-484127, 484129-484137, 484139-484142, 484145-484149, 484152, 484154, 484156-484159, 484161, 484162, 484164, 484165, 484167-484172, 484178-484182, 484184, 484185, 484188, 484190-484198, 484202-484204, 484209-484211, 484213, 484215, 484217-484221, 484227, 484231, 484232, 484234, 484235, 484237, 484240-484243, 484248-484250, 484257, 484263, 484265-484271, 484273-484276, 484281-484285, 484290, 484292, 484293, 484298, 484299, 484301, 484302, 484310, 484319-484325, 484327, 484336, 484338, 484342-484344, 484346-484357, 484359, 484362-484365, 484368, 484370-484387, 484390, 484404, 484411, 495425, 495428, 495429, 495430, 495436, 495438, 495440-495459, 495461-495473, 495475, 495476, 495479-495492, 495495-495511, 495514-495545, 495548-495580, 495584, 495585, 495587-495594, 495596-495626, 495630-495639, 495641-495644, 495648-495651, 495656, 495657, 495660-495662, 495664-495667, 495669-495671, 495676, 495677, 495684-495689, 495692-495707, 495711, 495713, 495714, 495717-495732, 495734, 495736-495739, 495742-495757, 495762-495766, 495772-495774, 495781-495786, 495788, 495789, 495791, 495793-495797, 495799, 495800, 495804, 495808-495813, 495817-495844, 495847-495860, 495862-495870, 495873-495883, 495886, 495899-495904, 495909, 495911-495914, 495918, 495920-495923, 495955, 495957, 495958, 495983, 495992, 496004, 496009, 496010, 496012, 496033, 500841, 500843, 500844, 500852, 500859, 500866, 500867, 500870, 500871, 500892, 500895, 500912, 500913, 500928, 500929, 500934, 500935, 500942, 500944-500946, 500950, 500953, 500957, 500960, 500961, 500966, 500974, 500975, 500979, 500982, 500985, 500986, 500989, 500990, 500994, 500995, 500997, 500998, 501004, 501007, 501008, 501016, 501018-501020, 501025, 501026, 501029-501031, 501033-501035, 501037-501041, 501043, 501055, 501061, 501062, 501064, 501067-501070, 501076, 501093-501098, 501100, 501103, 501104, 501106, 501108, 501111, 501117-501119, 501122-501130, 501140, 501154, 501155, 501158, 501165, 501171, 501176, 501177, 501182-501184, 501193, 501194, 501199, 501200, 501209, 501210, 501212-501214, 501217, 501224, 501227-501230, 501240, 501241, 501244, 501247-501249, 501254, 501256, 501264, 501270, 501287, 501289, 501290, 501297, 501319, 501322, 501326, 501332, 501335, 501342, 501345, 501353, 501357, 501370, 501382-501406, 501410-501412, 501414, 501426-501431, 501434-501443, 501445-501457, 501831, 501835, 501837, 501838, 501849-501853, 501855, 501861, 501867, 501871, 501880, 501883, 501884, 501886-501890, 501900, 501903, 501916, 501932-501934, 501944, 501946, 501947, 501950, 501951, 501957, 501959, 501960, 501966, 501968, 501976, 501977, 501979, 501981-501983, 501991, 501996, 502011, 502013-502015, 502019, 502024-502028, 502031, 502034, 502036-502042, 502045, 502046, 502050, 502053, 502055, 502056, 502062, 502065, 502068-502070, 502083-502085, 502095-502100, 502102, 502106, 502110, 502113, 502114, 502117, 502119, 502120, 502122, 502124, 502127, 502131, 502135, 502144, 502146, 502149, 502150, 502154-502156, 502158, 502163, 502164, 502167, 502172-502176, 502179, 502186, 502189, 502191, 502192, 502194, 502204, 502206, 502215, 502220, 502223, 502228, 502236, 502314, 502319, 502320, 502322, 502334, 502336, 507663, 507665, 507667, 507669, 507675, 507677, 507679, 507684, 507689-507696, 507705, 507709-507719, 507724, 507726, 522363, 522365, 522366, 522368-522375, 522383-522386, 522389, 522391, 522395, 522396, 522398-522413, 522416-522422, 522424-522440, 522442-522452, 522454, 522456, 522457, 522461-522467, 522469-522474, 522478-522490, 522492-522513, 522516-522518, 522521, 522522, 522525, 522529, 522530, 522533-522535, 522540-522550, 522552-522558, 522561-522565, 522573, 522577-522582, 522586-522593, 522597, 522598, 522602-522614, 522617-522625, 522627-522639, 522642-522645, 522657-522663, 522666-522668, 522671-522684, 522686-522702, 522704-522728, 522732, 522733, 522738-522740, 522744-522749, 522754, 522757-522761, 522763-522771, 522776-522778, 522780, 522782-522785, 522788-522797, 522801-522803, 522805, 522807-522809, 522813, 522821-522824, 522829-522831, 522835-522839, 522842, 522844, 522846-522850, 522852-522854, 522856, 522857, 522865-522873, 522875-522880, 522887-522897-522899, 522901, 522904-522906, 522909, 522913, 522914, 522917, 522924, 522925, 522927, 522931-522935, 522939-522943, 522945-522950, 522956, 522964, 522965, 522970, 522977-522982, 522986, 522987, 522996, 522997, 523000-523002, 523015, 523016, 523022, 523025-523027, 525388, 525391, 525394, 525395, 525399, 525401-525405, 525414-525416, 525419, 525420, 525423, 525424, 525431, 525434-525436, 525441-525444, 525450, 525461, 525468-525474, 525477, 525479, 525480, 525484, 525485, 525488-525491, 525498-525501, 525504-525507, 525511-525518, 525520, 525528, 525535-525537, 525539, 525541, 525542, 525544, 525547-525558, 525565, 525577-525579, 525606, 525609-525612, 525619, 525631, 525632, 525649, 525650, 525658, 525683, 525687, 525688, 525690, 525705-525711, 525733, 525737, 525740, 525741, and 525754.

In certain embodiments, the following antisense compounds or antisense oligonucleotides target a region of a DGAT2 nucleic acid and effect at least a 60% inhibition of a DGAT2 mRNA, SEQ ID NOs: 20, 38, 39, 41, 46-48, 61-64, 68, 69, 74, 75, 76, 103, 120, 121, 122, 131, 134, 144, 145, 150, 152, 153, 154, 181, 182, 183, 202-204, 221, 225, 226, 229, 236, 237, 246, 247, 251, 259, 262, 272, 277-280, 283, 383, 391, 405, 414, 425, 433, 438, 450, 452, 453, 455-479, 482-496, 504-507, 509-511, 514-516, 518-528, 531-535, 539-541, 545, 546, 555, 559, 561-568, 574, 575, 577, 578, 583, 584, 589, 594-596, 597, 601, 607, 608, 613-615, 622-625, 627, 652, 653, 660, 674, 706, 709-711, 718-720, 726, 738, 740-745, 749-752, 754-756, 758-769, 774, 789, 793, 794, 807-812, 815, 819, 820, 839, 841-846, 848-852, 878-880, 884, 885, 889, 890, 892-895, 897, 899, 900, 902, 904, 907, 910, 913-916, 923, 935-940, 960-964, 968, 972-977, 979-981, 983-985, 988, 991-1010, 1014, 1015, 1017, 1018, 1020, 1023-1025, 1032-1034, 1036-1038, 1040, 1043-1049, 1051-1054, 1057-1061, 1065, 1071-1073, 1078-1080, 1083, 1084, 1092-1098, 1103, 1107, 1108, 1117, 1118, 1136, 1141, 1142, 1148, 1149, 1153, 1155, 1159, 1165, 1172-1176, 1178, 1181, 1183-1189, 1192-1199, 1202-1215, 1218-1220, 1222, 1228, 1234-1236, 1238, 1240, 1242, 1247, 1254-1259, 1261-1265, 1267, 1269-1275, 1278-1283, 1287, 1288, 1290-1292, 1294-1299, 1301-1303, 1305, 1306, 1314, 1316, 1317, 1327, 1335, 1336, 1340-1343, 1349-1351, 1355-1359, 1367-1369, 1371, 1375, 1380, 1383-1393, 1396, 1397, 1400-1405, 1409, 1411-1413, 1415-1423, 1425-1428, 1431-1435, 1438, 1440, 1442-1445, 1447, 1448, 1450, 1451, 1453-1458, 1464-1468, 1470, 1471, 1474, 1476-1484, 1488-1490, 1495-1497, 1499, 1501, 1503-1507, 1513, 1517, 1518, 1520, 1521, 1523, 1526-1529, 1534-1536, 1543, 1549, 1551-1557, 1559-1562, 1567-1571, 1576, 1578, 1579, 1584, 1585, 1587, 1588, 1596, 1605-1611, 1613, 1622, 1624, 1628-1630, 1632-1643, 1645, 1648-1651, 1654, 1656-1673, 1676, 1677, 1690, 1697, 1698, 1701-1703, 1709, 1711, 1713-1746, 1748, 1749, 1752-1765, 1768-1784, 1787-1818, 1821-1853, 1857, 1858, 1860-1867, 1869-1899, 1903-1912, 1914-1917, 1921-1924, 1929, 1930, 1933-1935, 1937-1940, 1942-1944, 1949, 1950, 1957-1962, 1965-1980, 1984, 1986, 1987, 1990-2005, 2007, 2009-2012, 2015-2030, 2035-2039, 2045-2047, 2054-2059, 2061, 2062, 2064, 2066-2070, 2072, 2073, 2077, 2081-2086, 2090-2117, 2120-2133, 2135-2143, 2146-2156, 2159, 2172-2177, 2182, 2184-2187, 2191, 2193-2196, 2228, 2230, 2231, 2256, 2265, 2277, 2282, 2283, 2285, 2306, 2308, 2310-2334, 2338-2340, 2342, 2350, 2351, 2354-2359, 2362-2371, 2373-2385, 2402, 2405, 2409, 2415, 2418, 2425, 2428, 2436, 2440, 2453, 2465-2468, 2478, 2479, 2482, 2485-2487, 2492, 2494, 2502, 2508, 2525, 2527, 2528, 2535, 2543, 2544, 2547, 2554, 2560, 2565, 2566, 2571-2573, 2582, 2583, 2588, 2589, 2598, 2599, 2601-2603, 2606, 2613, 2615, 2632-2637, 2639, 2642, 2643, 2645, 2647, 2650, 2656-2658, 2661-2669, 2679, 2691, 2692, 2694, 2695, 2701, 2704, 2705, 2713, 2715-2717, 2722, 2723, 2726, 2727, 2728, 2730-2732, 2734-2739, 2748, 2754, 2755, 2757, 2760-2763, 2779, 2780, 2785, 2786, 2793, 2795-2797, 2801, 2804, 2808, 2811, 2812, 2817, 2825, 2826, 2830, 2833, 2836, 2837, 2840, 2841, 2846, 2848, 2849, 2857, 2864, 2871, 2872, 2875, 2876, 2897, 2900, 2917, 2918, 2929, 2933, 2935, 2936-2951, 2953, 2959, 2965, 2969, 2978, 2981, 2982, 2984-2988, 2998, 3001, 3014, 3030-3032, 3042, 3044, 3045, 3048, 3049, 3055, 3057, 3058, 3064, 3066, 3074, 3075, 3077, 3079, 3080, 3081, 3089, 3094, 3109, 3111-3113, 3117, 3122-3126, 3129, 3132, 3134-3140, 3143, 3144, 3148, 3151, 3153, 3154, 3160, 3163, 3166-3168, 3172-3174, 3181-3183, 3193-3198, 3200, 3204, 3208, 3211, 3212, 3215, 3217, 3218, 3220, 3222, 3225, 3229, 3233, 3242, 3244, 3247, 3248, 3252-3254, 3256, 3261, 3262, 3265, 3270-3274, 3277, 3284, 3287, 3289, 3290, 3292, 3302, 3304, 3313, 3318, 3321, 3326, 3334, 3388, 3390, 3392, 3393, 3396, 3398, 3404, 3408, 3410, 3412, 3417, 3418, 3420, 3422-3429, 3432, 3434, 3438, 3442-3452, 3464, 3466, 3468, 3470, 3471, 3473-3480, 3488-3491, 3494, 3496, 3500, 3501, 3503-3518, 3521-3527, 3529-3545, 3547-3557, 3559, 3561, 3562, 3566-3572, 3574-3579, 3583-3595, 3597-3618, 3621-3623, 3626, 3627, 3630, 3634, 3635, 3638-3640, 3645-3655, 3657-3663, 3666-3670, 3678, 3682-3687, 3691-3698, 3702, 3703, 3707-3719, 3722-3730, 3732-3744, 3747-3750, 3762-3768, 3771-3773, 3776-3789, 3791-3807, 3809-3833, 3837, 3838, 3843-3845, 3849-3854, 3859, 3862-3866, 3868-3876, 3881-3883, 3885, 3887-3890, 3893-3902, 3906-3908, 3910, 3912-3914, 3918, 3926-3929, 3934-3936, 3940-3944, 3947, 3949, 3951-3955, 3957-3959, 3961, 3962, 3970-3978, 3980-3985, 3992-3995, 3997-4000, 4002-4004, 4006, 4009-4011, 4014, 4018, 4019, 4022, 4029, 4030, 4032, 4036-4040, 4044-4048, 4050-4055, 4061, 4069, 4070, 4075, 4082, 4083, 4085, 4086, 4092, 4095-4097, 4105-4109, 4113, 4114, 4123, 4124, 4127-4129, 4143, 4146, 4149, 4150, 4154, 4156-4160, 4169-4171, 4174, 4175, 4178, 4179, 4186, 4189-4191, 4196-4199, 4205, 4222, 4229-4235, 4238, 4240, 4241, 4245, 4246, 4249-4252, 4259-4262, 4265-4268, 4272-4279, 4281, 4289, 4296-4298, 4300, 4302, 4303, 4305, 4308-4319, 4326, 4338-4340, 4364, 4367, 4368, 4372, 4373, 4380, 4392, 4393, 4410, 4411, 4419, 4444, 4448, 4449, 4451, 4466-4472, 4494, 4498, 4501, 4502, 4515, 4526-4530, 4532-4535, 4537, 4538-4541, 4544-4546, 4556-4573, 4575-4578, 4580-4583, 4588, 4589, 4592-4594, 4596, 4597, 4599-4601, 4604, 4605, 4612-4614, 4616, 4620, 4622-4625, 4634-4636, 4644, 4652, 4655, 4656, 4667-4670, and 4672.

In certain embodiments, the following antisense compounds or antisense oligonucleotides target a region of a DGAT2 nucleic acid and effect at least a 70% inhibition of a DGAT2 mRNA, ISIS NOs: 413236, 413433, 413446, 423437, 423440-423445, 423447, 423449, 423450, 423452-423454, 423460-423465, 423522-423528, 423601-423604, 472204, 472205, 472208, 472349-472351, 483803, 483811-483814, 483816-483818, 483825, 483826, 483828-483835, 483838-483842, 483846, 483848, 483852, 483862, 483866, 483869, 483870, 483872-483875, 483879, 483887-483890, 483892, 483895, 483897-483903, 483908-483913, 483916-483921, 483923, 483924, 483926-483928, 483934, 483948-483950, 483952, 483954, 483968-483970, 483972, 483973, 483975, 483977-483979, 483984-483989, 483992-483994, 483996, 483997, 484001, 484004, 484006, 484010, 484012, 484017, 484019, 484020, 484030, 484031, 484041, 484049, 484056, 484064, 484069, 484070, 484071, 484073, 484082, 484083, 484085, 484089, 484094, 484099-484102, 484104, 484105, 484107, 484110, 484111, 484114-484118, 484126, 484127, 484129-484131, 484133, 484135-484137, 484139-484142, 484145-484148, 484156-484158, 484161, 484167, 484169-484172, 484178, 484180-484182, 484185, 484190, 484192-484194, 484198, 484202-484204, 484209, 484211, 484215, 484217-484220, 484231, 484232, 484235, 484241, 484248, 484249, 484263, 484265, 484267-484271, 484273, 484274, 484276, 484283-484285, 484290, 484292, 484293, 484301, 484302, 484320-484322, 484324, 484327, 484336, 484342-484344, 484346, 484348-484350, 484352, 484353, 484355-484357, 484359, 484368, 484370-484378, 484381-484383, 484390, 495425, 495429, 495430, 495440-495443, 495445-495454, 495456, 495458, 495461-495473, 495476, 495479-495485, 495487-495492, 495495-495499, 495501-495511, 495514-495531, 495533-495545, 495548-495556, 495558, 495560-495566, 495568-495580, 495584, 495585, 495588-495592, 495597-495600, 495602-495610, 495612-495614,495616-495626, 495631-495633, 495636-495639, 495641-495643, 495649, 495650, 495656, 495657, 495661, 495664, 495666, 495669-495671, 495677, 495685, 495686, 495694, 495695, 495697, 495699-495702, 495705-495707, 495711, 495714, 495718-495720, 495724, 495730, 495731, 495736-495739, 495743-495746, 495748-495754, 495756, 495757, 495762, 495763, 495766, 495772, 495782, 495784, 495785, 495789, 495794, 495795, 495800, 495804, 495808-495813, 495817-495822, 495825-495833, 495835-495837, 495838-495844, 495848-495850, 495852-495857, 495859, 495860, 495867-495869, 495873-495878, 495882, 495899-495902, 495904, 495911, 495912, 495955, 495957, 495958, 495992, 500841, 500844, 500852, 500859, 500867, 500892, 500913, 500928, 500942, 500950, 500953, 500966, 500975, 500986, 500989, 500990, 500994, 500998, 501018-501020, 501025, 501030, 501033-501035, 501038-501041, 501062, 501064, 501067, 501069, 501093, 501094, 501097, 501098, 501100, 501103, 501111, 501118, 501122, 501123, 501127, 501128, 501154, 501165, 501171, 501176, 501183, 501184, 501199, 501200, 501210, 501212-501214, 501224, 501240, 501249, 501270, 501287, 501382-501385, 501387-501396,501398-501402, 501404-501406, 501410-501412, 501414, 501426-501430, 501435, 501436, 501438-501443, 501445, 501447-501452, 501454-501457, 501849, 501850, 501852, 501855, 501861, 501871, 501883, 501884, 501886, 501890, 501916, 501932, 501944, 501946, 501950, 501951, 501959, 501960, 501966, 501968, 501981-501983, 502013, 502015, 502025, 502026, 502037, 502040, 502045, 502046, 502056, 502083, 502098, 502099, 502106, 502110, 502119, 502120, 502131, 502135, 502154-502156, 502163, 502164, 502175, 502179, 502189, 502191, 502194, 502220, 502319, 502322, 502334, 507663, 507679, 507684, 507692-507696, 507710, 507716-507718, 507724, 522363, 522366, 522368, 522370, 522373-522375, 522383-522385, 522399, 522404-522406, 522408, 522409, 522411, 522418, 522421, 522422, 522424, 522427, 522428, 522434-522437, 522440, 522442, 522444-522446, 522450, 522452, 522457, 522462-522467, 522470, 522473, 522474, 522478, 522479, 522482, 522484-522490, 522492, 522494-522496, 522501, 522503-522505, 522509, 522510, 522518, 522529, 522534, 522540, 522542-522550,522552-522556, 522561, 522562, 522565, 522578-522582, 522587-522592, 522602-522610, 522612-522614, 522618, 522619, 522621, 522622, 522625, 522627, 522630-522638, 522642-522645, 522657, 522658, 522661-522663, 522666, 522667, 522671-522683, 522687-522694, 522696-522702, 522705, 522706, 522709, 522710, 522714-522719, 522722-522728, 522740, 522745-522748, 522754, 522757-522759, 522761, 522766-522771, 522776-522778, 522780, 522783, 522784, 522789, 522791, 522793, 522794, 522797, 522801, 522802, 522807, 522821, 522831, 522838, 522842, 522844, 522853, 522857, 522865, 522866, 522869-522872, 522877, 522878, 522888, 522889, 522894, 522897, 522898, 522905, 522913, 522917, 522924, 522925, 522932, 522939, 522940-522943, 522947, 522950, 522964, 522965, 522996, 523000, 523002, 523026, 525395, 525401, 525402, 525415, 525431, 525442, 525443, 525468-525472, 525474, 525477, 525479, 525480, 525499-525501, 525505, 525506, 525512, 525513, 525515, 525536, 525544, 525551-525554, 525578, 525612, 525631, 525688, 525705, 525708, 525711, 525733, and 525754.

In certain embodiments, the following antisense compounds or antisense oligonucleotides target a region of a DGAT2 nucleic acid and effect at least a 70% inhibition of a DGAT2 mRNA, SEQ ID NOs: 20, 38, 39, 46, 47, 62, 63, 103, 120, 121, 131, 144, 145, 150, 152, 153, 154, 182, 183, 202, 203, 204, 221, 225, 229, 246, 259, 283, 425, 438, 452, 453, 455-458, 460, 462-477, 479, 482-485, 487-496, 504-507, 509-511, 518, 519, 521-528, 531-535, 539, 541, 545, 555, 559, 562, 563, 565-568, 574, 575, 577, 594, 595, 597, 623, 624, 627, 653, 706, 710, 740, 742-744, 749-752, 754-756, 758, 760-766, 768, 769, 789, 808-811, 841-843, 845, 846, 848, 850-852, 880, 890, 893, 895, 897, 914-916, 939, 940, 960, 961, 973, 974, 981, 991-997, 1000, 1001, 1003-1008, 1015, 1020, 1024, 1032, 1034, 1036, 1043-1045, 1047-1049, 1052, 1059-1061, 1079, 1080, 1083, 1084, 1092, 1093, 1096, 1098, 1155, 1165, 1173-1176, 1178, 1181, 1183-1189, 1194-1199, 1202-1207, 1209, 1210, 1212-1214, 1220, 1234-1236, 1238, 1240, 1254-1256, 1258, 1259, 1261, 1263-1265, 1270-1275, 1278-1280, 1282, 1283, 1287, 1290, 1292, 1296, 1298, 1303, 1305, 1306, 1316, 1317, 1327, 1335, 1342, 1350, 1355-1357, 1359, 1368, 1369, 1371, 1375, 1380, 1385-1388, 1390, 1391, 1393, 1396, 1397, 1400-1404, 1412, 1413, 1415-1417, 1419, 1421-1423, 1425-1428, 1431-1434, 1442-1444, 1447, 1453, 1455-1458, 1464, 1466-1468, 1471, 1476, 1478-1480, 1484, 1488-1490, 1495, 1497, 1501, 1503-1506, 1517, 1518, 1521, 1527, 1534, 1535, 1549, 1551, 1553-1557, 1559, 1560, 1562, 1569-1571, 1576, 1578, 1579, 1587, 1588, 1606-1608, 1610, 1613, 1622, 1628-1630, 1632, 1634-1636, 1638, 1639, 1641-1643, 1645, 1654, 1656-1664, 1667-1669, 1676, 1677, 1698, 1702, 1703, 1713-1716, 1718-1727, 1729, 1731, 1734-1746, 1749, 1752-1758, 1760-1765, 1768-1772, 1774-1784, 1787-1804, 1806-1818, 1821-1829, 1831, 1833-1839, 1841-1853, 1857, 1858, 1861-1865, 1870-1873, 1875-1883, 1885-1887, 1889-1899, 1904-1906, 1909-1912, 1914-1916, 1922, 1923, 1929, 1930, 1934, 1937, 1939, 1942-1944, 1950, 1958, 1959, 1967, 1968, 1970, 1972-1975, 1978-1980, 1984, 1987, 1991-1993, 1997, 2003, 2004, 2009-2012, 2016-2019, 2021-2027, 2029, 2030, 2035, 2036, 2039, 2045, 2055, 2057, 2058, 2062, 2067, 2068, 2073, 2077, 2081-2086, 2090-2095, 2098-2106, 2108-2117, 2121-2123, 2125-2130, 2132, 2133, 2140-2142, 2146-2151, 2155, 2172-2175, 2177, 2184, 2185, 2228, 2230, 2231, 2265, 2308, 2310-2313, 2315-2324, 2326-2330, 2332-2334, 2338-2340, 2342, 2350, 2351, 2354-2358, 2363, 2364, 2366-2371, 2373, 2375-2380, 2382-2385, 2478, 2487, 2508, 2525, 2543, 2554, 2560, 2565, 2572, 2573, 2588, 2589, 2599, 2601-2603, 2613, 2632, 2633, 2636, 2637, 2639, 2642, 2650, 2657, 2661, 2662, 2666, 2667, 2691, 2695, 2715-2717, 2722, 2727, 2730-2732, 2735-2738, 2755, 2757, 2760, 2762, 2779, 2793, 2801, 2804, 2817, 2826, 2837, 2840, 2841, 2846, 2849, 2857, 2864, 2872, 2897, 2918, 2947, 2948, 2950, 2953, 2959, 2969, 2981, 2982, 2984, 2988, 3014, 3030, 3042, 3044, 3048, 3049, 3057, 3058, 3064, 3066, 3079-3081, 3111, 3113, 3123, 3124, 3135, 3138, 3143, 3144, 3154, 3173, 3181, 3196, 3197, 3204, 3208, 3217, 3218, 3229, 3233, 3252-3254, 3261, 3262, 3273, 3277, 3287, 3289, 3292, 3318, 3388, 3393, 3404, 3412, 3417, 3420, 3425-3429, 3432, 3443, 3449-3451, 3464, 3468, 3471, 3473, 3475, 3478-3480, 3488-3490, 3504, 3509-3511, 3513-3516, 3523, 3526, 3527, 3529, 3532, 3533, 3539-3542, 3545, 3547, 3549-3551, 3555, 3557, 3562, 3567-3572, 3575, 3578, 3579, 3583, 3584, 3587, 3589-3595, 3597, 3599-3601, 3606, 3608-3610, 3614, 3615, 3623, 3634, 3639, 3645, 3647-3655, 3657-3661, 3666, 3667, 3670, 3683-3687, 3692-3697, 3707-3715, 3717-3719, 3723, 3724, 3726, 3727, 3730, 3732, 3735-3743, 3747-3750, 3762, 3763, 3766-3768, 3771, 3772, 3776-3788, 3792-3799, 3801-3807, 3810, 3811, 3814, 3815, 3819-3824, 3827-3833, 3845, 3850-3853, 3859, 3862-3864, 3866, 3871-3876, 3881-3883, 3885, 3888, 3889, 3894, 3896, 3898, 3899, 3902, 3906, 3907, 3912, 3926, 3936, 3943, 3947, 3949, 3958, 3962, 3970, 3971, 3974-3977, 3982, 3983, 3993, 3994, 3999, 4002, 4003, 4010, 4018, 4022, 4029, 4030, 4037, 4044-4048, 4052, 4055, 4069, 4070, 4096, 4123, 4127, 4129, 4150, 4156, 4157, 4170, 4186, 4197, 4198, 4229-4233, 4235, 4238, 4240, 4241, 4260-4262, 4266, 4267, 4273, 4274, 4276, 4297, 4305, 4312-4315, 4339, 4373, 4392, 4449, 4466, 4469, 4472, 4494, 4515, 4526-4530, 4532, 4533, 4535, 4537-4540, 4545, 4546, 4558-4560, 4562-4570, 4573, 4575, 4576, 4578, 4580, 4582, 4588, 4589, 4592, 4596, 4600, 4601, 4604, 4612-4614, 4616, 4622-4625, 4634, 4635, 4652, 4667, and 4668.

In certain embodiments, the following antisense compounds or antisense oligonucleotides target a region of a DGAT2 nucleic acid and effect at least an 80% inhibition of a DGAT2 mRNA, ISIS NOs: 413433, 423463, 423464, 423523, 423524, 423526, 472351, 483817, 483825, 483826, 483828, 483830-483835, 483839-483841, 483848, 483852, 483866, 483869, 483870, 483873-483875, 483887, 483889, 483890, 483895, 483897, 483898, 483900, 483901, 483908-483910, 483913, 483916, 483919, 483921, 483923, 483924, 483927, 483952, 483968-483970, 483972, 483984, 483986-483988, 483992, 483993, 483996, 483997, 484004, 484017, 484031, 484041, 484049, 484064, 484070, 484085, 484094, 484099, 484100, 484115-484117, 484126, 484127, 484129-484131, 484133, 484137, 484139-484141, 484148, 484156-484158, 484167, 484169-484171, 484181, 484182, 484192, 484193, 484203, 484204, 484209, 484215, 484217, 484218, 484220, 484231, 484235, 484249, 484267-484271, 484273, 484283, 484284, 484292, 484293, 484301, 484327, 484336, 484343, 484344, 484348, 484350, 484353, 484357, 484368, 484377, 484378, 495425, 495429, 495440, 495442, 495446, 495449-495451, 495453, 495454, 495463, 495464, 495466, 495467, 495469-495472, 495481, 495482, 495484, 495485, 495488-495492, 495495-495498, 495505-495510, 495514-495531, 495533-495537, 495539-495541, 495543-495545, 495550-495556, 495560, 495561-495564, 495566, 495568-495578, 495585, 495591, 495598-495600, 495604, 495606, 495608, 495609, 495618-495622, 495639, 495649, 495650, 495685, 495686, 495697, 495702, 495705-495707, 495718, 495730, 495736, 495738, 495739, 495744, 495745, 495749, 495751-495753, 495756, 495785, 495808-495810, 495817-495820, 495822, 495825-495832, 495835-495844, 495849, 495852-495854, 495856, 495857, 495867-495869, 495874-495878, 495902, 495992, 500859, 500867, 500913, 500998, 501020, 501034, 501035, 501064, 501094, 501098, 501100, 501103, 501127, 501183, 501199, 501213, 501385, 501387-501393, 501396, 501398, 501404-501406, 501411, 501412, 501427-501430, 501435, 501436, 501438, 501440, 501442, 501443, 501447-501452, 501454-501855, 501861, 501884, 501944, 501950, 501983, 502040, 502046, 502056, 502083, 502099, 502119, 502154, 502164, 502175, 502179, 502189, 502191, 502319, 507692, 507694, 507696, 507717, 522366, 522373-522375, 522383, 522435-522437, 522444, 522445, 522450, 522465, 522473, 522484, 522485, 522495, 522501, 522509, 522529, 522546, 522550, 522553-522556, 522579-522582, 522587-522589, 522606-522610, 522618, 522621, 522627, 522630-522632, 522634, 522638, 522643, 522645, 522667, 522671, 522672, 522674-522683, 522687-522692, 522694, 522696-522700, 522705, 522709, 522715-522719, 522745, 522757, 522770, 522783, 522784, 522807, 522865, 522866, 522888, 522889, 522897, 522913, 522942, 522964, 523002, 525401, 525469, 525470, 525501, and 525612.

In certain embodiments, the following antisense compounds or antisense oligonucleotides target a region of a DGAT2 nucleic acid and effect at least a 80% inhibition of a DGAT2 mRNA, SEQ ID NOs: 103, 120, 121, 131, 144, 145, 150, 152, 153, 182, 204, 246, 259, 283, 425, 456, 457, 462, 463, 467-469, 487-490, 504, 506, 509, 510, 518, 519, 521, 523, 524-528, 532-534, 541, 545, 559, 562, 563, 566-568, 594, 742, 750, 751, 762, 808-810, 843, 845, 893, 915, 939, 973, 993-995, 997, 1000, 1001, 1005, 1006, 1008, 1034, 1060, 1061, 1079, 1084, 1173, 1175, 1176, 1181, 1183, 1184, 1186, 1187, 1194-1196, 1199, 1202, 1205, 1207, 1209, 1210, 1213, 1238, 1254-1256, 1258, 1270, 1272-1274, 1278, 1279, 1282, 1283, 1290, 1303, 1317, 1327, 1335, 1350, 1356, 1371, 1380, 1385, 1386, 1401-1403, 1412, 1413, 1415-1417, 1419, 1423, 1425-1427, 1434, 1442-1444, 1453, 1455-1457, 1467, 1468, 1478, 1479, 1489, 1490, 1495, 1501, 1503, 1504, 1506, 1517, 1521, 1535, 1553-1557, 1559, 1569, 1570, 1578, 1579, 1587, 1613, 1622, 1629, 1630, 1634, 1636, 1639, 1643, 1654, 1663, 1664, 1677, 1698, 1702, 1713, 1715, 1719, 1722-1724, 1726, 1727, 1736, 1737, 1739, 1740, 1742-1745, 1754, 1755, 1757, 1758, 1761-1765, 1768-1771, 1778-1783, 1787-1804, 1806-1810, 1812-1814, 1816-1818, 1823-1829, 1833-1837, 1839, 1841-1851, 1858, 1864, 1871-1873, 1877, 1879, 1881, 1882, 1891-1895, 1912, 1922, 1923, 1958, 1959, 1970, 1975, 1978-1980, 1991, 2003, 2009, 2011, 2012, 2017, 2018, 2022, 2024-2026, 2029, 2058, 2081-2083, 2090-2093, 2095, 2098-2105, 2108-2117, 2122, 2125-2127, 2129, 2130, 2140-2142, 2147-2151, 2175, 2265, 2313, 2315-2321, 2324, 2326, 2332-2334, 2339, 2340, 2355-2358, 2363, 2364, 2366, 2368, 2370, 2371, 2375-2380, 2382, 2383, 2572, 2588, 2602, 2633, 2637, 2639, 2642, 2666, 2695, 2717, 2731, 2732, 2757, 2864, 2872, 2918, 2953, 2959, 2982, 3042, 3048, 3081, 3138, 3144, 3154, 3181, 3197, 3217, 3252, 3262, 3273, 3277, 3287, 3289, 3404, 3417, 3425, 3427, 3429, 3450, 3471, 3478-3480, 3488, 3540-3542, 3549, 3550, 3555, 3570, 3578, 3589, 3590, 3600, 3606, 3614, 3634, 3651, 3655, 3658-3661, 3684-3687, 3692-3694, 3711-3715, 3723, 3726, 3732, 3735-3737, 3739, 3743, 3748, 3750, 3772, 3776, 3777, 3779-3788, 3792-3797, 3799, 3801-3803, 3805, 3810, 3814, 3820-3824, 3850, 3862, 3875, 3888, 3889, 3912, 3970, 3971, 3993, 3994, 4002, 4018, 4047, 4069, 4129, 4156, 4230, 4231, 4262, 4373, 4526, 4529, 4532, 4538, 4540, 4560, 4562-4564, 4566-4570, 4578, 4623, 4625, and 4667.

In certain embodiments, the following antisense compounds or antisense oligonucleotides target a region of a DGAT2 nucleic acid and effect at least a 90% inhibition of a DGAT2 mRNA, ISIS NOs: 413433, 423463, 483817, 483825, 483834, 483848, 483866, 483869, 483873, 483874, 483895, 483898, 483908, 483910, 483913, 483952, 484085, 484148, 484157, 484170, 484181, 484231, 484271, 484283, 484350, 484353, 495449, 495450, 495495, 495498, 495505, 495506, 495516-495520, 495522-495524, 495526, 495527, 495535, 495553-495555, 495562, 495563, 495570, 495571, 495575-495577, 495620, 495752, 495809, 495825, 495829, 495836, 495837, 495839-495842, 495853, 495857, 495876, 495878, 501385, 501387, 501404, 501412, 501427, 501430, 501442, 501443, 501447, 501448, 501450, 501452, 501861, 522632, 522688, and 522745.

In certain embodiments, the following antisense compounds or antisense oligonucleotides target a region of a DGAT2 nucleic acid and effect at least a 90% inhibition of a DGAT2 mRNA, SEQ ID NOs: 283, 425, 457, 467, 510, 518, 527, 541, 559, 562, 566, 567, 1181, 1184, 1194, 1196, 1199, 1238, 1371, 1434, 1443, 1456, 1467, 1517, 1557, 1569, 1636, 1639, 1722, 1723, 1768, 1771, 1778, 1779, 1789-1793, 1795-1797, 1799, 1800, 1808, 1826-1828, 1835, 1836, 1843, 1844, 1848-1850, 1893, 2025, 2082, 2098, 2102, 2109, 2110, 2112-2115, 2126, 2130, 2149, 2151, 2313, 2315, 2332, 2340, 2355, 2358, 2370, 2371, 2375, 2376, 2378, 2380, 2959, 3737, 3793, 3850, 4562, 4564, 4566, 4568, and 4569.

In certain embodiments, a compound comprises a modified oligonucleotide consisting of 8 to 80 linked nucleosides having at least an 8, 9, 10, 11, 12, 13, 14, 15, or 16 contiguous nucleobase portion complementary to an equal length portion within nucleotides 26778-26797, 23242-23261, 26630-26649, 15251-15270, 28026-28045, 35436-35455, 10820-10836, 23246-23262 of SEQ ID NO: 2 In certain embodiments, a compound comprises a modified oligonucleotide consisting of 10 to 30 linked nucleosides complementary within nucleotides 26778-26797, 23242-23261, 26630-26649, 15251-15270, 28026-28045, 35436-35455, 10820-10836, 23246-23262 of SEQ ID NO: 2.

In certain embodiments, a compound comprises a modified oligonucleotide consisting of 8 to 80 linked nucleosides having a nucleobase sequence comprising at least an 8, 9, 10, 11, 12, 13, 14, 15, or 16 contiguous nucleobase portion any one of SEQ ID NOs: 1423, 1371, 1415, 1849, 2959, 3292, 4198, and 4373.

In certain embodiments, a compound comprises a modified oligonucleotide consisting of 10 to 30 linked nucleosides having a nucleobase sequence comprising any one of SEQ ID NOs: 1423, 1371, 1415, 1849, 2959, 3292, 4198, and 4373.

In certain embodiments, a compound comprises a modified oligonucleotide having a nucleobase sequence consisting of any one of SEQ ID NOs: 1423, 1371, 1415, 1849, 2959, 3292, 4198, and 4373. In certain embodiments, a modified oligonucleotide targeted to DGAT2 is ISIS 484137, 484085, 484129, 495576, 501861, 502194, 525443, and 525612.

In certain embodiments, a modified oligonucleotide targeted to DGAT2 is ISIS 484137, 484085, 484129, 495576, 501861, 502194, 525443, and 525612. Out of about 5,000 antisense oligonucleotides that were screened as described in the Examples section below, ISIS 484137, 484085, 484129, 495576, 501861, 502194, 525443, and 525612 emerged as the top lead compounds. In particular, ISIS 484137 exhibited the best combination of properties in terms of potency and tolerability out of about 5,000 antisense oligonucleotides.

In certain embodiments, any of the foregoing compounds or oligonucleotides comprises at least one modified internucleoside linkage, at least one modified sugar, and/or at least one modified nucleobase.

In certain aspects, any of the foregoing compounds or oligonucleotides comprises at least one modified sugar. In certain aspects, at least one modified sugar comprises a 2'-O-methoxyethyl group. In certain aspects, at least one modified sugar is a bicyclic sugar, such as a 4'-CH($CH_3$)—O-2' group, a 4'-$CH_2$—O-2' group, or a 4'-$(CH_2)_2$—O-2' group.

In certain aspects, the modified oligonucleotide comprises at least one modified internucleoside linkage, such as a phosphorothioate internucleoside linkage.

In certain embodiments, any of the foregoing compounds or oligonucleotides comprises at least one modified nucleobase, such as 5-methylcytosine.

In certain embodiments, any of the foregoing compounds or oligonucleotides comprises:

a gap segment consisting of linked 2'-deoxynucleosides;
a 5' wing segment consisting of linked nucleosides; and
a 3' wing segment consisting of linked nucleosides;
wherein the gap segment is positioned between the 5' wing segment and the 3' wing segment and wherein each nucleoside of each wing segment comprises a modified sugar. In certain embodiments, the oligonucleotide consists of 8 to 80 linked nucleosides having a nucleobase sequence comprising the sequence recited in SEQ ID NO: 1423, 1371, 1415, 1849, 2959, 3292, 4198, and 4373. In certain aspects, the oligonucleotide consists of 10 to 30 linked nucleosides having a nucleobase sequence comprising the sequence recited in SEQ ID NO: 1423, 1371, 1415, 1849, 2959, 3292, 4198, and 4373.

In certain aspects, the modified oligonucleotide has a nucleobase sequence comprising the sequence recited in SEQ ID NO: 1423, 1371, 1415, 1849, 2959, or 3292, wherein the modified oligonucleotide comprises a gap segment consisting often linked 2'-deoxynucleosides;
a 5' wing segment consisting of five linked nucleosides; and
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage and wherein each cytosine is a 5-methylcytosine. In certain embodiments, the modified oligonucleotide consists of 20-80 linked nucleosides. In certain embodiments, the modified oligonucleotide consists of 20-30 linked nucleosides.

In certain aspects, the modified oligonucleotide has a nucleobase sequence comprising the sequence recited in SEQ ID NO: 4198 or 4373, wherein the modified oligonucleotide comprises a gap segment consisting often linked 2'-deoxynucleosides;
a 5' wing segment consisting of three linked nucleosides; and
a 3' wing segment consisting of four linked nucleosides;
wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage and wherein each cytosine is a 5-methylcytosine. In certain embodiments, the modified oligonucleotide consists of 17-80 linked nucleosides. In certain embodiments, the modified oligonucleotide consists of 17-30 linked nucleosides.

In certain embodiments, a compound comprises or consists of ISIS 484137 and has the following chemical structure or a salt thereof:

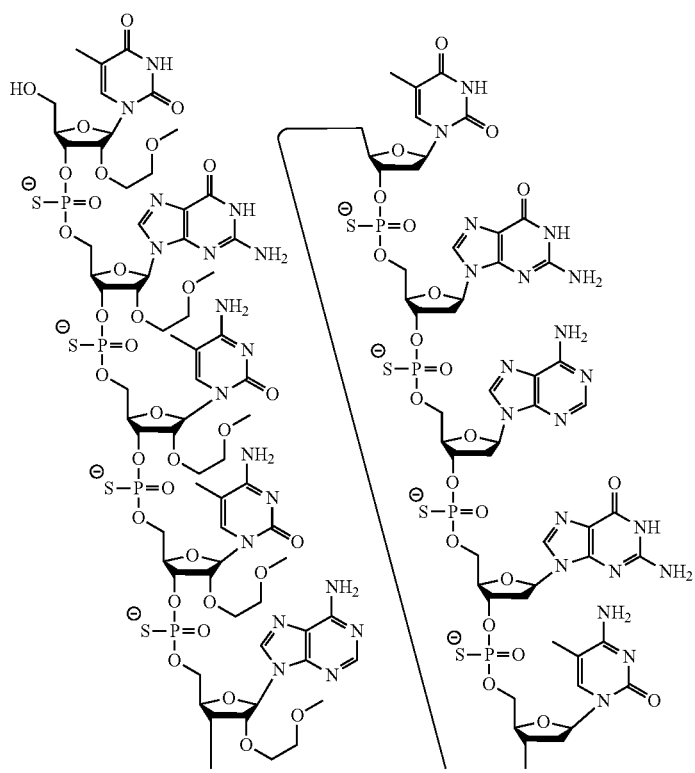

-continued

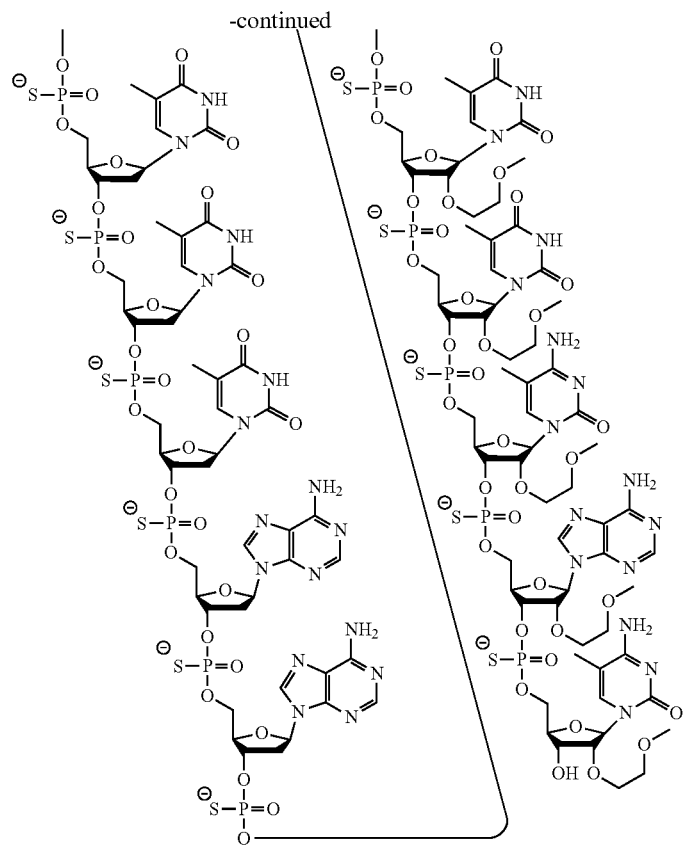

In certain embodiments, a compound comprises or consists of ISIS 484137, named by accepted oligonucleotide nomenclature, showing each 3'-0 to 5'-O-linked phosphorothioate diester internucleotide linkage as follows:

2'-O-(2-methoxyethyl)-5-methyl-P-thiouridylyl-(3'-O→5'-O)-2'-O-(2-methoxyethyl)-P-thioguanylyl-(3'-O→5'-O)-2'-O-(2-methoxyethyl)-5-methyl-P-thiocytidylyl-(3'-O→5'-O)-2'-O-(2-methoxyethyl)-5-methyl-P-thiocytidylyl-(3'-O→5'-O)-2'-O-(2-methoxyethyl)-P-thioadenylyl-(3'-O→5'-O)—P-thiothymidylyl-(3'-O→5'-O)—P-thiothymidylyl-(3'-O→5'-O)—P-thiothymidylyl-(3'-O→5'-O)-2'-deoxy-P-thioadenylyl-(3'-O→5'-O)-2'-deoxy-P-thioadenylyl-(3'-O→5'-O)—P-thiothymidylyl-(3'-O→5'-O)-2'-deoxy-P-thioguanylyl-(3'-O→5'-O)-2'-deoxy-P-thioadenylyl-(3'-O→5'-O)-2'-deoxy-P-thioguanylyl-(3'-O→5'-O)-2'-deoxy-5-methyl-P-thiocytidylyl-(3'-O→5'-O)-2'-O-(2-methoxyethyl)-5-methyl-P-thiouridylyl-(3'-O→5'-O)-2'-O-(2-methoxyethyl)-5-methyl-P-thiouridylyl-(3'-O→5'-O)-2'-O-(2-methoxyethyl)-5-methyl-P-thiocytidylyl-(3'-O→5'-O)-2'-O-(2-methoxyethyl)-P-thioadenylyl-(3'-O→5'-O)-2'-O-(2-methoxyethyl)-5-methyl-cytidine, 19 sodium salt.

In any of the foregoing embodiments, the compound or oligonucleotide can be at least 85%, at least 90%, at least 95%, at least 98%, at least 99%, or 100% complementary to a nucleic acid encoding DGAT2.

In any of the foregoing embodiments, the antisense compound can be a single-stranded oligonucleotide.

In any of the foregoing embodiments, the oligonucleotide can consist of 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides.

In certain embodiments, compounds or compositions provided herein comprise a salt of the modified oligonucleotide. In certain embodiments, the salt is a sodium salt. In certain embodiments, the salt is a potassium salt.

In certain embodiments, a compound comprises a modified oligonucleotide described herein and a conjugate group. In certain embodiments, the conjugate group is linked to the modified oligonucleotide at the 5' end of the modified oligonucleotide. In certain embodiments, the conjugate group is linked to the modified oligonucleotide at the 3' end of the modified oligonucleotide. In certain embodiments, the conjugate group comprises at least one N-Acetylgalactosamine (GalNAc), at least two N-Acetylgalactosamines (GalNAcs), or at least three N-Acetylgalactosamines (GalNAcs).

In certain embodiments, a compound having the following chemical structure comprises or consists of ISIS 484137 or salt thereof with a conjugate group comprising GalNAc as described herein:

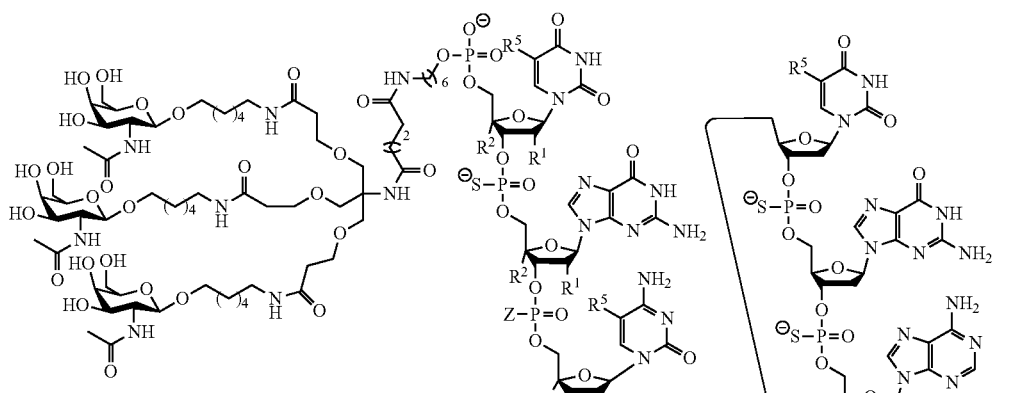
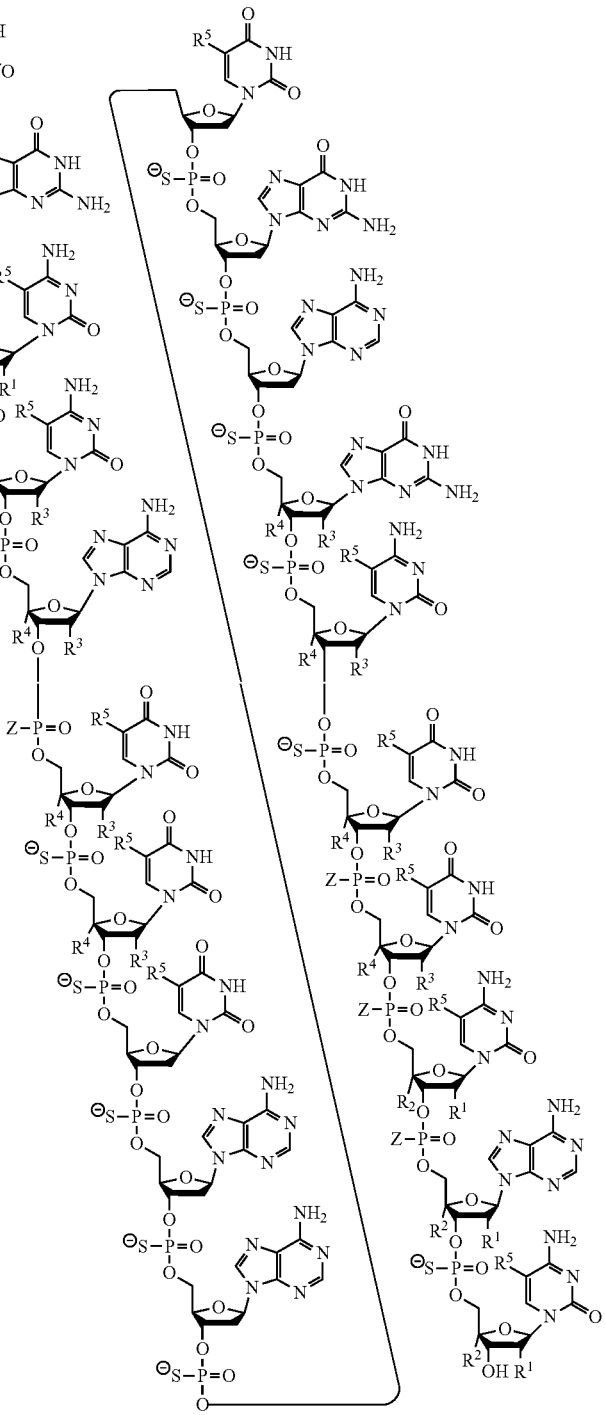

wherein for each pair of $R_1$ and $R_2$ on the same ring, independently for each ring, either $R_1$ is —OCH$_2$CH$_2$OCH$_3$ (MOE) and $R_2$ is H; or $R_1$ and $R_2$ together form a bridge, wherein $R_1$ is —O— and $R_2$ is —CH$_2$—, —CH(CH$_3$)—, or —CH$_2$CH$_2$—, and $R_1$ and $R_2$ are directly connected such that the resulting bridge is selected from: —O—CH$_2$—, —O—CH(CH$_3$)—, and —O—CH$_2$CH$_2$—; and for each pair of $R_3$ and $R_4$ on the same ring, independently for each ring: either $R_3$ is selected from H and —OCH$_2$CH$_2$OCH$_3$ and $R_4$ is H; or $R_3$ and $R_4$ together form a bridge, wherein $R_3$ is —O—, and $R_4$ is —CH$_2$—, —CH(CH$_3$)—, or —CH$_2$CH$_2$—, and $R_3$ and $R_4$ are directly connected such that the resulting bridge is selected from: —O—CH$_2$—, —O—CH(CH$_3$)—, and —O—CH$_2$CH$_2$—; and each $R_5$ is independently selected from H and —CH$_3$; and each Z is independently selected from S— and O—.

In certain embodiments, a compound comprises or consists of SEQ ID NO: 1423, 5'-GalNAc, and chemical modifications as represented by the following chemical structure:

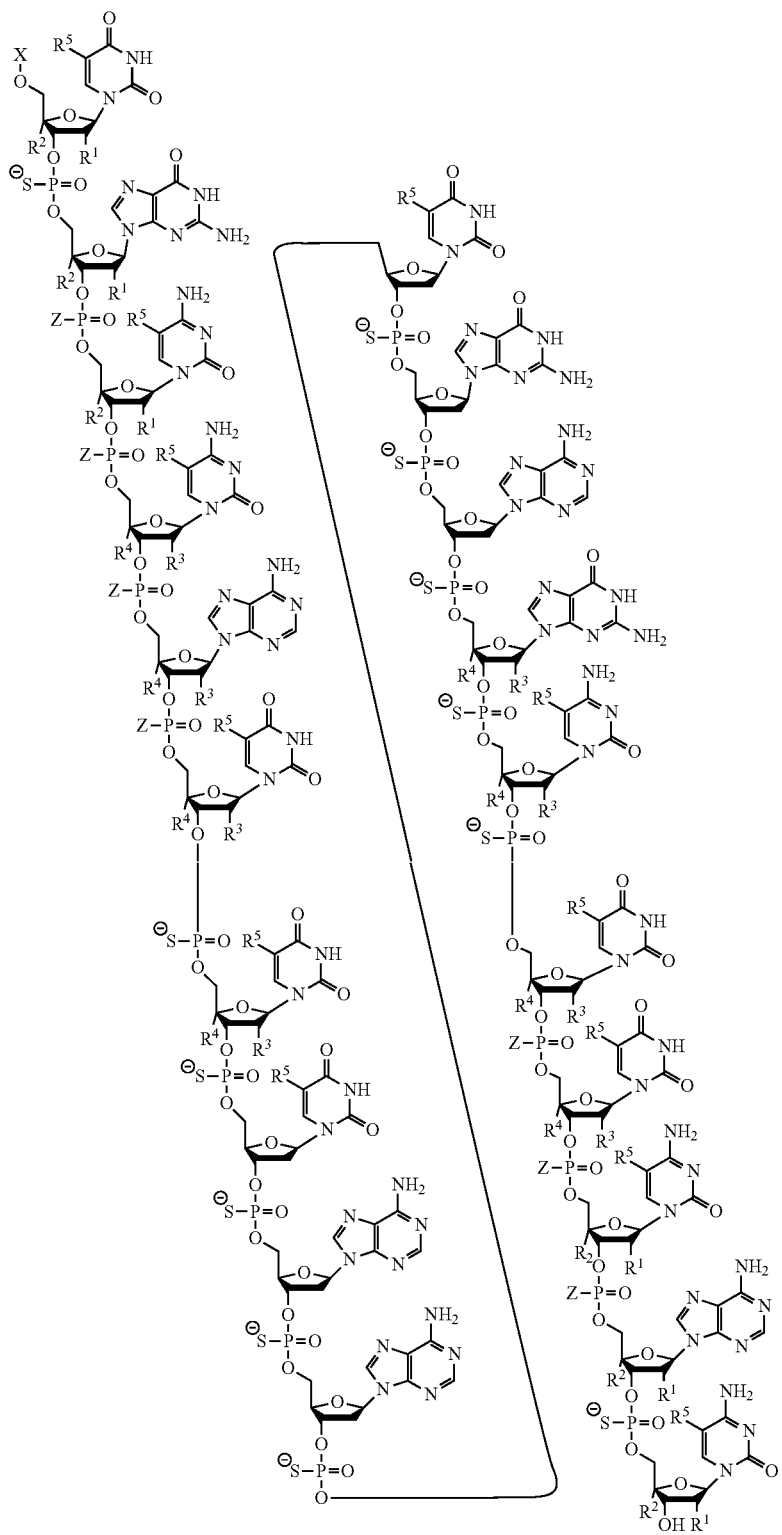

wherein for each pair of $R_1$ and $R_2$ on the same ring, independently for each ring, either $R_1$ is —OCH$_2$CH$_2$OCH$_3$ (MOE) and $R_2$ is H; or $R_1$ and $R_2$ together form a bridge, wherein $R_1$ is —O— and $R_2$ is —CH$_2$—, —CH(CH$_3$)—, or —CH$_2$CH$_2$—, and $R_1$ and $R_2$ are directly connected such that the resulting bridge is selected from: —O—CH$_2$—, —O—CH(CH$_3$)—, and —O—CH$_2$CH$_2$—; and for each pair of $R_3$ and $R_4$ on the same ring, independently for each ring: either $R_3$ is selected from H and —OCH$_2$CH$_2$OCH$_3$ and $R_4$ is H; or $R_3$ and $R_4$ together form a bridge, wherein $R_3$ is —O—, and $R_4$ is —CH$_2$—, —CH(CH$_3$)—, or —CH₂CH₂—, and R₃ and R₄ are directly connected such that the resulting bridge is selected from: —O—CH₂—, —O—CH(CH₃)—, and —O—CH₂CH₂—; and each R₅ is independently selected from H and —CH₃; and each Z is independently selected from S— and O—; and X is H or a conjugate group that optionally comprises a conjugate linker and/or cleavable moiety.

In certain embodiments, a compound comprises ISIS 769355 or salt thereof. In certain embodiments, a compound consists of ISIS 769355 or salt thereof. In certain embodiments, ISIS 769355 has the following chemical structure:

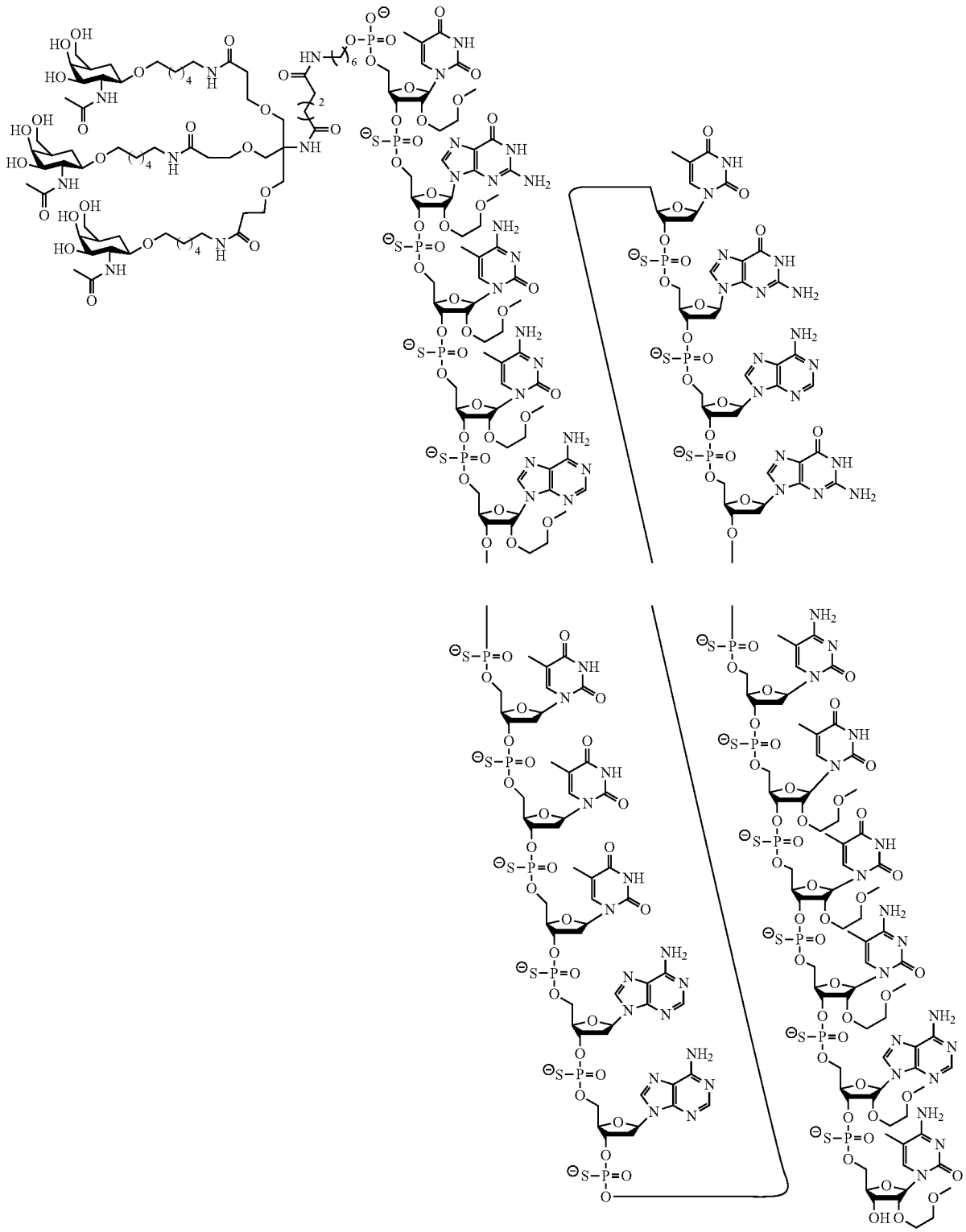

In certain embodiments, a compound comprises ISIS 769356 or salt thereof. In certain embodiments, a compound consists of ISIS 769356 or salt thereof. In certain embodiments, ISIS 769356 has the following chemical structure:
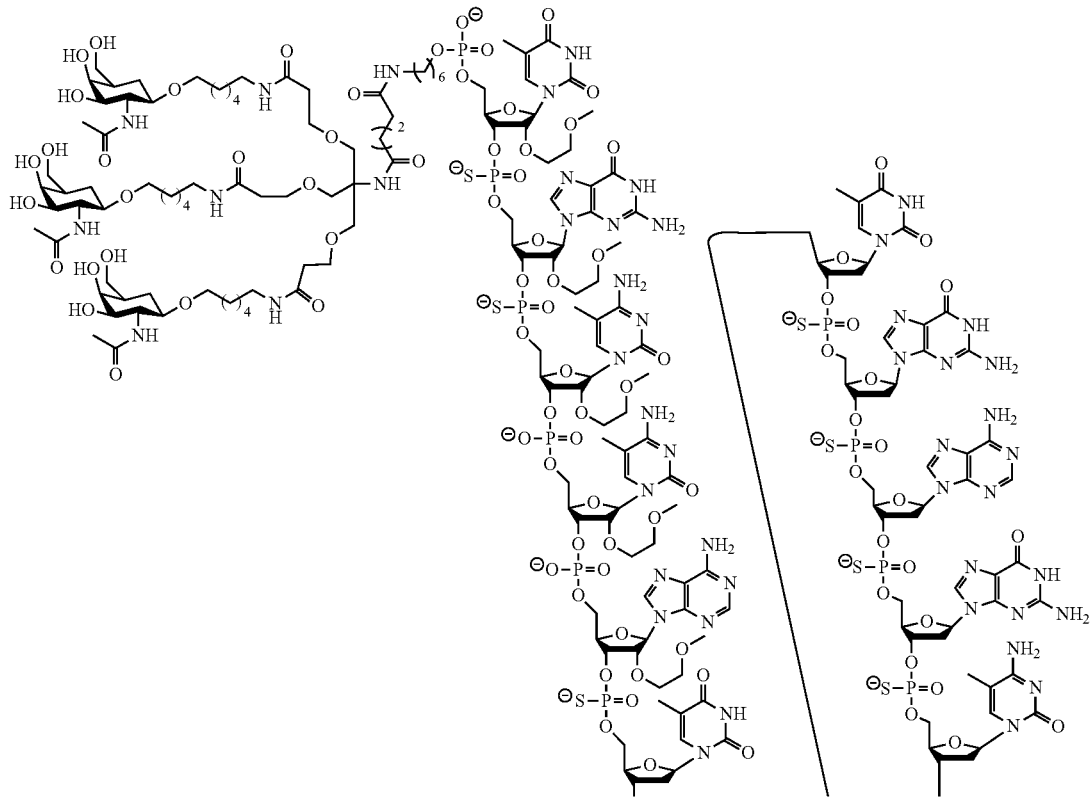
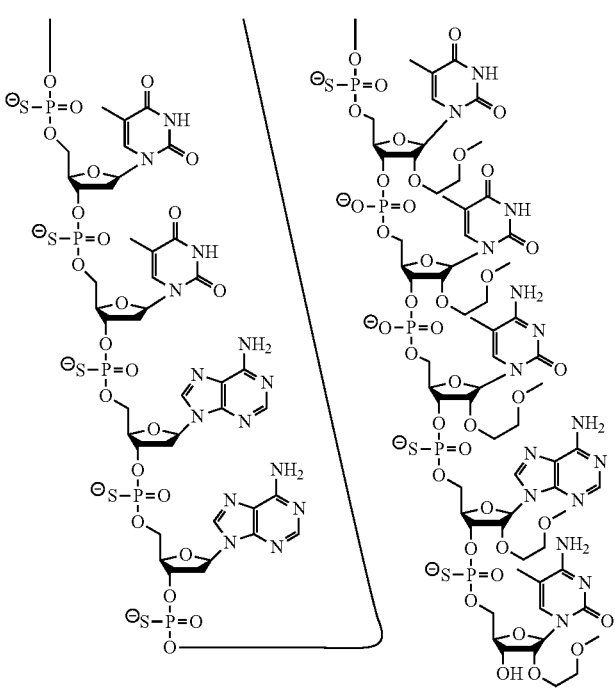

In certain embodiments, a compound comprises ISIS 769357 or salt thereof. In certain embodiments, a compound consists of ISIS 769357 or salt thereof. In certain embodiments, ISIS 769357 has the following chemical structure:
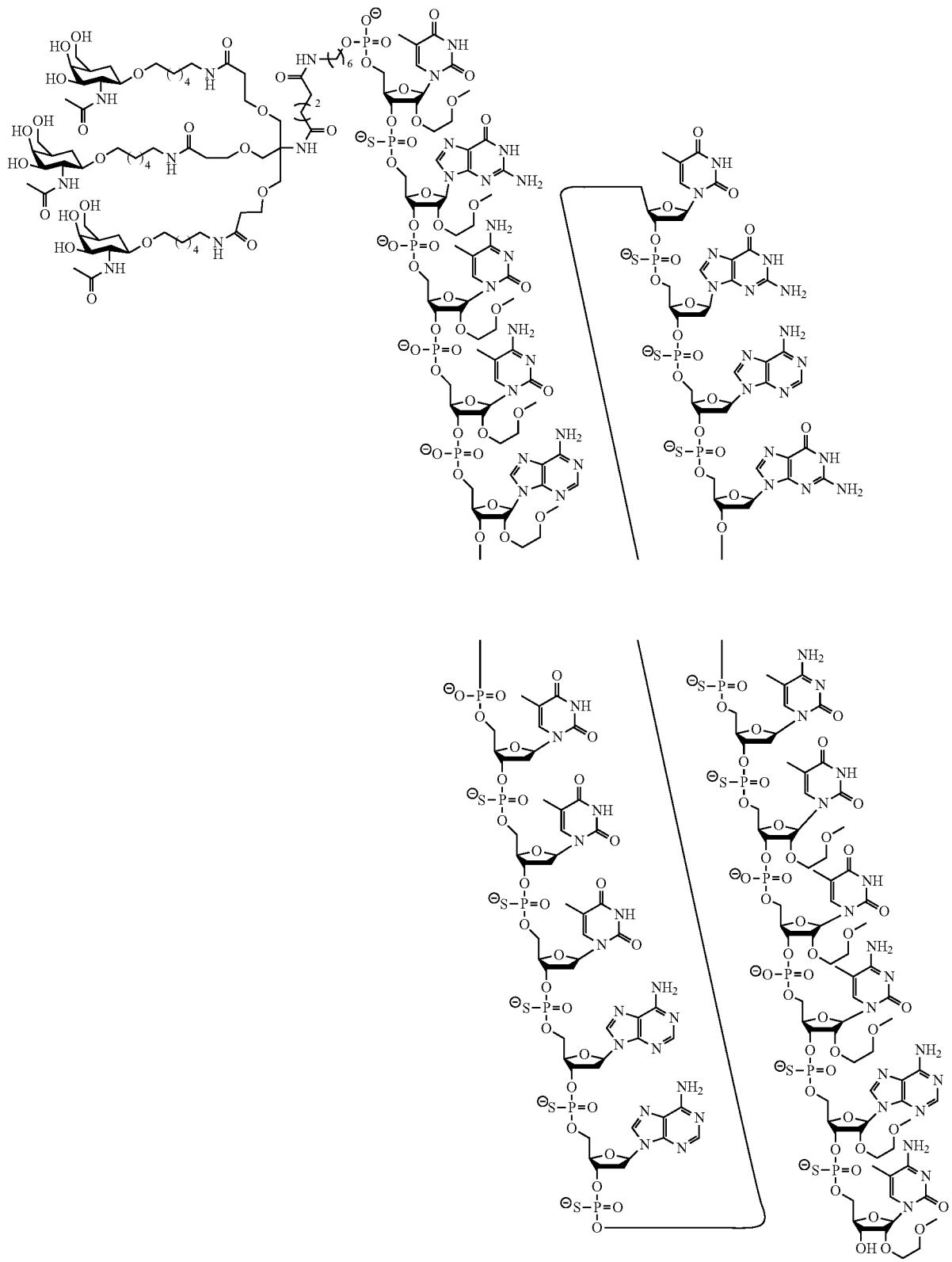

Certain embodiments provide compositions comprising any of the compounds comprising or consisting of a modified oligonucleotide targeted to DGAT2 or salt thereof and a conjugate group, and at least one of a pharmaceutically acceptable carrier or diluent.

In certain embodiments, the compounds or compositions as described herein are efficacious by virtue of having at least one of an in vitro $IC_{50}$ of less than 2 nM, less than 3 nM, less than 4 nM, less than 5 nM, less than 6 nM, less than 7 nM, less than 8 nM, less than 9 nM, less than 10 nM, less than 20 nM, less than 30 nM, less than 35 nM, less than 40 nM, less than 45 nM, less than 50 nM, less than 60 nM, less than 70 nM, less than 80 nM, less than 90 nM, less than 100 nM, less than 110 nM, less than 300 nM, less than 400 nM, less than 500 nM, less than 600 nM, less than 700 nM, less than 800 nM, less than 900 nM, less than 1 µM, less than 1.1 µM, less than 1.2 µM, less than 1.3 µM, less than 1.4 µM, less than 1.5 µM, less than 1.6 µM, less than 1.7 µM, less than 1.8 µM, less than 1.9 µM, less than 2 µM, less than 2.5 µM, less than 3 µM, less than 3.5 µM, less than 4 µM, less than 4.5 µM, less than 5 µM, less than 5.5 µM, less than 6 µM, less than 6.5 µM, or less than 10 µM.

In certain embodiments, the compounds or compositions as described herein are highly tolerable as demonstrated by having at least one of an increase an ALT or AST value of no more than 4 fold, 3 fold, or 2 fold over saline treated animals or an increase in liver, spleen, or kidney weight of no more than 30%, 20%, 15%, 12%, 10%, 5%, or 2%. In certain embodiments, the compounds or compositions as described herein are highly tolerable as demonstrated by having no increase of ALT or AST over saline treated animals. In certain embodiments, the compounds or compositions as described herein are highly tolerable as demonstrated by having no increase in liver, spleen, or kidney weight over saline treated animals.

Certain Indications

Certain embodiments provided herein relate to methods of treating, preventing, or ameliorating a disease associated with DGAT2 in an individual by administration of a DGAT2 specific inhibitor, such as an antisense compound targeted to DGAT2.

Examples of diseases associated with DGAT2 treatable, preventable, and/or ameliorable with the methods provided herein include nonalcoholic fatty liver diseases (NAFLD), nonalcoholic steatohepatitis (NASH), hepatic steatosis, fatty liver diseases, lipodystrophy syndromes, including congenital generalized lipodystrophy (CGL), acquired generalized lipodystrophy (AGL), familial partial lipodystrophy (FPL), and acquired partial lipodystrophy (PL), metabolic syndrome and cardiovascular diseases.

In certain embodiments, a method of treating, preventing, or ameliorating a disease associated with NAFLD in an individual comprises administering to the individual a specific inhibitor of DGAT2, thereby treating, preventing, or ameliorating the disease. In certain embodiments, a method of treating, preventing, or ameliorating a disease associated with lipodystrophy syndrome in an individual comprises administering to the individual a specific inhibitor of DGAT2, thereby treating, preventing, or ameliorating the disease. In certain embodiments, the lipodystrophy syndrome is partial lipodystrophy. In certain embodiments, the DGAT2 specific inhibitor is an antisense compound targeted to DGAT2, such as an antisense oligonucleotide targeted to DGAT2. In certain embodiments, the DGAT2 specific inhibitor is a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising at least 8 contiguous nucleobases of any of the nucleobase sequences of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising the nucleobase sequence of any one of SEQ ID NOs: 16-4679. In certain embodiments, the DGAT2 specific inhibitor is an antisense compound comprising a modified oligonucleotide consisting of the nucleobase sequence of any one of SEQ ID NOs: 16-4679. In certain embodiments, the DGAT2 specific inhibitor is an antisense compound comprising a modified oligonucleotide consisting of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising or consisting of a modified oligonucleotide and a conjugate group, wherein the modified oligonucleotide consists of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising a modified oligonucleotide having a nucleobase sequence consisting of any one of SEQ ID NOs: 1423, 1371, 1415, 1849, 2959, 3292, 4198, and 4373. In certain embodiments, the DGAT2 specific inhibitor is ISIS 484137, ISIS 484085, ISIS 484129, ISIS 495576, ISIS 501861, ISIS 502194, ISIS 525443, and ISIS 525612. In certain embodiments the DGAT2 specific inhibitor is ISIS 769355, ISIS 769356, and ISIS 769357. In any of the foregoing embodiments, the antisense compound can be a single-stranded oligonucleotide.

In certain embodiments, a method of treating, preventing, or ameliorating NAFLD/NASH comprises administering to the individual a DGAT2 specific inhibitor, thereby treating, preventing, or ameliorating NALFD/NASH. In certain embodiments, a method of treating, preventing, or ameliorating lipodystrophy comprises administering to the individual a DGAT2 specific inhibitor, thereby treating, preventing, or ameliorating lipodystrophy syndrome. In certain embodiments, the lipodystrophy syndrome is partial lipodystrophy. In certain embodiments, the DGAT2 specific inhibitor is an antisense compound targeted to DGAT2, such as an antisense oligonucleotide targeted to DGAT2. In certain embodiments, the DGAT2 specific inhibitor is a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising at least 8 contiguous nucleobases of any of the nucleobase sequences of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising the nucleobase sequence of any one of SEQ ID NOs: 16-4679. In certain embodiments, the DGAT2 specific inhibitor is an antisense compound comprising a modified oligonucleotide consisting of the nucleobase sequence of any one of SEQ ID NOs: 16-4679. In certain embodiments, the DGAT2 specific inhibitor is an antisense compound comprising a modified oligonucleotide consisting of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising or consisting of a modified oligonucleotide and a conjugate group, wherein the modified oligonucleotide consists of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising a modified oligonucleotide having a nucleobase sequence consisting of any one of SEQ ID NOs: 1423, 1371, 1415, 1849, 2959, 3292, 4198, and 4373. In certain embodiments, the DGAT2 specific inhibitor is ISIS 484137, ISIS 484085, ISIS 484129, ISIS 495576, ISIS 501861, ISIS 502194, ISIS 525443, and ISIS 525612. In certain embodiments the DGAT2 specific inhibitor is ISIS 769355, ISIS 769356, and ISIS 769357. In any of the foregoing embodiments, the antisense compound can be a single-stranded oligonucleotide. In certain aspects, the antisense compound is administered to the individual parenterally. In certain aspects, administering the antisense compound results in specific reduction of DGAT2 expression, reduction in the rate of triglyceride synthesis, improvement of hepatic steatosis and blood lipid levels, reduction of hepatic lipids, reversal of diet-induced hepatic insulin resistance, and improvement in hepatic insulin sensitivity. In certain aspects, administering the antisense compound results in reduction in liver steatosis and fibrosis. In certain aspects, administering the antisense compound results in improvements in ALT levels. In certain aspects, administering the antisense compound results in decrease in NAFLD Activity Score (NAS). In certain aspects, administering the antisense compound results in reduction in serum total cholesterol and triglycerides. In certain aspects, administering the antisense compound results in neutral insulin sensitivity and glycemic control. In certain aspects, administering the antisense compound results in improved insulin sensitivity and glycemic control. In certain aspects, the individual is identified as having or at risk of having a disease associated with NAFLD. In certain aspects, the individual is identified as having or at risk of having a disease associated with lipodystrophy syndrome.

In certain embodiments, a method of inhibiting expression of DGAT2 in an individual having, or at risk of having, a disease associated with NAFLD comprises administering a DGAT2 specific inhibitor to the individual, thereby inhibiting expression of DGAT2 in the individual. In certain embodiments, a method of inhibiting expression of DGAT2 in an individual having, or at risk of having, a disease associated with lipodystrophy syndrome comprises administering a DGAT2 specific inhibitor to the individual, thereby inhibiting expression of DGAT2 in the individual. In certain aspects, administering the inhibitor inhibits expression of DGAT2 in the liver. In certain aspects, administering the inhibitor inhibits expression of DGAT2 in adipose tissue. In certain aspects, the individual has, or is at risk of having lipodystrophy syndrome, partial lipodystrophy, liver steatosis, NAFLD, or NASH. In certain embodiments, the DGAT2 specific inhibitor is an antisense compound targeted to DGAT2, such as an antisense oligonucleotide targeted to DGAT2. In certain embodiments, the DGAT2 specific inhibitor is a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising at least 8 contiguous nucleobases of any of the nucleobase sequences of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising the nucleobase sequence of any one of SEQ ID NOs: 16-4679. In certain embodiments, the DGAT2 specific inhibitor is an antisense compound comprising a modified oligonucleotide consisting of the nucleobase sequence of any one of SEQ ID NOs: 16-4679. In certain embodiments, the DGAT2 specific inhibitor is an antisense compound comprising a modified oligonucleotide consisting of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising or consisting of a modified oligonucleotide and a conjugate group, wherein the modified oligonucleotide consists of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising a modified oligonucleotide having a nucleobase sequence consisting of any one of SEQ ID NOs: 1423, 1371, 1415, 1849, 2959, 3292, 4198, and 4373. In certain embodiments, the DGAT2 specific inhibitor is ISIS 484137, ISIS 484085, ISIS 484129, ISIS 495576, ISIS 501861, ISIS 502194, ISIS 525443, and ISIS 525612. In certain embodiments the DGAT2 specific inhibitor is ISIS 769355, ISIS 769356, and ISIS 769357. In any of the foregoing embodiments, the antisense compound can be a single-stranded oligonucleotide.

In certain embodiments, a method of reducing or inhibiting triglyceride synthesis, hepatic lipid synthesis and insulin resistance in the liver of an individual having, or at risk of having, a disease associated with DGAT2 comprises administering a DGAT2 specific inhibitor to the individual, thereby reducing or inhibiting triglyceride synthesis, hepatic lipid synthesis and insulin resistance in the liver of the individual. In certain embodiments, a method of reducing or inhibiting triglyceride synthesis, lipid synthesis and insulin resistance in the adipose tissue of an individual having, or at risk of having, a disease associated with DGAT2 comprises administering a DGAT2 specific inhibitor to the individual, thereby reducing or inhibiting triglyceride synthesis, lipid synthesis and insulin resistance in the adipose tissue of the individual. In certain aspects, administering the DGAT2 inhibitor leads to improvement in hepatic insulin signaling, hepatic insulin sensitivity and cardiovascular risk profile. In certain aspects, administering the DGAT2 specific inhibitor results in reduction in liver steatosis and fibrosis. In certain aspects, administering the DGAT2 specific inhibitor results in improvements in ALT levels. In certain aspects, administering the DGAT2 specific inhibitor results in decrease in NAFLD Activity Score (NAS). In certain aspects, administering the DGAT2 specific inhibitor results in reduction in serum total cholesterol and triglycerides. In certain aspects, administering the DGAT2 specific inhibitor results in neutral insulin sensitivity and glycemic control. In certain aspects, administering the antisense compound results in improved insulin sensitivity and glycemic control. In certain aspects, the individual has, or is at risk of having, NAFLD or NASH. In certain aspects, the individual has, or is at risk of having, lipodystrophy syndrome or partial lipodystrophy. In certain aspects, the inhibitor is an antisense compound targeted to DGAT2. In certain embodiments, the DGAT2 specific inhibitor is an antisense compound targeted to DGAT2, such as an antisense oligonucleotide targeted to DGAT2. In certain embodiments, the DGAT2 specific inhibitor is a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising at least 8 contiguous nucleobases of any of the nucleobase sequences of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising the nucleobase sequence of any one of SEQ ID NOs: 16-4679. In certain embodiments, the DGAT2 specific inhibitor is an antisense compound comprising a modified oligonucleotide consisting of the nucleobase sequence of any one of SEQ ID NOs: 16-4679. In certain embodiments, the DGAT2 specific inhibitor is an antisense compound comprising a modified oligonucleotide consisting of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising or consisting of a modified oligonucleotide and a conjugate group, wherein the modified oligonucleotide consists of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising a modified oligonucleotide having a nucleobase sequence consisting of any one of SEQ ID NOs: 1423, 1371, 1415, 1849, 2959, 3292, 4198, and 4373. In certain embodiments, the DGAT2 specific inhibitor is ISIS 484137, ISIS 484085, ISIS 484129, ISIS 495576, ISIS 501861, ISIS 502194, ISIS 525443, and ISIS 525612. In certain embodiments the DGAT2 specific inhibitor is ISIS 769355, ISIS 769356, and ISIS 769357. In any of the foregoing embodiments, the antisense compound can be a single-stranded oligonucleotide. In certain aspects, the antisense compound is administered to the individual parenterally.

Certain embodiments are drawn to a DGAT2 specific inhibitor for use in treating a disease associated with NAFLD. In certain aspects, the disease is NASH. In certain aspects, the disease is hepatic steatosis. In certain aspects, the disease is liver cirrhosis. In certain aspects, the disease is hepatocellular carcinoma. Certain embodiments are drawn to a DGAT2 specific inhibitor for use in treating a disease associated with lipodystrophy syndromes. In certain aspects, the disease is partial lipodystrophy. In certain aspects, the inhibitor is an antisense compound targeted to DGAT2. In certain embodiments, the DGAT2 specific inhibitor is an antisense compound targeted to DGAT2, such as an antisense oligonucleotide targeted to DGAT2. In certain embodiments, the DGAT2 specific inhibitor is a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising at least 8 contiguous nucleobases of any of the nucleobase sequences of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising the nucleobase sequence of any one of SEQ ID NOs: 16-4679. In certain embodiments, the DGAT2 specific inhibitor is an antisense compound comprising a modified oligonucleotide consisting of the nucleobase sequence of any one of SEQ ID NOs: 16-4679. In certain embodiments, the DGAT2 specific inhibitor is an antisense compound comprising a modified oligonucleotide consisting of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising or consisting of a modified oligonucleotide and a conjugate group, wherein the modified oligonucleotide consists of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising a modified oligonucleotide having a nucleobase sequence consisting of any one of SEQ ID NOs: 1423, 1371, 1415, 1849, 2959, 3292, 4198, and 4373. In certain embodiments, the DGAT2 specific inhibitor is ISIS 484137, ISIS 484085, ISIS 484129, ISIS 495576, ISIS 501861, ISIS 502194, ISIS 525443, and ISIS 525612. In certain embodiments the DGAT2 specific inhibitor is ISIS 769355, ISIS 769356, and ISIS 769357. In any of the foregoing embodiments, the antisense compound can be a single-stranded oligonucleotide. In certain aspects, the antisense compound is administered to the individual parenterally.

Certain embodiments are drawn to a DGAT2 specific inhibitor for reducing or inhibiting triglyceride synthesis, hepatic lipid synthesis and insulin resistance in the liver of an individual having, or at risk of having, a disease associated with NAFLD or lipodystrophy syndromes comprises administering a DGAT2 specific inhibitor to the individual, thereby reducing or inhibiting triglyceride synthesis, hepatic lipid synthesis and insulin resistance in the liver of the individual. Certain embodiments are drawn to a DGAT2 specific inhibitor for reducing or inhibiting triglyceride synthesis, lipid synthesis and insulin resistance in the adipose tissue of an individual having, or at risk of having, a disease associated with NAFLD or lipodystrophy syndromes comprises administering a DGAT2 specific inhibitor to the individual, thereby reducing or inhibiting triglyceride synthesis, lipid synthesis and insulin resistance in the adipose tissue of the individual. In certain embodiments, the DGAT2 specific inhibitor is an antisense compound targeted to DGAT2, such as an antisense oligonucleotide targeted to DGAT2. In certain embodiments, the DGAT2 specific inhibitor is a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising at least 8 contiguous nucleobases of any of the nucleobase sequences of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising the nucleobase sequence of any one of SEQ ID NOs: 16-4679. In certain embodiments, the DGAT2 specific inhibitor is an antisense compound comprising a modified oligonucleotide consisting of the nucleobase sequence of any one of SEQ ID NOs: 16-4679. In certain embodiments, the DGAT2 specific inhibitor is an antisense compound comprising a modified oligonucleotide consisting of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising or consisting of a modified oligonucleotide and a conjugate group, wherein the modified oligonucleotide consists of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising a modified oligonucleotide having a nucleobase sequence consisting of any one of SEQ ID NOs: 1423, 1371, 1415, 1849, 2959, 3292, 4198, and 4373. In certain embodiments, the DGAT2 specific inhibitor is ISIS 484137, ISIS 484085, ISIS 484129, ISIS 495576, ISIS 501861, ISIS 502194, ISIS 525443, and ISIS 525612. In certain embodiments the DGAT2 specific inhibitor is ISIS 769355, ISIS 769356, and ISIS 769357. In any of the foregoing embodiments, the antisense compound can be a single-stranded oligonucleotide.

Certain embodiments are drawn to use of a DGAT2 specific inhibitor for the manufacture of a medicament for treating a disease associated with NAFLD. In certain aspects, the disease is NASH. In certain aspects, the disease is hepatic steatosis. In certain aspects, the disease is liver cirrhosis. In certain aspects, the disease is hepatocellular carcinoma. Certain embodiments are drawn to use of a DGAT2 specific inhibitor for the manufacture of a medicament for treating a disease associated with lipodystrophy syndromes. In certain aspects, the disease is partial lipodystrophy. In certain aspects, the inhibitor is an antisense compound targeted to DGAT2. In certain embodiments, the DGAT2 specific inhibitor is an antisense compound targeted to DGAT2, such as an antisense oligonucleotide targeted to DGAT2. In certain embodiments, the DGAT2 specific inhibitor is a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising at least 8 contiguous nucleobases of any of the nucleobase sequences of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising the nucleobase sequence of any one of SEQ ID NOs: 16-4679. In certain embodiments, the DGAT2 specific inhibitor is an antisense compound comprising a modified oligonucleotide consisting of the nucleobase sequence of any one of SEQ ID NOs: 16-4679. In certain embodiments, the DGAT2 specific inhibitor is an antisense compound comprising a modified oligonucleotide consisting of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising or consisting of a modified oligonucleotide and a conjugate group, wherein the modified oligonucleotide consists of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising a modified oligonucleotide having a nucleobase sequence consisting of any one of SEQ ID NOs: 1423, 1371, 1415, 1849, 2959, 3292, 4198, and 4373. In certain embodiments, the DGAT2 specific inhibitor is ISIS 484137, ISIS 484085, ISIS 484129, ISIS 495576, ISIS 501861, ISIS 502194, ISIS 525443, and ISIS 525612. In certain embodiments the DGAT2 specific inhibitor is ISIS 769355, ISIS 769356, and ISIS 769357. In any of the foregoing embodiments, the antisense compound can be a single-stranded oligonucleotide. In certain aspects, the antisense compound is administered to the individual parenterally.

Certain embodiments are drawn to use of a DGAT2 specific inhibitor for the manufacture of a medicament for reducing or inhibiting triglyceride synthesis, hepatic lipid synthesis and insulin resistance in the liver of an individual having, or at risk of having, a disease associated with NAFLD or lipodystrophy syndromes. Certain embodiments are drawn to use of a DGAT2 specific inhibitor for the manufacture of a medicament for reducing or inhibiting triglyceride synthesis, hepatic lipid synthesis and insulin resistance in the liver of an individual having, or at risk of having, a disease associated with NAFLD or lipodystrophy syndromes. Certain embodiments are drawn to use of a DGAT2 specific inhibitor for the manufacture of a medicament for reducing or inhibiting triglyceride synthesis, lipid synthesis and insulin resistance in the adipose tissue of an individual having, or at risk of having, a disease associated with NAFLD or lipodystrophy syndromes. Certain embodiments are drawn to use of a DGAT2 specific inhibitor for the manufacture of a medicament for reducing or inhibiting triglyceride synthesis, lipid synthesis and insulin resistance in the adipose tissue of an individual having, or at risk of having, a disease associated with NAFLD or lipodystrophy syndromes. In certain embodiments, the DGAT2 specific inhibitor is an antisense compound targeted to DGAT2, such as an antisense oligonucleotide targeted to DGAT2. In certain embodiments, the DGAT2 specific inhibitor is a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising at least 8 contiguous nucleobases of any of the nucleobase sequences of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising the nucleobase sequence of any one of SEQ ID NOs: 16-4679. In certain embodiments, the DGAT2 specific inhibitor is an antisense compound comprising a modified oligonucleotide consisting of the nucleobase sequence of any one of SEQ ID NOs: 16-4679. In certain embodiments, the DGAT2 specific inhibitor is an antisense compound comprising a modified oligonucleotide consisting of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising or consisting of a modified oligonucleotide and a conjugate group, wherein the modified oligonucleotide consists of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising a modified oligonucleotide having a nucleobase sequence consisting of any one of SEQ ID NOs: 1423, 1371, 1415, 1849, 2959, 3292, 4198, and 4373. In certain embodiments, the DGAT2 specific inhibitor is ISIS 484137, ISIS 484085, ISIS 484129, ISIS 495576, ISIS 501861, ISIS 502194, ISIS 525443, and ISIS 525612. In certain embodiments the DGAT2 specific inhibitor is ISIS 769355, ISIS 769356, and ISIS 769357. In any of the foregoing embodiments, the antisense compound can be a single-stranded oligonucleotide.

In certain embodiments, a method of inhibiting expression of DGAT2 in a cell comprises contacting the cell with a DGAT2 specific inhibitor. In certain embodiments, the cell is a hepatocyte. In certain embodiments, the cell is in the liver of an individual. In certain embodiments, the cell is an adipose tissue cell of an individual. In certain embodiments, the cell is in the adipose tissue of an individual. In certain embodiments, the DGAT2 specific inhibitor is an antisense compound targeted to DGAT2, such as an antisense oligonucleotide targeted to DGAT2. In certain embodiments, the DGAT2 specific inhibitor is a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising at least 8 contiguous nucleobases of any of the nucleobase sequences of SEQ ID NOs: 16-4679. In certain embodiments, the DGAT2 specific inhibitor is an antisense compound comprising a modified oligonucleotide consisting of 10 to 30 linked nucleosides and having a nucleobase sequence comprising the nucleobase sequence of any one of SEQ ID NOs: 16-4679. In certain embodiments, the DGAT2 specific inhibitor is an antisense compound comprising a modified oligonucleotide consisting of the nucleobase sequence of any one of SEQ ID NOs: 16-4679. In certain embodiments, the DGAT2 specific inhibitor is an antisense compound comprising a modified oligonucleotide consisting of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising or consisting of a modified oligonucleotide and a conjugate group, wherein the modified oligonucleotide consists of 10 to 30 linked nucleosides having a nucleobase sequence comprising any one of SEQ ID NOs: 1423, 1371, 1415, 1849, 2959, 3292, 4198, and 4373. In certain embodiments, the DGAT2 specific inhibitor is an antisense compound comprising a modified oligonucleotide having a nucleobase sequence consisting of any one of SEQ ID NOs: 1423, 1371, 1415, 1849, 2959, 3292, 4198, and 4373. In certain embodiments, the DGAT2 specific inhibitor is ISIS 484137, ISIS 484085, ISIS 484129, ISIS 495576, ISIS 501861, ISIS 502194, ISIS 525443, and ISIS 525612. In certain embodiments the DGAT2 specific inhibitor is ISIS 769355, ISIS 769356, and ISIS 769357. In any of the foregoing embodiments, the antisense compound can be a single-stranded oligonucleotide. In certain aspects, the antisense compound is administered to the individual parenterally.

In any of the foregoing embodiments, the DGAT2 specific inhibitor can be an antisense compound targeted to DGAT2. In certain aspects, the antisense compound is an antisense oligonucleotide, for example an antisense oligonucleotide consisting of 8 to 80 linked nucleosides, 12 to 30 linked nucleosides, or 20 linked nucleosides. In certain aspects, the antisense oligonucleotide is at least 80%, 85%, 90%, 95% or 100% complementary to any of the nucleobase sequences recited in SEQ ID NOs: 1-4. In certain aspects, the antisense oligonucleotide comprises at least one modified internucleoside linkage, at least one modified sugar and/or at least one modified nucleobase. In certain aspects, the modified internucleoside linkage is a phosphorothioate internucleoside linkage, the modified sugar is a bicyclic sugar or a 2'-O-methoxyethyl, and the modified nucleobase is a 5-methylcytosine. In certain aspects, the modified oligonucleotide comprises a gap segment consisting of linked 2'-deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing embodiments, the antisense oligonucleotide consists of 12 to 30, 15 to 30, 15 to 25, 15 to 24, 16 to 24, 17 to 24, 18 to 24, 19 to 24, 20 to 24, 19 to 22, 20 to 22, 16 to 20, or 17 or 20 linked nucleosides. In certain aspects, the antisense oligonucleotide is at least 80%, 85%, 90%, 95% or 100% complementary to any of the nucleobase sequences recited in SEQ ID NOs: 1-4. In certain aspects, the antisense oligonucleotide comprises at least one modified internucleoside linkage, at least one modified sugar and/or at least one modified nucleobase. In certain aspects, the modified internucleoside linkage is a phosphorothioate internucleoside linkage, the modified sugar is a bicyclic sugar or a 2'-O-methoxyethyl, and the modified nucleobase is a 5-methylcytosine. In certain aspects, the modified oligonucleotide comprises a gap segment consisting of linked 2'-deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing methods or uses, the DGAT2 specific inhibitor can be a compound comprising or consisting of a modified oligonucleotide consisting of 10 to 30 linked nucleosides having a nucleobase sequence comprising any one of SEQ ID NOs: 16-4679, wherein the modified oligonucleotide comprises:
  a gap segment consisting of linked 2'-deoxynucleosides;
  a 5' wing segment consisting of linked nucleosides; and
  a 3' wing segment consisting of linked nucleosides;
    wherein the gap segment is positioned between the 5' wing segment and the 3' wing segment and wherein each nucleoside of each wing segment comprises a modified sugar.

In any of the foregoing methods or uses, the DGAT2 specific inhibitor can be a compound comprising a conjugate group and a modified oligonucleotide consisting of 10 to 30 linked nucleosides having a nucleobase sequence comprising any one of SEQ ID NOs: 16-4679, wherein the modified oligonucleotide comprises:
  a gap segment consisting of linked 2'-deoxynucleosides;
  a 5' wing segment consisting of linked nucleosides; and
  a 3' wing segment consisting of linked nucleosides;
  wherein the gap segment is positioned between the 5' wing segment and the 3' wing segment and wherein each nucleoside of each wing segment comprises a modified sugar.

In any of the foregoing methods or uses, the DGAT2 specific inhibitor can be a compound comprising or consisting of a modified oligonucleotide consisting of 10 to 30 linked nucleosides having a nucleobase sequence comprising any one of SEQ ID NOs: 1423, 1371, 1415, 1849, 2959, 3292, 4198, or 4373, wherein the modified oligonucleotide comprises:
  a gap segment consisting of linked 2'-deoxynucleosides;
  a 5' wing segment consisting of linked nucleosides; and
  a 3' wing segment consisting of linked nucleosides;
  wherein the gap segment is positioned between the 5' wing segment and the 3' wing segment and wherein each nucleoside of each wing segment comprises a modified sugar.

In any of the foregoing methods or uses, the DGAT2 specific inhibitor can be a compound comprising or consisting of a modified oligonucleotide consisting of 16 to 30 linked nucleosides having a nucleobase sequence comprising the sequence recited in SEQ ID NO: 1423, wherein the modified oligonucleotide comprises:
  a gap segment consisting often linked 2'-deoxynucleosides;
  a 5' wing segment consisting of five linked nucleosides; and
  a 3' wing segment consisting of five linked nucleosides;
  wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 20 linked nucleosides having a nucleobase sequence consisting of the sequence recited in SEQ ID NO: 1423, wherein the modified oligonucleotide comprises:
  a gap segment consisting often linked 2'-deoxynucleosides;
  a 5' wing segment consisting of five linked nucleosides; and
  a 3' wing segment consisting of five linked nucleosides;
  wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising a conjugate group and a modified oligonucleotide consisting of 20 linked nucleosides having a nucleobase sequence consisting of the sequence recited in SEQ ID NO: 1423, wherein the modified oligonucleotide comprises:
  a gap segment consisting often linked 2'-deoxynucleosides;
  a 5' wing segment consisting of five linked nucleosides; and
  a 3' wing segment consisting of five linked nucleosides;
  wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 16 to 30 linked nucleosides having a nucleobase sequence comprising the sequence recited in SEQ ID NO: 1371, wherein the modified oligonucleotide comprises:
  a gap segment consisting often linked 2'-deoxynucleosides;
  a 5' wing segment consisting of five linked nucleosides; and
  a 3' wing segment consisting of five linked nucleosides;
  wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 20 linked nucleosides having a nucleobase sequence consisting of the sequence recited in SEQ ID NO: 1371, wherein the modified oligonucleotide comprises:
  a gap segment consisting often linked 2'-deoxynucleosides;
  a 5' wing segment consisting of five linked nucleosides; and
  a 3' wing segment consisting of five linked nucleosides;
  wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 16 to 30 linked nucleosides having a nucleobase sequence comprising the sequence recited in SEQ ID NO: 1415, wherein the modified oligonucleotide comprises:
  a gap segment consisting often linked 2'-deoxynucleosides;
  a 5' wing segment consisting of five linked nucleosides; and
  a 3' wing segment consisting of five linked nucleosides;
  wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 20 linked nucleosides having a nucleobase sequence consisting of the sequence recited in SEQ ID NO: 1415, wherein the modified oligonucleotide comprises:

a gap segment consisting often linked 2'-deoxynucleosides;
a 5' wing segment consisting of five linked nucleosides; and
a 3' wing segment consisting of five linked nucleosides;
wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 16 to 30 linked nucleosides having a nucleobase sequence comprising the sequence recited in SEQ ID NO: 1849, wherein the modified oligonucleotide comprises:
a gap segment consisting often linked 2'-deoxynucleosides;
a 5' wing segment consisting of five linked nucleosides; and
a 3' wing segment consisting of five linked nucleosides;
wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 20 linked nucleosides having a nucleobase sequence consisting of the sequence recited in SEQ ID NO: 1849, wherein the modified oligonucleotide comprises:
a gap segment consisting often linked 2'-deoxynucleosides;
a 5' wing segment consisting of five linked nucleosides; and
a 3' wing segment consisting of five linked nucleosides;
wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 16 to 30 linked nucleosides having a nucleobase sequence comprising the sequence recited in SEQ ID NO: 2959, wherein the modified oligonucleotide comprises:
a gap segment consisting often linked 2'-deoxynucleosides;
a 5' wing segment consisting of five linked nucleosides; and
a 3' wing segment consisting of five linked nucleosides;
wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 20 linked nucleosides having a nucleobase sequence consisting of the sequence recited in SEQ ID NO: 2959, wherein the modified oligonucleotide comprises:
a gap segment consisting often linked 2'-deoxynucleosides;
a 5' wing segment consisting of five linked nucleosides; and
a 3' wing segment consisting of five linked nucleosides;
wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 16 to 30 linked nucleosides having a nucleobase sequence comprising the sequence recited in SEQ ID NO: 3292, wherein the modified oligonucleotide comprises:
a gap segment consisting often linked 2'-deoxynucleosides;
a 5' wing segment consisting of five linked nucleosides; and
a 3' wing segment consisting of five linked nucleosides;
wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 20 linked nucleosides having a nucleobase sequence consisting of the sequence recited in SEQ ID NO: 3292, wherein the modified oligonucleotide comprises:
a gap segment consisting often linked 2'-deoxynucleosides;
a 5' wing segment consisting of five linked nucleosides; and
a 3' wing segment consisting of five linked nucleosides;
wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 14 to 30 linked nucleosides having a nucleobase sequence comprising the sequence recited in SEQ ID NO: 4198, wherein the modified oligonucleotide comprises:
a gap segment consisting often linked 2'-deoxynucleosides;
a 5' wing segment consisting of three linked nucleosides; and
a 3' wing segment consisting of four linked nucleosides;
wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 17 linked nucleosides having a nucleobase sequence consisting of the sequence recited in SEQ ID NO: 4198, wherein the modified oligonucleotide comprises:
- a gap segment consisting often linked 2'-deoxynucleosides;
- a 5' wing segment consisting of three linked nucleosides; and
- a 3' wing segment consisting of four linked nucleosides;
- wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 14 to 30 linked nucleosides having a nucleobase sequence comprising the sequence recited in SEQ ID NO: 4373, wherein the modified oligonucleotide comprises:
- a gap segment consisting often linked 2'-deoxynucleosides;
- a 5' wing segment consisting of three linked nucleosides; and
- a 3' wing segment consisting of four linked nucleosides;
- wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor can be a compound comprising or consisting of a modified oligonucleotide consisting of 17 linked nucleosides having a nucleobase sequence consisting of the sequence recited in SEQ ID NO: 4373, wherein the modified oligonucleotide comprises:
- a gap segment consisting often linked 2'-deoxynucleosides;
- a 5' wing segment consisting of three linked nucleosides; and
- a 3' wing segment consisting of four linked nucleosides;
- wherein the gap segment is positioned between the 5' wing segment and the 3' wing segment; wherein each nucleoside of each wing segment comprises a 2'MOE sugar; wherein each internucleoside linkage is a phosphorothioate linkage; and wherein each cytosine is a 5-methylcytosine.

In any of the foregoing methods or uses, the DGAT2 specific inhibitor is administered subcutaneously, such as by subcutaneous injection.

Antisense Compounds

Oligomeric compounds include, but are not limited to, oligonucleotides, oligonucleosides, oligonucleotide analogs, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted.

In certain embodiments, an antisense compound is 10 to 30 subunits in length. In certain embodiments, an antisense compound is 12 to 30 subunits in length. In certain embodiments, an antisense compound is 12 to 22 subunits in length. In certain embodiments, an antisense compound is 14 to 30 subunits in length. In certain embodiments, an antisense compound is 14 to 20 subunits in length. In certain embodiments, an antisense compound is 15 to 30 subunits in length. In certain embodiments, an antisense compound is 15 to 20 subunits in length. In certain embodiments, an antisense compound is 16 to 30 subunits in length. In certain embodiments, an antisense compound is 16 to 20 subunits in length. In certain embodiments, an antisense compound is 17 to 30 subunits in length. In certain embodiments, an antisense compound is 17 to 20 subunits in length. In certain embodiments, an antisense compound is 18 to 30 subunits in length. In certain embodiments, an antisense compound is 18 to 21 subunits in length. In certain embodiments, an antisense compound is 18 to 20 subunits in length. In certain embodiments, an antisense compound is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound is 14 subunits in length. In certain embodiments, an antisense compound is 16 subunits in length. In certain embodiments, an antisense compound is 17 subunits in length. In certain embodiments, an antisense compound is 18 subunits in length. In certain embodiments, an antisense compound is 19 subunits in length. In certain embodiments, an antisense compound is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides, nucleosides, or nucleobases.

In certain embodiments, the antisense compound or oligomeric compound may further comprise additional features or elements, such as a conjugate group, that are attached to the oligonucleotide. In embodiments where a conjugate group comprises a nucleoside (i.e. a nucleoside that links the conjugate group to the oligonucleotide), the nucleoside of the conjugate group is not counted in the length of the oligonucleotide.

In certain embodiments antisense oligonucleotides may be shortened or truncated. For example, a single nucleoside may be deleted from the 5' end (5' truncation), or alternatively from the 3' end (3' truncation). A shortened or truncated antisense compound targeted to an DGAT2 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity (Woolf et al. (*Proc. Natl. Acad. Sci. USA* 89:7305-7309, 1992; Gautschi et al. *J. Natl. Cancer Inst.* 93:463-471, March 2001; Maher and Dolnick *Nuc. Acid. Res.* 16:3341-3358, 1988). However, seemingly small changes in oligonucleotide sequence, chemistry and motif can make large differences in one or more of the many properties required for clinical development (Seth et al. *J. Med. Chem.* 2009, 52, 10; Egli et al. *J. Am. Chem. Soc.* 2011, 133, 16642).

In certain embodiments, antisense compounds are single-stranded, consisting of one oligomeric compound. The oligonucleotide of such single-stranded antisense compounds is an antisense oligonucleotide. In certain embodiments, the antisense oligonucleotide of a single-stranded antisense compound is modified. In certain embodiments, the oligonucleotide of a single-stranded antisense compound or oligomeric compound comprises a self-complementary nucleobase sequence. In certain embodiments, antisense compounds are double-stranded, comprising two oligomeric compounds that form a duplex. In certain such embodiments, one oligomeric compound of a double-stranded antisense compound comprises one or more conjugate groups. In certain embodiments, each oligomeric compound of a double-stranded antisense compound comprises one or more conjugate groups. In certain embodiments, each oligonucleotide of a double-stranded antisense compound is a modified oligonucleotide. In certain embodiments, one oligonucleotide of a double-stranded antisense compound is a modified oligonucleotide. In certain embodiments, one oligonucleotide of a double-stranded antisense compound is an antisense oligonucleotide. In certain such embodiments, the antisense oligonucleotide is a modified oligonucleotide. Examples of single-stranded and double-stranded antisense compounds include but are not limited to antisense oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics.

In certain embodiments, a double-stranded compound can comprise any of the oligonucleotide sequences targeted to DGAT2 described herein. In certain embodiments, a double-stranded compound comprises a first strand comprising at least an 8, 9, 10, 11, 12, 13, 14, 15, 16, 17, 18, 19, or 20 contiguous nucleobase portion of any one of SEQ ID NOs: 16-4679 and a second strand. In certain embodiments, a double-stranded compound comprises a first strand comprising the nucleobase sequence of any one of SEQ ID NOs: 16-4679 and a second strand. In certain embodiments, the double-stranded compound comprises ribonucleotides in which the first strand has uracil (U) in place of thymine (T) in any one of SEQ ID NOs: 16-4679. In certain embodiments, a double-stranded compound comprises (i) a first strand comprising a nucleobase sequence complementary to the site on DGAT2 to which any of SEQ ID NOs: 16-4679 is targeted, and (ii) a second strand. In certain embodiments, the double-stranded compound comprises one or more modified nucleotides in which the 2' position in the sugar contains a halogen (such as fluorine group; 2'-F) or contains an alkoxy group (such as a methoxy group; 2'-OMe). In certain embodiments, the double-stranded compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the double-stranded compound comprises one or more linkages between adjacent nucleotides other than a naturally-occurring phosphodiester linkage. Examples of such linkages include phosphoramide, phosphorothioate, and phosphorodithioate linkages. The double-stranded compounds may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000. In certain embodiments, the first strand of the double-stranded compound is an siRNA guide strand and the second strand of the double-stranded compound is an siRNA passenger strand. In certain embodiments, the second strand of the double-stranded compound is complementary to the first strand. In certain embodiments, each strand of the double-stranded compound consists of 16, 17, 18, 19, 20, 21, 22, or 23 linked nucleosides. In certain embodiments, the first or second strand of the double-stranded compound can comprise a conjugate group.

In certain embodiments, a single-stranded RNAi (ssRNAi) compound can comprise any of the oligonucleotide sequences targeted to DGAT2 described herein. In certain embodiments, an ssRNAi compound comprises at least an 8, 9, 10, 11, 12, 13, 14, 15, 16, 17, 18, 19, or 20 contiguous nucleobase portion of any one of SEQ ID NOs: 16-4679. In certain embodiments, an ssRNAi compound comprises the nucleobase sequence of any one of SEQ ID NOs: 16-4679. In certain embodiments, the ssRNAi compound comprises ribonucleotides in which uracil (U) is in place of thymine (T) in any one of SEQ ID NOs: 16-4679. In certain embodiments, an ssRNAi compound comprises a nucleobase sequence complementary to the site on DGAT2 to which any of SEQ ID NOs: 16-4679 is targeted. In certain embodiments, an ssRNAi compound comprises one or more modified nucleotides in which the 2' position in the sugar contains a halogen (such as fluorine group; 2'-F) or contains an alkoxy group (such as a methoxy group; 2'-OMe). In certain embodiments, an ssRNAi compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the ssRNAi compound. In certain embodiments, the ssRNAi compound comprises one or more linkages between adjacent nucleotides other than a naturally-occurring phosphodiester linkage. Examples of such linkages include phosphoramide, phosphorothioate, and phosphorodithioate linkages. The ssRNAi compounds may also be chemically modified nucleic acid molecules as taught in U.S. Pat. No. 6,673,661. In other embodiments, the ssRNAi contains a capped strand, as disclosed, for example, by WO 00/63364, filed Apr. 19, 2000. In certain embodiments, the ssRNAi compound consists of 16, 17, 18, 19, 20, 21, 22, or 23 linked nucleosides. In certain embodiments, the ssRNAi compound can comprise a conjugate group.

In certain embodiments, antisense compounds comprise modified oligonucleotides. Certain modified oligonucleotides have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

In certain embodiments, antisense compounds and oligomeric compounds described herein comprise modified oligonucleotides. Such modified oligonucleotides may contain any combination of the modified sugar moieties, modified nucleobases, modified internucleoside linkages, motifs, and/or lengths described herein.

Certain Antisense Compound Mechanisms

In certain embodiments, antisense compounds are capable of hybridizing to a target nucleic acid, resulting in at least one antisense activity. In certain embodiments, antisense compounds specifically affect one or more target nucleic acid. Such specific antisense compounds comprises a nucleobase sequence that hybridizes to one or more target nucleic acid, resulting in one or more desired antisense activity and does not hybridize to one or more non-target nucleic acid or does not hybridize to one or more non-target nucleic acid in such a way that results in an undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, the invention provides antisense compounds that are sufficiently "DNA-like" to elicit RNase H activity. Further, in certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. In certain embodiments, antisense compounds that are loaded into RISC are RNAi compounds.

In certain embodiments, hybridization of an antisense compound to a target nucleic acid dose not result in recruitment of a protein that cleaves that target nucleic acid. In certain such embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain such embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

In certain embodiments, modified oligonucleotides having a gapmer sugar motif described herein have desirable properties compared to non-gapmer oligonucleotides or to gapmers having other sugar motifs. In certain circumstances, it is desirable to identify motifs resulting in a favorable combination of potent antisense activity and relatively low toxicity. In certain embodiments, compounds of the present invention have a favorable therapeutic index (measure of activity divided by measure of toxicity).

Target Nucleic Acids, Target Regions and Nucleotide Sequences

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

Nucleotide sequences that encode DGAT2 include, without limitation, the following: RefSeq No. NM_032564.3 (incorporated herein by reference; designated herein as SEQ ID NO: 1), nucleotides 5669186 to 5712008 of RefSeq No. NT_033927.5 (incorporated herein by reference; designated herein as SEQ ID NO: 2), nucleotides 20780400 to 20823450 of RefSeq No. NT_167190.1 (incorporated herein by reference; designated herein as SEQ ID NO: 4878), RefSeq No. AK091870.1 (incorporated herein by reference; designated herein as SEQ ID NO: 4879), and nucleotides 1232000 to 1268000 of RefSeq No. NW_001100387.1 (incorporated herein by reference; designated herein as SEQ ID NO: 3).

Hybridization

In some embodiments, hybridization occurs between an antisense compound disclosed herein and a DGAT2 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a DGAT2 nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

Non-complementary nucleobases between an antisense compound and a DGAT2 nucleic acid may be tolerated provided that the antisense compound remains able to specifically hybridize to a target nucleic acid. Moreover, an antisense compound may hybridize over one or more segments of a DGAT2 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a DGAT2 nucleic acid, a target region, target segment, or specified portion thereof. In certain such embodiments, the region of full complementarity is from 6 to 20 nucleobases in length. In certain such embodiments, the region of full complementarity is from 10 to 18 nucleobases in length. In certain such embodiments, the region of full complementarity is from 18 to 20 nucleobases in length. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to a DGAT2 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

In certain embodiments, antisense compounds comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the antisense compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the antisense compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a DGAT2 nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a DGAT2 nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are, or are at least, 70%, 75%, 80%, 85%, 90%, 91%, 92%, 93%, 94%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH$_2$—N(CH$_3$)—O—CH$_2$—), thiodiester (—O—C(=O)—S—), thionocarbamate (—O—

C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

In certain embodiments, antisense compounds targeted to a DGAT2 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, oligonucleotides having a gapmer nucleoside motif comprise a linkage motif comprising all phosphorothioate linkages except for one or two methylphosponate linkages. In certain embodiments, one methylphosphonate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds.

In certain embodiments, modified oligonucleotides comprise one or more modified nucleosides comprising a modified sugar moiety. Such modified oligonucleotides comprising one or more sugar-modified nucleosides may have desirable properties, such as enhanced nuclease stability or increased binding affinity with a target nucleic acid relative to oligonucleotides lacking such sugar-modified nucleosides. In certain embodiments, modified sugar moieties are linearly modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are linearly modified sugar moieties comprising a furanosyl ring with one or more acyclic substituent, including but not limited to substituents at the 2' and/or 5' positions. Examples of 2'-substituent groups suitable for linearly modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 5'-substituent groups suitable for linearly modified sugar moieties include but are not limited to: 5'-methyl (R or S), 5'-vinyl, and 5'-methoxy. In certain embodiments, linearly modified sugars comprise more than one non-bridging sugar substituent, for example, 2'-F-5'-methyl sugar moieties (see, e.g., PCT International Application WO 2008/101157, for additional 2', 5'-bis substituted sugar moieties and nucleosides).

In certain embodiments, a 2'-substituted nucleoside or 2'-linearly modified nucleoside comprises a sugar moiety comprising a linear 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-linearly modified nucleoside comprises a sugar moiety comprising a linear 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-linearly modified nucleoside comprises a sugar moiety comprising a linear 2'-substituent group selected from: F, OCH$_3$, and OCH$_2$CH$_2$OCH$_3$.

Nucleosides comprising modified sugar moieties, such as linearly modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., U.S. Pat. No. 7,399,845), 4'-C(CH$_3$)(CH$_3$)—O-2' and analogs thereof (see, e.g., WO2009/006478), 4'-CH$_2$—N(OCH$_3$)-2' and analogs thereof (see, e.g., WO2008/150759), 4'-CH$_2$—O—N(CH$_3$)-2' (see, e.g., US2004/0171570), 4'-CH$_2$—C(H)(CH$_3$)-2' (see, e.g., Chattopadhyaya, et al., J. Org. Chem., 2009, 74, 118-134), 4'-CH$_2$—C(=CH$_2$)-2' and analogs thereof (see, published PCT International Application WO 2008/154401), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, an LNA nucleoside (described above) may be in the α-L configuration or in the β-D configuration.

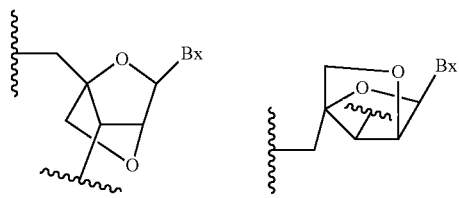

LNA (β-D-configuration)    α-L-LNA (α-L-configuration)
bridge = 4'-CH$_2$—O-2'    bridge = 4'-CH$_2$—O-2'

LNA (β-D-configuration) α-L-LNA (α-L-configuration) bridge=4'-CH$_2$—O-2' bridge=4'-CH$_2$—O-2'

α-L-methyleneoxy (4'-CH$_2$—O-2') or α-L-LNA bicyclic nucleosides have been incorporated into antisense oligonucleotides that showed antisense activity (Frieden et al., Nucleic Acids Research, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars). (see, e.g., WO 2007/134181, wherein LNA nucleosides are further substituted with, for example, a 5'-methyl or a 5'-vinyl group, and see, e.g., U.S. Pat. Nos. 7,547,684; 7,750,131; 8,030,467; 8,268,980; 7,666,854; and 8,088,746).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described above. For example, certain sugar surrogates comprise a 4'-sulfur atom and a substitution at the 2'-position (see, e.g., US2005/0130923) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see Leumann, C J. Bioorg. & Med. Chem. 2002, 10, 841-854), fluoro HNA:

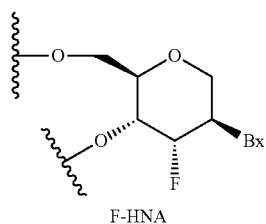

F-HNA ("F-HNA", see e.g., U.S. Pat. Nos. 8,088,904; 8,440,803; and 8,796,437, F-HNA can also be referred to as a F-THP or 3'-fluoro tetrahydropyran), and nucleosides comprising additional modified THP compounds having the formula:

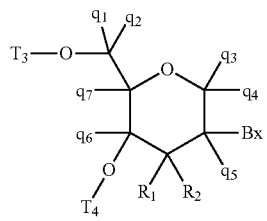

wherein, independently, for each of said modified THP nucleoside:
Bx is a nucleobase moiety;
$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and U.S. Pat. Nos. 5,698,685; 5,166,315; 5,185, 444; and 5,034,506). As used here, the term "morpholino" means a sugar surrogate having the following structure:

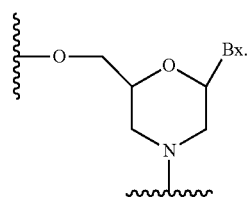

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in WO2011/133876.

Many other bicyclic and tricyclic sugar and sugar surrogate ring systems are known in the art that can be used in modified nucleosides (see, e.g., Leumann, J. C, *Bioorganic & Medicinal Chemistry,* 2002, 10, 841-854).

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds.

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering,* Kroschwitz, J. I., Ed., John Wiley & Sons, 1990, 858-859; Englisch et al., *Angewandte Chemie,* International Edition, 1991, 30, 613; Sanghvi, Y. S., Chapter 15, *Antisense Research and Applications,* Crooke, S. T. and Lebleu, B., Eds., CRC Press, 1993, 273-288; and those disclosed in Chapters 6 and 15, *Antisense Drug Technology,* Crooke S. T., Ed., CRC Press, 2008, 163-166 and 442-443.

Representative United States patents that teach the preparation of certain of the above noted modified nucleobases as well as other modified nucleobases include without limitation, US2003/0158403, U.S. Pat. Nos. 3,687,808; 4,845, 205; 5,130,302; 5,134,066; 5,175,273; 5,367,066; 5,432, 272; 5,434,257; 5,457,187; 5,459,255; 5,484,908; 5,502, 177; 5,525,711; 5,552,540; 5,587,469; 5,594,121; 5,596, 091; 5,614,617; 5,645,985; 5,681,941; 5,750,692; 5,763, 588; 5,830,653 and 6,005,096.

In certain embodiments, antisense compounds targeted to a DGAT2 nucleic acid comprise one or more modified nucleobases. In certain embodiments, the modified nucleobase is 5-methylcytosine. In certain embodiments, each cytosine is a 5-methylcytosine.

Certain Motifs

Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain such embodiments, each nucleoside to the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P═O). In certain embodiments, each internucleoside linking group of a modified oligonucleotide is a phosphorothioate (P═S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

Certain Oligonucleotides

Oligonucleotides are characterized by their motifs and overall lengths. In certain embodiments, such parameters are each independent of one another. Thus, unless otherwise indicated, each internucleoside linkage of an oligonucleotide having a gapmer motif may be modified or unmodified and may or may not follow the gapmer modification pattern of the sugar modifications. For example, the internucleoside linkages within the wing regions of a gapmer may be the same or different from one another and may be the same or different from the internucleoside linkages of the gap region. Likewise, such gapmer oligonucleotides may comprise one or more modified nucleobase independent of the gapmer pattern of the sugar modifications. Furthermore, unless otherwise indicated, each internucleoside linkage and each nucleobase of a fully modified oligonucleotide may be modified or unmodified. One of skill in the art will appreciate that such motifs may be combined to create a variety of oligonucleotides. Herein, if a description of an oligonucleotide is silent with respect to one or more parameter, such parameter is not limited. Thus, a modified oligonucleotide described only as having a gapmer motif without further description may have any length, internucleoside linkage motif, and nucleobase motif Unless otherwise indicated, all modifications are independent of nucleobase sequence.

In certain embodiments, oligonucleotides have a nucleobase sequence that is complementary to a second oligonucleotide or a target nucleic acid. In certain such embodiments, a region of an oligonucleotide has a nucleobase sequence that is complementary to a second oligonucleotide or a target nucleic acid. In certain embodiments, the nucleobase sequence of a region or entire length of an oligonucleotide is at least 50%, at least 60%, at least 70%, at least 80%, at least 90%, at least 95%, or 100% complementary to the second oligonucleotide or target nucleic acid. In certain embodiments, antisense compounds comprise two oligomeric compounds, wherein the two oligonucleotides of the oligomeric compounds are at least 80%, at least 90%, or 100% complementary to each other. In certain embodiments, one or both oligonucleotides of a double-stranded antisense compound comprise two nucleosides that are not complementary to the other oligonucleotide.

Conjugated Groups and Terminal Groups

In certain embodiments, antisense compounds and oligomeric compounds comprise conjugate groups and/or terminal groups. In certain such embodiments, oligonucleotides are covalently attached to one or more conjugate group. In certain embodiments, conjugate groups modify one or more properties of the attached oligonucleotide, including but not limited to pharmacodynamics, pharmacokinetics, stability, binding, absorption, cellular distribution, cellular uptake, charge and clearance. In certain embodiments, conjugate groups impart a new property on the attached oligonucleotide, e.g., fluorophores or reporter groups that enable detection of the oligonucleotide. Conjugate groups and/or terminal groups may be added to oligonucleotides having any of the modifications or motifs described above. Thus, for example, an antisense compound or oligomeric compound comprising an oligonucleotide having a gapmer motif may also comprise a conjugate group.

Conjugate groups include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Lett., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), an octadecylamine or hexylamino-carbonyl-oxycholesterol moiety (Crooke et al., J Pharmacol. Exp. Ther., 1996, 277, 923-937), a tocopherol group (Nishina et al., Molecular Therapy Nucleic Acids, 2015, 4, e220; doi: 10.1038/mtna.2014.72 and Nishina et al., Molecular Therapy, 2008, 16, 734-740), or a GalNAc cluster (e.g., WO2014/179620).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Conjugate groups are attached directly or via an optional conjugate linker to a parent compound, such as an oligonucleotide. In certain embodiments, conjugate groups are directly attached to oligonucleotides. In certain embodiments, conjugate groups are indirectly attached to oligonucleotides via conjugate linkers. In certain embodiments, the conjugate linker comprises a chain structure, such as a hydrocarbyl chain, or an oligomer of repeating units such as ethylene glycol or amino acid units. In certain embodiments, conjugate groups comprise a cleavable moiety. In certain embodiments, conjugate groups are attached to oligonucleotides via a cleavable moiety. In certain embodiments, conjugate linkers comprise a cleavable moiety. In certain such embodiments, conjugate linkers are attached to oligonucleotides via a cleavable moiety. In certain embodiments, oligonucleotides comprise a cleavable moiety, wherein the cleavable moiety is a nucleoside is attached to a cleavable internucleoside linkage, such as a phosphate internucleoside linkage. In certain embodiments, a conjugate group comprises a nucleoside or oligonucleotide, wherein the nucleoside or oligonucleotide of the conjugate group is indirectly attached to a parent oligonucleotide.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, a cleavable moiety is a cleavable bond. In certain embodiments, a cleavable moiety comprises a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate linker or conjugate group.

In certain embodiments, a cleavable moiety is a nucleoside. In certain such embodiments, the unmodified or modified nucleoside comprises an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. In certain embodiments, a cleavable moiety is 2'-deoxy nucleoside that is attached to either the 3' or 5'-terminal nucleoside of an oligonucleotide by a phosphate internucleoside linkage and covalently attached to the conjugate linker or conjugate group by a phosphate or phosphorothioate linkage. In certain such embodiments, the cleavable moiety is 2'-deoxyadenosine.

Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

In certain embodiments, a conjugate group is a cell-targeting moiety. In certain embodiments, a conjugate group, optional conjugate linker, and optional cleavable moiety have the general formula:

certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and

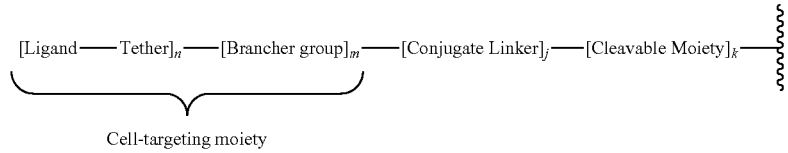

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian liver cell. In certain embodiments, each ligand has an affinity for the hepatic asialoglycoprotein receptor (ASGP-R). In certain embodiments, each ligand is a carbohydrate. In certain embodiments, each ligand is, independently selected from galactose, N-acetyl galactoseamine (GalNAc), mannose, glucose, glucoseamine and fucose. In certain embodiments, each ligand is N-acetyl galactoseamine (GalNAc). In certain embodiments, the cell-targeting moiety comprises 3 GalNAc ligands. In certain embodiments, the cell-targeting moiety comprises 2 GalNAc ligands. In certain embodiments, the cell-targeting moiety comprises 1 GalNAc ligand.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," *Bioconjugate Chemistry*, 2003, 14, 18-29, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, 47, 5798-5808, which are incorporated herein by reference in their entirety). In certain such embodiments, each ligand is an amino sugar or a thio sugar. For example, amino sugars may be selected from any number of compounds known in the art, such as sialic acid, α-D-galactosamine, 0-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, conjugate groups comprise a cell-targeting moiety having the formula:

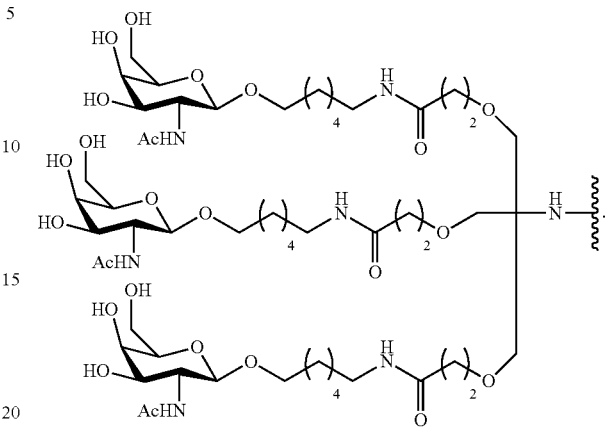

In certain embodiments, conjugate groups comprise a cell-targeting moiety having the formula:

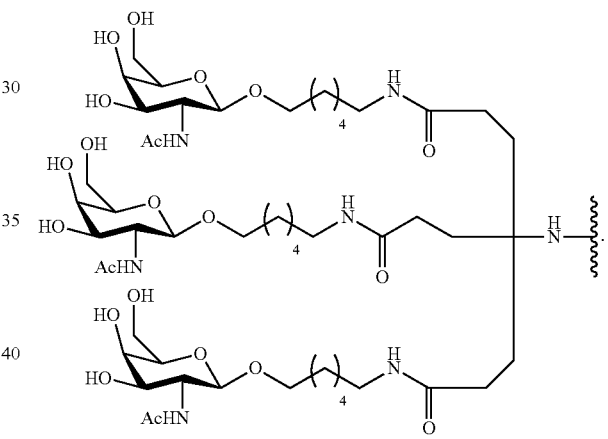

In certain embodiments, conjugate groups comprise a cell-targeting moiety having the formula:

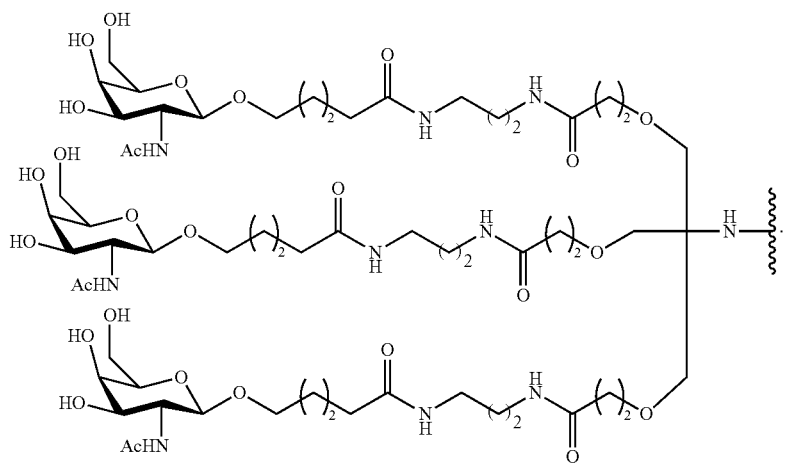

In certain embodiments, antisense compounds and oligomeric compounds comprise a conjugate group and conjugate linker described herein as "LICA-1". LICA-1 has the formula:

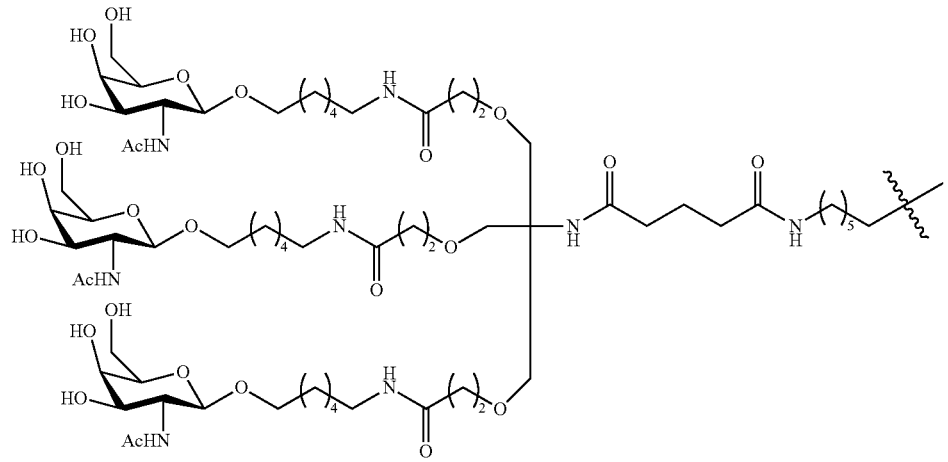

In certain embodiments, antisense compounds and oligomeric compounds comprising LICA-1 have the formula:

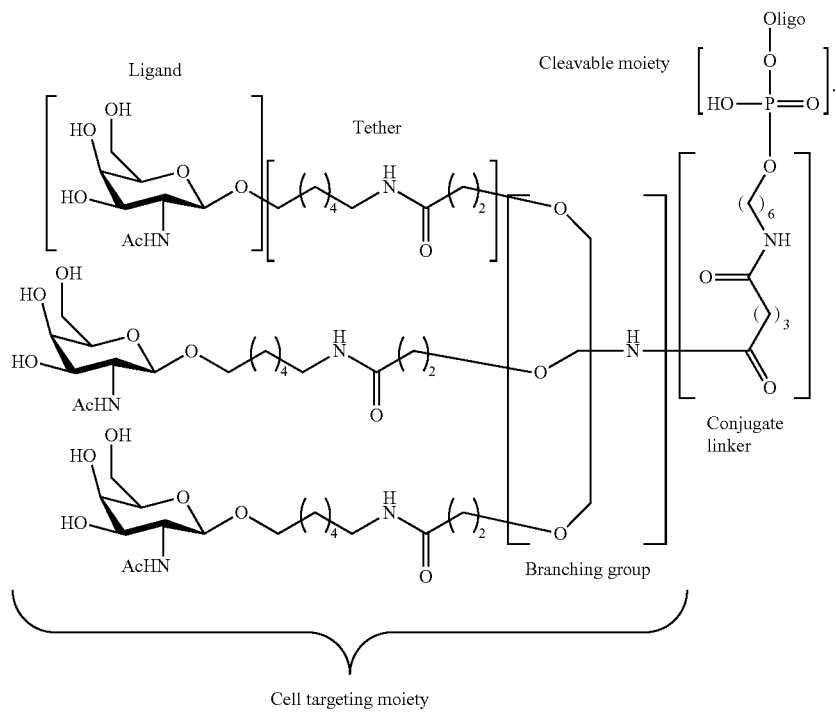

wherein oligo is an oligonucleotide.

Representative United States patents, United States patent application publications, international patent application publications, and other publications that teach the preparation of certain of the above noted conjugate groups, oligomeric compounds and antisense compounds comprising conjugate groups, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, WO 2013/033230 and WO 2012/037254, Biessen et al., *J Med. Chem.* 1995, 38, 1846-1852, Lee et al., *Bioorganic & Medicinal Chemistry* 2011, 19, 2494-2500, Rensen et al., *J Biol. Chem.* 2001, 276, 37577-37584, Rensen et al., *J Med. Chem.* 2004, 47, 5798-5808, Sliedregt et al., *J Med. Chem.* 1999, 42, 609-618, and Valentijn et al., *Tetrahedron*, 1997, 53, 759-770, each of which is incorporated by reference herein in its entirety.

In certain embodiments, antisense compounds and oligomeric compounds comprise modified oligonucleotides comprising a gapmer or fully modified motif and a conjugate group comprising at least one, two, or three GalNAc ligands. In certain embodiments antisense compounds and oligomeric compounds comprise a conjugate group found in any of the following references: Lee, *Carbohydr Res*, 1978, 67, 509-514; Connolly et al., *J Biol Chem*, 1982, 257, 939-945; Pavia et al., *Int J Pep Protein Res*, 1983, 22, 539-548; Lee et al., *Biochem*, 1984, 23, 4255-4261; Lee et al., *Glycoconjugate J*, 1987, 4, 317-328; Toyokuni et al., *Tetrahedron Lett*, 1990, 31, 2673-2676; Biessen et al., *J Med Chem*, 1995, 38, 1538-1546; Valentijn et al., *Tetrahedron*, 1997, 53, 759-770; Kim et al., *Tetrahedron Lett*, 1997, 38, 3487-3490; Lee et al., *Bioconjug Chem*, 1997, 8, 762-765; Kato et al., *Glycobiol*, 2001, 11, 821-829; Rensen et al., *J Biol Chem*, 2001, 276, 37577-37584; Lee et al., *Methods Enzymol*, 2003, 362, 38-43; Westerlind et al., *Glycoconj J*, 2004, 21, 227-241; Lee et al., *Bioorg Med Chem Lett*, 2006, 16(19), 5132-5135; Maierhofer et al., *Bioorg Med Chem*, 2007, 15, 7661-7676; Khorev et al., *Bioorg Med Chem*, 2008, 16, 5216-5231; Lee et al., *Bioorg Med Chem*, 2011, 19, 2494-2500; Komilova et al., *Analyt Biochem*, 2012, 425, 43-46; Pujol et al., *Angew Chemie Int Ed Engl*, 2012, 51, 7445-7448; Biessen et al., *J Med Chem*, 1995, 38, 1846-1852; Sliedregt et al., *J Med Chem*, 1999, 42, 609-618; Rensen et al., *J Med Chem*, 2004, 47, 5798-5808; Rensen et al., *Arterioscler Thromb Vasc Biol*, 2006, 26, 169-175; van Rossenberg et al., *Gene Ther*, 2004, 11, 457-464; Sato et al., *JAm Chem Soc*, 2004, 126, 14013-14022; Lee et al., *JOrg Chem*, 2012, 77, 7564-7571; Biessen et al., *FASEB J*, 2000, 14, 1784-1792; Rajur et al., *Bioconjug Chem*, 1997, 8, 935-940; Duff et al., *Methods Enzymol*, 2000, 313, 297-321; Maier et al., *Bioconjug Chem*, 2003, 14, 18-29; Jayaprakash et al., *Org Lett*, 2010, 12, 5410-5413; Manoharan, *Antisense Nucleic Acid Drug Dev*, 2002, 12, 103-128; Merwin et al., *Bioconjug Chem*, 1994, 5, 612-620; Tomiya et al., *Bioorg Med Chem*, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132; each of which is incorporated by reference in its entirety.

In certain embodiments, a modified oligonucleotide targeting DGAT2 described herein further comprises a GatNAc conjugate group. In certain embodiments, the GatNAc conjugate group is 5'-Trishexylamino-(THA)-C6 GalNAc$_3$. In certain embodiments, the 5'-Trishexylamino-(THA)-C6 GalNAc$_3$ conjugate has the formula

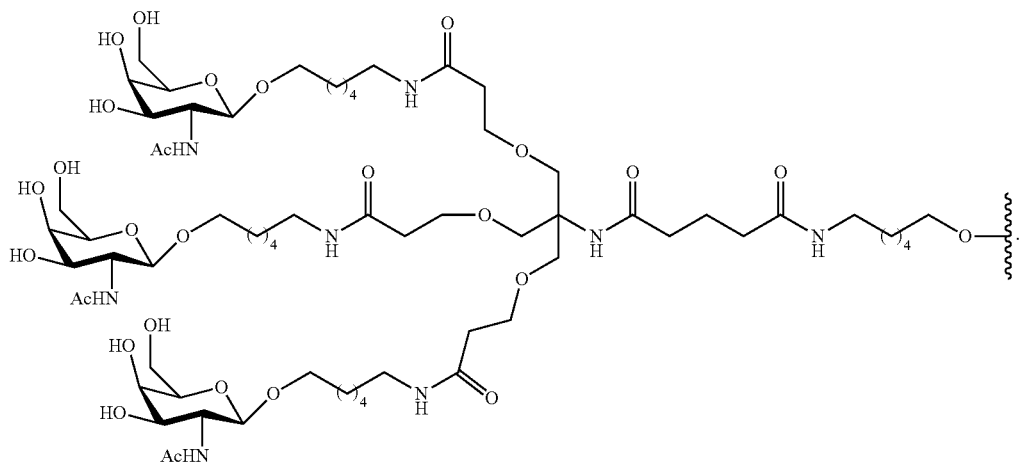

In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

Compositions and Methods for Formulating Pharmaceutical Compositions

In certain embodiments, the present invention provides pharmaceutical compositions comprising one or more antisense compound or a salt thereof. In certain such embodiments, the pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one antisense compound and sterile water. In certain embodiments, the sterile water is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

An antisense compound targeted to DGAT2 nucleic acid can be utilized in pharmaceutical compositions by combining the antisense compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising an antisense compound targeted to DGAT2 nucleic acid and a pharmaceutically acceptable diluent. In certain embodiments, the pharmaceutically acceptable diluent is water. In certain embodiments, the antisense compound is an antisense oligonucleotide provided herein.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In certain embodiments, the compounds or compositions further comprise a pharmaceutically acceptable carrier or diluent.

Certain Compounds

In vitro screens in human HepG2 cells were performed with about 5,000 antisense oligonucleotides that exhibited 100% complementarity to a human DGAT2 gene sequence. The new compounds were compared with previously designed compounds, which have been previously determined to be some of the most potent antisense compounds in vitro (see, e.g. published PCT application WO 2005/019418). From these in vitro screens, several antisense oligonucleotides that exhibited the greatest potency in reducing the expression of human DGAT2 mRNA were selected for in vivo tolerability assays.

The selected oligonucleotides were tested for tolerability in a CD1 mouse model, as well as a Sprague-Dawley rat model. In these models, body weights and organ weights, liver function markers (such as alanine transaminase, aspartate transaminase, and bilirubin), and kidney function markers (such as BUN and creatinine) were measured.

Final evaluation of all studies (Examples 1-15) led to the selection of eight oligonucleotides having a nucleobase sequence of SEQ ID NO: 1371 (ISIS 484085), SEQ ID NO: 1415 (ISIS 484129), SEQ ID NO: 1423 (ISIS484137), SEQ ID NO: 1844 (ISIS 495576), SEQ ID NO: 2959 (ISIS 501861), SEQ ID NO: 3292 (ISIS 502194), SEQ ID NO: 4198 (ISIS 525443), and SEQ ID NO: 4373 (ISIS 525612). The compounds are complementary to the regions 23242-23261, 26630-26649, 26778-26797, 15251-15270, 28026-28045, 35436-35455, 10820-10836, and 23246-23262. In certain embodiments, the compounds targeting the listed regions, as further described herein, comprise a modified oligonucleotide having some nucleobase portion of the sequence recited in the SEQ ID Nos, as further described herein. In certain embodiments, the compounds targeting the listed regions or having a nucleobase portion of a sequence recited in the listed SEQ ID Nos can be of various lengths, as further described herein, and can have one of various motifs, as further described herein. In certain embodiments, a compound targeting a region or having a nucleobase portion of a sequence in the listed SEQ ID Nos has the specific length and motif, as indicated by the ISIS Nos: 484085, 484129, 484137, 495576, 501861, 502194, 525443, and 525612.

These eight compounds were tested for activity, pharmacokinetic profile and tolerability in cynomolgus monkeys (Example 16). Specifically, ISIS 484137 was found to be potent and the most tolerable in this monkey study. Further evaluation of ISIS 484137 in a separate monkey study (Example 17) confirmed this finding.

The nucleotide sequence of ISIS 484137 is fully homologous to the rhesus monkey DGAT2 mRNA transcript. The cynomolgus monkey is regarded as a relevant preclinical safety model system for oligonucleotide therapeutics and the demonstrated pharmacologic activity of ISIS 484137 in this species makes it an appropriate species for safety assessment. General toxicology studies were conducted with ISIS 484137 in monkeys for 13 weeks of treatment and it was well tolerated with no overt adverse effects and no changes in routine laboratory parameters. ISIS 484137 reduced the expression of hepatic DGAT2 by about 70%.

The findings observed in mice and monkey toxicology studies following 13-weeks of ISIS 484137 treatment were, in general, non-specific class effects that are typical for 2'-MOE ASOs. There was no drug-related mortality or changes in clinical signs up to the highest doses tested (100 mg/kg in mice and 40 mg/kg in monkeys). There were no toxicologically significant findings at doses up to 12 mg/kg/wk for 13 weeks in the mouse and monkey studies, and therefore there is sufficient therapeutic margin to support the safe clinical use of ISIS 484137 at the proposed clinical doses and regimen.

The pharmacokinetic results confirm continuous and dose-dependent exposure to ISIS 484137 in the 13-week mouse and monkey studies. Pharmacokinetics observed in monkeys for antisense oligonucleotides typically well predict the observed plasma (and expected tissue) exposure levels in humans on the basis of mg/kg equivalent doses (Geary et al. 2003; 31: 1419-1428; Yu et al. Drug Metab Dispos 2007; 35: 460-468).

Thus, reduction of DGAT2 expression with ISIS 484137 provides a mechanism to reduce hepatic steatosis, thereby potentially attenuating subsequent inflammation and fibrosis. This mechanism of action could offer an attractive treatment option for patients who have significant hepatic steatosis associated with NAFLD and NASH.

EXAMPLES

The Examples below describe the screening process to identify the lead compounds targeted to DGAT2. Out of about 5,000 antisense oligonucleotides screened, ISIS 484085, ISIS 484129, ISIS 484137, ISIS 495576, ISIS 501861, ISIS 502194, ISIS 525443, and ISIS 525612 emerged as the top lead compounds. In particular, ISIS 484137 exhibited the best combination of properties in terms of potency and tolerability for DGAT2 out of about 5,000 antisense oligonucleotides.

Non-Limiting Disclosure and Incorporation by Reference

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG".

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Diacylglycerol Acyltransferase 2 in HepG2 Cells by MOE Gapmers Antisense oligonucleotides were designed targeting a diacylglycerol acyltransferase 2 (DGAT2) nucleic acid and were tested for their effects on DGAT2 mRNA in vitro. The antisense oligonucleotides were tested in a series of experiments that had similar culture conditions. The results for each experiment are presented in separate tables shown below. Cultured HepG2 cells at a density of 10,000 cells per well were transfected using Lipofectin reagent with 120 nM antisense oligonucleotide. After a treatment period of approximately 24 hours, RNA was isolated from the cells and DGAT2 mRNA levels were measured by quantitative real-time PCR. Human primer probe set RTS2367 (forward sequence GGCCTCCCGGAGACTGA, designated herein as SEQ ID NO: 4; reverse sequence AAGTGATTTGCAGCTGGTTCCT, designated herein as SEQ ID NO: 5; probe sequence AGGTGAACTGAGCCAGCCTTCGGG, designated herein as SEQ ID NO: 6) was used to measure mRNA levels. DGAT2 mRNA levels were adjusted according to total RNA content, as measured by RIBOGREEN®. Results are presented as percent inhibition of DGAT2, relative to untreated control cells.

ISIS oligonucleotides from an earlier published application, WO 2005/019418, were also included in this assay. These ISIS oligonucleotides are ISIS 217312-217322, ISIS 217324, ISIS 217325, ISIS 217328, ISIS 217333, ISIS 217336-217339, ISIS 217341-217343, ISIS 217346-217348, ISIS 217353-217355, ISIS 334177, ISIS 366710, ISIS 366714, ISIS 366722, ISIS 366728, ISIS 366730, ISIS 366741, ISIS 366746, ISIS 369220, ISIS 369221, ISIS 369255, ISIS 370727, ISIS 370747, ISIS 370784.

The newly designed chimeric antisense oligonucleotides in the Tables below were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted in the human gene sequence. Each gapmer listed in the Tables below is targeted to either the human DGAT2 mRNA, designated herein as SEQ ID NO: 1 (RefSeq No. NM_032564.3) or the human DGAT2 genomic sequence, designated herein as SEQ ID NO: 2 (RefSeq No. NT_033927.5 truncated from nucleotides 5669186 to 5712008). 'n/a' indicates that the antisense oligonucleotide does not target that particular gene sequence with 10000 complementarity.

TABLE 1

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 381726 | 278 | 297 | CGCAGGACCCCGGAGTAGGC | 75 | 9899 | 9918 | 38 |
| 217312 | 668 | 687 | TGGATGGGAAAGTAGTCTCG | 40 | 31600 | 31619 | 16 |
| 411887 | 669 | 688 | CTGGATGGGAAAGTAGTCTC | 38 | 31601 | 31620 | 50 |
| 411888 | 670 | 689 | GCTGGATGGGAAAGTAGTCT | 22 | n/a | n/a | 51 |
| 411889 | 671 | 690 | AGCTGGATGGGAAAGTAGTC | 31 | n/a | n/a | 52 |
| 411890 | 672 | 691 | CAGCTGGATGGGAAAGTAGT | 21 | n/a | n/a | 53 |
| 217313 | 673 | 692 | CCAGCTGGATGGGAAAGTAG | 24 | n/a | n/a | 17 |

TABLE 1-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 411891 | 674 | 693 | ACCAGCTGGATGGGAAAGTA | 21 | n/a | n/a | 54 |
| 380109 | 675 | 694 | CACCAGCTGGATGGGAAAGT | 31 | n/a | n/a | 35 |
| 411892 | 676 | 695 | TCACCAGCTGGATGGGAAAG | 22 | n/a | n/a | 55 |
| 411893 | 677 | 696 | TTCACCAGCTGGATGGGAAA | 26 | n/a | n/a | 56 |
| 217314 | 678 | 697 | CTTCACCAGCTGGATGGGAA | 36 | n/a | n/a | 18 |
| 369219 | 679 | 698 | TCTTCACCAGCTGGATGGGA | 50 | n/a | n/a | 32 |
| 411894 | 680 | 699 | GTCTTCACCAGCTGGATGGG | 42 | n/a | n/a | 57 |
| 411895 | 681 | 700 | TGTCTTCACCAGCTGGATGG | 55 | n/a | n/a | 58 |
| 411896 | 682 | 701 | GTGTCTTCACCAGCTGGATG | 49 | n/a | n/a | 59 |
| 217315 | 683 | 702 | TGTGTCTTCACCAGCTGGAT | 55 | n/a | n/a | 19 |
| 380110 | 684 | 703 | GTGTGTCTTCACCAGCTGGA | 53 | n/a | n/a | 36 |
| 411897 | 685 | 704 | TGTGTGTCTTCACCAGCTGG | 55 | n/a | n/a | 60 |
| 411873 | 686 | 705 | TTGTGTGTCTTCACCAGCTG | 63 | 37214 | 37233 | 46 |
| 411898 | 687 | 706 | GTTGTGTGTCTTCACCAGCT | 54 | 37215 | 37234 | 61 |
| 217316 | 688 | 707 | GGTTGTGTGTCTTCACCAGC | 64 | 37216 | 37235 | 20 |
| 381727 | 689 | 708 | AGGTTGTGTGTCTTCACCAG | 59 | 37217 | 37236 | 39 |
| 411899 | 690 | 709 | CAGGTTGTGTGTCTTCACCA | 68 | 37218 | 37237 | 62 |
| 411874 | 691 | 710 | GCAGGTTGTGTGTCTTCACC | 65 | 37219 | 37238 | 47 |
| 411900 | 692 | 711 | AGCAGGTTGTGTGTCTTCAC | 55 | 37220 | 37239 | 63 |
| 217317 | 693 | 712 | CAGCAGGTTGTGTGTCTTCA | 66 | 37221 | 37240 | 21 |
| 381728 | 694 | 713 | TCAGCAGGTTGTGTGTCTTC | 56 | 37222 | 37241 | 40 |
| 411901 | 695 | 714 | GTCAGCAGGTTGTGTGTCTT | 64 | 37223 | 37242 | 64 |
| 411875 | 696 | 715 | GGTCAGCAGGTTGTGTGTCT | 45 | 37224 | 37243 | 48 |
| 411902 | 697 | 716 | TGGTCAGCAGGTTGTGTGTC | 55 | 37225 | 37244 | 65 |
| 217318 | 698 | 717 | GTGGTCAGCAGGTTGTGTGT | 44 | 37226 | 37245 | 22 |
| 369220 | 699 | 718 | GGTGGTCAGCAGGTTGTGTG | 29 | 37227 | 37246 | 33 |
| 411903 | 700 | 719 | TGGTGGTCAGCAGGTTGTGT | 51 | 37228 | 37247 | 66 |
| 411904 | 701 | 720 | CTGGTGGTCAGCAGGTTGTG | 57 | 37229 | 37248 | 67 |
| 411905 | 702 | 721 | CCTGGTGGTCAGCAGGTTGT | 64 | 37230 | 37249 | 68 |
| 217319 | 703 | 722 | TCCTGGTGGTCAGCAGGTTG | 58 | 37231 | 37250 | 23 |
| 381729 | 704 | 723 | TTCCTGGTGGTCAGCAGGTT | 61 | 37232 | 37251 | 41 |
| 411906 | 705 | 724 | GTTCCTGGTGGTCAGCAGGT | 63 | 37233 | 37252 | 69 |
| 411907 | 706 | 725 | AGTTCCTGGTGGTCAGCAGG | 58 | 37234 | 37253 | 70 |
| 411908 | 707 | 726 | TAGTTCCTGGTGGTCAGCAG | 48 | 37235 | 37254 | 71 |
| 217320 | 708 | 727 | ATAGTTCCTGGTGGTCAGCA | 46 | 37236 | 37255 | 24 |
| 381730 | 709 | 728 | TATAGTTCCTGGTGGTCAGC | 56 | 37237 | 37256 | 42 |

TABLE 1-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 411909 | 710 | 729 | ATATAGTTCCTGGTGGTCAG | 53 | 37238 | 37257 | 72 |
| 411876 | 711 | 730 | GATATAGTTCCTGGTGGTCA | 57 | 37239 | 37258 | 49 |
| 411910 | 712 | 731 | AGATATAGTTCCTGGTGGTC | 56 | 37240 | 37259 | 73 |
| 217321 | 713 | 732 | AAGATATAGTTCCTGGTGGT | 41 | 37241 | 37260 | 25 |
| 381731 | 714 | 733 | AAAGATATAGTTCCTGGTGG | 54 | 37242 | 37261 | 43 |
| 411911 | 715 | 734 | CAAAGATATAGTTCCTGGTG | 61 | 37243 | 37262 | 74 |
| 411912 | 716 | 735 | CCAAAGATATAGTTCCTGGT | 66 | 37244 | 37263 | 75 |
| 411913 | 717 | 736 | TCCAAAGATATAGTTCCTGG | 63 | 37245 | 37264 | 76 |
| 217322 | 718 | 737 | ATCCAAAGATATAGTTCCTG | 39 | 37246 | 37265 | 26 |
| 369221 | 719 | 738 | TATCCAAAGATATAGTTCCT | 13 | 37247 | 37266 | 34 |
| 411914 | 720 | 739 | GTATCCAAAGATATAGTTCC | 8 | 37248 | 37267 | 77 |
| 411915 | 721 | 740 | GGTATCCAAAGATATAGTTC | 43 | 37249 | 37268 | 78 |
| 411916 | 722 | 741 | TGGTATCCAAAGATATAGTT | 42 | 37250 | 37269 | 79 |
| 217324 | 752 | 771 | AAGGCACCCAGGCCCATGAT | 46 | 37280 | 37299 | 27 |
| 381732 | 753 | 772 | GAAGGCACCCAGGCCCATGA | 38 | 37281 | 37300 | 44 |
| 380114 | 754 | 773 | AGAAGGCACCCAGGCCCATG | 38 | 37282 | 37301 | 37 |
| 411917 | 755 | 774 | CAGAAGGCACCCAGGCCCAT | 33 | 37283 | 37302 | 80 |
| 217325 | 875 | 894 | CCTCCAGACATCAGGTACTC | 29 | 37403 | 37422 | 28 |
| 217333 | 992 | 1011 | TTGCCAGGCATGGAGCTCAG | 37 | 38145 | 38164 | 29 |
| 381733 | 993 | 1012 | CTTGCCAGGCATGGAGCTCA | 51 | 38146 | 38165 | 45 |
| 411918 | 994 | 1013 | TCTTGCCAGGCATGGAGCTC | 47 | 38147 | 38166 | 81 |
| 411919 | 995 | 1014 | TTCTTGCCAGGCATGGAGCT | 54 | 38148 | 38167 | 82 |
| 217336 | 1139 | 1158 | TGGACCCATCGGCCCCAGGA | 52 | 39186 | 39205 | 30 |
| 411920 | 1140 | 1159 | CTGGACCCATCGGCCCCAGG | 41 | 39187 | 39206 | 83 |
| 411921 | 1141 | 1160 | TCTGGACCCATCGGCCCCAG | 20 | 39188 | 39207 | 84 |
| 411922 | 1142 | 1161 | TTCTGGACCCATCGGCCCCA | 27 | 39189 | 39208 | 85 |
| 411923 | 1143 | 1162 | CTTCTGGACCCATCGGCCCC | 30 | 39190 | 39209 | 86 |
| 217337 | 1144 | 1163 | TCTTCTGGACCCATCGGCCC | 37 | 39191 | 39210 | 31 |
| 411924 | 1145 | 1164 | TTCTTCTGGACCCATCGGCC | 44 | 39192 | 39211 | 87 |
| 411925 | 1146 | 1165 | CTTCTTCTGGACCCATCGGC | 27 | 39193 | 39212 | 88 |
| 411926 | 1147 | 1166 | ACTTCTTCTGGACCCATCGG | 28 | 39194 | 39213 | 89 |
| 411927 | 1148 | 1167 | AACTTCTTCTGGACCCATCG | 28 | 39195 | 39214 | 90 |

TABLE 2

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 217338 | 1149 | 1168 | GAACTTCTTCTGGACCCATC | 19 | 39196 | 39215 | 91 |
| 411928 | 1150 | 1169 | GGAACTTCTTCTGGACCCAT | 36 | 39197 | 39216 | 104 |
| 411929 | 1151 | 1170 | TGGAACTTCTTCTGGACCCA | 43 | 39198 | 39217 | 105 |
| 411930 | 1152 | 1171 | CTGGAACTTCTTCTGGACCC | 25 | 39199 | 39218 | 106 |
| 411931 | 1153 | 1172 | TCTGGAACTTCTTCTGGACC | 43 | 39200 | 39219 | 107 |
| 217339 | 1154 | 1173 | TTCTGGAACTTCTTCTGGAC | 37 | 39201 | 39220 | 92 |
| 217341 | 1226 | 1245 | GGCACCAGCCCCAGGTGTC | 30 | 39273 | 39292 | 93 |
| 411932 | 1227 | 1246 | GGGCACCAGCCCCAGGTGT | 34 | 39274 | 39293 | 108 |
| 411933 | 1228 | 1247 | AGGGCACCAGCCCCAGGTG | 29 | 39275 | 39294 | 109 |
| 411934 | 1229 | 1248 | TAGGGCACCAGCCCCAGGT | 32 | 39276 | 39295 | 110 |
| 411935 | 1230 | 1249 | GTAGGGCACCAGCCCCAGG | 23 | 39277 | 39296 | 111 |
| 217342 | 1231 | 1250 | AGTAGGGCACCAGCCCCAG | 0 | 39278 | 39297 | 94 |
| 411936 | 1232 | 1251 | GAGTAGGGCACCAGCCCCA | 0 | 39279 | 39298 | 112 |
| 411937 | 1233 | 1252 | GGAGTAGGGCACCAGCCCC | 17 | 39280 | 39299 | 113 |
| 411938 | 1234 | 1253 | TGGAGTAGGGCACCAGCCC | 28 | 39281 | 39300 | 114 |
| 411939 | 1235 | 1254 | TTGGAGTAGGGCACCAGCCC | 16 | 39282 | 39301 | 115 |
| 217343 | 1236 | 1255 | CTTGGAGTAGGGCACCAGCC | 35 | 39283 | 39302 | 95 |
| 411940 | 1237 | 1256 | GCTTGGAGTAGGGCACCAGC | 45 | 39284 | 39303 | 116 |
| 411941 | 1238 | 1257 | GGCTTGGAGTAGGGCACCAG | 56 | 39285 | 39304 | 117 |
| 366741 | 1245 | 1264 | GGTGATGGGCTTGGAGTAGG | 36 | 39292 | 39311 | 102 |
| 411942 | 1246 | 1265 | TGGTGATGGGCTTGGAGTAG | 28 | 39293 | 39312 | 118 |
| 411943 | 1247 | 1266 | GTGGTGATGGGCTTGGAGTA | 23 | 39294 | 39313 | 119 |
| 217346 | 1338 | 1357 | CAGGGCCTCCATGTACATGG | 37 | 41309 | 41328 | 96 |
| 369255 | 1339 | 1358 | CCAGGGCCTCCATGTACATG | 38 | 41310 | 41329 | 103 |
| 411944 | 1340 | 1359 | ACCAGGGCCTCCATGTACAT | 52 | 41311 | 41330 | 120 |
| 411945 | 1341 | 1360 | CACCAGGGCCTCCATGTACA | 53 | 41312 | 41331 | 121 |
| 411946 | 1342 | 1361 | TCACCAGGGCCTCCATGTAC | 37 | 41313 | 41332 | 122 |
| 217347 | 1343 | 1362 | TTCACCAGGGCCTCCATGTA | 20 | 41314 | 41333 | 97 |
| 411947 | 1344 | 1363 | CTTCACCAGGGCCTCCATGT | 46 | 41315 | 41334 | 123 |
| 411948 | 1345 | 1364 | GCTTCACCAGGGCCTCCATG | 31 | 41316 | 41335 | 124 |
| 411949 | 1346 | 1365 | AGCTTCACCAGGGCCTCCAT | 42 | 41317 | 41336 | 125 |
| 411950 | 1347 | 1366 | GAGCTTCACCAGGGCCTCCA | 52 | 41318 | 41337 | 126 |
| 217348 | 1348 | 1367 | AGAGCTTCACCAGGGCCTCC | 46 | 41319 | 41338 | 98 |
| 411951 | 1349 | 1368 | AAGAGCTTCACCAGGGCCTC | 44 | 41320 | 41339 | 127 |
| 217353 | 1498 | 1517 | AACCCACAGACACCCATGAC | 4 | 41469 | 41488 | 99 |
| 411952 | 1499 | 1518 | TAACCCACAGACACCCATGA | 14 | 41470 | 41489 | 128 |
| 411953 | 1500 | 1519 | ATAACCCACAGACACCCATG | 24 | 41471 | 41490 | 129 |

TABLE 2-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 411954 | 1501 | 1520 | AATAACCCACAGACACCCAT | 0 | 41472 | 41491 | 130 |
| 411955 | 1502 | 1521 | AAATAACCCACAGACACCCA | 10 | 41473 | 41492 | 131 |
| 217354 | 1503 | 1522 | TAAATAACCCACAGACACCC | 6 | 41474 | 41493 | 100 |
| 411956 | 1504 | 1523 | TTAAATAACCCACAGACACC | 0 | 41475 | 41494 | 132 |
| 411957 | 1505 | 1524 | TTTAAATAACCCACAGACAC | 14 | 41476 | 41495 | 133 |
| 411958 | 1506 | 1525 | TTTTAAATAACCCACAGACA | 10 | 41477 | 41496 | 134 |
| 411959 | 1507 | 1526 | CTTTTAAATAACCCACAGAC | 0 | 41478 | 41497 | 135 |
| 217355 | 1508 | 1527 | TCTTTTAAATAACCCACAGA | 10 | 41479 | 41498 | 101 |
| 411960 | 1509 | 1528 | TTCTTTTAAATAACCCACAG | 8 | 41480 | 41499 | 136 |
| 411961 | 1510 | 1529 | TTTCTTTTAAATAACCCACA | 1 | 41481 | 41500 | 137 |
| 411962 | 1511 | 1530 | ATTTCTTTTAAATAACCCAC | 1 | 41482 | 41501 | 138 |
| 411963 | 1512 | 1531 | AATTTCTTTTAAATAACCCA | 0 | 41483 | 41502 | 139 |
| 411964 | 1513 | 1532 | TAATTTCTTTTAAATAACCC | 0 | 41484 | 41503 | 140 |
| 411965 | 1514 | 1533 | ATAATTTCTTTTAAATAACC | 0 | 41485 | 41504 | 141 |
| 411966 | 1515 | 1534 | TATAATTTCTTTTAAATAAC | 0 | 41486 | 41505 | 142 |
| 411967 | 1516 | 1535 | TTATAATTTCTTTTAAATAA | 0 | 41487 | 41506 | 143 |

TABLE 3

Inhibition of DGAT2 mRNA by MOE gapmers targeting SEQ ID NO: 1 and 2

| ISIS NO | SEQ ID NO: 1 Start Site | SEQ ID NO: 1 Stop Site | Sequence | Motif | % inhibition | SEQ ID NO: 2 Start Site | SEQ ID NO: 2 Stop Site | SEQ ID NO |
|---|---|---|---|---|---|---|---|---|
| 413166 | 254 | 273 | ATGAGGGTCTTCATGGCTGA | 5-10-5 | 7 | 9875 | 9894 | 156 |
| 413167 | 266 | 285 | GAGTAGGCGGCTATGAGGGT | 5-10-5 | 11 | 9887 | 9906 | 157 |
| 413168 | 269 | 288 | CCGGAGTAGGCGGCTATGAG | 5-10-5 | 37 | 9890 | 9909 | 158 |
| 413169 | 272 | 291 | ACCCCGGAGTAGGCGGCTAT | 5-10-5 | 46 | 9893 | 9912 | 159 |
| 334177 | 275 | 294 | AGGACCCCGGAGTAGGCGGC | 5-10-5 | 52 | 9896 | 9915 | 145 |
| 413170 | 304 | 323 | GGTCAGCCTCGGCCTGACGC | 5-10-5 | 11 | 9925 | 9944 | 160 |
| 413171 | 307 | 326 | TCCGGTCAGCCTCGGCCTGA | 5-10-5 | 20 | 9928 | 9947 | 161 |
| 413172 | 310 | 329 | GGCTCCGGTCAGCCTCGGCC | 5-10-5 | 0 | 9931 | 9950 | 162 |
| 413173 | 331 | 350 | CAGGTCCTCCGTGAGAGCGC | 5-10-5 | 29 | 9952 | 9971 | 163 |
| 413174 | 339 | 358 | CGACAGCGCAGGTCCTCCGT | 5-10-5 | 48 | 9960 | 9979 | 164 |
| 413175 | 348 | 367 | CCCCTCGCGCGACAGCGCAG | 5-10-5 | 25 | 9969 | 9988 | 165 |
| 413176 | 355 | 374 | TCCCAGACCCCTCGCGCGAC | 5-10-5 | 36 | 9976 | 9995 | 166 |
| 413177 | 361 | 380 | CCCATCTCCCAGACCCCTCG | 5-10-5 | 12 | 9982 | 10001 | 167 |
| 413178 | 367 | 386 | CAGTGCCCCATCTCCCAGAC | 5-10-5 | 0 | n/a | n/a | 168 |

TABLE 3-continued

Inhibition of DGAT2 mRNA by MOE gapmers targeting SEQ ID NO: 1 and 2

| ISIS NO | SEQ ID NO: 1 Start Site | SEQ ID NO: 1 Stop Site | Sequence | Motif | % inhibition | SEQ ID NO: 2 Start Site | SEQ ID NO: 2 Stop Site | SEQ ID NO |
|---|---|---|---|---|---|---|---|---|
| 413179 | 370 | 389 | ATCCAGTGCCCCATCTCCCA | 5-10-5 | 16 | n/a | n/a | 169 |
| 413180 | 376 | 395 | TGCTGGATCCAGTGCCCCAT | 5-10-5 | 44 | n/a | n/a | 170 |
| 413181 | 379 | 398 | GGATGCTGGATCCAGTGCCC | 5-10-5 | 32 | n/a | n/a | 171 |
| 413182 | 382 | 401 | AGAGGATGCTGGATCCAGTG | 5-10-5 | 45 | 25508 | 25527 | 172 |
| 413183 | 385 | 404 | CGGAGAGGATGCTGGATCCA | 5-10-5 | 47 | 25511 | 25530 | 173 |
| 413184 | 396 | 415 | GTCCTGGAGGGCGGAGAGGA | 5-10-5 | 32 | 25522 | 25541 | 174 |
| 413185 | 404 | 423 | GAGAAGAGGTCCTGGAGGGC | 5-10-5 | 10 | 25530 | 25549 | 175 |
| 366710 | 425 | 444 | GACCTATTGAGCCAGGTGAC | 5-10-5 | 36 | 25551 | 25570 | 146 |
| 370727 | 443 | 462 | AGCTGCTTTTCCACCTTGGA | 2-16-2 | 45 | 25569 | 25588 | 152 |
| 366714 | 445 | 464 | GTAGCTGCTTTTCCACCTTG | 5-10-5 | 43 | 25571 | 25590 | 147 |
| 413186 | 448 | 467 | CCTGTAGCTGCTTTTCCACC | 5-10-5 | 29 | 25574 | 25593 | 176 |
| 413187 | 451 | 470 | TGACCTGTAGCTGCTTTTCC | 5-10-5 | 35 | 25577 | 25596 | 177 |
| 413188 | 455 | 474 | GAGATGACCTGTAGCTGCTT | 5-10-5 | 34 | 25581 | 25600 | 178 |
| 413189 | 458 | 477 | ACTGAGATGACCTGTAGCTG | 5-10-5 | 33 | 25584 | 25603 | 179 |
| 413190 | 461 | 480 | AGCACTGAGATGACCTGTAG | 5-10-5 | 36 | 25587 | 25606 | 180 |
| 413191 | 467 | 486 | CACTGGAGCACTGAGATGAC | 5-10-5 | 27 | 25593 | 25612 | 181 |
| 413192 | 473 | 492 | AGGACCCACTGGAGCACTGA | 5-10-5 | 40 | 25599 | 25618 | 182 |
| 413193 | 476 | 495 | GACAGGACCCACTGGAGCAC | 5-10-5 | 44 | 25602 | 25621 | 183 |
| 380089 | 482 | 501 | AGGAAGGACAGGACCCACTG | 5-10-5 | 38 | 25608 | 25627 | 155 |
| 413194 | 494 | 513 | ACTCCCAGTACAAGGAAGGA | 5-10-5 | 3 | n/a | n/a | 184 |
| 413195 | 497 | 516 | GCCACTCCCAGTACAAGGAA | 5-10-5 | 0 | n/a | n/a | 185 |
| 413196 | 500 | 519 | CAGGCCACTCCCAGTACAAG | 5-10-5 | 1 | n/a | n/a | 186 |
| 413197 | 503 | 522 | CTGCAGGCCACTCCCAGTAC | 5-10-5 | 40 | n/a | n/a | 187 |
| 413198 | 506 | 525 | GCACTGCAGGCCACTCCCAG | 5-10-5 | 37 | n/a | n/a | 188 |
| 413199 | 510 | 529 | GATGGCACTGCAGGCCACTC | 5-10-5 | 28 | 31077 | 31096 | 189 |
| 366722 | 530 | 549 | GTGCAGAATATGTACATGAG | 5-10-5 | 43 | 31097 | 31116 | 148 |
| 413200 | 554 | 573 | AGCACAGCGATGAGCCAGCA | 5-10-5 | 35 | 31121 | 31140 | 190 |
| 413201 | 570 | 589 | CAGCCAAGTGAAGTAGAGCA | 5-10-5 | 41 | 31137 | 31156 | 191 |
| 413202 | 573 | 592 | CACCAGCCAAGTGAAGTAGA | 5-10-5 | 23 | 31140 | 31159 | 192 |
| 413203 | 576 | 595 | AAACACCAGCCAAGTGAAGT | 5-10-5 | 9 | 31143 | 31162 | 193 |
| 413204 | 579 | 598 | GTCAAACACCAGCCAAGTGA | 5-10-5 | 15 | 31146 | 31165 | 194 |
| 413205 | 585 | 604 | GTTCCAGTCAAACACCAGCC | 5-10-5 | 31 | 31152 | 31171 | 195 |
| 413206 | 588 | 607 | TGTGTTCCAGTCAAACACCA | 5-10-5 | 23 | 31155 | 31174 | 196 |
| 413207 | 591 | 610 | GGGTGTGTTCCAGTCAAACA | 5-10-5 | 6 | 31158 | 31177 | 197 |
| 413208 | 594 | 613 | CTTGGGTGTGTTCCAGTCAA | 5-10-5 | 5 | 31161 | 31180 | 198 |
| 413209 | 615 | 634 | CTGTGACCTCCTGCCACCTT | 5-10-5 | 25 | 31547 | 31566 | 199 |
| 413210 | 618 | 637 | CCACTGTGACCTCCTGCCAC | 5-10-5 | 30 | 31550 | 31569 | 200 |

TABLE 3-continued

Inhibition of DGAT2 mRNA by MOE gapmers targeting SEQ ID NO: 1 and 2

| ISIS NO | SEQ ID NO: 1 Start Site | SEQ ID NO: 1 Stop Site | Sequence | Motif | % inhibition | SEQ ID NO: 2 Start Site | SEQ ID NO: 2 Stop Site | SEQ ID NO |
|---|---|---|---|---|---|---|---|---|
| 413211 | 621 | 640 | GACCCACTGTGACCTCCTGC | 5-10-5 | 25 | 31553 | 31572 | 201 |
| 413212 | 625 | 644 | TTCGGACCCACTGTGACCTC | 5-10-5 | 38 | 31557 | 31576 | 202 |
| 413213 | 629 | 648 | CAGTTTCGGACCCACTGTGA | 5-10-5 | 39 | 31561 | 31580 | 203 |
| 413214 | 632 | 651 | GCCCAGTTTCGGACCCACTG | 5-10-5 | 51 | 31564 | 31583 | 204 |
| 413215 | 635 | 654 | ACAGCCCAGTTTCGGACCCA | 5-10-5 | 27 | 31567 | 31586 | 205 |
| 413216 | 638 | 657 | CACACAGCCCAGTTTCGGAC | 5-10-5 | 24 | 31570 | 31589 | 206 |
| 413217 | 642 | 661 | GCGCCACACAGCCCAGTTTC | 5-10-5 | 31 | 31574 | 31593 | 207 |
| 413218 | 658 | 677 | AGTAGTCTCGAAAGTAGCGC | 5-10-5 | 39 | 31590 | 31609 | 208 |
| 413219 | 661 | 680 | GAAAGTAGTCTCGAAAGTAG | 5-10-5 | 0 | 31593 | 31612 | 209 |
| 413220 | 665 | 684 | ATGGGAAAGTAGTCTCGAAA | 5-10-5 | 0 | 31597 | 31616 | 210 |
| 366728 | 757 | 776 | TGCAGAAGGCACCCAGGCCC | 5-10-5 | 46 | 37285 | 37304 | 149 |
| 413221 | 780 | 799 | TTCTGTGGCCTCTGTGCTGA | 5-10-5 | 25 | 37308 | 37327 | 211 |
| 413222 | 783 | 802 | CACTTCTGTGGCCTCTGTGC | 5-10-5 | 38 | 37311 | 37330 | 212 |
| 413223 | 786 | 805 | GCTCACTTCTGTGGCCTCTG | 5-10-5 | 41 | 37314 | 37333 | 213 |
| 413224 | 789 | 808 | CTTGCTCACTTCTGTGGCCT | 5-10-5 | 48 | 37317 | 37336 | 214 |
| 413225 | 792 | 811 | CTTCTTGCTCACTTCTGTGG | 5-10-5 | 25 | 37320 | 37339 | 215 |
| 413226 | 798 | 817 | TGGGAACTTCTTGCTCACTT | 5-10-5 | 43 | 37326 | 37345 | 216 |
| 413227 | 801 | 820 | GCCTGGGAACTTCTTGCTCA | 5-10-5 | 47 | 37329 | 37348 | 217 |
| 413228 | 804 | 823 | TATGCCTGGGAACTTCTTGC | 5-10-5 | 26 | 37332 | 37351 | 218 |
| 413229 | 808 | 827 | GCCGTATGCCTGGGAACTTC | 5-10-5 | 29 | 37336 | 37355 | 219 |
| 413230 | 811 | 830 | AAGGCCGTATGCCTGGGAAC | 5-10-5 | 25 | 37339 | 37358 | 220 |
| 413231 | 814 | 833 | GGTAAGGCCGTATGCCTGGG | 5-10-5 | 41 | 37342 | 37361 | 221 |
| 217328 | 938 | 957 | GCATTGCCACTCCCATTCTT | 5-10-5 | 41 | 38091 | 38110 | 144 |
| 366730 | 979 | 998 | AGCTCAGAGACTCAGCCGCA | 5-10-5 | 39 | 38132 | 38151 | 150 |
| 370747 | 982 | 1001 | TGGAGCTCAGAGACTCAGCC | 2-16-2 | 37 | 38135 | 38154 | 153 |
| 366746 | 1366 | 1385 | TGGTCTTGTGCTTGTCGAAG | 5-10-5 | 41 | 41337 | 41356 | 151 |
| 370784 | 2128 | 2147 | GCTGCATCCATGTCATCAGC | 2-16-2 | 53 | 42099 | 42118 | 154 |

TABLE 4

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413232 | 817 | 836 | CCAGGTAAGGCCGTATGCCT | 78 | 37345 | 37364 | 225 |
| 413233 | 820 | 839 | TAGCCAGGTAAGGCCGTATG | 56 | 37348 | 37367 | 226 |
| 413234 | 823 | 842 | GTGTAGCCAGGTAAGGCCGT | 50 | 37351 | 37370 | 227 |
| 413235 | 827 | 846 | GCCAGTGTAGCCAGGTAAGG | 9 | 37355 | 37374 | 228 |

TABLE 4-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413236 | 861 | 880 | GTACTCCCTCAACACAGGCA | 72 | 37389 | 37408 | 229 |
| 413237 | 864 | 883 | CAGGTACTCCCTCAACACAG | 52 | 37392 | 37411 | 230 |
| 413238 | 867 | 886 | CATCAGGTACTCCCTCAACA | 35 | 37395 | 37414 | 231 |
| 413239 | 870 | 889 | AGACATCAGGTACTCCCTCA | 35 | 37398 | 37417 | 232 |
| 413240 | 878 | 897 | ATACCTCCAGACATCAGGTA | 50 | n/a | n/a | 233 |
| 413241 | 881 | 900 | CAGATACCTCCAGACATCAG | 38 | n/a | n/a | 234 |
| 413242 | 887 | 906 | ACAGGGCAGATACCTCCAGA | 58 | n/a | n/a | 235 |
| 413243 | 910 | 929 | AATAGTCTATGGTGTCCCGG | 63 | 38063 | 38082 | 236 |
| 413244 | 913 | 932 | GCAAATAGTCTATGGTGTCC | 60 | 38066 | 38085 | 237 |
| 413245 | 916 | 935 | AAAGCAAATAGTCTATGGTG | 46 | 38069 | 38088 | 238 |
| 413246 | 919 | 938 | TTGAAAGCAAATAGTCTATG | 42 | 38072 | 38091 | 239 |
| 413247 | 922 | 941 | TCTTTGAAAGCAAATAGTCT | 40 | 38075 | 38094 | 240 |
| 413248 | 925 | 944 | CATTCTTTGAAAGCAAATAG | 15 | 38078 | 38097 | 241 |
| 413249 | 928 | 947 | TCCCATTCTTTGAAAGCAAA | 31 | 38081 | 38100 | 242 |
| 413250 | 932 | 951 | CCACTCCCATTCTTTGAAAG | 34 | 38085 | 38104 | 243 |
| 413251 | 935 | 954 | TTGCCACTCCCATTCTTTGA | 39 | 38088 | 38107 | 244 |
| 217328 | 938 | 957 | GCATTGCCACTCCCATTCTT | 70 | 38091 | 38110 | 144 |
| 413252 | 976 | 995 | TCAGAGACTCAGCCGCACCC | 43 | 38129 | 38148 | 245 |
| 413253 | 987 | 1006 | AGGCATGGAGCTCAGAGACT | 69 | 38140 | 38159 | 246 |
| 413254 | 1002 | 1021 | GACTGCATTCTTGCCAGGCA | 60 | 38155 | 38174 | 247 |
| 413255 | 1005 | 1024 | GGTGACTGCATTCTTGCCAG | 25 | 38158 | 38177 | 248 |
| 413256 | 1012 | 1031 | TCCGCAGGGTGACTGCATTC | 48 | 38165 | 38184 | 249 |
| 369241 | 1019 | 1038 | TTGCGGTTCCGCAGGGTGAC | 70 | 38172 | 38191 | 222 |
| 413257 | 1022 | 1041 | CCCTTGCGGTTCCGCAGGGT | 36 | 38175 | 38194 | 250 |
| 413258 | 1025 | 1044 | AAGCCCTTGCGGTTCCGCAG | 67 | 38178 | 38197 | 251 |
| 413259 | 1028 | 1047 | ACAAAGCCCTTGCGGTTCCG | 35 | 38181 | 38200 | 252 |
| 413260 | 1034 | 1053 | AGTTTCACAAAGCCCTTGCG | 25 | 38187 | 38206 | 253 |
| 413261 | 1037 | 1056 | GCCAGTTTCACAAAGCCCTT | 34 | 38190 | 38209 | 254 |
| 413262 | 1040 | 1059 | AGGGCCAGTTTCACAAAGCC | 33 | 38193 | 38212 | 255 |
| 413263 | 1043 | 1062 | CGCAGGGCCAGTTTCACAAA | 31 | 38196 | 38215 | 256 |
| 413264 | 1088 | 1107 | TCATTCTCTCCAAAGGAGTA | 18 | 39135 | 39154 | 257 |
| 413265 | 1091 | 1110 | ACTTCATTCTCTCCAAAGGA | 45 | 39138 | 39157 | 258 |
| 413266 | 1095 | 1114 | GTACACTTCATTCTCTCCAA | 82 | 39142 | 39161 | 259 |
| 413267 | 1101 | 1120 | CTGCTTGTACACTTCATTCT | 58 | 39148 | 39167 | 260 |
| 413268 | 1105 | 1124 | TCACCTGCTTGTACACTTCA | 40 | 39152 | 39171 | 261 |
| 413269 | 1111 | 1130 | CGAAGATCACCTGCTTGTAC | 63 | 39158 | 39177 | 262 |
| 413270 | 1114 | 1133 | CCTCGAAGATCACCTGCTTG | 53 | 39161 | 39180 | 263 |

TABLE 4-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413271 | 1117 | 1136 | CCTCCTCGAAGATCACCTGC | 49 | 39164 | 39183 | 264 |
| 413272 | 1120 | 1139 | AGCCCTCCTCGAAGATCACC | 39 | 39167 | 39186 | 265 |
| 413273 | 1123 | 1142 | AGGAGCCCTCCTCGAAGATC | 31 | 39170 | 39189 | 266 |
| 413274 | 1126 | 1145 | CCCAGGAGCCCTCCTCGAAG | 54 | 39173 | 39192 | 267 |
| 413275 | 1129 | 1148 | GGCCCCAGGAGCCCTCCTCG | 40 | 39176 | 39195 | 268 |
| 411877 | 1136 | 1155 | ACCCATCGGCCCCAGGAGCC | 59 | 39183 | 39202 | 223 |
| 413276 | 1157 | 1176 | TATTTCTGGAACTTCTTCTG | 22 | 39204 | 39223 | 269 |
| 413277 | 1160 | 1179 | ATGTATTTCTGGAACTTCTT | 45 | 39207 | 39226 | 270 |
| 413278 | 1171 | 1190 | GGGCGAAACCAATGTATTTC | 24 | 39218 | 39237 | 271 |
| 413279 | 1208 | 1227 | TCGGAGGAGAAGAGGCCTCG | 60 | 39255 | 39274 | 272 |
| 413280 | 1211 | 1230 | GTGTCGGAGGAGAAGAGGCC | 52 | 39258 | 39277 | 273 |
| 413281 | 1215 | 1234 | CCAGGTGTCGGAGGAGAAGA | 53 | 39262 | 39281 | 274 |
| 413282 | 1222 | 1241 | CCAGCCCCAGGTGTCGGAG | 50 | 39269 | 39288 | 275 |
| 413283 | 1250 | 1269 | ACAGTGGTGATGGGCTTGGA | 52 | 39297 | 39316 | 276 |
| 413284 | 1273 | 1292 | GGATGGTGATGGGCTCTCCC | 67 | 41244 | 41263 | 277 |
| 411879 | 1330 | 1349 | CCATGTACATGGTGTGGTAC | 52 | 41301 | 41320 | 224 |
| 413285 | 1334 | 1353 | GCCTCCATGTACATGGTGTG | 63 | 41305 | 41324 | 278 |
| 413286 | 1363 | 1382 | TCTTGTGCTTGTCGAAGAGC | 62 | 41334 | 41353 | 279 |
| 413287 | 1399 | 1418 | CCTCCAGGACCTCAGTCTCC | 66 | 41370 | 41389 | 280 |
| 413288 | 1403 | 1422 | TTCACCTCCAGGACCTCAGT | 46 | 41374 | 41393 | 281 |
| 413289 | 1407 | 1426 | TCAGTTCACCTCCAGGACCT | 46 | 41378 | 41397 | 282 |
| 413290 | 1412 | 1431 | CTGGCTCAGTTCACCTCCAG | 90 | 41383 | 41402 | 283 |
| 413291 | 1537 | 1556 | TGTAATGGTTTAGCAAAATT | 26 | 41508 | 41527 | 284 |
| 413292 | 1555 | 1574 | TTAAAAAGACCTAACATTG | 0 | 41526 | 41545 | 285 |
| 413293 | 1559 | 1578 | CTTCTTAAAAAGACCTAAC | 26 | 41530 | 41549 | 286 |
| 413294 | 1563 | 1582 | TTTCCTTCTTAAAAAGACC | 9 | 41534 | 41553 | 287 |
| 413295 | 1567 | 1586 | ACTTTTTCCTTCTTAAAAAA | 0 | 41538 | 41557 | 288 |
| 413296 | 1572 | 1591 | TACTGACTTTTCCTTCTTA | 39 | 41543 | 41562 | 289 |
| 413297 | 1616 | 1635 | CCACCACCTAGAACAGGGCA | 55 | 41587 | 41606 | 290 |
| 413298 | 1653 | 1672 | AGGTTAGCTGAGCCACCCAG | 59 | 41624 | 41643 | 291 |
| 413299 | 1840 | 1859 | GTCCTGCAGTTTCAGGACTA | 54 | 41811 | 41830 | 292 |
| 413300 | 1844 | 1863 | ACTGGTCCTGCAGTTTCAGG | 55 | 41815 | 41834 | 293 |
| 413301 | 1860 | 1879 | TCCCCTTGGCAGAGAAACTG | 47 | 41831 | 41850 | 294 |
| 413302 | 1864 | 1883 | CTCCTCCCCTTGGCAGAGAA | 43 | 41835 | 41854 | 295 |
| 413303 | 1868 | 1887 | CCAACTCCTCCCCTTGGCAG | 28 | 41839 | 41858 | 296 |

TABLE 4-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413304 | 1872 | 1891 | CTCTCCAACTCCTCCCCTTG | 25 | 41843 | 41862 | 297 |
| 413305 | 1875 | 1894 | GTGCTCTCCAACTCCTCCCC | 34 | 41846 | 41865 | 298 |

TABLE 5

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413347 | n/a | n/a | AGCCTGCCACAGGGCCCTTT | 37 | 10050 | 10069 | 339 |
| 413348 | n/a | n/a | AGGACAGGGCAGACACACCT | 44 | 10396 | 10415 | 340 |
| 413349 | n/a | n/a | GATTTGTACTTGAATCCAGG | 34 | 10703 | 10722 | 341 |
| 413350 | n/a | n/a | ACACGCAGACCAGGACAGCT | 46 | 10747 | 10766 | 342 |
| 413351 | n/a | n/a | TTTGGATAGTCGATTTACCA | 41 | 10943 | 10962 | 343 |
| 413352 | n/a | n/a | AAGATTCATAACTATATCTA | 6 | 11045 | 11064 | 344 |
| 413353 | n/a | n/a | AAAAACATGACAGCCAGGGT | 31 | 11558 | 11577 | 345 |
| 413354 | n/a | n/a | GACTTCCCTTCACAGAATCC | 5 | 11983 | 12002 | 346 |
| 413355 | n/a | n/a | CAGGCAGGTGTCAGAGGGCT | 21 | 12250 | 12269 | 347 |
| 413356 | n/a | n/a | TAGCCTGGCTTTGATAACCC | 42 | 12892 | 12911 | 348 |
| 413357 | n/a | n/a | CATAGGCCAGGAGGAAGAGT | 35 | 13206 | 13225 | 349 |
| 413358 | n/a | n/a | TTGCTTAAACAGATAAGCAC | 17 | 13541 | 13560 | 350 |
| 413359 | n/a | n/a | AATGTCACAAGTTCACAAAC | 4 | 14428 | 14447 | 351 |
| 413360 | n/a | n/a | CTGACCTCAGGGTGATCAAG | 31 | 14721 | 14740 | 352 |
| 413361 | n/a | n/a | CCAAGCAGGAGCTGGACAGA | 19 | 15143 | 15162 | 353 |
| 413362 | n/a | n/a | TCATTTCATAGATGAGGAGA | 34 | 15215 | 15234 | 354 |
| 413363 | n/a | n/a | AGGAGTTTGTGTTTCCCATT | 39 | 15320 | 15339 | 355 |
| 413364 | n/a | n/a | GGCAGGGCTTAGAATGGCTA | 48 | 15359 | 15378 | 356 |
| 413365 | n/a | n/a | ACCATTTTCACAAGGAGAAG | 30 | 15572 | 15591 | 357 |
| 413366 | n/a | n/a | TTCAAAAAGTAGCTACTGCA | 47 | 15738 | 15757 | 358 |
| 413367 | n/a | n/a | TCCAGGACCCTGGACATGAT | 50 | 15813 | 15832 | 359 |
| 413368 | n/a | n/a | AGAGCCAGCACACAGCTATG | 20 | 16251 | 16270 | 360 |
| 413369 | n/a | n/a | AGTCTAGTTGGAAAAGTAGA | 16 | 16545 | 16564 | 361 |
| 413370 | n/a | n/a | AGATGCCACTTCATCAAGGC | 24 | 17722 | 17741 | 362 |
| 413371 | n/a | n/a | GAAGTCAGGCCAAGTGCCAA | 26 | 17744 | 17763 | 363 |
| 413372 | n/a | n/a | TGATTCTTACCTGCAATGAG | 22 | 18221 | 18240 | 364 |
| 413373 | n/a | n/a | CCAAGTAAGCCTCGGTGTCC | 32 | 18329 | 18348 | 365 |
| 413374 | n/a | n/a | TGAGTAGTCAAAGGTGGCTT | 30 | 19019 | 19038 | 366 |
| 413375 | n/a | n/a | ATGCCTGAGGGCAGCAGTGT | 45 | 19907 | 19926 | 367 |
| 413376 | n/a | n/a | TGACCAGGAAGGCCACACCT | 15 | 19967 | 19986 | 368 |

TABLE 5-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413377 | n/a | n/a | GGCTTCACCGTCCCACAGCA | 39 | 20409 | 20428 | 369 |
| 413378 | n/a | n/a | CAGGACTTGGTACCTGATTC | 35 | 20883 | 20902 | 370 |
| 413379 | n/a | n/a | TGGCTGGGAGGAGTCCAGCA | 10 | 21131 | 21150 | 371 |
| 413380 | n/a | n/a | GGGTCAAGGTCACTCAGCCA | 33 | 21660 | 21679 | 372 |
| 413381 | n/a | n/a | TATTTGAAGATAAAGTCAGA | 0 | 22021 | 22040 | 373 |
| 413382 | n/a | n/a | GGGATGATAAACACTAAGGT | 37 | 22093 | 22112 | 374 |
| 217328 | 938 | 957 | GCATTGCCACTCCCATTCTT | 59 | 38091 | 38110 | 144 |
| 413306 | 1992 | 2011 | CTGGAGGCCAGTCCAGGCTC | 23 | 41963 | 41982 | 299 |
| 413307 | 1995 | 2014 | ATCCTGGAGGCCAGTCCAGG | 18 | 41966 | 41985 | 300 |
| 413308 | 2006 | 2025 | CCCCCATCCTCATCCTGGAG | 7 | 41977 | 41996 | 301 |
| 413309 | 2010 | 2029 | GCCACCCCCATCCTCATCCT | 0 | 41981 | 42000 | 302 |
| 413310 | 2014 | 2033 | CATTGCCACCCCCATCCTCA | 9 | 41985 | 42004 | 303 |
| 413311 | 2040 | 2059 | GGGCAGTCCTTTCCCCTGCA | 37 | 42011 | 42030 | 304 |
| 413312 | 2081 | 2100 | TAGCTCATGGTGGCGGCATC | 35 | 42052 | 42071 | 305 |
| 413313 | 2087 | 2106 | TCCACCTAGCTCATGGTGGC | 21 | 42058 | 42077 | 306 |
| 413314 | 2091 | 2110 | TTACTCCACCTAGCTCATGG | 6 | 42062 | 42081 | 307 |
| 413315 | 2099 | 2118 | AAAACCAGTTACTCCACCTA | 0 | 42070 | 42089 | 308 |
| 413316 | 2102 | 2121 | AGAAAAACCAGTTACTCCAC | 4 | 42073 | 42092 | 309 |
| 413317 | 2113 | 2132 | TCAGCCACCCAAGAAAAACC | 0 | 42084 | 42103 | 310 |
| 413318 | 2120 | 2139 | CATGTCATCAGCCACCCAAG | 16 | 42091 | 42110 | 311 |
| 413319 | 2128 | 2147 | GCTGCATCCATGTCATCAGC | 43 | 42099 | 42118 | 154 |
| 413320 | 2131 | 2150 | TGTGCTGCATCCATGTCATC | 36 | 42102 | 42121 | 312 |
| 413321 | 2136 | 2155 | GAGTCTGTGCTGCATCCATG | 48 | 42107 | 42126 | 313 |
| 413322 | 2143 | 2162 | CAAGGCTGAGTCTGTGCTGC | 24 | 42114 | 42133 | 314 |
| 413323 | 2146 | 2165 | GGCCAAGGCTGAGTCTGTGC | 17 | 42117 | 42136 | 315 |
| 413324 | 2149 | 2168 | CCAGGCCAAGGCTGAGTCTG | 27 | 42120 | 42139 | 316 |
| 413325 | 2182 | 2201 | AAGGTAAACTGAGGCCACCA | 37 | 42153 | 42172 | 317 |
| 413326 | 2185 | 2204 | GGGAAGGTAAACTGAGGCCA | 32 | 42156 | 42175 | 318 |
| 413327 | 2236 | 2255 | AGGCCCCTTCTGAAGAGGGA | 43 | 42207 | 42226 | 319 |
| 413328 | 2239 | 2258 | GCCAGGCCCCTTCTGAAGAG | 36 | 42210 | 42229 | 320 |
| 413329 | 2242 | 2261 | AAGGCCAGGCCCCTTCTGAA | 32 | 42213 | 42232 | 321 |
| 413330 | 2246 | 2265 | TCAGAAGGCCAGGCCCCTTC | 20 | 42217 | 42236 | 322 |
| 413331 | 2252 | 2271 | TGCTGCTCAGAAGGCCAGGC | 42 | 42223 | 42242 | 323 |
| 413332 | 2257 | 2276 | TAATCTGCTGCTCAGAAGGC | 36 | 42228 | 42247 | 324 |
| 413333 | 2265 | 2284 | TTTGGAACTAATCTGCTGCT | 50 | 42236 | 42255 | 325 |
| 413334 | 2274 | 2293 | GCCACCTGCTTTGGAACTAA | 41 | 42245 | 42264 | 326 |
| 413335 | 2301 | 2320 | ACAGAAAAGTGAGGCTTGGG | 40 | 42272 | 42291 | 327 |

TABLE 5-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413336 | 2304 | 2323 | GGCACAGAAAAGTGAGGCTT | 32 | 42275 | 42294 | 328 |
| 413337 | 2307 | 2326 | GAAGGCACAGAAAAGTGAGG | 11 | 42278 | 42297 | 329 |
| 413338 | 2310 | 2329 | CAGGAAGGCACAGAAAAGTG | 28 | 42281 | 42300 | 330 |
| 413339 | 2313 | 2332 | CCTCAGGAAGGCACAGAAAA | 40 | 42284 | 42303 | 331 |
| 413340 | 2317 | 2336 | ACCCCCTCAGGAAGGCACAG | 25 | 42288 | 42307 | 332 |
| 413341 | 2323 | 2342 | GGCCCAACCCCCTCAGGAAG | 19 | 42294 | 42313 | 333 |
| 413342 | 2373 | 2392 | TCTCATCAAGAGATAACAGA | 6 | 42344 | 42363 | 334 |
| 413343 | 2376 | 2395 | TGATCTCATCAAGAGATAAC | 17 | 42347 | 42366 | 335 |
| 413344 | 2399 | 2418 | TACAAAAGTCTGACATGGTG | 40 | 42370 | 42389 | 336 |
| 413345 | 2402 | 2421 | ATATACAAAAGTCTGACATG | 21 | 42373 | 42392 | 337 |
| 413346 | 2406 | 2425 | AGGCATATACAAAAGTCTGA | 38 | 42377 | 42396 | 338 |

TABLE 6

Inhibition of DGAT2 mRNA by 5-10-5 MOE gapmers targeting SEQ ID NO: 1 and 2

| ISIS NO | SEQ ID NO: 2 Start Site | SEQ ID NO: 2 Stop Site | Sequence | % inhibition | SEQ ID NO |
|---|---|---|---|---|---|
| 413383 | 22161 | 22180 | ACCCAGAGATGGTGATAAGG | 53 | 375 |
| 413384 | 22521 | 22540 | AAGTGAACCCTCACTTCCCA | 35 | 376 |
| 413385 | 22840 | 22859 | ACATATCCCCAACTGAAACA | 21 | 377 |
| 413386 | 22849 | 22868 | TCACTGATGACATATCCCCA | 52 | 378 |
| 413387 | 22862 | 22881 | GAGTATAGAAATTTCACTGA | 44 | 379 |
| 413388 | 22877 | 22896 | TGCAGCTTGGAGGAGGAGTA | 36 | 380 |
| 413389 | 23151 | 23172 | GCATTTTAACAAGATCCCCA | 34 | 381 |
| 413390 | 23167 | 23186 | CTGAATCAAAATCTGCATTT | 28 | 382 |
| 413391 | 23182 | 23201 | TCCAGACTGGATTTACTGAA | 60 | 383 |
| 413392 | 23550 | 23569 | TTATCCTTGAGGGTCTCATA | 45 | 384 |
| 413393 | 23560 | 23579 | CATCACATGCTTATCCTTGA | 41 | 385 |
| 413394 | 23669 | 23688 | TTCCCCAGAGCAGCTCTGAG | 27 | 386 |
| 413395 | 23726 | 23745 | GCGGCAGAGCCAGGACTGAA | 35 | 387 |
| 413396 | 23812 | 23831 | GTCATCCAGTATAGCCTAAT | 44 | 388 |
| 413397 | 23957 | 23975 | TAAAGAGGCTGGGCCATAGA | 21 | 389 |
| 413398 | 24122 | 24141 | TCAAACCTAGGTTCAGACTT | 47 | 390 |
| 413399 | 24204 | 24223 | AGGAAGGAAATGCTAGGCCT | 64 | 391 |
| 413400 | 24642 | 24661 | ACAGGAAGCCTGGTGACTGC | 54 | 392 |
| 413401 | 24790 | 24809 | CAGGCAGCCTGAAGGACACT | 49 | 393 |
| 413402 | 25074 | 25093 | AGGACAGAGGTTCAACATCC | 53 | 394 |

TABLE 6-continued

Inhibition of DGAT2 mRNA by 5-10-5 MOE gapmers targeting SEQ ID NO: 1 and 2

| ISIS NO | SEQ ID NO: 2 Start Site | SEQ ID NO: 2 Stop Site | Sequence | % inhibition | SEQ ID NO |
|---------|------------------------|------------------------|----------|--------------|-----------|
| 413403 | 25234 | 25253 | AGACCACATGAAGTATCTAA | 50 | 395 |
| 413404 | 25376 | 25395 | GCTATAGAATCAGACAGACC | 46 | 396 |
| 413405 | 25488 | 25507 | CCTACAGCAGAGGGAAGATG | 13 | 397 |
| 413406 | 25493 | 25512 | CAGTGCCTACAGCAGAGGGA | 0 | 398 |
| 413407 | 25504 | 25523 | GATGCTGGATCCAGTGCCTA | 53 | 399 |
| 413408 | 25953 | 25972 | GTGGGAAAGGCACAGGCTTT | 53 | 400 |
| 413409 | 26393 | 26412 | GATGGCAACCTAAGGAGTGA | 37 | 401 |
| 413410 | 26893 | 26912 | GTTCTTGGGCCTAAAGGTGA | 34 | 402 |
| 413411 | 27564 | 27583 | ATTAGCAGTAGCTCAGGAGA | 48 | 403 |
| 413412 | 27677 | 27696 | CTGGTCCAGGGAGAGACCAA | 25 | 404 |
| 413413 | 27711 | 27730 | AGAGGGTTCCATGGCACAAA | 67 | 405 |
| 413414 | 28186 | 28205 | AATTTCCTTACAGGGTATTG | 46 | 406 |
| 413415 | 28461 | 28480 | TCATGAGAAGCTTAGAAGGC | 58 | 407 |
| 413416 | 28524 | 28543 | CAACAGGCTCTGGTTCCATG | 56 | 408 |
| 413417 | 28920 | 28939 | CAGGCCCCACTGCTTAGAGG | 48 | 409 |
| 413418 | 29446 | 29465 | AAATGGTAGCCCCTTGTTGC | 32 | 410 |
| 413419 | 29503 | 29522 | TTTCCCATGGGAGAAGATAA | 55 | 411 |
| 413420 | 30361 | 30380 | AGCGCAGAGCCCATCAGCCT | 48 | 412 |
| 413421 | 30620 | 30639 | CAGGGTGACTTTGCCCCATT | 43 | 413 |
| 413422 | 30974 | 30993 | TGGCACTAAGCTAGGCACAC | 62 | 414 |
| 413423 | 31184 | 31203 | AGGGAGGCCTTGCACTTACC | 13 | 415 |
| 413424 | 31240 | 31259 | TGAGGCCCTTCAGCTTGTGC | 49 | 416 |
| 413425 | 31370 | 31389 | AAACCCTCGACTGAGTGTGA | 37 | 417 |
| 413426 | 31531 | 31550 | CCTTCCAGGGAATAAAATAC | 3 | 418 |
| 413427 | 31534 | 31553 | CCACCTTCCAGGGAATAAAA | 22 | 419 |
| 413428 | 31537 | 31556 | CTGCCACCTTCCAGGGAATA | 27 | 420 |
| 413429 | 31620 | 31639 | AACACTCACAGCACTTTACC | 4 | 421 |
| 413430 | 31769 | 31788 | TGGATACTCAGAAGAGCAGT | 37 | 422 |
| 413431 | 31935 | 31954 | CAGAGTTATCCTCAATTCAC | 34 | 423 |
| 413432 | 32145 | 32164 | ACACCAGGATCTCAGTCACT | 42 | 424 |
| 413433 | 32431 | 32450 | GCCTGGACAAGTCCTGCCCA | 70 | 425 |
| 413434 | 32528 | 32547 | GAAACAGGCAGTAGGAAATC | 23 | 426 |
| 413435 | 32644 | 32663 | ATGGAGTGACAGGGCAGGAA | 59 | 427 |
| 413436 | 32939 | 32958 | AGGCCACAGTGGCAACAGAG | 54 | 428 |
| 413437 | 33067 | 33086 | GTTCTTTTGGAAGGGTGGAG | 52 | 429 |
| 413438 | 33164 | 33183 | GGAGCCCTCACAGGGCCAGG | 38 | 430 |
| 413439 | 33364 | 33383 | GGACAGGAGGGTCACACACA | 45 | 431 |

TABLE 6-continued

Inhibition of DGAT2 mRNA by 5-10-5 MOE gapmers targeting SEQ ID NO: 1 and 2

| ISIS NO | SEQ ID NO: 2 Start Site | SEQ ID NO: 2 Stop Site | Sequence | % inhibition | SEQ ID NO |
|---|---|---|---|---|---|
| 413440 | 33671 | 33690 | AGATGGACAGGTGATTCTAA | 50 | 432 |
| 413441 | 33739 | 33758 | TTAAGCTTTGTGACCTTGGG | 67 | 433 |
| 413442 | 34101 | 34120 | GGGAAGGATACCGCCAATGA | 57 | 434 |
| 413443 | 34311 | 34330 | CAGTGGGCCCCAGGTGGCTC | 46 | 435 |
| 413444 | 34642 | 34661 | GGTGGGAAACTTGGAAACTT | 37 | 436 |
| 413445 | 35355 | 35374 | ACAATTCCTGGATAACAAGG | 41 | 437 |
| 413446 | 35362 | 35381 | TAGAAATACAATTCCTGGAT | 71 | 438 |
| 413447 | 35568 | 35587 | TGTCCTTATCAAAATCCCTC | 38 | 439 |
| 413448 | 36267 | 36286 | GCTGAGAGAGACAATGAGTA | 54 | 440 |
| 413449 | 36858 | 36877 | GATTATTCTAAAACTCAAAT | 0 | 441 |
| 413450 | 37202 | 37221 | ACCAGCTGCAAGGATGACCT | 49 | 442 |
| 413451 | 37457 | 37476 | GAGGCTCAGGCCTTGACAAC | 12 | 443 |
| 413452 | 37604 | 37623 | TGTTATCCGAGTTGAATTCT | 45 | 444 |
| 413453 | 37818 | 37837 | GTTTTGGGAACTCATGCATT | 50 | 445 |
| 413454 | 37837 | 37856 | CAGCTAATGATACAAGGTTG | 55 | 446 |
| 413455 | 37880 | 37899 | GCTATTCATTTTTCTGAGCC | 47 | 447 |
| 217328 | 38091 | 38110 | GCATTGCCACTCCCATTCTT | 67 | 144 |
| 413456 | 39033 | 39052 | AGAGGCCCTGGACACTGGCC | 32 | 448 |
| 413457 | 39040 | 39059 | TCAGCCTAGAGGCCCTGGAC | 26 | 449 |
| 413458 | 39300 | 39319 | CCAACAGTGGTGATGGGCTT | 60 | 450 |
| 413459 | 39305 | 39324 | GCTTACCAACAGTGGTGATG | 21 | 451 |

Example 2: Antisense Inhibition of Human Diacylglycerol Acyltransferase 2 in HepG2 Cells by MOE Gapmers Antisense oligonucleotides were designed targeting a diacylglycerol acyltransferase 2 (DGAT2) nucleic acid and were tested for their effects on DGAT2 mRNA in vitro. The antisense oligonucleotides were tested in a series of experiments that had similar culture conditions. The results for each experiment are presented in separate tables shown below. Cultured HepG2 cells at a density of 10,000 cells per well were transfected using Lipofectin reagent with 120 nM antisense oligonucleotide. After a treatment period of approximately 24 hours, RNA was isolated from the cells and DGAT2 mRNA levels were measured by quantitative real-time PCR. Human primer probe set RTS2988_MGB (forward sequence AACTGGCCCTGCGTCATG, designated herein as SEQ ID NO: 7; reverse sequence CTTGTACACTTCATTCTCCAAAGG, designated herein as SEQ ID NO: 8; probe sequence CTGACCTGGTTCCC, designated herein as SEQ ID NO: 9) was used to measure mRNA levels. DGAT2 mRNA levels were adjusted according to total RNA content, as measured by RIBOGREEN®. Results are presented as percent inhibition of DGAT2, relative to untreated control cells.

ISIS oligonucleotides from an earlier published application, WO 2005/019418, were also included in this assay. These ISIS oligonucleotides are ISIS 217316, ISIS 217317, ISIS 217328, ISIS 217329, ISIS 334177, ISIS 334178, ISIS 366730, ISIS 366731, and ISIS 369255. As shown in the Tables below, several newly designed antisense oligonucleotides demonstrated similar or greater potency that any of these benchmark oligonucleotides.

The newly designed chimeric antisense oligonucleotides in the Tables below were designed as 5-10-5 MOE, 3-14-3 MOE, or 2-13-5 MOE gapmers. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. The 3-14-3 MOE gapmers are 20 nucleosides in length, wherein the central gap segment comprises of fourteen 2'-deoxynucleosides and is flanked by wing segments on the 5' direction and the 3' direction comprising three nucleosides each. The 2-13-5 MOE gapmers are 20 nucleosides in length, wherein the central gap segment comprises of thirteen 2'-deoxynucleosides and is flanked by wing segments on the 5' direction and the 3' direction comprising two and three nucleosides respectively. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted in the human gene sequence. Each gapmer listed in the Tables below is targeted to either the human DGAT2 mRNA, designated herein as SEQ ID NO: 1 (RefSeq No. NM_032564.3) or the human DGAT2 genomic sequence, designated herein as SEQ ID NO: 2 (RefSeq No. NT_033927.5 truncated from nucleotides 5669186 to 5712008). 'n/a' indicates that the antisense oligonucleotide does not target that particular gene sequence with 100% complementarity.

TABLE 8

Inhibition of DGAT2 mRNA by MOE gapmers targeting SEQ ID NO: 1 and 2

| ISIS NO | SEQ ID NO: 1 Start Site | SEQ ID NO: 1 Stop Site | Motif | Sequence | % inhibition | SEQ ID NO: 2 Start Site | SEQ ID NO: 2 Stop Site | SEQ ID NO |
|---|---|---|---|---|---|---|---|---|
| 423460 | n/a | n/a | 5-10-5 | TGGACAAGTCCTGCCCATCT | 72 | 32428 | 32447 | 464 |
| 423520 | n/a | n/a | 3-14-3 | TGGACAAGTCCTGCCCATCT | 69 | 32428 | 32447 | 464 |
| 423598 | n/a | n/a | 2-13-5 | TGGACAAGTCCTGCCCATCT | 51 | 32428 | 32447 | 464 |
| 423461 | n/a | n/a | 5-10-5 | CTGGACAAGTCCTGCCCATC | 77 | 32429 | 32448 | 465 |
| 423521 | n/a | n/a | 3-14-3 | CTGGACAAGTCCTGCCCATC | 67 | 32429 | 32448 | 465 |
| 423599 | n/a | n/a | 2-13-5 | CTGGACAAGTCCTGCCCATC | 58 | 32429 | 32448 | 465 |
| 423462 | n/a | n/a | 5-10-5 | CCTGGACAAGTCCTGCCCAT | 73 | 32430 | 32449 | 466 |
| 423522 | n/a | n/a | 3-14-3 | CCTGGACAAGTCCTGCCCAT | 70 | 32430 | 32449 | 466 |
| 423600 | n/a | n/a | 2-13-5 | CCTGGACAAGTCCTGCCCAT | 59 | 32430 | 32449 | 466 |
| 413433 | n/a | n/a | 5-10-5 | GCCTGGACAAGTCCTGCCCA | 86 | 32431 | 32450 | 425 |
| 423523 | n/a | n/a | 3-14-3 | GCCTGGACAAGTCCTGCCCA | 84 | 32431 | 32450 | 425 |
| 423601 | n/a | n/a | 2-13-5 | GCCTGGACAAGTCCTGCCCA | 78 | 32431 | 32450 | 425 |
| 423463 | n/a | n/a | 5-10-5 | AGCCTGGACAAGTCCTGCCC | 79 | 32432 | 32451 | 467 |
| 423524 | n/a | n/a | 3-14-3 | AGCCTGGACAAGTCCTGCCC | 82 | 32432 | 32451 | 467 |
| 423602 | n/a | n/a | 2-13-5 | AGCCTGGACAAGTCCTGCCC | 75 | 32432 | 32451 | 467 |
| 423464 | n/a | n/a | 5-10-5 | CAGCCTGGACAAGTCCTGCC | 84 | 32433 | 32452 | 468 |
| 423525 | n/a | n/a | 3-14-3 | CAGCCTGGACAAGTCCTGCC | 72 | 32433 | 32452 | 468 |
| 423603 | n/a | n/a | 2-13-5 | CAGCCTGGACAAGTCCTGCC | 72 | 32433 | 32452 | 468 |
| 423465 | n/a | n/a | 5-10-5 | GCAGCCTGGACAAGTCCTGC | 70 | 32434 | 32453 | 469 |
| 423526 | n/a | n/a | 3-14-3 | GCAGCCTGGACAAGTCCTGC | 83 | 32434 | 32453 | 469 |
| 423604 | n/a | n/a | 2-13-5 | GCAGCCTGGACAAGTCCTGC | 77 | 32434 | 32453 | 469 |
| 423466 | n/a | n/a | 5-10-5 | TGCAGCCTGGACAAGTCCTG | 67 | 32435 | 32454 | 470 |
| 423527 | n/a | n/a | 3-14-3 | TGCAGCCTGGACAAGTCCTG | 77 | 32435 | 32454 | 470 |
| 413191 | 467 | 486 | 5-10-5 | CACTGGAGCACTGAGATGAC | 48 | 25593 | 25612 | 181 |
| 423502 | 467 | 486 | 3-14-3 | CACTGGAGCACTGAGATGAC | 55 | 25593 | 25612 | 181 |
| 423580 | 467 | 486 | 2-13-5 | CACTGGAGCACTGAGATGAC | 61 | 25593 | 25612 | 181 |
| 423449 | 468 | 487 | 5-10-5 | CCACTGGAGCACTGAGATGA | 71 | 25594 | 25613 | 452 |
| 423503 | 468 | 487 | 3-14-3 | CCACTGGAGCACTGAGATGA | 62 | 25594 | 25613 | 452 |
| 423581 | 468 | 487 | 2-13-5 | CCACTGGAGCACTGAGATGA | 54 | 25594 | 25613 | 452 |
| 423450 | 469 | 488 | 5-10-5 | CCCACTGGAGCACTGAGATG | 78 | 25595 | 25614 | 453 |
| 423504 | 469 | 488 | 3-14-3 | CCCACTGGAGCACTGAGATG | 75 | 25595 | 25614 | 453 |
| 423582 | 469 | 488 | 2-13-5 | CCCACTGGAGCACTGAGATG | 70 | 25595 | 25614 | 453 |

TABLE 8-continued

Inhibition of DGAT2 mRNA by MOE gapmers targeting SEQ ID NO: 1 and 2

| ISIS NO | SEQ ID NO: 1 Start Site | SEQ ID NO: 1 Stop Site | Motif | Sequence | % inhibition | SEQ ID NO: 2 Start Site | SEQ ID NO: 2 Stop Site | SEQ ID NO |
|---|---|---|---|---|---|---|---|---|
| 334178 | 470 | 489 | 5-10-5 | ACCCACTGGAGCACTGAGAT | 72 | 25596 | 25615 | 454 |
| 423505 | 470 | 489 | 3-14-3 | ACCCACTGGAGCACTGAGAT | 59 | 25596 | 25615 | 454 |
| 423583 | 470 | 489 | 2-13-5 | ACCCACTGGAGCACTGAGAT | 52 | 25596 | 25615 | 454 |
| 423451 | 471 | 490 | 5-10-5 | GACCCACTGGAGCACTGAGA | 69 | 25597 | 25616 | 455 |
| 423506 | 471 | 490 | 3-14-3 | GACCCACTGGAGCACTGAGA | 56 | 25597 | 25616 | 455 |
| 423584 | 471 | 490 | 2-13-5 | GACCCACTGGAGCACTGAGA | 70 | 25597 | 25616 | 455 |
| 423452 | 472 | 491 | 5-10-5 | GGACCCACTGGAGCACTGAG | 84 | 25598 | 25617 | 456 |
| 423507 | 472 | 491 | 3-14-3 | GGACCCACTGGAGCACTGAG | 82 | 25598 | 25617 | 456 |
| 423585 | 472 | 491 | 2-13-5 | GGACCCACTGGAGCACTGAG | 86 | 25598 | 25617 | 456 |
| 413192 | 473 | 492 | 5-10-5 | AGGACCCACTGGAGCACTGA | 70 | 25599 | 25618 | 182 |
| 423508 | 473 | 492 | 3-14-3 | AGGACCCACTGGAGCACTGA | 82 | 25599 | 25618 | 182 |
| 423586 | 473 | 492 | 2-13-5 | AGGACCCACTGGAGCACTGA | 75 | 25599 | 25618 | 182 |
| 423453 | 474 | 493 | 5-10-5 | CAGGACCCACTGGAGCACTG | 80 | 25600 | 25619 | 457 |
| 423509 | 474 | 493 | 3-14-3 | CAGGACCCACTGGAGCACTG | 71 | 25600 | 25619 | 457 |
| 423587 | 474 | 493 | 2-13-5 | CAGGACCCACTGGAGCACTG | 78 | 25600 | 25619 | 457 |
| 423454 | 475 | 494 | 5-10-5 | ACAGGACCCACTGGAGCACT | 79 | 25601 | 25620 | 458 |
| 423510 | 475 | 494 | 3-14-3 | ACAGGACCCACTGGAGCACT | 61 | 25601 | 25620 | 458 |
| 423588 | 475 | 494 | 2-13-5 | ACAGGACCCACTGGAGCACT | 68 | 25601 | 25620 | 458 |
| 413193 | 476 | 495 | 5-10-5 | GACAGGACCCACTGGAGCAC | 69 | 25602 | 25621 | 183 |
| 423511 | 476 | 495 | 3-14-3 | GACAGGACCCACTGGAGCAC | 58 | 25602 | 25621 | 183 |
| 423589 | 476 | 495 | 2-13-5 | GACAGGACCCACTGGAGCAC | 73 | 25602 | 25621 | 183 |
| 413212 | 625 | 644 | 5-10-5 | TTCGGACCCACTGTGACCTC | 75 | 31557 | 31576 | 202 |
| 423512 | 625 | 644 | 3-14-3 | TTCGGACCCACTGTGACCTC | 64 | 31557 | 31576 | 202 |
| 423590 | 625 | 644 | 2-13-5 | TTCGGACCCACTGTGACCTC | 71 | 31557 | 31576 | 202 |
| 423455 | 626 | 645 | 5-10-5 | TTTCGGACCCACTGTGACCT | 65 | 31558 | 31577 | 459 |
| 423513 | 626 | 645 | 3-14-3 | TTTCGGACCCACTGTGACCT | 61 | 31558 | 31577 | 459 |
| 423591 | 626 | 645 | 2-13-5 | TTTCGGACCCACTGTGACCT | 68 | 31558 | 31577 | 459 |
| 423456 | 627 | 646 | 5-10-5 | GTTTCGGACCCACTGTGACC | 65 | 31559 | 31578 | 460 |
| 423514 | 627 | 646 | 3-14-3 | GTTTCGGACCCACTGTGACC | 71 | 31559 | 31578 | 460 |
| 423592 | 627 | 646 | 2-13-5 | GTTTCGGACCCACTGTGACC | 70 | 31559 | 31578 | 460 |
| 423457 | 628 | 647 | 5-10-5 | AGTTTCGGACCCACTGTGAC | 63 | 31560 | 31579 | 461 |
| 423515 | 628 | 647 | 3-14-3 | AGTTTCGGACCCACTGTGAC | 60 | 31560 | 31579 | 461 |
| 423593 | 628 | 647 | 2-13-5 | AGTTTCGGACCCACTGTGAC | 64 | 31560 | 31579 | 461 |
| 413213 | 629 | 648 | 5-10-5 | CAGTTTCGGACCCACTGTGA | 74 | 31561 | 31580 | 203 |
| 423516 | 629 | 648 | 3-14-3 | CAGTTTCGGACCCACTGTGA | 58 | 31561 | 31580 | 203 |
| 423594 | 629 | 648 | 2-13-5 | CAGTTTCGGACCCACTGTGA | 77 | 31561 | 31580 | 203 |
| 423458 | 630 | 649 | 5-10-5 | CCAGTTTCGGACCCACTGTG | 83 | 31562 | 31581 | 462 |

TABLE 8-continued

Inhibition of DGAT2 mRNA by MOE gapmers targeting SEQ ID NO: 1 and 2

| ISIS NO | SEQ ID NO: 1 Start Site | SEQ ID NO: 1 Stop Site | Motif | Sequence | % inhibition | SEQ ID NO: 2 Start Site | SEQ ID NO: 2 Stop Site | SEQ ID NO |
|---|---|---|---|---|---|---|---|---|
| 423517 | 630 | 649 | 3-14-3 | CCAGTTTCGGACCCACTGTG | 82 | 31562 | 31581 | 462 |
| 423595 | 630 | 649 | 2-13-5 | CCAGTTTCGGACCCACTGTG | 80 | 31562 | 31581 | 462 |
| 423459 | 631 | 650 | 5-10-5 | CCCAGTTTCGGACCCACTGT | 85 | 31563 | 31582 | 463 |
| 423518 | 631 | 650 | 3-14-3 | CCCAGTTTCGGACCCACTGT | 76 | 31563 | 31582 | 463 |
| 423596 | 631 | 650 | 2-13-5 | CCCAGTTTCGGACCCACTGT | 70 | 31563 | 31582 | 463 |
| 413214 | 632 | 651 | 5-10-5 | GCCCAGTTTCGGACCCACTG | 89 | 31564 | 31583 | 204 |
| 423519 | 632 | 651 | 3-14-3 | GCCCAGTTTCGGACCCACTG | 81 | 31564 | 31583 | 204 |
| 423597 | 632 | 651 | 2-13-5 | GCCCAGTTTCGGACCCACTG | 82 | 31564 | 31583 | 204 |
| 217328 | 938 | 957 | 5-10-5 | GCATTGCCACTCCCATTCTT | 82 | 38091 | 38110 | 144 |

TABLE 9

Inhibition of DGAT2 mRNA by MOE gapmers targeting SEQ ID NO: 1 and 2

| ISIS NO | SEQ ID NO: 1 Start Site | SEQ ID NO: 1 Stop Site | Motif | Sequence | % inhibition | SEQ ID NO: 2 Start Site | SEQ ID NO: 2 Stop Site | SEQ ID NO |
|---|---|---|---|---|---|---|---|---|
| 334177 | 275 | 294 | 5-10-5 | AGGACCCCGGAGTAGGCGGC | 76 | 9896 | 9915 | 145 |
| 423528 | 275 | 294 | 3-14-3 | AGGACCCCGGAGTAGGCGGC | 76 | 9896 | 9915 | 145 |
| 423606 | 275 | 294 | 2-13-5 | AGGACCCCGGAGTAGGCGGC | 81 | 9896 | 9915 | 145 |
| 423467 | 276 | 295 | 5-10-5 | CAGGACCCCGGAGTAGGCGG | 75 | 9897 | 9916 | 471 |
| 423529 | 276 | 295 | 3-14-3 | CAGGACCCCGGAGTAGGCGG | 53 | 9897 | 9916 | 471 |
| 423607 | 276 | 295 | 2-13-5 | CAGGACCCCGGAGTAGGCGG | 76 | 9897 | 9916 | 471 |
| 423468 | 277 | 296 | 5-10-5 | GCAGGACCCCGGAGTAGGCG | 58 | 9898 | 9917 | 472 |
| 423530 | 277 | 296 | 3-14-3 | GCAGGACCCCGGAGTAGGCG | 70 | 9898 | 9917 | 472 |
| 423608 | 277 | 296 | 2-13-5 | GCAGGACCCCGGAGTAGGCG | 68 | 9898 | 9917 | 472 |
| 381726 | 278 | 297 | 5-10-5 | CGCAGGACCCCGGAGTAGGC | 70 | 9899 | 9918 | 38 |
| 423531 | 278 | 297 | 3-14-3 | CGCAGGACCCCGGAGTAGGC | 65 | 9899 | 9918 | 38 |
| 423609 | 278 | 297 | 2-13-5 | CGCAGGACCCCGGAGTAGGC | 71 | 9899 | 9918 | 38 |
| 423469 | 279 | 298 | 5-10-5 | GCGCAGGACCCCGGAGTAGG | 79 | 9900 | 9919 | 473 |
| 423532 | 279 | 298 | 3-14-3 | GCGCAGGACCCCGGAGTAGG | 71 | 9900 | 9919 | 473 |
| 423610 | 279 | 298 | 2-13-5 | GCGCAGGACCCCGGAGTAGG | 72 | 9900 | 9919 | 473 |
| 423470 | 280 | 299 | 5-10-5 | CGCGCAGGACCCCGGAGTAG | 74 | 9901 | 9920 | 474 |
| 423533 | 280 | 299 | 3-14-3 | CGCGCAGGACCCCGGAGTAG | 69 | 9901 | 9920 | 474 |
| 423611 | 280 | 299 | 2-13-5 | CGCGCAGGACCCCGGAGTAG | 67 | 9901 | 9920 | 474 |
| 423471 | 281 | 300 | 5-10-5 | CCGCGCAGGACCCCGGAGTA | 75 | 9902 | 9921 | 475 |
| 423534 | 281 | 300 | 3-14-3 | CCGCGCAGGACCCCGGAGTA | 71 | 9902 | 9921 | 475 |
| 411873 | 686 | 705 | 5-10-5 | TTGTGTGTCTTCACCAGCTG | 73 | 37214 | 37233 | 46 |
| 423542 | 686 | 705 | 3-14-3 | TTGTGTGTCTTCACCAGCTG | 60 | 37214 | 37233 | 46 |

TABLE 9-continued

Inhibition of DGAT2 mRNA by MOE gapmers targeting SEQ ID NO: 1 and 2

| ISIS NO | SEQ ID NO: 1 Start Site | SEQ ID NO: 1 Stop Site | Motif | Sequence | % inhibition | SEQ ID NO: 2 Start Site | SEQ ID NO: 2 Stop Site | SEQ ID NO |
|---|---|---|---|---|---|---|---|---|
| 423620 | 686 | 705 | 2-13-5 | TTGTGTGTCTTCACCAGCTG | 71 | 37214 | 37233 | 46 |
| 411898 | 687 | 706 | 5-10-5 | GTTGTGTGTCTTCACCAGCT | 68 | 37215 | 37234 | 61 |
| 423543 | 687 | 706 | 3-14-3 | GTTGTGTGTCTTCACCAGCT | 56 | 37215 | 37234 | 61 |
| 423621 | 687 | 706 | 2-13-5 | GTTGTGTGTCTTCACCAGCT | 65 | 37215 | 37234 | 61 |
| 217316 | 688 | 707 | 5-10-5 | GGTTGTGTGTCTTCACCAGC | 70 | 37216 | 37235 | 20 |
| 423544 | 688 | 707 | 3-14-3 | GGTTGTGTGTCTTCACCAGC | 70 | 37216 | 37235 | 20 |
| 423622 | 688 | 707 | 2-13-5 | GGTTGTGTGTCTTCACCAGC | 68 | 37216 | 37235 | 20 |
| 381727 | 689 | 708 | 5-10-5 | AGGTTGTGTGTCTTCACCAG | 74 | 37217 | 37236 | 39 |
| 423545 | 689 | 708 | 3-14-3 | AGGTTGTGTGTCTTCACCAG | 61 | 37217 | 37236 | 39 |
| 423623 | 689 | 708 | 2-13-5 | AGGTTGTGTGTCTTCACCAG | 61 | 37217 | 37236 | 39 |
| 411899 | 690 | 709 | 5-10-5 | CAGGTTGTGTGTCTTCACCA | 76 | 37218 | 37237 | 62 |
| 423546 | 690 | 709 | 3-14-3 | CAGGTTGTGTGTCTTCACCA | 68 | 37218 | 37237 | 62 |
| 423624 | 690 | 709 | 2-13-5 | CAGGTTGTGTGTCTTCACCA | 62 | 37218 | 37237 | 62 |
| 411874 | 691 | 710 | 5-10-5 | GCAGGTTGTGTGTCTTCACC | 73 | 37219 | 37238 | 47 |
| 423547 | 691 | 710 | 3-14-3 | GCAGGTTGTGTGTCTTCACC | 69 | 37219 | 37238 | 47 |
| 423625 | 691 | 710 | 2-13-5 | GCAGGTTGTGTGTCTTCACC | 56 | 37219 | 37238 | 47 |
| 411900 | 692 | 711 | 5-10-5 | AGCAGGTTGTGTGTCTTCAC | 77 | 37220 | 37239 | 63 |
| 423548 | 692 | 711 | 3-14-3 | AGCAGGTTGTGTGTCTTCAC | 63 | 37220 | 37239 | 63 |
| 423626 | 692 | 711 | 2-13-5 | AGCAGGTTGTGTGTCTTCAC | 44 | 37220 | 37239 | 63 |
| 217317 | 693 | 712 | 5-10-5 | CAGCAGGTTGTGTGTCTTCA | 75 | 37221 | 37240 | 21 |
| 423549 | 693 | 712 | 3-14-3 | CAGCAGGTTGTGTGTCTTCA | 47 | 37221 | 37240 | 21 |
| 423627 | 693 | 712 | 2-13-5 | CAGCAGGTTGTGTGTCTTCA | 57 | 37221 | 37240 | 21 |
| 381728 | 694 | 713 | 5-10-5 | TCAGCAGGTTGTGTGTCTTC | 56 | 37222 | 37241 | 40 |
| 423550 | 694 | 713 | 3-14-3 | TCAGCAGGTTGTGTGTCTTC | 54 | 37222 | 37241 | 40 |
| 423628 | 694 | 713 | 2-13-5 | TCAGCAGGTTGTGTGTCTTC | 57 | 37222 | 37241 | 40 |
| 411901 | 695 | 714 | 5-10-5 | GTCAGCAGGTTGTGTGTCTT | 59 | 37223 | 37242 | 64 |
| 423551 | 695 | 714 | 3-14-3 | GTCAGCAGGTTGTGTGTCTT | 61 | 37223 | 37242 | 64 |
| 423629 | 695 | 714 | 2-13-5 | GTCAGCAGGTTGTGTGTCTT | 58 | 37223 | 37242 | 64 |
| 411875 | 696 | 715 | 5-10-5 | GGTCAGCAGGTTGTGTGTCT | 62 | 37224 | 37243 | 48 |
| 423552 | 696 | 715 | 3-14-3 | GGTCAGCAGGTTGTGTGTCT | 57 | 37224 | 37243 | 48 |
| 423630 | 696 | 715 | 2-13-5 | GGTCAGCAGGTTGTGTGTCT | 45 | 37224 | 37243 | 48 |
| 411902 | 697 | 716 | 5-10-5 | TGGTCAGCAGGTTGTGTGTC | 43 | 37225 | 37244 | 65 |
| 423553 | 697 | 716 | 3-14-3 | TGGTCAGCAGGTTGTGTGTC | 57 | 37225 | 37244 | 65 |
| 423631 | 697 | 716 | 2-13-5 | TGGTCAGCAGGTTGTGTGTC | 57 | 37225 | 37244 | 65 |
| 413231 | 814 | 833 | 5-10-5 | GGTAAGGCCGTATGCCTGGG | 71 | 37342 | 37361 | 221 |
| 423535 | 814 | 833 | 3-14-3 | GGTAAGGCCGTATGCCTGGG | 51 | 37342 | 37361 | 221 |
| 423613 | 814 | 833 | 2-13-5 | GGTAAGGCCGTATGCCTGGG | 53 | 37342 | 37361 | 221 |

TABLE 9-continued

Inhibition of DGAT2 mRNA by MOE gapmers targeting SEQ ID NO: 1 and 2

| ISIS NO | SEQ ID NO: 1 Start Site | SEQ ID NO: 1 Stop Site | Motif | Sequence | % inhibition | SEQ ID NO: 2 Start Site | SEQ ID NO: 2 Stop Site | SEQ ID NO |
|---|---|---|---|---|---|---|---|---|
| 423472 | 815 | 834 | 5-10-5 | AGGTAAGGCCGTATGCCTGG | 72 | 37343 | 37362 | 476 |
| 423536 | 815 | 834 | 3-14-3 | AGGTAAGGCCGTATGCCTGG | 67 | 37343 | 37362 | 476 |
| 423614 | 815 | 834 | 2-13-5 | AGGTAAGGCCGTATGCCTGG | 63 | 37343 | 37362 | 476 |
| 423473 | 816 | 835 | 5-10-5 | CAGGTAAGGCCGTATGCCTG | 63 | 37344 | 37363 | 477 |
| 423537 | 816 | 835 | 3-14-3 | CAGGTAAGGCCGTATGCCTG | 72 | 37344 | 37363 | 477 |
| 423615 | 816 | 835 | 2-13-5 | CAGGTAAGGCCGTATGCCTG | 59 | 37344 | 37363 | 477 |
| 413232 | 817 | 836 | 5-10-5 | CCAGGTAAGGCCGTATGCCT | 76 | 37345 | 37364 | 225 |
| 423538 | 817 | 836 | 3-14-3 | CCAGGTAAGGCCGTATGCCT | 71 | 37345 | 37364 | 225 |
| 423616 | 817 | 836 | 2-13-5 | CCAGGTAAGGCCGTATGCCT | 64 | 37345 | 37364 | 225 |
| 423474 | 818 | 837 | 5-10-5 | GCCAGGTAAGGCCGTATGCC | 68 | 37346 | 37365 | 478 |
| 423539 | 818 | 837 | 3-14-3 | GCCAGGTAAGGCCGTATGCC | 61 | 37346 | 37365 | 478 |
| 423617 | 818 | 837 | 2-13-5 | GCCAGGTAAGGCCGTATGCC | 66 | 37346 | 37365 | 478 |
| 423475 | 819 | 838 | 5-10-5 | AGCCAGGTAAGGCCGTATGC | 70 | 37347 | 37366 | 479 |
| 423540 | 819 | 838 | 3-14-3 | AGCCAGGTAAGGCCGTATGC | 51 | 37347 | 37366 | 479 |
| 423618 | 819 | 838 | 2-13-5 | AGCCAGGTAAGGCCGTATGC | 67 | 37347 | 37366 | 479 |
| 413233 | 820 | 839 | 5-10-5 | TAGCCAGGTAAGGCCGTATG | 60 | 37348 | 37367 | 226 |
| 423541 | 820 | 839 | 3-14-3 | TAGCCAGGTAAGGCCGTATG | 49 | 37348 | 37367 | 226 |
| 423619 | 820 | 839 | 2-13-5 | TAGCCAGGTAAGGCCGTATG | 51 | 37348 | 37367 | 226 |
| 217328 | 938 | 957 | 5-10-5 | GCATTGCCACTCCCATTCTT | 82 | 38091 | 38110 | 144 |

TABLE 10

Inhibition of DGAT2 mRNA by MOE gapmers targeting SEQ ID NO: 1 and 2

| ISIS NO | SEQ ID NO: 1 Start Site | SEQ ID NO: 1 Stop Site | Motif | Sequence | % inhibition | SEQ ID NO: 2 Start Site | SEQ ID NO: 2 Stop Site | SEQ ID NO |
|---|---|---|---|---|---|---|---|---|
| 413251 | 935 | 954 | 5-10-5 | TTGCCACTCCCATTCTTTGA | 57 | 38088 | 38107 | 244 |
| 423476 | 935 | 954 | 3-14-3 | TTGCCACTCCCATTCTTTGA | 59 | 38088 | 38107 | 244 |
| 423554 | 935 | 954 | 2-13-5 | TTGCCACTCCCATTCTTTGA | 57 | 38088 | 38107 | 244 |
| 423435 | 936 | 955 | 5-10-5 | ATTGCCACTCCCATTCTTTG | 35 | 38089 | 38108 | 480 |
| 423477 | 936 | 955 | 3-14-3 | ATTGCCACTCCCATTCTTTG | 40 | 38089 | 38108 | 480 |
| 423555 | 936 | 955 | 2-13-5 | ATTGCCACTCCCATTCTTTG | 53 | 38089 | 38108 | 480 |
| 423436 | 937 | 956 | 5-10-5 | CATTGCCACTCCCATTCTTT | 44 | 38090 | 38109 | 481 |
| 423478 | 937 | 956 | 3-14-3 | CATTGCCACTCCCATTCTTT | 46 | 38090 | 38109 | 481 |
| 423556 | 937 | 956 | 2-13-5 | CATTGCCACTCCCATTCTTT | 40 | 38090 | 38109 | 481 |
| 217328 | 938 | 957 | 5-10-5 | GCATTGCCACTCCCATTCTT | 85 | 38091 | 38110 | 144 |
| 423479 | 938 | 957 | 3-14-3 | GCATTGCCACTCCCATTCTT | 85 | 38091 | 38110 | 144 |
| 423557 | 938 | 957 | 2-13-5 | GCATTGCCACTCCCATTCTT | 61 | 38091 | 38110 | 144 |
| 380133 | 939 | 958 | 5-10-5 | AGCATTGCCACTCCCATTCT | 74 | 38092 | 38111 | 482 |

TABLE 10-continued

Inhibition of DGAT2 mRNA by MOE gapmers targeting SEQ ID NO: 1 and 2

| ISIS NO | SEQ ID NO: 1 Start Site | SEQ ID NO: 1 Stop Site | Motif | Sequence | % inhibition | SEQ ID NO: 2 Start Site | SEQ ID NO: 2 Stop Site | SEQ ID NO |
|---|---|---|---|---|---|---|---|---|
| 423480 | 939 | 958 | 3-14-3 | AGCATTGCCACTCCCATTCT | 67 | 38092 | 38111 | 482 |
| 423558 | 939 | 958 | 2-13-5 | AGCATTGCCACTCCCATTCT | 50 | 38092 | 38111 | 482 |
| 423437 | 940 | 959 | 5-10-5 | TAGCATTGCCACTCCCATTC | 71 | 38093 | 38112 | 483 |
| 423481 | 940 | 959 | 3-14-3 | TAGCATTGCCACTCCCATTC | 68 | 38093 | 38112 | 483 |
| 423559 | 940 | 959 | 2-13-5 | TAGCATTGCCACTCCCATTC | 60 | 38093 | 38112 | 483 |
| 423438 | 941 | 960 | 5-10-5 | ATAGCATTGCCACTCCCATT | 57 | 38094 | 38113 | 484 |
| 423482 | 941 | 960 | 3-14-3 | ATAGCATTGCCACTCCCATT | 71 | 38094 | 38113 | 484 |
| 423560 | 941 | 960 | 2-13-5 | ATAGCATTGCCACTCCCATT | 57 | 38094 | 38113 | 484 |
| 423439 | 942 | 961 | 5-10-5 | GATAGCATTGCCACTCCCAT | 66 | 38095 | 38114 | 485 |
| 423483 | 942 | 961 | 3-14-3 | GATAGCATTGCCACTCCCAT | 75 | 38095 | 38114 | 485 |
| 423561 | 942 | 961 | 2-13-5 | GATAGCATTGCCACTCCCAT | 62 | 38095 | 38114 | 485 |
| 217329 | 943 | 962 | 5-10-5 | TGATAGCATTGCCACTCCCA | 64 | 38096 | 38115 | 486 |
| 423484 | 943 | 962 | 3-14-3 | TGATAGCATTGCCACTCCCA | 66 | 38096 | 38115 | 486 |
| 423562 | 943 | 962 | 2-13-5 | TGATAGCATTGCCACTCCCA | 69 | 38096 | 38115 | 486 |
| 413252 | 976 | 995 | 5-10-5 | TCAGAGACTCAGCCGCACCC | 55 | 38129 | 38148 | 245 |
| 423485 | 976 | 995 | 3-14-3 | TCAGAGACTCAGCCGCACCC | 41 | 38129 | 38148 | 245 |
| 423563 | 976 | 995 | 2-13-5 | TCAGAGACTCAGCCGCACCC | 56 | 38129 | 38148 | 245 |
| 423440 | 977 | 996 | 5-10-5 | CTCAGAGACTCAGCCGCACC | 80 | 38130 | 38149 | 487 |
| 423486 | 977 | 996 | 3-14-3 | CTCAGAGACTCAGCCGCACC | 70 | 38130 | 38149 | 487 |
| 423564 | 977 | 996 | 2-13-5 | CTCAGAGACTCAGCCGCACC | 43 | 38130 | 38149 | 487 |
| 423441 | 978 | 997 | 5-10-5 | GCTCAGAGACTCAGCCGCAC | 86 | 38131 | 38150 | 488 |
| 423487 | 978 | 997 | 3-14-3 | GCTCAGAGACTCAGCCGCAC | 69 | 38131 | 38150 | 488 |
| 423565 | 978 | 997 | 2-13-5 | GCTCAGAGACTCAGCCGCAC | 82 | 38131 | 38150 | 488 |
| 366730 | 979 | 998 | 5-10-5 | AGCTCAGAGACTCAGCCGCA | 85 | 38132 | 38151 | 150 |
| 423488 | 979 | 998 | 3-14-3 | AGCTCAGAGACTCAGCCGCA | 77 | 38132 | 38151 | 150 |
| 423566 | 979 | 998 | 2-13-5 | AGCTCAGAGACTCAGCCGCA | 86 | 38132 | 38151 | 150 |
| 423442 | 980 | 999 | 5-10-5 | GAGCTCAGAGACTCAGCCGC | 81 | 38133 | 38152 | 489 |
| 423489 | 980 | 999 | 3-14-3 | GAGCTCAGAGACTCAGCCGC | 89 | 38133 | 38152 | 489 |
| 423567 | 980 | 999 | 2-13-5 | GAGCTCAGAGACTCAGCCGC | 89 | 38133 | 38152 | 489 |
| 423443 | 981 | 1000 | 5-10-5 | GGAGCTCAGAGACTCAGCCG | 73 | 38134 | 38153 | 490 |
| 423490 | 981 | 1000 | 3-14-3 | GGAGCTCAGAGACTCAGCCG | 81 | 38134 | 38153 | 490 |
| 423568 | 981 | 1000 | 2-13-5 | GGAGCTCAGAGACTCAGCCG | 65 | 38134 | 38153 | 490 |
| 423444 | 982 | 1001 | 5-10-5 | TGGAGCTCAGAGACTCAGCC | 77 | 38135 | 38154 | 153 |
| 423491 | 982 | 1001 | 3-14-3 | TGGAGCTCAGAGACTCAGCC | 76 | 38135 | 38154 | 153 |
| 423569 | 982 | 1001 | 2-13-5 | TGGAGCTCAGAGACTCAGCC | 82 | 38135 | 38154 | 153 |
| 423445 | 983 | 1002 | 5-10-5 | ATGGAGCTCAGAGACTCAGC | 78 | 38136 | 38155 | 491 |
| 423492 | 983 | 1002 | 3-14-3 | ATGGAGCTCAGAGACTCAGC | 71 | 38136 | 38155 | 491 |

TABLE 10-continued

Inhibition of DGAT2 mRNA by MOE gapmers targeting SEQ ID NO: 1 and 2

| ISIS NO | SEQ ID NO: 1 Start Site | SEQ ID NO: 1 Stop Site | Motif | Sequence | % inhibition | SEQ ID NO: 2 Start Site | SEQ ID NO: 2 Stop Site | SEQ ID NO |
|---|---|---|---|---|---|---|---|---|
| 423570 | 983 | 1002 | 2-13-5 | ATGGAGCTCAGAGACTCAGC | 73 | 38136 | 38155 | 491 |
| 366731 | 984 | 1003 | 5-10-5 | CATGGAGCTCAGAGACTCAG | 65 | 38137 | 38156 | 492 |
| 423493 | 984 | 1003 | 3-14-3 | CATGGAGCTCAGAGACTCAG | 62 | 38137 | 38156 | 492 |
| 423571 | 984 | 1003 | 2-13-5 | CATGGAGCTCAGAGACTCAG | 71 | 38137 | 38156 | 492 |
| 423446 | 985 | 1004 | 5-10-5 | GCATGGAGCTCAGAGACTCA | 69 | 38138 | 38157 | 493 |
| 423494 | 985 | 1004 | 3-14-3 | GCATGGAGCTCAGAGACTCA | 51 | 38138 | 38157 | 493 |
| 423572 | 985 | 1004 | 2-13-5 | GCATGGAGCTCAGAGACTCA | 77 | 38138 | 38157 | 493 |
| 423447 | 986 | 1005 | 5-10-5 | GGCATGGAGCTCAGAGACTC | 77 | 38139 | 38158 | 494 |
| 423495 | 986 | 1005 | 3-14-3 | GGCATGGAGCTCAGAGACTC | 74 | 38139 | 38158 | 494 |
| 423573 | 986 | 1005 | 2-13-5 | GGCATGGAGCTCAGAGACTC | 77 | 38139 | 38158 | 494 |
| 413253 | 987 | 1006 | 5-10-5 | AGGCATGGAGCTCAGAGACT | 83 | 38140 | 38159 | 246 |
| 423496 | 987 | 1006 | 3-14-3 | AGGCATGGAGCTCAGAGACT | 66 | 38140 | 38159 | 246 |
| 423574 | 987 | 1006 | 2-13-5 | AGGCATGGAGCTCAGAGACT | 78 | 38140 | 38159 | 246 |
| 423448 | 988 | 1007 | 5-10-5 | CAGGCATGGAGCTCAGAGAC | 57 | 38141 | 38160 | 495 |
| 423497 | 988 | 1007 | 3-14-3 | CAGGCATGGAGCTCAGAGAC | 76 | 38141 | 38160 | 495 |
| 423575 | 988 | 1007 | 2-13-5 | CAGGCATGGAGCTCAGAGAC | 70 | 38141 | 38160 | 495 |
| 369255 | 1339 | 1358 | 5-10-5 | CCAGGGCCTCCATGTACATG | 83 | 41310 | 41329 | 103 |
| 423498 | 1339 | 1358 | 3-14-3 | CCAGGGCCTCCATGTACATG | 86 | 41310 | 41329 | 103 |
| 423576 | 1339 | 1358 | 2-13-5 | CCAGGGCCTCCATGTACATG | 69 | 41310 | 41329 | 103 |
| 411944 | 1340 | 1359 | 5-10-5 | ACCAGGGCCTCCATGTACAT | 85 | 41311 | 41330 | 120 |
| 423499 | 1340 | 1359 | 3-14-3 | ACCAGGGCCTCCATGTACAT | 84 | 41311 | 41330 | 120 |
| 423577 | 1340 | 1359 | 2-13-5 | ACCAGGGCCTCCATGTACAT | 50 | 41311 | 41330 | 120 |
| 411945 | 1341 | 1360 | 5-10-5 | CACCAGGGCCTCCATGTACA | 80 | 41312 | 41331 | 121 |
| 423500 | 1341 | 1360 | 3-14-3 | CACCAGGGCCTCCATGTACA | 41 | 41312 | 41331 | 121 |
| 423578 | 1341 | 1360 | 2-13-5 | CACCAGGGCCTCCATGTACA | 69 | 41312 | 41331 | 121 |
| 411946 | 1342 | 1361 | 5-10-5 | TCACCAGGGCCTCCATGTAC | 65 | 41313 | 41332 | 122 |
| 423501 | 1342 | 1361 | 3-14-3 | TCACCAGGGCCTCCATGTAC | 68 | 41313 | 41332 | 122 |
| 423579 | 1342 | 1361 | 2-13-5 | TCACCAGGGCCTCCATGTAC | 3 | 41313 | 41332 | 122 |

Example 3: Antisense Inhibition of Human DGAT2 in HepG2 Cells by MOE Gapmers

Antisense oligonucleotides were designed targeting a DGAT2 nucleic acid and were tested for their effects on DGAT2 mRNA in vitro. The antisense oligonucleotides were tested in a series of experiments that had similar culture conditions. Previously disclosed oligonucleotides, ISIS 217317, 217328, ISIS 366722, ISIS 366710, ISIS 366714, ISIS 366728, ISIS 366746, and ISIS 369255 were included in this study as benchmark oligonucleotides. The results for each experiment are presented in separate tables shown below. Cultured HepG2 cells at a density of 20,000 cells per well were transfected using electroporation with 4,500 nM antisense oligonucleotide. After a treatment period of approximately 24 hours, RNA was isolated from the cells and DGAT2 mRNA levels were measured by quantitative real-time PCR. Human primer probe set RTS2988_MGB was used to measure mRNA levels. The potency of some oligonucleotides was measured with human primer probe set RTS2367 (forward sequence GGCCTCCCGGAGACTGA, designated herein as SEQ ID NO: 4; reverse sequence AAGTGATTTGCAGCTGGTTCCT, designated herein as SEQ ID NO: 5; probe sequence AGGTGAACT-GAGCCAGCCTTCGGG, designated herein as SEQ ID NO: 6). DGAT2 mRNA levels were adjusted according to total RNA content, as measured by RIBOGREEN®. Results are presented as percent inhibition of DGAT2, relative to untreated control cells. The results show several antisense oligonucleotides demonstrate greater potency than the benchmark oligonucleotides.

The newly designed chimeric antisense oligonucleotides in the Tables below were designed as 5-10-5 MOE gapmers. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted in the human gene sequence. Each gapmer listed in the Tables below is targeted to SEQ ID NO: 1, SEQ ID NO: 2, or both. 'n/a' indicates that the antisense oligonucleotide does not target that particular gene sequence with 100% complementarity. In case the sequence alignment for a target gene sequence in a particular table is not shown, it is understood that none of the oligonucleotides presented in that table align with 100% complementarity with that target gene sequence.

TABLE 7

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 334177 | 9896 | 9915 | AGGACCCCGGAGTAGGCGGC | 76 | 145 |
| 366710 | 25551 | 25570 | GACCTATTGAGCCAGGTGAC | 60 | 146 |
| 366722 | 31097 | 31116 | GTGCAGAATATGTACATGAG | 50 | 148 |
| 413433 | 32431 | 32450 | GCCTGGACAAGTCCTGCCCA | 80 | 425 |
| 523014 | 35670 | 35689 | TTCTACTCAAAAATATACAT | 23 | 4084 |
| 495875 | 36249 | 36268 | TAAGGGTATTCTGCTCATAA | 73 | 2148 |
| 495876 | 36250 | 36269 | GTAAGGGTATTCTGCTCATA | 83 | 2149 |
| 495877 | 36251 | 36270 | AGTAAGGGTATTCTGCTCAT | 82 | 2150 |
| 495878 | 36252 | 36271 | GAGTAAGGGTATTCTGCTCA | 89 | 2151 |
| 523015 | 36254 | 36273 | ATGAGTAAGGGTATTCTGCT | 68 | 4085 |
| 523016 | 36255 | 36274 | AATGAGTAAGGGTATTCTGC | 65 | 4086 |
| 523017 | 36256 | 36275 | CAATGAGTAAGGGTATTCTG | 39 | 4087 |
| 523018 | 36257 | 36276 | ACAATGAGTAAGGGTATTCT | 25 | 4088 |
| 495879 | 36259 | 36278 | AGACAATGAGTAAGGGTATT | 64 | 2152 |
| 495880 | 36260 | 36279 | GAGACAATGAGTAAGGGTAT | 62 | 2153 |
| 495881 | 36261 | 36280 | AGAGACAATGAGTAAGGGTA | 64 | 2154 |
| 495882 | 36262 | 36281 | GAGAGACAATGAGTAAGGGT | 66 | 2155 |
| 523019 | 36513 | 36532 | CAGCCCTGTGCCAGCCAGCC | 37 | 4089 |
| 523020 | 36514 | 36533 | ACAGCCCTGTGCCAGCCAGC | 17 | 4090 |
| 523021 | 36515 | 36534 | GACAGCCCTGTGCCAGCCAG | 52 | 4091 |
| 523022 | 36516 | 36535 | CGACAGCCCTGTGCCAGCCA | 62 | 4092 |
| 495886 | 36518 | 36537 | AGCGACAGCCCTGTGCCAGC | 57 | 2159 |
| 495887 | 36519 | 36538 | AAGCGACAGCCCTGTGCCAG | 46 | 2160 |
| 495888 | 36520 | 36539 | CAAGCGACAGCCCTGTGCCA | 28 | 2161 |
| 495889 | 36521 | 36540 | ACAAGCGACAGCCCTGTGCC | 46 | 2162 |
| 523023 | 36579 | 36598 | ACTTTCCCACAGTCAGCTGG | 59 | 4093 |
| 523024 | 36580 | 36599 | AACTTTCCCACAGTCAGCTG | 51 | 4094 |
| 523025 | 36581 | 36600 | AAACTTTCCCACAGTCAGCT | 68 | 4095 |
| 523026 | 36582 | 36601 | GAAACTTTCCCACAGTCAGC | 73 | 4096 |

TABLE 7-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 523027 | 36584 | 36603 | TGGAAACTTTCCCACAGTCA | 68 | 4097 |
| 523028 | 36585 | 36604 | ATGGAAACTTTCCCACAGTC | 52 | 4098 |
| 523029 | 36586 | 36605 | AATGGAAACTTTCCCACAGT | 23 | 4099 |
| 523030 | 36587 | 36606 | AAATGGAAACTTTCCCACAG | 36 | 4100 |
| 523031 | 36842 | 36861 | AAATCCAACCCTTGTCACTC | 28 | 4101 |
| 523032 | 36843 | 36862 | CAAATCCAACCCTTGTCACT | 22 | 4102 |
| 523033 | 36844 | 36863 | TCAAATCCAACCCTTGTCAC | 21 | 4103 |
| 523034 | 36845 | 36864 | CTCAAATCCAACCCTTGTCA | 38 | 4104 |
| 523035 | 37120 | 37139 | TGGATGTGTCATTTCCCCTG | 69 | 4105 |
| 217328 | 38091 | 38110 | GCATTGCCACTCCCATTCTT | 73 | 144 |
| 423444 | 38135 | 38154 | TGGAGCTCAGAGACTCAGCC | 56 | 153 |
| 522979 | 39671 | 39690 | AGTGCAAGAGTTACCTCCTC | 67 | 4106 |
| 522980 | 39672 | 39691 | CAGTGCAAGAGTTACCTCCT | 67 | 4107 |
| 522981 | 39673 | 39692 | GCAGTGCAAGAGTTACCTCC | 60 | 4108 |
| 522982 | 39674 | 39693 | AGCAGTGCAAGAGTTACCTC | 63 | 4109 |
| 522983 | 39681 | 39700 | ATCAGTTAGCAGTGCAAGAG | 46 | 4110 |
| 522984 | 39682 | 39701 | TATCAGTTAGCAGTGCAAGA | 43 | 4111 |
| 522985 | 39683 | 39702 | CTATCAGTTAGCAGTGCAAG | 52 | 4112 |
| 522986 | 39684 | 39703 | CCTATCAGTTAGCAGTGCAA | 64 | 4113 |
| 522987 | 39686 | 39705 | TTCCTATCAGTTAGCAGTGC | 61 | 4114 |
| 522988 | 39687 | 39706 | ATTCCTATCAGTTAGCAGTG | 47 | 4115 |
| 522989 | 39688 | 39707 | AATTCCTATCAGTTAGCAGT | 16 | 4116 |
| 522990 | 39689 | 39708 | TAATTCCTATCAGTTAGCAG | 11 | 4117 |
| 522991 | 39814 | 39833 | TCTATGCTGCAGTCATATTA | 28 | 4118 |
| 522992 | 39815 | 39834 | GTCTATGCTGCAGTCATATT | 20 | 4119 |
| 522993 | 39816 | 39835 | GGTCTATGCTGCAGTCATAT | 45 | 4120 |
| 522994 | 39817 | 39836 | AGGTCTATGCTGCAGTCATA | 40 | 4121 |
| 522995 | 39819 | 39838 | ACAGGTCTATGCTGCAGTCA | 56 | 4122 |
| 522996 | 39820 | 39839 | GACAGGTCTATGCTGCAGTC | 70 | 4123 |
| 522997 | 39821 | 39840 | TGACAGGTCTATGCTGCAGT | 65 | 4124 |
| 522998 | 39822 | 39841 | CTGACAGGTCTATGCTGCAG | 54 | 4125 |
| 522999 | 39829 | 39848 | CACTCTTCTGACAGGTCTAT | 54 | 4126 |
| 523000 | 39830 | 39849 | CCACTCTTCTGACAGGTCTA | 70 | 4127 |
| 523001 | 39831 | 39850 | TCCACTCTTCTGACAGGTCT | 69 | 4128 |
| 523002 | 39832 | 39851 | TTCCACTCTTCTGACAGGTC | 84 | 4129 |
| 523003 | 39834 | 39853 | TTTTCCACTCTTCTGACAGG | 35 | 4130 |
| 523004 | 39835 | 39854 | GTTTTCCACTCTTCTGACAG | 25 | 4131 |

TABLE 7-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 523005 | 39836 | 39855 | TGTTTTCCACTCTTCTGACA | 24 | 4132 |
| 523006 | 40329 | 40348 | ATCTCTTCCATCTCCACTGC | 30 | 4133 |
| 523007 | 40330 | 40349 | CATCTCTTCCATCTCCACTG | 32 | 4134 |
| 523008 | 40331 | 40350 | ACATCTCTTCCATCTCCACT | 39 | 4135 |
| 523009 | 40332 | 40351 | CACATCTCTTCCATCTCCAC | 40 | 4136 |
| 523010 | 40334 | 40353 | TGCACATCTCTTCCATCTCC | 50 | 4137 |
| 523011 | 40335 | 40354 | ATGCACATCTCTTCCATCTC | 35 | 4138 |
| 523012 | 40336 | 40355 | CATGCACATCTCTTCCATCT | 43 | 4139 |
| 523013 | 40337 | 40356 | TCATGCACATCTCTTCCATC | 28 | 4140 |
| 369255 | 41310 | 41329 | CCAGGGCCTCCATGTACATG | 33 | 103 |
| 411947 | 41315 | 41334 | CTTCACCAGGGCCTCCATGT | 22 | 123 |
| 366746 | 41337 | 41356 | TGGTCTTGTGCTTGTCGAAG | 46 | 151 |

TABLE 11

Inhibition of DGAT2 mRNA by 5-10-5 MOE gapmers targeting SEQ ID NOs: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413433 | n/a | n/a | GCCTGGACAAGTCCTGCCCA | 82 | 32431 | 32450 | 425 |
| 472154 | 105 | 124 | GACACCTGGAGCTGCGGCCG | 51 | 9726 | 9745 | 573 |
| 472155 | 106 | 125 | GGACACCTGGAGCTGCGGCC | 79 | 9727 | 9746 | 574 |
| 472156 | 107 | 126 | AGGACACCTGGAGCTGCGGC | 79 | 9728 | 9747 | 575 |
| 472157 | 108 | 127 | TAGGACACCTGGAGCTGCGG | 56 | 9729 | 9748 | 576 |
| 472158 | 110 | 129 | GCTAGGACACCTGGAGCTGC | 76 | 9731 | 9750 | 577 |
| 472159 | 111 | 130 | GGCTAGGACACCTGGAGCTG | 63 | 9732 | 9751 | 578 |
| 472160 | 161 | 180 | CAGGGCTTCGCGCAGAGCAC | 46 | 9782 | 9801 | 579 |
| 472161 | 162 | 181 | CCAGGGCTTCGCGCAGAGCA | 42 | 9783 | 9802 | 580 |
| 472162 | 164 | 183 | GGCCAGGGCTTCGCGCAGAG | 6 | 9785 | 9804 | 581 |
| 472163 | 253 | 272 | TGAGGGTCTTCATGGCTGAA | 40 | 9874 | 9893 | 582 |
| 472164 | 255 | 274 | TATGAGGGTCTTCATGGCTG | 69 | 9876 | 9895 | 583 |
| 472165 | 256 | 275 | CTATGAGGGTCTTCATGGCT | 62 | 9877 | 9896 | 584 |
| 472166 | 257 | 276 | GCTATGAGGGTCTTCATGGC | 53 | 9878 | 9897 | 585 |
| 472167 | 259 | 278 | CGGCTATGAGGGTCTTCATG | 59 | 9880 | 9899 | 586 |
| 472168 | 260 | 279 | GCGGCTATGAGGGTCTTCAT | 54 | 9881 | 9900 | 587 |
| 472169 | 261 | 280 | GGCGGCTATGAGGGTCTTCA | 57 | 9882 | 9901 | 588 |
| 472170 | 262 | 281 | AGGCGGCTATGAGGGTCTTC | 69 | 9883 | 9902 | 589 |
| 472171 | 264 | 283 | GTAGGCGGCTATGAGGGTCT | 32 | 9885 | 9904 | 590 |
| 472172 | 265 | 284 | AGTAGGCGGCTATGAGGGTC | 23 | 9886 | 9905 | 591 |

TABLE 11-continued

Inhibition of DGAT2 mRNA by 5-10-5 MOE gapmers targeting SEQ ID NOs: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472173 | 267 | 286 | GGAGTAGGCGGCTATGAGGG | 15 | 9888 | 9907 | 592 |
| 472174 | 268 | 287 | CGGAGTAGGCGGCTATGAGG | 48 | 9889 | 9908 | 593 |
| 472175 | 270 | 289 | CCCGGAGTAGGCGGCTATGA | 80 | 9891 | 9910 | 594 |
| 472176 | 271 | 290 | CCCCGGAGTAGGCGGCTATG | 75 | 9892 | 9911 | 595 |
| 472177 | 273 | 292 | GACCCCGGAGTAGGCGGCTA | 69 | 9894 | 9913 | 596 |
| 472178 | 274 | 293 | GGACCCCGGAGTAGGCGGCT | 76 | 9895 | 9914 | 597 |
| 334177 | 275 | 294 | AGGACCCCGGAGTAGGCGGC | 74 | 9896 | 9915 | 145 |
| 472179 | 305 | 324 | CGGTCAGCCTCGGCCTGACG | 30 | 9926 | 9945 | 598 |
| 472180 | 306 | 325 | CCGGTCAGCCTCGGCCTGAC | 5 | 9927 | 9946 | 599 |
| 472181 | 308 | 327 | CTCCGGTCAGCCTCGGCCTG | 43 | 9929 | 9948 | 600 |
| 472182 | 309 | 328 | GCTCCGGTCAGCCTCGGCCT | 61 | 9930 | 9949 | 601 |
| 472183 | 311 | 330 | TGGCTCCGGTCAGCCTCGGC | 48 | 9932 | 9951 | 602 |
| 472184 | 312 | 331 | CTGGCTCCGGTCAGCCTCGG | 28 | 9933 | 9952 | 603 |
| 472185 | 313 | 332 | GCTGGCTCCGGTCAGCCTCG | 35 | 9934 | 9953 | 604 |
| 472186 | 314 | 333 | CGCTGGCTCCGGTCAGCCTC | 44 | 9935 | 9954 | 605 |
| 472187 | 315 | 334 | GCGCTGGCTCCGGTCAGCCT | 43 | 9936 | 9955 | 606 |
| 472188 | 332 | 351 | GCAGGTCCTCCGTGAGAGCG | 63 | 9953 | 9972 | 607 |
| 472189 | 333 | 352 | CGCAGGTCCTCCGTGAGAGC | 68 | 9954 | 9973 | 608 |
| 472190 | 334 | 353 | GCGCAGGTCCTCCGTGAGAG | 40 | 9955 | 9974 | 609 |
| 472191 | 335 | 354 | AGCGCAGGTCCTCCGTGAGA | 39 | 9956 | 9975 | 610 |
| 472192 | 336 | 355 | CAGCGCAGGTCCTCCGTGAG | 54 | 9957 | 9976 | 611 |
| 472193 | 337 | 356 | ACAGCGCAGGTCCTCCGTGA | 36 | 9958 | 9977 | 612 |
| 472194 | 338 | 357 | GACAGCGCAGGTCCTCCGTG | 63 | 9959 | 9978 | 613 |
| 472195 | 340 | 359 | GCGACAGCGCAGGTCCTCCG | 62 | 9961 | 9980 | 614 |
| 472196 | 341 | 360 | CGCGACAGCGCAGGTCCTCC | 65 | 9962 | 9981 | 615 |
| 472197 | 342 | 361 | GCGCGACAGCGCAGGTCCTC | 57 | 9963 | 9982 | 616 |
| 472198 | 343 | 362 | CGCGCGACAGCGCAGGTCCT | 58 | 9964 | 9983 | 617 |
| 472199 | 344 | 363 | TCGCGCGACAGCGCAGGTCC | 53 | 9965 | 9984 | 618 |
| 472200 | 345 | 364 | CTCGCGCGACAGCGCAGGTC | 52 | 9966 | 9985 | 619 |
| 472201 | 346 | 365 | CCTCGCGCGACAGCGCAGGT | 26 | 9967 | 9986 | 620 |
| 472202 | 347 | 366 | CCCTCGCGCGACAGCGCAGG | 32 | 9968 | 9987 | 621 |
| 472203 | 349 | 368 | ACCCCTCGCGCGACAGCGCA | 67 | 9970 | 9989 | 622 |
| 472204 | 350 | 369 | GACCCCTCGCGCGACAGCGC | 72 | 9971 | 9990 | 623 |
| 472205 | 351 | 370 | AGACCCCTCGCGCGACAGCG | 74 | 9972 | 9991 | 624 |
| 472206 | 352 | 371 | CAGACCCCTCGCGCGACAGC | 67 | 9973 | 9992 | 625 |
| 472207 | 353 | 372 | CCAGACCCCTCGCGCGACAG | 53 | 9974 | 9993 | 626 |
| 472208 | 354 | 373 | CCCAGACCCCTCGCGCGACA | 70 | 9975 | 9994 | 627 |

TABLE 11-continued

Inhibition of DGAT2 mRNA by 5-10-5 MOE gapmers targeting SEQ ID NOs: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472209 | 356 | 375 | CTCCCAGACCCCTCGCGCGA | 50 | 9977 | 9996 | 628 |
| 472210 | 357 | 376 | TCTCCCAGACCCCTCGCGCG | 31 | 9978 | 9997 | 629 |
| 472211 | 358 | 377 | ATCTCCCAGACCCCTCGCGC | 54 | 9979 | 9998 | 630 |
| 472212 | 359 | 378 | CATCTCCCAGACCCCTCGCG | 51 | 9980 | 9999 | 631 |
| 472213 | 360 | 379 | CCATCTCCCAGACCCCTCGC | 42 | 9981 | 10000 | 632 |
| 472214 | 362 | 381 | CCCCATCTCCCAGACCCCTC | 48 | 9983 | 10002 | 633 |
| 472215 | 363 | 382 | GCCCCATCTCCCAGACCCCT | 32 | n/a | n/a | 634 |
| 472216 | 364 | 383 | TGCCCCATCTCCCAGACCCC | 46 | n/a | n/a | 635 |
| 472217 | 365 | 384 | GTGCCCCATCTCCCAGACCC | 43 | n/a | n/a | 636 |
| 472218 | 366 | 385 | AGTGCCCCATCTCCCAGACC | 19 | n/a | n/a | 637 |
| 472219 | 368 | 387 | CCAGTGCCCCATCTCCCAGA | 9 | n/a | n/a | 638 |
| 472220 | 369 | 388 | TCCAGTGCCCCATCTCCCAG | 0 | n/a | n/a | 639 |
| 472221 | 371 | 390 | GATCCAGTGCCCCATCTCCC | 0 | n/a | n/a | 640 |
| 472222 | 372 | 391 | GGATCCAGTGCCCCATCTCC | 2 | n/a | n/a | 641 |
| 472223 | 374 | 393 | CTGGATCCAGTGCCCCATCT | 31 | n/a | n/a | 642 |
| 472224 | 375 | 394 | GCTGGATCCAGTGCCCCATC | 39 | n/a | n/a | 643 |
| 472225 | 377 | 396 | ATGCTGGATCCAGTGCCCCA | 36 | n/a | n/a | 644 |
| 472226 | 378 | 397 | GATGCTGGATCCAGTGCCCC | 18 | n/a | n/a | 645 |
| 472227 | 380 | 399 | AGGATGCTGGATCCAGTGCC | 41 | 25506 | 25525 | 646 |
| 472228 | 381 | 400 | GAGGATGCTGGATCCAGTGC | 17 | 25507 | 25526 | 647 |
| 472229 | 383 | 402 | GAGAGGATGCTGGATCCAGT | 6 | 25509 | 25528 | 648 |

TABLE 12

Inhibition of DGAT2 mRNA by 5-10-5 MOE gapmers targeting SEQ ID NOs: 1 and 2

| ISIS NO | SEQ ID NO: 1 Start Site | SEQ ID NO: 1 Stop Site | Sequence | # inhibition | SEQ ID NO: 2 Start Site | SEQ ID NO: 2 Stop Site | SEQ ID NO |
|---|---|---|---|---|---|---|---|
| 413433 | n/a | n/a | GCCTGGACAAGTCCTGCCCA | 75 | 32431 | 32450 | 425 |
| 472373 | 782 | 801 | ACTTCTGTGGCCTCTGTGCT | 31 | 37310 | 37329 | 649 |
| 472374 | 784 | 803 | TCACTTCTGTGGCCTCTGTG | 42 | 37312 | 37331 | 650 |
| 472375 | 785 | 804 | CTCACTTCTGTGGCCTCTGT | 53 | 37313 | 37332 | 651 |
| 472376 | 787 | 806 | TGCTCACTTCTGTGGCCTCT | 66 | 37315 | 37334 | 652 |
| 472377 | 788 | 807 | TTGCTCACTTCTGTGGCCTC | 78 | 37316 | 37335 | 653 |
| 472378 | 790 | 809 | TCTTGCTCACTTCTGTGGCC | 57 | 37318 | 37337 | 654 |
| 472379 | 791 | 810 | TTCTTGCTCACTTCTGTGGC | 43 | 37319 | 37338 | 655 |
| 472380 | 793 | 812 | ACTTCTTGCTCACTTCTGTG | 41 | 37321 | 37340 | 656 |
| 472381 | 794 | 813 | AACTTCTTGCTCACTTCTGT | 14 | 37322 | 37341 | 657 |
| 472382 | 796 | 815 | GGAACTTCTTGCTCACTTCT | 39 | 37324 | 37343 | 658 |

TABLE 12-continued

Inhibition of DGAT2 mRNA by 5-10-5 MOE gapmers targeting SEQ ID NOs: 1 and 2

| ISIS NO | SEQ ID NO: 1 Start Site | SEQ ID NO: 1 Stop Site | Sequence | # inhibition | SEQ ID NO: 2 Start Site | SEQ ID NO: 2 Stop Site | SEQ ID NO |
|---|---|---|---|---|---|---|---|
| 472383 | 797 | 816 | GGGAACTTCTTGCTCACTTC | 47 | 37325 | 37344 | 659 |
| 472384 | 799 | 818 | CTGGGAACTTCTTGCTCACT | 65 | 37327 | 37346 | 660 |
| 472385 | 800 | 819 | CCTGGGAACTTCTTGCTCAC | 0 | 37328 | 37347 | 661 |
| 472386 | 802 | 821 | TGCCTGGGAACTTCTTGCTC | 54 | 37330 | 37349 | 662 |
| 472387 | 803 | 822 | ATGCCTGGGAACTTCTTGCT | 24 | 37331 | 37350 | 663 |
| 472388 | 805 | 824 | GTATGCCTGGGAACTTCTTG | 26 | 37333 | 37352 | 664 |
| 472389 | 806 | 825 | CGTATGCCTGGGAACTTCTT | 46 | 37334 | 37353 | 665 |
| 472390 | 807 | 826 | CCGTATGCCTGGGAACTTCT | 41 | 37335 | 37354 | 666 |
| 472391 | 809 | 828 | GGCCGTATGCCTGGGAACTT | 47 | 37337 | 37356 | 667 |
| 472392 | 810 | 829 | AGGCCGTATGCCTGGGAACT | 45 | 37338 | 37357 | 668 |
| 472393 | 812 | 831 | TAAGGCCGTATGCCTGGGAA | 38 | 37340 | 37359 | 669 |
| 472394 | 813 | 832 | GTAAGGCCGTATGCCTGGGA | 53 | 37341 | 37360 | 670 |
| 472395 | 821 | 840 | GTAGCCAGGTAAGGCCGTAT | 53 | 37349 | 37368 | 671 |
| 472396 | 822 | 841 | TGTAGCCAGGTAAGGCCGTA | 41 | 37350 | 37369 | 672 |
| 472397 | 824 | 843 | AGTGTAGCCAGGTAAGGCCG | 36 | 37352 | 37371 | 673 |
| 472398 | 825 | 844 | CAGTGTAGCCAGGTAAGGCC | 63 | 37353 | 37372 | 674 |
| 472399 | 826 | 845 | CCAGTGTAGCCAGGTAAGGC | 45 | 37354 | 37373 | 675 |
| 472400 | 862 | 881 | GGTACTCCCTCAACACAGGC | 42 | 37390 | 37409 | 676 |
| 472401 | 863 | 882 | AGGTACTCCCTCAACACAGG | 11 | 37391 | 37410 | 677 |
| 472402 | 865 | 884 | TCAGGTACTCCCTCAACACA | 20 | 37393 | 37412 | 678 |
| 472403 | 866 | 885 | ATCAGGTACTCCCTCAACAC | 13 | 37394 | 37413 | 679 |
| 472404 | 868 | 887 | ACATCAGGTACTCCCTCAAC | 11 | 37396 | 37415 | 680 |
| 472405 | 869 | 888 | GACATCAGGTACTCCCTCAA | 27 | 37397 | 37416 | 681 |
| 472406 | 871 | 890 | CAGACATCAGGTACTCCCTC | 39 | 37399 | 37418 | 682 |
| 472407 | 872 | 891 | CCAGACATCAGGTACTCCCT | 46 | 37400 | 37419 | 683 |
| 472408 | 873 | 892 | TCCAGACATCAGGTACTCCC | 32 | 37401 | 37420 | 684 |
| 472409 | 874 | 893 | CTCCAGACATCAGGTACTCC | 29 | 37402 | 37421 | 685 |
| 472410 | 879 | 898 | GATACCTCCAGACATCAGGT | 33 | n/a | n/a | 686 |
| 472411 | 880 | 899 | AGATACCTCCAGACATCAGG | 17 | n/a | n/a | 687 |
| 472412 | 882 | 901 | GCAGATACCTCCAGACATCA | 9 | n/a | n/a | 688 |
| 472413 | 883 | 902 | GGCAGATACCTCCAGACATC | 44 | n/a | n/a | 689 |
| 472414 | 885 | 904 | AGGGCAGATACCTCCAGACA | 0 | n/a | n/a | 690 |
| 472415 | 886 | 905 | CAGGGCAGATACCTCCAGAC | 16 | n/a | n/a | 691 |
| 472416 | 888 | 907 | GACAGGGCAGATACCTCCAG | 1 | n/a | n/a | 692 |
| 472417 | 889 | 908 | TGACAGGGCAGATACCTCCA | 31 | n/a | n/a | 693 |
| 472418 | 911 | 930 | AAATAGTCTATGGTGTCCCG | 25 | 38064 | 38083 | 694 |
| 472419 | 912 | 931 | CAAATAGTCTATGGTGTCCC | 32 | 38065 | 38084 | 695 |

TABLE 12-continued

Inhibition of DGAT2 mRNA by 5-10-5 MOE gapmers targeting SEQ ID NOs: 1 and 2

| ISIS NO | SEQ ID NO: 1 Start Site | SEQ ID NO: 1 Stop Site | Sequence | # inhibition | SEQ ID NO: 2 Start Site | SEQ ID NO: 2 Stop Site | SEQ ID NO |
|---|---|---|---|---|---|---|---|
| 472420 | 914 | 933 | AGCAAATAGTCTATGGTGTC | 54 | 38067 | 38086 | 696 |
| 472421 | 915 | 934 | AAGCAAATAGTCTATGGTGT | 22 | 38068 | 38087 | 697 |
| 472422 | 917 | 936 | GAAAGCAAATAGTCTATGGT | 24 | 38070 | 38089 | 698 |
| 472423 | 918 | 937 | TGAAAGCAAATAGTCTATGG | 19 | 38071 | 38090 | 699 |
| 472424 | 920 | 939 | TTTGAAAGCAAATAGTCTAT | 17 | 38073 | 38092 | 700 |
| 472425 | 921 | 940 | CTTTGAAAGCAAATAGTCTA | 0 | 38074 | 38093 | 701 |
| 472426 | 923 | 942 | TTCTTTGAAAGCAAATAGTC | 24 | 38076 | 38095 | 702 |
| 472427 | 924 | 943 | ATTCTTTGAAAGCAAATAGT | 9 | 38077 | 38096 | 703 |
| 472428 | 926 | 945 | CCATTCTTTGAAAGCAAATA | 31 | 38079 | 38098 | 704 |
| 472429 | 927 | 946 | CCCATTCTTTGAAAGCAAAT | 48 | 38080 | 38099 | 705 |
| 380132 | 929 | 948 | CTCCCATTCTTTGAAAGCAA | 75 | 38082 | 38101 | 706 |
| 472430 | 930 | 949 | ACTCCCATTCTTTGAAAGCA | 35 | 38083 | 38102 | 707 |
| 472431 | 931 | 950 | CACTCCCATTCTTTGAAAGC | 35 | 38084 | 38103 | 708 |
| 472432 | 933 | 952 | GCCACTCCCATTCTTTGAAA | 69 | 38086 | 38105 | 709 |
| 472433 | 934 | 953 | TGCCACTCCCATTCTTTGAA | 73 | 38087 | 38106 | 710 |
| 217328 | 938 | 957 | GCATTGCCACTCCCATTCTT | 76 | 38091 | 38110 | 144 |
| 472434 | 944 | 963 | ATGATAGCATTGCCACTCCC | 65 | 38097 | 38116 | 711 |
| 472435 | 945 | 964 | GATGATAGCATTGCCACTCC | 50 | 38098 | 38117 | 712 |
| 472436 | 946 | 965 | TGATGATAGCATTGCCACTC | 56 | 38099 | 38118 | 713 |
| 380134 | 947 | 966 | ATGATGATAGCATTGCCACT | 34 | 38100 | 38119 | 714 |
| 472437 | 949 | 968 | CGATGATGATAGCATTGCCA | 56 | 38102 | 38121 | 715 |
| 472438 | 950 | 969 | ACGATGATGATAGCATTGCC | 51 | 38103 | 38122 | 716 |
| 472439 | 951 | 970 | CACGATGATGATAGCATTGC | 56 | 38104 | 38123 | 717 |
| 472440 | 952 | 971 | CCACGATGATGATAGCATTG | 63 | 38105 | 38124 | 718 |
| 472441 | 974 | 993 | AGAGACTCAGCCGCACCCCC | 63 | 38127 | 38146 | 719 |
| 472442 | 975 | 994 | CAGAGACTCAGCCGCACCCC | 66 | 38128 | 38147 | 720 |
| 366730 | 979 | 998 | AGCTCAGAGACTCAGCCGCA | 67 | 38132 | 38151 | 150 |
| 423442 | 980 | 999 | GAGCTCAGAGACTCAGCCGC | 52 | 38133 | 38152 | 489 |
| 423444 | 982 | 1001 | TGGAGCTCAGAGACTCAGCC | 63 | 38135 | 38154 | 153 |
| 472443 | 989 | 1008 | CCAGGCATGGAGCTCAGAGA | 47 | 38142 | 38161 | 721 |

TABLE 13

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413433 | n/a | n/a | GCCTGGACAAGTCCTGCCCA | 94 | 32431 | 32450 | 425 |
| 472230 | 384 | 403 | GGAGAGGATGCTGGATCCAG | 38 | 25510 | 25529 | 722 |
| 472231 | 386 | 405 | GCGGAGAGGATGCTGGATCC | 41 | 25512 | 25531 | 723 |
| 472232 | 387 | 406 | GGCGGAGAGGATGCTGGATC | 28 | 25513 | 25532 | 724 |
| 472233 | 389 | 408 | AGGGCGGAGAGGATGCTGGA | 0 | 25515 | 25534 | 725 |
| 472234 | 390 | 409 | GAGGGCGGAGAGGATGCTGG | 66 | 25516 | 25535 | 726 |
| 472235 | 391 | 410 | GGAGGGCGGAGAGGATGCTG | 28 | 25517 | 25536 | 727 |
| 472236 | 392 | 411 | TGGAGGGCGGAGAGGATGCT | 35 | 25518 | 25537 | 728 |
| 472237 | 394 | 413 | CCTGGAGGGCGGAGAGGATG | 9 | 25520 | 25539 | 729 |
| 472238 | 395 | 414 | TCCTGGAGGGCGGAGAGGAT | 0 | 25521 | 25540 | 730 |
| 472239 | 397 | 416 | GGTCCTGGAGGGCGGAGAGG | 0 | 25523 | 25542 | 731 |
| 472240 | 398 | 417 | AGGTCCTGGAGGGCGGAGAG | 32 | 25524 | 25543 | 732 |
| 472241 | 399 | 418 | GAGGTCCTGGAGGGCGGAGA | 33 | 25525 | 25544 | 733 |
| 472242 | 400 | 419 | AGAGGTCCTGGAGGGCGGAG | 0 | 25526 | 25545 | 734 |
| 472243 | 401 | 420 | AAGAGGTCCTGGAGGGCGGA | 35 | 25527 | 25546 | 735 |
| 472244 | 402 | 421 | GAAGAGGTCCTGGAGGGCGG | 16 | 25528 | 25547 | 736 |
| 472245 | 403 | 422 | AGAAGAGGTCCTGGAGGGCG | 53 | 25529 | 25548 | 737 |
| 366710 | 425 | 444 | GACCTATTGAGCCAGGTGAC | 62 | 25551 | 25570 | 146 |
| 472246 | 426 | 445 | GGACCTATTGAGCCAGGTGA | 63 | 25552 | 25571 | 738 |
| 472247 | 427 | 446 | TGGACCTATTGAGCCAGGTG | 58 | 25553 | 25572 | 739 |
| 472248 | 428 | 447 | TTGGACCTATTGAGCCAGGT | 71 | 25554 | 25573 | 740 |
| 472249 | 429 | 448 | CTTGGACCTATTGAGCCAGG | 63 | 25555 | 25574 | 741 |
| 472250 | 431 | 450 | ACCTTGGACCTATTGAGCCA | 80 | 25557 | 25576 | 742 |
| 472251 | 432 | 451 | CACCTTGGACCTATTGAGCC | 70 | 25558 | 25577 | 743 |
| 472252 | 433 | 452 | CCACCTTGGACCTATTGAGC | 74 | 25559 | 25578 | 744 |
| 472253 | 434 | 453 | TCCACCTTGGACCTATTGAG | 68 | 25560 | 25579 | 745 |
| 472254 | 436 | 455 | TTTCCACCTTGGACCTATTG | 41 | 25562 | 25581 | 746 |
| 472255 | 437 | 456 | TTTTCCACCTTGGACCTATT | 43 | 25563 | 25582 | 747 |
| 472256 | 438 | 457 | CTTTTCCACCTTGGACCTAT | 48 | 25564 | 25583 | 748 |
| 472257 | 439 | 458 | GCTTTTCCACCTTGGACCTA | 75 | 25565 | 25584 | 749 |
| 472258 | 441 | 460 | CTGCTTTTCCACCTTGGACC | 83 | 25567 | 25586 | 750 |
| 472259 | 442 | 461 | GCTGCTTTTCCACCTTGGAC | 83 | 25568 | 25587 | 751 |
| 472260 | 443 | 462 | AGCTGCTTTTCCACCTTGGA | 84 | 25569 | 25588 | 152 |
| 472261 | 444 | 463 | TAGCTGCTTTTCCACCTTGG | 76 | 25570 | 25589 | 752 |
| 366714 | 445 | 464 | GTAGCTGCTTTTCCACCTTG | 70 | 25571 | 25590 | 147 |
| 472262 | 446 | 465 | TGTAGCTGCTTTTCCACCTT | 39 | 25572 | 25591 | 753 |

TABLE 13-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472263 | 447 | 466 | CTGTAGCTGCTTTTCCACCT | 72 | 25573 | 25592 | 754 |
| 380086 | 449 | 468 | ACCTGTAGCTGCTTTTCCAC | 70 | 25575 | 25594 | 755 |
| 472264 | 450 | 469 | GACCTGTAGCTGCTTTTCCA | 77 | 25576 | 25595 | 756 |
| 472265 | 452 | 471 | ATGACCTGTAGCTGCTTTTC | 57 | 25578 | 25597 | 757 |
| 472266 | 453 | 472 | GATGACCTGTAGCTGCTTTT | 74 | 25579 | 25598 | 758 |
| 472267 | 454 | 473 | AGATGACCTGTAGCTGCTTT | 67 | 25580 | 25599 | 759 |
| 472268 | 456 | 475 | TGAGATGACCTGTAGCTGCT | 77 | 25582 | 25601 | 760 |
| 472269 | 457 | 476 | CTGAGATGACCTGTAGCTGC | 78 | 25583 | 25602 | 761 |
| 472270 | 459 | 478 | CACTGAGATGACCTGTAGCT | 80 | 25585 | 25604 | 762 |
| 472271 | 460 | 479 | GCACTGAGATGACCTGTAGC | 77 | 25586 | 25605 | 763 |
| 472272 | 462 | 481 | GAGCACTGAGATGACCTGTA | 71 | 25588 | 25607 | 764 |
| 472273 | 463 | 482 | GGAGCACTGAGATGACCTGT | 75 | 25589 | 25608 | 765 |
| 472274 | 465 | 484 | CTGGAGCACTGAGATGACCT | 72 | 25591 | 25610 | 766 |
| 472275 | 466 | 485 | ACTGGAGCACTGAGATGACC | 62 | 25592 | 25611 | 767 |
| 423453 | 474 | 493 | CAGGACCCACTGGAGCACTG | 92 | 25600 | 25619 | 457 |
| 472276 | 477 | 496 | GGACAGGACCCACTGGAGCA | 72 | 25603 | 25622 | 768 |
| 472277 | 478 | 497 | AGGACAGGACCCACTGGAGC | 74 | 25604 | 25623 | 769 |
| 472278 | 480 | 499 | GAAGGACAGGACCCACTGGA | 53 | 25606 | 25625 | 770 |
| 472279 | 481 | 500 | GGAAGGACAGGACCCACTGG | 48 | 25607 | 25626 | 771 |
| 472280 | 483 | 502 | AAGGAAGGACAGGACCCACT | 54 | 25609 | 25628 | 772 |
| 472281 | 484 | 503 | CAAGGAAGGACAGGACCCAC | 40 | 25610 | 25629 | 773 |
| 472282 | 485 | 504 | ACAAGGAAGGACAGGACCCA | 65 | 25611 | 25630 | 774 |
| 472283 | 487 | 506 | GTACAAGGAAGGACAGGACC | 55 | 25613 | 25632 | 775 |
| 472284 | 488 | 507 | AGTACAAGGAAGGACAGGAC | 35 | 25614 | 25633 | 776 |
| 472285 | 489 | 508 | CAGTACAAGGAAGGACAGGA | 40 | 25615 | 25634 | 777 |
| 472286 | 490 | 509 | CCAGTACAAGGAAGGACAGG | 32 | 25616 | 25635 | 778 |
| 472287 | 492 | 511 | TCCCAGTACAAGGAAGGACA | 58 | n/a | n/a | 779 |
| 472288 | 493 | 512 | CTCCCAGTACAAGGAAGGAC | 33 | n/a | n/a | 780 |
| 472289 | 495 | 514 | CACTCCCAGTACAAGGAAGG | 47 | n/a | n/a | 781 |
| 472290 | 496 | 515 | CCACTCCCAGTACAAGGAAG | 4 | n/a | n/a | 782 |
| 472291 | 498 | 517 | GGCCACTCCCAGTACAAGGA | 12 | n/a | n/a | 783 |
| 472292 | 499 | 518 | AGGCCACTCCCAGTACAAGG | 2 | n/a | n/a | 784 |
| 472293 | 501 | 520 | GCAGGCCACTCCCAGTACAA | 0 | n/a | n/a | 785 |
| 472294 | 502 | 521 | TGCAGGCCACTCCCAGTACA | 0 | n/a | n/a | 786 |
| 472295 | 504 | 523 | ACTGCAGGCCACTCCCAGTA | 43 | n/a | n/a | 787 |

TABLE 13-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472296 | 505 | 524 | CACTGCAGGCCACTCCCAGT | 14 | n/a | n/a | 788 |
| 472297 | 507 | 526 | GGCACTGCAGGCCACTCCCA | 73 | n/a | n/a | 789 |
| 472298 | 508 | 527 | TGGCACTGCAGGCCACTCCC | 25 | n/a | n/a | 790 |
| 472299 | 509 | 528 | ATGGCACTGCAGGCCACTCC | 46 | 31076 | 31095 | 791 |
| 472300 | 511 | 530 | GGATGGCACTGCAGGCCACT | 43 | 31078 | 31097 | 792 |
| 472301 | 512 | 531 | AGGATGGCACTGCAGGCCAC | 61 | 31079 | 31098 | 793 |
| 472302 | 513 | 532 | GAGGATGGCACTGCAGGCCA | 69 | 31080 | 31099 | 794 |

TABLE 14

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413433 | n/a | n/a | GCCTGGACAAGTCCTGCCCA | 90 | 32431 | 32450 | 425 |
| 472303 | 514 | 533 | TGAGGATGGCACTGCAGGCC | 45 | 31081 | 31100 | 795 |
| 472304 | 516 | 535 | CATGAGGATGGCACTGCAGG | 24 | 31083 | 31102 | 796 |
| 472305 | 517 | 536 | ACATGAGGATGGCACTGCAG | 19 | 31084 | 31103 | 797 |
| 472306 | 518 | 537 | TACATGAGGATGGCACTGCA | 59 | 31085 | 31104 | 798 |
| 472307 | 521 | 540 | ATGTACATGAGGATGGCACT | 32 | 31088 | 31107 | 799 |
| 472308 | 522 | 541 | TATGTACATGAGGATGGCAC | 22 | 31089 | 31108 | 800 |
| 472309 | 523 | 542 | ATATGTACATGAGGATGGCA | 39 | 31090 | 31109 | 801 |
| 472310 | 524 | 543 | AATATGTACATGAGGATGGC | 34 | 31091 | 31110 | 802 |
| 472311 | 526 | 545 | AGAATATGTACATGAGGATG | 1 | 31093 | 31112 | 803 |
| 472312 | 527 | 546 | CAGAATATGTACATGAGGAT | 48 | 31094 | 31113 | 804 |
| 472313 | 528 | 547 | GCAGAATATGTACATGAGGA | 44 | 31095 | 31114 | 805 |
| 472314 | 529 | 548 | TGCAGAATATGTACATGAGG | 43 | 31096 | 31115 | 806 |
| 366722 | 530 | 549 | GTGCAGAATATGTACATGAG | 65 | 31097 | 31116 | 148 |
| 472315 | 552 | 571 | CACAGCGATGAGCCAGCAAT | 65 | 31119 | 31138 | 807 |
| 472316 | 553 | 572 | GCACAGCGATGAGCCAGCAA | 84 | 31120 | 31139 | 808 |
| 472317 | 555 | 574 | GAGCACAGCGATGAGCCAGC | 87 | 31122 | 31141 | 809 |
| 472318 | 556 | 575 | AGAGCACAGCGATGAGCCAG | 83 | 31123 | 31142 | 810 |
| 472319 | 558 | 577 | GTAGAGCACAGCGATGAGCC | 73 | 31125 | 31144 | 811 |
| 472320 | 559 | 578 | AGTAGAGCACAGCGATGAGC | 68 | 31126 | 31145 | 812 |
| 472321 | 560 | 579 | AAGTAGAGCACAGCGATGAG | 48 | 31127 | 31146 | 813 |
| 472322 | 561 | 580 | GAAGTAGAGCACAGCGATGA | 22 | 31128 | 31147 | 814 |

TABLE 14-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472323 | 563 | 582 | GTGAAGTAGAGCACAGCGAT | 64 | 31130 | 31149 | 815 |
| 472324 | 564 | 583 | AGTGAAGTAGAGCACAGCGA | 51 | 31131 | 31150 | 816 |
| 472325 | 565 | 584 | AAGTGAAGTAGAGCACAGCG | 39 | 31132 | 31151 | 817 |
| 472326 | 566 | 585 | CAAGTGAAGTAGAGCACAGC | 26 | 31133 | 31152 | 818 |
| 472327 | 568 | 587 | GCCAAGTGAAGTAGAGCACA | 64 | 31135 | 31154 | 819 |
| 472328 | 569 | 588 | AGCCAAGTGAAGTAGAGCAC | 65 | 31136 | 31155 | 820 |
| 472329 | 571 | 590 | CCAGCCAAGTGAAGTAGAGC | 51 | 31138 | 31157 | 821 |
| 472330 | 572 | 591 | ACCAGCCAAGTGAAGTAGAG | 47 | 31139 | 31158 | 822 |
| 472331 | 574 | 593 | ACACCAGCCAAGTGAAGTAG | 35 | 31141 | 31160 | 823 |
| 472332 | 575 | 594 | AACACCAGCCAAGTGAAGTA | 34 | 31142 | 31161 | 824 |
| 472333 | 577 | 596 | CAAACACCAGCCAAGTGAAG | 33 | 31144 | 31163 | 825 |
| 472334 | 578 | 597 | TCAAACACCAGCCAAGTGAA | 34 | 31145 | 31164 | 826 |
| 472335 | 580 | 599 | AGTCAAACACCAGCCAAGTG | 39 | 31147 | 31166 | 827 |
| 472336 | 581 | 600 | CAGTCAAACACCAGCCAAGT | 37 | 31148 | 31167 | 828 |
| 472337 | 583 | 602 | TCCAGTCAAACACCAGCCAA | 53 | 31150 | 31169 | 829 |
| 472338 | 584 | 603 | TTCCAGTCAAACACCAGCCA | 52 | 31151 | 31170 | 830 |
| 472339 | 586 | 605 | TGTTCCAGTCAAACACCAGC | 38 | 31153 | 31172 | 831 |
| 472340 | 587 | 606 | GTGTTCCAGTCAAACACCAG | 43 | 31154 | 31173 | 832 |
| 472341 | 589 | 608 | GTGTGTTCCAGTCAAACACC | 26 | 31156 | 31175 | 833 |
| 472342 | 590 | 609 | GGTGTGTTCCAGTCAAACAC | 41 | 31157 | 31176 | 834 |
| 472343 | 592 | 611 | TGGGTGTGTTCCAGTCAAAC | 7 | 31159 | 31178 | 835 |
| 472344 | 593 | 612 | TTGGGTGTGTTCCAGTCAAA | 15 | 31160 | 31179 | 836 |
| 472345 | 595 | 614 | TCTTGGGTGTGTTCCAGTCA | 54 | 31162 | 31181 | 837 |
| 472346 | 596 | 615 | TTCTTGGGTGTGTTCCAGTC | 47 | 31163 | 31182 | 838 |
| 472347 | 616 | 635 | ACTGTGACCTCCTGCCACCT | 66 | 31548 | 31567 | 839 |
| 472348 | 617 | 636 | CACTGTGACCTCCTGCCACC | 55 | 31549 | 31568 | 840 |
| 472349 | 619 | 638 | CCCACTGTGACCTCCTGCCA | 79 | 31551 | 31570 | 841 |
| 472350 | 620 | 639 | ACCCACTGTGACCTCCTGCC | 77 | 31552 | 31571 | 842 |
| 472351 | 622 | 641 | GGACCCACTGTGACCTCCTG | 80 | 31554 | 31573 | 843 |
| 472352 | 623 | 642 | CGGACCCACTGTGACCTCCT | 63 | 31555 | 31574 | 844 |
| 472353 | 624 | 643 | TCGGACCCACTGTGACCTCC | 82 | 31556 | 31575 | 845 |
| 423459 | 631 | 650 | CCCAGTTTCGGACCCACTGT | 49 | 31563 | 31582 | 463 |
| 472354 | 633 | 652 | AGCCCAGTTTCGGACCCACT | 79 | 31565 | 31584 | 846 |
| 472355 | 634 | 653 | CAGCCCAGTTTCGGACCCAC | 48 | 31566 | 31585 | 847 |
| 472356 | 636 | 655 | CACAGCCCAGTTTCGGACCC | 72 | 31568 | 31587 | 848 |

TABLE 14-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472357 | 637 | 656 | ACACAGCCCAGTTTCGGACC | 63 | 31569 | 31588 | 849 |
| 472358 | 639 | 658 | CCACACAGCCCAGTTTCGGA | 75 | 31571 | 31590 | 850 |
| 472359 | 640 | 659 | GCCACACAGCCCAGTTTCGG | 74 | 31572 | 31591 | 851 |
| 472360 | 641 | 660 | CGCCACACAGCCCAGTTTCG | 77 | 31573 | 31592 | 852 |
| 472361 | 659 | 678 | AAGTAGTCTCGAAAGTAGCG | 7 | 31591 | 31610 | 853 |
| 472362 | 660 | 679 | AAAGTAGTCTCGAAAGTAGC | 0 | 31592 | 31611 | 854 |
| 472363 | 662 | 681 | GGAAAGTAGTCTCGAAAGTA | 15 | 31594 | 31613 | 855 |
| 472364 | 663 | 682 | GGGAAAGTAGTCTCGAAAGT | 0 | 31595 | 31614 | 856 |
| 472365 | 664 | 683 | TGGGAAAGTAGTCTCGAAAG | 57 | 31596 | 31615 | 857 |
| 472366 | 666 | 685 | GATGGGAAAGTAGTCTCGAA | 17 | 31598 | 31617 | 858 |
| 472367 | 667 | 686 | GGATGGGAAAGTAGTCTCGA | 21 | 31599 | 31618 | 859 |
| 411897 | 685 | 704 | TGTGTGTCTTCACCAGCTGG | 41 | n/a | n/a | 60 |
| 217317 | 693 | 712 | CAGCAGGTTGTGTGTCTTCA | 57 | 37221 | 37240 | 21 |
| 411901 | 695 | 714 | GTCAGCAGGTTGTGTGTCTT | 45 | 37223 | 37242 | 64 |
| 411902 | 697 | 716 | TGGTCAGCAGGTTGTGTGTC | 28 | 37225 | 37244 | 65 |
| 472368 | 724 | 743 | GGTGGTATCCAAAGATATAG | 50 | 37252 | 37271 | 860 |
| 472369 | 725 | 744 | GGGTGGTATCCAAAGATATA | 27 | 37253 | 37272 | 861 |
| 366728 | 757 | 776 | TGCAGAAGGCACCCAGGCCC | 63 | 37285 | 37304 | 149 |
| 472370 | 758 | 777 | TTGCAGAAGGCACCCAGGCC | 31 | 37286 | 37305 | 862 |
| 472371 | 759 | 778 | GTTGCAGAAGGCACCCAGGC | 46 | 37287 | 37306 | 863 |
| 472372 | 781 | 800 | CTTCTGTGGCCTCTGTGCTG | 33 | 37309 | 37328 | 864 |

TABLE 15

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413433 | n/a | n/a | GCCTGGACAAGTCCTGCCCA | 89 | 32431 | 32450 | 425 |
| 472521 | 1210 | 1229 | TGTCGGAGGAGAAGAGGCCT | 32 | 39257 | 39276 | 865 |
| 472522 | 1212 | 1231 | GGTGTCGGAGGAGAAGAGGC | 0 | 39259 | 39278 | 866 |
| 472523 | 1213 | 1232 | AGGTGTCGGAGGAGAAGAGG | 0 | 39260 | 39279 | 867 |
| 472524 | 1214 | 1233 | CAGGTGTCGGAGGAGAAGAG | 9 | 39261 | 39280 | 868 |
| 472525 | 1216 | 1235 | CCCAGGTGTCGGAGGAGAAG | 3 | 39263 | 39282 | 869 |
| 472526 | 1217 | 1236 | CCCCAGGTGTCGGAGGAGAA | 36 | 39264 | 39283 | 870 |
| 472527 | 1219 | 1238 | GCCCCCAGGTGTCGGAGGAG | 10 | 39266 | 39285 | 871 |

TABLE 15-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472528 | 1220 | 1239 | AGCCCCCAGGTGTCGGAGGA | 13 | 39267 | 39286 | 872 |
| 472529 | 1221 | 1240 | CAGCCCCCAGGTGTCGGAGG | 32 | 39268 | 39287 | 873 |
| 472530 | 1223 | 1242 | ACCAGCCCCCAGGTGTCGGA | 40 | 39270 | 39289 | 874 |
| 472531 | 1251 | 1270 | AACAGTGGTGATGGGCTTGG | 17 | 39298 | 39317 | 875 |
| 472532 | 1252 | 1271 | CAACAGTGGTGATGGGCTTG | 28 | 39299 | 39318 | 876 |
| 472533 | 1323 | 1342 | CATGGTGTGGTACAGGTCGA | 42 | 41294 | 41313 | 877 |
| 472534 | 1324 | 1343 | ACATGGTGTGGTACAGGTCG | 63 | 41295 | 41314 | 878 |
| 411878 | 1325 | 1344 | TACATGGTGTGGTACAGGTC | 63 | 41296 | 41315 | 879 |
| 472535 | 1326 | 1345 | GTACATGGTGTGGTACAGGT | 70 | 41297 | 41316 | 880 |
| 472536 | 1328 | 1347 | ATGTACATGGTGTGGTACAG | 56 | 41299 | 41318 | 881 |
| 472537 | 1329 | 1348 | CATGTACATGGTGTGGTACA | 50 | 41300 | 41319 | 882 |
| 472538 | 1331 | 1350 | TCCATGTACATGGTGTGGTA | 53 | 41302 | 41321 | 883 |
| 472539 | 1332 | 1351 | CTCCATGTACATGGTGTGGT | 68 | 41303 | 41322 | 884 |
| 472540 | 1333 | 1352 | CCTCCATGTACATGGTGTGG | 63 | 41304 | 41323 | 885 |
| 472541 | 1335 | 1354 | GGCCTCCATGTACATGGTGT | 48 | 41306 | 41325 | 886 |
| 472542 | 1336 | 1355 | GGGCCTCCATGTACATGGTG | 51 | 41307 | 41326 | 887 |
| 472543 | 1337 | 1356 | AGGGCCTCCATGTACATGGT | 56 | 41308 | 41327 | 888 |
| 369255 | 1339 | 1358 | CCAGGGCCTCCATGTACATG | 35 | 41310 | 41329 | 103 |
| 411944 | 1340 | 1359 | ACCAGGGCCTCCATGTACAT | 47 | 41311 | 41330 | 120 |
| 411947 | 1344 | 1363 | CTTCACCAGGGCCTCCATGT | 22 | 41315 | 41334 | 123 |
| 411948 | 1345 | 1364 | GCTTCACCAGGGCCTCCATG | 43 | 41316 | 41335 | 124 |
| 411950 | 1347 | 1366 | GAGCTTCACCAGGGCCTCCA | 47 | 41318 | 41337 | 126 |
| 411951 | 1349 | 1368 | AAGAGCTTCACCAGGGCCTC | 51 | 41320 | 41339 | 127 |
| 472544 | 1352 | 1371 | TCGAAGAGCTTCACCAGGGC | 60 | 41323 | 41342 | 889 |
| 472545 | 1353 | 1372 | GTCGAAGAGCTTCACCAGGG | 73 | 41324 | 41343 | 890 |
| 472546 | 1355 | 1374 | TTGTCGAAGAGCTTCACCAG | 45 | 41326 | 41345 | 891 |
| 472547 | 1356 | 1375 | CTTGTCGAAGAGCTTCACCA | 65 | 41327 | 41346 | 892 |
| 472548 | 1357 | 1376 | GCTTGTCGAAGAGCTTCACC | 86 | 41328 | 41347 | 893 |
| 472549 | 1358 | 1377 | TGCTTGTCGAAGAGCTTCAC | 68 | 41329 | 41348 | 894 |
| 472550 | 1360 | 1379 | TGTGCTTGTCGAAGAGCTTC | 70 | 41331 | 41350 | 895 |
| 472551 | 1361 | 1380 | TTGTGCTTGTCGAAGAGCTT | 40 | 41332 | 41351 | 896 |
| 472552 | 1362 | 1381 | CTTGTGCTTGTCGAAGAGCT | 77 | 41333 | 41352 | 897 |
| 366746 | 1366 | 1385 | TGGTCTTGTGCTTGTCGAAG | 37 | 41337 | 41356 | 151 |
| 472553 | 1368 | 1387 | CTTGGTCTTGTGCTTGTCGA | 58 | 41339 | 41358 | 898 |
| 472554 | 1369 | 1388 | ACTTGGTCTTGTGCTTGTCG | 60 | 41340 | 41359 | 899 |

TABLE 15-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472555 | 1370 | 1389 | AACTTGGTCTTGTGCTTGTC | 61 | 41341 | 41360 | 900 |
| 472556 | 1372 | 1391 | CGAACTTGGTCTTGTGCTTG | 55 | 41343 | 41362 | 901 |
| 472557 | 1373 | 1392 | CCGAACTTGGTCTTGTGCTT | 63 | 41344 | 41363 | 902 |
| 472558 | 1374 | 1393 | GCCGAACTTGGTCTTGTGCT | 59 | 41345 | 41364 | 903 |
| 472559 | 1375 | 1394 | GGCCGAACTTGGTCTTGTGC | 60 | 41346 | 41365 | 904 |
| 472560 | 1377 | 1396 | GAGGCCGAACTTGGTCTTGT | 53 | 41348 | 41367 | 905 |
| 472561 | 1378 | 1397 | GGAGGCCGAACTTGGTCTTG | 35 | 41349 | 41368 | 906 |
| 472562 | 1400 | 1419 | ACCTCCAGGACCTCAGTCTC | 66 | 41371 | 41390 | 907 |
| 472563 | 1401 | 1420 | CACCTCCAGGACCTCAGTCT | 19 | 41372 | 41391 | 908 |
| 472564 | 1402 | 1421 | TCACCTCCAGGACCTCAGTC | 40 | 41373 | 41392 | 909 |
| 472565 | 1404 | 1423 | GTTCACCTCCAGGACCTCAG | 60 | 41375 | 41394 | 910 |
| 472566 | 1405 | 1424 | AGTTCACCTCCAGGACCTCA | 23 | 41376 | 41395 | 911 |
| 472567 | 1406 | 1425 | CAGTTCACCTCCAGGACCTC | 13 | 41377 | 41396 | 912 |
| 472568 | 1408 | 1427 | CTCAGTTCACCTCCAGGACC | 67 | 41379 | 41398 | 913 |
| 472569 | 1409 | 1428 | GCTCAGTTCACCTCCAGGAC | 71 | 41380 | 41399 | 914 |
| 472570 | 1410 | 1429 | GGCTCAGTTCACCTCCAGGA | 84 | 41381 | 41400 | 915 |
| 472571 | 1411 | 1430 | TGGCTCAGTTCACCTCCAGG | 74 | 41382 | 41401 | 916 |
| 411955 | 1502 | 1521 | AAATAACCCACAGACACCCA | 81 | 41473 | 41492 | 131 |
| 411958 | 1506 | 1525 | TTTTAAATAACCCACAGACA | 68 | 41477 | 41496 | 134 |
| 472572 | 1538 | 1557 | TTGTAATGGTTTAGCAAAAT | 7 | 41509 | 41528 | 917 |
| 472573 | 1539 | 1558 | ATTGTAATGGTTTAGCAAAA | 47 | 41510 | 41529 | 918 |
| 472574 | 1540 | 1559 | CATTGTAATGGTTTAGCAAA | 18 | 41511 | 41530 | 919 |
| 472575 | 1541 | 1560 | ACATTGTAATGGTTTAGCAA | 40 | 41512 | 41531 | 920 |
| 472576 | 1543 | 1562 | TAACATTGTAATGGTTTAGC | 58 | 41514 | 41533 | 921 |
| 472577 | 1544 | 1563 | CTAACATTGTAATGGTTTAG | 49 | 41515 | 41534 | 922 |
| 472578 | 1545 | 1564 | CCTAACATTGTAATGGTTTA | 67 | 41516 | 41535 | 923 |
| 472579 | 1546 | 1565 | ACCTAACATTGTAATGGTTT | 27 | 41517 | 41536 | 924 |
| 472580 | 1548 | 1567 | AGACCTAACATTGTAATGGT | 54 | 41519 | 41538 | 925 |
| 472581 | 1549 | 1568 | AAGACCTAACATTGTAATGG | 46 | 41520 | 41539 | 926 |
| 472582 | 1550 | 1569 | AAAGACCTAACATTGTAATG | 34 | 41521 | 41540 | 927 |
| 472583 | 1551 | 1570 | AAAAGACCTAACATTGTAAT | 33 | 41522 | 41541 | 928 |
| 472584 | 1553 | 1572 | AAAAAAGACCTAACATTGTA | 53 | 41524 | 41543 | 929 |
| 472585 | 1554 | 1573 | TAAAAAAGACCTAACATTGT | 58 | 41525 | 41544 | 930 |
| 472586 | 1556 | 1575 | CTTAAAAAAGACCTAACATT | 25 | 41527 | 41546 | 931 |
| 472587 | 1557 | 1576 | TCTTAAAAAAGACCTAACAT | 23 | 41528 | 41547 | 932 |

Example 4: Antisense Inhibition of Human DGAT2 in HepG2 Cells by MOE Gapmers

Antisense oligonucleotides were designed targeting a DGAT2 nucleic acid and were tested for their effects on DGAT2 mRNA in vitro. The antisense oligonucleotides were tested in a series of experiments that had similar culture conditions. ISIS 413433, which consistently demonstrated higher potency than any of the previously disclosed oligonucleotides in the studies above was included in this study as a benchmark oligonucleotide. Antisense oligonucleotides that demonstrated about the same or greater potency than ISIS 413433 were therefore considered for further experimentation.

The results for each experiment are presented in separate tables shown below. Cultured HepG2 cells at a density of 20,000 cells per well were transfected using electroporation with 4,500 nM antisense oligonucleotide. After a treatment period of approximately 24 hours, RNA was isolated from the cells and DGAT2 mRNA levels were measured by quantitative real-time PCR. Human primer probe set RTS2988_MGB was used to measure mRNA levels. The potency of some oligonucleotides was measured with human primer probe set RTS2367 (forward sequence GGCCTCCCGGAGACTGA, designated herein as SEQ ID NO: 4; reverse sequence AAGTGATTTGCAGCTGGTTCCT, designated herein as SEQ ID NO: 5; probe sequence AGGTGAACTGAGCCAGCCTTCGGG, designated herein as SEQ ID NO: 6). DGAT2 mRNA levels were adjusted according to total RNA content, as measured by RIBOGREEN®. Results are presented as percent inhibition of DGAT2, relative to untreated control cells. The results show several antisense oligonucleotides demonstrate greater potency than the benchmark oligonucleotides.

The newly designed chimeric antisense oligonucleotides in the Tables below were designed as 5-10-5 MOE gapmers or 3-10-4 MOE gapmers. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. The 3-10-4 MOE gapmers are 17 nucleosides in length, wherein the central gap segment comprises of ten 2'-deoxynucleosides and is flanked by wing segments on the 5' direction and the 3' direction comprising three and four nucleosides respectively. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to SEQ ID NO: 1, SEQ ID NO: 2, or both. 'n/a' indicates that the antisense oligonucleotide does not target that particular gene sequence with 100% complementarity. In case the sequence alignment for a target gene in a particular table is not shown, it is understood that none of the oligonucleotides presented in that table align with 100% complementarity with that target gene.

TABLE 16

Inhibition of DGAT2 mRNA by 5-10-5 MOE gapmers targeting SEQ ID NO: 2

| ISIS NO | SEQ ID NO: 1 Start Site | SEQ ID NO: 1 Stop Site | Sequence | SEQ ID NO: 2 Start Site | SEQ ID NO: 2 Stop Site | % inhibition | SEQ ID NO |
|---|---|---|---|---|---|---|---|
| 483799 | 221 | 240 | ACGGCCCCGCGGGAAGCCGC | 9842 | 9861 | 8 | 569 |
| 483800 | 226 | 245 | CAGTCACGGCCCCGCGGGAA | 9847 | 9866 | 46 | 570 |
| 483801 | 231 | 250 | CCGCCCAGTCACGGCCCCGC | 9852 | 9871 | 0 | 571 |
| 483802 | 236 | 255 | GAAGCCCGCCCAGTCACGGC | 9857 | 9876 | 50 | 572 |
| 413433 | n/a | n/a | GCCTGGACAAGTCCTGCCCA | 32431 | 32450 | 85 | 425 |
| 483803 | n/a | n/a | ACCCCATCTCCCAGACCCCT | 9984 | 10003 | 75 | 496 |
| 483804 | n/a | n/a | CACTCACCCCATCTCCCAGA | 9989 | 10008 | 46 | 497 |
| 483805 | n/a | n/a | CAGGTCCATAACCCCTGCGC | 10014 | 10033 | 51 | 498 |
| 483806 | n/a | n/a | TCTCGCAGGTCCATAACCCC | 10019 | 10038 | 6 | 499 |
| 483807 | n/a | n/a | AATCTTCTCGCAGGTCCATA | 10024 | 10043 | 50 | 500 |
| 483808 | n/a | n/a | CAGAAAATCTTCTCGCAGGT | 10029 | 10048 | 49 | 501 |
| 483809 | n/a | n/a | CTTTCCAGAAAATCTTCTCG | 10034 | 10053 | 37 | 502 |
| 483810 | n/a | n/a | GGGCCCTTTCCAGAAAATCT | 10039 | 10058 | 40 | 503 |
| 483811 | n/a | n/a | CCACAGGGCCCTTTCCAGAA | 10044 | 10063 | 85 | 504 |
| 483812 | n/a | n/a | GCCTGCCACAGGGCCCTTTC | 10049 | 10068 | 76 | 505 |
| 483813 | n/a | n/a | CACCAGCCTGCCACAGGGCC | 10054 | 10073 | 80 | 506 |
| 483814 | n/a | n/a | CACGGATGAGGGAAACAAGC | 10160 | 10179 | 73 | 507 |

TABLE 16-continued

Inhibition of DGAT2 mRNA by 5-10-5 MOE gapmers targeting SEQ ID NO: 2

| ISIS NO | SEQ ID NO: 1 Start Site | SEQ ID NO: 1 Stop Site | Sequence | SEQ ID NO: 2 Start Site | SEQ ID NO: 2 Stop Site | % inhibition | SEQ ID NO |
|---|---|---|---|---|---|---|---|
| 483815 | n/a | n/a | AATATCCCTAATAACTAAGA | 10205 | 10224 | 35 | 508 |
| 483816 | n/a | n/a | TCTCGAATATCCCTAATAAC | 10210 | 10229 | 84 | 509 |
| 483817 | n/a | n/a | GGAGTTCTCGAATATCCCTA | 10215 | 10234 | 96 | 510 |
| 483818 | n/a | n/a | AAACCCATACCATCCTGCCC | 10327 | 10346 | 76 | 511 |
| 483819 | n/a | n/a | TGGTGGCTGTCTCAGGAGAC | 10351 | 10370 | 49 | 512 |
| 483820 | n/a | n/a | CCGTCTGGTGGCTGTCTCAG | 10356 | 10375 | 36 | 513 |
| 483821 | n/a | n/a | GGCAGACACACCTGTTCCAG | 10389 | 10408 | 64 | 514 |
| 483822 | n/a | n/a | GACAGGGCAGACACACCTGT | 10394 | 10413 | 64 | 515 |
| 483823 | n/a | n/a | CAGAGGACAGGGCAGACACA | 10399 | 10418 | 69 | 516 |
| 483824 | n/a | n/a | CCAGAGCCTGGGCGAGAGGA | 10430 | 10449 | 45 | 517 |
| 483825 | n/a | n/a | CAGGGTCCTCTCCGCTGCCT | 10490 | 10509 | 91 | 518 |
| 483826 | n/a | n/a | CTGAGGACCTCAGTTCTACC | 10522 | 10541 | 83 | 519 |
| 483827 | n/a | n/a | ATTCACTGAGGACCTCAGTT | 10527 | 10546 | 67 | 520 |
| 483828 | n/a | n/a | GCGCGATTCACTGAGGACCT | 10532 | 10551 | 88 | 521 |
| 483829 | n/a | n/a | ACTCTGCGCGATTCACTGAG | 10537 | 10556 | 73 | 522 |
| 483830 | n/a | n/a | CTCCCACTTCAGTTTCTCCA | 10645 | 10664 | 83 | 523 |
| 483831 | n/a | n/a | GCTTCCTCCCACTTCAGTTT | 10650 | 10669 | 86 | 524 |
| 483832 | n/a | n/a | GGCATGCTTCCTCCCACTTC | 10655 | 10674 | 89 | 525 |
| 483833 | n/a | n/a | ACTTAGGCATGCTTCCTCCC | 10660 | 10679 | 89 | 526 |
| 483834 | n/a | n/a | GGAAAACTTAGGCATGCTTC | 10665 | 10684 | 92 | 527 |
| 483835 | n/a | n/a | GCTAAGGAAAACTTAGGCAT | 10670 | 10689 | 85 | 528 |
| 483836 | n/a | n/a | CATCAGCTAAGGAAAACTTA | 10675 | 10694 | 53 | 529 |
| 483837 | n/a | n/a | CAAGGCATCAGCTAAGGAAA | 10680 | 10699 | 27 | 530 |
| 483838 | n/a | n/a | ATTTGTACTTGAATCCAGGG | 10702 | 10721 | 77 | 531 |
| 483839 | n/a | n/a | GTGATGACTTCCCAGGGTCT | 10727 | 10746 | 87 | 532 |
| 483840 | n/a | n/a | CAGCTGTGATGACTTCCCAG | 10732 | 10751 | 84 | 533 |
| 483841 | n/a | n/a | CAGGACAGCTGTGATGACTT | 10737 | 10756 | 80 | 534 |
| 483842 | n/a | n/a | CAGACCAGGACAGCTGTGAT | 10742 | 10761 | 72 | 535 |
| 483843 | n/a | n/a | CACACGCAGACCAGGACAGC | 10748 | 10767 | 54 | 536 |
| 483844 | n/a | n/a | AGACACACGCAGACCAGG | 10753 | 10772 | 44 | 537 |
| 483845 | n/a | n/a | ATGCAAGACACACGCAGA | 10758 | 10777 | 45 | 538 |
| 483846 | n/a | n/a | GCTTCATGCAAGACACACAC | 10763 | 10782 | 78 | 539 |
| 483847 | n/a | n/a | ATGTCAGAGAGGCTCAGCAA | 10814 | 10833 | 67 | 540 |
| 483848 | n/a | n/a | AATCCATGTCAGAGAGGCTC | 10819 | 10838 | 93 | 541 |
| 483849 | n/a | n/a | AGAAAAATCCATGTCAGAGA | 10824 | 10843 | 37 | 542 |
| 483850 | n/a | n/a | ACTAAAGAAAAATCCATGTC | 10829 | 10848 | 49 | 543 |

TABLE 16-continued

Inhibition of DGAT2 mRNA by 5-10-5 MOE gapmers targeting SEQ ID NO: 2

| ISIS NO | SEQ ID NO: 1 Start Site | SEQ ID NO: 1 Stop Site | Sequence | SEQ ID NO: 2 Start Site | SEQ ID NO: 2 Stop Site | % inhibition | SEQ ID NO |
|---|---|---|---|---|---|---|---|
| 483851 | n/a | n/a | TAGTTACTAAAGAAAAATCC | 10834 | 10853 | 21 | 544 |
| 483852 | n/a | n/a | GGATAGTCGATTTACCAGAA | 10940 | 10959 | 88 | 545 |
| 483853 | n/a | n/a | TCTTTGGATAGTCGATTTAC | 10945 | 10964 | 66 | 546 |
| 483854 | n/a | n/a | ACTAAAATGCTAATAGGAAG | 10968 | 10987 | 2 | 547 |
| 483855 | n/a | n/a | GATATACTAAAATGCTAATA | 10973 | 10992 | 9 | 548 |
| 483856 | n/a | n/a | CAAGAGATATACTAAAATGC | 10978 | 10997 | 32 | 549 |
| 483857 | n/a | n/a | ATGATCAAGAGATATACTAA | 10983 | 11002 | 36 | 550 |
| 483858 | n/a | n/a | AGAAAATGATCAAGAGATAT | 10988 | 11007 | 6 | 551 |
| 483859 | n/a | n/a | TATAAAGAAAATGATCAAGA | 10993 | 11012 | 6 | 552 |
| 483860 | n/a | n/a | ATGTGTATAAAGAAAATGAT | 10998 | 11017 | 0 | 553 |
| 483861 | n/a | n/a | ATGCAATGTGTATAAAGAAA | 11003 | 11022 | 36 | 554 |
| 483862 | n/a | n/a | TATCTATGCAATGTGTATAA | 11008 | 11027 | 75 | 555 |
| 483863 | n/a | n/a | ATTCATAACTATATCTACAG | 11042 | 11061 | 52 | 556 |
| 483864 | n/a | n/a | ACAAGATTCATAACTATATC | 11047 | 11066 | 31 | 557 |
| 483865 | n/a | n/a | AGAAAACAAGATTCATAACT | 11052 | 11071 | 33 | 558 |
| 483866 | n/a | n/a | CCTCGATGTTACATTAAGGG | 11074 | 11093 | 90 | 559 |
| 483867 | n/a | n/a | GGAAACCTCGATGTTACATT | 11079 | 11098 | 59 | 560 |
| 483868 | n/a | n/a | ATTGCAACCACTAGGACATT | 11123 | 11142 | 60 | 561 |
| 483869 | n/a | n/a | GGGTTATTGCAACCACTAGG | 11128 | 11147 | 91 | 562 |
| 483870 | n/a | n/a | CACAGTTAAAGTGTGGTACA | 11158 | 11177 | 86 | 563 |
| 483871 | n/a | n/a | TAGGTCACAGTTAAAGTGTG | 11163 | 11182 | 60 | 564 |
| 483872 | n/a | n/a | ATGCCTAGGTCACAGTTAAA | 11168 | 11187 | 74 | 565 |
| 483873 | n/a | n/a | TGCCAATGCCTAGGTCACAG | 11173 | 11192 | 90 | 566 |
| 483874 | n/a | n/a | AGCAATGCCAATGCCTAGGT | 11178 | 11197 | 91 | 567 |
| 483875 | n/a | n/a | CACAGCGATAATCACACAAG | 11199 | 11218 | 87 | 568 |

TABLE 17

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413433 | n/a | n/a | GCCTGGACAAGTCCTGCCCA | 89 | 32431 | 32450 | 425 |
| 472665 | 1870 | 1889 | CTCCAACTCCTCCCCTTGGC | 56 | 41841 | 41860 | 933 |
| 472666 | 1871 | 1890 | TCTCCAACTCCTCCCCTTGG | 37 | 41842 | 41861 | 934 |
| 472667 | 1873 | 1892 | GCTCTCCAACTCCTCCCCTT | 63 | 41844 | 41863 | 935 |

TABLE 17-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472668 | 1874 | 1893 | TGCTCTCCAACTCCTCCCCT | 65 | 41845 | 41864 | 936 |
| 472669 | 1917 | 1936 | CATTCCAGATGCCTACTACT | 63 | 41888 | 41907 | 937 |
| 472670 | 1918 | 1937 | GCATTCCAGATGCCTACTAC | 68 | 41889 | 41908 | 938 |
| 472671 | 1919 | 1938 | AGCATTCCAGATGCCTACTA | 81 | 41890 | 41909 | 939 |
| 472672 | 1920 | 1939 | GAGCATTCCAGATGCCTACT | 77 | 41891 | 41910 | 940 |
| 472673 | 1993 | 2012 | CCTGGAGGCCAGTCCAGGCT | 33 | 41964 | 41983 | 941 |
| 472674 | 1994 | 2013 | TCCTGGAGGCCAGTCCAGGC | 22 | 41965 | 41984 | 942 |
| 472675 | 1996 | 2015 | CATCCTGGAGGCCAGTCCAG | 14 | 41967 | 41986 | 943 |
| 472676 | 1997 | 2016 | TCATCCTGGAGGCCAGTCCA | 47 | 41968 | 41987 | 944 |
| 472677 | 1999 | 2018 | CCTCATCCTGGAGGCCAGTC | 57 | 41970 | 41989 | 945 |
| 472678 | 2000 | 2019 | TCCTCATCCTGGAGGCCAGT | 37 | 41971 | 41990 | 946 |
| 472679 | 2001 | 2020 | ATCCTCATCCTGGAGGCCAG | 50 | 41972 | 41991 | 947 |
| 472680 | 2002 | 2021 | CATCCTCATCCTGGAGGCCA | 56 | 41973 | 41992 | 948 |
| 472681 | 2004 | 2023 | CCCATCCTCATCCTGGAGGC | 29 | 41975 | 41994 | 949 |
| 472682 | 2005 | 2024 | CCCCATCCTCATCCTGGAGG | 21 | 41976 | 41995 | 950 |
| 472683 | 2007 | 2026 | ACCCCCATCCTCATCCTGGA | 24 | 41978 | 41997 | 951 |
| 472684 | 2008 | 2027 | CACCCCCATCCTCATCCTGG | 8 | 41979 | 41998 | 952 |
| 472685 | 2009 | 2028 | CCACCCCCATCCTCATCCTG | 39 | 41980 | 41999 | 953 |
| 472686 | 2011 | 2030 | TGCCACCCCCATCCTCATCC | 46 | 41982 | 42001 | 954 |
| 472687 | 2012 | 2031 | TTGCCACCCCCATCCTCATC | 48 | 41983 | 42002 | 955 |
| 472688 | 2013 | 2032 | ATTGCCACCCCCATCCTCAT | 57 | 41984 | 42003 | 956 |
| 472689 | 2015 | 2034 | TCATTGCCACCCCCATCCTC | 43 | 41986 | 42005 | 957 |
| 472690 | 2016 | 2035 | GTCATTGCCACCCCCATCCT | 29 | 41987 | 42006 | 958 |
| 472691 | 2017 | 2036 | TGTCATTGCCACCCCCATCC | 51 | 41988 | 42007 | 959 |
| 472692 | 2019 | 2038 | GGTGTCATTGCCACCCCCAT | 74 | 41990 | 42009 | 960 |
| 472693 | 2079 | 2098 | GCTCATGGTGGCGGCATCCT | 77 | 42050 | 42069 | 961 |
| 472694 | 2080 | 2099 | AGCTCATGGTGGCGGCATCC | 66 | 42051 | 42070 | 962 |
| 472695 | 2082 | 2101 | CTAGCTCATGGTGGCGGCAT | 65 | 42053 | 42072 | 963 |
| 472696 | 2083 | 2102 | CCTAGCTCATGGTGGCGGCA | 68 | 42054 | 42073 | 964 |
| 472697 | 2085 | 2104 | CACCTAGCTCATGGTGGCGG | 49 | 42056 | 42075 | 965 |
| 472698 | 2086 | 2105 | CCACCTAGCTCATGGTGGCG | 44 | 42057 | 42076 | 966 |
| 472699 | 2088 | 2107 | CTCCACCTAGCTCATGGTGG | 18 | 42059 | 42078 | 967 |
| 472700 | 2089 | 2108 | ACTCCACCTAGCTCATGGTG | 61 | 42060 | 42079 | 968 |
| 472701 | 2090 | 2109 | TACTCCACCTAGCTCATGGT | 46 | 42061 | 42080 | 969 |
| 472702 | 2092 | 2111 | GTTACTCCACCTAGCTCATG | 51 | 42063 | 42082 | 970 |

TABLE 17-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472703 | 2093 | 2112 | AGTTACTCCACCTAGCTCAT | 58 | 42064 | 42083 | 971 |
| 472704 | 2094 | 2113 | CAGTTACTCCACCTAGCTCA | 66 | 42065 | 42084 | 972 |
| 472705 | 2095 | 2114 | CCAGTTACTCCACCTAGCTC | 80 | 42066 | 42085 | 973 |
| 472706 | 2097 | 2116 | AACCAGTTACTCCACCTAGC | 71 | 42068 | 42087 | 974 |
| 472707 | 2098 | 2117 | AAACCAGTTACTCCACCTAG | 68 | 42069 | 42088 | 975 |
| 472708 | 2100 | 2119 | AAAAACCAGTTACTCCACCT | 67 | 42071 | 42090 | 976 |
| 472709 | 2101 | 2120 | GAAAAACCAGTTACTCCACC | 68 | 42072 | 42091 | 977 |
| 472710 | 2103 | 2122 | AAGAAAAACCAGTTACTCCA | 53 | 42074 | 42093 | 978 |
| 472711 | 2104 | 2123 | CAAGAAAAACCAGTTACTCC | 61 | 42075 | 42094 | 979 |
| 472712 | 2106 | 2125 | CCCAAGAAAAACCAGTTACT | 67 | 42077 | 42096 | 980 |
| 472713 | 2107 | 2126 | ACCCAAGAAAAACCAGTTAC | 71 | 42078 | 42097 | 981 |
| 472714 | 2108 | 2127 | CACCCAAGAAAAACCAGTTA | 56 | 42079 | 42098 | 982 |
| 472715 | 2109 | 2128 | CCACCCAAGAAAAACCAGTT | 61 | 42080 | 42099 | 983 |
| 472716 | 2111 | 2130 | AGCCACCCAAGAAAAACCAG | 62 | 42082 | 42101 | 984 |
| 472717 | 2112 | 2131 | CAGCCACCCAAGAAAAACCA | 69 | 42083 | 42102 | 985 |
| 472718 | 2114 | 2133 | ATCAGCCACCCAAGAAAAAC | 58 | 42085 | 42104 | 986 |
| 472719 | 2115 | 2134 | CATCAGCCACCCAAGAAAAA | 46 | 42086 | 42105 | 987 |
| 472720 | 2116 | 2135 | TCATCAGCCACCCAAGAAAA | 64 | 42087 | 42106 | 988 |
| 472721 | 2118 | 2137 | TGTCATCAGCCACCCAAGAA | 48 | 42089 | 42108 | 989 |
| 472722 | 2119 | 2138 | ATGTCATCAGCCACCCAAGA | 50 | 42090 | 42109 | 990 |
| 472723 | 2121 | 2140 | CCATGTCATCAGCCACCCAA | 79 | 42092 | 42111 | 991 |
| 472724 | 2122 | 2141 | TCCATGTCATCAGCCACCCA | 79 | 42093 | 42112 | 992 |
| 472725 | 2123 | 2142 | ATCCATGTCATCAGCCACCC | 83 | 42094 | 42113 | 993 |
| 472726 | 2124 | 2143 | CATCCATGTCATCAGCCACC | 80 | 42095 | 42114 | 994 |
| 472727 | 2126 | 2145 | TGCATCCATGTCATCAGCCA | 81 | 42097 | 42116 | 995 |
| 472728 | 2127 | 2146 | CTGCATCCATGTCATCAGCC | 78 | 42098 | 42117 | 996 |
| 413319 | 2128 | 2147 | GCTGCATCCATGTCATCAGC | 74 | 42099 | 42118 | 154 |
| 472729 | 2129 | 2148 | TGCTGCATCCATGTCATCAG | 80 | 42100 | 42119 | 997 |
| 472730 | 2130 | 2149 | GTGCTGCATCCATGTCATCA | 68 | 42101 | 42120 | 998 |
| 472731 | 2132 | 2151 | CTGTGCTGCATCCATGTCAT | 64 | 42103 | 42122 | 999 |
| 472732 | 2133 | 2152 | TCTGTGCTGCATCCATGTCA | 80 | 42104 | 42123 | 1000 |
| 472733 | 2134 | 2153 | GTCTGTGCTGCATCCATGTC | 83 | 42105 | 42124 | 1001 |
| 472734 | 2135 | 2154 | AGTCTGTGCTGCATCCATGT | 68 | 42106 | 42125 | 1002 |
| 472735 | 2137 | 2156 | TGAGTCTGTGCTGCATCCAT | 71 | 42108 | 42127 | 1003 |
| 472736 | 2138 | 2157 | CTGAGTCTGTGCTGCATCCA | 78 | 42109 | 42128 | 1004 |
| 472737 | 2139 | 2158 | GCTGAGTCTGTGCTGCATCC | 80 | 42110 | 42129 | 1005 |

TABLE 17-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472738 | 2140 | 2159 | GGCTGAGTCTGTGCTGCATC | 84 | 42111 | 42130 | 1006 |
| 472739 | 2141 | 2160 | AGGCTGAGTCTGTGCTGCAT | 76 | 42112 | 42131 | 1007 |
| 472740 | 2142 | 2161 | AAGGCTGAGTCTGTGCTGCA | 81 | 42113 | 42132 | 1008 |

TABLE 18

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 413433 | n/a | n/a | GCCTGGACAAGTCCTGCCCA | 89 | 32431 | 32450 | 425 |
| 411901 | 695 | 714 | GTCAGCAGGTTGTGTGTCTT | 64 | 37223 | 37242 | 64 |
| 472741 | 2144 | 2163 | CCAAGGCTGAGTCTGTGCTG | 60 | 42115 | 42134 | 1009 |
| 472742 | 2145 | 2164 | GCCAAGGCTGAGTCTGTGCT | 63 | 42116 | 42135 | 1010 |
| 472743 | 2147 | 2166 | AGGCCAAGGCTGAGTCTGTG | 55 | 42118 | 42137 | 1011 |
| 472744 | 2148 | 2167 | CAGGCCAAGGCTGAGTCTGT | 39 | 42119 | 42138 | 1012 |
| 472745 | 2150 | 2169 | TCCAGGCCAAGGCTGAGTCT | 56 | 42121 | 42140 | 1013 |
| 472746 | 2151 | 2170 | CTCCAGGCCAAGGCTGAGTC | 62 | 42122 | 42141 | 1014 |
| 472747 | 2152 | 2171 | GCTCCAGGCCAAGGCTGAGT | 77 | 42123 | 42142 | 1015 |
| 472748 | 2153 | 2172 | TGCTCCAGGCCAAGGCTGAG | 43 | 42124 | 42143 | 1016 |
| 472749 | 2155 | 2174 | TGTGCTCCAGGCCAAGGCTG | 63 | 42126 | 42145 | 1017 |
| 472750 | 2156 | 2175 | ATGTGCTCCAGGCCAAGGCT | 69 | 42127 | 42146 | 1018 |
| 472751 | 2181 | 2200 | AGGTAAACTGAGGCCACCAG | 35 | 42152 | 42171 | 1019 |
| 472752 | 2183 | 2202 | GAAGGTAAACTGAGGCCACC | 72 | 42154 | 42173 | 1020 |
| 472753 | 2184 | 2203 | GGAAGGTAAACTGAGGCCAC | 45 | 42155 | 42174 | 1021 |
| 472754 | 2214 | 2233 | TCTTCCTCACATCCAGAATC | 49 | 42185 | 42204 | 1022 |
| 472755 | 2215 | 2234 | CTCTTCCTCACATCCAGAAT | 62 | 42186 | 42205 | 1023 |
| 472756 | 2237 | 2256 | CAGGCCCCTTCTGAAGAGGG | 73 | 42208 | 42227 | 1024 |
| 472757 | 2238 | 2257 | CCAGGCCCCTTCTGAAGAGG | 68 | 42209 | 42228 | 1025 |
| 472758 | 2240 | 2259 | GGCCAGGCCCCTTCTGAAGA | 41 | 42211 | 42230 | 1026 |
| 472759 | 2241 | 2260 | AGGCCAGGCCCCTTCTGAAG | 51 | 42212 | 42231 | 1027 |
| 472760 | 2243 | 2262 | GAAGGCCAGGCCCCTTCTGA | 32 | 42214 | 42233 | 1028 |
| 472761 | 2244 | 2263 | AGAAGGCCAGGCCCCTTCTG | 28 | 42215 | 42234 | 1029 |
| 472762 | 2245 | 2264 | CAGAAGGCCAGGCCCCTTCT | 24 | 42216 | 42235 | 1030 |
| 472763 | 2247 | 2266 | CTCAGAAGGCCAGGCCCCTT | 54 | 42218 | 42237 | 1031 |

TABLE 18-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472764 | 2248 | 2267 | GCTCAGAAGGCCAGGCCCCT | 72 | 42219 | 42238 | 1032 |
| 472765 | 2250 | 2269 | CTGCTCAGAAGGCCAGGCCC | 60 | 42221 | 42240 | 1033 |
| 472766 | 2251 | 2270 | GCTGCTCAGAAGGCCAGGCC | 81 | 42222 | 42241 | 1034 |
| 472767 | 2253 | 2272 | CTGCTGCTCAGAAGGCCAGG | 51 | 42224 | 42243 | 1035 |
| 472768 | 2254 | 2273 | TCTGCTGCTCAGAAGGCCAG | 79 | 42225 | 42244 | 1036 |
| 472769 | 2255 | 2274 | ATCTGCTGCTCAGAAGGCCA | 63 | 42226 | 42245 | 1037 |
| 472770 | 2256 | 2275 | AATCTGCTGCTCAGAAGGCC | 69 | 42227 | 42246 | 1038 |
| 472771 | 2258 | 2277 | CTAATCTGCTGCTCAGAAGG | 57 | 42229 | 42248 | 1039 |
| 472772 | 2259 | 2278 | ACTAATCTGCTGCTCAGAAG | 63 | 42230 | 42249 | 1040 |
| 472773 | 2260 | 2279 | AACTAATCTGCTGCTCAGAA | 52 | 42231 | 42250 | 1041 |
| 472774 | 2261 | 2280 | GAACTAATCTGCTGCTCAGA | 45 | 42232 | 42251 | 1042 |
| 472775 | 2262 | 2281 | GGAACTAATCTGCTGCTCAG | 70 | 42233 | 42252 | 1043 |
| 472776 | 2263 | 2282 | TGGAACTAATCTGCTGCTCA | 73 | 42234 | 42253 | 1044 |
| 472777 | 2264 | 2283 | TTGGAACTAATCTGCTGCTC | 70 | 42235 | 42254 | 1045 |
| 472778 | 2266 | 2285 | CTTTGGAACTAATCTGCTGC | 69 | 42237 | 42256 | 1046 |
| 472779 | 2267 | 2286 | GCTTTGGAACTAATCTGCTG | 70 | 42238 | 42257 | 1047 |
| 472780 | 2268 | 2287 | TGCTTTGGAACTAATCTGCT | 76 | 42239 | 42258 | 1048 |
| 472781 | 2269 | 2288 | CTGCTTTGGAACTAATCTGC | 71 | 42240 | 42259 | 1049 |
| 472782 | 2270 | 2289 | CCTGCTTTGGAACTAATCTG | 55 | 42241 | 42260 | 1050 |
| 472783 | 2272 | 2291 | CACCTGCTTTGGAACTAATC | 65 | 42243 | 42262 | 1051 |
| 472784 | 2273 | 2292 | CCACCTGCTTTGGAACTAAT | 78 | 42244 | 42263 | 1052 |
| 472785 | 2275 | 2294 | GGCCACCTGCTTTGGAACTA | 66 | 42246 | 42265 | 1053 |
| 472786 | 2276 | 2295 | GGGCCACCTGCTTTGGAACT | 67 | 42247 | 42266 | 1054 |
| 472787 | 2296 | 2315 | AAAGTGAGGCTTGGGTTCGG | 58 | 42267 | 42286 | 1055 |
| 472788 | 2297 | 2316 | AAAAGTGAGGCTTGGGTTCG | 54 | 42268 | 42287 | 1056 |
| 472789 | 2299 | 2318 | AGAAAAGTGAGGCTTGGGTT | 65 | 42270 | 42289 | 1057 |
| 472790 | 2300 | 2319 | CAGAAAAGTGAGGCTTGGGT | 61 | 42271 | 42290 | 1058 |
| 472791 | 2302 | 2321 | CACAGAAAAGTGAGGCTTGG | 70 | 42273 | 42292 | 1059 |
| 472792 | 2303 | 2322 | GCACAGAAAAGTGAGGCTTG | 81 | 42274 | 42293 | 1060 |
| 472793 | 2305 | 2324 | AGGCACAGAAAAGTGAGGCT | 82 | 42276 | 42295 | 1061 |
| 472794 | 2306 | 2325 | AAGGCACAGAAAAGTGAGGC | 58 | 42277 | 42296 | 1062 |
| 472795 | 2308 | 2327 | GGAAGGCACAGAAAAGTGAG | 29 | 42279 | 42298 | 1063 |
| 472796 | 2309 | 2328 | AGGAAGGCACAGAAAAGTGA | 24 | 42280 | 42299 | 1064 |
| 472797 | 2311 | 2330 | TCAGGAAGGCACAGAAAAGT | 67 | 42282 | 42301 | 1065 |
| 472798 | 2312 | 2331 | CTCAGGAAGGCACAGAAAAG | 32 | 42283 | 42302 | 1066 |
| 472799 | 2314 | 2333 | CCCTCAGGAAGGCACAGAAA | 48 | 42285 | 42304 | 1067 |

TABLE 18-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472800 | 2315 | 2334 | CCCCTCAGGAAGGCACAGAA | 55 | 42286 | 42305 | 1068 |
| 472801 | 2316 | 2335 | CCCCCTCAGGAAGGCACAGA | 57 | 42287 | 42306 | 1069 |
| 472802 | 2318 | 2337 | AACCCCCTCAGGAAGGCACA | 57 | 42289 | 42308 | 1070 |
| 472803 | 2319 | 2338 | CAACCCCCTCAGGAAGGCAC | 63 | 42290 | 42309 | 1071 |
| 472804 | 2320 | 2339 | CCAACCCCCTCAGGAAGGCA | 66 | 42291 | 42310 | 1072 |
| 472805 | 2321 | 2340 | CCCAACCCCCTCAGGAAGGC | 67 | 42292 | 42311 | 1073 |
| 472806 | 2322 | 2341 | GCCCAACCCCCTCAGGAAGG | 1 | 42293 | 42312 | 1074 |
| 472807 | 2372 | 2391 | CTCATCAAGAGATAACAGAA | 47 | 42343 | 42362 | 1075 |
| 472808 | 2374 | 2393 | ATCTCATCAAGAGATAACAG | 56 | 42345 | 42364 | 1076 |
| 472809 | 2375 | 2394 | GATCTCATCAAGAGATAACA | 48 | 42346 | 42365 | 1077 |
| 472810 | 2377 | 2396 | ATGATCTCATCAAGAGATAA | 69 | 42348 | 42367 | 1078 |
| 472811 | 2398 | 2417 | ACAAAAGTCTGACATGGTGC | 82 | 42369 | 42388 | 1079 |
| 472812 | 2400 | 2419 | ATACAAAAGTCTGACATGGT | 74 | 42371 | 42390 | 1080 |
| 472813 | 2401 | 2420 | TATACAAAAGTCTGACATGG | 52 | 42372 | 42391 | 1081 |
| 472814 | 2403 | 2422 | CATATACAAAAGTCTGACAT | 45 | 42374 | 42393 | 1082 |
| 472815 | 2404 | 2423 | GCATATACAAAAGTCTGACA | 78 | 42375 | 42394 | 1083 |
| 472816 | 2405 | 2424 | GGCATATACAAAAGTCTGAC | 81 | 42376 | 42395 | 1084 |

TABLE 19

Inhibition of DGAT2 mRNA by 3-10-4 MOE gapmers targeting SEQ ID NOs: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 496047 | 1000 | 1016 | CATTCTTGCCAGGCATG | 42 | 38153 | 38169 | 1102 |
| 496048 | 1003 | 1019 | CTGCATTCTTGCCAGGC | 61 | 38156 | 38172 | 1103 |
| 496049 | 1004 | 1020 | ACTGCATTCTTGCCAGG | 43 | 38157 | 38173 | 1104 |
| 496050 | 1005 | 1021 | GACTGCATTCTTGCCAG | 31 | 38158 | 38174 | 1105 |
| 496051 | 1015 | 1031 | TCCGCAGGGTGACTGCA | 59 | 38168 | 38184 | 1106 |
| 496052 | 1016 | 1032 | TTCCGCAGGGTGACTGC | 60 | 38169 | 38185 | 1107 |
| 496053 | 1017 | 1033 | GTTCCGCAGGGTGACTG | 64 | 38170 | 38186 | 1108 |
| 496054 | 1096 | 1112 | ACACTTCATTCTCTCCA | 39 | 39143 | 39159 | 1109 |
| 496055 | 1097 | 1113 | TACACTTCATTCTCTCC | 39 | 39144 | 39160 | 1110 |
| 496056 | 1098 | 1114 | GTACACTTCATTCTCTC | 44 | 39145 | 39161 | 1111 |
| 496057 | 1099 | 1115 | TGTACACTTCATTCTCT | 36 | 39146 | 39162 | 1112 |

TABLE 19-continued

Inhibition of DGAT2 mRNA by 3-10-4 MOE gapmers targeting SEQ ID NOs: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 496058 | 1100 | 1116 | TTGTACACTTCATTCTC | 28 | 39147 | 39163 | 1113 |
| 496059 | 1101 | 1117 | CTTGTACACTTCATTCT | 35 | 39148 | 39164 | 1114 |
| 496060 | 1102 | 1118 | GCTTGTACACTTCATTC | 48 | 39149 | 39165 | 1115 |
| 496061 | 1103 | 1119 | TGCTTGTACACTTCATT | 40 | 39150 | 39166 | 1116 |
| 496062 | 1104 | 1120 | CTGCTTGTACACTTCAT | 63 | 39151 | 39167 | 1117 |
| 496063 | 1105 | 1121 | CCTGCTTGTACACTTCA | 62 | 39152 | 39168 | 1118 |
| 496064 | 1106 | 1122 | ACCTGCTTGTACACTTC | 47 | 39153 | 39169 | 1119 |
| 496065 | 1107 | 1123 | CACCTGCTTGTACACTT | 39 | 39154 | 39170 | 1120 |
| 496066 | 1108 | 1124 | TCACCTGCTTGTACACT | 43 | 39155 | 39171 | 1121 |
| 496067 | 1109 | 1125 | ATCACCTGCTTGTACAC | 23 | 39156 | 39172 | 1122 |
| 496068 | 1119 | 1135 | CTCCTCGAAGATCACCT | 9 | 39166 | 39182 | 1123 |
| 496069 | 1120 | 1136 | CCTCCTCGAAGATCACC | 26 | 39167 | 39183 | 1124 |
| 496070 | 1121 | 1137 | CCCTCCTCGAAGATCAC | 25 | 39168 | 39184 | 1125 |
| 496071 | 1357 | 1373 | TGTCGAAGAGCTTCACC | 36 | 41328 | 41344 | 1126 |
| 496072 | 1358 | 1374 | TTGTCGAAGAGCTTCAC | 7 | 41329 | 41345 | 1127 |
| 496073 | 1359 | 1375 | CTTGTCGAAGAGCTTCA | 22 | 41330 | 41346 | 1128 |
| 496074 | 1362 | 1378 | GTGCTTGTCGAAGAGCT | 44 | 41333 | 41349 | 1129 |
| 496075 | 1363 | 1379 | TGTGCTTGTCGAAGAGC | 33 | 41334 | 41350 | 1130 |
| 496076 | 1364 | 1380 | TTGTGCTTGTCGAAGAG | 10 | 41335 | 41351 | 1131 |
| 496077 | 1410 | 1426 | TCAGTTCACCTCCAGGA | 11 | 41381 | 41397 | 1132 |
| 496078 | 1411 | 1427 | CTCAGTTCACCTCCAGG | 11 | 41382 | 41398 | 1133 |
| 496079 | 1412 | 1428 | GCTCAGTTCACCTCCAG | 25 | 41383 | 41399 | 1134 |
| 496080 | 1413 | 1429 | GGCTCAGTTCACCTCCA | 56 | 41384 | 41400 | 1135 |
| 496081 | 1502 | 1518 | TAACCCACAGACACCCA | 61 | 41473 | 41489 | 1136 |
| 496082 | 1503 | 1519 | ATAACCCACAGACACCC | 55 | 41474 | 41490 | 1137 |
| 496083 | 1504 | 1520 | AATAACCCACAGACACC | 59 | 41475 | 41491 | 1138 |
| 496084 | 1627 | 1643 | AGATTTAGCCACCACCT | 17 | 41598 | 41614 | 1139 |
| 496085 | 1628 | 1644 | CAGATTTAGCCACCACC | 58 | 41599 | 41615 | 1140 |
| 496086 | 1629 | 1645 | CCAGATTTAGCCACCAC | 60 | 41600 | 41616 | 1141 |
| 496087 | 1630 | 1646 | CCCAGATTTAGCCACCA | 62 | 41601 | 41617 | 1142 |
| 496088 | 1631 | 1647 | GCCCAGATTTAGCCACC | 28 | 41602 | 41618 | 1143 |
| 496089 | 1853 | 1869 | AGAGAAACTGGTCCTGC | 0 | 41824 | 41840 | 1144 |
| 496090 | 1854 | 1870 | CAGAGAAACTGGTCCTG | 0 | 41825 | 41841 | 1145 |
| 496091 | 1855 | 1871 | GCAGAGAAACTGGTCCT | 42 | 41826 | 41842 | 1146 |
| 496092 | 2123 | 2139 | CATGTCATCAGCCACCC | 52 | 42094 | 42110 | 1147 |
| 496093 | 2124 | 2140 | CCATGTCATCAGCCACC | 62 | 42095 | 42111 | 1148 |

TABLE 19-continued

Inhibition of DGAT2 mRNA by 3-10-4 MOE gapmers targeting SEQ ID NOs: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 496094 | 2125 | 2141 | TCCATGTCATCAGCCAC | 60 | 42096 | 42112 | 1149 |
| 496095 | 2134 | 2150 | TGTGCTGCATCCATGTC | 53 | 42105 | 42121 | 1150 |
| 496096 | 2135 | 2151 | CTGTGCTGCATCCATGT | 21 | 42106 | 42122 | 1151 |
| 496097 | 2136 | 2152 | TCTGTGCTGCATCCATG | 33 | 42107 | 42123 | 1152 |
| 496098 | 2140 | 2156 | TGAGTCTGTGCTGCATC | 60 | 42111 | 42127 | 1153 |
| 496099 | 2141 | 2157 | CTGAGTCTGTGCTGCAT | 58 | 42112 | 42128 | 1154 |
| 496100 | 2142 | 2158 | GCTGAGTCTGTGCTGCA | 72 | 42113 | 42129 | 1155 |
| 496101 | 2305 | 2321 | CACAGAAAAGTGAGGCT | 53 | 42276 | 42292 | 1156 |
| 496102 | 2306 | 2322 | GCACAGAAAAGTGAGGC | 49 | 42277 | 42293 | 1157 |
| 496103 | 2307 | 2323 | GGCACAGAAAAGTGAGG | 28 | 42278 | 42294 | 1158 |
| 496104 | 2398 | 2414 | AAAGTCTGACATGGTGC | 65 | 42369 | 42385 | 1159 |
| 496105 | 2399 | 2415 | AAAAGTCTGACATGGTG | 54 | 42370 | 42386 | 1160 |
| 496106 | 2400 | 2416 | CAAAAGTCTGACATGGT | 39 | 42371 | 42387 | 1161 |
| 496036 | 474 | 490 | GACCCACTGGAGCACTG | 49 | 25600 | 25616 | 1091 |
| 496037 | 475 | 491 | GGACCCACTGGAGCACT | 76 | 25601 | 25617 | 1092 |
| 496038 | 476 | 492 | AGGACCCACTGGAGCAC | 72 | 25602 | 25618 | 1093 |
| 496039 | 553 | 569 | CAGCGATGAGCCAGCAA | 67 | 31120 | 31136 | 1094 |
| 496040 | 554 | 570 | ACAGCGATGAGCCAGCA | 67 | 31121 | 31137 | 1095 |
| 496041 | 555 | 571 | CACAGCGATGAGCCAGC | 78 | 31122 | 31138 | 1096 |
| 496042 | 556 | 572 | GCACAGCGATGAGCCAG | 61 | 31123 | 31139 | 1097 |
| 496043 | 557 | 573 | AGCACAGCGATGAGCCA | 70 | 31124 | 31140 | 1098 |
| 496044 | 558 | 574 | GAGCACAGCGATGAGCC | 48 | 31125 | 31141 | 1099 |
| 496045 | 998 | 1014 | TTCTTGCCAGGCATGGA | 39 | 38151 | 38167 | 1100 |
| 496046 | 999 | 1015 | ATTCTTGCCAGGCATGG | 31 | 38152 | 38168 | 1101 |
| 413433 | n/a | n/a | GCCTGGACAAGTCCTGCCCA | 68 | 32431 | 32450 | 425 |
| 496107 | n/a | n/a | CAGGGCCCTTTCCAGAA | 34 | 10044 | 10060 | 1085 |
| 496108 | n/a | n/a | ACAGGGCCCTTTCCAGA | 39 | 10045 | 10061 | 1086 |
| 496109 | n/a | n/a | CACAGGGCCCTTTCCAG | 39 | 10046 | 10062 | 1087 |
| 496110 | n/a | n/a | CGAATATCCCTAATAAC | 14 | 10210 | 10226 | 1088 |
| 496111 | n/a | n/a | TCGAATATCCCTAATAA | 9 | 10211 | 10227 | 1089 |
| 496112 | n/a | n/a | CTCGAATATCCCTAATA | 17 | 10212 | 10228 | 1090 |

TABLE 20

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 483876 | 14332 | 14351 | GTGAGATCCCCAGAGAGGAA | 26 | 1162 |
| 483877 | 14337 | 14356 | AAGGAGTGAGATCCCCAGAG | 34 | 1163 |
| 483878 | 14360 | 14379 | TTCTGACCCTATTTTCCAGA | 52 | 1164 |
| 483879 | 14385 | 14404 | CCCTCCATCCTTGAGAATCT | 76 | 1165 |
| 483880 | 14427 | 14446 | ATGTCACAAGTTCACAAACA | 49 | 1166 |
| 483881 | 14432 | 14451 | CATGAATGTCACAAGTTCAC | 38 | 1167 |
| 483882 | 14437 | 14456 | ACTAACATGAATGTCACAAG | 35 | 1168 |
| 483883 | 14442 | 14461 | CAAGGACTAACATGAATGTC | 0 | 1169 |
| 483884 | 14447 | 14466 | AATGACAAGGACTAACATGA | 24 | 1170 |
| 483885 | 14452 | 14471 | GGACAAATGACAAGGACTAA | 12 | 1171 |
| 483886 | 14457 | 14476 | ACACAGGACAAATGACAAGG | 62 | 1172 |
| 483887 | 14462 | 14481 | GTGTAACACAGGACAAATGA | 82 | 1173 |
| 483888 | 14467 | 14486 | TGAATGTGTAACACAGGACA | 75 | 1174 |
| 483889 | 14503 | 14522 | CAGGGTCTGCCACTCTCTAC | 88 | 1175 |
| 483890 | 14508 | 14527 | TAGAGCAGGGTCTGCCACTC | 85 | 1176 |
| 483891 | 14532 | 14551 | TCAGTGAAGCCTTCCTGGAT | 31 | 1177 |
| 483892 | 14537 | 14556 | CTTCCTCAGTGAAGCCTTCC | 72 | 1178 |
| 483893 | 14542 | 14561 | AGTCCCTTCCTCAGTGAAGC | 59 | 1179 |
| 483894 | 14547 | 14566 | CCCCAAGTCCCTTCCTCAGT | 51 | 1180 |
| 483895 | 14648 | 14667 | CACAGTCATCTTGTGTACAT | 93 | 1181 |
| 483896 | 14653 | 14672 | CTCTGCACAGTCATCTTGTG | 59 | 1182 |
| 483897 | 14658 | 14677 | GATCACTCTGCACAGTCATC | 83 | 1183 |
| 483898 | 14663 | 14682 | GCTCAGATCACTCTGCACAG | 94 | 1184 |
| 483899 | 14668 | 14687 | TCATTGCTCAGATCACTCTG | 71 | 1185 |
| 483900 | 14673 | 14692 | TCCTGTCATTGCTCAGATCA | 81 | 1186 |
| 483901 | 14678 | 14697 | GTCTTTCCTGTCATTGCTCA | 86 | 1187 |
| 483902 | 14715 | 14734 | TCAGGGTGATCAAGCTCCCC | 70 | 1188 |
| 483903 | 14720 | 14739 | TGACCTCAGGGTGATCAAGC | 75 | 1189 |
| 483904 | 14725 | 14744 | TTCCCTGACCTCAGGGTGAT | 49 | 1190 |
| 483905 | 14730 | 14749 | AAGACTTCCCTGACCTCAGG | 46 | 1191 |
| 483906 | 14735 | 14754 | CCAGGAAGACTTCCCTGACC | 65 | 1192 |
| 483907 | 14740 | 14759 | CTCTTCCAGGAAGACTTCCC | 68 | 1193 |
| 483908 | 14745 | 14764 | GTCACCTCTTCCAGGAAGAC | 94 | 1194 |
| 483909 | 14750 | 14769 | TGAATGTCACCTCTTCCAGG | 84 | 1195 |
| 483910 | 14755 | 14774 | CGGACTGAATGTCACCTCTT | 95 | 1196 |
| 483911 | 14760 | 14779 | AGATCCGGACTGAATGTCAC | 79 | 1197 |

TABLE 20-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 483912 | 14765 | 14784 | TTTCCAGATCCGGACTGAAT | 79 | 1198 |
| 483913 | 14770 | 14789 | TCATCTTTCCAGATCCGGAC | 95 | 1199 |
| 483914 | 14775 | 14794 | TCTATTCATCTTTCCAGATC | 55 | 1200 |
| 483915 | 14802 | 14821 | TGAATGTTCTTGCCTGTCTT | 48 | 1201 |
| 483916 | 14807 | 14826 | GTACCTGAATGTTCTTGCCT | 85 | 1202 |
| 483917 | 14812 | 14831 | TTCCTGTACCTGAATGTTCT | 71 | 1203 |
| 483918 | 14852 | 14871 | TGCCTCTCCCATCCAAATCT | 75 | 1204 |
| 483919 | 14882 | 14901 | GTTGGTCACTCAGAGGCCCT | 86 | 1205 |
| 483920 | 14953 | 14972 | ACAGGCCTGGATCCAGCATC | 77 | 1206 |
| 483921 | 14986 | 15005 | TCTTCCTCCTGCTGCAGACA | 86 | 1207 |
| 483922 | 14991 | 15010 | TCAAGTCTTCCTCCTGCTGC | 68 | 1208 |
| 483923 | 14996 | 15015 | AGCTCTCAAGTCTTCCTCCT | 87 | 1209 |
| 483924 | 15001 | 15020 | CCATGAGCTCTCAAGTCTTC | 82 | 1210 |
| 483925 | 15006 | 15025 | CTTTCCCATGAGCTCTCAAG | 68 | 1211 |
| 483926 | 15011 | 15030 | GGCTCCTTTCCCATGAGCTC | 77 | 1212 |
| 483927 | 15016 | 15035 | CACCAGGCTCCTTTCCCATG | 84 | 1213 |
| 483928 | 15021 | 15040 | AACTGCACCAGGCTCCTTTC | 70 | 1214 |
| 483929 | 15026 | 15045 | AAACTAACTGCACCAGGCTC | 65 | 1215 |
| 483930 | 15031 | 15050 | CCAATAAACTAACTGCACCA | 36 | 1216 |
| 483931 | 15036 | 15055 | GGAGGCCAATAAACTAACTG | 37 | 1217 |
| 483932 | 15041 | 15060 | GTGCTGGAGGCCAATAAACT | 60 | 1218 |
| 483933 | 15046 | 15065 | TCAAAGTGCTGGAGGCCAAT | 66 | 1219 |
| 483934 | 15073 | 15092 | AGCCAGCAGCTCCATACCAG | 70 | 1220 |
| 483935 | 15078 | 15097 | AAATCAGCCAGCAGCTCCAT | 56 | 1221 |
| 483936 | 15083 | 15102 | CCCTCAAATCAGCCAGCAGC | 62 | 1222 |
| 483937 | 15088 | 15107 | TGAGGCCCTCAAATCAGCCA | 52 | 1223 |
| 483938 | 15093 | 15112 | GCCCATGAGGCCCTCAAATC | 44 | 1224 |
| 483939 | 15098 | 15117 | GCCCTGCCCATGAGGCCCTC | 44 | 1225 |
| 483940 | 15103 | 15122 | CCTGGGCCCTGCCCATGAGG | 28 | 1226 |
| 483941 | 15144 | 15163 | GCCAAGCAGGAGCTGGACAG | 35 | 1227 |
| 483942 | 15178 | 15197 | TAGTGGCTTGCTGAGGCTGC | 67 | 1228 |
| 483943 | 15183 | 15202 | AAGGGTAGTGGCTTGCTGAG | 31 | 1229 |
| 483944 | 15188 | 15207 | TAAGGAAGGGTAGTGGCTTG | 5 | 1230 |
| 483945 | 15199 | 15218 | GAGACTGAGGGTAAGGAAGG | 31 | 1231 |
| 483946 | 15204 | 15223 | ATGAGGAGACTGAGGGTAAG | 41 | 1232 |
| 483947 | 15209 | 15228 | CATAGATGAGGAGACTGAGG | 42 | 1233 |

TABLE 20-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 483948 | 15214 | 15233 | CATTTCATAGATGAGGAGAC | 71 | 1234 |
| 483949 | 15219 | 15238 | TTGCTCATTTCATAGATGAG | 78 | 1235 |
| 483950 | 15224 | 15243 | CACTTTTGCTCATTTCATAG | 74 | 1236 |
| 483951 | 15247 | 15266 | ATAATCTGCACAGGTTCTTA | 47 | 1237 |
| 483952 | 15252 | 15271 | GCACCATAATCTGCACAGGT | 92 | 1238 |
| 413433 | 32431 | 32450 | GCCTGGACAAGTCCTGCCCA | 87 | 425 |

TABLE 21

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 483953 | 17938 | 17957 | GGGTCTAGGTGAGTGAGAAA | 42 | 1239 |
| 483954 | 17960 | 17979 | ATCTGGACCTAATGTCTGCC | 71 | 1240 |
| 483955 | 17965 | 17984 | GGCCCATCTGGACCTAATGT | 41 | 1241 |
| 483956 | 17970 | 17989 | ACCTGGGCCCATCTGGACCT | 61 | 1242 |
| 483957 | 18042 | 18061 | CTCTTGGGCTCCTTGAGGCA | 33 | 1243 |
| 483958 | 18047 | 18066 | ACAGCCTCTTGGGCTCCTTG | 33 | 1244 |
| 483959 | 18052 | 18071 | TGTGAACAGCCTCTTGGGCT | 49 | 1245 |
| 483960 | 18057 | 18076 | AGAGGTGTGAACAGCCTCTT | 0 | 1246 |
| 483961 | 18078 | 18097 | GCCAGAAAGATGCCAGCTAA | 67 | 1247 |
| 483962 | 18083 | 18102 | AGAGAGCCAGAAAGATGCCA | 57 | 1248 |
| 483963 | 18113 | 18132 | AAAAGGGCCAGAATGTCTGG | 24 | 1249 |
| 483964 | 18136 | 18155 | TAAGGAATCTAAATAACTTA | 21 | 1250 |
| 483965 | 18141 | 18160 | TGTCATAAGGAATCTAAATA | 16 | 1251 |
| 483966 | 18146 | 18165 | AGGATTGTCATAAGGAATCT | 54 | 1252 |
| 483967 | 18151 | 18170 | AATCCAGGATTGTCATAAGG | 59 | 1253 |
| 483968 | 18156 | 18175 | GCTTTAATCCAGGATTGTCA | 80 | 1254 |
| 483969 | 18161 | 18180 | CCTTAGCTTTAATCCAGGAT | 86 | 1255 |
| 483970 | 18166 | 18185 | GTCCTCCTTAGCTTTAATCC | 80 | 1256 |
| 483971 | 18171 | 18190 | TCAGTGTCCTCCTTAGCTTT | 65 | 1257 |
| 483972 | 18176 | 18195 | GGGACTCAGTGTCCTCCTTA | 81 | 1258 |
| 483973 | 18181 | 18200 | TCCCTGGGACTCAGTGTCCT | 77 | 1259 |
| 483974 | 18220 | 18239 | GATTCTTACCTGCAATGAGA | 36 | 1260 |
| 483975 | 18225 | 18244 | GCTCTGATTCTTACCTGCAA | 70 | 1261 |
| 483976 | 18230 | 18249 | CCCTGGCTCTGATTCTTACC | 60 | 1262 |

TABLE 21-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 483977 | 18235 | 18254 | TCAAACCCTGGCTCTGATTC | 70 | 1263 |
| 483978 | 18240 | 18259 | AGGATTCAAACCCTGGCTCT | 72 | 1264 |
| 483979 | 18286 | 18305 | ATGCCTGCCCTGCCTAGGAA | 75 | 1265 |
| 483980 | 18291 | 18310 | AAATAATGCCTGCCCTGCCT | 37 | 1266 |
| 483981 | 18296 | 18315 | GGGTAAAATAATGCCTGCCC | 65 | 1267 |
| 483982 | 18301 | 18320 | TTGATGGGTAAAATAATGCC | 9 | 1268 |
| 483983 | 18306 | 18325 | CCTGTTTGATGGGTAAAATA | 60 | 1269 |
| 483984 | 18311 | 18330 | CCTCTCCTGTTTGATGGGTA | 89 | 1270 |
| 483985 | 18316 | 18335 | GGTGTCCTCTCCTGTTTGAT | 78 | 1271 |
| 483986 | 18321 | 18340 | GCCTCGGTGTCCTCTCCTGT | 84 | 1272 |
| 483987 | 18326 | 18345 | AGTAAGCCTCGGTGTCCTCT | 87 | 1273 |
| 483988 | 18331 | 18350 | TACCAAGTAAGCCTCGGTGT | 87 | 1274 |
| 483989 | 18336 | 18355 | TTAATTACCAAGTAAGCCTC | 74 | 1275 |
| 483990 | 18369 | 18388 | TTCATAAAAAGTAAAGATCT | 51 | 1276 |
| 483991 | 18374 | 18393 | AGAGCTTCATAAAAAGTAAA | 0 | 1277 |
| 483992 | 18379 | 18398 | AGCCAAGAGCTTCATAAAAA | 87 | 1278 |
| 483993 | 18417 | 18436 | TCACCAGATTGTTGTGGGAA | 84 | 1279 |
| 483994 | 18422 | 18441 | CTACCTCACCAGATTGTTGT | 75 | 1280 |
| 483995 | 18427 | 18446 | AATACCTACCTCACCAGATT | 63 | 1281 |
| 483996 | 18432 | 18451 | GGGCTAATACCTACCTCACC | 81 | 1282 |
| 483997 | 18450 | 18469 | TTCCTCATCTATACAGTGGG | 85 | 1283 |
| 483998 | 18455 | 18474 | TCAGCTTCCTCATCTATACA | 52 | 1284 |
| 483999 | 18460 | 18479 | AAGCTTCAGCTTCCTCATCT | 35 | 1285 |
| 484000 | 18465 | 18484 | TATACAAGCTTCAGCTTCCT | 44 | 1286 |
| 484001 | 18470 | 18489 | CTTCCTATACAAGCTTCAGC | 77 | 1287 |
| 484002 | 18475 | 18494 | AGTCACTTCCTATACAAGCT | 64 | 1288 |
| 484003 | 18513 | 18532 | AGAACCTGGCCTCTAACTCG | 42 | 1289 |
| 484004 | 18581 | 18600 | CATACTGGCATCTGGCAGGG | 84 | 1290 |
| 484005 | 18586 | 18605 | ACCTCCATACTGGCATCTGG | 66 | 1291 |
| 484006 | 18591 | 18610 | ACCTCACCTCCATACTGGCA | 79 | 1292 |
| 484007 | 18747 | 18766 | ATGAAGAAAATAATTTGGG | 0 | 1293 |
| 484008 | 18821 | 18840 | TTAACTTCTGCTGAGGGAGA | 63 | 1294 |
| 484009 | 18826 | 18845 | GATGCTTAACTTCTGCTGAG | 68 | 1295 |
| 484010 | 18831 | 18850 | GTTAGGATGCTTAACTTCTG | 78 | 1296 |
| 484011 | 18836 | 18855 | GTTAAGTTAGGATGCTTAAC | 65 | 1297 |
| 484012 | 18869 | 18888 | ATAGGCCTGGATGCCCAAGT | 78 | 1298 |

TABLE 21-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| | 20779 | 20798 | | | |
| 484013 | 18880 20790 | 18899 20809 | CAGAGGCAGCTATAGGCCTG | 69 | 1299 |
| 484014 | 18885 | 18904 | TGCCTCAGAGGCAGCTATAG | 30 | 1300 |
| 484015 | 18890 | 18909 | TGTCCTGCCTCAGAGGCAGC | 65 | 1301 |
| 484016 | 18895 | 18914 | GATGATGTCCTGCCTCAGAG | 61 | 1302 |
| 484017 | 18900 | 18919 | CAGCAGATGATGTCCTGCCT | 85 | 1303 |
| 484018 | 18982 | 19001 | GGGACAGAGCTAAGACCCAA | 58 | 1304 |
| 484019 | 19013 | 19032 | GTCAAAGGTGGCTTCCTGGG | 74 | 1305 |
| 484020 | 19018 | 19037 | GAGTAGTCAAAGGTGGCTTC | 78 | 1306 |
| 484021 | 19023 | 19042 | GGAATGAGTAGTCAAAGGTG | 27 | 1307 |
| 484022 | 19028 | 19047 | AAGTTGGAATGAGTAGTCAA | 14 | 1308 |
| 484023 | 19041 | 19060 | GCTGAGAATAAAGAAGTTGG | 55 | 1309 |
| 484024 | 19046 | 19065 | TAGAAGCTGAGAATAAAGAA | 36 | 1310 |
| 484025 | 19051 | 19070 | TGAAATAGAAGCTGAGAATA | 20 | 1311 |
| 484026 | 19112 | 19131 | GGAGTTCTAATGAGGCAGAC | 50 | 1312 |
| 484027 | 19117 | 19136 | TGCAGGGAGTTCTAATGAGG | 53 | 1313 |
| 484028 | 19122 | 19141 | AGCCTTGCAGGGAGTTCTAA | 62 | 1314 |
| 484029 | 19127 | 19146 | AACAAAGCCTTGCAGGGAGT | 30 | 1315 |
| 413433 | 32431 | 32450 | GCCTGGACAAGTCCTGCCCA | 76 | 425 |

TABLE 22

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 484030 | 22439 | 22458 | ATGGCAAGTGCTTCCGTGGG | 79 | 1316 |
| 484031 | 22444 | 22463 | ACCAAATGGCAAGTGCTTCC | 82 | 1317 |
| 484032 | 22449 | 22468 | CAAATACCAAATGGCAAGTG | 34 | 1318 |
| 484033 | 22474 | 22493 | CTGCAAGGTGGTGAGCTCTA | 28 | 1319 |
| 484034 | 22513 | 22532 | CCTCACTTCCCATCTGCCTG | 24 | 1320 |
| 484035 | 22518 | 22537 | TGAACCCTCACTTCCCATCT | 14 | 1321 |
| 484036 | 22523 | 22542 | CCAAGTGAACCCTCACTTCC | 12 | 1322 |
| 484037 | 22528 | 22547 | GTCTACCAAGTGAACCCTCA | 20 | 1323 |
| 484038 | 22533 | 22552 | ATGCAGTCTACCAAGTGAAC | 39 | 1324 |
| 484039 | 22538 | 22557 | GGGAAATGCAGTCTACCAAG | 55 | 1325 |
| 484040 | 22543 | 22562 | CAAGTGGGAAATGCAGTCTA | 53 | 1326 |

TABLE 22-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 484041 | 22548 | 22567 | GCCAACAAGTGGGAAATGCA | 85 | 1327 |
| 484042 | 22573 | 22592 | CCAACTACCGCCCACAGCTC | 43 | 1328 |
| 484043 | 22578 | 22597 | CAGCCCCAACTACCGCCCAC | 29 | 1329 |
| 484044 | 22583 | 22602 | TTATCCAGCCCCAACTACCG | 10 | 1330 |
| 484045 | 22588 | 22607 | CTGCCTTATCCAGCCCCAAC | 43 | 1331 |
| 484046 | 22593 | 22612 | TCACCCTGCCTTATCCAGCC | 51 | 1332 |
| 484047 | 22713 | 22732 | TCTTGTTCAACCCTCACCCC | 45 | 1333 |
| 484048 | 22766 | 22785 | CTTATTAGGTGTCTTAAAAT | 43 | 1334 |
| 484049 | 22771 | 22790 | CTAAGCTTATTAGGTGTCTT | 85 | 1335 |
| 484050 | 22776 | 22795 | CTCTGCTAAGCTTATTAGGT | 69 | 1336 |
| 484051 | 22820 | 22839 | ACTGAGAAGACCTAAAAATT | 0 | 1337 |
| 484052 | 22825 | 22844 | AAACAACTGAGAAGACCTAA | 45 | 1338 |
| 484053 | 22830 | 22849 | AACTGAAACAACTGAGAAGA | 32 | 1339 |
| 484054 | 22835 | 22854 | TCCCCAACTGAAACAACTGA | 65 | 1340 |
| 484055 | 22841 | 22860 | GACATATCCCCAACTGAAAC | 67 | 1341 |
| 484056 | 22846 | 22865 | CTGATGACATATCCCCAACT | 71 | 1342 |
| 484057 | 22851 | 22870 | TTTCACTGATGACATATCCC | 69 | 1343 |
| 484058 | 22856 | 22875 | AGAAATTTCACTGATGACAT | 56 | 1344 |
| 484059 | 22861 | 22880 | AGTATAGAAATTTCACTGAT | 18 | 1345 |
| 484060 | 22866 | 22885 | GGAGGAGTATAGAAATTTCA | 53 | 1346 |
| 484061 | 22871 | 22890 | TTGGAGGAGGAGTATAGAAA | 48 | 1347 |
| 484062 | 22876 | 22895 | GCAGCTTGGAGGAGGAGTAT | 32 | 1348 |
| 484063 | 22881 | 22900 | CCCATGCAGCTTGGAGGAGG | 68 | 1349 |
| 484064 | 22886 | 22905 | CAGCCCCATGCAGCTTGGA | 84 | 1350 |
| 484065 | 22891 | 22910 | AGGGCCAGCCCCATGCAGC | 67 | 1351 |
| 484066 | 22916 | 22935 | TTATCTAGCTCCCTACCTTG | 57 | 1352 |
| 484067 | 22968 | 22987 | TGAAGCCAGTGGTTTGAGGG | 30 | 1353 |
| 484068 | 22992 | 23011 | TGCTTCCCGTTGCAGACAGG | 34 | 1354 |
| 484069 | 23095 | 23114 | GTCCAAACACTCAGGTAGGG | 72 | 1355 |
| 484070 | 23100 | 23119 | CTTCAGTCCAAACACTCAGG | 85 | 1356 |
| 484071 | 23128 | 23147 | TTAAGTCTGAGAAACACCAC | 77 | 1357 |
| 484072 | 23133 | 23152 | GGTGATTAAGTCTGAGAAAC | 64 | 1358 |
| 484073 | 23138 | 23157 | CCCCAGGTGATTAAGTCTGA | 73 | 1359 |
| 484074 | 23143 | 23162 | AAGATCCCCAGGTGATTAAG | 26 | 1360 |
| 484075 | 23148 | 23167 | TTAACAAGATCCCCAGGTGA | 22 | 1361 |
| 484076 | 23154 | 23173 | TGCATTTTAACAAGATCCCC | 0 | 1362 |

TABLE 22-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 484077 | 23159 | 23178 | AAATCTGCATTTTAACAAGA | 20 | 1363 |
| 484078 | 23164 | 23183 | AATCAAAATCTGCATTTTAA | 40 | 1364 |
| 484079 | 23169 | 23188 | TACTGAATCAAAATCTGCAT | 53 | 1365 |
| 484080 | 23174 | 23193 | GGATTTACTGAATCAAAATC | 31 | 1366 |
| 484081 | 23179 | 23198 | AGACTGGATTTACTGAATCA | 65 | 1367 |
| 484082 | 23184 | 23203 | GCTCCAGACTGGATTTACTG | 72 | 1368 |
| 484083 | 23232 | 23251 | AGCAGCATCAGCATCACCTG | 79 | 1369 |
| 484084 | 23237 | 23256 | GGAACAGCAGCATCAGCATC | 39 | 1370 |
| 484085 | 23242 | 23261 | GTCTGGGAACAGCAGCATCA | 90 | 1371 |
| 484086 | 23271 | 23290 | TACTCTAGCACTTTCCTACT | 53 | 1372 |
| 484087 | 23276 | 23295 | AAATGTACTCTAGCACTTTC | 41 | 1373 |
| 484088 | 23281 | 23300 | AGACAAAATGTACTCTAGCA | 58 | 1374 |
| 484089 | 23305 | 23324 | GGCTGGATGCCCTGGCTAGA | 79 | 1375 |
| 484090 | 23310 | 23329 | AGGCAGGCTGGATGCCCTGG | 55 | 1376 |
| 484091 | 23315 | 23334 | ATCTGAGGCAGGCTGGATGC | 59 | 1377 |
| 484092 | 23417 | 23436 | ATCTTCCAGCAGCTGGCTCT | 28 | 1378 |
| 484093 | 23422 | 23441 | AAGTCATCTTCCAGCAGCTG | 41 | 1379 |
| 484094 | 23427 | 23446 | TGGACAAGTCATCTTCCAGC | 85 | 1380 |
| 484095 | 23470 | 23489 | AAGTCCAAGCACAGGCTTGA | 44 | 1381 |
| 484096 | 23475 | 23494 | AAGTGAAGTCCAAGCACAGG | 39 | 1382 |
| 484097 | 23480 | 23499 | GAGGGAAGTGAAGTCCAAGC | 63 | 1383 |
| 484098 | 23547 | 23566 | TCCTTGAGGGTCTCATAACC | 66 | 1384 |
| 484099 | 23552 | 23571 | GCTTATCCTTGAGGGTCTCA | 84 | 1385 |
| 484100 | 23557 | 23576 | CACATGCTTATCCTTGAGGG | 82 | 1386 |
| 484101 | 23562 | 23581 | TTCATCACATGCTTATCCTT | 75 | 1387 |
| 484102 | 23567 | 23586 | ATGAGTTCATCACATGCTTA | 78 | 1388 |
| 484103 | 23597 | 23616 | TCAACCTGCCCAGCAGTGGG | 62 | 1389 |
| 484104 | 23641 | 23660 | CTCTGTACACAGGACACAGT | 70 | 1390 |
| 484105 | 23646 | 23665 | AAAGGCTCTGTACACAGGAC | 79 | 1391 |
| 484106 | 23651 | 23670 | AGTGCAAAGGCTCTGTACAC | 66 | 1392 |
| 413433 | 32431 | 32450 | GCCTGGACAAGTCCTGCCCA | 86 | 425 |

TABLE 23

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 413433 | 32431 | 32450 | GCCTGGACAAGTCCTGCCCA | 84 | 425 |
| 484107 | 26390 | 26409 | GGCAACCTAAGGAGTGAGGG | 71 | 1393 |
| 484108 | 26395 | 26414 | TGGATGGCAACCTAAGGAGT | 40 | 1394 |
| 484109 | 26400 | 26419 | TGGCCTGGATGGCAACCTAA | 57 | 1395 |
| 484110 | 26479 | 26498 | GCTATGCTGAGAGCACAGGG | 79 | 1396 |
| 484111 | 26484 | 26503 | TACCTGCTATGCTGAGAGCA | 71 | 1397 |
| 484112 | 26489 | 26508 | GAAGCTACCTGCTATGCTGA | 46 | 1398 |
| 484113 | 26494 | 26513 | CTGAGGAAGCTACCTGCTAT | 36 | 1399 |
| 484114 | 26516 | 26535 | CAGGTTCATCTGCCTTGACG | 70 | 1400 |
| 484115 | 26521 | 26540 | TGGAGCAGGTTCATCTGCCT | 83 | 1401 |
| 484116 | 26526 | 26545 | TGCTCTGGAGCAGGTTCATC | 81 | 1402 |
| 484117 | 26531 | 26550 | TGTGATGCTCTGGAGCAGGT | 80 | 1403 |
| 484118 | 26536 | 26555 | CACTCTGTGATGCTCTGGAG | 74 | 1404 |
| 484119 | 26541 | 26560 | GAATGCACTCTGTGATGCTC | 68 | 1405 |
| 484120 | 26566 | 26585 | CAGAGGGACTGGCTCACAGG | 21 | 1406 |
| 484121 | 26590 | 26609 | TACAGTCCCGAAGAGTGGGT | 38 | 1407 |
| 484122 | 26595 | 26614 | GCCTATACAGTCCCGAAGAG | 51 | 1408 |
| 484123 | 26600 | 26619 | TACCAGCCTATACAGTCCCG | 60 | 1409 |
| 484124 | 26605 | 26624 | TCCCCTACCAGCCTATACAG | 59 | 1410 |
| 484125 | 26610 | 26629 | GATGATCCCTACCAGCCTA | 68 | 1411 |
| 484126 | 26615 | 26634 | GTCCTGATGATCCCCTACCA | 80 | 1412 |
| 484127 | 26620 | 26639 | GGTAAGTCCTGATGATCCCC | 86 | 1413 |
| 484128 | 26625 | 26644 | GACATGGTAAGTCCTGATGA | 54 | 1414 |
| 484129 | 26630 | 26649 | GCACTGACATGGTAAGTCCT | 87 | 1415 |
| 484130 | 26635 | 26654 | GCTCAGCACTGACATGGTAA | 85 | 1416 |
| 484131 | 26640 | 26659 | CAGCTGCTCAGCACTGACAT | 80 | 1417 |
| 484132 | 26645 | 26664 | AAGGACAGCTGCTCAGCACT | 60 | 1418 |
| 484133 | 26711 | 26730 | GTGAAGTTCTATCCCTTGGC | 89 | 1419 |
| 484134 | 26716 | 26735 | CACCTGTGAAGTTCTATCCC | 69 | 1420 |
| 484135 | 26721 | 26740 | TTTCTCACCTGTGAAGTTCT | 79 | 1421 |
| 484136 | 26755 | 26774 | AGCAGGTAGTTGATGAACCT | 70 | 1422 |
| 484137 | 26778 | 26797 | TGCCATTTAATGAGCTTCAC | 86 | 1423 |
| 484138 | 26783 | 26802 | AACTCTGCCATTTAATGAGC | 55 | 1424 |
| 484139 | 26788 | 26807 | ATCCAACTCTGCCATTTAA | 81 | 1425 |
| 484140 | 26811 | 26830 | GAATGCACTGAGTTTCTGCT | 89 | 1426 |
| 484141 | 26849 | 26868 | CACTAATTCTGGGCTTCCAG | 87 | 1427 |
| 484142 | 26854 | 26873 | CAGTTCACTAATTCTGGGCT | 79 | 1428 |

TABLE 23-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
| --- | --- | --- | --- | --- | --- |
| 484143 | 26859 | 26878 | AGCCCCAGTTCACTAATTCT | 52 | 1429 |
| 484144 | 26864 | 26883 | GTTTCAGCCCCAGTTCACTA | 54 | 1430 |
| 484145 | 26869 | 26888 | TGGCTGTTTCAGCCCCAGTT | 70 | 1431 |
| 484146 | 26874 | 26893 | AAGACTGGCTGTTTCAGCCC | 79 | 1432 |
| 484147 | 26879 | 26898 | AGGTGAAGACTGGCTGTTTC | 76 | 1433 |
| 484148 | 26884 | 26903 | CCTAAAGGTGAAGACTGGCT | 91 | 1434 |
| 484149 | 26889 | 26908 | TTGGGCCTAAAGGTGAAGAC | 64 | 1435 |
| 484150 | 26894 | 26913 | CGTTCTTGGGCCTAAAGGTG | 57 | 1436 |
| 484151 | 26899 | 26918 | AAGCCCGTTCTTGGGCCTAA | 23 | 1437 |
| 484152 | 26926 | 26945 | TTAAGGGTTCATGGATCCCC | 66 | 1438 |
| 484153 | 26931 | 26950 | TAATTTTAAGGGTTCATGGA | 29 | 1439 |
| 484154 | 27005 | 27024 | CTGTAAGACTTTGAGGACAG | 60 | 1440 |
| 484155 | 27010 | 27029 | TGTCCCTGTAAGACTTTGAG | 43 | 1441 |
| 484156 | 27046 | 27065 | GTTCTTCCAACCAGTGTTTG | 84 | 1442 |
| 484157 | 27051 | 27070 | GCTCAGTTCTTCCAACCAGT | 94 | 1443 |
| 484158 | 27056 | 27075 | AGTTTGCTCAGTTCTTCCAA | 85 | 1444 |
| 484159 | 27061 | 27080 | TGTTTAGTTTGCTCAGTTCT | 68 | 1445 |
| 484160 | 27101 | 27120 | AAATGCAAGCCATGTTAGGG | 54 | 1446 |
| 484161 | 27106 | 27125 | TGGCCAAATGCAAGCCATGT | 72 | 1447 |
| 484162 | 27111 | 27130 | GTAAGTGGCCAAATGCAAGC | 67 | 1448 |
| 484163 | 27116 | 27135 | TTCTAGTAAGTGGCCAAATG | 57 | 1449 |
| 484164 | 27174 | 27193 | CAGGCCTCCACTTCCTTTTT | 66 | 1450 |
| 484165 | 27211 | 27230 | TCTTCTCATGTGACCCCAAG | 69 | 1451 |
| 484166 | 27216 | 27235 | TACTTTCTTCTCATGTGACC | 59 | 1452 |
| 484167 | 27221 | 27240 | CCCAGTACTTTCTTCTCATG | 85 | 1453 |
| 484168 | 27226 | 27245 | CTGGTCCCAGTACTTTCTTC | 63 | 1454 |
| 484169 | 27231 | 27250 | TTGTCCTGGTCCCAGTACTT | 86 | 1455 |
| 484170 | 27236 | 27255 | GGTTCTTGTCCTGGTCCCAG | 90 | 1456 |
| 484171 | 27241 | 27260 | CCCTGGGTTCTTGTCCTGGT | 82 | 1457 |
| 484172 | 27246 | 27265 | GGAGTCCCTGGGTTCTTGTC | 74 | 1458 |
| 484173 | 27251 | 27270 | AGGCTGGAGTCCCTGGGTTC | 53 | 1459 |
| 484174 | 27256 | 27275 | CTGGGAGGCTGGAGTCCCTG | 55 | 1460 |
| 484175 | 27352 | 27371 | ACCAGCCAGGCCCAGACCCA | 34 | 1461 |
| 484176 | 27357 | 27376 | TCCCTACCAGCCAGGCCCAG | 17 | 1462 |
| 484177 | 27362 | 27381 | TCAGCTCCCTACCAGCCAGG | 47 | 1463 |
| 484178 | 27367 | 27386 | GCTGCTCAGCTCCCTACCAG | 74 | 1464 |

TABLE 23-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
| --- | --- | --- | --- | --- | --- |
| 484179 | 27372 | 27391 | TACAAGCTGCTCAGCTCCCT | 67 | 1465 |
| 484180 | 27377 | 27396 | TGTTCTACAAGCTGCTCAGC | 73 | 1466 |
| 484181 | 27382 | 27401 | GCTGGTGTTCTACAAGCTGC | 92 | 1467 |
| 484182 | 27387 | 27406 | CGTGAGCTGGTGTTCTACAA | 80 | 1468 |
| 484183 | 27437 | 27456 | TCTGATCAATTATTAACCTA | 21 | 1469 |

TABLE 24

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
| --- | --- | --- | --- | --- | --- |
| 484184 | 29480 | 29499 | TGGATGTAGACTCTCCATGA | 61 | 1470 |
| 484185 | 29485 | 29504 | AAGGCTGGATGTAGACTCTC | 72 | 1471 |
| 484186 | 29490 | 29509 | AAGATAAGGCTGGATGTAGA | 28 | 1472 |
| 484187 | 29495 | 29514 | GGGAGAAGATAAGGCTGGAT | 50 | 1473 |
| 484188 | 29500 | 29519 | CCCATGGGAGAAGATAAGGC | 62 | 1474 |
| 484189 | 29505 | 29524 | GGTTTCCCATGGGAGAAGAT | 50 | 1475 |
| 484190 | 29538 | 29557 | CATGCTCTCTTCTCACCATG | 71 | 1476 |
| 484191 | 29543 | 29562 | GATGTCATGCTCTCTTCTCA | 66 | 1477 |
| 484192 | 29548 | 29567 | CTCTGGATGTCATGCTCTCT | 82 | 1478 |
| 484193 | 29570 | 29589 | CCAGGTGCTGTAGGCTGCCT | 84 | 1479 |
| 484194 | 29575 | 29594 | TGGTCCCAGGTGCTGTAGGC | 75 | 1480 |
| 484195 | 29580 | 29599 | CCTGGTGGTCCCAGGTGCTG | 62 | 1481 |
| 484196 | 29607 | 29626 | AGGCCAACCCTTGCTGTGTG | 63 | 1482 |
| 484197 | 29612 | 29631 | AAGGGAGGCCAACCCTTGCT | 60 | 1483 |
| 484198 | 29635 | 29654 | TAGGACTTTTTCCACTGCCC | 72 | 1484 |
| 484199 | 29640 | 29659 | CCTTCTAGGACTTTTTCCAC | 41 | 1485 |
| 484200 | 29663 | 29682 | GTTTGGTGGGAGAAGCATGG | 25 | 1486 |
| 484201 | 29668 | 29687 | CTCATGTTTGGTGGGAGAAG | 45 | 1487 |
| 484202 | 29673 | 29692 | AGGTACTCATGTTTGGTGGG | 77 | 1488 |
| 484203 | 29678 | 29697 | GCAGCAGGTACTCATGTTTG | 86 | 1489 |
| 484204 | 29683 | 29702 | CAAGGGCAGCAGGTACTCAT | 81 | 1490 |
| 484205 | 29762 | 29781 | ACATATCATCTCTTGCCTGT | 59 | 1491 |
| 484206 | 29767 | 29786 | TATCTACATATCATCTCTTG | 31 | 1492 |
| 484207 | 29772 | 29791 | CATACTATCTACATATCATC | 10 | 1493 |
| 484208 | 29777 | 29796 | AATATCATACTATCTACATA | 21 | 1494 |
| 484209 | 29782 | 29801 | TCCCCAATATCATACTATCT | 84 | 1495 |

TABLE 24-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
| --- | --- | --- | --- | --- | --- |
| 484210 | 29804 | 29823 | ACCTCAGCTCTTCAAGAAGT | 61 | 1496 |
| 484211 | 29809 | 29828 | CTCAGACCTCAGCTCTTCAA | 76 | 1497 |
| 484212 | 29814 | 29833 | CCTATCTCAGACCTCAGCTC | 58 | 1498 |
| 484213 | 29819 | 29838 | TAAGGCCTATCTCAGACCTC | 66 | 1499 |
| 484214 | 29824 | 29843 | ACCTTTAAGGCCTATCTCAG | 4 | 1500 |
| 484215 | 29829 | 29848 | ACCCAACCTTTAAGGCCTAT | 86 | 1501 |
| 484216 | 29834 | 29853 | TTTTTACCCAACCTTTAAGG | 53 | 1502 |
| 484217 | 29839 | 29858 | TCCATTTTTTACCCAACCTT | 87 | 1503 |
| 484218 | 29844 | 29863 | CTCTTTCCATTTTTTACCCA | 80 | 1504 |
| 484219 | 29849 | 29868 | CTTCTCTCTTTCCATTTTTT | 75 | 1505 |
| 484220 | 29854 | 29873 | CAGGGCTTCTCTCTTTCCAT | 83 | 1506 |
| 484221 | 29859 | 29878 | CTCAGCAGGGCTTCTCTCTT | 66 | 1507 |
| 484222 | 29864 | 29883 | CTGCCCTCAGCAGGGCTTCT | 0 | 1508 |
| 484223 | 29869 | 29888 | ACTAGCTGCCCTCAGCAGGG | 28 | 1509 |
| 484224 | 29902 | 29921 | TTGTGCCATGCCTGCTTTAT | 39 | 1510 |
| 484225 | 30358 | 30377 | GCAGAGCCCATCAGCCTCCC | 44 | 1511 |
| 484226 | 30363 | 30382 | AAAGCGCAGAGCCCATCAGC | 48 | 1512 |
| 484227 | 30407 | 30426 | CTGGCTCCCTTCCAACATAA | 64 | 1513 |
| 484228 | 30412 | 30431 | GAGGGCTGGCTCCCTTCCAA | 41 | 1514 |
| 484229 | 30417 | 30436 | AGGAGGAGGGCTGGCTCCCT | 12 | 1515 |
| 484230 | 30422 | 30441 | TGCCCAGGAGGAGGGCTGGC | 4 | 1516 |
| 484231 | 30483 | 30502 | TAGGCTTTAGAAATTCACCA | 91 | 1517 |
| 484232 | 30514 | 30533 | CAGGTCTGACTCTACAGTCC | 78 | 1518 |
| 484233 | 30519 | 30538 | AAACACAGGTCTGACTCTAC | 55 | 1519 |
| 484234 | 30524 | 30543 | GATTCAAACACAGGTCTGAC | 62 | 1520 |
| 484235 | 30529 | 30548 | GCCAGGATTCAAACACAGGT | 82 | 1521 |
| 484236 | 30534 | 30553 | GCAGAGCCAGGATTCAAACA | 55 | 1522 |
| 484237 | 30539 | 30558 | CAGTGGCAGAGCCAGGATTC | 66 | 1523 |
| 484238 | 30544 | 30563 | CAGGACAGTGGCAGAGCCAG | 27 | 1524 |
| 484239 | 30549 | 30568 | CCCAGCAGGACAGTGGCAGA | 39 | 1525 |
| 484240 | 30554 | 30573 | GGTCACCCAGCAGGACAGTG | 65 | 1526 |
| 484241 | 30559 | 30578 | CCCAAGGTCACCCAGCAGGA | 76 | 1527 |
| 484242 | 30564 | 30583 | ACTTGCCCAAGGTCACCCAG | 68 | 1528 |
| 484243 | 30569 | 30588 | AGATAACTTGCCCAAGGTCA | 62 | 1529 |
| 484244 | 30610 | 30629 | TTGCCCCATTTTAGAGATAA | 26 | 1530 |
| 484245 | 30615 | 30634 | TGACTTTGCCCCATTTTAGA | 0 | 1531 |

TABLE 24-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 484246 | 30621 | 30640 | GCAGGGTGACTTTGCCCCAT | 35 | 1532 |
| 484247 | 30644 | 30663 | TGAGCCACTGTCTCAAGTGT | 42 | 1533 |
| 484248 | 30669 | 30688 | TGCCTCTGCATCTCAAGACT | 75 | 1534 |
| 484249 | 30674 | 30693 | CCCAGTGCCTCTGCATCTCA | 83 | 1535 |
| 484250 | 30712 | 30731 | CCAGCCCAGACACTGTGGAT | 60 | 1536 |
| 484251 | 30717 | 30736 | AGCACCCAGCCCAGACACTG | 59 | 1537 |
| 484252 | 30749 | 30768 | TACTGTCCCCTCCTTGTGTG | 16 | 1538 |
| 484253 | 30773 | 30792 | TTCAGCTTCTTGTGAAGCTG | 0 | 1539 |
| 484254 | 30778 | 30797 | TAGGCTTCAGCTTCTTGTGA | 25 | 1540 |
| 484255 | 30783 | 30802 | GGAGATAGGCTTCAGCTTCT | 58 | 1541 |
| 484256 | 30788 | 30807 | CCAAAGGAGATAGGCTTCAG | 49 | 1542 |
| 484257 | 30887 | 30906 | AGCAGATTCCTGGGACAAGA | 62 | 1543 |
| 484258 | 30922 | 30941 | GAGAAATAGCTACAGGAATG | 36 | 1544 |
| 484259 | 30927 | 30946 | ACCCTGAGAAATAGCTACAG | 22 | 1545 |
| 484260 | 30932 | 30951 | CACAAACCCTGAGAAATAGC | 0 | 1546 |
| 413433 | 32431 | 32450 | GCCTGGACAAGTCCTGCCCA | 88 | 425 |

TABLE 25

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 484261 | 32253 | 32272 | AAGACTGGGCTTAGGCTAAG | 50 | 1547 |
| 484262 | 32303 | 32322 | TCAGGAAAAGGAGAAGGAAC | 36 | 1548 |
| 484263 | 32336 | 32355 | AGCTTCAAATTTTCTGCAGT | 72 | 1549 |
| 484264 | 32399 | 32418 | AGTTTCTTTACCTCCAAAAT | 48 | 1550 |
| 413433 | 32431 | 32450 | GCCTGGACAAGTCCTGCCCA | 87 | 425 |
| 423463 | 32432 | 32451 | AGCCTGGACAAGTCCTGCCC | 90 | 467 |
| 423464 | 32433 | 32452 | CAGCCTGGACAAGTCCTGCC | 86 | 468 |
| 423465 | 32434 | 32453 | GCAGCCTGGACAAGTCCTGC | 74 | 469 |
| 484265 | 32436 | 32455 | ATGCAGCCTGGACAAGTCCT | 74 | 1551 |
| 484266 | 32441 | 32460 | AGACTATGCAGCCTGGACAA | 63 | 1552 |
| 484267 | 32446 | 32465 | ATACTAGACTATGCAGCCTG | 82 | 1553 |
| 484268 | 32451 | 32470 | CCATCATACTAGACTATGCA | 87 | 1554 |
| 484269 | 32456 | 32475 | TGTTGCCATCATACTAGACT | 83 | 1555 |
| 484270 | 32461 | 32480 | TGCAATGTTGCCATCATACT | 89 | 1556 |
| 484271 | 32466 | 32485 | GTGGTTGCAATGTTGCCATC | 90 | 1557 |

TABLE 25-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 484272 | 32471 | 32490 | GGATGGTGGTTGCAATGTTG | 55 | 1558 |
| 484273 | 32476 | 32495 | AGCCTGGATGGTGGTTGCAA | 86 | 1559 |
| 484274 | 32481 | 32500 | CAATAAGCCTGGATGGTGGT | 79 | 1560 |
| 484275 | 32486 | 32505 | GAATTCATAAGCCTGGATG | 66 | 1561 |
| 484276 | 32510 | 32529 | TCAGTGGAAAAGAACCTGGG | 71 | 1562 |
| 484277 | 32515 | 32534 | GGAAATCAGTGGAAAAGAAC | 55 | 1563 |
| 484278 | 32520 | 32539 | CAGTAGGAAATCAGTGGAAA | 54 | 1564 |
| 484279 | 32525 | 32544 | ACAGGCAGTAGGAAATCAGT | 51 | 1565 |
| 484280 | 32530 | 32549 | GAGAAACAGGCAGTAGGAAA | 56 | 1566 |
| 484281 | 32586 | 32605 | GACCCAGGAAGCTGGAATCA | 66 | 1567 |
| 484282 | 32591 | 32610 | AGGGAGACCCAGGAAGCTGG | 60 | 1568 |
| 484283 | 32619 | 32638 | ACTGAGATCTCCAGCAGCAA | 90 | 1569 |
| 484284 | 32645 | 32664 | AATGGAGTGACAGGGCAGGA | 82 | 1570 |
| 484285 | 32670 | 32689 | AGGGAGCAATGGTGGCAGGT | 71 | 1571 |
| 484286 | 32675 | 32694 | TGGACAGGGAGCAATGGTGG | 46 | 1572 |
| 484287 | 32680 | 32699 | TGCACTGGACAGGGAGCAAT | 36 | 1573 |
| 484288 | 32685 | 32704 | AGCCCTGCACTGGACAGGGA | 41 | 1574 |
| 484289 | 32706 | 32725 | TTGTGTCCCCATGCCCAGCA | 58 | 1575 |
| 484290 | 32711 | 32730 | CTGACTTGTGTCCCCATGCC | 78 | 1576 |
| 484291 | 32716 | 32735 | CAGGGCTGACTTGTGTCCCC | 52 | 1577 |
| 484292 | 32752 | 32771 | ACAAAGTCTATCAGGATGCA | 83 | 1578 |
| 484293 | 32757 | 32776 | AAGTGACAAAGTCTATCAGG | 83 | 1579 |
| 484294 | 32781 | 32800 | GTCTGCCCATGGCCCCATGG | 31 | 1580 |
| 484295 | 32786 | 32805 | AGAAAGTCTGCCCATGGCCC | 45 | 1581 |
| 484296 | 32791 | 32810 | GCTTGAGAAAGTCTGCCCAT | 35 | 1582 |
| 484297 | 32796 | 32815 | AGCAGGCTTGAGAAAGTCTG | 18 | 1583 |
| 484298 | 32801 | 32820 | GGCTCAGCAGGCTTGAGAAA | 60 | 1584 |
| 484299 | 32806 | 32825 | GATGAGGCTCAGCAGGCTTG | 68 | 1585 |
| 484300 | 32811 | 32830 | TTGCAGATGAGGCTCAGCAG | 48 | 1586 |
| 484301 | 32816 | 32835 | CCATTTTGCAGATGAGGCTC | 80 | 1587 |
| 484302 | 32821 | 32840 | CAGCTCCATTTTGCAGATGA | 77 | 1588 |
| 484303 | 32878 | 32897 | AGAACAGTCTATCATCACTC | 34 | 1589 |
| 484304 | 32899 | 32918 | GAGGTGAGAGAGAAAGCAGA | 11 | 1590 |
| 484305 | 32904 | 32923 | CCCCTGAGGTGAGAGAGAAA | 46 | 1591 |
| 484306 | 32909 | 32928 | CCTGGCCCCTGAGGTGAGAG | 38 | 1592 |
| 484307 | 32914 | 32933 | TGGAGCCTGGCCCCTGAGGT | 12 | 1593 |

TABLE 25-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 484308 | 32919 | 32938 | AACACTGGAGCCTGGCCCCT | 18 | 1594 |
| 484309 | 32924 | 32943 | CAGAGAACACTGGAGCCTGG | 35 | 1595 |
| 484310 | 32929 | 32948 | GGCAACAGAGAACACTGGAG | 62 | 1596 |
| 484311 | 32934 | 32953 | ACAGTGGCAACAGAGAACAC | 0 | 1597 |
| 484312 | 32940 | 32959 | CAGGCCACAGTGGCAACAGA | 3 | 1598 |
| 484313 | 32945 | 32964 | AGGACCAGGCCACAGTGGCA | 31 | 1599 |
| 484314 | 32950 | 32969 | TCCAGAGGACCAGGCCACAG | 22 | 1600 |
| 484315 | 32973 | 32992 | GGGCTACTGGCCTCCTGGAG | 47 | 1601 |
| 484316 | 33038 | 33057 | CAAAGGACACCTGCCTGTCC | 46 | 1602 |
| 484317 | 33043 | 33062 | GATAGCAAAGGACACCTGCC | 48 | 1603 |
| 484318 | 33065 | 33084 | TCTTTTGGAAGGGTGGAGAT | 16 | 1604 |
| 484319 | 33070 | 33089 | TTGGTTCTTTTGGAAGGGTG | 62 | 1605 |
| 484320 | 33096 | 33115 | GATGTGAGAAGGACACAGGG | 79 | 1606 |
| 484321 | 33101 | 33120 | ACAGAGATGTGAGAAGGACA | 77 | 1607 |
| 484322 | 33106 | 33125 | TTGGAACAGAGATGTGAGAA | 71 | 1608 |
| 484323 | 33111 | 33130 | ACTTCTTGGAACAGAGATGT | 69 | 1609 |
| 484324 | 33161 | 33180 | GCCCTCACAGGGCCAGGTTG | 77 | 1610 |
| 484325 | 33170 | 33189 | CCCCAGGGAGCCCTCACAGG | 68 | 1611 |
| 484326 | 33175 | 33194 | TAGTGCCCCAGGGAGCCCTC | 51 | 1612 |
| 484327 | 33180 | 33199 | TGTCCTAGTGCCCCAGGGAG | 86 | 1613 |
| 484328 | 33217 | 33236 | TCAACACCCCAGCCTGCCTC | 56 | 1614 |
| 484329 | 33222 | 33241 | GAGGCTCAACACCCCAGCCT | 47 | 1615 |
| 484330 | 33360 | 33379 | AGGAGGGTCACACACACCCC | 56 | 1616 |
| 484331 | 33388 | 33407 | GCAAGAGGCCAGGAAAAGGG | 53 | 1617 |
| 484332 | 33393 | 33412 | TACTGGCAAGAGGCCAGGAA | 53 | 1618 |
| 484333 | 33398 | 33417 | ATGATTACTGGCAAGAGGCC | 45 | 1619 |
| 484334 | 33403 | 33422 | ATTACATGATTACTGGCAAG | 30 | 1620 |

TABLE 26

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 413433 | 32431 | 32450 | GCCTGGACAAGTCCTGCCCA | 94 | 425 |
| 484335 | 35661 | 35680 | AAAATATACATGCTCTTTTT | 52 | 1621 |
| 484336 | 35666 | 35685 | ACTCAAAATATACATGCTC | 88 | 1622 |
| 484337 | 35671 | 35690 | TTTCTACTCAAAATATACA | 28 | 1623 |

TABLE 26-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 484338 | 35676 | 35695 | TCCTTTTTCTACTCAAAAAT | 64 | 1624 |
| 484339 | 36215 | 36234 | TTCTGATTAGAAAAATAATA | 15 | 1625 |
| 484340 | 36220 | 36239 | TTTTATTCTGATTAGAAAAA | 33 | 1626 |
| 484341 | 36243 | 36262 | TATTCTGCTCATAAAAACAT | 44 | 1627 |
| 484342 | 36248 | 36267 | AAGGGTATTCTGCTCATAAA | 78 | 1628 |
| 484343 | 36253 | 36272 | TGAGTAAGGGTATTCTGCTC | 89 | 1629 |
| 484344 | 36258 | 36277 | GACAATGAGTAAGGGTATTC | 88 | 1630 |
| 484345 | 36263 | 36282 | AGAGAGACAATGAGTAAGGG | 46 | 1631 |
| 484346 | 36268 | 36287 | GGCTGAGAGAGACAATGAGT | 72 | 1632 |
| 484347 | 36318 | 36337 | AGCCTGTGACACCTACCCTG | 68 | 1633 |
| 484348 | 36354 | 36373 | ATGCAGTGTCCCTAAACCCT | 82 | 1634 |
| 484349 | 36359 | 36378 | GGGTGATGCAGTGTCCCTAA | 73 | 1635 |
| 484350 | 36409 | 36428 | TGGCTTCCTCAGGGCCCACC | 90 | 1636 |
| 484351 | 36454 | 36473 | CCTGACCTGTGGTACTAAGG | 68 | 1637 |
| 484352 | 36512 | 36531 | AGCCCTGTGCCAGCCAGCCT | 74 | 1638 |
| 484353 | 36517 | 36536 | GCGACAGCCCTGTGCCAGCC | 92 | 1639 |
| 484354 | 36522 | 36541 | GACAAGCGACAGCCCTGTGC | 60 | 1640 |
| 484355 | 36573 | 36592 | CCACAGTCAGCTGGGCTCAG | 72 | 1641 |
| 484356 | 36578 | 36597 | CTTTCCCACAGTCAGCTGGG | 70 | 1642 |
| 484357 | 36583 | 36602 | GGAAACTTTCCCACAGTCAG | 89 | 1643 |
| 484358 | 36588 | 36607 | CAAATGGAAACTTTCCCACA | 56 | 1644 |
| 484359 | 36617 | 36636 | GGCCTGGAAAAGGGACACTG | 71 | 1645 |
| 484360 | 36622 | 36641 | CCCCTGGCCTGGAAAAGGGA | 48 | 1646 |
| 484361 | 36627 | 36646 | CTACTCCCCTGGCCTGGAAA | 21 | 1647 |
| 484362 | 36632 | 36651 | ACCTCCTACTCCCCTGGCCT | 67 | 1648 |
| 484363 | 36637 | 36656 | AGCCCACCTCCTACTCCCCT | 68 | 1649 |
| 484364 | 36642 | 36661 | CAGGCAGCCCACCTCCTACT | 66 | 1650 |
| 484365 | 36647 | 36666 | TGAGACAGGCAGCCCACCTC | 66 | 1651 |
| 484366 | 36652 | 36671 | CAGAATGAGACAGGCAGCCC | 56 | 1652 |
| 484367 | 36676 | 36695 | CTCTGTGGGCTCCTCCACAG | 45 | 1653 |
| 484368 | 36681 | 36700 | CTGTGCTCTGTGGGCTCCTC | 81 | 1654 |
| 484369 | 36686 | 36705 | TGGCCCTGTGCTCTGTGGGC | 42 | 1655 |
| 484370 | 36691 | 36710 | TTACTTGGCCCTGTGCTCTG | 75 | 1656 |
| 484371 | 36733 | 36752 | ACTGTCAGTCTCTCCAAACT | 73 | 1657 |
| 484372 | 36738 | 36757 | CCCCCACTGTCAGTCTCTCC | 78 | 1658 |
| 484373 | 36743 | 36762 | CTCTGCCCCCACTGTCAGTC | 72 | 1659 |

TABLE 26-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 484374 | 36748 | 36767 | GCAAGCTCTGCCCCCACTGT | 71 | 1660 |
| 484375 | 36753 | 36772 | TGGCTGCAAGCTCTGCCCCC | 70 | 1661 |
| 484376 | 36758 | 36777 | GGCCTTGGCTGCAAGCTCTG | 76 | 1662 |
| 484377 | 36841 | 36860 | AATCCACCCTTGTCACTCT | 88 | 1663 |
| 484378 | 36846 | 36865 | ACTCAAATCCAACCCTTGTC | 81 | 1664 |
| 484379 | 36855 | 36874 | TATTCTAAAACTCAAATCCA | 61 | 1665 |
| 484380 | 36860 | 36879 | GTGATTATTCTAAAACTCAA | 65 | 1666 |
| 484381 | 36865 | 36884 | CCAGAGTGATTATTCTAAAA | 73 | 1667 |
| 484382 | 36896 | 36915 | CCTCCCTCTGGGCCCATCCT | 74 | 1668 |
| 484383 | 36923 | 36942 | TTTGCACTCTGCCAGCCTCC | 78 | 1669 |
| 484384 | 36928 | 36947 | TCTTCTTTGCACTCTGCCAG | 69 | 1670 |
| 484385 | 36969 | 36988 | TGCCCTTGTTCCTCTCAGTC | 68 | 1671 |
| 484386 | 36974 | 36993 | ATGTTTGCCCTTGTTCCTCT | 62 | 1672 |
| 484387 | 37022 | 37041 | GTTGGGCAGTCACCATTTGC | 63 | 1673 |
| 484388 | 37027 | 37046 | CTGGTGTTGGGCAGTCACCA | 30 | 1674 |
| 484389 | 37032 | 37051 | CAGTGCTGGTGTTGGGCAGT | 30 | 1675 |
| 484390 | 37054 | 37073 | CAGACTCTCATCCCCAGGGC | 72 | 1676 |
| 484391 | 37119 | 37138 | GGATGTGTCATTTCCCCTGG | 86 | 1677 |
| 484392 | 37174 | 37193 | AGGAAACTGGCTGGGAGAGG | 20 | 1678 |
| 484393 | 37179 | 37198 | GTCAGAGGAAACTGGCTGGG | 48 | 1679 |
| 484394 | 37184 | 37203 | CTTGGGTCAGAGGAAACTGG | 37 | 1680 |
| 484395 | 37189 | 37208 | ATGACCTTGGGTCAGAGGAA | 38 | 1681 |
| 484396 | 37194 | 37213 | CAAGGATGACCTTGGGTCAG | 36 | 1682 |
| 484397 | 37199 | 37218 | AGCTGCAAGGATGACCTTGG | 48 | 1683 |
| 484398 | 37204 | 37223 | TCACCAGCTGCAAGGATGAC | 24 | 1684 |
| 484399 | 37440 | 37459 | AACAGTGCCCAGCAGGAGCA | 14 | 1685 |
| 484400 | 37445 | 37464 | TTGACAACAGTGCCCAGCAG | 19 | 1686 |
| 484401 | 37450 | 37469 | AGGCCTTGACAACAGTGCCC | 36 | 1687 |
| 484402 | 37455 | 37474 | GGCTCAGGCCTTGACAACAG | 57 | 1688 |
| 484403 | 37460 | 37479 | GGAGAGGCTCAGGCCTTGAC | 53 | 1689 |
| 484404 | 37485 | 37504 | GGCTCCCTGTGTCACCCTGC | 61 | 1690 |
| 484405 | 37490 | 37509 | GTGTTGGCTCCCTGTGTCAC | 39 | 1691 |
| 484406 | 37495 | 37514 | ATGGTGTGTTGGCTCCCTGT | 36 | 1692 |
| 484407 | 37500 | 37519 | AAGGAATGGTGTGTTGGCTC | 48 | 1693 |
| 484408 | 37505 | 37524 | GCACCAAGGAATGGTGTGTT | 30 | 1694 |
| 484409 | 37510 | 37529 | GCCCAGCACCAAGGAATGGT | 48 | 1695 |

TABLE 26-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 484410 | 37515 | 37534 | TGCAGGCCCAGCACCAAGGA | 55 | 1696 |
| 484411 | 37520 | 37539 | CCCAATGCAGGCCCAGCACC | 67 | 1697 |

TABLE 27

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495425 | 10040 | 10059 | AGGGCCCTTTCCAGAAAATC | 84 | 1698 |
| 495426 | 10041 | 10060 | CAGGGCCCTTTCCAGAAAAT | 29 | 1699 |
| 495427 | 10042 | 10061 | ACAGGGCCCTTTCCAGAAAA | 14 | 1700 |
| 495428 | 10043 | 10062 | CACAGGGCCCTTTCCAGAAA | 64 | 1701 |
| 495429 | 10045 | 10064 | GCCACAGGGCCCTTTCCAGA | 86 | 1702 |
| 495430 | 10046 | 10065 | TGCCACAGGGCCCTTTCCAG | 77 | 1703 |
| 495431 | 10047 | 10066 | CTGCCACAGGGCCCTTTCCA | 50 | 1704 |
| 495432 | 10048 | 10067 | CCTGCCACAGGGCCCTTTCC | 44 | 1705 |
| 495433 | 10206 | 10225 | GAATATCCCTAATAACTAAG | 18 | 1706 |
| 495434 | 10207 | 10226 | CGAATATCCCTAATAACTAA | 8 | 1707 |
| 495435 | 10208 | 10227 | TCGAATATCCCTAATAACTA | 18 | 1708 |
| 495436 | 10209 | 10228 | CTCGAATATCCCTAATAACT | 66 | 1709 |
| 495437 | 10211 | 10230 | TTCTCGAATATCCCTAATAA | 31 | 1710 |
| 495438 | 10212 | 10231 | GTTCTCGAATATCCCTAATA | 69 | 1711 |
| 495439 | 10213 | 10232 | AGTTCTCGAATATCCCTAAT | 36 | 1712 |
| 495440 | 10214 | 10233 | GAGTTCTCGAATATCCCTAA | 84 | 1713 |
| 495441 | 10216 | 10235 | AGGAGTTCTCGAATATCCCT | 79 | 1714 |
| 495442 | 10217 | 10236 | GAGGAGTTCTCGAATATCCC | 83 | 1715 |
| 495443 | 10218 | 10237 | GGAGGAGTTCTCGAATATCC | 78 | 1716 |
| 495444 | 10219 | 10238 | GGGAGGAGTTCTCGAATATC | 64 | 1717 |
| 495445 | 10491 | 10510 | GCAGGGTCCTCTCCGCTGCC | 70 | 1718 |
| 495446 | 10492 | 10511 | TGCAGGGTCCTCTCCGCTGC | 80 | 1719 |
| 495447 | 10528 | 10547 | GATTCACTGAGGACCTCAGT | 71 | 1720 |
| 495448 | 10529 | 10548 | CGATTCACTGAGGACCTCAG | 78 | 1721 |
| 495449 | 10530 | 10549 | GCGATTCACTGAGGACCTCA | 94 | 1722 |
| 495450 | 10531 | 10550 | CGCGATTCACTGAGGACCTC | 90 | 1723 |
| 495451 | 10533 | 10552 | TGCGCGATTCACTGAGGACC | 82 | 1724 |
| 495452 | 10534 | 10553 | CTGCGCGATTCACTGAGGAC | 77 | 1725 |
| 495453 | 10535 | 10554 | TCTGCGCGATTCACTGAGGA | 81 | 1726 |

TABLE 27-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495454 | 10536 | 10555 | CTCTGCGCGATTCACTGAGG | 85 | 1727 |
| 495455 | 10646 | 10665 | CCTCCCACTTCAGTTTCTCC | 64 | 1728 |
| 495456 | 10647 | 10666 | TCCTCCCACTTCAGTTTCTC | 71 | 1729 |
| 495457 | 10648 | 10667 | TTCCTCCCACTTCAGTTTCT | 63 | 1730 |
| 495458 | 10649 | 10668 | CTTCCTCCCACTTCAGTTTC | 70 | 1731 |
| 495459 | 10651 | 10670 | TGCTTCCTCCCACTTCAGTT | 63 | 1732 |
| 495460 | 10652 | 10671 | ATGCTTCCTCCCACTTCAGT | 55 | 1733 |
| 495461 | 10653 | 10672 | CATGCTTCCTCCCACTTCAG | 70 | 1734 |
| 495462 | 10654 | 10673 | GCATGCTTCCTCCCACTTCA | 78 | 1735 |
| 495463 | 10656 | 10675 | AGGCATGCTTCCTCCCACTT | 81 | 1736 |
| 495464 | 10657 | 10676 | TAGGCATGCTTCCTCCCACT | 85 | 1737 |
| 495465 | 10658 | 10677 | TTAGGCATGCTTCCTCCCAC | 78 | 1738 |
| 495466 | 10659 | 10678 | CTTAGGCATGCTTCCTCCCA | 83 | 1739 |
| 495467 | 10661 | 10680 | AACTTAGGCATGCTTCCTCC | 82 | 1740 |
| 495468 | 10662 | 10681 | AAACTTAGGCATGCTTCCTC | 76 | 1741 |
| 495469 | 10663 | 10682 | AAAACTTAGGCATGCTTCCT | 83 | 1742 |
| 495470 | 10664 | 10683 | GAAAACTTAGGCATGCTTCC | 87 | 1743 |
| 495471 | 10666 | 10685 | AGGAAAACTTAGGCATGCTT | 83 | 1744 |
| 495472 | 10667 | 10686 | AAGGAAAACTTAGGCATGCT | 85 | 1745 |
| 495473 | 10668 | 10687 | TAAGGAAAACTTAGGCATGC | 76 | 1746 |
| 495474 | 10669 | 10688 | CTAAGGAAAACTTAGGCATG | 59 | 1747 |
| 495475 | 10671 | 10690 | AGCTAAGGAAAACTTAGGCA | 65 | 1748 |
| 495476 | 10672 | 10691 | CAGCTAAGGAAAACTTAGGC | 70 | 1749 |
| 495477 | 10673 | 10692 | TCAGCTAAGGAAAACTTAGG | 40 | 1750 |
| 495478 | 10674 | 10693 | ATCAGCTAAGGAAAACTTAG | 25 | 1751 |
| 495479 | 10728 | 10747 | TGTGATGACTTCCCAGGGTC | 75 | 1752 |
| 495480 | 10729 | 10748 | CTGTGATGACTTCCCAGGGT | 72 | 1753 |
| 495481 | 10730 | 10749 | GCTGTGATGACTTCCCAGGG | 87 | 1754 |
| 495482 | 10731 | 10750 | AGCTGTGATGACTTCCCAGG | 80 | 1755 |
| 495483 | 10733 | 10752 | ACAGCTGTGATGACTTCCCA | 79 | 1756 |
| 495484 | 10734 | 10753 | GACAGCTGTGATGACTTCCC | 86 | 1757 |
| 495485 | 10735 | 10754 | GGACAGCTGTGATGACTTCC | 80 | 1758 |
| 495486 | 10736 | 10755 | AGGACAGCTGTGATGACTTC | 62 | 1759 |
| 495487 | 10815 | 10834 | CATGTCAGAGAGGCTCAGCA | 72 | 1760 |
| 495488 | 10816 | 10835 | CCATGTCAGAGAGGCTCAGC | 87 | 1761 |
| 495489 | 10817 | 10836 | TCCATGTCAGAGAGGCTCAG | 86 | 1762 |

TABLE 27-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495490 | 10818 | 10837 | ATCCATGTCAGAGAGGCTCA | 88 | 1763 |
| 495491 | 10820 | 10839 | AAATCCATGTCAGAGAGGCT | 85 | 1764 |
| 495492 | 10821 | 10840 | AAAATCCATGTCAGAGAGGC | 86 | 1765 |
| 495493 | 10822 | 10841 | AAAAATCCATGTCAGAGAGG | 57 | 1766 |
| 495494 | 10823 | 10842 | GAAAAATCCATGTCAGAGAG | 52 | 1767 |
| 495495 | 10941 | 10960 | TGGATAGTCGATTTACCAGA | 92 | 1768 |
| 495496 | 10942 | 10961 | TTGGATAGTCGATTTACCAG | 89 | 1769 |
| 495497 | 10944 | 10963 | CTTTGGATAGTCGATTTACC | 89 | 1770 |
| 495498 | 11075 | 11094 | ACCTCGATGTTACATTAAGG | 90 | 1771 |
| 495499 | 11076 | 11095 | AACCTCGATGTTACATTAAG | 72 | 1772 |
| 495500 | 11077 | 11096 | AAACCTCGATGTTACATTAA | 64 | 1773 |
| 495501 | 11078 | 11097 | GAAACCTCGATGTTACATTA | 71 | 1774 |
| 413433 | 32431 | 32450 | GCCTGGACAAGTCCTGCCCA | 74 | 425 |

TABLE 28

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495502 | 11124 | 11143 | TATTGCAACCACTAGGACAT | 78 | 1775 |
| 495503 | 11125 | 11144 | TTATTGCAACCACTAGGACA | 72 | 1776 |
| 495504 | 11126 | 11145 | GTTATTGCAACCACTAGGAC | 79 | 1777 |
| 495505 | 11127 | 11146 | GGTTATTGCAACCACTAGGA | 91 | 1778 |
| 495506 | 11129 | 11148 | TGGGTTATTGCAACCACTAG | 91 | 1779 |
| 495507 | 11130 | 11149 | GTGGGTTATTGCAACCACTA | 86 | 1780 |
| 495508 | 11131 | 11150 | GGTGGGTTATTGCAACCACT | 85 | 1781 |
| 495509 | 11159 | 11178 | TCACAGTTAAAGTGTGGTAC | 82 | 1782 |
| 495510 | 11160 | 11179 | GTCACAGTTAAAGTGTGGTA | 84 | 1783 |
| 495511 | 11161 | 11180 | GGTCACAGTTAAAGTGTGGT | 78 | 1784 |
| 495512 | 11162 | 11181 | AGGTCACAGTTAAAGTGTGG | 7 | 1785 |
| 495513 | 11169 | 11188 | AATGCCTAGGTCACAGTTAA | 46 | 1786 |
| 495514 | 11170 | 11189 | CAATGCCTAGGTCACAGTTA | 80 | 1787 |
| 495515 | 11171 | 11190 | CCAATGCCTAGGTCACAGTT | 88 | 1788 |
| 495516 | 11172 | 11191 | GCCAATGCCTAGGTCACAGT | 94 | 1789 |
| 495517 | 11174 | 11193 | ATGCCAATGCCTAGGTCACA | 92 | 1790 |
| 495518 | 11175 | 11194 | AATGCCAATGCCTAGGTCAC | 93 | 1791 |
| 495519 | 11176 | 11195 | CAATGCCAATGCCTAGGTCA | 92 | 1792 |

TABLE 28-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495520 | 11177 | 11196 | GCAATGCCAATGCCTAGGTC | 92 | 1793 |
| 495521 | 11200 | 11219 | CCACAGCGATAATCACACAA | 84 | 1794 |
| 495522 | 11201 | 11220 | ACCACAGCGATAATCACACA | 92 | 1795 |
| 495523 | 11202 | 11221 | AACCACAGCGATAATCACAC | 94 | 1796 |
| 495524 | 11203 | 11222 | TAACCACAGCGATAATCACA | 91 | 1797 |
| 495525 | 14504 | 14523 | GCAGGGTCTGCCACTCTCTA | 86 | 1798 |
| 495526 | 14505 | 14524 | AGCAGGGTCTGCCACTCTCT | 92 | 1799 |
| 495527 | 14506 | 14525 | GAGCAGGGTCTGCCACTCTC | 91 | 1800 |
| 495528 | 14507 | 14526 | AGAGCAGGGTCTGCCACTCT | 82 | 1801 |
| 495529 | 14649 | 14668 | GCACAGTCATCTTGTGTACA | 86 | 1802 |
| 495530 | 14650 | 14669 | TGCACAGTCATCTTGTGTAC | 81 | 1803 |
| 495531 | 14651 | 14670 | CTGCACAGTCATCTTGTGTA | 80 | 1804 |
| 495532 | 14652 | 14671 | TCTGCACAGTCATCTTGTGT | 64 | 1805 |
| 495533 | 14659 | 14678 | AGATCACTCTGCACAGTCAT | 81 | 1806 |
| 495534 | 14660 | 14679 | CAGATCACTCTGCACAGTCA | 87 | 1807 |
| 495535 | 14661 | 14680 | TCAGATCACTCTGCACAGTC | 90 | 1808 |
| 495536 | 14662 | 14681 | CTCAGATCACTCTGCACAGT | 86 | 1809 |
| 495537 | 14664 | 14683 | TGCTCAGATCACTCTGCACA | 87 | 1810 |
| 495538 | 14665 | 14684 | TTGCTCAGATCACTCTGCAC | 78 | 1811 |
| 495539 | 14666 | 14685 | ATTGCTCAGATCACTCTGCA | 84 | 1812 |
| 495540 | 14667 | 14686 | CATTGCTCAGATCACTCTGC | 88 | 1813 |
| 495541 | 14741 | 14760 | CCTCTTCCAGGAAGACTTCC | 80 | 1814 |
| 495542 | 14742 | 14761 | ACCTCTTCCAGGAAGACTTC | 72 | 1815 |
| 495543 | 14743 | 14762 | CACCTCTTCCAGGAAGACTT | 88 | 1816 |
| 495544 | 14744 | 14763 | TCACCTCTTCCAGGAAGACT | 86 | 1817 |
| 495545 | 14746 | 14765 | TGTCACCTCTTCCAGGAAGA | 82 | 1818 |
| 495546 | 14747 | 14766 | ATGTCACCTCTTCCAGGAAG | 42 | 1819 |
| 495547 | 14748 | 14767 | AATGTCACCTCTTCCAGGAA | 50 | 1820 |
| 495548 | 14749 | 14768 | GAATGTCACCTCTTCCAGGA | 74 | 1821 |
| 495549 | 14751 | 14770 | CTGAATGTCACCTCTTCCAG | 75 | 1822 |
| 495550 | 14752 | 14771 | ACTGAATGTCACCTCTTCCA | 81 | 1823 |
| 495551 | 14753 | 14772 | GACTGAATGTCACCTCTTCC | 81 | 1824 |
| 495552 | 14754 | 14773 | GGACTGAATGTCACCTCTTC | 88 | 1825 |
| 495553 | 14756 | 14775 | CCGGACTGAATGTCACCTCT | 90 | 1826 |
| 495554 | 14757 | 14776 | TCCGGACTGAATGTCACCTC | 91 | 1827 |
| 495555 | 14758 | 14777 | ATCCGGACTGAATGTCACCT | 91 | 1828 |

TABLE 28-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495556 | 14759 | 14778 | GATCCGGACTGAATGTCACC | 85 | 1829 |
| 495557 | 14766 | 14785 | CTTTCCAGATCCGGACTGAA | 67 | 1830 |
| 495558 | 14767 | 14786 | TCTTTCCAGATCCGGACTGA | 77 | 1831 |
| 495559 | 14768 | 14787 | ATCTTTCCAGATCCGGACTG | 69 | 1832 |
| 495560 | 14769 | 14788 | CATCTTTCCAGATCCGGACT | 88 | 1833 |
| 495561 | 14771 | 14790 | TTCATCTTTCCAGATCCGGA | 89 | 1834 |
| 495562 | 14772 | 14791 | ATTCATCTTTCCAGATCCGG | 94 | 1835 |
| 495563 | 14773 | 14792 | TATTCATCTTTCCAGATCCG | 92 | 1836 |
| 495564 | 14774 | 14793 | CTATTCATCTTTCCAGATCC | 84 | 1837 |
| 495565 | 14992 | 15011 | CTCAAGTCTTCCTCCTGCTG | 79 | 1838 |
| 495566 | 14993 | 15012 | TCTCAAGTCTTCCTCCTGCT | 83 | 1839 |
| 495567 | 14994 | 15013 | CTCTCAAGTCTTCCTCCTGC | 63 | 1840 |
| 495568 | 14995 | 15014 | GCTCTCAAGTCTTCCTCCTG | 86 | 1841 |
| 495569 | 14997 | 15016 | GAGCTCTCAAGTCTTCCTCC | 84 | 1842 |
| 495570 | 14998 | 15017 | TGAGCTCTCAAGTCTTCCTC | 90 | 1843 |
| 495571 | 14999 | 15018 | ATGAGCTCTCAAGTCTTCCT | 91 | 1844 |
| 495572 | 15000 | 15019 | CATGAGCTCTCAAGTCTTCC | 85 | 1845 |
| 495573 | 15248 | 15267 | CATAATCTGCACAGGTTCTT | 84 | 1846 |
| 495574 | 15249 | 15268 | CCATAATCTGCACAGGTTCT | 87 | 1847 |
| 495575 | 15250 | 15269 | ACCATAATCTGCACAGGTTC | 91 | 1848 |
| 495576 | 15251 | 15270 | CACCATAATCTGCACAGGTT | 94 | 1849 |
| 495577 | 15253 | 15272 | TGCACCATAATCTGCACAGG | 90 | 1850 |
| 495578 | 15254 | 15273 | CTGCACCATAATCTGCACAG | 86 | 1851 |
| 413433 | 32431 | 32450 | GCCTGGACAAGTCCTGCCCA | 92 | 425 |

TABLE 29

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495579 | 15255 | 15274 | TCTGCACCATAATCTGCACA | 78 | 1852 |
| 495580 | 15256 | 15275 | ATCTGCACCATAATCTGCAC | 73 | 1853 |
| 495581 | 18152 | 18171 | TAATCCAGGATTGTCATAAG | 53 | 1854 |
| 495582 | 18153 | 18172 | TTAATCCAGGATTGTCATAA | 54 | 1855 |
| 495583 | 18154 | 18173 | TTTAATCCAGGATTGTCATA | 40 | 1856 |
| 495584 | 18155 | 18174 | CTTTAATCCAGGATTGTCAT | 70 | 1857 |
| 495585 | 18157 | 18176 | AGCTTTAATCCAGGATTGTC | 81 | 1858 |

TABLE 29-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495586 | 18158 | 18177 | TAGCTTTAATCCAGGATTGT | 37 | 1859 |
| 495587 | 18159 | 18178 | TTAGCTTTAATCCAGGATTG | 60 | 1860 |
| 495588 | 18160 | 18179 | CTTAGCTTTAATCCAGGATT | 75 | 1861 |
| 495589 | 18162 | 18181 | TCCTTAGCTTTAATCCAGGA | 78 | 1862 |
| 495590 | 18163 | 18182 | CTCCTTAGCTTTAATCCAGG | 77 | 1863 |
| 495591 | 18164 | 18183 | CCTCCTTAGCTTTAATCCAG | 82 | 1864 |
| 495592 | 18165 | 18184 | TCCTCCTTAGCTTTAATCCA | 73 | 1865 |
| 495593 | 18167 | 18186 | TGTCCTCCTTAGCTTTAATC | 69 | 1866 |
| 495594 | 18168 | 18187 | GTGTCCTCCTTAGCTTTAAT | 61 | 1867 |
| 495595 | 18169 | 18188 | AGTGTCCTCCTTAGCTTTAA | 51 | 1868 |
| 495596 | 18170 | 18189 | CAGTGTCCTCCTTAGCTTTA | 61 | 1869 |
| 495597 | 18172 | 18191 | CTCAGTGTCCTCCTTAGCTT | 76 | 1870 |
| 495598 | 18173 | 18192 | ACTCAGTGTCCTCCTTAGCT | 81 | 1871 |
| 495599 | 18174 | 18193 | GACTCAGTGTCCTCCTTAGC | 83 | 1872 |
| 495600 | 18175 | 18194 | GGACTCAGTGTCCTCCTTAG | 80 | 1873 |
| 495601 | 18177 | 18196 | TGGGACTCAGTGTCCTCCTT | 64 | 1874 |
| 495602 | 18178 | 18197 | CTGGGACTCAGTGTCCTCCT | 72 | 1875 |
| 495603 | 18179 | 18198 | CCTGGGACTCAGTGTCCTCC | 77 | 1876 |
| 495604 | 18180 | 18199 | CCCTGGGACTCAGTGTCCTC | 88 | 1877 |
| 495605 | 18307 | 18326 | TCCTGTTTGATGGGTAAAAT | 77 | 1878 |
| 495606 | 18308 | 18327 | CTCCTGTTTGATGGGTAAAA | 83 | 1879 |
| 495607 | 18309 | 18328 | TCTCCTGTTTGATGGGTAAA | 78 | 1880 |
| 495608 | 18310 | 18329 | CTCTCCTGTTTGATGGGTAA | 81 | 1881 |
| 495609 | 18312 | 18331 | TCCTCTCCTGTTTGATGGGT | 83 | 1882 |
| 495610 | 18313 | 18332 | GTCCTCTCCTGTTTGATGGG | 77 | 1883 |
| 495611 | 18314 | 18333 | TGTCCTCTCCTGTTTGATGG | 69 | 1884 |
| 495612 | 18315 | 18334 | GTGTCCTCTCCTGTTTGATG | 76 | 1885 |
| 495613 | 18317 | 18336 | CGGTGTCCTCTCCTGTTTGA | 77 | 1886 |
| 495614 | 18318 | 18337 | TCGGTGTCCTCTCCTGTTTG | 72 | 1887 |
| 495615 | 18319 | 18338 | CTCGGTGTCCTCTCCTGTTT | 69 | 1888 |
| 495616 | 18320 | 18339 | CCTCGGTGTCCTCTCCTGTT | 77 | 1889 |
| 495617 | 18322 | 18341 | AGCCTCGGTGTCCTCTCCTG | 72 | 1890 |
| 495618 | 18323 | 18342 | AAGCCTCGGTGTCCTCTCCT | 84 | 1891 |
| 495619 | 18324 | 18343 | TAAGCCTCGGTGTCCTCTCC | 88 | 1892 |
| 495620 | 18325 | 18344 | GTAAGCCTCGGTGTCCTCTC | 91 | 1893 |
| 495621 | 18327 | 18346 | AAGTAAGCCTCGGTGTCCTC | 86 | 1894 |

TABLE 29-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495622 | 18328 | 18347 | CAAGTAAGCCTCGGTGTCCT | 81 | 1895 |
| 495623 | 18330 | 18349 | ACCAAGTAAGCCTCGGTGTC | 79 | 1896 |
| 495624 | 18418 | 18437 | CTCACCAGATTGTTGTGGGA | 79 | 1897 |
| 495625 | 18419 | 18438 | CCTCACCAGATTGTTGTGGG | 77 | 1898 |
| 495626 | 18420 | 18439 | ACCTCACCAGATTGTTGTGG | 79 | 1899 |
| 495627 | 18421 | 18440 | TACCTCACCAGATTGTTGTG | 47 | 1900 |
| 495628 | 18428 | 18447 | TAATACCTACCTCACCAGAT | 56 | 1901 |
| 495629 | 18429 | 18448 | CTAATACCTACCTCACCAGA | 49 | 1902 |
| 495630 | 18430 | 18449 | GCTAATACCTACCTCACCAG | 60 | 1903 |
| 495631 | 18431 | 18450 | GGCTAATACCTACCTCACCA | 70 | 1904 |
| 495632 | 18451 | 18470 | CTTCCTCATCTATACAGTGG | 72 | 1905 |
| 495633 | 18452 | 18471 | GCTTCCTCATCTATACAGTG | 72 | 1906 |
| 495634 | 18453 | 18472 | AGCTTCCTCATCTATACAGT | 63 | 1907 |
| 495635 | 18454 | 18473 | CAGCTTCCTCATCTATACAG | 66 | 1908 |
| 495636 | 18582 | 18601 | CCATACTGGCATCTGGCAGG | 78 | 1909 |
| 495637 | 18583 | 18602 | TCCATACTGGCATCTGGCAG | 73 | 1910 |
| 495638 | 18584 | 18603 | CTCCATACTGGCATCTGGCA | 78 | 1911 |
| 495639 | 18585 | 18604 | CCTCCATACTGGCATCTGGC | 82 | 1912 |
| 495640 | 18587 | 18606 | CACCTCCATACTGGCATCTG | 51 | 1913 |
| 495641 | 18588 | 18607 | TCACCTCCATACTGGCATCT | 71 | 1914 |
| 495642 | 18589 | 18608 | CTCACCTCCATACTGGCATC | 72 | 1915 |
| 495643 | 18590 | 18609 | CCTCACCTCCATACTGGCAT | 70 | 1916 |
| 495644 | 18592 | 18611 | CACCTCACCTCCATACTGGC | 68 | 1917 |
| 495645 | 18593 | 18612 | CCACCTCACCTCCATACTGG | 54 | 1918 |
| 495646 | 18594 | 18613 | CCCACCTCACCTCCATACTG | 45 | 1919 |
| 495647 | 18595 | 18614 | ACCCACCTCACCTCCATACT | 37 | 1920 |
| 495648 | 18827 | 18846 | GGATGCTTAACTTCTGCTGA | 67 | 1921 |
| 495649 | 18828 | 18847 | AGGATGCTTAACTTCTGCTG | 83 | 1922 |
| 495650 | 18829 | 18848 | TAGGATGCTTAACTTCTGCT | 84 | 1923 |
| 495651 | 18830 | 18849 | TTAGGATGCTTAACTTCTGC | 68 | 1924 |
| 495652 | 18832 | 18851 | AGTTAGGATGCTTAACTTCT | 50 | 1925 |
| 495653 | 18833 | 18852 | AAGTTAGGATGCTTAACTTC | 49 | 1926 |
| 495654 | 18834 | 18853 | TAAGTTAGGATGCTTAACTT | 49 | 1927 |
| 495655 | 18835 | 18854 | TTAAGTTAGGATGCTTAACT | 42 | 1928 |
| 413433 | 32431 | 32450 | GCCTGGACAAGTCCTGCCCA | 82 | 425 |

TABLE 30

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 423461 | 32429 | 32448 | CTGGACAAGTCCTGCCCATC | 73 | 465 |
| 423462 | 32430 | 32449 | CCTGGACAAGTCCTGCCCAT | 70 | 466 |
| 413433 | 32431 | 32450 | GCCTGGACAAGTCCTGCCCA | 87 | 425 |
| 495656 | 18870 20780 | 18889 20799 | TATAGGCCTGGATGCCCAAG | 70 | 1929 |
| 495657 | 18871 20781 | 18890 20800 | CTATAGGCCTGGATGCCCAA | 72 | 1930 |
| 495658 | 18896 | 18915 | AGATGATGTCCTGCCTCAGA | 30 | 1931 |
| 495659 | 18897 | 18916 | CAGATGATGTCCTGCCTCAG | 37 | 1932 |
| 495660 | 18898 | 18917 | GCAGATGATGTCCTGCCTCA | 65 | 1933 |
| 495661 | 18899 | 18918 | AGCAGATGATGTCCTGCCTC | 72 | 1934 |
| 495662 | 19014 | 19033 | AGTCAAAGGTGGCTTCCTGG | 67 | 1935 |
| 495663 | 19015 | 19034 | TAGTCAAAGGTGGCTTCCTG | 57 | 1936 |
| 495664 | 19016 | 19035 | GTAGTCAAAGGTGGCTTCCT | 75 | 1937 |
| 495665 | 19017 | 19036 | AGTAGTCAAAGGTGGCTTCC | 66 | 1938 |
| 495666 | 19020 | 19039 | ATGAGTAGTCAAAGGTGGCT | 73 | 1939 |
| 495667 | 19021 | 19040 | AATGAGTAGTCAAAGGTGGC | 64 | 1940 |
| 495668 | 19022 | 19041 | GAATGAGTAGTCAAAGGTGG | 31 | 1941 |
| 495669 | 20775 | 20794 | GCCTGGATGCCCAAGTTAGA | 72 | 1942 |
| 495670 | 20776 | 20795 | GGCCTGGATGCCCAAGTTAG | 73 | 1943 |
| 495671 | 20777 | 20796 | AGGCCTGGATGCCCAAGTTA | 77 | 1944 |
| 495672 | 20778 | 20797 | TAGGCCTGGATGCCCAAGTT | 57 | 1945 |
| 495673 | 22544 | 22563 | ACAAGTGGGAAATGCAGTCT | 48 | 1946 |
| 495674 | 22545 | 22564 | AACAAGTGGGAAATGCAGTC | 42 | 1947 |
| 495675 | 22546 | 22565 | CAACAAGTGGGAAATGCAGT | 35 | 1948 |
| 495676 | 22547 | 22566 | CCAACAAGTGGGAAATGCAG | 62 | 1949 |
| 495677 | 22549 | 22568 | TGCCAACAAGTGGGAAATGC | 70 | 1950 |
| 495678 | 22550 | 22569 | CTGCCAACAAGTGGGAAATG | 52 | 1951 |
| 495679 | 22551 | 22570 | TCTGCCAACAAGTGGGAAAT | 39 | 1952 |
| 495680 | 22552 | 22571 | CTCTGCCAACAAGTGGGAAA | 34 | 1953 |
| 495681 | 22767 | 22786 | GCTTATTAGGTGTCTTAAAA | 51 | 1954 |
| 495682 | 22768 | 22787 | AGCTTATTAGGTGTCTTAAA | 56 | 1955 |
| 495683 | 22769 | 22788 | AAGCTTATTAGGTGTCTTAA | 59 | 1956 |
| 495684 | 22770 | 22789 | TAAGCTTATTAGGTGTCTTA | 63 | 1957 |
| 495685 | 22772 | 22791 | GCTAAGCTTATTAGGTGTCT | 86 | 1958 |
| 495686 | 22773 | 22792 | TGCTAAGCTTATTAGGTGTC | 80 | 1959 |
| 495687 | 22774 | 22793 | CTGCTAAGCTTATTAGGTGT | 68 | 1960 |
| 495688 | 22775 | 22794 | TCTGCTAAGCTTATTAGGTG | 64 | 1961 |

TABLE 30-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495689 | 22882 | 22901 | CCCCATGCAGCTTGGAGGAG | 60 | 1962 |
| 495690 | 22883 | 22902 | CCCCCATGCAGCTTGGAGGA | 53 | 1963 |
| 495691 | 22884 | 22903 | GCCCCCATGCAGCTTGGAGG | 43 | 1964 |
| 495692 | 22885 | 22904 | AGCCCCCATGCAGCTTGGAG | 61 | 1965 |
| 495693 | 22887 | 22906 | CCAGCCCCCATGCAGCTTGG | 66 | 1966 |
| 495694 | 22888 | 22907 | GCCAGCCCCCATGCAGCTTG | 78 | 1967 |
| 495695 | 22889 | 22908 | GGCCAGCCCCCATGCAGCTT | 71 | 1968 |
| 495696 | 22890 | 22909 | GGGCCAGCCCCCATGCAGCT | 63 | 1969 |
| 495697 | 23096 | 23115 | AGTCCAAACACTCAGGTAGG | 82 | 1970 |
| 495698 | 23097 | 23116 | CAGTCCAAACACTCAGGTAG | 68 | 1971 |
| 495699 | 23098 | 23117 | TCAGTCCAAACACTCAGGTA | 74 | 1972 |
| 495700 | 23099 | 23118 | TTCAGTCCAAACACTCAGGT | 72 | 1973 |
| 495701 | 23238 | 23257 | GGGAACAGCAGCATCAGCAT | 77 | 1974 |
| 495702 | 23239 | 23258 | TGGGAACAGCAGCATCAGCA | 83 | 1975 |
| 495703 | 23240 | 23259 | CTGGGAACAGCAGCATCAGC | 68 | 1976 |
| 495704 | 23241 | 23260 | TCTGGGAACAGCAGCATCAG | 65 | 1977 |
| 495705 | 23243 | 23262 | GGTCTGGGAACAGCAGCATC | 84 | 1978 |
| 495706 | 23244 | 23263 | TGGTCTGGGAACAGCAGCAT | 81 | 1979 |
| 495707 | 23245 | 23264 | GTGGTCTGGGAACAGCAGCA | 84 | 1980 |
| 495708 | 23423 | 23442 | CAAGTCATCTTCCAGCAGCT | 57 | 1981 |
| 495709 | 23424 | 23443 | ACAAGTCATCTTCCAGCAGC | 36 | 1982 |
| 495710 | 23425 | 23444 | GACAAGTCATCTTCCAGCAG | 38 | 1983 |
| 495711 | 23426 | 23445 | GGACAAGTCATCTTCCAGCA | 77 | 1984 |
| 495712 | 23428 | 23447 | CTGGACAAGTCATCTTCCAG | 53 | 1985 |
| 495713 | 23429 | 23448 | GCTGGACAAGTCATCTTCCA | 66 | 1986 |
| 495714 | 23430 | 23449 | GGCTGGACAAGTCATCTTCC | 76 | 1987 |
| 495715 | 23431 | 23450 | GGGCTGGACAAGTCATCTTC | 45 | 1988 |
| 495716 | 23548 | 23567 | ATCCTTGAGGGTCTCATAAC | 58 | 1989 |
| 495717 | 23549 | 23568 | TATCCTTGAGGGTCTCATAA | 61 | 1990 |
| 495718 | 23551 | 23570 | CTTATCCTTGAGGGTCTCAT | 83 | 1991 |
| 495719 | 23553 | 23572 | TGCTTATCCTTGAGGGTCTC | 79 | 1992 |
| 495720 | 23554 | 23573 | ATGCTTATCCTTGAGGGTCT | 73 | 1993 |
| 495721 | 23555 | 23574 | CATGCTTATCCTTGAGGGTC | 64 | 1994 |
| 495722 | 23556 | 23575 | ACATGCTTATCCTTGAGGGT | 60 | 1995 |
| 495723 | 26396 | 26415 | CTGGATGGCAACCTAAGGAG | 61 | 1996 |
| 495724 | 26397 | 26416 | CCTGGATGGCAACCTAAGGA | 74 | 1997 |

TABLE 30-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495725 | 26398 | 26417 | GCCTGGATGGCAACCTAAGG | 61 | 1998 |
| 495726 | 26399 | 26418 | GGCCTGGATGGCAACCTAAG | 60 | 1999 |
| 495727 | 26401 | 26420 | CTGGCCTGGATGGCAACCTA | 69 | 2000 |
| 495728 | 26480 | 26499 | TGCTATGCTGAGAGCACAGG | 69 | 2001 |
| 495729 | 26481 | 26500 | CTGCTATGCTGAGAGCACAG | 64 | 2002 |
| 495730 | 26482 | 26501 | CCTGCTATGCTGAGAGCACA | 81 | 2003 |

TABLE 31

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % Inhibition | SEQ ID NO |
|---|---|---|---|---|---|
| 495731 | 26483 | 26502 | ACCTGCTATGCTGAGAGCAC | 75 | 2004 |
| 495732 | 26485 | 26504 | CTACCTGCTATGCTGAGAGC | 69 | 2005 |
| 495733 | 26486 | 26505 | GCTACCTGCTATGCTGAGAG | 54 | 2006 |
| 495734 | 26487 | 26506 | AGCTACCTGCTATGCTGAGA | 67 | 2007 |
| 495735 | 26488 | 26507 | AAGCTACCTGCTATGCTGAG | 44 | 2008 |
| 495736 | 26517 | 26536 | GCAGGTTCATCTGCCTTGAC | 88 | 2009 |
| 495737 | 26518 | 26537 | AGCAGGTTCATCTGCCTTGA | 75 | 2010 |
| 495738 | 26519 | 26538 | GAGCAGGTTCATCTGCCTTG | 84 | 2011 |
| 495739 | 26520 | 26539 | GGAGCAGGTTCATCTGCCTT | 80 | 2012 |
| 495740 | 26532 | 26551 | CTGTGATGCTCTGGAGCAGG | 56 | 2013 |
| 495741 | 26533 | 26552 | TCTGTGATGCTCTGGAGCAG | 49 | 2014 |
| 495742 | 26534 | 26553 | CTCTGTGATGCTCTGGAGCA | 66 | 2015 |
| 495743 | 26535 | 26554 | ACTCTGTGATGCTCTGGAGC | 74 | 2016 |
| 495744 | 26537 | 26556 | GCACTCTGTGATGCTCTGGA | 85 | 2017 |
| 495745 | 26538 | 26557 | TGCACTCTGTGATGCTCTGG | 80 | 2018 |
| 495746 | 26539 | 26558 | ATGCACTCTGTGATGCTCTG | 70 | 2019 |
| 495747 | 26540 | 26559 | AATGCACTCTGTGATGCTCT | 60 | 2020 |
| 495748 | 26626 | 26645 | TGACATGGTAAGTCCTGATG | 79 | 2021 |
| 495749 | 26627 | 26646 | CTGACATGGTAAGTCCTGAT | 86 | 2022 |
| 495750 | 26628 | 26647 | ACTGACATGGTAAGTCCTGA | 79 | 2023 |
| 495751 | 26629 | 26648 | CACTGACATGGTAAGTCCTG | 84 | 2024 |
| 495752 | 26631 | 26650 | AGCACTGACATGGTAAGTCC | 90 | 2025 |
| 495753 | 26632 | 26651 | CAGCACTGACATGGTAAGTC | 86 | 2026 |
| 495754 | 26633 | 26652 | TCAGCACTGACATGGTAAGT | 73 | 2027 |
| 495755 | 26634 | 26653 | CTCAGCACTGACATGGTAAG | 63 | 2028 |
| 495756 | 26779 | 26798 | CTGCCATTTAATGAGCTTCA | 86 | 2029 |
| 495757 | 26780 | 26799 | TCTGCCATTTAATGAGCTTC | 77 | 2030 |
| 495758 | 26781 | 26800 | CTCTGCCATTTAATGAGCTT | 50 | 2031 |
| 495759 | 26782 | 26801 | ACTCTGCCATTTAATGAGCT | 43 | 2032 |
| 495760 | 26784 | 26803 | CAACTCTGCCATTTAATGAG | 34 | 2033 |
| 495761 | 26785 | 26804 | CCAACTCTGCCATTTAATGA | 39 | 2034 |

TABLE 31-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % Inhibition | SEQ ID NO |
|---|---|---|---|---|---|
| 495762 | 26786 | 26805 | CCCAACTCTGCCATTTAATG | 74 | 2035 |
| 495763 | 26787 | 26806 | TCCCAACTCTGCCATTTAAT | 76 | 2036 |
| 495764 | 26789 | 26808 | AATCCCAACTCTGCCATTTA | 62 | 2037 |
| 495765 | 26790 | 26809 | AAATCCCAACTCTGCCATTT | 61 | 2038 |
| 495766 | 26927 | 26946 | TTTAAGGGTTCATGGATCCC | 70 | 2039 |
| 495767 | 26928 | 26947 | TTTTAAGGGTTCATGGATCC | 48 | 2040 |
| 495768 | 26929 | 26948 | ATTTTAAGGGTTCATGGATC | 23 | 2041 |
| 495769 | 26930 | 26949 | AATTTTAAGGGTTCATGGAT | 9 | 2042 |
| 495770 | 27247 | 27266 | TGGAGTCCCTGGGTTCTTGT | 51 | 2043 |
| 495771 | 27248 | 27267 | CTGGAGTCCCTGGGTTCTTG | 52 | 2044 |
| 495772 | 27249 | 27268 | GCTGGAGTCCCTGGGTTCTT | 72 | 2045 |
| 495773 | 27250 | 27269 | GGCTGGAGTCCCTGGGTTCT | 64 | 2046 |
| 495774 | 27252 | 27271 | GAGGCTGGAGTCCCTGGGTT | 64 | 2047 |
| 495775 | 27253 | 27272 | GGAGGCTGGAGTCCCTGGGT | 45 | 2048 |
| 495776 | 27255 | 27274 | TGGGAGGCTGGAGTCCCTGG | 24 | 2049 |
| 495777 | 27353 | 27372 | TACCAGCCAGGCCCAGACCC | 8 | 2050 |
| 495778 | 27354 | 27373 | CTACCAGCCAGGCCCAGACC | 7 | 2051 |
| 495779 | 27355 | 27374 | CCTACCAGCCAGGCCCAGAC | 6 | 2052 |
| 495780 | 27356 | 27375 | CCCTACCAGCCAGGCCCAGA | 9 | 2053 |
| 495781 | 27378 | 27397 | GTGTTCTACAAGCTGCTCAG | 64 | 2054 |
| 495782 | 27379 | 27398 | GGTGTTCTACAAGCTGCTCA | 77 | 2055 |
| 495783 | 27380 | 27399 | TGGTGTTCTACAAGCTGCTC | 68 | 2056 |
| 495784 | 27381 | 27400 | CTGGTGTTCTACAAGCTGCT | 74 | 2057 |
| 495785 | 27383 | 27402 | AGCTGGTGTTCTACAAGCTG | 80 | 2058 |
| 495786 | 27384 | 27403 | GAGCTGGTGTTCTACAAGCT | 61 | 2059 |
| 495787 | 27385 | 27404 | TGAGCTGGTGTTCTACAAGC | 58 | 2060 |
| 495788 | 27386 | 27405 | GTGAGCTGGTGTTCTACAAG | 62 | 2061 |
| 495789 | 27438 | 27457 | GTCTGATCAATTATTAACCT | 71 | 2062 |
| 495790 | 27439 | 27458 | GGTCTGATCAATTATTAACC | 57 | 2063 |
| 495791 | 27440 | 27459 | GGGTCTGATCAATTATTAAC | 60 | 2064 |
| 495792 | 27441 | 27460 | TGGGTCTGATCAATTATTAA | 40 | 2065 |
| 495793 | 29674 | 29693 | CAGGTACTCATGTTTGGTGG | 63 | 2066 |
| 495794 | 29675 | 29694 | GCAGGTACTCATGTTTGGTG | 75 | 2067 |
| 495795 | 29676 | 29695 | AGCAGGTACTCATGTTTGGT | 73 | 2068 |
| 495796 | 29677 | 29696 | CAGCAGGTACTCATGTTTGG | 66 | 2069 |
| 495797 | 29679 | 29698 | GGCAGCAGGTACTCATGTTT | 60 | 2070 |
| 495798 | 29680 | 29699 | GGGCAGCAGGTACTCATGTT | 58 | 2071 |
| 495799 | 29681 | 29700 | AGGGCAGCAGGTACTCATGT | 63 | 2072 |
| 495800 | 29682 | 29701 | AAGGGCAGCAGGTACTCATG | 75 | 2073 |
| 495801 | 29778 | 29797 | CAATATCATACTATCTACAT | 11 | 2074 |
| 495802 | 29779 | 29798 | CCAATATCATACTATCTACA | 13 | 2075 |
| 495803 | 29780 | 29799 | CCCAATATCATACTATCTAC | 51 | 2076 |
| 495804 | 29781 | 29800 | CCCCAATATCATACTATCTA | 71 | 2077 |
| 495805 | 29783 | 29802 | TTCCCCAATATCATACTATC | 50 | 2078 |
| 495806 | 29825 | 29844 | AACCTTTAAGGCCTATCTCA | 32 | 2079 |
| 495807 | 29826 | 29845 | CAACCTTTAAGGCCTATCTC | 25 | 2080 |
| 413433 | 32431 | 32450 | GCCTGGACAAGTCCTGCCCA | 84 | 425 |

TABLE 32

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495808 | 29827 | 29846 | CCAACCTTTAAGGCCTATCT | 82 | 2081 |
| 495809 | 29828 | 29847 | CCCAACCTTTAAGGCCTATC | 90 | 2082 |
| 495810 | 29830 | 29849 | TACCCAACCTTTAAGGCCTA | 82 | 2083 |
| 495811 | 29831 | 29850 | TTACCCAACCTTTAAGGCCT | 75 | 2084 |
| 495812 | 29832 | 29851 | TTTACCCAACCTTTAAGGCC | 73 | 2085 |
| 495813 | 29833 | 29852 | TTTTACCCAACCTTTAAGGC | 70 | 2086 |
| 495814 | 29835 | 29854 | TTTTTTACCCAACCTTTAAG | 32 | 2087 |
| 495815 | 29836 | 29855 | ATTTTTTACCCAACCTTTAA | 27 | 2088 |
| 495816 | 29837 | 29856 | CATTTTTTACCCAACCTTTA | 54 | 2089 |
| 495817 | 29838 | 29857 | CCATTTTTTACCCAACCTTT | 81 | 2090 |
| 495818 | 29840 | 29859 | TTCCATTTTTTACCCAACCT | 89 | 2091 |
| 495819 | 29841 | 29860 | TTTCCATTTTTTACCCAACC | 88 | 2092 |
| 495820 | 29842 | 29861 | CTTTCCATTTTTTACCCAAC | 85 | 2093 |
| 495821 | 29843 | 29862 | TCTTTCCATTTTTTACCCAA | 74 | 2094 |
| 495822 | 30484 | 30503 | TTAGGCTTTAGAAATTCACC | 85 | 2095 |
| 495823 | 30485 | 30504 | ATTAGGCTTTAGAAATTCAC | 69 | 2096 |
| 413433 | 32431 | 32450 | GCCTGGACAAGTCCTGCCCA | 89 | 425 |
| 495824 | 32437 | 32456 | TATGCAGCCTGGACAAGTCC | 65 | 2097 |
| 495825 | 32447 | 32466 | CATACTAGACTATGCAGCCT | 91 | 2098 |
| 495826 | 32448 | 32467 | TCATACTAGACTATGCAGCC | 88 | 2099 |
| 495827 | 32449 | 32468 | ATCATACTAGACTATGCAGC | 86 | 2100 |
| 495828 | 32450 | 32469 | CATCATACTAGACTATGCAG | 82 | 2101 |
| 495829 | 32452 | 32471 | GCCATCATACTAGACTATGC | 92 | 2102 |
| 495830 | 32453 | 32472 | TGCCATCATACTAGACTATG | 81 | 2103 |
| 495831 | 32454 | 32473 | TTGCCATCATACTAGACTAT | 82 | 2104 |
| 495832 | 32455 | 32474 | GTTGCCATCATACTAGACTA | 88 | 2105 |
| 495833 | 32457 | 32476 | ATGTTGCCATCATACTAGAC | 78 | 2106 |
| 495834 | 32458 | 32477 | AATGTTGCCATCATACTAGA | 68 | 2107 |
| 495835 | 32459 | 32478 | CAATGTTGCCATCATACTAG | 85 | 2108 |
| 495836 | 32460 | 32479 | GCAATGTTGCCATCATACTA | 91 | 2109 |
| 495837 | 32462 | 32481 | TTGCAATGTTGCCATCATAC | 95 | 2110 |
| 495838 | 32463 | 32482 | GTTGCAATGTTGCCATCATA | 86 | 2111 |
| 495839 | 32464 | 32483 | GGTTGCAATGTTGCCATCAT | 94 | 2112 |
| 495840 | 32465 | 32484 | TGGTTGCAATGTTGCCATCA | 94 | 2113 |
| 495841 | 32467 | 32486 | GGTGGTTGCAATGTTGCCAT | 91 | 2114 |
| 495842 | 32468 | 32487 | TGGTGGTTGCAATGTTGCCA | 92 | 2115 |
| 495843 | 32469 | 32488 | ATGGTGGTTGCAATGTTGCC | 84 | 2116 |
| 495844 | 32470 | 32489 | GATGGTGGTTGCAATGTTGC | 82 | 2117 |
| 495845 | 32472 | 32491 | TGGATGGTGGTTGCAATGTT | 51 | 2118 |
| 495846 | 32473 | 32492 | CTGGATGGTGGTTGCAATGT | 48 | 2119 |
| 495847 | 32474 | 32493 | CCTGGATGGTGGTTGCAATG | 64 | 2120 |
| 495848 | 32475 | 32494 | GCCTGGATGGTGGTTGCAAT | 76 | 2121 |
| 495849 | 32477 | 32496 | AAGCCTGGATGGTGGTTGCA | 89 | 2122 |
| 495850 | 32478 | 32497 | TAAGCCTGGATGGTGGTTGC | 71 | 2123 |
| 495851 | 32479 | 32498 | ATAAGCCTGGATGGTGGTTG | 69 | 2124 |
| 495852 | 32480 | 32499 | AATAAGCCTGGATGGTGGTT | 85 | 2125 |

TABLE 32-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495853 | 32620 | 32639 | AACTGAGATCTCCAGCAGCA | 93 | 2126 |
| 495854 | 32621 | 32640 | AAACTGAGATCTCCAGCAGC | 82 | 2127 |
| 495855 | 32622 | 32641 | TAAACTGAGATCTCCAGCAG | 79 | 2128 |
| 495856 | 32623 | 32642 | TTAAACTGAGATCTCCAGCA | 81 | 2129 |
| 495857 | 32753 | 32772 | GACAAAGTCTATCAGGATGC | 90 | 2130 |
| 495858 | 32754 | 32773 | TGACAAAGTCTATCAGGATG | 67 | 2131 |
| 495859 | 32755 | 32774 | GTGACAAAGTCTATCAGGAT | 73 | 2132 |
| 495860 | 32756 | 32775 | AGTGACAAAGTCTATCAGGA | 72 | 2133 |
| 495861 | 32758 | 32777 | AAAGTGACAAAGTCTATCAG | 58 | 2134 |
| 495862 | 32759 | 32778 | GAAAGTGACAAAGTCTATCA | 67 | 2135 |
| 495863 | 32760 | 32779 | AGAAAGTGACAAAGTCTATC | 63 | 2136 |
| 495864 | 33176 | 33195 | CTAGTGCCCCAGGGAGCCCT | 63 | 2137 |
| 495865 | 33177 | 33196 | CCTAGTGCCCCAGGGAGCCC | 67 | 2138 |
| 495866 | 33178 | 33197 | TCCTAGTGCCCCAGGGAGCC | 60 | 2139 |
| 495867 | 33179 | 33198 | GTCCTAGTGCCCCAGGGAGC | 83 | 2140 |
| 495868 | 33181 | 33200 | TTGTCCTAGTGCCCCAGGGA | 87 | 2141 |
| 495869 | 33182 | 33201 | TTTGTCCTAGTGCCCCAGGG | 82 | 2142 |
| 495870 | 33183 | 33202 | TTTTGTCCTAGTGCCCCAGG | 66 | 2143 |
| 495871 | 36244 | 36263 | GTATTCTGCTCATAAAAACA | 42 | 2144 |
| 495872 | 36245 | 36264 | GGTATTCTGCTCATAAAAAC | 56 | 2145 |
| 495873 | 36246 | 36265 | GGGTATTCTGCTCATAAAAA | 72 | 2146 |
| 495874 | 36247 | 36266 | AGGGTATTCTGCTCATAAAA | 82 | 2147 |
| 495875 | 36249 | 36268 | TAAGGGTATTCTGCTCATAA | 89 | 2148 |
| 495876 | 36250 | 36269 | GTAAGGGTATTCTGCTCATA | 90 | 2149 |
| 495877 | 36251 | 36270 | AGTAAGGGTATTCTGCTCAT | 85 | 2150 |
| 495878 | 36252 | 36271 | GAGTAAGGGTATTCTGCTCA | 94 | 2151 |
| 495879 | 36259 | 36278 | AGACAATGAGTAAGGGTATT | 67 | 2152 |
| 495880 | 36260 | 36279 | GAGACAATGAGTAAGGGTAT | 47 | 2153 |
| 495881 | 36261 | 36280 | AGAGACAATGAGTAAGGGTA | 60 | 2154 |
| 495882 | 36262 | 36281 | GAGAGACAATGAGTAAGGGT | 77 | 2155 |
| 495883 | 36264 | 36283 | GAGAGAGACAATGAGTAAGG | 64 | 2156 |
| 495884 | 36265 | 36284 | TGAGAGAGACAATGAGTAAG | 31 | 2157 |

TABLE 33

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 413433 | 32431 | 32450 | GCCTGGACAAGTCCTGCCCA | 87 | 425 |
| 495885 | 36266 | 36285 | CTGAGAGAGACAATGAGTAA | 51 | 2158 |
| 495886 | 36518 | 36537 | AGCGACAGCCCTGTGCCAGC | 67 | 2159 |
| 495887 | 36519 | 36538 | AAGCGACAGCCCTGTGCCAG | 43 | 2160 |
| 495888 | 36520 | 36539 | CAAGCGACAGCCCTGTGCCA | 15 | 2161 |
| 495889 | 36521 | 36540 | ACAAGCGACAGCCCTGTGCC | 25 | 2162 |
| 495890 | 36523 | 36542 | GGACAAGCGACAGCCCTGTG | 44 | 2163 |
| 495891 | 36524 | 36543 | AGGACAAGCGACAGCCCTGT | 42 | 2164 |
| 495892 | 36648 | 36667 | ATGAGACAGGCAGCCCACCT | 53 | 2165 |
| 495893 | 36649 | 36668 | AATGAGACAGGCAGCCCACC | 56 | 2166 |

TABLE 33-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495894 | 36650 | 36669 | GAATGAGACAGGCAGCCCAC | 46 | 2167 |
| 495895 | 36651 | 36670 | AGAATGAGACAGGCAGCCCA | 56 | 2168 |
| 495896 | 36653 | 36672 | ACAGAATGAGACAGGCAGCC | 42 | 2169 |
| 495897 | 36654 | 36673 | CACAGAATGAGACAGGCAGC | 47 | 2170 |
| 495898 | 36655 | 36674 | TCACAGAATGAGACAGGCAG | 24 | 2171 |
| 495899 | 36677 | 36696 | GCTCTGTGGGCTCCTCCACA | 72 | 2172 |
| 495900 | 36678 | 36697 | TGCTCTGTGGGCTCCTCCAC | 70 | 2173 |
| 495901 | 36679 | 36698 | GTGCTCTGTGGGCTCCTCCA | 76 | 2174 |
| 495902 | 36680 | 36699 | TGTGCTCTGTGGGCTCCTCC | 81 | 2175 |
| 495903 | 36682 | 36701 | CCTGTGCTCTGTGGGCTCCT | 65 | 2176 |
| 495904 | 36683 | 36702 | CCCTGTGCTCTGTGGGCTCC | 70 | 2177 |
| 495905 | 36684 | 36703 | GCCCTGTGCTCTGTGGGCTC | 31 | 2178 |
| 495906 | 36685 | 36704 | GGCCCTGTGCTCTGTGGGCT | 32 | 2179 |
| 495907 | 36687 | 36706 | TTGGCCCTGTGCTCTGTGGG | 46 | 2180 |
| 495908 | 36688 | 36707 | CTTGGCCCTGTGCTCTGTGG | 41 | 2181 |
| 495909 | 36689 | 36708 | ACTTGGCCCTGTGCTCTGTG | 66 | 2182 |
| 495910 | 36690 | 36709 | TACTTGGCCCTGTGCTCTGT | 52 | 2183 |
| 495911 | 36734 | 36753 | CACTGTCAGTCTCTCCAAAC | 75 | 2184 |
| 495912 | 36735 | 36754 | CCACTGTCAGTCTCTCCAAA | 75 | 2185 |
| 495913 | 36736 | 36755 | CCCACTGTCAGTCTCTCCAA | 60 | 2186 |
| 495914 | 36737 | 36756 | CCCCACTGTCAGTCTCTCCA | 63 | 2187 |
| 495915 | 36739 | 36758 | GCCCCACTGTCAGTCTCTC | 48 | 2188 |
| 495916 | 36740 | 36759 | TGCCCCACTGTCAGTCTCT | 46 | 2189 |
| 495917 | 36741 | 36760 | CTGCCCCACTGTCAGTCTC | 55 | 2190 |
| 495918 | 36742 | 36761 | TCTGCCCCACTGTCAGTCT | 68 | 2191 |
| 495919 | 36754 | 36773 | TTGGCTGCAAGCTCTGCCCC | 59 | 2192 |
| 495920 | 36755 | 36774 | CTTGGCTGCAAGCTCTGCCC | 63 | 2193 |
| 495921 | 36756 | 36775 | CCTTGGCTGCAAGCTCTGCC | 65 | 2194 |
| 495922 | 36757 | 36776 | GCCTTGGCTGCAAGCTCTGC | 65 | 2195 |
| 495923 | 36759 | 36778 | GGGCCTTGGCTGCAAGCTCT | 65 | 2196 |
| 495924 | 36856 | 36875 | TTATTCTAAAACTCAAATCC | 8 | 2197 |
| 495925 | 36857 | 36876 | ATTATTCTAAAACTCAAATC | 11 | 2198 |
| 495926 | 36859 | 36878 | TGATTATTCTAAAACTCAAA | 2 | 2199 |
| 495927 | 36861 | 36880 | AGTGATTATTCTAAAACTCA | 55 | 2200 |
| 495928 | 36862 | 36881 | GAGTGATTATTCTAAAACTC | 36 | 2201 |
| 495929 | 36863 | 36882 | AGAGTGATTATTCTAAAACT | 0 | 2202 |
| 495930 | 36864 | 36883 | CAGAGTGATTATTCTAAAAC | 28 | 2203 |
| 495931 | 37023 | 37042 | TGTTGGGCAGTCACCATTTG | 1 | 2204 |
| 495932 | 37024 | 37043 | GTGTTGGGCAGTCACCATTT | 17 | 2205 |
| 495933 | 37025 | 37044 | GGTGTTGGGCAGTCACCATT | 20 | 2206 |
| 495934 | 37026 | 37045 | TGGTGTTGGGCAGTCACCAT | 2 | 2207 |
| 495935 | 37185 | 37204 | CCTTGGGTCAGAGGAAACTG | 5 | 2208 |
| 495936 | 37186 | 37205 | ACCTTGGGTCAGAGGAAACT | 12 | 2209 |
| 495937 | 37187 | 37206 | GACCTTGGGTCAGAGGAAAC | 15 | 2210 |
| 495938 | 37188 | 37207 | TGACCTTGGGTCAGAGGAAA | 2 | 2211 |
| 495939 | 37190 | 37209 | GATGACCTTGGGTCAGAGGA | 18 | 2212 |

TABLE 33-continued

Inhibition of DGAT2 mRNA by 5-10-5
MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495940 | 37191 | 37210 | GGATGACCTTGGGTCAGAGG | 16 | 2213 |
| 495941 | 37192 | 37211 | AGGATGACCTTGGGTCAGAG | 13 | 2214 |
| 495942 | 37193 | 37212 | AAGGATGACCTTGGGTCAGA | 8 | 2215 |
| 495943 | 37195 | 37214 | GCAAGGATGACCTTGGGTCA | 26 | 2216 |
| 495944 | 37196 | 37215 | TGCAAGGATGACCTTGGGTC | 24 | 2217 |
| 495945 | 37197 | 37216 | CTGCAAGGATGACCTTGGGT | 32 | 2218 |
| 495946 | 37198 | 37217 | GCTGCAAGGATGACCTTGGG | 16 | 2219 |
| 495947 | 37200 | 37219 | CAGCTGCAAGGATGACCTTG | 7 | 2220 |
| 495948 | 37201 | 37220 | CCAGCTGCAAGGATGACCTT | 0 | 2221 |
| 495949 | 37203 | 37222 | CACCAGCTGCAAGGATGACC | 27 | 2222 |
| 495950 | 37491 | 37510 | TGTGTTGGCTCCCTGTGTCA | 38 | 2223 |
| 495951 | 37492 | 37511 | GTGTGTTGGCTCCCTGTGTC | 11 | 2224 |
| 495952 | 37493 | 37512 | GGTGTGTTGGCTCCCTGTGT | 40 | 2225 |
| 495953 | 37494 | 37513 | TGGTGTGTTGGCTCCCTGTG | 29 | 2226 |
| 495954 | 37496 | 37515 | AATGGTGTGTTGGCTCCCTG | 49 | 2227 |
| 495955 | 37497 | 37516 | GAATGGTGTGTTGGCTCCCT | 76 | 2228 |
| 495956 | 37498 | 37517 | GGAATGGTGTGTTGGCTCCC | 44 | 2229 |
| 495957 | 37499 | 37518 | AGGAATGGTGTGTTGGCTCC | 72 | 2230 |
| 495958 | 37501 | 37520 | CAAGGAATGGTGTGTTGGCT | 74 | 2231 |
| 495959 | 37502 | 37521 | CCAAGGAATGGTGTGTTGGC | 8 | 2232 |
| 495960 | 37503 | 37522 | ACCAAGGAATGGTGTGTTGG | 21 | 2233 |
| 495961 | 37504 | 37523 | CACCAAGGAATGGTGTGTTG | 18 | 2234 |

TABLE 34

Inhibition of DGAT2 mRNA by 5-10-5
MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 423460 | 32428 | 32447 | TGGACAAGTCCTGCCCATCT | 65 | 464 |
| 423461 | 32429 | 32448 | CTGGACAAGTCCTGCCCATC | 70 | 465 |
| 423462 | 32430 | 32449 | CCTGGACAAGTCCTGCCCAT | 54 | 466 |
| 413433 | 32431 | 32450 | GCCTGGACAAGTCCTGCCCA | 80 | 425 |
| 495962 | 37506 | 37525 | AGCACCAAGGAATGGTGTGT | 6 | 2235 |
| 495963 | 37507 | 37526 | CAGCACCAAGGAATGGTGTG | 19 | 2236 |
| 495964 | 37508 | 37527 | CCAGCACCAAGGAATGGTGT | 13 | 2237 |
| 495965 | 37509 | 37528 | CCCAGCACCAAGGAATGGTG | 26 | 2238 |
| 495966 | 37511 | 37530 | GGCCCAGCACCAAGGAATGG | 14 | 2239 |
| 495967 | 37512 | 37531 | AGGCCCAGCACCAAGGAATG | 4 | 2240 |
| 495968 | 37513 | 37532 | CAGGCCCAGCACCAAGGAAT | 8 | 2241 |
| 495969 | 37514 | 37533 | GCAGGCCCAGCACCAAGGAA | 33 | 2242 |
| 495970 | 37516 | 37535 | ATGCAGGCCCAGCACCAAGG | 33 | 2243 |
| 495971 | 37517 | 37536 | AATGCAGGCCCAGCACCAAG | 14 | 2244 |
| 495972 | 37518 | 37537 | CAATGCAGGCCCAGCACCAA | 16 | 2245 |
| 495973 | 37519 | 37538 | CCAATGCAGGCCCAGCACCA | 45 | 2246 |
| 495974 | 40192 | 40211 | CTGAACTTCCCCTCCCAAAC | 16 | 2247 |
| 495975 | 40197 | 40216 | CAAATCTGAACTTCCCCTCC | 0 | 2248 |
| 495976 | 40202 | 40221 | AAATGCAAATCTGAACTTCC | 30 | 2249 |
| 495977 | 40223 | 40242 | GCAGCTCCAAGGATCATTTT | 44 | 2250 |
| 495978 | 40228 | 40247 | ATCCAGCAGCTCCAAGGATC | 45 | 2251 |
| 495979 | 40233 | 40252 | CTTCCATCCAGCAGCTCCAA | 51 | 2252 |
| 495980 | 40238 | 40257 | CCCATCTTCCATCCAGCAGC | 49 | 2253 |

TABLE 34-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 495981 | 40243 | 40262 | TCTAACCCATCTTCCATCCA | 28 | 2254 |
| 495982 | 40248 | 40267 | ATTTTTCTAACCCATCTTCC | 21 | 2255 |
| 495983 | 40253 | 40272 | CTTCCATTTTTCTAACCCAT | 64 | 2256 |
| 495984 | 40293 | 40312 | GCCACTGGCTACCAAAACAG | 37 | 2257 |
| 495985 | 40298 | 40317 | TCCAAGCCACTGGCTACCAA | 41 | 2258 |
| 495986 | 40303 | 40322 | CTTGGTCCAAGCCACTGGCT | 43 | 2259 |
| 495987 | 40308 | 40327 | ACTCCCTTGGTCCAAGCCAC | 44 | 2260 |
| 495988 | 40313 | 40332 | CTGCTACTCCCTTGGTCCAA | 40 | 2261 |
| 495989 | 40318 | 40337 | CTCCACTGCTACTCCCTTGG | 11 | 2262 |
| 495990 | 40323 | 40342 | TCCATCTCCACTGCTACTCC | 39 | 2263 |
| 495991 | 40328 | 40347 | TCTCTTCCATCTCCACTGCT | 36 | 2264 |
| 495992 | 40333 | 40352 | GCACATCTCTTCCATCTCCA | 82 | 2265 |
| 495993 | 40338 | 40357 | ATCATGCACATCTCTTCCAT | 39 | 2266 |
| 495994 | 40359 | 40378 | TATTTCTGAAATTTTTCCCA | 17 | 2267 |
| 495995 | 40364 | 40383 | AATGCTATTTCTGAAATTTT | 10 | 2268 |
| 495996 | 40386 | 40405 | CAATCCATTCCTATGTCCTG | 24 | 2269 |
| 495997 | 40391 | 40410 | ATACCCAATCCATTCCTATG | 13 | 2270 |
| 495998 | 40396 | 40415 | TCTCCATACCCAATCCATTC | 45 | 2271 |
| 495999 | 40401 | 40420 | CTGCATCTCCATACCCAATC | 59 | 2272 |
| 496000 | 40406 | 40425 | TCCTGCTGCATCTCCATACC | 38 | 2273 |
| 496001 | 40411 | 40430 | TCTTATCCTGCTGCATCTCC | 15 | 2274 |
| 496002 | 40416 | 40435 | TATTTTCTTATCCTGCTGCA | 46 | 2275 |
| 496003 | 40421 | 40440 | TGCTTTATTTTCTTATCCTG | 47 | 2276 |
| 496004 | 40444 | 40463 | ACCAGCATTTATGATCTGTG | 67 | 2277 |
| 496005 | 40807 | 40826 | GACATGCTTTAAAAAGTGTA | 25 | 2278 |
| 496006 | 40812 | 40831 | AATGTGACATGCTTTAAAAA | 23 | 2279 |
| 496007 | 40899 | 40918 | AGCCATTCCTGCCTCTCTGA | 12 | 2280 |
| 496008 | 40904 | 40923 | GGGCAAGCCATTCCTGCCTC | 5 | 2281 |
| 496009 | 40909 | 40928 | GCTCTGGGCAAGCCATTCCT | 60 | 2282 |
| 496010 | 40914 | 40933 | GCTCTGCTCTGGGCAAGCCA | 66 | 2283 |
| 496011 | 40919 | 40938 | CTTTTGCTCTGCTCTGGGCA | 50 | 2284 |
| 496012 | 40924 | 40943 | CTTTGCTTTTGCTCTGCTCT | 67 | 2285 |
| 496013 | 40929 | 40948 | AACATCTTTGCTTTTGCTCT | 59 | 2286 |
| 496014 | 40934 | 40953 | AAGTAAACATCTTTGCTTTT | 15 | 2287 |
| 496015 | 40939 | 40958 | GGATCAAGTAAACATCTTTG | 42 | 2288 |
| 496016 | 40967 | 40986 | TCTGCTAGGAGGGTCTATGA | 20 | 2289 |
| 496017 | 40972 | 40991 | TGCATTCTGCTAGGAGGGTC | 39 | 2290 |
| 496018 | 40977 | 40996 | CCCACTGCATTCTGCTAGGA | 27 | 2291 |
| 496019 | 40982 | 41001 | TTGAACCCACTGCATTCTGC | 6 | 2292 |
| 496020 | 40987 | 41006 | ACTGGTTGAACCCACTGCAT | 0 | 2293 |
| 496021 | 40992 | 41011 | TCAAGACTGGTTGAACCCAC | 8 | 2294 |
| 496022 | 40997 | 41016 | TGGGATCAAGACTGGTTGAA | 0 | 2295 |
| 496023 | 41002 | 41021 | GCAGATGGGATCAAGACTGG | 0 | 2296 |
| 496024 | 41007 | 41026 | AAGCTGCAGATGGGATCAAG | 0 | 2297 |
| 496025 | 41012 | 41031 | GTGCTAAGCTGCAGATGGGA | 39 | 2298 |
| 496026 | 41043 | 41062 | GCATGTGAAGGGACCCACCC | 14 | 2299 |

TABLE 34-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 496027 | 41064 | 41083 | TGAAAAGACTGAGGCCCAGG | 1 | 2300 |
| 496028 | 41069 | 41088 | ACAGATGAAAAGACTGAGGC | 21 | 2301 |
| 496029 | 41074 | 41093 | CTATTACAGATGAAAAGACT | 0 | 2302 |
| 496030 | 41079 | 41098 | GTCCCCTATTACAGATGAAA | 34 | 2303 |
| 496031 | 41084 | 41103 | TGGTTGTCCCCTATTACAGA | 39 | 2304 |
| 496032 | 41089 | 41108 | ATCTCTGGTTGTCCCCTATT | 21 | 2305 |
| 496033 | 41094 | 41113 | GCTGCATCTCTGGTTGTCCC | 65 | 2306 |
| 496034 | 41099 | 41118 | TATGTGCTGCATCTCTGGTT | 51 | 2307 |
| 496035 | 42398 | 42417 | TCTCACTTTCATTTATTTTC | 70 | 2308 |

TABLE 35

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501381 | 24794 | 24813 | GCTTCAGGCAGCCTGAAGGA | 46 | 2309 |
| 501382 | 24799 | 24818 | AGTGAGCTTCAGGCAGCCTG | 75 | 2310 |
| 501383 | 24823 | 24842 | GCTTCCCCAAAGGGCCCAGT | 70 | 2311 |
| 501384 | 24828 | 24847 | CCTTTGCTTCCCCAAAGGGC | 71 | 2312 |
| 501385 | 24878 | 24897 | CCTCATCTCAGTGCCCAAAG | 90 | 2313 |
| 501386 | 25018 | 25037 | AGCATCCCCAATCCCTGCTC | 65 | 2314 |
| 501387 | 25023 | 25042 | CTTTGAGCATCCCCAATCCC | 91 | 2315 |
| 501388 | 25028 | 25047 | GTGTACTTTGAGCATCCCCA | 82 | 2316 |
| 501389 | 25033 | 25052 | TCCAAGTGTACTTTGAGCAT | 85 | 2317 |
| 501390 | 25069 | 25088 | AGAGGTTCAACATCCAATTT | 81 | 2318 |
| 501391 | 25075 | 25094 | AAGGACAGAGGTTCAACATC | 88 | 2319 |
| 501392 | 25080 | 25099 | AGGCCAAGGACAGAGGTTCA | 82 | 2320 |
| 501393 | 25085 | 25104 | CTGTGAGGCCAAGGACAGAG | 88 | 2321 |
| 501394 | 25090 | 25109 | TCTGTCTGTGAGGCCAAGGA | 77 | 2322 |
| 501395 | 25095 | 25114 | TGCTATCTGTCTGTGAGGCC | 77 | 2323 |
| 501396 | 25183 | 25202 | GTCTCTCATAATTGCCAGTT | 82 | 2324 |
| 501397 | 25188 | 25207 | GGGAAGTCTCTCATAATTGC | 67 | 2325 |
| 501398 | 25193 | 25212 | GCCTTGGGAAGTCTCTCATA | 85 | 2326 |
| 501399 | 25198 | 25217 | GCTAGGCCTTGGGAAGTCTC | 76 | 2327 |
| 501400 | 25226 | 25245 | TGAAGTATCTAAAGAGGCTA | 71 | 2328 |
| 501401 | 25231 | 25250 | CCACATGAAGTATCTAAAGA | 74 | 2329 |
| 501402 | 25236 | 25255 | GGAGACCACATGAAGTATCT | 75 | 2330 |
| 501403 | 25241 | 25260 | ATTTTGGAGACCACATGAAG | 68 | 2331 |
| 501404 | 25246 | 25265 | GGGTCATTTTGGAGACCACA | 91 | 2332 |
| 501405 | 25267 | 25286 | ATGGGAATGGTATCGCACTC | 85 | 2333 |
| 501406 | 25272 | 25291 | ACACAATGGGAATGGTATCG | 80 | 2334 |
| 501407 | 25297 | 25316 | CCCCTGTGCCCTGGTTTCTA | 49 | 2335 |
| 501408 | 25302 | 25321 | ATGCTCCCCTGTGCCCTGGT | 44 | 2336 |
| 501409 | 25307 | 25326 | TCTGCATGCTCCCCTGTGCC | 44 | 2337 |
| 501410 | 25312 | 25331 | GGCTGTCTGCATGCTCCCCT | 76 | 2338 |
| 501411 | 25375 | 25394 | CTATAGAATCAGACAGACCT | 83 | 2339 |
| 501412 | 25380 | 25399 | ATCAGCTATAGAATCAGACA | 90 | 2340 |

TABLE 35-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501413 | 25424 | 25443 | CAAACCTCACCTCCCACAGG | 33 | 2341 |
| 501414 | 25429 | 25448 | CAGTACAAACCTCACCTCCC | 70 | 2342 |
| 501415 | 25468 | 25487 | TCAGTCCACTGTCACCCTTC | 33 | 2343 |
| 501416 | 25473 | 25492 | AGATGTCAGTCCACTGTCAC | 13 | 2344 |
| 501417 | 25478 | 25497 | AGGGAAGATGTCAGTCCACT | 0 | 2345 |
| 501418 | 25483 | 25502 | AGCAGAGGGAAGATGTCAGT | 0 | 2346 |
| 501419 | 25489 | 25508 | GCCTACAGCAGAGGGAAGAT | 29 | 2347 |
| 501420 | 25494 | 25513 | CCAGTGCCTACAGCAGAGGG | 38 | 2348 |
| 501421 | 25499 | 25518 | TGGATCCAGTGCCTACAGCA | 41 | 2349 |
| 501422 | 25505 | 25524 | GGATGCTGGATCCAGTGCCT | 74 | 2350 |
| 501423 | 25618 | 25637 | ACCCAGTACAAGGAAGGACA | 78 | 2351 |
| 501424 | 25623 | 25642 | AGCTTACCCAGTACAAGGAA | 31 | 2352 |
| 501425 | 25628 | 25647 | GGCCCAGCTTACCCAGTACA | 48 | 2353 |
| 501426 | 25717 | 25736 | CTCTTATTCCCTCACCCCTG | 77 | 2354 |
| 501427 | 25782 | 25801 | CACTTGATCTGGGACCCAAA | 96 | 2355 |
| 501428 | 25787 | 25806 | TAGAGCACTTGATCTGGGAC | 80 | 2356 |
| 501429 | 25841 | 25860 | ACTATCACACCACCTCCCAC | 85 | 2357 |
| 501430 | 25846 | 25865 | TGGGAACTATCACACCACCT | 95 | 2358 |
| 501431 | 25851 | 25870 | GTAAATGGGAACTATCACAC | 64 | 2359 |
| 501432 | 25856 | 25875 | CATCTGTAAATGGGAACTAT | 49 | 2360 |
| 501433 | 25861 | 25880 | TTTCCCATCTGTAAATGGGA | 0 | 2361 |
| 501434 | 25866 | 25885 | TGAGGTTTCCCATCTGTAAA | 61 | 2362 |
| 501435 | 25900 | 25919 | GACCTTGGGCAAGTTACCTA | 88 | 2363 |
| 501436 | 25905 | 25924 | TGTGTGACCTTGGGCAAGTT | 82 | 2364 |
| 501437 | 25910 | 25929 | AAATCTGTGTGACCTTGGGC | 67 | 2365 |
| 501438 | 25915 | 25934 | GATTCAAATCTGTGTGACCT | 89 | 2366 |
| 501439 | 25920 | 25939 | ACAGGGATTCAAATCTGTGT | 73 | 2367 |
| 501440 | 25950 | 25969 | GGAAAGGCACAGGCTTTGGG | 88 | 2368 |
| 501441 | 25981 | 26000 | AATGTCTGTTGGTGGGCAGG | 77 | 2369 |
| 501442 | 26005 | 26024 | GGCAAAGTAACATACCTGCT | 94 | 2370 |
| 501443 | 26010 | 26029 | CTTAAGGCAAAGTAACATAC | 91 | 2371 |
| 501444 | 26069 | 26088 | TGTAAGGTCACAGAGCTTGT | 54 | 2372 |
| 501445 | 26102 | 26121 | GGAAACTAACACTCAGAGAG | 70 | 2373 |
| 501446 | 26107 | 26126 | AATGAGGAAACTAACACTCA | 62 | 2374 |
| 501447 | 26165 | 26184 | TTTCTTATCTTCAATCCTCA | 95 | 2375 |
| 501448 | 26170 | 26189 | TCTCATTTCTTATCTTCAAT | 92 | 2376 |
| 501449 | 26175 | 26194 | GGTGCTCTCATTTCTTATCT | 81 | 2377 |
| 501450 | 26200 | 26219 | CCCATCATGACCAGGCCCTG | 91 | 2378 |
| 501451 | 26300 | 26319 | AGGCCTCGGGAAGCACCTGG | 89 | 2379 |
| 501452 | 26305 | 26324 | GGAGCAGGCCTCGGGAAGCA | 90 | 2380 |
| 501453 | 26331 | 26350 | ATGTGGGCTGTGCTGAGAGA | 64 | 2381 |
| 501454 | 26353 | 26372 | AGAAAAGCAACCAAAGCAC | 89 | 2382 |
| 501455 | 26358 | 26377 | CCTGCAGAAAAAGCAACCAA | 81 | 2383 |
| 501456 | 26363 | 26382 | CCAGACCTGCAGAAAAAGCA | 76 | 2384 |
| 501457 | 26385 | 26404 | CCTAAGGAGTGAGGGTATCT | 79 | 2385 |
| 413433 | 32431 | 32450 | GCCTGGACAAGTCCTGCCCA | 48 | 425 |

TABLE 36

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501303 | 23656 | 23675 | CTCTGAGTGCAAAGGCTCTG | 40 | 2386 |
| 501304 | 23661 | 23680 | AGCAGCTCTGAGTGCAAAGG | 48 | 2387 |
| 501305 | 23666 | 23685 | CCCAGAGCAGCTCTGAGTGC | 45 | 2388 |
| 501306 | 23671 | 23690 | CTTTCCCCAGAGCAGCTCTG | 25 | 2389 |
| 501307 | 23694 | 23713 | TGACCCTGCTTAGAGGACCT | 29 | 2390 |
| 501308 | 23699 | 23718 | ATTCCTGACCCTGCTTAGAG | 5 | 2391 |
| 501309 | 23704 | 23723 | CCAGCATTCCTGACCCTGCT | 14 | 2392 |
| 501310 | 23709 | 23728 | GAAACCCAGCATTCCTGACC | 18 | 2393 |
| 501311 | 23714 | 23733 | GGACTGAAACCCAGCATTCC | 11 | 2394 |
| 501312 | 23719 | 23738 | AGCCAGGACTGAAACCCAGC | 34 | 2395 |
| 501313 | 23724 | 23743 | GGCAGAGCCAGGACTGAAAC | 47 | 2396 |
| 501314 | 23729 | 23748 | TAGGCGGCAGAGCCAGGACT | 43 | 2397 |
| 501315 | 23734 | 23753 | GGCAGTAGGCGGCAGAGCCA | 28 | 2398 |
| 501316 | 23770 | 23789 | ACCAGAGACAGGCACTGACT | 59 | 2399 |
| 501317 | 23792 | 23811 | TGGACAGCCAGGGAGACTGG | 36 | 2400 |
| 501318 | 23797 | 23816 | CTAATTGGACAGCCAGGGAG | 20 | 2401 |
| 501319 | 23802 | 23821 | ATAGCCTAATTGGACAGCCA | 63 | 2402 |
| 501320 | 23807 | 23826 | CCAGTATAGCCTAATTGGAC | 40 | 2403 |
| 501321 | 23813 | 23832 | GGTCATCCAGTATAGCCTAA | 53 | 2404 |
| 501322 | 23855 | 23874 | GACTTGCCCAGCAACCCATC | 65 | 2405 |
| 501323 | 23860 | 23879 | CTCCAGACTTGCCCAGCAAC | 28 | 2406 |
| 501324 | 23865 | 23884 | CCCACCTCCAGACTTGCCCA | 26 | 2407 |
| 501325 | 23870 | 23889 | ACTTTCCCACCTCCAGACTT | 18 | 2408 |
| 501326 | 23875 | 23894 | ATAGGACTTTCCCACCTCCA | 61 | 2409 |
| 501327 | 23880 | 23899 | CCTTCATAGGACTTTCCCAC | 56 | 2410 |
| 501328 | 23885 | 23904 | TCCTACCTTCATAGGACTTT | 40 | 2411 |
| 501329 | 23890 | 23909 | AAAAATCCTACCTTCATAGG | 0 | 2412 |
| 501330 | 23921 | 23940 | TGCCTCATAATTGCTCCTTC | 49 | 2413 |
| 501331 | 23926 | 23945 | AGGTCTGCCTCATAATTGCT | 8 | 2414 |
| 501332 | 23931 | 23950 | TCCAGAGGTCTGCCTCATAA | 64 | 2415 |
| 501333 | 23957 | 23976 | ATAAAGAGGCTGGGCCATAG | 8 | 2416 |
| 501334 | 23981 | 24000 | CAGGATGTGAACTCACAAAA | 59 | 2417 |
| 501335 | 24024 | 24043 | GTAGCATCTAATAACACCAC | 61 | 2418 |
| 501336 | 24029 | 24048 | GTTCAGTAGCATCTAATAAC | 59 | 2419 |
| 501337 | 24034 | 24053 | TGGGTGTTCAGTAGCATCTA | 50 | 2420 |
| 501338 | 24089 | 24108 | TATGTGACCCCAGGCAAGCT | 32 | 2421 |
| 501339 | 24094 | 24113 | CTCACTATGTGACCCCAGGC | 59 | 2422 |
| 501340 | 24099 | 24118 | TTCTACTCACTATGTGACCC | 56 | 2423 |
| 501341 | 24104 | 24123 | TTTGGTTCTACTCACTATGT | 57 | 2424 |
| 501342 | 24109 | 24128 | CAGACTTTGGTTCTACTCAC | 63 | 2425 |
| 501343 | 24114 | 24133 | AGGTTCAGACTTTGGTTCTA | 58 | 2426 |
| 501344 | 24119 | 24138 | AACCTAGGTTCAGACTTTGG | 59 | 2427 |
| 501345 | 24124 | 24143 | AGTCAAACCTAGGTTCAGAC | 68 | 2428 |
| 501346 | 24129 | 24148 | AGAAGAGTCAAACCTAGGTT | 56 | 2429 |
| 501347 | 24134 | 24153 | TTAGCAGAAGAGTCAAACCT | 38 | 2430 |
| 501348 | 24139 | 24158 | TTAGTTTAGCAGAAGAGTCA | 36 | 2431 |

TABLE 36-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501349 | 24164 | 24183 | GTGTGATGCATCAGAGGGAA | 40 | 2432 |
| 501350 | 24169 | 24188 | CCCTGGTGTGATGCATCAGA | 50 | 2433 |
| 501351 | 24174 | 24193 | CCTTTCCCTGGTGTGATGCA | 53 | 2434 |
| 501352 | 24197 | 24216 | AAATGCTAGGCCTCAAGATG | 17 | 2435 |
| 501353 | 24202 | 24221 | GAAGGAAATGCTAGGCCTCA | 64 | 2436 |
| 501354 | 24207 | 24226 | GGAAGGAAGGAAATGCTAGG | 31 | 2437 |
| 501355 | 24212 | 24231 | TAGGAGGAAGGAAGGAAATG | 11 | 2438 |
| 501356 | 24217 | 24236 | ACTTTTAGGAGGAAGGAAGG | 0 | 2439 |
| 501357 | 24222 | 24241 | CTTTGACTTTTAGGAGGAAG | 60 | 2440 |
| 501358 | 24227 | 24246 | AACTGCTTTGACTTTTAGGA | 39 | 2441 |
| 501359 | 24232 | 24251 | TTAACAACTGCTTTGACTTT | 30 | 2442 |
| 501360 | 24237 | 24256 | GAAAGTTAACAACTGCTTTG | 37 | 2443 |
| 501361 | 24447 | 24466 | TACCATCTGCTCTGTGAAAG | 21 | 2444 |
| 501362 | 24452 | 24471 | CTTCATACCATCTGCTCTGT | 29 | 2445 |
| 501363 | 24483 | 24502 | CAAGCACCTACTGTGTGCCC | 13 | 2446 |
| 501364 | 24488 | 24507 | TTCACCAAGCACCTACTGTG | 21 | 2447 |
| 501365 | 24493 | 24512 | ACATCTTCACCAAGCACCTA | 0 | 2448 |
| 501366 | 24516 | 24535 | CCACTACATGCCCTTTGCTC | 51 | 2449 |
| 501367 | 24557 | 24576 | CTGAAGAAGTGGGCCACCTC | 52 | 2450 |
| 501368 | 24582 | 24601 | ACCCATACCCCATTCCTTCC | 22 | 2451 |
| 501369 | 24587 | 24606 | TCCTCACCCATACCCCATTC | 9 | 2452 |
| 501370 | 24636 | 24655 | AGCCTGGTGACTGCAGGAGA | 61 | 2453 |
| 501371 | 24641 | 24660 | CAGGAAGCCTGGTGACTGCA | 45 | 2454 |
| 501372 | 24666 | 24685 | TCCAGCAGCTGATGGGCAGT | 43 | 2455 |
| 501373 | 24671 | 24690 | TGGACTCCAGCAGCTGATGG | 19 | 2456 |
| 501374 | 24695 | 24714 | CTTGGTGCCCCTAGGATGAC | 33 | 2457 |
| 501375 | 24700 | 24719 | ATTGGCTTGGTGCCCCTAGG | 8 | 2458 |
| 501376 | 24705 | 24724 | ACTTAATTGGCTTGGTGCCC | 36 | 2459 |
| 501377 | 24774 | 24793 | CACTGAGGGCTGTAATTATG | 21 | 2460 |
| 501378 | 24779 | 24798 | AAGGACACTGAGGGCTGTAA | 24 | 2461 |
| 501379 | 24784 | 24803 | GCCTGAAGGACACTGAGGGC | 2 | 2462 |
| 501380 | 24789 | 24808 | AGGCAGCCTGAAGGACACTG | 14 | 2463 |
| 413433 | 32431 | 32450 | GCCTGGACAAGTCCTGCCCA | 81 | 425 |

TABLE 37

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501226 | 21041 | 21060 | TGTTCCTGACTCCTGGGTGG | 26 | 2464 |
| 501227 | 21046 | 21065 | CTGACTGTTCCTGACTCCTG | 61 | 2465 |
| 501228 | 21091 | 21110 | TGCTGCAATCAGATGCCACC | 65 | 2466 |
| 501229 | 21096 | 21115 | GCCGATGCTGCAATCAGATG | 68 | 2467 |
| 501230 | 21101 | 21120 | GGGATGCCGATGCTGCAATC | 69 | 2468 |
| 501231 | 21119 | 21138 | GTCCAGCAGAAGCTGGTGGG | 19 | 2469 |
| 501232 | 21124 | 21143 | GAGGAGTCCAGCAGAAGCTG | 15 | 2470 |
| 501233 | 21129 | 21148 | GCTGGGAGGAGTCCAGCAGA | 12 | 2471 |
| 501234 | 21134 | 21153 | CTGTGGCTGGGAGGAGTCCA | 14 | 2472 |

TABLE 37-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501235 | 21139 | 21158 | CCCAGCTGTGGCTGGAGGA | 0 | 2473 |
| 501236 | 21144 | 21163 | TCTGCCCCAGCTGTGGCTGG | 0 | 2474 |
| 501237 | 21149 | 21168 | CTTCCTCTGCCCCAGCTGTG | 41 | 2475 |
| 501238 | 21154 | 21173 | CAGTACTTCCTCTGCCCCAG | 40 | 2476 |
| 501239 | 21159 | 21178 | GCTGTCAGTACTTCCTCTGC | 50 | 2477 |
| 501240 | 21164 | 21183 | ACCTGGCTGTCAGTACTTCC | 70 | 2478 |
| 501241 | 21169 | 21188 | TTGCCACCTGGCTGTCAGTA | 68 | 2479 |
| 501242 | 21174 | 21193 | AGTCCTTGCCACCTGGCTGT | 50 | 2480 |
| 501243 | 21179 | 21198 | CTGCCAGTCCTTGCCACCTG | 53 | 2481 |
| 501244 | 21184 | 21203 | AAACACTGCCAGTCCTTGCC | 63 | 2482 |
| 501245 | 21213 | 21232 | GGAAGTGAGGGTTCAGTTGG | 30 | 2483 |
| 501246 | 21369 | 21388 | CTCTCTGGGCTTCAGTTTCC | 45 | 2484 |
| 501247 | 21374 | 21393 | CTCACCTCTCTGGGCTTCAG | 61 | 2485 |
| 501248 | 21379 | 21398 | GTCTCCTCACCTCTCTGGGC | 61 | 2486 |
| 501249 | 21384 | 21403 | GCTAAGTCTCCTCACCTCTC | 71 | 2487 |
| 501250 | 21490 | 21509 | ATCTGTTTTCCTTCAGAGGG | 55 | 2488 |
| 501251 | 21565 | 21584 | TTCCTTCTCTCTGCTCCCCA | 55 | 2489 |
| 501252 | 21570 | 21589 | CCAAGTTCCTTCTCTCTGCT | 15 | 2490 |
| 501253 | 21575 | 21594 | TGTCCCCAAGTTCCTTCTCT | 32 | 2491 |
| 501254 | 21659 | 21678 | GGTCAAGGTCACTCAGCCAG | 62 | 2492 |
| 501255 | 21681 | 21700 | CCCTATTTTGATGGTGATAC | 57 | 2493 |
| 501256 | 21708 | 21727 | TGGACTCCTGTGAGTTTGGC | 67 | 2494 |
| 501257 | 21713 | 21732 | GCACTTGGACTCCTGTGAGT | 25 | 2495 |
| 501258 | 21718 | 21737 | CACAGGCACTTGGACTCCTG | 27 | 2496 |
| 501259 | 21723 | 21742 | CCTTGCACAGGCACTTGGAC | 18 | 2497 |
| 501260 | 21728 | 21747 | CATGCCCTTGCACAGGCACT | 14 | 2498 |
| 501261 | 21733 | 21752 | CCCTCCATGCCCTTGCACAG | 29 | 2499 |
| 501262 | 21755 | 21774 | AGGCCCATAAAGCTTTGGGA | 49 | 2500 |
| 501263 | 21760 | 21779 | ACAAGAGGCCCATAAAGCTT | 26 | 2501 |
| 501264 | 21765 | 21784 | GATGCACAAGAGGCCCATAA | 65 | 2502 |
| 501265 | 21770 | 21789 | GGTATGATGCACAAGAGGCC | 58 | 2503 |
| 501266 | 21821 | 21840 | CTGGCCACTCTTCAGGCCCC | 32 | 2504 |
| 501267 | 21826 | 21845 | GTGCTCTGGCCACTCTTCAG | 0 | 2505 |
| 501268 | 21873 | 21892 | GATCCATATCTGGATCCCCA | 2 | 2506 |
| 501269 | 21878 | 21897 | GGTCTGATCCATATCTGGAT | 20 | 2507 |
| 501270 | 21933 | 21952 | GCTGATTACAAGCTGATTCT | 77 | 2508 |
| 501271 | 21938 | 21957 | TAACTGCTGATTACAAGCTG | 39 | 2509 |
| 501272 | 21996 | 22015 | ACAATGGAGAAACAAAAGAG | 6 | 2510 |
| 501273 | 22019 | 22038 | TTTGAAGATAAAGTCAGACC | 35 | 2511 |
| 501274 | 22075 | 22094 | GTCTATGCAGGCCTGGAATT | 54 | 2512 |
| 501275 | 22080 | 22099 | CTAAGGTCTATGCAGGCCTG | 53 | 2513 |
| 501276 | 22085 | 22104 | AAACACTAAGGTCTATGCAG | 32 | 2514 |
| 501277 | 22090 | 22109 | ATGATAAACACTAAGGTCTA | 43 | 2515 |
| 501278 | 22095 | 22114 | CTGGGATGATAAACACTAAG | 53 | 2516 |
| 501279 | 22100 | 22119 | CTTCTCTGGGATGATAAACA | 0 | 2517 |
| 501280 | 22105 | 22124 | CTTTCCTTCTCTGGGATGAT | 0 | 2518 |

TABLE 37-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501281 | 22126 | 22145 | AAGCCTTTGGAAAGAGAAGG | 31 | 2519 |
| 501282 | 22131 | 22150 | CCAGGAAGCCTTTGGAAAGA | 31 | 2520 |
| 501283 | 22136 | 22155 | GTCTTCCAGGAAGCCTTTGG | 51 | 2521 |
| 501284 | 22141 | 22160 | CAGCAGTCTTCCAGGAAGCC | 54 | 2522 |
| 501285 | 22146 | 22165 | TAAGGCAGCAGTCTTCCAGG | 59 | 2523 |
| 501286 | 22151 | 22170 | GGTGATAAGGCAGCAGTCTT | 56 | 2524 |
| 501287 | 22156 | 22175 | GAGATGGTGATAAGGCAGCA | 78 | 2525 |
| 501288 | 22162 | 22181 | AACCCAGAGATGGTGATAAG | 23 | 2526 |
| 501289 | 22167 | 22186 | TTCAAAACCCAGAGATGGTG | 64 | 2527 |
| 501290 | 22172 | 22191 | CATCCTTCAAAACCCAGAGA | 62 | 2528 |
| 501291 | 22194 | 22213 | CTGATAATGAGATAAAGCAA | 3 | 2529 |
| 501292 | 22231 | 22250 | CAGAGGCCCTTCCCTGCTTT | 42 | 2530 |
| 501293 | 22266 | 22285 | TGGGAGCCCCCAGTCCACCT | 48 | 2531 |
| 501294 | 22271 | 22290 | GCCAGTGGGAGCCCCCAGTC | 0 | 2532 |
| 501295 | 22311 | 22330 | TGGCCTGGGAGCTGGCCTGG | 13 | 2533 |
| 501296 | 22349 | 22368 | CTCTCAGGCAATCCCAACCT | 27 | 2534 |
| 501297 | 22354 | 22373 | AGGCCCTCTCAGGCAATCCC | 62 | 2535 |
| 501298 | 22359 | 22378 | GGCCCAGGCCCTCTCAGGCA | 34 | 2536 |
| 501299 | 22364 | 22383 | TCTCAGGCCCAGGCCCTCTC | 27 | 2537 |
| 501300 | 22403 | 22422 | CTCCTGGAGAGGGAAGCTGG | 31 | 2538 |
| 501301 | 22408 | 22427 | GGAGGCTCCTGGAGAGGGAA | 0 | 2539 |
| 501302 | 22413 | 22432 | AGTTGGGAGGCTCCTGGAGA | 0 | 2540 |
| 413433 | 32431 | 32450 | GCCTGGACAAGTCCTGCCCA | 80 | 425 |

TABLE 38

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 484013 | 18880 20790 | 18899 20809 | CAGAGGCAGCTATAGGCCTG | 43 | 1299 |
| 495657 | 18871 20781 | 18890 20800 | CTATAGGCCTGGATGCCCAA | 72 | 1930 |
| 501152 | 19132 | 19151 | GCTGGAACAAAGCCTTGCAG | 52 | 2541 |
| 501153 | 19261 | 19280 | AAGAAGAGGTCGCAGAGTGA | 17 | 2542 |
| 501154 | 19360 | 19379 | GCTACTGGCATTGCTCCTCC | 75 | 2543 |
| 501155 | 19392 | 19411 | ACATGTGGCATTTGTTAGGT | 66 | 2544 |
| 501156 | 19421 | 19440 | GGAACATTAAATTTTAAAAC | 20 | 2545 |
| 501157 | 19775 | 19794 | TAGGATGAGGGTGATAATCC | 37 | 2546 |
| 501158 | 19804 | 19823 | CCTAACTCTAGCTTTGGTTT | 63 | 2547 |
| 501159 | 19809 | 19828 | AGTCACCTAACTCTAGCTTT | 20 | 2548 |
| 501160 | 19854 | 19873 | GCCCTGGGCCAGCTCTGCCC | 15 | 2549 |
| 501161 | 19867 | 19886 | TCTGAGAAAGAGGGCCCTGG | 26 | 2550 |
| 501162 | 19872 | 19891 | CTAAATCTGAGAAAGAGGGC | 0 | 2551 |
| 501163 | 19903 | 19922 | CTGAGGGCAGCAGTGTCTGA | 35 | 2552 |
| 501164 | 19908 | 19927 | CATGCCTGAGGGCAGCAGTG | 54 | 2553 |
| 501165 | 19913 | 19932 | TCTCACATGCCTGAGGGCAG | 74 | 2554 |
| 501166 | 19963 | 19982 | CAGGAAGGCCACACCTCGGG | 23 | 2555 |
| 501167 | 19968 | 19987 | GTGACCAGGAAGGCCACACC | 12 | 2556 |
| 501168 | 19973 | 19992 | TCAAAGTGACCAGGAAGGCC | 33 | 2557 |
| 501169 | 19978 | 19997 | TGATATCAAAGTGACCAGGA | 22 | 2558 |
| 501170 | 19983 | 20002 | ATATCTGATATCAAAGTGAC | 3 | 2559 |
| 501171 | 19988 | 20007 | GCCCAATATCTGATATCAAA | 74 | 2560 |
| 501172 | 20044 | 20063 | GACCCAGGGCCCAGCCCAGG | 18 | 2561 |

TABLE 38-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501173 | 20049 | 20068 | TCTCAGACCCAGGGCCCAGC | 55 | 2562 |
| 501174 | 20093 | 20112 | TGAGACTGGATTCCACCCCC | 24 | 2563 |
| 501175 | 20227 | 20246 | TACAATGCTACGCTGTTGAG | 36 | 2564 |
| 501176 | 20232 | 20251 | ATCTCTACAATGCTACGCTG | 73 | 2565 |
| 501177 | 20237 | 20256 | TCATCATCTCTACAATGCTA | 65 | 2566 |
| 501178 | 20242 | 20261 | GTCCCTCATCATCTCTACAA | 22 | 2567 |
| 501179 | 20247 | 20266 | TCCCAGTCCCTCATCATCTC | 49 | 2568 |
| 501180 | 20252 | 20271 | CAGGCTCCCAGTCCCTCATC | 16 | 2569 |
| 501181 | 20257 | 20276 | GTATTCAGGCTCCCAGTCCC | 7 | 2570 |
| 501182 | 20296 | 20315 | TGCTTGAGGTCAGGGTGTGG | 65 | 2571 |
| 501183 | 20301 | 20320 | TCACTTGCTTGAGGTCAGGG | 83 | 2572 |
| 501184 | 20306 | 20325 | CAAAATCACTTGCTTGAGGT | 72 | 2573 |
| 501185 | 20311 | 20330 | AGAGGCAAAATCACTTGCTT | 59 | 2574 |
| 501186 | 20397 | 20416 | CCACAGCACTCTCTGGGAAG | 30 | 2575 |
| 501187 | 20402 | 20421 | CCGTCCCACAGCACTCTCTG | 27 | 2576 |
| 501188 | 20407 | 20426 | CTTCACCGTCCCACAGCACT | 39 | 2577 |
| 501189 | 20442 | 20461 | GGAAAGCAATCCCCTTCTCC | 41 | 2578 |
| 501190 | 20447 | 20466 | CACCCGGAAAGCAATCCCCT | 18 | 2579 |
| 501191 | 20452 | 20471 | TTTACCACCCGGAAAGCAAT | 12 | 2580 |
| 501192 | 20457 | 20476 | GCTCTTTTACCACCCGGAAA | 55 | 2581 |
| 501193 | 20462 | 20481 | GAGCAGCTCTTTTACCACCC | 66 | 2582 |
| 501194 | 20541 | 20560 | GCAGCACTTGCTTTACACAC | 60 | 2583 |
| 501195 | 20546 | 20565 | CCCAGGCAGCACTTGCTTTA | 33 | 2584 |
| 501196 | 20551 | 20570 | CTGCTCCCAGGCAGCACTTG | 0 | 2585 |
| 501197 | 20639 | 20658 | ACAACCCTGCTACCTACAGA | 23 | 2586 |
| 501198 | 20644 | 20663 | GGAACACAACCCTGCTACCT | 37 | 2587 |
| 501199 | 20668 | 20687 | GTACAAGTTTCTCCACCTAT | 80 | 2588 |
| 501200 | 20673 | 20692 | CCTAGGTACAAGTTTCTCCA | 79 | 2589 |
| 501201 | 20714 | 20733 | GGACTGACCCCAGAGATGGG | 22 | 2590 |
| 501202 | 20719 | 20738 | ACTGAGGACTGACCCCAGAG | 0 | 2591 |
| 501203 | 20724 | 20743 | CCATCACTGAGGACTGACCC | 33 | 2592 |
| 501204 | 20729 | 20748 | CAGCCCCATCACTGAGGACT | 18 | 2593 |
| 501205 | 20771 | 20790 | GGATGCCCAAGTTAGACTGG | 24 | 2594 |
| 495670 | 20776 | 20795 | GGCCTGGATGCCCAAGTTAG | 69 | 1943 |
| 501206 | 20802 | 20821 | CCAGAGCAGCCTCAGAGGCA | 55 | 2595 |
| 501207 | 20807 | 20826 | CAAATCCAGAGCAGCCTCAG | 13 | 2596 |
| 501208 | 20812 | 20831 | ATAAGCAAATCCAGAGCAGC | 18 | 2597 |
| 501209 | 20817 | 20836 | AATCCATAAGCAAATCCAGA | 60 | 2598 |
| 501210 | 20822 | 20841 | GAGCAAATCCATAAGCAAAT | 70 | 2599 |
| 501211 | 20827 | 20846 | TAGCTGAGCAAATCCATAAG | 58 | 2600 |
| 501212 | 20832 | 20851 | CTGCATAGCTGAGCAAATCC | 79 | 2601 |
| 501213 | 20837 | 20856 | GTTTACTGCATAGCTGAGCA | 84 | 2602 |
| 501214 | 20842 | 20861 | TAGAGGTTTACTGCATAGCT | 75 | 2603 |
| 501215 | 20868 | 20887 | GATTCATCTGTGGTAAGAGG | 55 | 2604 |
| 501216 | 20873 | 20892 | TACCTGATTCATCTGTGGTA | 44 | 2605 |
| 501217 | 20878 | 20897 | CTTGGTACCTGATTCATCTG | 64 | 2606 |

TABLE 38-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501218 | 20884 | 20903 | CCAGGACTTGGTACCTGATT | 54 | 2607 |
| 501219 | 20889 | 20908 | GGGTGCCAGGACTTGGTACC | 26 | 2608 |
| 501220 | 20913 | 20932 | GCCATCCCACTGCCAGTGAC | 23 | 2609 |
| 501221 | 20937 | 20956 | ACAGCACCAATGTCACTTTA | 55 | 2610 |
| 501222 | 20950 | 20969 | TCTGCACACTCCCACAGCAC | 52 | 2611 |
| 501223 | 20955 | 20974 | CTCTCTCTGCACACTCCCAC | 59 | 2612 |
| 501224 | 20960 | 20979 | CTGCACTCTCTCTGCACACT | 76 | 2613 |
| 413433 | 32431 | 32450 | GCCTGGACAAGTCCTGCCCA | 77 | 425 |

TABLE 39

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501075 | 16484 | 16503 | GTCCTGGCCTCTACCCTGAA | 57 | 2614 |
| 501076 | 16510 | 16529 | GAAGGACTGGGATGCTAGGT | 65 | 2615 |
| 501077 | 16515 | 16534 | GGCATGAAGGACTGGGATGC | 49 | 2616 |
| 501078 | 16520 | 16539 | AGGGAGGCATGAAGGACTGG | 22 | 2617 |
| 501079 | 16525 | 16544 | GAAACAGGGAGGCATGAAGG | 21 | 2618 |
| 501080 | 16530 | 16549 | GTAGAGAAACAGGGAGGCAT | 34 | 2619 |
| 501081 | 16535 | 16554 | GAAAAGTAGAGAAACAGGGA | 0 | 2620 |
| 501082 | 16540 | 16559 | AGTTGGAAAAGTAGAGAAAC | 11 | 2621 |
| 501083 | 16546 | 16565 | GAGTCTAGTTGGAAAAGTAG | 1 | 2622 |
| 501084 | 16551 | 16570 | ACTGTGAGTCTAGTTGGAAA | 33 | 2623 |

TABLE 39-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501085 | 16556 | 16575 | CAGAGACTGTGAGTCTAGTT | 51 | 2624 |
| 501086 | 16561 | 16580 | CAGCACAGAGACTGTGAGTC | 59 | 2625 |
| 501087 | 16566 | 16585 | GACTGCAGCACAGAGACTGT | 29 | 2626 |
| 501088 | 16571 | 16590 | AGTCAGACTGCAGCACAGAG | 25 | 2627 |
| 501089 | 16576 | 16595 | AGTTTAGTCAGACTGCAGCA | 35 | 2628 |
| 501090 | 16673 | 16692 | GATGCCTTCCAGGAGGAAGG | 19 | 2629 |
| 501091 | 16678 | 16697 | TTAGGGATGCCTTCCAGGAG | 31 | 2630 |
| 501092 | 16683 | 16702 | TGTTCTTAGGGATGCCTTCC | 44 | 2631 |
| 501093 | 16808 | 16827 | AGGCTGAGTTCTGCTCCTGG | 72 | 2632 |
| 501094 | 16813 | 16832 | GCTAGAGGCTGAGTTCTGCT | 83 | 2633 |
| 501095 | 16818 | 16837 | CATCTGCTAGAGGCTGAGTT | 67 | 2634 |
| 501096 | 16823 | 16842 | TTGGGCATCTGCTAGAGGCT | 65 | 2635 |
| 501097 | 16828 | 16847 | GCTTCTTGGGCATCTGCTAG | 75 | 2636 |
| 501098 | 16833 | 16852 | CCTCTGCTTCTTGGGCATCT | 84 | 2637 |
| 501099 | 16896 | 16915 | TTTCTAAGTACCCTTTACAC | 34 | 2638 |
| 501100 | 16901 | 16920 | AGTGCTTTCTAAGTACCCTT | 86 | 2639 |
| 501101 | 16941 | 16960 | GGAGAGAGAAGGGTGGAACC | 26 | 2640 |
| 501102 | 16949 | 16968 | AGAGGAAGGGAGAGAGAAGG | 13 | 2641 |
| 501103 | 17007 | 17026 | GGGAAAGGTCTTCTCCAGCT | 89 | 2642 |
| 501104 | 17012 | 17031 | CAGGAGGGAAAGGTCTTCTC | 60 | 2643 |
| 501105 | 17017 | 17036 | GGAATCAGGAGGGAAAGGTC | 25 | 2644 |
| 501106 | 17038 | 17057 | GGGTCAAGCAGAGCTTTCTG | 66 | 2645 |
| 501107 | 17109 | 17128 | ATGAATAAACAGGGCCTAGA | 37 | 2646 |

TABLE 39-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501108 | 17114 | 17133 | CTGTGATGAATAAACAGGGC | 67 | 2647 |
| 501109 | 17138 | 17157 | TGAATGACTGAATGCTTGAG | 39 | 2648 |
| 501110 | 17143 | 17162 | TTTGCTGAATGACTGAATGC | 53 | 2649 |
| 501111 | 17207 | 17226 | TCTCATTCATCTGGGCCCTG | 72 | 2650 |
| 501112 | 17244 | 17263 | TGGGAAAAGGTATGTGTGTG | 16 | 2651 |
| 501113 | 17249 | 17268 | CATTATGGGAAAAGGTATGT | 8 | 2652 |
| 501114 | 17254 | 17273 | TTTCTCATTATGGGAAAAGG | 38 | 2653 |
| 501115 | 17259 | 17278 | AGCCCTTTCTCATTATGGGA | 47 | 2654 |
| 501116 | 17264 | 17283 | TACTCAGCCCTTTCTCATTA | 43 | 2655 |
| 501117 | 17269 | 17288 | CCCTGTACTCAGCCCTTTCT | 65 | 2656 |
| 501118 | 17274 | 17293 | CTCACCCCTGTACTCAGCCC | 73 | 2657 |
| 501119 | 17279 | 17298 | CCCATCTCACCCCTGTACTC | 66 | 2658 |
| 501120 | 17284 | 17303 | CCTGTCCCATCTCACCCCTG | 13 | 2659 |
| 501121 | 17289 | 17308 | CCCTGCCTGTCCCATCTCAC | 36 | 2660 |
| 501122 | 17328 | 17347 | AGTCTTCCTTCTCCTCCACC | 75 | 2661 |
| 501123 | 17333 | 17352 | TGGAAAGTCTTCCTTCTCCT | 72 | 2662 |
| 501124 | 17338 | 17357 | TTCTCTGGAAAGTCTTCCTT | 66 | 2663 |
| 501125 | 17420 | 17439 | TTGGTCAGTCTTTTAGCACA | 64 | 2664 |
| 501126 | 17425 | 17444 | CTAGTTTGGTCAGTCTTTTA | 68 | 2665 |
| 501127 | 17450 | 17469 | AGGTAGAGTTCTATTGCTTC | 81 | 2666 |
| 501128 | 17530 | 17549 | GTCTCCACTTGGTGCCTCAC | 72 | 2667 |
| 501129 | 17535 | 17554 | AAGCTGTCTCCACTTGGTGC | 61 | 2668 |
| 501130 | 17540 | 17559 | ACAGGAAGCTGTCTCCACTT | 69 | 2669 |
| 501131 | 17545 | 17564 | CTCACACAGGAAGCTGTCTC | 44 | 2670 |
| 501132 | 17614 | 17633 | AGCTGCCATCTCTGGAGGGT | 15 | 2671 |
| 501133 | 17619 | 17638 | GGCAAAGCTGCCATCTCTGG | 52 | 2672 |
| 501134 | 17624 | 17643 | GTCATGGCAAAGCTGCCATC | 7 | 2673 |
| 501135 | 17664 | 17683 | CCTTTCAGCGGGAGTCCACA | 44 | 2674 |
| 501136 | 17687 | 17706 | TTCCAGGCTCCTCCAGGCAG | 36 | 2675 |
| 501137 | 17692 | 17711 | CTCTCTTCCAGGCTCCTCCA | 44 | 2676 |
| 501138 | 17720 | 17739 | ATGCCACTTCATCAAGGCTG | 33 | 2677 |
| 501139 | 17725 | 17744 | AAGAGATGCCACTTCATCAA | 36 | 2678 |
| 501140 | 17730 | 17749 | TGCCAAAGAGATGCCACTTC | 63 | 2679 |
| 501141 | 17735 | 17754 | CCAAGTGCCAAAGAGATGCC | 39 | 2680 |
| 501142 | 17740 | 17759 | TCAGGCAAGTGCCAAAGAG | 30 | 2681 |
| 501143 | 17745 | 17764 | GGAAGTCAGGCCAAGTGCCA | 38 | 2682 |
| 501144 | 17750 | 17769 | GTCTAGGAAGTCAGGCCAAG | 46 | 2683 |
| 501145 | 17755 | 17774 | GGGAGGTCTAGGAAGTCAGG | 19 | 2684 |
| 501146 | 17760 | 17779 | CCCCAGGGAGGTCTAGGAAG | 32 | 2685 |
| 501147 | 17765 | 17784 | TCCAGCCCCAGGGAGGTCTA | 30 | 2686 |
| 501148 | 17770 | 17789 | GCTCTTCCAGCCCCAGGGAG | 36 | 2687 |
| 501149 | 17804 | 17823 | AGAGTGAGGGTCAGTACATA | 15 | 2688 |
| 501150 | 17809 | 17828 | GTAGCAGAGTGAGGGTCAGT | 28 | 2689 |
| 501151 | 17933 | 17952 | TAGGTGAGTGAGAAAGTCAC | 16 | 2690 |
| 413433 | 32431 | 32450 | GCCTGGACAAGTCCTGCCCA | 78 | 425 |

TABLE 40

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 500994 | 15257 | 15276 | CATCTGCACCATAATCTGCA | 72 | 2691 |
| 500995 | 15292 | 15311 | TTTACCCAAAAGGTTCACAG | 64 | 2692 |
| 500996 | 15297 | 15316 | ATTGATTTACCCAAAAGGTT | 32 | 2693 |
| 500997 | 15318 | 15337 | GAGTTTGTGTTTCCCATTTC | 69 | 2694 |
| 500998 | 15323 | 15342 | AAAAGGAGTTTGTGTTTCCC | 81 | 2695 |
| 500999 | 15328 | 15347 | ATAAGAAAAGGAGTTTGTGT | 30 | 2696 |
| 501000 | 15333 | 15352 | CTCTAATAAGAAAGGAGTT | 33 | 2697 |
| 501001 | 15338 | 15357 | TTCTGCTCTAATAAGAAAAG | 12 | 2698 |
| 501002 | 15343 | 15362 | GCTAATTCTGCTCTAATAAG | 28 | 2699 |
| 501003 | 15348 | 15367 | GAATGGCTAATTCTGCTCTA | 48 | 2700 |
| 501004 | 15353 | 15372 | GCTTAGAATGGCTAATTCTG | 69 | 2701 |
| 501005 | 15358 | 15377 | GCAGGGCTTAGAATGGCTAA | 59 | 2702 |
| 501006 | 15363 | 15382 | CAGAGGCAGGGCTTAGAATG | 56 | 2703 |
| 501007 | 15368 | 15387 | GGAAGCAGAGGCAGGGCTTA | 68 | 2704 |
| 501008 | 15373 | 15392 | ACATGGAAGCAGAGGCAGG | 66 | 2705 |
| 501009 | 15378 | 15397 | AGGTCACATGGAAGCAGAG | 57 | 2706 |
| 501010 | 15431 | 15450 | TCCTCACTGTGCAGATGAGA | 30 | 2707 |
| 501011 | 15436 | 15455 | AGTCCTCCTCACTGTGCAGA | 48 | 2708 |
| 501012 | 15441 | 15460 | CAACCAGTCCTCCTCACTGT | 33 | 2709 |
| 501013 | 15446 | 15465 | CATCTCAACCAGTCCTCCTC | 52 | 2710 |
| 501014 | 15504 | 15523 | TTAGGGACAAGAATGGAATC | 23 | 2711 |
| 501015 | 15509 | 15528 | AGCAGTTAGGGACAAGAATG | 10 | 2712 |
| 501016 | 15514 | 15533 | CCCACAGCAGTTAGGGACAA | 63 | 2713 |
| 501017 | 15568 | 15587 | TTTTCACAAGGAGAAGCTGA | 47 | 2714 |
| 501018 | 15573 | 15592 | CACCATTTTCACAAGGAGAA | 76 | 2715 |
| 501019 | 15578 | 15597 | GAGTGCACCATTTTCACAAG | 71 | 2716 |
| 501020 | 15646 | 15665 | ATCACAATATATGGGCAAGC | 82 | 2717 |
| 501021 | 15651 | 15670 | TCCCCATCACAATATATGGG | 39 | 2718 |
| 501022 | 15671 | 15690 | CAAGGAATCTCCAAAATACG | 37 | 2719 |
| 501023 | 15703 | 15722 | ATGGCAACACTACTAGCTTG | 27 | 2720 |
| 501024 | 15708 | 15727 | CTGCCATGGCAACACTACTA | 56 | 2721 |
| 501025 | 15729 | 15748 | TAGCTACTGCAGTGGAAGGG | 71 | 2722 |
| 501026 | 15734 | 15753 | AAAAGTAGCTACTGCAGTGG | 69 | 2723 |
| 501027 | 15739 | 15758 | ATTCAAAAGTAGCTACTGC | 59 | 2724 |
| 501028 | 15744 | 15763 | AGCACATTCAAAAGTAGCT | 59 | 2725 |
| 501029 | 15804 | 15823 | CTGGACATGATTGCTGAGGA | 63 | 2726 |

TABLE 40-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501030 | 15809 | 15828 | GGACCCTGGACATGATTGCT | 74 | 2727 |
| 501031 | 15814 | 15833 | ATCCAGGACCCTGGACATGA | 69 | 2728 |
| 501032 | 15839 | 15858 | TTCCTGATACCGAACATGGA | 22 | 2729 |
| 501033 | 15876 | 15895 | GGTAAGGCCAAGGAAGTGAG | 78 | 2730 |
| 501034 | 15881 | 15900 | CAAGAGGTAAGGCCAAGGAA | 80 | 2731 |
| 501035 | 15933 | 15952 | ACCTGGGTTTTGTGTATTC | 82 | 2732 |
| 501036 | 15938 | 15957 | CATACACCTGGGTTTTGTG | 57 | 2733 |
| 501037 | 15943 | 15962 | TACTCCATACACCTGGGTTT | 69 | 2734 |
| 501038 | 15991 | 16010 | TTATCCACAGAAGATCTCCC | 75 | 2735 |
| 501039 | 16046 | 16065 | CTGAGTGCTGCTAACTTGGG | 70 | 2736 |
| 501040 | 16051 | 16070 | GAAATCTGAGTGCTGCTAAC | 78 | 2737 |
| 501041 | 16082 | 16101 | CACTAAATTAGGAAGCTGGG | 79 | 2738 |
| 501043 | 16105 | 16124 | CCCTCTCTAGGTTTCCCCAT | 63 | 2739 |
| 501045 | 16110 | 16129 | TCCTCCCCTCTCTAGGTTTC | 34 | 2740 |
| 501047 | 16115 | 16134 | CCTCTTCCTCCCCTCTCTAG | 24 | 2741 |
| 501049 | 16120 | 16139 | CTAAGCCTCTTCCTCCCCTC | 33 | 2742 |
| 501050 | 16171 | 16190 | GCCTGCTGCAGGGAGCCAGG | 4 | 2743 |
| 501051 | 16208 | 16227 | GGCCATCAGGACCCTGCAGG | 30 | 2744 |
| 501052 | 16213 | 16232 | AAGTGGGCCATCAGGACCCT | 5 | 2745 |
| 501053 | 16227 | 16246 | GTGTGCCAGGTGGGAAGTGG | 0 | 2746 |
| 501054 | 16232 | 16251 | GCTAGGTGTGCCAGGTGGGA | 38 | 2747 |
| 501055 | 16237 | 16256 | GCTATGCTAGGTGTGCCAGG | 62 | 2748 |
| 501056 | 16242 | 16261 | ACACAGCTATGCTAGGTGTG | 22 | 2749 |
| 501057 | 16247 | 16266 | CCAGCACACAGCTATGCTAG | 25 | 2750 |
| 501058 | 16252 | 16271 | GAGAGCCAGCACACAGCTAT | 44 | 2751 |
| 501059 | 16257 | 16276 | TACTGGAGAGCCAGCACACA | 57 | 2752 |
| 501060 | 16262 | 16281 | CAAACTACTGGAGAGCCAGC | 59 | 2753 |
| 501061 | 16288 | 16307 | TGGGACATCTGGCCCAAAGG | 67 | 2754 |
| 501062 | 16293 | 16312 | CCCACTGGGACATCTGGCCC | 77 | 2755 |
| 501063 | 16305 | 16324 | CTTAAAGCAGGGCCCACTGG | 49 | 2756 |
| 501064 | 16310 | 16329 | GTATCCTTAAAGCAGGGCCC | 80 | 2757 |
| 501065 | 16364 | 16383 | TTCTTTTCTGAAAAGATTAA | 16 | 2758 |
| 501066 | 16369 | 16388 | GTGAGTTCTTTTCTGAAAAG | 48 | 2759 |
| 501067 | 16428 | 16447 | ACTGGTGCCTAAGAGCCCTA | 76 | 2760 |
| 501068 | 16433 | 16452 | CCTCCACTGGTGCCTAAGAG | 66 | 2761 |
| 501069 | 16438 | 16457 | CACTCCCTCCACTGGTGCCT | 71 | 2762 |

TABLE 40-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
| --- | --- | --- | --- | --- | --- |
| 501070 | 16459 | 16478 | AGAAGACAGCCAGTCAGAGC | 67 | 2763 |
| 501071 | 16464 | 16483 | GGCAGAGAAGACAGCCAGTC | 53 | 2764 |
| 501072 | 16469 | 16488 | CTGAAGGCAGAGAAGACAGC | 11 | 2765 |
| 501073 | 16474 | 16493 | CTACCCTGAAGGCAGAGAAG | 0 | 2766 |
| 501074 | 16479 | 16498 | GGCCTCTACCCTGAAGGCAG | 1 | 2767 |
| 413433 | 32431 | 32450 | GCCTGGACAAGTCCTGCCCA | 79 | 425 |

TABLE 41

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
| --- | --- | --- | --- | --- | --- |
| 500917 | 12407 | 12426 | TGTCAGAAAGGACTCCTCTG | 37 | 2768 |
| 500918 | 12412 | 12431 | ACAGCTGTCAGAAAGGACTC | 47 | 2769 |
| 500919 | 12417 | 12436 | CCTCAACAGCTGTCAGAAAG | 22 | 2770 |
| 500920 | 12439 | 12458 | ACCCACCCCAGCCTGTTGCA | 56 | 2771 |
| 500921 | 12474 | 12493 | CAAGCAGATCCACAGTGATG | 16 | 2772 |
| 500922 | 12479 | 12498 | AGTTTCAAGCAGATCCACAG | 37 | 2773 |
| 500923 | 12500 | 12519 | CCCCCAACAATCTAGCCACT | 41 | 2774 |
| 500924 | 12505 | 12524 | AGTTACCCCAACAATCTAG | 16 | 2775 |
| 500925 | 12510 | 12529 | TTCCCAGTTACCCCCAACAA | 16 | 2776 |
| 500926 | 12515 | 12534 | CTCAGTTCCCAGTTACCCCC | 44 | 2777 |
| 500927 | 12520 | 12539 | CAACCCTCAGTTCCCAGTTA | 26 | 2778 |
| 500928 | 12549 | 12568 | TCTGACTTAGGACTAGGTTA | 70 | 2779 |
| 500929 | 12554 | 12573 | CTCATTCTGACTTAGGACTA | 64 | 2780 |
| 500930 | 12559 | 12578 | ATGTTCTCATTCTGACTTAG | 44 | 2781 |
| 500931 | 12564 | 12583 | GAGTAATGTTCTCATTCTGA | 44 | 2782 |
| 500932 | 12569 | 12588 | CATGAGAGTAATGTTCTCAT | 44 | 2783 |
| 500933 | 12618 | 12637 | GGAAGTGATGTAGGTGAGGG | 23 | 2784 |
| 500934 | 12671 | 12690 | AGCCTAGATGAGCCCTTGGT | 65 | 2785 |
| 500935 | 12676 | 12695 | TTCTCAGCCTAGATGAGCCC | 69 | 2786 |
| 500936 | 12681 | 12700 | CTCCTTTCTCAGCCTAGATG | 52 | 2787 |
| 500937 | 12686 | 12705 | TGGCCCTCCTTTCTCAGCCT | 54 | 2788 |
| 500938 | 12691 | 12710 | ACTCTTGGCCCTCCTTTCTC | 26 | 2789 |
| 500939 | 12696 | 12715 | ACATTACTCTTGGCCCTCCT | 59 | 2790 |
| 500940 | 12779 | 12798 | TTGCTGTTGAATTTGAGGGC | 53 | 2791 |

TABLE 41-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 500941 | 12784 | 12803 | AGTACTTGCTGTTGAATTTG | 45 | 2792 |
| 500942 | 12806 | 12825 | CAGCACTAATTTTTACAACT | 78 | 2793 |
| 500943 | 12834 | 12853 | ATCTGTAACATGAGGGTTGG | 36 | 2794 |
| 500944 | 12839 | 12858 | ATCCCATCTGTAACATGAGG | 69 | 2795 |
| 500945 | 12844 | 12863 | CAGTGATCCCATCTGTAACA | 67 | 2796 |
| 500946 | 12890 | 12909 | GCCTGGCTTTGATAACCCTG | 63 | 2797 |
| 500947 | 12895 | 12914 | TTCTAGCCTGGCTTTGATAA | 20 | 2798 |
| 500948 | 12917 | 12936 | CAGACTGGGAGATGGATCTG | 31 | 2799 |
| 500949 | 12922 | 12941 | GGCCACAGACTGGGAGATGG | 47 | 2800 |
| 500950 | 12927 | 12946 | AGTCAGGCCACAGACTGGGA | 72 | 2801 |
| 500951 | 12932 | 12951 | TAAGGAGTCAGGCCACAGAC | 47 | 2802 |
| 500952 | 12937 | 12956 | TGGCTTAAGGAGTCAGGCCA | 43 | 2803 |
| 500953 | 12942 | 12961 | TCTCTTGGCTTAAGGAGTCA | 71 | 2804 |
| 500954 | 12977 | 12996 | GCCCTGCACTCAGCCCTTCA | 19 | 2805 |
| 500955 | 12982 | 13001 | ACAGAGCCCTGCACTCAGCC | 54 | 2806 |
| 500956 | 13026 | 13045 | GACAACCTTCACTCATTCAG | 35 | 2807 |
| 500957 | 13098 | 13117 | ATCCACTAGGGCAGGCTTGG | 69 | 2808 |
| 500958 | 13202 | 13221 | GGCCAGGAGGAAGAGTTTGG | 39 | 2809 |
| 500959 | 13207 | 13226 | TCATAGGCCAGGAGGAAGAG | 20 | 2810 |
| 500960 | 13212 | 13231 | TTACTTCATAGGCCAGGAGG | 63 | 2811 |
| 500961 | 13239 | 13258 | TGGCAGTGGAGGCTGTTCAC | 63 | 2812 |
| 500962 | 13306 | 13325 | GCAGGAACAGGAAGACCACC | 0 | 2813 |
| 500963 | 13311 | 13330 | ATGCTGCAGGAACAGGAAGA | 51 | 2814 |
| 500964 | 13316 | 13335 | GAGTAATGCTGCAGGAACAG | 35 | 2815 |
| 500965 | 13321 | 13340 | ATTGGGAGTAATGCTGCAGG | 55 | 2816 |
| 500966 | 13441 | 13460 | TGGCTCTCTAGATAGGGTGG | 75 | 2817 |
| 500967 | 13485 | 13504 | TAAAAGAAGATGTGGTGATT | 0 | 2818 |
| 500968 | 13490 | 13509 | AAAAATAAAGAAGATGTGG | 0 | 2819 |
| 500969 | 13495 | 13514 | GCTATAAAAATAAAGAAGA | 0 | 2820 |
| 500970 | 13500 | 13519 | TAAAGGCTATAAAAATAAAA | 0 | 2821 |
| 500971 | 13542 | 13561 | ATTGCTTAAACAGATAAGCA | 6 | 2822 |
| 500972 | 13547 | 13566 | AGACAATTGCTTAAACAGAT | 32 | 2823 |
| 500973 | 13916 | 13935 | GTTCCTGTTTCCAAGGGACT | 59 | 2824 |
| 500974 | 13921 | 13940 | ACAAGGTTCCTGTTTCCAAG | 69 | 2825 |
| 500975 | 13926 | 13945 | GACAGACAAGGTTCCTGTTT | 72 | 2826 |
| 500976 | 13931 | 13950 | AGAAAGACAGACAAGGTTCC | 51 | 2827 |

TABLE 41-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 500977 | 13936 | 13955 | CACTGAGAAAGACAGACAAG | 0 | 2828 |
| 500978 | 13941 | 13960 | CACAGCACTGAGAAAGACAG | 36 | 2829 |
| 500979 | 13962 | 13981 | GCCAGGCACTGTGCTAGATG | 63 | 2830 |
| 500980 | 13967 | 13986 | CCAGTGCCAGGCACTGTGCT | 37 | 2831 |
| 500981 | 13972 | 13991 | TATTACCAGTGCCAGGCACT | 13 | 2832 |
| 500982 | 13977 | 13996 | GTACCTATTACCAGTGCCAG | 64 | 2833 |
| 500983 | 13982 | 14001 | ACTAAGTACCTATTACCAGT | 7 | 2834 |
| 500984 | 14054 | 14073 | AGCTAAAAGCAGGGCTTCCT | 0 | 2835 |
| 500985 | 14177 | 14196 | GCTCCTTGCCAGACTGTGGG | 60 | 2836 |
| 500986 | 14182 | 14201 | AGCCAGCTCCTTGCCAGACT | 75 | 2837 |
| 500987 | 14187 | 14206 | CTTGGAGCCAGCTCCTTGCC | 54 | 2838 |
| 500988 | 14192 | 14211 | TCAGCCTTGGAGCCAGCTCC | 35 | 2839 |
| 500989 | 14197 | 14216 | GCCACTCAGCCTTGGAGCCA | 76 | 2840 |
| 500990 | 14239 | 14258 | GGAAGCAGTAAGGGTGACCA | 73 | 2841 |
| 500991 | 14246 | 14265 | AGCCCTGGGAAGCAGTAAGG | 11 | 2842 |
| 500992 | 14251 | 14270 | TAATAAGCCCTGGGAAGCAG | 0 | 2843 |
| 500993 | 14327 | 14346 | ATCCCCAGAGAGGAAGTGAA | 0 | 2844 |
| 413433 | 32431 | 32450 | GCCTGGACAAGTCCTGCCCA | 80 | 425 |

TABLE 42

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 500840 | 11204 | 11223 | ATAACCACAGCGATAATCAC | 45 | 2845 |
| 500841 | 11209 | 11228 | GGCAGATAACCACAGCGATA | 79 | 2846 |
| 500842 | 11228 | 11247 | CAGCACCCACACCAAGAGGG | 38 | 2847 |
| 500843 | 11318 | 11337 | TCAGAGGCTACTGGCTGGAT | 69 | 2848 |
| 500844 | 11323 | 11342 | GGCTGTCAGAGGCTACTGGC | 75 | 2849 |
| 500845 | 11346 | 11365 | AAAAGGACTCAAGTGAGAGA | 24 | 2850 |
| 500846 | 11351 | 11370 | AACAGAAAGGACTCAAGTG | 4 | 2851 |
| 500847 | 11356 | 11375 | CAGGGAACAGAAAAGGACTC | 30 | 2852 |
| 500848 | 11361 | 11380 | GGACACAGGGAACAGAAAAG | 2 | 2853 |
| 500849 | 11366 | 11385 | TCAAAGGACACAGGGAACAG | 24 | 2854 |
| 500850 | 11371 | 11390 | GGACATCAAAGGACACAGGG | 3 | 2855 |

TABLE 42-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 500851 | 11376 | 11395 | CCTAAGGACATCAAAGGACA | 3 | 2856 |
| 500852 | 11413 | 11432 | GCATGAACAAGGGCAAGTCC | 74 | 2857 |
| 500853 | 11457 | 11476 | AGAACATCCCTATCCCACTG | 37 | 2858 |
| 500854 | 11462 | 11481 | CACAGAGAACATCCCTATCC | 59 | 2859 |
| 500855 | 11509 | 11528 | CCTGTGGATGGCAGAGCCGA | 32 | 2860 |
| 500856 | 11514 | 11533 | CCCAGCCTGTGGATGGCAGA | 21 | 2861 |
| 500857 | 11519 | 11538 | CAGCTCCCAGCCTGTGGATG | 0 | 2862 |
| 500858 | 11553 | 11572 | CATGACAGCCAGGGTCACTG | 57 | 2863 |
| 500859 | 11559 | 11578 | CAAAAACATGACAGCCAGGG | 80 | 2864 |
| 500860 | 11564 | 11583 | TAAGTCAAAACATGACAGC | 24 | 2865 |
| 500861 | 11569 | 11588 | AACTCTAAGTCAAAAACATG | 0 | 2866 |
| 500862 | 11574 | 11593 | GAACAAACTCTAAGTCAAAA | 5 | 2867 |
| 500863 | 11579 | 11598 | CTAAGGAACAAACTCTAAGT | 19 | 2868 |
| 500864 | 11584 | 11603 | TTCTCCTAAGGAACAAACTC | 31 | 2869 |
| 500865 | 11589 | 11608 | ACAAGTTCTCCTAAGGAACA | 28 | 2870 |
| 500866 | 11594 | 11613 | AGAGTACAAGTTCTCCTAAG | 66 | 2871 |
| 500867 | 11599 | 11618 | TCGCTAGAGTACAAGTTCTC | 81 | 2872 |
| 500868 | 11635 | 11654 | TCCTGACATGATATTAAGTG | 50 | 2873 |
| 500869 | 11640 | 11659 | AATGTTCCTGACATGATATT | 5 | 2874 |
| 500870 | 11707 | 11726 | ATGATGTAAATCCTTGCACC | 68 | 2875 |
| 500871 | 11712 | 11731 | ATTCCATGATGTAAATCCTT | 63 | 2876 |
| 500872 | 11717 | 11736 | CCTACATTCCATGATGTAAA | 45 | 2877 |
| 500873 | 11722 | 11741 | CCCTTCCTACATTCCATGAT | 56 | 2878 |
| 500874 | 11727 | 11746 | ACCAGCCCTTCCTACATTCC | 54 | 2879 |
| 500875 | 11732 | 11751 | TTCATACCAGCCCTTCCTAC | 22 | 2880 |
| 500876 | 11755 | 11774 | AAGCTGAACTGACTGGTTTG | 41 | 2881 |
| 500877 | 11760 | 11779 | CCAGAAAGCTGAACTGACTG | 0 | 2882 |
| 500878 | 11765 | 11784 | AGATCCCAGAAAGCTGAACT | 29 | 2883 |
| 500879 | 11770 | 11789 | AAAGTAGATCCCAGAAAGCT | 15 | 2884 |
| 500880 | 11775 | 11794 | TCACCAAAGTAGATCCCAGA | 58 | 2885 |
| 500881 | 11780 | 11799 | ATCTTTCACCAAAGTAGATC | 33 | 2886 |
| 500882 | 11785 | 11804 | ACCCAATCTTTCACCAAAGT | 18 | 2887 |
| 500883 | 11790 | 11809 | ACTCCACCCAATCTTTCACC | 49 | 2888 |
| 500884 | 11795 | 11814 | CCCCTACTCCACCCAATCTT | 14 | 2889 |
| 500885 | 11800 | 11819 | GCCCTCCCCTACTCCACCCA | 32 | 2890 |
| 500886 | 11805 | 11824 | TCAGTGCCCTCCCCTACTCC | 26 | 2891 |

TABLE 42-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
| --- | --- | --- | --- | --- | --- |
| 500887 | 11827 | 11846 | TGCCCAGATAACAAAATGTG | 29 | 2892 |
| 500888 | 11832 | 11851 | GGAGATGCCCAGATAACAAA | 56 | 2893 |
| 500889 | 11857 | 11876 | CAAGGATCTAGAAGGCAGGT | 59 | 2894 |
| 500890 | 11862 | 11881 | AGGACCAAGGATCTAGAAGG | 28 | 2895 |
| 500891 | 11867 | 11886 | CTTCAAGGACCAAGGATCTA | 30 | 2896 |
| 500892 | 11872 | 11891 | AGTATCTTCAAGGACCAAGG | 72 | 2897 |
| 500893 | 11893 | 11912 | AGGCAAACTAGGCCACTGGG | 20 | 2898 |
| 500894 | 11898 | 11917 | CACAGAGGCAAACTAGGCCA | 4 | 2899 |
| 500895 | 11920 | 11939 | CTCACAACAGTGGGACCTTA | 69 | 2900 |
| 500896 | 11925 | 11944 | ACCAGCTCACAACAGTGGGA | 43 | 2901 |
| 500897 | 11930 | 11949 | TGTTCACCAGCTCACAACAG | 8 | 2902 |
| 500898 | 11964 | 11983 | CATGGTCTCTACTTGAATAC | 14 | 2903 |
| 500899 | 11969 | 11988 | GAATCCATGGTCTCTACTTG | 18 | 2904 |
| 500900 | 11974 | 11993 | TCACAGAATCCATGGTCTCT | 42 | 2905 |
| 500901 | 11979 | 11998 | TCCCTTCACAGAATCCATGG | 36 | 2906 |
| 500902 | 11984 | 12003 | GGACTTCCCTTCACAGAATC | 23 | 2907 |
| 500903 | 11989 | 12008 | TCACAGGACTTCCCTTCACA | 47 | 2908 |
| 500904 | 12070 | 12089 | ACCTACCCATACTCCCACAG | 31 | 2909 |
| 500905 | 12075 | 12094 | CACCCACCTACCCATACTCC | 15 | 2910 |
| 500906 | 12080 | 12099 | GCATGCACCCACCTACCCAT | 41 | 2911 |
| 500907 | 12085 | 12104 | CCCCAGCATGCACCCACCTA | 14 | 2912 |
| 500908 | 12090 | 12109 | GCTTCCCCCAGCATGCACCC | 36 | 2913 |
| 500909 | 12138 | 12157 | GGCACAGGACAGCCCTCCAA | 54 | 2914 |
| 500910 | 12169 | 12188 | TGTCCTGATGAACTCTGCAA | 54 | 2915 |
| 500911 | 12242 | 12261 | TGTCAGAGGGCTCTTCTGAA | 0 | 2916 |
| 500912 | 12247 | 12266 | GCAGGTGTCAGAGGGCTCTT | 60 | 2917 |
| 500913 | 12285 | 12304 | TCTCATGCTAGGTCCTGTGC | 80 | 2918 |
| 500914 | 12392 | 12411 | CTCTGCTACATCAAAACTTG | 25 | 2919 |
| 500915 | 12397 | 12416 | GACTCCTCTGCTACATCAAA | 38 | 2920 |
| 500916 | 12402 | 12421 | GAAAGGACTCCTCTGCTACA | 23 | 2921 |
| 413433 | 32431 | 32450 | GCCTGGACAAGTCCTGCCCA | 75 | 425 |

TABLE 43

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501824 | 27442 | 27461 | TTGGGTCTGATCAATTATTA | 14 | 2922 |
| 501825 | 27447 | 27466 | TGTGGTTGGGTCTGATCAAT | 50 | 2923 |
| 501826 | 27458 | 27477 | GGTTTCTGGGCTGTGGTTGG | 20 | 2924 |
| 501827 | 27469 | 27488 | GATGCTGGGCCGGTTTCTGG | 40 | 2925 |
| 501828 | 27551 | 27570 | CAGGAGATCTGCCTGTCCAA | 48 | 2926 |
| 501829 | 27556 | 27575 | TAGCTCAGGAGATCTGCCTG | 32 | 2927 |
| 501830 | 27561 | 27580 | AGCAGTAGCTCAGGAGATCT | 50 | 2928 |
| 501831 | 27566 | 27585 | TAATTAGCAGTAGCTCAGGA | 65 | 2929 |
| 501832 | 27613 | 27632 | AGGTTTGAGAGGCAGAGGGA | 6 | 2930 |
| 501833 | 27618 | 27637 | CCAGCAGGTTTGAGAGGCAG | 29 | 2931 |
| 501834 | 27623 | 27642 | TTCTGCCAGCAGGTTTGAGA | 40 | 2932 |
| 501835 | 27628 | 27647 | TGAGCTTCTGCCAGCAGGTT | 64 | 2933 |
| 501836 | 27633 | 27652 | CCAGGTGAGCTTCTGCCAGC | 43 | 2934 |
| 501837 | 27638 | 27657 | GCTTGCCAGGTGAGCTTCTG | 61 | 2935 |
| 501838 | 27643 | 27662 | TCTTTGCTTGCCAGGTGAGC | 67 | 2936 |
| 501839 | 27673 | 27692 | TCCAGGGAGAGACCAACAGG | 7 | 2937 |
| 501840 | 27678 | 27697 | TCTGGTCCAGGGAGAGACCA | 0 | 2938 |
| 501841 | 27683 | 27702 | AAATCTCTGGTCCAGGGAGA | 26 | 2939 |
| 501842 | 27688 | 27707 | GTGAAAAATCTCTGGTCCAG | 12 | 2940 |
| 501843 | 27693 | 27712 | AAGTGGTGAAAAATCTCTGG | 5 | 2941 |
| 501844 | 27698 | 27717 | GCACAAAGTGGTGAAAAATC | 41 | 2942 |
| 501845 | 27703 | 27722 | CCATGGCACAAAGTGGTGAA | 41 | 2943 |
| 501846 | 27708 | 27727 | GGGTTCCATGGCACAAAGTG | 1 | 2944 |
| 501847 | 27761 | 27780 | ATTAAATACTCTAAAACACT | 0 | 2945 |
| 501848 | 27766 | 27785 | CTTGTATTAAATACTCTAAA | 5 | 2946 |
| 501849 | 27771 | 27790 | TGCACCTTGTATTAAATACT | 77 | 2947 |
| 501850 | 27776 | 27795 | TCCAATGCACCTTGTATTAA | 79 | 2948 |
| 501851 | 27781 | 27800 | TGAAATCCAATGCACCTTGT | 69 | 2949 |
| 501852 | 27786 | 27805 | TCCTTTGAAATCCAATGCAC | 76 | 2950 |
| 501853 | 27791 | 27810 | TAGTTTCCTTTGAAATCCAA | 64 | 2951 |
| 501854 | 27849 | 27868 | TGTTACTACATGTCTAATCA | 32 | 2952 |
| 501855 | 27854 | 27873 | GCACCTGTTACTACATGTCT | 87 | 2953 |
| 501856 | 27859 | 27878 | AAAAGGCACCTGTTACTACA | 57 | 2954 |
| 501857 | 27864 | 27883 | TAATAAAAGGCACCTGTTA | 32 | 2955 |
| 501858 | 27992 | 28011 | AAATAACAAGGTATTTTCA | 1 | 2956 |
| 501859 | 27997 | 28016 | CAAATAAATAACAAGGTAT | 14 | 2957 |

TABLE 43-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501860 | 28002 | 28021 | TGACACAAATAAATAACAAA | 18 | 2958 |
| 501861 | 28026 | 28045 | TCACAGAATTATCAGCAGTA | 92 | 2959 |
| 501862 | 28031 | 28050 | ATAAATCACAGAATTATCAG | 0 | 2960 |
| 501863 | 28054 | 28073 | CATTTCCTTCACTTACCAAT | 41 | 2961 |
| 501864 | 28078 | 28097 | CACTTATCTCTTATGGAAAT | 47 | 2962 |
| 501865 | 28083 | 28102 | ATTTTCACTTATCTCTTATG | 35 | 2963 |
| 501866 | 28088 | 28107 | TCTAAATTTTCACTTATCTC | 48 | 2964 |
| 501867 | 28093 | 28112 | TGACATCTAAATTTTCACTT | 63 | 2965 |
| 501868 | 28098 | 28117 | ACAAATGACATCTAAATTTT | 0 | 2966 |
| 501869 | 28103 | 28122 | GGGAAACAAATGACATCTAA | 58 | 2967 |
| 501870 | 28127 | 28146 | ACACAATATCCATGGACTTG | 59 | 2968 |
| 501871 | 28132 | 28151 | CTGACACACAATATCCATGG | 75 | 2969 |
| 501872 | 28185 | 28204 | ATTTCCTTACAGGGTATTGG | 53 | 2970 |
| 501873 | 28210 | 28229 | GGCCAAGCCCCATTCCTAAG | 7 | 2971 |
| 501874 | 28215 | 28234 | TTGCTGGCCAAGCCCCATTC | 0 | 2972 |
| 501875 | 28220 | 28239 | GCCACTTGCTGGCCAAGCCC | 22 | 2973 |
| 501876 | 28269 | 28288 | GGTGAAGAGCATGGACTCTG | 41 | 2974 |
| 501877 | 28293 | 28312 | GCAGGGAAGGCAGCAGTGTG | 39 | 2975 |
| 501878 | 28298 | 28317 | CAATGGCAGGGAAGGCAGCA | 55 | 2976 |
| 501879 | 28358 | 28377 | ACTTGTGATACAAAATTCTG | 41 | 2977 |
| 501880 | 28363 | 28382 | AAGACACTTGTGATACAAAA | 66 | 2978 |
| 501881 | 28454 | 28473 | AAGCTTAGAAGGCCCTGCTT | 44 | 2979 |
| 501882 | 28459 | 28478 | ATGAGAAGCTTAGAAGGCCC | 41 | 2980 |
| 501883 | 28464 | 28483 | AGCTCATGAGAAGCTTAGAA | 74 | 2981 |
| 501884 | 28469 | 28488 | TGCTGAGCTCATGAGAAGCT | 82 | 2982 |
| 501885 | 28474 | 28493 | ACTGTTGCTGAGCTCATGAG | 37 | 2983 |
| 501886 | 28479 | 28498 | AAACCACTGTTGCTGAGCTC | 78 | 2984 |
| 501887 | 28484 | 28503 | AGTAAAACCACTGTTGCTG | 60 | 2985 |
| 501888 | 28489 | 28508 | GCTGCAGTAAAACCACTGT | 66 | 2986 |
| 501889 | 28515 | 28534 | CTGGTTCCATGCTCTTAGGT | 63 | 2987 |
| 501890 | 28520 | 28539 | AGGCTCTGGTTCCATGCTCT | 71 | 2988 |
| 501891 | 28525 | 28544 | ACAACAGGCTCTGGTTCCAT | 38 | 2989 |
| 501892 | 28530 | 28549 | TCTGAACAACAGGCTCTGGT | 19 | 2990 |
| 501893 | 28535 | 28554 | TGTCCTCTGAACAACAGGCT | 52 | 2991 |
| 501894 | 28540 | 28559 | ATCCTTGTCCTCTGAACAAC | 36 | 2992 |
| 501895 | 28545 | 28564 | GCCTAATCCTTGTCCTCTGA | 54 | 2993 |

TABLE 43-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
| --- | --- | --- | --- | --- | --- |
| 501896 | 28550 | 28569 | TCAGAGCCTAATCCTTGTCC | 53 | 2994 |
| 501897 | 28555 | 28574 | CTTTCTCAGAGCCTAATCCT | 39 | 2995 |
| 501898 | 28560 | 28579 | CCTTCCTTTCTCAGAGCCTA | 50 | 2996 |
| 501899 | 28565 | 28584 | AATGACCTTCCTTTCTCAGA | 19 | 2997 |
| 501900 | 28570 | 28589 | CACCAAATGACCTTCCTTTC | 66 | 2998 |
| 413433 | 32431 | 32450 | GCCTGGACAAGTCCTGCCCA | 79 | 425 |

TABLE 44

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
| --- | --- | --- | --- | --- | --- |
| 501901 | 28575 | 28594 | AAATCCACCAAATGACCTTC | 42 | 2999 |
| 501902 | 28580 | 28599 | GAACTAAATCCACCAAATGA | 13 | 3000 |
| 501903 | 28585 | 28604 | AGGATGAACTAAATCCACCA | 65 | 3001 |
| 501904 | 28590 | 28609 | GCAAAAGGATGAACTAAATC | 4 | 3002 |
| 501905 | 28595 | 28614 | GAAGAGCAAAAGGATGAACT | 0 | 3003 |
| 501906 | 28600 | 28619 | CACAGGAAGAGCAAAAGGAT | 0 | 3004 |
| 501907 | 28605 | 28624 | CCAAACACAGGAAGAGCAAA | 0 | 3005 |
| 501908 | 28610 | 28629 | AGAAACCAAACACAGGAAGA | 33 | 3006 |
| 501909 | 28615 | 28634 | GCCCCAGAAACCAAACACAG | 20 | 3007 |
| 501910 | 28620 | 28639 | CTCCAGCCCCAGAAACCAAA | 45 | 3008 |
| 501911 | 28625 | 28644 | AATCTCTCCAGCCCCAGAAA | 36 | 3009 |
| 501912 | 28787 | 28806 | CCTGGCCTTTCTCAGCTGGG | 25 | 3010 |
| 501913 | 28792 | 28811 | TCTAGCCTGGCCTTTCTCAG | 0 | 3011 |
| 501914 | 28797 | 28816 | TGAATTCTAGCCTGGCCTTT | 44 | 3012 |
| 501915 | 28802 | 28821 | GAGACTGAATTCTAGCCTGG | 48 | 3013 |
| 501916 | 28807 | 28826 | ATCCAGAGACTGAATTCTAG | 71 | 3014 |
| 501917 | 28829 | 28848 | AGAAGAAGAGGCCTGATGGG | 29 | 3015 |
| 501918 | 28834 | 28853 | GATGGAGAAGAAGAGGCCTG | 59 | 3016 |
| 501919 | 28839 | 28858 | GCCTGGATGGAGAAGAAGAG | 0 | 3017 |
| 501920 | 28844 | 28863 | AGGCAGCCTGGATGGAGAAG | 5 | 3018 |
| 501921 | 28849 | 28868 | TGCTGAGGCAGCCTGGATGG | 26 | 3019 |
| 501922 | 28854 | 28873 | TCTGCTGCTGAGGCAGCCTG | 12 | 3020 |
| 501923 | 28859 | 28878 | CTTACTCTGCTGCTGAGGCA | 47 | 3021 |
| 501924 | 28864 | 28883 | TTGTCCTTACTCTGCTGCTG | 55 | 3022 |

TABLE 44-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501925 | 28901 | 28920 | GGCTGGTCTCTCTGGGAAGG | 25 | 3023 |
| 501926 | 28906 | 28925 | TAGAGGGCTGGTCTCTCTGG | 40 | 3024 |
| 501927 | 28911 | 28930 | CTGCTTAGAGGGCTGGTCTC | 40 | 3025 |
| 501928 | 28916 | 28935 | CCCCACTGCTTAGAGGGCTG | 34 | 3026 |
| 501929 | 28921 | 28940 | CCAGGCCCCACTGCTTAGAG | 26 | 3027 |
| 501930 | 28926 | 28945 | GAGCTCCAGGCCCCACTGCT | 7 | 3028 |
| 501931 | 28986 | 29005 | GGAAACCTAGCTTCCAGAAA | 53 | 3029 |
| 501932 | 29010 | 29029 | TTTAGGCTATGGTCTGAGCA | 78 | 3030 |
| 501933 | 29015 | 29034 | TGAGGTTTAGGCTATGGTCT | 68 | 3031 |
| 501934 | 29044 | 29063 | GATGCTCCAGGTGGGCCAGA | 68 | 3032 |
| 501935 | 29049 | 29068 | AGGTGGATGCTCCAGGTGGG | 0 | 3033 |
| 501936 | 29054 | 29073 | CCTCTAGGTGGATGCTCCAG | 18 | 3034 |
| 501937 | 29059 | 29078 | GGCATCCTCTAGGTGGATGC | 22 | 3035 |
| 501938 | 29064 | 29083 | CTAGTGGCATCCTCTAGGTG | 50 | 3036 |
| 501939 | 29069 | 29088 | CTCCTCTAGTGGCATCCTCT | 33 | 3037 |
| 501940 | 29074 | 29093 | CCAGGCTCCTCTAGTGGCAT | 55 | 3038 |
| 501941 | 29079 | 29098 | GGCATCCAGGCTCCTCTAGT | 53 | 3039 |
| 501942 | 29103 | 29122 | GACTCTAGCCCCCCAGACTC | 29 | 3040 |
| 501943 | 29139 | 29158 | TCTGCCTGATTCCCTTTCTT | 30 | 3041 |
| 501944 | 29144 | 29163 | AGCAGTCTGCCTGATTCCCT | 81 | 3042 |
| 501945 | 29149 | 29168 | TGTTCAGCAGTCTGCCTGAT | 50 | 3043 |
| 501946 | 29154 | 29173 | CTTACTGTTCAGCAGTCTGC | 70 | 3044 |
| 501947 | 29159 | 29178 | TCATACTTACTGTTCAGCAG | 65 | 3045 |
| 501948 | 29164 | 29183 | CAAAGTCATACTTACTGTTC | 29 | 3046 |
| 501949 | 29169 | 29188 | GCCTACAAAGTCATACTTAC | 17 | 3047 |
| 501950 | 29193 | 29212 | GGTGAATAGCTATGTCTAAA | 80 | 3048 |
| 501951 | 29198 | 29217 | AGCTTGGTGAATAGCTATGT | 76 | 3049 |
| 501952 | 29222 | 29241 | AGCAAACTGTGAAAAGCTTA | 59 | 3050 |
| 501953 | 29227 | 29246 | TTAAAAGCAAACTGTGAAAA | 2 | 3051 |
| 501954 | 29232 | 29251 | GCCTGTTAAAAGCAAACTGT | 48 | 3052 |
| 501955 | 29237 | 29256 | CAAGAGCCTGTTAAAAGCAA | 12 | 3053 |
| 501956 | 29242 | 29261 | GCCTACAAGAGCCTGTTAAA | 30 | 3054 |
| 501957 | 29247 | 29266 | GTGCAGCCTACAAGAGCCTG | 69 | 3055 |
| 501958 | 29252 | 29271 | AGCATGTGCAGCCTACAAGA | 57 | 3056 |
| 501959 | 29257 | 29276 | AGGGAAGCATGTGCAGCCTA | 76 | 3057 |
| 501960 | 29262 | 29281 | TTTCTAGGGAAGCATGTGCA | 76 | 3058 |

TABLE 44-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501961 | 29267 | 29286 | ACAAGTTTCTAGGGAAGCAT | 40 | 3059 |
| 501962 | 29272 | 29291 | GGAAGACAAGTTTCTAGGGA | 52 | 3060 |
| 501963 | 29277 | 29296 | AGAAGGGAAGACAAGTTTCT | 30 | 3061 |
| 501964 | 29282 | 29301 | ATCGCAGAAGGGAAGACAAG | 28 | 3062 |
| 501965 | 29327 | 29346 | AGTGACGAGATGTCCAATTT | 59 | 3063 |
| 501966 | 29361 | 29380 | ACAACTCTCTTGTTGGGAGG | 71 | 3064 |
| 501967 | 29366 | 29385 | AGGGTACAACTCTCTTGTTG | 59 | 3065 |
| 501968 | 29371 | 29390 | AAAACAGGGTACAACTCTCT | 73 | 3066 |
| 501969 | 29376 | 29395 | AGCTAAAAACAGGGTACAAC | 13 | 3067 |
| 501970 | 29383 | 29402 | CCAGGGTAGCTAAAAACAGG | 3 | 3068 |
| 501971 | 29388 | 29407 | TCTCCCCAGGGTAGCTAAAA | 0 | 3069 |
| 501972 | 29393 | 29412 | CAGCCTCTCCCCAGGGTAGC | 33 | 3070 |
| 501973 | 29417 | 29436 | TAGCCCTGTTCTAGACTCCT | 36 | 3071 |
| 501974 | 29440 | 29459 | TAGCCCCTTGTTGCCCCCCA | 43 | 3072 |
| 501975 | 29445 | 29464 | AATGGTAGCCCCTTGTTGCC | 11 | 3073 |
| 501976 | 29450 | 29469 | AGGGAAATGGTAGCCCCTTG | 63 | 3074 |
| 501977 | 29475 | 29494 | GTAGACTCTCCATGAGCCTA | 60 | 3075 |
| 413433 | 32431 | 32450 | GCCTGGACAAGTCCTGCCCA | 77 | 425 |

TABLE 45

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501978 | 30937 | 30956 | GGGCCCACAAACCCTGAGAA | 20 | 3076 |
| 501979 | 30962 | 30981 | AGGCACACCCAGGGCCATGG | 68 | 3077 |
| 501980 | 30967 | 30986 | AAGCTAGGCACACCCAGGGC | 48 | 3078 |
| 501981 | 30972 | 30991 | GCACTAAGCTAGGCACACCC | 77 | 3079 |
| 501982 | 30977 | 30996 | CTGTGGCACTAAGCTAGGCA | 78 | 3080 |
| 501983 | 30982 | 31001 | GTTTACTGTGGCACTAAGCT | 80 | 3081 |
| 501984 | 30987 | 31006 | TGAGTGTTTACTGTGGCACT | 56 | 3082 |
| 501985 | 31026 | 31045 | ACTGGGCTTCATCTCCCCTC | 0 | 3083 |
| 501986 | 31031 | 31050 | GTCCTACTGGGCTTCATCTC | 28 | 3084 |
| 501987 | 31074 | 31093 | GGCACTGCAGGCCACTCCTG | 41 | 3085 |
| 501988 | 31185 | 31204 | AAGGGAGGCCTTGCACTTAC | 26 | 3086 |

TABLE 45-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 501989 | 31236 | 31255 | GCCCTTCAGCTTGTGCAGGG | 36 | 3087 |
| 501990 | 31241 | 31260 | ATGAGGCCCTTCAGCTTGTG | 57 | 3088 |
| 501991 | 31246 | 31265 | TCAGGATGAGGCCCTTCAGC | 67 | 3089 |
| 501992 | 31251 | 31270 | AGCACTCAGGATGAGGCCCT | 50 | 3090 |
| 501993 | 31274 | 31293 | ACAAAGTGGGTGTTAAAGA | 22 | 3091 |
| 501994 | 31279 | 31298 | TTTTCACAAAGTGGGTGTTA | 40 | 3092 |
| 501995 | 31315 | 31334 | GCTTTTAACCTCCCCCCAAA | 6 | 3093 |
| 501996 | 31366 | 31385 | CCTCGACTGAGTGTGAACTC | 66 | 3094 |
| 501997 | 31371 | 31390 | CAAACCCTCGACTGAGTGTG | 46 | 3095 |
| 501998 | 31376 | 31395 | TTATGCAAACCCTCGACTGA | 24 | 3096 |
| 501999 | 31490 | 31509 | ACATTTGGGCAAGGCAGACA | 14 | 3097 |
| 502000 | 31525 | 31544 | AGGGAATAAAATACAGAGTT | 0 | 3098 |
| 502001 | 31530 | 31549 | CTTCCAGGGAATAAAATACA | 0 | 3099 |
| 502002 | 31535 | 31554 | GCCACCTTCCAGGGAATAAA | 0 | 3100 |
| 502003 | 31540 | 31559 | CTCCTGCCACCTTCCAGGGA | 0 | 3101 |
| 502004 | 31545 | 31564 | GTGACCTCCTGCCACCTTCC | 54 | 3102 |
| 502005 | 31606 | 31625 | TTTACCTGGATGGGAAAGTA | 0 | 3103 |
| 502006 | 31612 | 31631 | CAGCACTTTACCTGGATGGG | 2 | 3104 |
| 502007 | 31617 | 31636 | ACTCACAGCACTTTACCTGG | 0 | 3105 |
| 502008 | 31622 | 31641 | ACAACACTCACAGCACTTTA | 1 | 3106 |
| 502009 | 31688 | 31707 | ACTTGCTTCCCTGTGGGTGG | 0 | 3107 |
| 502010 | 31693 | 31712 | TCTAAACTTGCTTCCCTGTG | 16 | 3108 |
| 502011 | 31698 | 31717 | CTTGGTCTAAACTTGCTTCC | 60 | 3109 |
| 502012 | 31703 | 31722 | ACCAACTTGGTCTAAACTTG | 57 | 3110 |
| 502013 | 31768 | 31787 | GGATACTCAGAAGAGCAGTG | 79 | 3111 |
| 502014 | 31792 | 31811 | CCTCAGGGCTGGCCCAAAGA | 61 | 3112 |
| 502015 | 31797 | 31816 | CAGGACCTCAGGGCTGGCCC | 74 | 3113 |
| 502016 | 31802 | 31821 | CCTGTCAGGACCTCAGGGCT | 40 | 3114 |
| 502017 | 31807 | 31826 | ATTTCCCTGTCAGGACCTCA | 46 | 3115 |
| 502018 | 31828 | 31847 | TGAAAGCCAAACTGAGCCAC | 55 | 3116 |
| 502019 | 31866 | 31885 | AGCTTGCAGACCAGGCAGGG | 60 | 3117 |
| 502020 | 31871 | 31890 | AGCCCAGCTTGCAGACCAGG | 55 | 3118 |
| 502021 | 31876 | 31895 | TCACCAGCCCAGCTTGCAGA | 30 | 3119 |
| 502022 | 31881 | 31900 | GTGCCTCACCAGCCCAGCTT | 49 | 3120 |
| 502023 | 31904 | 31923 | ACATGCATCAGGGCCAGATG | 35 | 3121 |
| 502024 | 31932 | 31951 | AGTTATCCTCAATTCACCAG | 66 | 3122 |

TABLE 45-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 502025 | 31937 | 31956 | GCCAGAGTTATCCTCAATTC | 76 | 3123 |
| 502026 | 31942 | 31961 | ATCCTGCCAGAGTTATCCTC | 71 | 3124 |
| 502027 | 31947 | 31966 | TCAGGATCCTGCCAGAGTTA | 63 | 3125 |
| 502028 | 31952 | 31971 | AACCTTCAGGATCCTGCCAG | 60 | 3126 |
| 502029 | 31957 | 31976 | GGGAAAACCTTCAGGATCCT | 51 | 3127 |
| 502030 | 31975 | 31994 | ACAGGTCTTTCCCCTGTGGG | 31 | 3128 |
| 502031 | 31980 | 31999 | GCCAGACAGGTCTTTCCCCT | 65 | 3129 |
| 502032 | 32052 | 32071 | CTTCAGCACCCCTACCTTCT | 45 | 3130 |
| 502033 | 32057 | 32076 | CCACTCTTCAGCACCCCTAC | 53 | 3131 |
| 502034 | 32062 | 32081 | TGCCTCCACTCTTCAGCACC | 60 | 3132 |
| 502035 | 32110 | 32129 | ATATACACCACCCTGCACCC | 30 | 3133 |
| 502036 | 32115 | 32134 | AGCAAATATACACCACCCTG | 67 | 3134 |
| 502037 | 32120 | 32139 | ACAACAGCAAATATACACCA | 73 | 3135 |
| 502038 | 32125 | 32144 | GACTCACAACAGCAAATATA | 68 | 3136 |
| 502039 | 32130 | 32149 | TCACTGACTCACAACAGCAA | 60 | 3137 |
| 502040 | 32135 | 32154 | CTCAGTCACTGACTCACAAC | 83 | 3138 |
| 502041 | 32140 | 32159 | AGGATCTCAGTCACTGACTC | 68 | 3139 |
| 502042 | 32146 | 32165 | CACACCAGGATCTCAGTCAC | 61 | 3140 |
| 502043 | 32167 | 32186 | CCAGCCACTGCCCCCAGGCA | 38 | 3141 |
| 502044 | 32172 | 32191 | GTTACCCAGCCACTGCCCCC | 33 | 3142 |
| 502045 | 32177 | 32196 | GCAGGGTTACCCAGCCACTG | 76 | 3143 |
| 502046 | 32182 | 32201 | AGGATGCAGGGTTACCCAGC | 80 | 3144 |
| 502047 | 32187 | 32206 | AGTGAAGGATGCAGGGTTAC | 13 | 3145 |
| 502048 | 32192 | 32211 | AATGCAGTGAAGGATGCAGG | 52 | 3146 |
| 502049 | 32223 | 32242 | AGGAGCTGGCCCTGCCACCC | 48 | 3147 |
| 502050 | 32228 | 32247 | GCAGAAGGAGCTGGCCCTGC | 64 | 3148 |
| 502051 | 32233 | 32252 | GATGAGCAGAAGGAGCTGGC | 56 | 3149 |
| 502052 | 32238 | 32257 | CTAAGGATGAGCAGAAGGAG | 42 | 3150 |
| 502053 | 32243 | 32262 | TTAGGCTAAGGATGAGCAGA | 60 | 3151 |
| 502054 | 32248 | 32267 | TGGGCTTAGGCTAAGGATGA | 53 | 3152 |
| 413433 | 32431 | 32450 | GCCTGGACAAGTCCTGCCCA | 79 | 425 |

TABLE 46

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 413433 | 32431 | 32450 | GCCTGGACAAGTCCTGCCCA | 77 | 425 |
| 502055 | 33408 | 33427 | TCTTCATTACATGATTACTG | 66 | 3153 |
| 502056 | 33413 | 33432 | GCAGATCTTCATTACATGAT | 81 | 3154 |
| 502057 | 33449 | 33468 | ACCAGGAAGGGAGTAGGTGG | 0 | 3155 |
| 502058 | 33454 | 33473 | GTCCCACCAGGAAGGGAGTA | 0 | 3156 |
| 502059 | 33459 | 33478 | CCAGAGTCCCACCAGGAAGG | 0 | 3157 |
| 502060 | 33464 | 33483 | AAAGACCAGAGTCCCACCAG | 15 | 3158 |
| 502061 | 33489 | 33508 | GGGCCAGATGAGCTGTTCTG | 26 | 3159 |
| 502062 | 33513 | 33532 | GTGCCAACAGAAGGGATACA | 68 | 3160 |
| 502063 | 33518 | 33537 | CACCTGTGCCAACAGAAGGG | 36 | 3161 |
| 502064 | 33523 | 33542 | AACCCCACCTGTGCCAACAG | 53 | 3162 |
| 502065 | 33557 | 33576 | GGCTGGTGGTCTCGGTGGCT | 61 | 3163 |
| 502066 | 33562 | 33581 | CAGGTGGCTGGTGGTCTCGG | 38 | 3164 |
| 502067 | 33567 | 33586 | TCTTCCAGGTGGCTGGTGGT | 32 | 3165 |
| 502068 | 33572 | 33591 | GCTCCTCTTCCAGGTGGCTG | 61 | 3166 |
| 502069 | 33577 | 33596 | TGTCTGCTCCTCTTCCAGGT | 63 | 3167 |
| 502070 | 33582 | 33601 | GGCACTGTCTGCTCCTCTTC | 64 | 3168 |
| 502071 | 33636 | 33655 | TTCCTAGTCTCCTCTCCAAG | 24 | 3169 |
| 502072 | 33658 | 33677 | ATTCTAAGCTTAGAGAGAGT | 28 | 3170 |
| 502073 | 33663 | 33682 | AGGTGATTCTAAGCTTAGAG | 53 | 3171 |
| 502074 | 33668 | 33687 | TGGACAGGTGATTCTAAGCT | 66 | 3172 |
| 502075 | 33673 | 33692 | GCAGATGGACAGGTGATTCT | 72 | 3173 |
| 502076 | 33678 | 33697 | ATGAGGCAGATGGACAGGTG | 66 | 3174 |
| 502077 | 33683 | 33702 | GTGAAATGAGGCAGATGGAC | 52 | 3175 |
| 502078 | 33688 | 33707 | TATCAGTGAAATGAGGCAGA | 16 | 3176 |
| 502079 | 33693 | 33712 | AAGCCTATCAGTGAAATGAG | 8 | 3177 |
| 502080 | 33698 | 33717 | TCAGTAAGCCTATCAGTGAA | 0 | 3178 |
| 502081 | 33703 | 33722 | GTGCCTCAGTAAGCCTATCA | 56 | 3179 |
| 502082 | 33708 | 33727 | TCTCTGTGCCTCAGTAAGCC | 32 | 3180 |
| 502083 | 33729 | 33748 | TGACCTTGGGATAGTCCCTC | 84 | 3181 |
| 502084 | 33734 | 33753 | CTTTGTGACCTTGGGATAGT | 61 | 3182 |
| 502085 | 33740 | 33759 | CTTAAGCTTTGTGACCTTGG | 69 | 3183 |
| 502086 | 33745 | 33764 | TACTACTTAAGCTTTGTGAC | 59 | 3184 |
| 502087 | 33750 | 33769 | CCTGCTACTACTTAAGCTTT | 30 | 3185 |
| 502088 | 33755 | 33774 | CTAGTCCTGCTACTACTTAA | 43 | 3186 |
| 502089 | 33760 | 33779 | CTACACTAGTCCTGCTACTA | 16 | 3187 |

TABLE 46-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 502090 | 33765 | 33784 | GGTTCCTACACTAGTCCTGC | 59 | 3188 |
| 502091 | 33802 | 33821 | CAGGAGTAAGACCATGGGCC | 59 | 3189 |
| 502092 | 33807 | 33826 | TAACACAGGAGTAAGACCAT | 57 | 3190 |
| 502093 | 33812 | 33831 | GAAAGTAACACAGGAGTAAG | 45 | 3191 |
| 502094 | 33817 | 33836 | ATGGTGAAAGTAACACAGGA | 54 | 3192 |
| 502095 | 33846 | 33865 | TGCTTAAGTTTACACAGCAC | 66 | 3193 |
| 502096 | 33851 | 33870 | AGGCTTGCTTAAGTTTACAC | 62 | 3194 |
| 502097 | 33856 | 33875 | AGCAAAGGCTTGCTTAAGTT | 65 | 3195 |
| 502098 | 33861 | 33880 | AGAAGAGCAAAGGCTTGCTT | 79 | 3196 |
| 502099 | 33866 | 33885 | CCCACAGAAGAGCAAAGGCT | 80 | 3197 |
| 502100 | 33871 | 33890 | TCAGACCCACAGAAGAGCAA | 69 | 3198 |
| 502101 | 33893 | 33912 | AGCAGTGCATAGAGGAAAAA | 16 | 3199 |
| 502102 | 33898 | 33917 | ACCACAGCAGTGCATAGAGG | 60 | 3200 |
| 502103 | 33903 | 33922 | GTCCCACCACAGCAGTGCAT | 49 | 3201 |
| 502104 | 33908 | 33927 | GGCTTGTCCCACCACAGCAG | 42 | 3202 |
| 502105 | 33913 | 33932 | AGATAGGCTTGTCCCACCAC | 54 | 3203 |
| 502106 | 33918 | 33937 | TGCTCAGATAGGCTTGTCCC | 71 | 3204 |
| 502107 | 33958 | 33977 | CAAGTCACTCTTTATACCCT | 53 | 3205 |
| 502108 | 33963 | 33982 | CCTATCAAGTCACTCTTTAT | 18 | 3206 |
| 502109 | 33968 | 33987 | ACATTCCTATCAAGTCACTC | 58 | 3207 |
| 502110 | 34017 | 34036 | CCCAACACGATGCCCAGGCC | 70 | 3208 |
| 502111 | 34053 | 34072 | TCCTCTTGCTGCCTGTTTCC | 34 | 3209 |
| 502112 | 34058 | 34077 | TTGTGTCCTCTTGCTGCCTG | 59 | 3210 |
| 502113 | 34063 | 34082 | TGCTCTTGTGTCCTCTTGCT | 68 | 3211 |
| 502114 | 34098 | 34117 | AAGGATACCGCCAATGAAGG | 65 | 3212 |
| 502115 | 34155 | 34174 | TCATGTCACACTCCCCTCCC | 58 | 3213 |
| 502116 | 34179 | 34198 | CATCTGACCAGCTCTGATCT | 52 | 3214 |
| 502117 | 34184 | 34203 | GTAGGCATCTGACCAGCTCT | 68 | 3215 |
| 502118 | 34189 | 34208 | AGAATGTAGGCATCTGACCA | 57 | 3216 |
| 502119 | 34211 | 34230 | TGCCCTTGCTGTAGGACCCA | 84 | 3217 |
| 502120 | 34216 | 34235 | GTCAATGCCCTTGCTGTAGG | 70 | 3218 |
| 502121 | 34221 | 34240 | TGCAAGTCAATGCCCTTGCT | 44 | 3219 |
| 502122 | 34226 | 34245 | CACAGTGCAAGTCAATGCCC | 62 | 3220 |
| 502123 | 34231 | 34250 | TGGGACACAGTGCAAGTCAA | 55 | 3221 |
| 502124 | 34267 | 34286 | AGGCTCTGATGGGACATTTG | 65 | 3222 |
| 502125 | 34301 | 34320 | CAGGTGGCTCTTTAAATCAT | 59 | 3223 |

TABLE 46-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 502126 | 34306 | 34325 | GGCCCCAGGTGGCTCTTTAA | 32 | 3224 |
| 502127 | 34312 | 34331 | CCAGTGGGCCCCAGGTGGCT | 63 | 3225 |
| 502128 | 34317 | 34336 | GTCACCCAGTGGGCCCCAGG | 46 | 3226 |
| 502129 | 34340 | 34359 | CCTGGGCTGCTGGATGAAGA | 0 | 3227 |
| 502130 | 34345 | 34364 | TTTTCCCTGGGCTGCTGGAT | 28 | 3228 |
| 502131 | 34350 | 34369 | TGCACTTTTCCCTGGGCTGC | 70 | 3229 |

TABLE 47

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 413433 | 32431 | 32450 | GCCTGGACAAGTCCTGCCCA | 78 | 425 |
| 502132 | 34391 | 34410 | TCACAGCAAATTATCCTGCA | 49 | 3230 |
| 502133 | 34396 | 34415 | GGAGGTCACAGCAAATTATC | 41 | 3231 |
| 502134 | 34401 | 34420 | CCTGTGGAGGTCACAGCAAA | 52 | 3232 |
| 502135 | 34460 | 34479 | TAAGCCATTCCTTGGATGAC | 72 | 3233 |
| 502136 | 34465 | 34484 | AGGTCTAAGCCATTCCTTGG | 58 | 3234 |
| 502137 | 34470 | 34489 | CTGAAAGGTCTAAGCCATTC | 59 | 3235 |
| 502138 | 34553 | 34572 | TTTGTCCCCTTCCTATGGCT | 49 | 3236 |
| 502139 | 34605 | 34624 | CAGGCCTGGGATAGTTACCC | 8 | 3237 |
| 502140 | 34610 | 34629 | ATGGCCAGGCCTGGGATAGT | 33 | 3238 |
| 502141 | 34615 | 34634 | AGCTGATGGCCAGGCCTGGG | 7 | 3239 |
| 502142 | 34620 | 34639 | TCCTGAGCTGATGGCCAGGC | 40 | 3240 |
| 502143 | 34625 | 34644 | CTTGCTCCTGAGCTGATGGC | 20 | 3241 |
| 502144 | 34630 | 34649 | GGAAACTTGCTCCTGAGCTG | 62 | 3242 |
| 502145 | 34635 | 34654 | AACTTGGAAACTTGCTCCTG | 52 | 3243 |
| 502146 | 34640 | 34659 | TGGGAAACTTGGAAACTTGC | 66 | 3244 |
| 502147 | 34676 | 34695 | GGCATTGAGGGAAGAGCTGG | 42 | 3245 |
| 502148 | 34681 | 34700 | AGGCAGGCATTGAGGGAAGA | 53 | 3246 |
| 502149 | 34686 | 34705 | AAGGCAGGCAGGCATTGAGG | 62 | 3247 |
| 502150 | 34691 | 34710 | TGAAAAGGCAGGCAGGCAT | 63 | 3248 |
| 502151 | 34696 | 34715 | TTTGATGAAAAGGCAGGCA | 49 | 3249 |
| 502152 | 34701 | 34720 | CTAGTTTTGATGAAAAGGC | 53 | 3250 |
| 502153 | 34706 | 34725 | TTGTGCTAGTTTTGATGAAA | 41 | 3251 |
| 502154 | 34739 | 34758 | TAGCTCTCAGTGAAGCTGGA | 83 | 3252 |

TABLE 47-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 502155 | 34826 | 34845 | GAGCAGATCTCAAAATCTCG | 70 | 3253 |
| 502156 | 34868 | 34887 | ACAGCAGCAGTCTAATCCAT | 73 | 3254 |
| 502157 | 34873 | 34892 | GGGAAACAGCAGCAGTCTAA | 49 | 3255 |
| 502158 | 34878 | 34897 | TAAATGGGAAACAGCAGCAG | 62 | 3256 |
| 502159 | 34883 | 34902 | CCAAATAAATGGGAAACAGC | 15 | 3257 |
| 502160 | 34888 | 34907 | ACTCCCCAAATAAATGGGAA | 13 | 3258 |
| 502161 | 34893 | 34912 | CAGCTACTCCCCAAATAAAT | 0 | 3259 |
| 502162 | 34898 | 34917 | ACTCTCAGCTACTCCCCAAA | 56 | 3260 |
| 502163 | 34903 | 34922 | AACCAACTCTCAGCTACTCC | 76 | 3261 |
| 502164 | 34931 | 34950 | CAAACAGATTAAAGTTGCTC | 80 | 3262 |
| 502165 | 35006 | 35025 | AATGTGAGCAAGACTCCCTC | 58 | 3263 |
| 502166 | 35167 | 35186 | TTGGGAGCCTCCTGGCAGAG | 0 | 3264 |
| 502167 | 35192 | 35211 | GCCCAGGTTTTCTGTGACTC | 65 | 3265 |
| 502168 | 35197 | 35216 | CAAGAGCCCAGGTTTTCTGT | 53 | 3266 |
| 502169 | 35220 | 35239 | GTCACTGGCCACCAGCAGAA | 44 | 3267 |
| 502170 | 35225 | 35244 | GCAGAGTCACTGGCCACCAG | 59 | 3268 |
| 502171 | 35230 | 35249 | TGGAAGCAGAGTCACTGGCC | 48 | 3269 |
| 502172 | 35263 | 35282 | TGCAAAGTGCCCCTTCCCTG | 67 | 3270 |
| 502173 | 35268 | 35287 | AGTGCTGCAAAGTGCCCCTT | 61 | 3271 |
| 502174 | 35273 | 35292 | ACCTGAGTGCTGCAAAGTGC | 61 | 3272 |
| 502175 | 35278 | 35297 | CTCCCACCTGAGTGCTGCAA | 83 | 3273 |
| 502176 | 35283 | 35302 | TGACACTCCCACCTGAGTGC | 60 | 3274 |
| 502177 | 35288 | 35307 | ATCAATGACACTCCCACCTG | 59 | 3275 |
| 502178 | 35318 | 35337 | TTTTGGCTGCCCTGCCTCAA | 36 | 3276 |
| 502179 | 35323 | 35342 | GGTCTTTTGGCTGCCCTGC | 82 | 3277 |
| 502180 | 35345 | 35364 | GATAACAAGGAATGAACACG | 8 | 3278 |
| 502181 | 35350 | 35369 | TCCTGGATAACAAGGAATGA | 36 | 3279 |
| 502182 | 35356 | 35375 | TACAATTCCTGGATAACAAG | 0 | 3280 |
| 502183 | 35361 | 35380 | AGAAATACAATTCCTGGATA | 9 | 3281 |
| 502184 | 35366 | 35385 | CTTCTAGAAATACAATTCCT | 37 | 3282 |
| 502185 | 35371 | 35390 | ACAAACTTCTAGAAATACAA | 0 | 3283 |
| 502186 | 35376 | 35395 | GTGAAACAAACTTCTAGAAA | 62 | 3284 |
| 502187 | 35401 | 35420 | TTTGTCCACATATCTGATTG | 40 | 3285 |
| 502188 | 35406 | 35425 | TTATCTTTGTCCACATATCT | 44 | 3286 |
| 502189 | 35411 | 35430 | ATACCTTATCTTTGTCCACA | 81 | 3287 |
| 502190 | 35416 | 35435 | AATAAATACCTTATCTTTGT | 0 | 3288 |

TABLE 47-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 502191 | 35421 | 35440 | GCTTCAATAAATACCTTATC | 88 | 3289 |
| 502192 | 35426 | 35445 | GTAATGCTTCAATAAATACC | 67 | 3290 |
| 502193 | 35431 | 35450 | TAGAAGTAATGCTTCAATAA | 0 | 3291 |
| 502194 | 35436 | 35455 | CCTCTTAGAAGTAATGCTTC | 75 | 3292 |
| 502195 | 35441 | 35460 | ATTTCCCTCTTAGAAGTAAT | 30 | 3293 |
| 502196 | 35446 | 35465 | CCAAAATTTCCCTCTTAGAA | 39 | 3294 |
| 502197 | 35519 | 35538 | TATTCTACAGCACAGCTCTC | 24 | 3295 |
| 502198 | 35560 | 35579 | TCAAAATCCCTCAGTTCCAT | 25 | 3296 |
| 502199 | 35565 | 35584 | CCTTATCAAAATCCCTCAGT | 53 | 3297 |
| 502200 | 35570 | 35589 | TCTGTCCTTATCAAAATCCC | 23 | 3298 |
| 502201 | 35575 | 35594 | AGCTATCTGTCCTTATCAAA | 8 | 3299 |
| 502202 | 35607 | 35626 | ATCATTTTATATCATTTTC | 0 | 3300 |
| 502203 | 35612 | 35631 | TTGATATCATTTTTATATCA | 0 | 3301 |
| 502204 | 35617 | 35636 | ATGGGTTGATATCATTTTTA | 61 | 3302 |
| 502205 | 35622 | 35641 | GTTATATGGGTTGATATCAT | 48 | 3303 |
| 502206 | 35627 | 35646 | TTGAGGTTATATGGGTTGAT | 68 | 3304 |
| 502207 | 35632 | 35651 | CAAAATTGAGGTTATATGGG | 19 | 3305 |
| 502208 | 35656 | 35675 | ATACATGCTCTTTTTCAAAA | 45 | 3306 |

TABLE 48

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition (RTS2988_MGB) | % inhibition (RTS2367) | SEQ ID NO |
|---|---|---|---|---|---|---|
| 413433 | 32431 | 32450 | GCCTGGACAAGTCCTGCCCA | 72 | 77 | 425 |
| 502209 | 37525 | 37544 | CATCTCCCAATGCAGGCCCA | 37 | 34 | 3307 |
| 502210 | 37555 | 37574 | GCCCTGACCCACCATGTCTG | 0 | 27 | 3308 |
| 502211 | 37560 | 37579 | CCTCAGCCCTGACCCACCAT | 19 | 51 | 3309 |
| 502212 | 37565 | 37584 | CTCCTCCTCAGCCCTGACCC | 0 | 8 | 3310 |
| 502213 | 37570 | 37589 | CAGCTCTCCTCCTCAGCCCT | 20 | 33 | 3311 |
| 502214 | 37575 | 37594 | ATGGACAGCTCTCCTCCTCA | 31 | 46 | 3312 |
| 502215 | 37580 | 37599 | ACCATATGGACAGCTCTCCT | 57 | 68 | 3313 |
| 502216 | 37695 | 37714 | GTGCCATGGACAACAATCAG | 0 | 0 | 3314 |
| 502217 | 37700 | 37719 | TTACAGTGCCATGGACAACA | 0 | 23 | 3315 |
| 502218 | 37705 | 37724 | GACAATTACAGTGCCATGGA | 15 | 7 | 3316 |

TABLE 48-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition (RTS2988_MGB) | % inhibition (RTS2367) | SEQ ID NO |
|---|---|---|---|---|---|---|
| 502219 | 37740 | 37759 | AATGCATCAGTCTGGTGGGA | 53 | 59 | 3317 |
| 502220 | 37745 | 37764 | ATCCCAATGCATCAGTCTGG | 66 | 73 | 3318 |
| 502221 | 37804 | 37823 | TGCATTTGGCAAACATTCCC | 36 | 50 | 3319 |
| 502222 | 37809 | 37828 | ACTCATGCATTTGGCAAACA | 42 | 0 | 3320 |
| 502223 | 37814 | 37833 | TGGGAACTCATGCATTTGGC | 62 | 65 | 3321 |
| 502224 | 37819 | 37838 | TGTTTTGGGAACTCATGCAT | 3 | 25 | 3322 |
| 502225 | 37824 | 37843 | AAGGTTGTTTTGGGAACTCA | 44 | 42 | 3323 |
| 502226 | 37829 | 37848 | GATACAAGGTTGTTTTGGGA | 29 | 44 | 3324 |
| 502227 | 37834 | 37853 | CTAATGATACAAGGTTGTTT | 29 | 41 | 3325 |
| 502228 | 37839 | 37858 | TGCAGCTAATGATACAAGGT | 68 | 67 | 3326 |
| 502229 | 37844 | 37863 | TAAAATGCAGCTAATGATAC | 21 | 18 | 3327 |
| 502230 | 37849 | 37868 | ATCTGTAAAATGCAGCTAAT | 13 | 38 | 3328 |
| 502231 | 37854 | 37873 | TCCTCATCTGTAAAATGCAG | 48 | 43 | 3329 |
| 502232 | 37859 | 37878 | CAGTTTCCTCATCTGTAAAA | 8 | 19 | 3330 |
| 502233 | 37864 | 37883 | AGCCTCAGTTTCCTCATCTG | 42 | 44 | 3331 |
| 502234 | 37869 | 37888 | TTCTGAGCCTCAGTTTCCTC | 34 | 54 | 3332 |
| 502235 | 37874 | 37893 | CATTTTTCTGAGCCTCAGTT | 46 | 45 | 3333 |
| 502236 | 37879 | 37898 | CTATTCATTTTTCTGAGCCT | 56 | 65 | 3334 |
| 502237 | 37884 | 37903 | GTAAGCTATTCATTTTTCTG | 50 | 53 | 3335 |
| 502238 | 37889 | 37908 | TCTGTGTAAGCTATTCATTT | 44 | 55 | 3336 |
| 502239 | 37894 | 37913 | CTGGTTCTGTGTAAGCTATT | 55 | 55 | 3337 |
| 502240 | 37899 | 37918 | GTTGTCTGGTTCTGTGTAAG | 31 | 38 | 3338 |
| 502241 | 37904 | 37923 | TTGGAGTTGTCTGGTTCTGT | 52 | 52 | 3339 |
| 502242 | 37989 | 38008 | TGGATCCACTCCCCATCCCC | 0 | 30 | 3340 |
| 502243 | 37994 | 38013 | GCCCATGGATCCACTCCCCA | 0 | 0 | 3341 |
| 502244 | 37999 | 38018 | GGGTTGCCCATGGATCCACT | 0 | 10 | 3342 |
| 502245 | 38004 | 38023 | AGTCAGGGTTGCCCATGGAT | 9 | 13 | 3343 |
| 502246 | 38270 | 38289 | CCAAGGAGTCTGCTGCCCTG | 15 | 16 | 3344 |
| 502247 | 38292 | 38311 | GTCTGGGTCCTGTCTTCAGG | 17 | 15 | 3345 |
| 502248 | 38326 | 38345 | CAGAATGACTGACTCCCTTC | 10 | 19 | 3346 |
| 502249 | 38356 | 38375 | GCAGTCTGGGCTCCAACATC | 0 | 5 | 3347 |
| 502250 | 38361 | 38380 | ACTGTGCAGTCTGGGCTCCA | 0 | 7 | 3348 |
| 502251 | 38366 | 38385 | CCCACACTGTGCAGTCTGGG | 5 | 10 | 3349 |
| 502252 | 38371 | 38390 | CTTGGCCCACACTGTGCAGT | 4 | 8 | 3350 |
| 502253 | 38376 | 38395 | GCAAACTTGGCCCACACTGT | 2 | 0 | 3351 |
| 502254 | 38381 | 38400 | CATGGGCAAACTTGGCCCAC | 21 | 22 | 3352 |

TABLE 48-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition (RTS2988_MGB) | % inhibition (RTS2367) | SEQ ID NO |
|---|---|---|---|---|---|---|
| 502255 | 38386 | 38405 | ACACACATGGGCAAACTTGG | 0 | 0 | 3353 |
| 502256 | 38391 | 38410 | CCCAGACACACATGGGCAAA | 0 | 0 | 3354 |
| 502257 | 38396 | 38415 | GCCCACCCAGACACACATGG | 0 | 5 | 3355 |
| 502258 | 38401 | 38420 | TCTGTGCCCACCCAGACACA | 0 | 13 | 3356 |
| 502259 | 38406 | 38425 | TTGCATCTGTGCCCACCCAG | 5 | 22 | 3357 |
| 502260 | 38411 | 38430 | ACAGGTTGCATCTGTGCCCA | 33 | 45 | 3358 |
| 502261 | 38478 | 38497 | GGCCCCAGGTGGTCCAGTCC | 0 | 4 | 3359 |
| 502262 | 38483 | 38502 | ATTCTGGCCCCAGGTGGTCC | 0 | 10 | 3360 |
| 502263 | 38505 | 38524 | TGGTCTCCCAGCAAAATGAT | 0 | 0 | 3361 |
| 502264 | 38510 | 38529 | CCTCCTGGTCTCCCAGCAAA | 0 | 0 | 3362 |
| 502265 | 38515 | 38534 | CCTGACCTCCTGGTCTCCCA | 0 | 7 | 3363 |
| 502266 | 38520 | 38539 | TCCTTCCTGACCTCCTGGTC | 3 | 16 | 3364 |
| 502267 | 38525 | 38544 | CACCCTCCTTCCTGACCTCC | 0 | 3 | 3365 |
| 502268 | 38595 | 38614 | TTCCAAAGCCTGAGGTAAGG | 18 | 36 | 3366 |
| 502269 | 38600 | 38619 | TCTTCTTCCAAAGCCTGAGG | 14 | 40 | 3367 |
| 502270 | 38605 | 38624 | CAGCCTCTTCTTCCAAAGCC | 10 | 9 | 3368 |
| 502271 | 38630 | 38649 | CTGGCCCAGGGCTGAGCCTG | 0 | 0 | 3369 |
| 502272 | 38676 | 38695 | TCCCTGAAGGCAGGGACTGG | 0 | 10 | 3370 |
| 502273 | 38681 | 38700 | GGTGCTCCCTGAAGGCAGGG | 24 | 28 | 3371 |
| 502274 | 38686 | 38705 | CCCTTGGTGCTCCCTGAAGG | 0 | 15 | 3372 |
| 502275 | 38726 | 38745 | CACACTGTGTTGTCACTGTC | 41 | 44 | 3373 |
| 502276 | 38731 | 38750 | CTCAGCACACTGTGTTGTCA | 38 | 48 | 3374 |
| 502277 | 38736 | 38755 | ACAGTCTCAGCACACTGTGT | 6 | 21 | 3375 |
| 502278 | 38759 | 38778 | AGCCCTGGACTCACCATTGT | 0 | 4 | 3376 |
| 502279 | 38764 | 38783 | CTCTCAGCCCTGGACTCACC | 6 | 8 | 3377 |
| 502280 | 38809 | 38828 | GCCTCTGCCAGGAAGTTCTC | 8 | 6 | 3378 |
| 502281 | 38814 | 38833 | GGCCTGCCTCTGCCAGGAAG | 0 | 51 | 3379 |
| 502282 | 38819 | 38838 | TGCAGGGCCTGCCTCTGCCA | 9 | 2 | 3380 |
| 502283 | 38843 | 38862 | GAATGCCTGTTTTCCACCTC | 34 | 53 | 3381 |
| 502284 | 38848 | 38867 | CTCTGGAATGCCTGTTTTCC | 19 | 27 | 3382 |
| 502285 | 38874 | 38893 | AGGCAAAGGGAAGGCTGAGC | 4 | 23 | 3383 |

TABLE 49

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition (RTS2988_MGB) | % inhibition (RTS2367) | SEQ ID NO |
|---|---|---|---|---|---|---|
| 413433 | 32431 | 32450 | GCCTGGACAAGTCCTGCCCA | 74 | 73 | 425 |
| 502286 | 38879 | 38898 | CCCCCAGGCAAAGGGAAGGC | 0 | 16 | 3384 |
| 502287 | 38928 | 38947 | GCCTTCTGCCCCACTGCTAG | 0 | 6 | 3385 |
| 502288 | 38933 | 38952 | GATGGGCCTTCTGCCCCACT | 0 | 0 | 3386 |
| 502289 | 38938 | 38957 | GTTCTGATGGGCCTTCTGCC | 0 | 15 | 3387 |
| 502290 | 38943 | 38962 | ACCAGGTTCTGATGGGCCTT | 0 | 42 | 3388 |
| 502291 | 38948 | 38967 | TCTCTACCAGGTTCTGATGG | 0 | 2 | 3389 |
| 502292 | 39030 | 39049 | GGCCCTGGACACTGGCCAAG | 0 | 12 | 3390 |
| 502293 | 39035 | 39054 | CTAGAGGCCCTGGACACTGG | 0 | 16 | 3391 |
| 502294 | 39041 | 39060 | GTCAGCCTAGAGGCCCTGGA | 18 | 40 | 3392 |
| 502295 | 39082 | 39101 | CCAGGGTCTGTCATACCCTA | 0 | 0 | 3393 |
| 502296 | 39087 | 39106 | AGAGGCCAGGGTCTGTCATA | 0 | 0 | 3394 |
| 502297 | 39097 | 39116 | TCTGGAAGGGAGAGGCCAGG | 0 | 0 | 3395 |
| 502298 | 39301 | 39320 | ACCAACAGTGGTGATGGGCT | 7 | 24 | 3396 |
| 502299 | 39306 | 39325 | GGCTTACCAACAGTGGTGAT | 0 | 0 | 3397 |
| 502300 | 39337 | 39356 | GTTCAGGACAGCCCTTGGTC | 25 | 35 | 3398 |
| 502301 | 39342 | 39361 | CCTGTGTTCAGGACAGCCCT | 26 | 31 | 3399 |
| 502302 | 39347 | 39366 | GGCACCCTGTGTTCAGGACA | 41 | 52 | 3400 |
| 502303 | 39377 | 39396 | AATCCCGTCTCTACTGCTGA | 18 | 39 | 3401 |
| 502304 | 39401 | 39420 | TCAGAGCCAGGTGGCCTGCA | 30 | 27 | 3402 |
| 502305 | 39406 | 39425 | GGCCATCAGAGCCAGGTGGC | 0 | 33 | 3403 |
| 502306 | 39411 | 39430 | GGCATGGCCATCAGAGCCAG | 0 | 12 | 3404 |
| 502307 | 39416 | 39435 | CTAAGGGCATGGCCATCAGA | 0 | 23 | 3405 |
| 502308 | 39421 | 39440 | CATGGCTAAGGGCATGGCCA | 0 | 10 | 3406 |
| 502309 | 39426 | 39445 | GTCCTCATGGCTAAGGGCAT | 26 | 29 | 3407 |
| 502310 | 39431 | 39450 | TCAAAGTCCTCATGGCTAAG | 0 | 37 | 3408 |
| 502311 | 39436 | 39455 | ACACTTCAAAGTCCTCATGG | 33 | 52 | 3409 |
| 502312 | 39441 | 39460 | ACCCAACACTTCAAAGTCCT | 44 | 57 | 3410 |
| 502313 | 39446 | 39465 | TCAGCACCCAACACTTCAAA | 35 | 47 | 3411 |
| 502314 | 39514 | 39533 | ATCACAGAGCTTGGTTCATC | 61 | 62 | 3412 |
| 502315 | 39539 | 39558 | GACTGCAGATTTTCTTTCCT | 18 | 40 | 3413 |
| 502316 | 39577 | 39596 | GTCTTCCCTGATAGACTAGT | 43 | 46 | 3414 |
| 502317 | 39614 | 39633 | TCCTCATCACATTCCCCCAC | 37 | 59 | 3415 |
| 502318 | 39665 | 39684 | AGAGTTACCTCCTCCCTGGG | 14 | 25 | 3416 |
| 502319 | 39670 | 39689 | GTGCAAGAGTTACCTCCTCC | 71 | 81 | 3417 |
| 502320 | 39675 | 39694 | TAGCAGTGCAAGAGTTACCT | 61 | 67 | 3418 |

TABLE 49-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition (RTS2988_MGB) | % inhibition (RTS2367) | SEQ ID NO |
|---|---|---|---|---|---|---|
| 502321 | 39680 | 39699 | TCAGTTAGCAGTGCAAGAGT | 38 | 53 | 3419 |
| 502322 | 39685 | 39704 | TCCTATCAGTTAGCAGTGCA | 73 | 75 | 3420 |
| 502323 | 39690 | 39709 | ATAATTCCTATCAGTTAGCA | 32 | 35 | 3421 |
| 502324 | 39695 | 39714 | GCTAGATAATTCCTATCAGT | 25 | 17 | 3422 |
| 502325 | 39700 | 39719 | ATTTTGCTAGATAATTCCTA | 0 | 0 | 3423 |
| 502326 | 39705 | 39724 | CCTCTATTTTGCTAGATAAT | 1 | 26 | 3424 |
| 502327 | 39727 | 39746 | TTCTGATAAAAATTCTCTTC | 10 | 13 | 3425 |
| 502328 | 39732 | 39751 | ATTGTTTCTGATAAAAATTC | 0 | 0 | 3426 |
| 502329 | 39737 | 39756 | AGGCTATTGTTTCTGATAAA | 34 | 31 | 3427 |
| 502330 | 39813 | 39832 | CTATGCTGCAGTCATATTAA | 35 | 26 | 3428 |
| 502331 | 39818 | 39837 | CAGGTCTATGCTGCAGTCAT | 58 | 45 | 3429 |
| 502332 | 39823 | 39842 | TCTGACAGGTCTATGCTGCA | 46 | 50 | 3430 |
| 502333 | 39828 | 39847 | ACTCTTCTGACAGGTCTATG | 47 | 50 | 3431 |
| 502334 | 39833 | 39852 | TTTCCACTCTTCTGACAGGT | 54 | 72 | 3432 |
| 502335 | 39906 | 39925 | ATTCTTTAGAATCCTCTAAA | 0 | 10 | 3433 |
| 502336 | 39911 | 39930 | AGGTAATTCTTTAGAATCCT | 41 | 62 | 3434 |
| 502337 | 39965 | 39984 | AAGGGCCCATGTGCTCCTGG | 14 | 33 | 3435 |
| 502338 | 39970 | 39989 | CTGCCAAGGGCCCATGTGCT | 10 | 30 | 3436 |
| 502339 | 39975 | 39994 | GTCCACTGCCAAGGGCCCAT | 37 | 51 | 3437 |
| 502340 | 39980 | 39999 | CTCAAGTCCACTGCCAAGGG | 0 | 9 | 3438 |
| 502341 | 39985 | 40004 | GGCCCCTCAAGTCCACTGCC | 0 | 14 | 3439 |
| 502342 | 39990 | 40009 | GCTTTGGCCCCTCAAGTCCA | 13 | 27 | 3440 |
| 502343 | 40041 | 40060 | TAAAAGTACAAGGCAGGACA | 26 | 25 | 3441 |
| 502344 | 40063 | 40082 | TCCCTGTTGCTTTGTCTCTA | 20 | 26 | 3442 |
| 502345 | 40068 | 40087 | CTGCCTCCCTGTTGCTTTGT | 24 | 31 | 3443 |
| 502346 | 40073 | 40092 | TCCTGCTGCCTCCCTGTTGC | 0 | 21 | 3444 |
| 502347 | 40078 | 40097 | AATGTTCCTGCTGCCTCCCT | 0 | 0 | 3445 |
| 502348 | 40083 | 40102 | ATGGAAATGTTCCTGCTGCC | 33 | 33 | 3446 |
| 502349 | 40088 | 40107 | TGTGCATGGAAATGTTCCTG | 39 | 38 | 3447 |
| 502350 | 40093 | 40112 | ACACCTGTGCATGGAAATGT | 7 | 24 | 3448 |
| 502351 | 40098 | 40117 | CAGCCACACCTGTGCATGGA | 56 | 54 | 3449 |
| 502352 | 40103 | 40122 | CTCCCCAGCCACACCTGTGC | 10 | 21 | 3450 |
| 502353 | 40108 | 40127 | AGCCCCTCCCCAGCCACACC | 2 | 0 | 3451 |
| 502354 | 40130 | 40149 | CTTCACATTGCCCACAGGAC | 39 | 41 | 3452 |
| 502355 | 40135 | 40154 | AATTCCTTCACATTGCCCAC | 14 | 19 | 3453 |

TABLE 49-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition (RTS2988_MGB) | % inhibition (RTS2367) | SEQ ID NO |
|---|---|---|---|---|---|---|
| 502356 | 40140 | 40159 | GAGCAAATTCCTTCACATTG | 0 | 0 | 3454 |
| 502357 | 40145 | 40164 | GTGAAGAGCAAATTCCTTCA | 0 | 13 | 3455 |
| 502358 | 40150 | 40169 | TCAAGGTGAAGAGCAAATTC | 0 | 7 | 3456 |
| 502359 | 40155 | 40174 | CATTCTCAAGGTGAAGAGCA | 32 | 20 | 3457 |
| 502360 | 40160 | 40179 | CTCTCCATTCTCAAGGTGAA | 0 | 0 | 3458 |
| 502361 | 40182 | 40201 | CCTCCCAAACACTCTCTGGT | 11 | 11 | 3459 |
| 502362 | 40187 | 40206 | CTTCCCCTCCCAAACACTCT | 2 | 15 | 3460 |

TABLE 50

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 507659 | 26616 | 26635 | AGTCCTGATGATCCCCTACC | 44 | 3384 |
| 507660 | 26617 | 26636 | AAGTCCTGATGATCCCCTAC | 54 | 3385 |
| 507661 | 26618 | 26637 | TAAGTCCTGATGATCCCCTA | 53 | 3386 |
| 507662 | 26619 | 26638 | GTAAGTCCTGATGATCCCCT | 59 | 3387 |
| 507663 | 26621 | 26640 | TGGTAAGTCCTGATGATCCC | 73 | 3388 |
| 507664 | 26622 | 26641 | ATGGTAAGTCCTGATGATCC | 49 | 3389 |
| 507665 | 26623 | 26642 | CATGGTAAGTCCTGATGATC | 68 | 3390 |
| 507666 | 26624 | 26643 | ACATGGTAAGTCCTGATGAT | 35 | 3391 |
| 495752 | 26631 | 26650 | AGCACTGACATGGTAAGTCC | 67 | 3392 |
| 495753 | 26632 | 26651 | CAGCACTGACATGGTAAGTC | 75 | 3393 |
| 495754 | 26633 | 26652 | TCAGCACTGACATGGTAAGT | 50 | 3394 |
| 495755 | 26634 | 26653 | CTCAGCACTGACATGGTAAG | 35 | 3395 |
| 507667 | 26636 | 26655 | TGCTCAGCACTGACATGGTA | 60 | 3396 |
| 507668 | 26637 | 26656 | CTGCTCAGCACTGACATGGT | 56 | 3397 |
| 507669 | 26638 | 26657 | GCTGCTCAGCACTGACATGG | 69 | 3398 |
| 507670 | 26639 | 26658 | AGCTGCTCAGCACTGACATG | 54 | 3399 |
| 507671 | 26712 | 26731 | TGTGAAGTTCTATCCCTTGG | 52 | 3400 |
| 507672 | 26713 | 26732 | CTGTGAAGTTCTATCCCTTG | 40 | 3401 |
| 507673 | 26714 | 26733 | CCTGTGAAGTTCTATCCCTT | 28 | 3402 |
| 507674 | 26715 | 26734 | ACCTGTGAAGTTCTATCCCT | 27 | 3403 |
| 495756 | 26779 | 26798 | CTGCCATTTAATGAGCTTCA | 80 | 3404 |
| 495757 | 26780 | 26799 | TCTGCCATTTAATGAGCTTC | 56 | 3405 |
| 495758 | 26781 | 26800 | CTCTGCCATTTAATGAGCTT | 22 | 3406 |
| 495759 | 26782 | 26801 | ACTCTGCCATTTAATGAGCT | 13 | 3407 |
| 507675 | 26812 | 26831 | GGAATGCACTGAGTTTCTGC | 64 | 3408 |
| 507676 | 26813 | 26832 | GGGAATGCACTGAGTTTCTG | 39 | 3409 |
| 507677 | 26850 | 26869 | TCACTAATTCTGGGCTTCCA | 66 | 3410 |
| 507678 | 26851 | 26870 | TTCACTAATTCTGGGCTTCC | 51 | 3411 |
| 507679 | 26852 | 26871 | GTTCACTAATTCTGGGCTTC | 70 | 3412 |
| 507680 | 26853 | 26872 | AGTTCACTAATTCTGGGCTT | 37 | 3413 |
| 507681 | 26880 | 26899 | AAGGTGAAGACTGGCTGTTT | 4 | 3414 |
| 507682 | 26881 | 26900 | AAAGGTGAAGACTGGCTGTT | 43 | 3415 |
| 507683 | 26882 | 26901 | TAAAGGTGAAGACTGGCTGT | 46 | 3416 |
| 507684 | 26883 | 26902 | CTAAAGGTGAAGACTGGCTG | 70 | 3417 |
| 507685 | 26885 | 26904 | GCCTAAAGGTGAAGACTGGC | 42 | 3418 |
| 507686 | 26886 | 26905 | GGCCTAAAGGTGAAGACTGG | 18 | 3419 |
| 507687 | 26887 | 26906 | GGGCCTAAAGGTGAAGACTG | 31 | 3420 |
| 507688 | 26888 | 26907 | TGGGCCTAAAGGTGAAGACT | 37 | 3421 |
| 507689 | 27047 | 27066 | AGTTCTTCCAACCAGTGTTT | 66 | 3422 |
| 507690 | 27048 | 27067 | CAGTTCTTCCAACCAGTGTT | 69 | 3423 |
| 507691 | 27049 | 27068 | TCAGTTCTTCCAACCAGTGT | 63 | 3424 |
| 507692 | 27050 | 27069 | CTCAGTTCTTCCAACCAGTG | 83 | 3425 |
| 507693 | 27052 | 27071 | TGCTCAGTTCTTCCAACCAG | 79 | 3426 |

TABLE 50-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 507694 | 27053 | 27072 | TTGCTCAGTTCTTCCAACCA | 80 | 3427 |
| 507695 | 27054 | 27073 | TTTGCTCAGTTCTTCCAACC | 78 | 3428 |
| 507696 | 27055 | 27074 | GTTTGCTCAGTTCTTCCAAC | 85 | 3429 |
| 507697 | 27057 | 27076 | TAGTTTGCTCAGTTCTTCCA | 30 | 3430 |
| 507698 | 27058 | 27077 | TTAGTTTGCTCAGTTCTTCC | 55 | 3431 |
| 507699 | 27059 | 27078 | TTTAGTTTGCTCAGTTCTTC | 27 | 3432 |
| 507700 | 27060 | 27079 | GTTTAGTTTGCTCAGTTCTT | 48 | 3433 |
| 507701 | 27217 | 27236 | GTACTTTCTTCTCATGTGAC | 9 | 3434 |
| 507702 | 27218 | 27237 | AGTACTTTCTTCTCATGTGA | 0 | 3435 |
| 507703 | 27219 | 27238 | CAGTACTTTCTTCTCATGTG | 0 | 3436 |
| 507704 | 27220 | 27239 | CCAGTACTTTCTTCTCATGT | 53 | 3437 |
| 507705 | 27222 | 27241 | TCCCAGTACTTTCTTCTCAT | 67 | 3438 |
| 507706 | 27223 | 27242 | GTCCCAGTACTTTCTTCTCA | 57 | 3439 |
| 507707 | 27224 | 27243 | GGTCCCAGTACTTTCTTCTC | 58 | 3440 |
| 507708 | 27225 | 27244 | TGGTCCCAGTACTTTCTTCT | 49 | 3441 |
| 507709 | 27227 | 27246 | CCTGGTCCCAGTACTTTCTT | 65 | 3442 |
| 507710 | 27228 | 27247 | TCCTGGTCCCAGTACTTTCT | 77 | 3443 |
| 507711 | 27229 | 27248 | GTCCTGGTCCCAGTACTTTC | 69 | 3444 |
| 507712 | 27230 | 27249 | TGTCCTGGTCCCAGTACTTT | 64 | 3445 |
| 507713 | 27232 | 27251 | CTTGTCCTGGTCCCAGTACT | 61 | 3446 |
| 507714 | 27233 | 27252 | TCTTGTCCTGGTCCCAGTAC | 61 | 3447 |
| 507715 | 27234 | 27253 | TTCTTGTCCTGGTCCCAGTA | 67 | 3448 |
| 507716 | 27235 | 27254 | GTTCTTGTCCTGGTCCCAGT | 76 | 3449 |
| 507717 | 27237 | 27256 | GGGTTCTTGTCCTGGTCCCA | 80 | 3450 |
| 507718 | 27238 | 27257 | TGGGTTCTTGTCCTGGTCCC | 71 | 3451 |
| 507719 | 27239 | 27258 | CTGGGTTCTTGTCCTGGTCC | 62 | 3452 |
| 507720 | 27240 | 27259 | CCTGGGTTCTTGTCCTGGTC | 55 | 3453 |
| 413433 | 32431 | 32450 | GCCTGGACAAGTCCTGCCCA | 69 | 425 |
| 507721 | 35662 | 35681 | AAAAATATACATGCTCTTTT | 0 | 3461 |
| 507722 | 35663 | 35682 | CAAAAATATACATGCTCTTT | 29 | 3462 |
| 507723 | 35664 | 35683 | TCAAAAATATACATGCTCTT | 45 | 3463 |
| 507724 | 35665 | 35684 | CTCAAAAATATACATGCTCT | 74 | 3464 |
| 507725 | 35667 | 35686 | TACTCAAAAATATACATGCT | 51 | 3465 |
| 507726 | 35668 | 35687 | CTACTCAAAAATATACATGC | 63 | 3466 |
| 507727 | 35669 | 35688 | TCTACTCAAAAATATACATG | 0 | 3467 |

TABLE 51

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522363 | 12807 | 12826 | CCAGCACTAATTTTTACAAC | 72 | 3468 |
| 522364 | 12808 | 12827 | TCCAGCACTAATTTTTACAA | 49 | 3469 |
| 522365 | 12809 | 12828 | ATCCAGCACTAATTTTTACA | 65 | 3470 |
| 522366 | 13442 | 13461 | GTGGCTCTCTAGATAGGGTG | 80 | 3471 |
| 522367 | 14193 | 14212 | CTCAGCCTTGGAGCCAGCTC | 59 | 3472 |
| 522368 | 14194 | 14213 | ACTCAGCCTTGGAGCCAGCT | 72 | 3473 |
| 522369 | 14195 | 14214 | CACTCAGCCTTGGAGCCAGC | 63 | 3474 |
| 522370 | 14196 | 14215 | CCACTCAGCCTTGGAGCCAG | 71 | 3475 |
| 522371 | 14198 | 14217 | TGCCACTCAGCCTTGGAGCC | 67 | 3476 |
| 522372 | 14199 | 14218 | TTGCCACTCAGCCTTGGAGC | 62 | 3477 |
| 522373 | 15319 | 15338 | GGAGTTTGTGTTTCCCATTT | 83 | 3478 |
| 522374 | 15321 | 15340 | AAGGAGTTTGTGTTTCCCAT | 83 | 3479 |
| 522375 | 15322 | 15341 | AAAGGAGTTTGTGTTTCCCA | 83 | 3480 |
| 522376 | 15324 | 15343 | GAAAAGGAGTTTGTGTTTCC | 50 | 3481 |
| 522377 | 15325 | 15344 | AGAAAAGGAGTTTGTGTTTC | 17 | 3482 |
| 522378 | 15326 | 15345 | AAGAAAAGGAGTTTGTGTTT | 30 | 3483 |
| 522379 | 15327 | 15346 | TAAGAAAAGGAGTTTGTGTT | 21 | 3484 |
| 522380 | 15569 | 15588 | ATTTTCACAAGGAGAAGCTG | 40 | 3485 |
| 522381 | 15570 | 15589 | CATTTTCACAAGGAGAAGCT | 44 | 3486 |
| 522382 | 15571 | 15590 | CCATTTTCACAAGGAGAAGC | 32 | 3487 |
| 522383 | 15574 | 15593 | GCACCATTTTCACAAGGAGA | 84 | 3488 |
| 522384 | 15575 | 15594 | TGCACCATTTTCACAAGGAG | 77 | 3489 |
| 522385 | 15576 | 15595 | GTGCACCATTTTCACAAGGA | 72 | 3490 |
| 522386 | 15577 | 15596 | AGTGCACCATTTTCACAAGG | 65 | 3491 |
| 522387 | 15647 | 15666 | CATCACAATATATGGGCAAG | 44 | 3492 |
| 522388 | 15648 | 15667 | CCATCACAATATATGGGCAA | 51 | 3493 |
| 522389 | 15649 | 15668 | CCCATCACAATATATGGGCA | 60 | 3494 |
| 522390 | 15650 | 15669 | CCCCATCACAATATATGGGC | 55 | 3495 |
| 522391 | 15877 | 15896 | AGGTAAGGCCAAGGAAGTGA | 69 | 3496 |
| 522392 | 15878 | 15897 | GAGGTAAGGCCAAGGAAGTG | 50 | 3497 |
| 522393 | 15879 | 15898 | AGAGGTAAGGCCAAGGAAGT | 43 | 3498 |
| 522394 | 15880 | 15899 | AAGAGGTAAGGCCAAGGAAG | 57 | 3499 |
| 522395 | 15934 | 15953 | CACCTGGGTTTTTGTGTATT | 66 | 3500 |
| 522396 | 15935 | 15954 | ACACCTGGGTTTTTGTGTAT | 61 | 3501 |
| 522397 | 15936 | 15955 | TACACCTGGGTTTTTGTGTA | 37 | 3502 |
| 522398 | 15937 | 15956 | ATACACCTGGGTTTTTGTGT | 69 | 3503 |

TABLE 51-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522399 | 16047 | 16066 | TCTGAGTGCTGCTAACTTGG | 77 | 3504 |
| 522400 | 16048 | 16067 | ATCTGAGTGCTGCTAACTTG | 65 | 3505 |
| 522401 | 16049 | 16068 | AATCTGAGTGCTGCTAACTT | 62 | 3506 |
| 522402 | 16050 | 16069 | AAATCTGAGTGCTGCTAACT | 60 | 3507 |
| 522403 | 16052 | 16071 | TGAAATCTGAGTGCTGCTAA | 68 | 3508 |
| 522404 | 16053 | 16072 | TTGAAATCTGAGTGCTGCTA | 74 | 3509 |
| 522405 | 16054 | 16073 | GTTGAAATCTGAGTGCTGCT | 78 | 3510 |
| 522406 | 16083 | 16102 | GCACTAAATTAGGAAGCTGG | 77 | 3511 |
| 522407 | 16084 | 16103 | AGCACTAAATTAGGAAGCTG | 65 | 3512 |
| 522408 | 16289 | 16308 | CTGGGACATCTGGCCCAAAG | 72 | 3513 |
| 522409 | 16290 | 16309 | ACTGGGACATCTGGCCCAAA | 71 | 3514 |
| 522410 | 16291 | 16310 | CACTGGGACATCTGGCCCAA | 66 | 3515 |
| 522411 | 16292 | 16311 | CCACTGGGACATCTGGCCCA | 71 | 3516 |
| 522412 | 16294 | 16313 | GCCCACTGGGACATCTGGCC | 61 | 3517 |
| 522413 | 16295 | 16314 | GGCCCACTGGGACATCTGGC | 68 | 3518 |
| 522414 | 16306 | 16325 | CCTTAAAGCAGGGCCCACTG | 50 | 3519 |
| 522415 | 16307 | 16326 | TCCTTAAAGCAGGGCCCACT | 58 | 3520 |
| 522416 | 16308 | 16327 | ATCCTTAAAGCAGGGCCCAC | 67 | 3521 |
| 522417 | 16309 | 16328 | TATCCTTAAAGCAGGGCCCA | 63 | 3522 |
| 522418 | 16429 | 16448 | CACTGGTGCCTAAGAGCCCT | 70 | 3523 |
| 522419 | 16430 | 16449 | CCACTGGTGCCTAAGAGCCC | 63 | 3524 |
| 522420 | 16431 | 16450 | TCCACTGGTGCCTAAGAGCC | 61 | 3525 |
| 522421 | 16432 | 16451 | CTCCACTGGTGCCTAAGAGC | 73 | 3526 |
| 522422 | 16809 | 16828 | GAGGCTGAGTTCTGCTCCTG | 77 | 3527 |
| 522423 | 16810 | 16829 | AGAGGCTGAGTTCTGCTCCT | 59 | 3528 |
| 522424 | 16811 | 16830 | TAGAGGCTGAGTTCTGCTCC | 71 | 3529 |
| 522425 | 16812 | 16831 | CTAGAGGCTGAGTTCTGCTC | 60 | 3530 |
| 522426 | 16814 | 16833 | TGCTAGAGGCTGAGTTCTGC | 65 | 3531 |
| 522427 | 16815 | 16834 | CTGCTAGAGGCTGAGTTCTG | 71 | 3532 |
| 522428 | 16816 | 16835 | TCTGCTAGAGGCTGAGTTCT | 74 | 3533 |
| 522429 | 16817 | 16836 | ATCTGCTAGAGGCTGAGTTC | 67 | 3534 |
| 522430 | 16824 | 16843 | CTTGGGCATCTGCTAGAGGC | 69 | 3535 |
| 522431 | 16825 | 16844 | TCTTGGGCATCTGCTAGAGG | 66 | 3536 |
| 522432 | 16826 | 16845 | TTCTTGGGCATCTGCTAGAG | 65 | 3537 |
| 522433 | 16827 | 16846 | CTTCTTGGGCATCTGCTAGA | 62 | 3538 |
| 522434 | 16829 | 16848 | TGCTTCTTGGGCATCTGCTA | 71 | 3539 |
| 522435 | 16830 | 16849 | CTGCTTCTTGGGCATCTGCT | 81 | 3540 |
| 522436 | 16831 | 16850 | TCTGCTTCTTGGGCATCTGC | 80 | 3541 |
| 522437 | 16832 | 16851 | CTCTGCTTCTTGGGCATCTG | 82 | 3542 |
| 522438 | 16834 | 16853 | TCCTCTGCTTCTTGGGCATC | 67 | 3543 |
| 522439 | 16835 | 16854 | CTCCTCTGCTTCTTGGGCAT | 68 | 3544 |
| 413433 | 32431 | 32450 | GCCTGGACAAGTCCTGCCCA | 82 | 425 |

TABLE 52

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522440 | 16836 | 16855 | TCTCCTCTGCTTCTTGGGCA | 78 | 3545 |
| 522441 | 16897 | 16916 | CTTTCTAAGTACCCTTTACA | 37 | 3546 |
| 522442 | 16898 | 16917 | GCTTTCTAAGTACCCTTTAC | 71 | 3547 |
| 522443 | 16899 | 16918 | TGCTTTCTAAGTACCCTTTA | 62 | 3548 |
| 522444 | 16900 | 16919 | GTGCTTTCTAAGTACCCTTT | 85 | 3549 |
| 522445 | 16902 | 16921 | CAGTGCTTTCTAAGTACCCT | 86 | 3550 |
| 522446 | 17008 | 17027 | AGGGAAAGGTCTTCTCCAGC | 74 | 3551 |
| 522447 | 17009 | 17028 | GAGGGAAAGGTCTTCTCCAG | 67 | 3552 |
| 522448 | 17010 | 17029 | GGAGGGAAAGGTCTTCTCCA | 62 | 3553 |
| 522449 | 17011 | 17030 | AGGAGGGAAAGGTCTTCTCC | 60 | 3554 |
| 522450 | 17208 | 17227 | GTCTCATTCATCTGGGCCCT | 80 | 3555 |
| 522451 | 17209 | 17228 | TGTCTCATTCATCTGGGCCC | 65 | 3556 |
| 522452 | 17210 | 17229 | ATGTCTCATTCATCTGGGCC | 72 | 3557 |
| 522453 | 17270 | 17289 | CCCCTGTACTCAGCCCTTTC | 49 | 3558 |
| 522454 | 17271 | 17290 | ACCCCTGTACTCAGCCCTTT | 60 | 3559 |
| 522455 | 17272 | 17291 | CACCCCTGTACTCAGCCCTT | 51 | 3560 |
| 522456 | 17273 | 17292 | TCACCCCTGTACTCAGCCCT | 61 | 3561 |
| 522457 | 17275 | 17294 | TCTCACCCCTGTACTCAGCC | 70 | 3562 |
| 522458 | 17276 | 17295 | ATCTCACCCCTGTACTCAGC | 58 | 3563 |
| 522459 | 17277 | 17296 | CATCTCACCCCTGTACTCAG | 51 | 3564 |
| 522460 | 17278 | 17297 | CCATCTCACCCCTGTACTCA | 54 | 3565 |
| 522461 | 17329 | 17348 | AAGTCTTCCTTCTCCTCCAC | 65 | 3566 |

TABLE 52-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522462 | 17330 | 17349 | AAAGTCTTCCTTCTCCTCCA | 71 | 3567 |
| 522463 | 17331 | 17350 | GAAAGTCTTCCTTCTCCTCC | 75 | 3568 |
| 522464 | 17332 | 17351 | GGAAAGTCTTCCTTCTCCTC | 75 | 3569 |
| 522465 | 17451 | 17470 | CAGGTAGAGTTCTATTGCTT | 80 | 3570 |
| 522466 | 17452 | 17471 | CCAGGTAGAGTTCTATTGCT | 77 | 3571 |
| 522467 | 19361 | 19380 | GGCTACTGGCATTGCTCCTC | 74 | 3572 |
| 522468 | 19362 | 19381 | TGGCTACTGGCATTGCTCCT | 56 | 3573 |
| 522469 | 19363 | 19382 | GTGGCTACTGGCATTGCTCC | 68 | 3574 |
| 522470 | 19364 | 19383 | GGTGGCTACTGGCATTGCTC | 74 | 3575 |
| 522471 | 19909 | 19928 | ACATGCCTGAGGGCAGCAGT | 68 | 3576 |
| 522472 | 19910 | 19929 | CACATGCCTGAGGGCAGCAG | 69 | 3577 |
| 522473 | 19911 | 19930 | TCACATGCCTGAGGGCAGCA | 81 | 3578 |
| 522474 | 19912 | 19931 | CTCACATGCCTGAGGGCAGC | 79 | 3579 |
| 522475 | 19984 | 20003 | AATATCTGATATCAAAGTGA | 14 | 3580 |
| 522476 | 19985 | 20004 | CAATATCTGATATCAAAGTG | 14 | 3581 |
| 522477 | 19986 | 20005 | CCAATATCTGATATCAAAGT | 41 | 3582 |
| 522478 | 19987 | 20006 | CCCAATATCTGATATCAAAG | 74 | 3583 |
| 522479 | 19989 | 20008 | TGCCCAATATCTGATATCAA | 73 | 3584 |
| 522480 | 19990 | 20009 | TTGCCCAATATCTGATATCA | 65 | 3585 |
| 522481 | 20297 | 20316 | TTGCTTGAGGTCAGGGTGTG | 62 | 3586 |
| 522482 | 20298 | 20317 | CTTGCTTGAGGTCAGGGTGT | 72 | 3587 |
| 522483 | 20299 | 20318 | ACTTGCTTGAGGTCAGGGTG | 68 | 3588 |
| 522484 | 20300 | 20319 | CACTTGCTTGAGGTCAGGGT | 84 | 3589 |
| 522485 | 20302 | 20321 | ATCACTTGCTTGAGGTCAGG | 82 | 3590 |
| 522486 | 20303 | 20322 | AATCACTTGCTTGAGGTCAG | 77 | 3591 |
| 522487 | 20304 | 20323 | AAATCACTTGCTTGAGGTCA | 75 | 3592 |
| 522488 | 20305 | 20324 | AAAATCACTTGCTTGAGGTC | 71 | 3593 |
| 522489 | 20669 | 20688 | GGTACAAGTTTCTCCACCTA | 75 | 3594 |
| 522490 | 20670 | 20689 | AGGTACAAGTTTCTCCACCT | 74 | 3595 |
| 522491 | 20671 | 20690 | TAGGTACAAGTTTCTCCACC | 47 | 3596 |
| 522492 | 20672 | 20691 | CTAGGTACAAGTTTCTCCAC | 72 | 3597 |
| 522493 | 20828 | 20847 | ATAGCTGAGCAAATCCATAA | 63 | 3598 |
| 522494 | 20829 | 20848 | CATAGCTGAGCAAATCCATA | 73 | 3599 |
| 522495 | 20830 | 20849 | GCATAGCTGAGCAAATCCAT | 80 | 3600 |
| 522496 | 20831 | 20850 | TGCATAGCTGAGCAAATCCA | 72 | 3601 |
| 522497 | 20833 | 20852 | ACTGCATAGCTGAGCAAATC | 63 | 3602 |
| 522498 | 20834 | 20853 | TACTGCATAGCTGAGCAAAT | 67 | 3603 |
| 522499 | 20835 | 20854 | TTACTGCATAGCTGAGCAAA | 65 | 3604 |
| 522500 | 20836 | 20855 | TTTACTGCATAGCTGAGCAA | 65 | 3605 |
| 522501 | 20838 | 20857 | GGTTTACTGCATAGCTGAGC | 85 | 3606 |
| 522502 | 20839 | 20858 | AGGTTTACTGCATAGCTGAG | 65 | 3607 |
| 522503 | 20840 | 20859 | GAGGTTTACTGCATAGCTGA | 72 | 3608 |
| 522504 | 20841 | 20860 | AGAGGTTTACTGCATAGCTG | 75 | 3609 |
| 522505 | 20843 | 20862 | ATAGAGGTTTACTGCATAGC | 71 | 3610 |
| 522506 | 20844 | 20863 | CATAGAGGTTTACTGCATAG | 65 | 3611 |
| 522507 | 20956 | 20975 | ACTCTCTGCACACTCCCA | 62 | 3612 |
| 522508 | 20957 | 20976 | CACTCTCTGCACACTCCC | 61 | 3613 |
| 522509 | 20958 | 20977 | GCACTCTCTGCACACTCC | 80 | 3614 |
| 522510 | 20959 | 20978 | TGCACTCTCTGCACACTC | 76 | 3615 |
| 522511 | 21934 | 21953 | TGCTGATTACAAGCTGATTC | 64 | 3616 |
| 522512 | 21935 | 21954 | CTGCTGATTACAAGCTGATT | 67 | 3617 |
| 522513 | 21936 | 21955 | ACTGCTGATTACAAGCTGAT | 61 | 3618 |
| 522514 | 21937 | 21956 | AACTGCTGATTACAAGCTGA | 55 | 3619 |
| 522515 | 22152 | 22171 | TGGTGATAAGGCAGCAGTCT | 53 | 3620 |
| 522516 | 22153 | 22172 | ATGGTGATAAGGCAGCAGTC | 62 | 3621 |
| 413433 | 32431 | 32450 | GCCTGGACAAGTCCTGCCCA | 81 | 425 |

TABLE 53

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522517 | 22154 | 22173 | GATGGTGATAAGGCAGCAGT | 67 | 3622 |
| 522518 | 22155 | 22174 | AGATGGTGATAAGGCAGCAG | 71 | 3623 |
| 522519 | 22157 | 22176 | AGAGATGGTGATAAGGCAGC | 58 | 3624 |
| 522520 | 22158 | 22177 | CAGAGATGGTGATAAGGCAG | 38 | 3625 |
| 522521 | 22159 | 22178 | CCAGAGATGGTGATAAGGCA | 60 | 3626 |
| 522522 | 22160 | 22179 | CCCAGAGATGGTGATAAGGC | 67 | 3627 |
| 522523 | 23856 | 23875 | AGACTTGCCCAGCAACCCAT | 49 | 3628 |
| 522524 | 23857 | 23876 | CAGACTTGCCCAGCAACCCA | 58 | 3629 |

TABLE 53-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522525 | 23858 | 23877 | CCAGACTTGCCCAGCAACCC | 61 | 3630 |
| 522526 | 23859 | 23878 | TCCAGACTTGCCCAGCAACC | 57 | 3631 |
| 522527 | 24120 | 24139 | AAACCTAGGTTCAGACTTTG | 51 | 3632 |
| 522528 | 24121 | 24140 | CAAACCTAGGTTCAGACTTT | 48 | 3633 |
| 522529 | 24123 | 24142 | GTCAAACCTAGGTTCAGACT | 84 | 3634 |
| 522530 | 24125 | 24144 | GAGTCAAACCTAGGTTCAGA | 66 | 3635 |
| 522531 | 24126 | 24145 | AGAGTCAAACCTAGGTTCAG | 48 | 3636 |
| 522532 | 24127 | 24146 | AAGAGTCAAACCTAGGTTCA | 50 | 3637 |
| 522533 | 24128 | 24147 | GAAGAGTCAAACCTAGGTTC | 61 | 3638 |
| 522534 | 25019 | 25038 | GAGCATCCCCAATCCCTGCT | 72 | 3639 |
| 522535 | 25020 | 25039 | TGAGCATCCCCAATCCCTGC | 63 | 3640 |
| 522536 | 25021 | 25040 | TTGAGCATCCCCAATCCCTG | 56 | 3641 |
| 522537 | 25022 | 25041 | TTTGAGCATCCCCAATCCCT | 48 | 3642 |
| 522538 | 25024 | 25043 | ACTTTGAGCATCCCCAATCC | 42 | 3643 |
| 522539 | 25025 | 25044 | TACTTTGAGCATCCCCAATC | 53 | 3644 |
| 522540 | 25026 | 25045 | GTACTTTGAGCATCCCCAAT | 70 | 3645 |
| 522541 | 25027 | 25046 | TGTACTTTGAGCATCCCCAA | 68 | 3646 |
| 522542 | 25029 | 25048 | AGTGTACTTTGAGCATCCCC | 77 | 3647 |
| 522543 | 25030 | 25049 | AAGTGTACTTTGAGCATCCC | 70 | 3648 |
| 522544 | 25031 | 25050 | CAAGTGTACTTTGAGCATCC | 73 | 3649 |
| 522545 | 25032 | 25051 | CCAAGTGTACTTTGAGCATC | 76 | 3650 |
| 522546 | 25034 | 25053 | CTCCAAGTGTACTTTGAGCA | 82 | 3651 |
| 522547 | 25070 | 25089 | CAGAGGTTCAACATCCAATT | 74 | 3652 |
| 522548 | 25071 | 25090 | ACAGAGGTTCAACATCCAAT | 74 | 3653 |
| 522549 | 25072 | 25091 | GACAGAGGTTCAACATCCAA | 73 | 3654 |
| 522550 | 25073 | 25092 | GGACAGAGGTTCAACATCCA | 82 | 3655 |
| 522551 | 25076 | 25095 | CAAGGACAGAGGTTCAACAT | 53 | 3656 |
| 522552 | 25077 | 25096 | CCAAGGACAGAGGTTCAACA | 72 | 3657 |
| 522553 | 25078 | 25097 | GCCAAGGACAGAGGTTCAAC | 84 | 3658 |
| 522554 | 25079 | 25098 | GGCCAAGGACAGAGGTTCAA | 82 | 3659 |
| 522555 | 25081 | 25100 | GAGGCCAAGGACAGAGGTTC | 80 | 3660 |
| 522556 | 25082 | 25101 | TGAGGCCAAGGACAGAGGTT | 82 | 3661 |
| 522557 | 25083 | 25102 | GTGAGGCCAAGGACAGAGGT | 67 | 3662 |
| 522558 | 25084 | 25103 | TGTGAGGCCAAGGACAGAGG | 63 | 3663 |
| 522559 | 25086 | 25105 | TCTGTGAGGCCAAGGACAGA | 54 | 3664 |
| 522560 | 25087 | 25106 | GTCTGTGAGGCCAAGGACAG | 58 | 3665 |
| 522561 | 25088 | 25107 | TGTCTGTGAGGCCAAGGACA | 71 | 3666 |
| 522562 | 25089 | 25108 | CTGTCTGTGAGGCCAAGGAC | 74 | 3667 |
| 522563 | 25184 | 25203 | AGTCTCTCATAATTGCCAGT | 69 | 3668 |
| 522564 | 25185 | 25204 | AAGTCTCTCATAATTGCCAG | 69 | 3669 |
| 522565 | 25186 | 25205 | GAAGTCTCTCATAATTGCCA | 71 | 3670 |
| 522566 | 25187 | 25206 | GGAAGTCTCTCATAATTGCC | 46 | 3671 |
| 522567 | 25189 | 25208 | TGGGAAGTCTCTCATAATTG | 37 | 3672 |
| 522568 | 25190 | 25209 | TTGGGAAGTCTCTCATAATT | 22 | 3673 |
| 522569 | 25191 | 25210 | CTTGGGAAGTCTCTCATAAT | 23 | 3674 |
| 522570 | 25192 | 25211 | CCTTGGGAAGTCTCTCATAA | 35 | 3675 |
| 522571 | 25194 | 25213 | GGCCTTGGGAAGTCTCTCAT | 51 | 3676 |
| 522572 | 25195 | 25214 | AGGCCTTGGGAAGTCTCTCA | 55 | 3677 |
| 522573 | 25196 | 25215 | TAGGCCTTGGGAAGTCTCTC | 61 | 3678 |
| 522574 | 25197 | 25216 | CTAGGCCTTGGGAAGTCTCT | 43 | 3679 |
| 522575 | 25242 | 25261 | CATTTTGGAGACCACATGAA | 31 | 3680 |
| 522576 | 25243 | 25262 | TCATTTTGGAGACCACATGA | 41 | 3681 |
| 522577 | 25244 | 25263 | GTCATTTTGGAGACCACATG | 60 | 3682 |
| 522578 | 25245 | 25264 | GGTCATTTTGGAGACCACAT | 70 | 3683 |
| 522579 | 25268 | 25287 | AATGGGAATGGTATCGCACT | 84 | 3684 |
| 522580 | 25269 | 25288 | CAATGGGAATGGTATCGCAC | 87 | 3685 |
| 522581 | 25270 | 25289 | ACAATGGGAATGGTATCGCA | 85 | 3686 |
| 522582 | 25271 | 25290 | CACAATGGGAATGGTATCGC | 86 | 3687 |
| 522583 | 25377 | 25396 | AGCTATAGAATCAGACAGAC | 53 | 3688 |
| 522584 | 25378 | 25397 | CAGCTATAGAATCAGACAGA | 56 | 3689 |
| 522585 | 25379 | 25398 | TCAGCTATAGAATCAGACAG | 48 | 3690 |
| 522586 | 25381 | 25400 | CATCAGCTATAGAATCAGAC | 64 | 3691 |
| 522587 | 25783 | 25802 | GCACTTGATCTGGGACCCAA | 87 | 3692 |
| 522588 | 25784 | 25803 | AGCACTTGATCTGGGACCCA | 88 | 3693 |
| 522589 | 25785 | 25804 | GAGCACTTGATCTGGGACCC | 86 | 3694 |
| 522590 | 25786 | 25805 | AGAGCACTTGATCTGGGACC | 76 | 3695 |
| 522591 | 25788 | 25807 | GTAGAGCACTTGATCTGGGA | 74 | 3696 |
| 522592 | 25789 | 25808 | GGTAGAGCACTTGATCTGGG | 79 | 3697 |
| 522593 | 25790 | 25809 | GGGTAGAGCACTTGATCTGG | 61 | 3698 |
| 413433 | 32431 | 32450 | GCCTGGACAAGTCCTGCCCA | 84 | 425 |

TABLE 54

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522594 | 25842 | 25861 | AACTATCACACCACCTCCCA | 44 | 3699 |
| 522595 | 25843 | 25862 | GAACTATCACACCACCTCCC | 42 | 3700 |
| 522596 | 25844 | 25863 | GGAACTATCACACCACCTCC | 47 | 3701 |
| 522591 | 25845 | 25864 | GGGAACTATCACACCACCTC | 61 | 3702 |
| 522598 | 25847 | 25866 | ATGGGAACTATCACACCACC | 64 | 3703 |
| 522599 | 25848 | 25867 | AATGGGAACTATCACACCAC | 33 | 3704 |
| 522600 | 25849 | 25868 | AAATGGGAACTATCACACCA | 37 | 3705 |
| 522601 | 25850 | 25869 | TAAATGGGAACTATCACACC | 16 | 3706 |
| 522602 | 25901 | 25920 | TGACCTTGGGCAAGTTACCT | 74 | 3707 |
| 522603 | 25902 | 25921 | GTGACCTTGGGCAAGTTACC | 76 | 3708 |
| 522604 | 25903 | 25922 | TGTGACCTTGGGCAAGTTAC | 77 | 3709 |
| 522605 | 25904 | 25923 | GTGTGACCTTGGGCAAGTTA | 78 | 3710 |
| 522606 | 25906 | 25925 | CTGTGTGACCTTGGGCAAGT | 80 | 3711 |
| 522607 | 25907 | 25926 | TCTGTGTGACCTTGGGCAAG | 81 | 3712 |
| 522608 | 25908 | 25927 | ATCTGTGTGACCTTGGGCAA | 81 | 3713 |
| 522609 | 25909 | 25928 | AATCTGTGTGACCTTGGGCA | 87 | 3714 |
| 522610 | 25911 | 25930 | CAAATCTGTGTGACCTTGGG | 85 | 3715 |
| 522611 | 25912 | 25931 | TCAAATCTGTGTGACCTTGG | 69 | 3716 |
| 522612 | 25913 | 25932 | TTCAAATCTGTGTGACCTTG | 75 | 3717 |
| 522613 | 25914 | 25933 | ATTCAAATCTGTGTGACCTT | 79 | 3718 |
| 522614 | 25916 | 25935 | GGATTCAAATCTGTGTGACC | 75 | 3719 |
| 522615 | 25917 | 25936 | GGGATTCAAATCTGTGTGAC | 54 | 3720 |
| 522616 | 25918 | 25937 | AGGGATTCAAATCTGTGTGA | 57 | 3721 |
| 522617 | 25919 | 25938 | CAGGGATTCAAATCTGTGTG | 63 | 3722 |
| 522618 | 25951 | 25970 | GGGAAAGGCACAGGCTTTGG | 81 | 3723 |
| 522619 | 25952 | 25971 | TGGGAAAGGCACAGGCTTTG | 70 | 3724 |
| 522620 | 25954 | 25973 | TGTGGGAAAGGCACAGGCTT | 66 | 3725 |
| 522621 | 26006 | 26025 | AGGCAAAGTAACATACCTGC | 87 | 3726 |
| 522622 | 26007 | 26026 | AAGGCAAAGTAACATACCTG | 76 | 3727 |
| 522623 | 26008 | 26027 | TAAGGCAAAGTAACATACCT | 62 | 3728 |
| 522624 | 26009 | 26028 | TTAAGGCAAAGTAACATACC | 69 | 3729 |
| 522625 | 26011 | 26030 | CCTTAAGGCAAAGTAACATA | 73 | 3730 |
| 522626 | 26012 | 26031 | ACCTTAAGGCAAAGTAACAT | 45 | 3731 |
| 522627 | 26166 | 26185 | ATTTCTTATCTTCAATCCTC | 84 | 3732 |
| 522628 | 26167 | 26186 | CATTTCTTATCTTCAATCCT | 64 | 3733 |
| 522629 | 26168 | 26187 | TCATTTCTTATCTTCAATCC | 62 | 3734 |
| 522630 | 26169 | 26188 | CTCATTTCTTATCTTCAATC | 81 | 3735 |
| 522631 | 26171 | 26190 | CTCTCATTTCTTATCTTCAA | 86 | 3736 |
| 522632 | 26172 | 26191 | GCTCTCATTTCTTATCTTCA | 90 | 3737 |
| 522633 | 26173 | 26192 | TGCTCTCATTTCTTATCTTC | 78 | 3738 |
| 522634 | 26174 | 26193 | GTGCTCTCATTTCTTATCTT | 80 | 3739 |
| 522635 | 26176 | 26195 | AGGTGCTCTCATTTCTTATC | 78 | 3740 |
| 522636 | 26177 | 26196 | CAGGTGCTCTCATTTCTTAT | 73 | 3741 |
| 522637 | 26178 | 26197 | CCAGGTGCTCTCATTTCTTA | 74 | 3742 |
| 522638 | 26179 | 26198 | GCCAGGTGCTCTCATTTCTT | 84 | 3743 |
| 522639 | 26201 | 26220 | GCCCATCATGACCAGGCCCT | 60 | 3744 |
| 522640 | 26202 | 26221 | GGCCCATCATGACCAGGCCC | 21 | 3745 |
| 522641 | 26203 | 26222 | GGGCCCATCATGACCAGGCC | 41 | 3746 |
| 522642 | 26301 | 26320 | CAGGCCTCGGGAAGCACCTG | 71 | 3747 |
| 522643 | 26302 | 26321 | GCAGGCCTCGGGAAGCACCT | 86 | 3748 |
| 522644 | 26303 | 26322 | AGCAGGCCTCGGGAAGCACC | 77 | 3749 |
| 522645 | 26304 | 26323 | GAGCAGGCCTCGGGAAGCAC | 80 | 3750 |
| 522646 | 26354 | 26373 | CAGAAAAGCAACCAAAGCA | 31 | 3751 |
| 522647 | 26355 | 26374 | GCAGAAAAGCAACCAAAGC | 31 | 3752 |
| 522648 | 26356 | 26375 | TGCAGAAAAGCAACCAAAG | 34 | 3753 |
| 522649 | 26357 | 26376 | CTGCAGAAAAGCAACCAAA | 52 | 3754 |
| 522650 | 26359 | 26378 | ACCTGCAGAAAAGCAACCA | 32 | 3755 |
| 522651 | 26360 | 26379 | GACCTGCAGAAAAGCAACC | 24 | 3756 |
| 522652 | 26361 | 26380 | AGACCTGCAGAAAAGCAAC | 17 | 3757 |
| 522653 | 26362 | 26381 | CAGACCTGCAGAAAAGCAA | 23 | 3758 |
| 522654 | 26386 | 26405 | ACCTAAGGAGTGAGGGTATC | 46 | 3759 |
| 522655 | 26387 | 26406 | AACCTAAGGAGTGAGGGTAT | 58 | 3760 |
| 522656 | 26388 | 26407 | CAACCTAAGGAGTGAGGGTA | 59 | 3761 |
| 522657 | 26389 | 26408 | GCAACCTAAGGAGTGAGGGT | 73 | 3762 |
| 522658 | 27639 | 27658 | TGCTTGCCAGGTGAGCTTCT | 76 | 3763 |
| 522659 | 27640 | 27659 | TTGCTTGCCAGGTGAGCTTC | 65 | 3764 |
| 522660 | 27641 | 27660 | TTTGCTTGCCAGGTGAGCTT | 65 | 3765 |
| 522661 | 27642 | 27661 | CTTTGCTTGCCAGGTGAGCT | 77 | 3766 |
| 522662 | 27644 | 27663 | GTCTTTGCTTGCCAGGTGAG | 74 | 3767 |
| 522663 | 27645 | 27664 | GGTCTTTGCTTGCCAGGTGA | 75 | 3768 |
| 522664 | 27767 | 27786 | CCTTGTATTAAATACTCTAA | 59 | 3769 |

TABLE 54-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522665 | 27768 | 27787 | ACCTTGTATTAAATACTCTA | 57 | 3770 |
| 522666 | 27769 | 27788 | CACCTTGTATTAAATACTCT | 78 | 3771 |
| 522667 | 27770 | 27789 | GCACCTTGTATTAAATACTC | 83 | 3772 |
| 522668 | 27772 | 27791 | ATGCACCTTGTATTAAATAC | 69 | 3773 |
| 522669 | 27773 | 27792 | AATGCACCTTGTATTAAATA | 41 | 3774 |
| 522670 | 27774 | 27793 | CAATGCACCTTGTATTAAAT | 59 | 3775 |
| 413433 | 32431 | 32450 | GCCTGGACAAGTCCTGCCCA | 83 | 425 |

TABLE 55

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522671 | 27775 | 27794 | CCAATGCACCTTGTATTAAA | 83 | 3776 |
| 522672 | 27777 | 27796 | ATCCAATGCACCTTGTATTA | 85 | 3777 |
| 522673 | 27778 | 27797 | AATCCAATGCACCTTGTATT | 77 | 3778 |
| 522674 | 27779 | 27798 | AAATCCAATGCACCTTGTAT | 80 | 3779 |
| 522675 | 27780 | 27799 | GAAATCCAATGCACCTTGTA | 85 | 3780 |
| 522676 | 27782 | 27801 | TTGAAATCCAATGCACCTTG | 86 | 3781 |
| 522677 | 27783 | 27802 | TTTGAAATCCAATGCACCTT | 87 | 3782 |
| 522678 | 27784 | 27803 | CTTTGAAATCCAATGCACCT | 82 | 3783 |
| 522679 | 27785 | 27804 | CCTTTGAAATCCAATGCACC | 88 | 3784 |
| 522680 | 27787 | 27806 | TTCCTTTGAAATCCAATGCA | 82 | 3785 |
| 522681 | 27788 | 27807 | TTTCCTTTGAAATCCAATGC | 82 | 3786 |
| 522682 | 27789 | 27808 | GTTTCCTTTGAAATCCAATG | 87 | 3787 |
| 522683 | 27790 | 27809 | AGTTTCCTTTGAAATCCAAT | 82 | 3788 |
| 522684 | 27850 | 27869 | CTGTTACTACATGTCTAATC | 61 | 3789 |
| 522685 | 27851 | 27870 | CCTGTTACTACATGTCTAAT | 51 | 3790 |
| 522686 | 27852 | 27871 | ACCTGTTACTACATGTCTAA | 68 | 3791 |
| 522687 | 27853 | 27872 | CACCTGTTACTACATGTCTA | 82 | 3792 |
| 522688 | 27855 | 27874 | GGCACCTGTTACTACATGTC | 90 | 3793 |
| 522689 | 27856 | 27875 | AGGCACCTGTTACTACATGT | 88 | 3794 |
| 522690 | 27857 | 27876 | AAGGCACCTGTTACTACATG | 82 | 3795 |
| 522691 | 27858 | 27877 | AAAGGCACCTGTTACTACAT | 80 | 3796 |
| 522692 | 28027 | 28046 | ATCACAGAATTATCAGCAGT | 84 | 3797 |

TABLE 55-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522693 | 28028 | 28047 | AATCACAGAATTATCAGCAG | 79 | 3798 |
| 522694 | 28029 | 28048 | AAATCACAGAATTATCAGCA | 86 | 3799 |
| 522695 | 28030 | 28049 | TAAATCACAGAATTATCAGC | 64 | 3800 |
| 522696 | 28128 | 28147 | CACACAATATCCATGGACTT | 80 | 3801 |
| 522697 | 28129 | 28148 | ACACACAATATCCATGGACT | 88 | 3802 |
| 522698 | 28130 | 28149 | GACACACAATATCCATGGAC | 89 | 3803 |
| 522699 | 28131 | 28150 | TGACACACAATATCCATGGA | 75 | 3804 |
| 522700 | 28133 | 28152 | CCTGACACACAATATCCATG | 80 | 3805 |
| 522701 | 28134 | 28153 | GCCTGACACACAATATCCAT | 79 | 3806 |
| 522702 | 28135 | 28154 | AGCCTGACACACAATATCCA | 72 | 3807 |
| 522703 | 28460 | 28479 | CATGAGAAGCTTAGAAGGCC | 59 | 3808 |
| 522704 | 28462 | 28481 | CTCATGAGAAGCTTAGAAGG | 63 | 3809 |
| 522705 | 28463 | 28482 | GCTCATGAGAAGCTTAGAAG | 83 | 3810 |
| 522706 | 28465 | 28484 | GAGCTCATGAGAAGCTTAGA | 70 | 3811 |
| 522707 | 28466 | 28485 | TGAGCTCATGAGAAGCTTAG | 60 | 3812 |
| 522708 | 28467 | 28486 | CTGAGCTCATGAGAAGCTTA | 69 | 3813 |
| 522709 | 28468 | 28487 | GCTGAGCTCATGAGAAGCTT | 80 | 3814 |
| 522710 | 28470 | 28489 | TTGCTGAGCTCATGAGAAGC | 74 | 3815 |
| 522711 | 28471 | 28490 | GTTGCTGAGCTCATGAGAAG | 66 | 3816 |
| 522712 | 28472 | 28491 | TGTTGCTGAGCTCATGAGAA | 60 | 3817 |
| 522713 | 28473 | 28492 | CTGTTGCTGAGCTCATGAGA | 65 | 3818 |
| 522714 | 28475 | 28494 | CACTGTTGCTGAGCTCATGA | 73 | 3819 |
| 522715 | 28476 | 28495 | CCACTGTTGCTGAGCTCATG | 86 | 3820 |
| 522716 | 28477 | 28496 | ACCACTGTTGCTGAGCTCAT | 86 | 3821 |
| 522717 | 28478 | 28497 | AACCACTGTTGCTGAGCTCA | 87 | 3822 |
| 522718 | 28480 | 28499 | AAAACCACTGTTGCTGAGCT | 80 | 3823 |
| 522719 | 28481 | 28500 | AAAACCACTGTTGCTGAGC | 83 | 3824 |
| 522720 | 28482 | 28501 | TAAAACCACTGTTGCTGAG | 69 | 3825 |
| 522721 | 28483 | 28502 | GTAAAACCACTGTTGCTGA | 69 | 3826 |
| 522722 | 28516 | 28535 | TCTGGTTCCATGCTCTTAGG | 70 | 3827 |
| 522723 | 28517 | 28536 | CTCTGGTTCCATGCTCTTAG | 74 | 3828 |
| 522724 | 28518 | 28537 | GCTCTGGTTCCATGCTCTTA | 78 | 3829 |
| 522725 | 28519 | 28538 | GGCTCTGGTTCCATGCTCTT | 75 | 3830 |
| 522726 | 28521 | 28540 | CAGGCTCTGGTTCCATGCTC | 73 | 3831 |
| 522727 | 28522 | 28541 | ACAGGCTCTGGTTCCATGCT | 78 | 3832 |

TABLE 55-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522728 | 28523 | 28542 | AACAGGCTCTGGTTCCATGC | 78 | 3833 |
| 522729 | 28581 | 28600 | TGAACTAAATCCACCAAATG | 22 | 3834 |
| 522730 | 28582 | 28601 | ATGAACTAAATCCACCAAAT | 46 | 3835 |
| 522731 | 28583 | 28602 | GATGAACTAAATCCACCAAA | 46 | 3836 |
| 522732 | 28584 | 28603 | GGATGAACTAAATCCACCAA | 67 | 3837 |
| 522733 | 28586 | 28605 | AAGGATGAACTAAATCCACC | 65 | 3838 |
| 522734 | 28587 | 28606 | AAAGGATGAACTAAATCCAC | 43 | 3839 |
| 522735 | 28588 | 28607 | AAAAGGATGAACTAAATCCA | 33 | 3840 |
| 522736 | 28589 | 28608 | CAAAAGGATGAACTAAATCC | 16 | 3841 |
| 522737 | 28803 | 28822 | AGAGACTGAATTCTAGCCTG | 59 | 3842 |
| 522738 | 28804 | 28823 | CAGAGACTGAATTCTAGCCT | 67 | 3843 |
| 522739 | 28805 | 28824 | CCAGAGACTGAATTCTAGCC | 67 | 3844 |
| 522740 | 28806 | 28825 | TCCAGAGACTGAATTCTAGC | 77 | 3845 |
| 522741 | 28808 | 28827 | TATCCAGAGACTGAATTCTA | 52 | 3846 |
| 522742 | 28809 | 28828 | GTATCCAGAGACTGAATTCT | 46 | 3847 |
| 522743 | 28810 | 28829 | GGTATCCAGAGACTGAATTC | 50 | 3848 |
| 522744 | 28811 | 28830 | GGGTATCCAGAGACTGAATT | 65 | 3849 |
| 522745 | 29011 | 29030 | GTTTAGGCTATGGTCTGAGC | 90 | 3850 |
| 522746 | 29012 | 29031 | GGTTTAGGCTATGGTCTGAG | 78 | 3851 |
| 522747 | 29013 | 29032 | AGGTTTAGGCTATGGTCTGA | 71 | 3852 |
| 413433 | 32431 | 32450 | GCCTGGACAAGTCCTGCCCA | 84 | 425 |

TABLE 56

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522748 | 29014 | 29033 | GAGGTTTAGGCTATGGTCTG | 71 | 3853 |
| 522749 | 29016 | 29035 | ATGAGGTTTAGGCTATGGTC | 67 | 3854 |
| 522750 | 29045 | 29064 | GGATGCTCCAGGTGGGCCAG | 59 | 3855 |
| 522751 | 29046 | 29065 | TGGATGCTCCAGGTGGGCCA | 52 | 3856 |
| 522752 | 29047 | 29066 | GTGGATGCTCCAGGTGGGCC | 57 | 3857 |
| 522753 | 29048 | 29067 | GGTGGATGCTCCAGGTGGGC | 52 | 3858 |
| 522754 | 29140 | 29159 | GTCTGCCTGATTCCCTTTCT | 75 | 3859 |
| 522755 | 29141 | 29160 | AGTCTGCCTGATTCCCTTTC | 58 | 3860 |
| 522756 | 29142 | 29161 | CAGTCTGCCTGATTCCCTTT | 59 | 3861 |
| 522757 | 29143 | 29162 | GCAGTCTGCCTGATTCCCTT | 85 | 3862 |
| 522758 | 29145 | 29164 | CAGCAGTCTGCCTGATTCCC | 79 | 3863 |
| 522759 | 29146 | 29165 | TCAGCAGTCTGCCTGATTCC | 72 | 3864 |
| 522760 | 29147 | 29166 | TTCAGCAGTCTGCCTGATTC | 61 | 3865 |
| 522761 | 29148 | 29167 | GTTCAGCAGTCTGCCTGATT | 71 | 3866 |
| 522762 | 29150 | 29169 | CTGTTCAGCAGTCTGCCTGA | 55 | 3867 |
| 522763 | 29151 | 29170 | ACTGTTCAGCAGTCTGCCTG | 62 | 3868 |
| 522764 | 29152 | 29171 | TACTGTTCAGCAGTCTGCCT | 64 | 3869 |
| 522765 | 29153 | 29172 | TTACTGTTCAGCAGTCTGCC | 61 | 3870 |
| 522766 | 29155 | 29174 | ACTTACTGTTCAGCAGTCTG | 73 | 3871 |
| 522767 | 29156 | 29175 | TACTTACTGTTCAGCAGTCT | 75 | 3872 |
| 522768 | 29157 | 29176 | ATACTTACTGTTCAGCAGTC | 74 | 3873 |
| 522769 | 29158 | 29177 | CATACTTACTGTTCAGCAGT | 74 | 3874 |
| 522770 | 29160 | 29179 | GTCATACTTACTGTTCAGCA | 89 | 3875 |
| 522771 | 29161 | 29180 | AGTCATACTTACTGTTCAGC | 74 | 3876 |
| 522772 | 29162 | 29181 | AAGTCATACTTACTGTTCAG | 39 | 3877 |
| 522773 | 29163 | 29182 | AAAGTCATACTTACTGTTCA | 43 | 3878 |
| 522774 | 29194 | 29213 | TGGTGAATAGCTATGTCTAA | 54 | 3879 |
| 522775 | 29195 | 29214 | TTGGTGAATAGCTATGTCTA | 58 | 3880 |
| 522776 | 29196 | 29215 | CTTGGTGAATAGCTATGTCT | 71 | 3881 |
| 522777 | 29197 | 29216 | GCTTGGTGAATAGCTATGTC | 77 | 3882 |
| 522778 | 29199 | 29218 | TAGCTTGGTGAATAGCTATG | 70 | 3883 |
| 522779 | 29200 | 29219 | GTAGCTTGGTGAATAGCTAT | 50 | 3884 |
| 522780 | 29201 | 29220 | GGTAGCTTGGTGAATAGCTA | 71 | 3885 |
| 522781 | 29243 | 29262 | AGCCTACAAGAGCCTGTTAA | 39 | 3886 |
| 522782 | 29244 | 29263 | CAGCCTACAAGAGCCTGTTA | 67 | 3887 |
| 522783 | 29245 | 29264 | GCAGCCTACAAGAGCCTGTT | 82 | 3888 |
| 522784 | 29246 | 29265 | TGCAGCCTACAAGAGCCTGT | 82 | 3889 |
| 522785 | 29248 | 29267 | TGTGCAGCCTACAAGAGCCT | 64 | 3890 |
| 522786 | 29249 | 29268 | ATGTGCAGCCTACAAGAGCC | 59 | 3891 |
| 522787 | 29250 | 29269 | CATGTGCAGCCTACAAGAGC | 39 | 3892 |
| 522788 | 29251 | 29270 | GCATGTGCAGCCTACAAGAG | 64 | 3893 |
| 522789 | 29253 | 29272 | AAGCATGTGCAGCCTACAAG | 70 | 3894 |
| 522790 | 29254 | 29273 | GAAGCATGTGCAGCCTACAA | 66 | 3895 |

TABLE 56-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522791 | 29255 | 29274 | GGAAGCATGTGCAGCCTACA | 78 | 3896 |
| 522792 | 29256 | 29275 | GGGAAGCATGTGCAGCCTAC | 69 | 3897 |
| 522793 | 29258 | 29277 | TAGGGAAGCATGTGCAGCCT | 74 | 3898 |
| 522794 | 29259 | 29278 | CTAGGGAAGCATGTGCAGCC | 72 | 3899 |
| 522795 | 29260 | 29279 | TCTAGGGAAGCATGTGCAGC | 65 | 3900 |
| 522796 | 29261 | 29280 | TTCTAGGGAAGCATGTGCAG | 61 | 3901 |
| 522797 | 29263 | 29282 | GTTTCTAGGGAAGCATGTGC | 72 | 3902 |
| 522798 | 29264 | 29283 | AGTTTCTAGGGAAGCATGTG | 40 | 3903 |
| 522799 | 29265 | 29284 | AAGTTTCTAGGGAAGCATGT | 46 | 3904 |
| 522800 | 29266 | 29285 | CAAGTTTCTAGGGAAGCATG | 42 | 3905 |
| 522801 | 29362 | 29381 | TACAACTCTCTTGTTGGGAG | 70 | 3906 |
| 522802 | 29363 | 29382 | GTACAACTCTCTTGTTGGGA | 73 | 3907 |
| 522803 | 29364 | 29383 | GGTACAACTCTCTTGTTGGG | 63 | 3908 |
| 522804 | 29365 | 29384 | GGGTACAACTCTCTTGTTGG | 57 | 3909 |
| 522805 | 29367 | 29386 | CAGGGTACAACTCTCTTGTT | 64 | 3910 |
| 522806 | 29368 | 29387 | ACAGGGTACAACTCTCTTGT | 57 | 3911 |
| 522807 | 29369 | 29388 | AACAGGGTACAACTCTCTTG | 85 | 3912 |
| 522808 | 29370 | 29389 | AAACAGGGTACAACTCTCTT | 63 | 3913 |
| 522809 | 29372 | 29391 | AAAAACAGGGTACAACTCTC | 62 | 3914 |
| 522810 | 29373 | 29392 | TAAAAACAGGGTACAACTCT | 32 | 3915 |
| 522811 | 29374 | 29393 | CTAAAAACAGGGTACAACTC | 21 | 3916 |
| 522812 | 29375 | 29394 | GCTAAAAACAGGGTACAACT | 31 | 3917 |
| 522813 | 29476 | 29495 | TGTAGACTCTCCATGAGCCT | 65 | 3918 |
| 522814 | 29477 | 29496 | ATGTAGACTCTCCATGAGCC | 45 | 3919 |
| 522815 | 29478 | 29497 | GATGTAGACTCTCCATGAGC | 25 | 3920 |
| 522816 | 29479 | 29498 | GGATGTAGACTCTCCATGAG | 42 | 3921 |
| 522817 | 30968 | 30987 | TAAGCTAGGCACACCCAGGG | 43 | 3922 |
| 522818 | 30969 | 30988 | CTAAGCTAGGCACACCCAGG | 23 | 3923 |
| 522819 | 30970 | 30989 | ACTAAGCTAGGCACACCCAG | 33 | 3924 |
| 522820 | 30971 | 30990 | CACTAAGCTAGGCACACCCA | 48 | 3925 |
| 522821 | 30973 | 30992 | GGCACTAAGCTAGGCACACC | 78 | 3926 |
| 522822 | 30975 | 30994 | GTGGCACTAAGCTAGGCACA | 69 | 3927 |
| 522823 | 30976 | 30995 | TGTGGCACTAAGCTAGGCAC | 66 | 3928 |
| 522824 | 30978 | 30997 | ACTGTGGCACTAAGCTAGGC | 69 | 3929 |
| 413433 | 32431 | 32450 | GCCTGGACAAGTCCTGCCCA | 85 | 425 |

TABLE 57

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522825 | 30979 | 30998 | TACTGTGGCACTAAGCTAGG | 53 | 3930 |
| 522826 | 30980 | 30999 | TTACTGTGGCACTAAGCTAG | 36 | 3931 |
| 522827 | 30981 | 31000 | TTTACTGTGGCACTAAGCTA | 40 | 3932 |
| 522828 | 30983 | 31002 | TGTTTACTGTGGCACTAAGC | 59 | 3933 |
| 522829 | 30984 | 31003 | GTGTTTACTGTGGCACTAAG | 68 | 3934 |
| 522830 | 30985 | 31004 | AGTGTTTACTGTGGCACTAA | 67 | 3935 |
| 522831 | 30986 | 31005 | GAGTGTTTACTGTGGCACTA | 72 | 3936 |
| 522832 | 31770 | 31789 | ATGGATACTCAGAAGAGCAG | 34 | 3937 |
| 522833 | 31771 | 31790 | GATGGATACTCAGAAGAGCA | 46 | 3938 |
| 522834 | 31793 | 31812 | ACCTCAGGGCTGGCCCAAAG | 47 | 3939 |
| 522835 | 31794 | 31813 | GACCTCAGGGCTGGCCCAAA | 67 | 3940 |
| 522836 | 31795 | 31814 | GGACCTCAGGGCTGGCCCAA | 66 | 3941 |
| 522837 | 31796 | 31815 | AGGACCTCAGGGCTGGCCCA | 68 | 3942 |
| 522838 | 31798 | 31817 | TCAGGACCTCAGGGCTGGCC | 78 | 3943 |
| 522839 | 31799 | 31818 | GTCAGGACCTCAGGGCTGGC | 66 | 3944 |
| 522840 | 31800 | 31819 | TGTCAGGACCTCAGGGCTGG | 53 | 3945 |
| 522841 | 31801 | 31820 | CTGTCAGGACCTCAGGGCTG | 49 | 3946 |
| 522842 | 31933 | 31952 | GAGTTATCCTCAATTCACCA | 74 | 3947 |
| 522843 | 31934 | 31953 | AGAGTTATCCTCAATTCACC | 59 | 3948 |
| 522844 | 31936 | 31955 | CCAGAGTTATCCTCAATTCA | 71 | 3949 |
| 522845 | 31938 | 31957 | TGCCAGAGTTATCCTCAATT | 52 | 3950 |
| 522846 | 31939 | 31958 | CTGCCAGAGTTATCCTCAAT | 62 | 3951 |
| 522847 | 31940 | 31959 | CCTGCCAGAGTTATCCTCAA | 64 | 3952 |
| 522848 | 31941 | 31960 | TCCTGCCAGAGTTATCCTCA | 68 | 3953 |
| 522849 | 31943 | 31962 | GATCCTGCCAGAGTTATCCT | 69 | 3954 |
| 522850 | 31944 | 31963 | GGATCCTGCCAGAGTTATCC | 62 | 3955 |
| 522851 | 31945 | 31964 | AGGATCCTGCCAGAGTTATC | 45 | 3956 |
| 522852 | 31946 | 31965 | CAGGATCCTGCCAGAGTTAT | 60 | 3957 |
| 522853 | 32116 | 32135 | CAGCAAATATACACCACCCT | 70 | 3958 |
| 522854 | 32117 | 32136 | ACAGCAAATATACACCACCC | 66 | 3959 |
| 522855 | 32118 | 32137 | AACAGCAAATATACACCACC | 56 | 3960 |
| 522856 | 32119 | 32138 | CAACAGCAAATATACACCAC | 66 | 3961 |
| 522857 | 32121 | 32140 | CACAACAGCAAATATACACC | 70 | 3962 |
| 522858 | 32122 | 32141 | TCACAACAGCAAATATACAC | 55 | 3963 |
| 522859 | 32123 | 32142 | CTCACAACAGCAAATATACA | 41 | 3964 |
| 522860 | 32124 | 32143 | ACTCACAACAGCAAATATAC | 48 | 3965 |

TABLE 57-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522861 | 32126 | 32145 | TGACTCACAACAGCAAATAT | 21 | 3966 |
| 522862 | 32127 | 32146 | CTGACTCACAACAGCAAATA | 33 | 3967 |
| 522863 | 32128 | 32147 | ACTGACTCACAACAGCAAAT | 44 | 3968 |
| 522864 | 32129 | 32148 | CACTGACTCACAACAGCAAA | 54 | 3969 |
| 522865 | 32131 | 32150 | GTCACTGACTCACAACAGCA | 85 | 3970 |
| 522866 | 32132 | 32151 | AGTCACTGACTCACAACAGC | 80 | 3971 |
| 522867 | 32133 | 32152 | CAGTCACTGACTCACAACAG | 62 | 3972 |
| 522868 | 32134 | 32153 | TCAGTCACTGACTCACAACA | 62 | 3973 |
| 522869 | 32136 | 32155 | TCTCAGTCACTGACTCACAA | 71 | 3974 |
| 522870 | 32137 | 32156 | ATCTCAGTCACTGACTCACA | 77 | 3975 |
| 522871 | 32138 | 32157 | GATCTCAGTCACTGACTCAC | 75 | 3976 |
| 522872 | 32139 | 32158 | GGATCTCAGTCACTGACTCA | 73 | 3977 |
| 522873 | 32173 | 32192 | GGTTACCCAGCCACTGCCCC | 65 | 3978 |
| 522874 | 32174 | 32193 | GGGTTACCCAGCCACTGCCC | 54 | 3979 |
| 522875 | 32175 | 32194 | AGGGTTACCCAGCCACTGCC | 61 | 3980 |
| 522876 | 32176 | 32195 | CAGGGTTACCCAGCCACTGC | 65 | 3981 |
| 522877 | 32178 | 32197 | TGCAGGGTTACCCAGCCACT | 74 | 3982 |
| 522878 | 32179 | 32198 | ATGCAGGGTTACCCAGCCAC | 73 | 3983 |
| 522879 | 32180 | 32199 | GATGCAGGGTTACCCAGCCA | 67 | 3984 |
| 522880 | 32181 | 32200 | GGATGCAGGGTTACCCAGCC | 69 | 3985 |
| 522881 | 32183 | 32202 | AAGGATGCAGGGTTACCCAG | 58 | 3986 |
| 522882 | 32184 | 32203 | GAAGGATGCAGGGTTACCCA | 58 | 3987 |
| 522883 | 32185 | 32204 | TGAAGGATGCAGGGTTACCC | 51 | 3988 |
| 522884 | 32186 | 32205 | GTGAAGGATGCAGGGTTACC | 43 | 3989 |
| 413433 | 32431 | 32450 | GCCTGGACAAGTCCTGCCCA | 80 | 425 |
| 522885 | 33409 | 33428 | ATCTTCATTACATGATTACT | 59 | 3990 |
| 522886 | 33410 | 33429 | GATCTTCATTACATGATTAC | 58 | 3991 |
| 522887 | 33411 | 33430 | AGATCTTCATTACATGATTA | 69 | 3992 |
| 522888 | 33412 | 33431 | CAGATCTTCATTACATGATT | 81 | 3993 |
| 522889 | 33414 | 33433 | GGCAGATCTTCATTACATGA | 83 | 3994 |
| 522890 | 33669 | 33688 | ATGGACAGGTGATTCTAAGC | 69 | 3995 |
| 522891 | 33670 | 33689 | GATGGACAGGTGATTCTAAG | 56 | 3996 |
| 522892 | 33672 | 33691 | CAGATGGACAGGTGATTCTA | 62 | 3997 |
| 522893 | 33674 | 33693 | GGCAGATGGACAGGTGATTC | 67 | 3998 |
| 522894 | 33675 | 33694 | AGGCAGATGGACAGGTGATT | 76 | 3999 |
| 522895 | 33676 | 33695 | GAGGCAGATGGACAGGTGAT | 69 | 4000 |
| 522896 | 33677 | 33696 | TGAGGCAGATGGACAGGTGA | 50 | 4001 |
| 522897 | 33730 | 33749 | GTGACCTTGGGATAGTCCCT | 88 | 4002 |
| 522898 | 33731 | 33750 | TGTGACCTTGGGATAGTCCC | 76 | 4003 |
| 522899 | 33732 | 33751 | TTGTGACCTTGGGATAGTCC | 69 | 4004 |
| 522900 | 33733 | 33752 | TTTGTGACCTTGGGATAGTC | 52 | 4005 |
| 522901 | 33857 | 33876 | GAGCAAAGGCTTGCTTAAGT | 60 | 4006 |

TABLE 58

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 413433 | 32431 | 32450 | GCCTGGACAAGTCCTGCCCA | 77 | 425 |
| 522902 | 33858 | 33877 | AGAGCAAAGGCTTGCTTAAG | 40 | 4007 |
| 522903 | 33859 | 33878 | AAGAGCAAAGGCTTGCTTAA | 41 | 4008 |
| 522904 | 33860 | 33879 | GAAGAGCAAAGGCTTGCTTA | 67 | 4009 |
| 522905 | 33862 | 33881 | CAGAAGAGCAAAGGCTTGCT | 74 | 4010 |
| 522906 | 33863 | 33882 | ACAGAAGAGCAAAGGCTTGC | 61 | 4011 |
| 522907 | 33864 | 33883 | CACAGAAGAGCAAAGGCTTG | 33 | 4012 |
| 522908 | 33865 | 33884 | CCACAGAAGAGCAAAGGCTT | 58 | 4013 |

TABLE 58-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522909 | 33867 | 33886 | ACCCACAGAAGAGCAAAGGC | 63 | 4014 |
| 522910 | 33868 | 33887 | GACCCACAGAAGAGCAAAGG | 40 | 4015 |
| 522911 | 33869 | 33888 | AGACCCACAGAAGAGCAAAG | 37 | 4016 |
| 522912 | 33870 | 33889 | CAGACCCACAGAAGAGCAAA | 37 | 4017 |
| 522913 | 34212 | 34231 | ATGCCCTTGCTGTAGGACCC | 84 | 4018 |
| 522914 | 34213 | 34232 | AATGCCCTTGCTGTAGGACC | 69 | 4019 |
| 522915 | 34214 | 34233 | CAATGCCCTTGCTGTAGGAC | 59 | 4020 |
| 522916 | 34215 | 34234 | TCAATGCCCTTGCTGTAGGA | 56 | 4021 |
| 522917 | 34740 | 34759 | TTAGCTCTCAGTGAAGCTGG | 76 | 4022 |
| 522918 | 34869 | 34888 | AACAGCAGCAGTCTAATCCA | 49 | 4023 |
| 522919 | 34870 | 34889 | AAACAGCAGCAGTCTAATCC | 50 | 4024 |
| 522920 | 34871 | 34890 | GAAACAGCAGCAGTCTAATC | 30 | 4025 |
| 522921 | 34872 | 34891 | GGAAACAGCAGCAGTCTAAT | 33 | 4026 |
| 522922 | 34899 | 34918 | AACTCTCAGCTACTCCCCAA | 46 | 4027 |
| 522923 | 34900 | 34919 | CAACTCTCAGCTACTCCCCA | 56 | 4028 |
| 522924 | 34901 | 34920 | CCAACTCTCAGCTACTCCCC | 75 | 4029 |
| 522925 | 34902 | 34921 | ACCAACTCTCAGCTACTCCC | 75 | 4030 |
| 522926 | 34932 | 34951 | GCAAACAGATTAAAGTTGCT | 55 | 4031 |
| 522927 | 34933 | 34952 | GGCAAACAGATTAAAGTTGC | 63 | 4032 |
| 522928 | 35274 | 35293 | CACCTGAGTGCTGCAAAGTG | 47 | 4033 |
| 522929 | 35275 | 35294 | CCACCTGAGTGCTGCAAAGT | 55 | 4034 |
| 522930 | 35276 | 35295 | CCCACCTGAGTGCTGCAAAG | 58 | 4035 |
| 522931 | 35277 | 35296 | TCCCACCTGAGTGCTGCAAA | 60 | 4036 |
| 522932 | 35279 | 35298 | ACTCCCACCTGAGTGCTGCA | 77 | 4037 |
| 522933 | 35280 | 35299 | CACTCCCACCTGAGTGCTGC | 62 | 4038 |
| 522934 | 35281 | 35300 | ACACTCCCACCTGAGTGCTG | 64 | 4039 |
| 522935 | 35282 | 35301 | GACACTCCCACCTGAGTGCT | 69 | 4040 |
| 522936 | 35319 | 35338 | TTTTTGGCTGCCCTGCCTCA | 35 | 4041 |
| 522937 | 35320 | 35339 | CTTTTTGGCTGCCCTGCCTC | 56 | 4042 |
| 522938 | 35321 | 35340 | TCTTTTTGGCTGCCCTGCCT | 58 | 4043 |
| 522939 | 35322 | 35341 | GTCTTTTTGGCTGCCCTGCC | 74 | 4044 |
| 522940 | 35324 | 35343 | TGGTCTTTTTGGCTGCCCTG | 72 | 4045 |
| 522941 | 35325 | 35344 | TTGGTCTTTTTGGCTGCCCT | 79 | 4046 |
| 522942 | 35326 | 35345 | GTTGGTCTTTTTGGCTGCCC | 81 | 4047 |
| 522943 | 35327 | 35346 | CGTTGGTCTTTTTGGCTGCC | 79 | 4048 |
| 522944 | 35407 | 35426 | CTTATCTTTGTCCACATATC | 57 | 4049 |
| 522945 | 35408 | 35427 | CCTTATCTTTGTCCACATAT | 66 | 4050 |

TABLE 58-continued

Inhibition of DGAT2 mRNA by 5-10-5 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 522946 | 35409 | 35428 | ACCTTATCTTTGTCCACATA | 60 | 4051 |
| 522947 | 35410 | 35429 | TACCTTATCTTTGTCCACAT | 75 | 4052 |
| 522948 | 35412 | 35431 | AATACCTTATCTTTGTCCAC | 67 | 4053 |
| 522949 | 35413 | 35432 | AAATACCTTATCTTTGTCCA | 61 | 4054 |
| 522950 | 35414 | 35433 | TAAATACCTTATCTTTGTCC | 71 | 4055 |
| 522951 | 35415 | 35434 | ATAAATACCTTATCTTTGTC | 16 | 4056 |
| 522952 | 35417 | 35436 | CAATAAATACCTTATCTTTG | 22 | 4057 |
| 522953 | 35418 | 35437 | TCAATAAATACCTTATCTTT | 3 | 4058 |
| 522954 | 35419 | 35438 | TTCAATAAATACCTTATCTT | 12 | 4059 |
| 522955 | 35420 | 35439 | CTTCAATAAATACCTTATCT | 47 | 4060 |
| 522956 | 35422 | 35441 | TGCTTCAATAAATACCTTAT | 65 | 4061 |
| 522957 | 35423 | 35442 | ATGCTTCAATAAATACCTTA | 55 | 4062 |
| 522958 | 35424 | 35443 | AATGCTTCAATAAATACCTT | 42 | 4063 |
| 522959 | 35425 | 35444 | TAATGCTTCAATAAATACCT | 42 | 4064 |
| 522960 | 35432 | 35451 | TTAGAAGTAATGCTTCAATA | 37 | 4065 |
| 522961 | 35433 | 35452 | CTTAGAAGTAATGCTTCAAT | 44 | 4066 |
| 522962 | 35434 | 35453 | TCTTAGAAGTAATGCTTCAA | 44 | 4067 |
| 522963 | 35435 | 35454 | CTCTTAGAAGTAATGCTTCA | 59 | 4068 |
| 522964 | 35437 | 35456 | CCCTCTTAGAAGTAATGCTT | 80 | 4069 |
| 522965 | 35438 | 35457 | TCCCTCTTAGAAGTAATGCT | 73 | 4070 |
| 522966 | 35439 | 35458 | TTCCCTCTTAGAAGTAATGC | 59 | 4071 |
| 522967 | 35440 | 35459 | TTTCCCTCTTAGAAGTAATG | 48 | 4072 |
| 522968 | 37835 | 37854 | GCTAATGATACAAGGTTGTT | 57 | 4073 |
| 522969 | 37836 | 37855 | AGCTAATGATACAAGGTTGT | 54 | 4074 |
| 522970 | 37838 | 37857 | GCAGCTAATGATACAAGGTT | 65 | 4075 |
| 522971 | 37840 | 37859 | ATGCAGCTAATGATACAAGG | 57 | 4076 |
| 522972 | 37841 | 37860 | AATGCAGCTAATGATACAAG | 33 | 4077 |
| 522973 | 37842 | 37861 | AAATGCAGCTAATGATACAA | 24 | 4078 |
| 522974 | 37843 | 37862 | AAAATGCAGCTAATGATACA | 22 | 4079 |
| 522975 | 39666 | 39685 | AAGAGTTACCTCCTCCCTGG | 30 | 4080 |
| 522976 | 39667 | 39686 | CAAGAGTTACCTCCTCCCTG | 36 | 4081 |
| 522977 | 39668 | 39687 | GCAAGAGTTACCTCCTCCCT | 62 | 4082 |
| 522978 | 39669 | 39688 | TGCAAGAGTTACCTCCTCCC | 61 | 4083 |

TABLE 59

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525386 | 10047 | 10063 | CCACAGGGCCCTTTCCA | 49 | 4141 |
| 525387 | 10048 | 10064 | GCCACAGGGCCCTTTCC | 53 | 4142 |
| 525388 | 10215 | 10231 | GTTCTCGAATATCCCTA | 67 | 4143 |
| 525389 | 10216 | 10232 | AGTTCTCGAATATCCCT | 55 | 4144 |
| 525390 | 10217 | 10233 | GAGTTCTCGAATATCCC | 52 | 4145 |
| 525391 | 10218 | 10234 | GGAGTTCTCGAATATCC | 60 | 4146 |
| 525392 | 10219 | 10235 | AGGAGTTCTCGAATATC | 34 | 4147 |
| 525393 | 10220 | 10236 | GAGGAGTTCTCGAATAT | 41 | 4148 |
| 525394 | 10490 | 10506 | GGTCCTCTCCGCTGCCT | 62 | 4149 |
| 525395 | 10491 | 10507 | GGGTCCTCTCCGCTGCC | 70 | 4150 |
| 525396 | 10492 | 10508 | AGGGTCCTCTCCGCTGC | 57 | 4151 |
| 525397 | 10529 | 10545 | TTCACTGAGGACCTCAG | 29 | 4152 |
| 525398 | 10530 | 10546 | ATTCACTGAGGACCTCA | 44 | 4153 |
| 525399 | 10531 | 10547 | GATTCACTGAGGACCTC | 66 | 4154 |
| 525400 | 10532 | 10548 | CGATTCACTGAGGACCT | 48 | 4155 |
| 525401 | 10533 | 10549 | GCGATTCACTGAGGACC | 83 | 4156 |
| 525402 | 10534 | 10550 | CGCGATTCACTGAGGAC | 71 | 4157 |
| 525403 | 10535 | 10551 | GCGCGATTCACTGAGGA | 68 | 4158 |
| 525404 | 10536 | 10552 | TGCGCGATTCACTGAGG | 65 | 4159 |
| 525405 | 10537 | 10553 | CTGCGCGATTCACTGAG | 60 | 4160 |
| 525406 | 10538 | 10554 | TCTGCGCGATTCACTGA | 45 | 4161 |
| 525407 | 10650 | 10666 | TCCTCCCACTTCAGTTT | 28 | 4162 |
| 525408 | 10651 | 10667 | TTCCTCCCACTTCAGTT | 18 | 4163 |
| 525409 | 10652 | 10668 | CTTCCTCCCACTTCAGT | 30 | 4164 |
| 525410 | 10654 | 10670 | TGCTTCCTCCCACTTCA | 30 | 4165 |
| 525411 | 10655 | 10671 | ATGCTTCCTCCCACTTC | 37 | 4166 |
| 525412 | 10656 | 10672 | CATGCTTCCTCCCACTT | 32 | 4167 |
| 525413 | 10657 | 10673 | GCATGCTTCCTCCCACT | 59 | 4168 |
| 525414 | 10658 | 10674 | GGCATGCTTCCTCCCAC | 69 | 4169 |
| 525415 | 10659 | 10675 | AGGCATGCTTCCTCCCA | 71 | 4170 |
| 525416 | 10660 | 10676 | TAGGCATGCTTCCTCCC | 62 | 4171 |
| 525417 | 10661 | 10677 | TTAGGCATGCTTCCTCC | 53 | 4172 |
| 525418 | 10662 | 10678 | CTTAGGCATGCTTCCTC | 53 | 4173 |
| 525419 | 10663 | 10679 | ACTTAGGCATGCTTCCT | 63 | 4174 |
| 525420 | 10664 | 10680 | AACTTAGGCATGCTTCC | 62 | 4175 |
| 525421 | 10665 | 10681 | AAACTTAGGCATGCTTC | 50 | 4176 |
| 525422 | 10666 | 10682 | AAAACTTAGGCATGCTT | 58 | 4177 |

TABLE 59-continued

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525423 | 10667 | 10683 | GAAAACTTAGGCATGCT | 68 | 4178 |
| 525424 | 10668 | 10684 | GGAAAACTTAGGCATGC | 65 | 4179 |
| 525425 | 10669 | 10685 | AGGAAAACTTAGGCATG | 41 | 4180 |
| 525426 | 10670 | 10686 | AAGGAAAACTTAGGCAT | 15 | 4181 |
| 525427 | 10671 | 10687 | TAAGGAAAACTTAGGCA | 15 | 4182 |
| 525428 | 10672 | 10688 | CTAAGGAAAACTTAGGC | 12 | 4183 |
| 525429 | 10728 | 10744 | GATGACTTCCCAGGGTC | 32 | 4184 |
| 525430 | 10729 | 10745 | TGATGACTTCCCAGGGT | 41 | 4185 |
| 525431 | 10730 | 10746 | GTGATGACTTCCCAGGG | 78 | 4186 |
| 525432 | 10731 | 10747 | TGTGATGACTTCCCAGG | 51 | 4187 |
| 525433 | 10732 | 10748 | CTGTGATGACTTCCCAG | 41 | 4188 |
| 525434 | 10733 | 10749 | GCTGTGATGACTTCCCA | 63 | 4189 |
| 525435 | 10734 | 10750 | AGCTGTGATGACTTCCC | 61 | 4190 |
| 525436 | 10735 | 10751 | CAGCTGTGATGACTTCC | 60 | 4191 |
| 525437 | 10736 | 10752 | ACAGCTGTGATGACTTC | 31 | 4192 |
| 525438 | 10737 | 10753 | GACAGCTGTGATGACTT | 0 | 4193 |
| 525439 | 10816 | 10832 | TGTCAGAGAGGCTCAGC | 59 | 4194 |
| 525440 | 10817 | 10833 | ATGTCAGAGAGGCTCAG | 41 | 4195 |
| 525441 | 10818 | 10834 | CATGTCAGAGAGGCTCA | 60 | 4196 |
| 525442 | 10819 | 10835 | CCATGTCAGAGAGGCTC | 73 | 4197 |
| 525443 | 10820 | 10836 | TCCATGTCAGAGAGGCT | 75 | 4198 |
| 525444 | 10821 | 10837 | ATCCATGTCAGAGAGGC | 64 | 4199 |
| 525445 | 10822 | 10838 | AATCCATGTCAGAGAGG | 44 | 4200 |
| 525446 | 10823 | 10839 | AAATCCATGTCAGAGAG | 10 | 4201 |
| 525447 | 10940 | 10956 | TAGTCGATTTACCAGAA | 31 | 4202 |
| 525448 | 10941 | 10957 | ATAGTCGATTTACCAGA | 31 | 4203 |
| 525449 | 10942 | 10958 | GATAGTCGATTTACCAG | 43 | 4204 |
| 525450 | 10943 | 10959 | GGATAGTCGATTTACCA | 62 | 4205 |
| 525451 | 10944 | 10960 | TGGATAGTCGATTTACC | 48 | 4206 |
| 525452 | 10945 | 10961 | TTGGATAGTCGATTTAC | 36 | 4207 |
| 525453 | 10946 | 10962 | TTTGGATAGTCGATTTA | 16 | 4208 |
| 525454 | 11074 | 11090 | CGATGTTACATTAAGGG | 26 | 4209 |
| 525455 | 11075 | 11091 | TCGATGTTACATTAAGG | 24 | 4210 |
| 525456 | 11076 | 11092 | CTCGATGTTACATTAAG | 11 | 4211 |
| 496041 | 31122 | 31138 | CACAGCGATGAGCCAGC | 52 | 1096 |
| 413433 | 32431 | 32450 | GCCTGGACAAGTCCTGCCCA | 69 | 425 |

TABLE 59-continued

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525765 | 36860 | 36876 | ATTATTCTAAAACTCAA | 11 | 4212 |
| 525766 | 36861 | 36877 | GATTATTCTAAAACTCA | 6 | 4213 |
| 525767 | 36862 | 36878 | TGATTATTCTAAAACTC | 7 | 4214 |
| 525768 | 37022 | 37038 | GGGCAGTCACCATTTGC | 14 | 4215 |
| 525769 | 37023 | 37039 | TGGGCAGTCACCATTTG | 12 | 4216 |
| 525770 | 37024 | 37040 | TTGGGCAGTCACCATTT | 7 | 4217 |

TABLE 60

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525457 | 11077 | 11093 | CCTCGATGTTACATTAA | 44 | 4218 |
| 525458 | 11127 | 11143 | TATTGCAACCACTAGGA | 36 | 4219 |
| 525459 | 11128 | 11144 | TTATTGCAACCACTAGG | 41 | 4220 |
| 525460 | 11129 | 11145 | GTTATTGCAACCACTAG | 49 | 4221 |
| 525461 | 11130 | 11146 | GGTTATTGCAACCACTA | 61 | 4222 |
| 525462 | 11158 | 11174 | AGTTAAAGTGTGGTACA | 4 | 4223 |
| 525463 | 11159 | 11175 | CAGTTAAAGTGTGGTAC | 37 | 4224 |
| 525464 | 11160 | 11176 | ACAGTTAAAGTGTGGTA | 14 | 4225 |
| 525465 | 11171 | 11187 | ATGCCTAGGTCACAGTT | 55 | 4226 |
| 525466 | 11172 | 11188 | AATGCCTAGGTCACAGT | 48 | 4227 |
| 525467 | 11173 | 11189 | CAATGCCTAGGTCACAG | 44 | 4228 |
| 525468 | 11174 | 11190 | CCAATGCCTAGGTCACA | 73 | 4229 |
| 525469 | 11175 | 11191 | GCCAATGCCTAGGTCAC | 89 | 4230 |
| 525470 | 11176 | 11192 | TGCCAATGCCTAGGTCA | 82 | 4231 |
| 525471 | 11177 | 11193 | ATGCCAATGCCTAGGTC | 79 | 4232 |
| 525472 | 11178 | 11194 | AATGCCAATGCCTAGGT | 76 | 4233 |
| 525473 | 11179 | 11195 | CAATGCCAATGCCTAGG | 69 | 4234 |
| 525474 | 11180 | 11196 | GCAATGCCAATGCCTAG | 78 | 4235 |
| 525475 | 11199 | 11215 | AGCGATAATCACACAAG | 54 | 4236 |
| 525476 | 11200 | 11216 | CAGCGATAATCACACAA | 58 | 4237 |
| 525477 | 11201 | 11217 | ACAGCGATAATCACACA | 72 | 4238 |
| 525478 | 11202 | 11218 | CACAGCGATAATCACAC | 49 | 4239 |
| 525479 | 11203 | 11219 | CCACAGCGATAATCACA | 79 | 4240 |
| 525480 | 11204 | 11220 | ACCACAGCGATAATCAC | 76 | 4241 |
| 525481 | 11205 | 11221 | AACCACAGCGATAATCA | 40 | 4242 |

TABLE 60-continued

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525482 | 14503 | 14519 | GGTCTGCCACTCTCTAC | 49 | 4243 |
| 525483 | 14504 | 14520 | GGGTCTGCCACTCTCTA | 47 | 4244 |
| 525484 | 14505 | 14521 | AGGGTCTGCCACTCTCT | 64 | 4245 |
| 525485 | 14648 | 14664 | AGTCATCTTGTGTACAT | 60 | 4246 |
| 525486 | 14649 | 14665 | CAGTCATCTTGTGTACA | 49 | 4247 |
| 525487 | 14650 | 14666 | ACAGTCATCTTGTGTAC | 52 | 4248 |
| 525488 | 14663 | 14679 | CAGATCACTCTGCACAG | 62 | 4249 |
| 525489 | 14664 | 14680 | TCAGATCACTCTGCACA | 65 | 4250 |
| 525490 | 14665 | 14681 | CTCAGATCACTCTGCAC | 61 | 4251 |
| 525491 | 14667 | 14683 | TGCTCAGATCACTCTGC | 60 | 4252 |
| 525492 | 14668 | 14684 | TTGCTCAGATCACTCTG | 51 | 4253 |
| 525493 | 14669 | 14685 | ATTGCTCAGATCACTCT | 54 | 4254 |
| 525494 | 14745 | 14761 | ACCTCTTCCAGGAAGAC | 41 | 4255 |
| 525495 | 14746 | 14762 | CACCTCTTCCAGGAAGA | 44 | 4256 |
| 525496 | 14747 | 14763 | TCACCTCTTCCAGGAAG | 28 | 4257 |
| 525497 | 14755 | 14771 | ACTGAATGTCACCTCTT | 57 | 4258 |
| 525498 | 14756 | 14772 | GACTGAATGTCACCTCT | 62 | 4259 |
| 525499 | 14757 | 14773 | GGACTGAATGTCACCTC | 71 | 4260 |
| 525500 | 14758 | 14774 | CGGACTGAATGTCACCT | 74 | 4261 |
| 525501 | 14759 | 14775 | CCGGACTGAATGTCACC | 80 | 4262 |
| 525502 | 14760 | 14776 | TCCGGACTGAATGTCAC | 39 | 4263 |
| 525503 | 14770 | 14786 | TCTTTCCAGATCCGGAC | 53 | 4264 |
| 525504 | 14771 | 14787 | ATCTTTCCAGATCCGGA | 62 | 4265 |
| 525505 | 14772 | 14788 | CATCTTTCCAGATCCGG | 70 | 4266 |
| 525506 | 14773 | 14789 | TCATCTTTCCAGATCCG | 71 | 4267 |
| 525507 | 14774 | 14790 | TTCATCTTTCCAGATCC | 63 | 4268 |
| 525508 | 14775 | 14791 | ATTCATCTTTCCAGATC | 23 | 4269 |
| 525509 | 14996 | 15012 | TCTCAAGTCTTCCTCCT | 33 | 4270 |
| 525510 | 14997 | 15013 | CTCTCAAGTCTTCCTCC | 46 | 4271 |
| 525511 | 14998 | 15014 | GCTCTCAAGTCTTCCTC | 65 | 4272 |
| 525512 | 14999 | 15015 | AGCTCTCAAGTCTTCCT | 72 | 4273 |
| 525513 | 15000 | 15016 | GAGCTCTCAAGTCTTCC | 73 | 4274 |
| 525514 | 15001 | 15017 | TGAGCTCTCAAGTCTTC | 64 | 4275 |
| 525515 | 15250 | 15266 | ATAATCTGCACAGGTTC | 72 | 4276 |
| 525516 | 15251 | 15267 | CATAATCTGCACAGGTT | 67 | 4277 |
| 525517 | 15252 | 15268 | CCATAATCTGCACAGGT | 69 | 4278 |

TABLE 60-continued

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525518 | 15253 | 15269 | ACCATAATCTGCACAGG | 68 | 4279 |
| 525519 | 15254 | 15270 | CACCATAATCTGCACAG | 49 | 4280 |
| 525520 | 15255 | 15271 | GCACCATAATCTGCACA | 60 | 4281 |
| 525521 | 18156 | 18172 | TTAATCCAGGATTGTCA | 55 | 4282 |
| 525522 | 18157 | 18173 | TTTAATCCAGGATTGTC | 57 | 4283 |
| 525523 | 18158 | 18174 | CTTTAATCCAGGATTGT | 26 | 4284 |
| 525524 | 18161 | 18177 | TAGCTTTAATCCAGGAT | 42 | 4285 |
| 525525 | 18162 | 18178 | TTAGCTTTAATCCAGGA | 28 | 4286 |
| 525526 | 18163 | 18179 | CTTAGCTTTAATCCAGG | 45 | 4287 |
| 525527 | 18164 | 18180 | CCTTAGCTTTAATCCAG | 27 | 4288 |
| 525528 | 18165 | 18181 | TCCTTAGCTTTAATCCA | 60 | 4289 |
| 525529 | 18166 | 18182 | CTCCTTAGCTTTAATCC | 23 | 4290 |
| 525530 | 18167 | 18183 | CCTCCTTAGCTTTAATC | 32 | 4291 |
| 525531 | 18168 | 18184 | TCCTCCTTAGCTTTAAT | 28 | 4292 |
| 525532 | 18174 | 18190 | TCAGTGTCCTCCTTAGC | 39 | 4293 |
| 525533 | 18175 | 18191 | CTCAGTGTCCTCCTTAG | 32 | 4294 |
| 496041 | 31122 | 31138 | CACAGCGATGAGCCAGC | 64 | 1096 |
| 413433 | 32431 | 32450 | GCCTGGACAAGTCCTGCCCA | 78 | 425 |

TABLE 61

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525534 | 18176 | 18192 | ACTCAGTGTCCTCCTTA | 35 | 4295 |
| 525535 | 18177 | 18193 | GACTCAGTGTCCTCCTT | 64 | 4296 |
| 525536 | 18178 | 18194 | GGACTCAGTGTCCTCCT | 73 | 4297 |
| 525537 | 18180 | 18196 | TGGGACTCAGTGTCCTC | 62 | 4298 |
| 525538 | 18181 | 18197 | CTGGGACTCAGTGTCCT | 59 | 4299 |
| 525539 | 18182 | 18198 | CCTGGGACTCAGTGTCC | 63 | 4300 |
| 525540 | 18308 | 18324 | CTGTTTGATGGGTAAAA | 20 | 4301 |
| 525541 | 18309 | 18325 | CCTGTTTGATGGGTAAA | 62 | 4302 |
| 525542 | 18310 | 18326 | TCCTGTTTGATGGGTAA | 68 | 4303 |
| 525543 | 18311 | 18327 | CTCCTGTTTGATGGGTA | 39 | 4304 |
| 525544 | 18312 | 18328 | TCTCCTGTTTGATGGGT | 73 | 4305 |
| 525545 | 18313 | 18329 | CTCTCCTGTTTGATGGG | 47 | 4306 |
| 525546 | 18314 | 18330 | CCTCTCCTGTTTGATGG | 43 | 4307 |

TABLE 61-continued

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525547 | 18321 | 18337 | TCGGTGTCCTCTCCTGT | 63 | 4308 |
| 525548 | 18322 | 18338 | CTCGGTGTCCTCTCCTG | 64 | 4309 |
| 525549 | 18323 | 18339 | CCTCGGTGTCCTCTCCT | 60 | 4310 |
| 525550 | 18324 | 18340 | GCCTCGGTGTCCTCTCC | 68 | 4311 |
| 525551 | 18325 | 18341 | AGCCTCGGTGTCCTCTC | 78 | 4312 |
| 525552 | 18326 | 18342 | AAGCCTCGGTGTCCTCT | 73 | 4313 |
| 525553 | 18327 | 18343 | TAAGCCTCGGTGTCCTC | 70 | 4314 |
| 525554 | 18328 | 18344 | GTAAGCCTCGGTGTCCT | 75 | 4315 |
| 525555 | 18329 | 18345 | AGTAAGCCTCGGTGTCC | 64 | 4316 |
| 525556 | 18417 | 18433 | CCAGATTGTTGTGGGAA | 66 | 4317 |
| 525557 | 18418 | 18434 | ACCAGATTGTTGTGGGA | 68 | 4318 |
| 525558 | 18419 | 18435 | CACCAGATTGTTGTGGG | 63 | 4319 |
| 525559 | 18432 | 18448 | CTAATACCTACCTCACC | 35 | 4320 |
| 525560 | 18433 | 18449 | GCTAATACCTACCTCAC | 25 | 4321 |
| 525561 | 18434 | 18450 | GGCTAATACCTACCTCA | 34 | 4322 |
| 525562 | 18450 | 18466 | CTCATCTATACAGTGGG | 58 | 4323 |
| 525563 | 18451 | 18467 | CCTCATCTATACAGTGG | 51 | 4324 |
| 525564 | 18452 | 18468 | TCCTCATCTATACAGTG | 28 | 4325 |
| 525565 | 18581 | 18597 | ACTGGCATCTGGCAGGG | 69 | 4326 |
| 525566 | 18582 | 18598 | TACTGGCATCTGGCAGG | 52 | 4327 |
| 525567 | 18583 | 18599 | ATACTGGCATCTGGCAG | 31 | 4328 |
| 525568 | 18591 | 18607 | TCACCTCCATACTGGCA | 21 | 4329 |
| 525569 | 18592 | 18608 | CTCACCTCCATACTGGC | 20 | 4330 |
| 525570 | 18593 | 18609 | CCTCACCTCCATACTGG | 6 | 4331 |
| 525571 | 18828 | 18844 | ATGCTTAACTTCTGCTG | 48 | 4332 |
| 525572 | 18829 | 18845 | GATGCTTAACTTCTGCT | 46 | 4333 |
| 525573 | 18830 | 18846 | GGATGCTTAACTTCTGC | 53 | 4334 |
| 525574 | 18831 | 18847 | AGGATGCTTAACTTCTG | 40 | 4335 |
| 525575 | 18832 | 18848 | TAGGATGCTTAACTTCT | 40 | 4336 |
| 525576 | 18833 | 18849 | TTAGGATGCTTAACTTC | 20 | 4337 |
| 525577 | 18869 20779 | 18885 20795 | GGCCTGGATGCCCAAGT | 65 | 4338 |
| 525578 | 18870 20780 | 18886 20796 | AGGCCTGGATGCCCAAG | 71 | 4339 |
| 525579 | 18871 20781 | 18887 20797 | TAGGCCTGGATGCCCAA | 66 | 4340 |
| 525580 | 18900 | 18916 | CAGATGATGTCCTGCCT | 25 | 4341 |
| 525581 | 18901 | 18917 | GCAGATGATGTCCTGCC | 55 | 4342 |

TABLE 61-continued

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525582 | 18902 | 18918 | AGCAGATGATGTCCTGC | 38 | 4343 |
| 525583 | 19018 | 19034 | TAGTCAAAGGTGGCTTC | 44 | 4344 |
| 525584 | 19019 | 19035 | GTAGTCAAAGGTGGCTT | 57 | 4345 |
| 525585 | 19020 | 19036 | AGTAGTCAAAGGTGGCT | 55 | 4346 |
| 525589 | 22548 | 22564 | AACAAGTGGGAAATGCA | 17 | 4347 |
| 525590 | 22549 | 22565 | CAACAAGTGGGAAATGC | 19 | 4348 |
| 525591 | 22550 | 22566 | CCAACAAGTGGGAAATG | 23 | 4349 |
| 525592 | 22771 | 22787 | AGCTTATTAGGTGTCTT | 42 | 4350 |
| 525593 | 22772 | 22788 | AAGCTTATTAGGTGTCT | 53 | 4351 |
| 525594 | 22773 | 22789 | TAAGCTTATTAGGTGTC | 44 | 4352 |
| 525595 | 22774 | 22790 | CTAAGCTTATTAGGTGT | 36 | 4353 |
| 525596 | 22886 | 22902 | CCCCCATGCAGCTTGGA | 29 | 4354 |
| 525597 | 22887 | 22903 | GCCCCCATGCAGCTTGG | 43 | 4355 |
| 525598 | 22888 | 22904 | AGCCCCCATGCAGCTTG | 50 | 4356 |
| 525599 | 23096 | 23112 | CCAAACACTCAGGTAGG | 49 | 4357 |
| 525600 | 23097 | 23113 | TCCAAACACTCAGGTAG | 41 | 4358 |
| 525601 | 23098 | 23114 | GTCCAAACACTCAGGTA | 54 | 4359 |
| 525602 | 23100 | 23116 | CAGTCCAAACACTCAGG | 47 | 4360 |
| 525603 | 23101 | 23117 | TCAGTCCAAACACTCAG | 57 | 4361 |
| 525604 | 23102 | 23118 | TTCAGTCCAAACACTCA | 49 | 4362 |
| 525605 | 23239 | 23255 | GAACAGCAGCATCAGCA | 47 | 4363 |
| 525606 | 23240 | 23256 | GGAACAGCAGCATCAGC | 67 | 4364 |
| 525607 | 23241 | 23257 | GGGAACAGCAGCATCAG | 40 | 4365 |
| 525608 | 23242 | 23258 | TGGGAACAGCAGCATCA | 44 | 4366 |
| 525609 | 23243 | 23259 | CTGGGAACAGCAGCATC | 69 | 4367 |
| 525610 | 23244 | 23260 | TCTGGGAACAGCAGCAT | 65 | 4368 |
| 525586 | 36855 | 36871 | TCTAAAACTCAAATCCA | 0 | 4369 |
| 525587 | 36856 | 36872 | TTCTAAAACTCAAATCC | 0 | 4370 |
| 525588 | 36857 | 36873 | ATTCTAAAACTCAAATC | 0 | 4371 |
| 496041 | 31122 | 31138 | CACAGCGATGAGCCAGC | 64 | 1096 |
| 413433 | 32431 | 32450 | GCCTGGACAAGTCCTGCCCA | 78 | 425 |

TABLE 62

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525611 | 23245 | 23261 | GTCTGGGAACAGCAGCA | 65 | 4372 |
| 525612 | 23246 | 23262 | GGTCTGGGAACAGCAGC | 83 | 4373 |
| 525613 | 23247 | 23263 | TGGTCTGGGAACAGCAG | 42 | 4374 |
| 525614 | 23427 | 23443 | ACAAGTCATCTTCCAGC | 16 | 4375 |
| 525615 | 23428 | 23444 | GACAAGTCATCTTCCAG | 24 | 4376 |
| 525616 | 23429 | 23445 | GGACAAGTCATCTTCCA | 37 | 4377 |
| 525617 | 23551 | 23567 | ATCCTTGAGGGTCTCAT | 55 | 4378 |
| 525618 | 23552 | 23568 | TATCCTTGAGGGTCTCA | 55 | 4379 |
| 525619 | 23553 | 23569 | TTATCCTTGAGGGTCTC | 65 | 4380 |
| 525620 | 23554 | 23570 | CTTATCCTTGAGGGTCT | 46 | 4381 |
| 525621 | 26400 | 26416 | CCTGGATGGCAACCTAA | 42 | 4382 |
| 525622 | 26401 | 26417 | GCCTGGATGGCAACCTA | 33 | 4383 |
| 525623 | 26402 | 26418 | GGCCTGGATGGCAACCT | 43 | 4384 |
| 525624 | 26484 | 26500 | CTGCTATGCTGAGAGCA | 44 | 4385 |
| 525625 | 26485 | 26501 | CCTGCTATGCTGAGAGC | 42 | 4386 |
| 525626 | 26486 | 26502 | ACCTGCTATGCTGAGAG | 8 | 4387 |
| 525627 | 26516 | 26532 | GTTCATCTGCCTTGACG | 44 | 4388 |
| 525628 | 26517 | 26533 | GGTTCATCTGCCTTGAC | 56 | 4389 |
| 525629 | 26518 | 26534 | AGGTTCATCTGCCTTGA | 33 | 4390 |
| 525630 | 26519 | 26535 | CAGGTTCATCTGCCTTG | 55 | 4391 |
| 525631 | 26520 | 26536 | GCAGGTTCATCTGCCTT | 75 | 4392 |
| 525632 | 26521 | 26537 | AGCAGGTTCATCTGCCT | 62 | 4393 |
| 525633 | 26536 | 26552 | TCTGTGATGCTCTGGAG | 33 | 4394 |
| 525634 | 26537 | 26553 | CTCTGTGATGCTCTGGA | 43 | 4395 |
| 525635 | 26538 | 26554 | ACTCTGTGATGCTCTGG | 46 | 4396 |
| 525636 | 26539 | 26555 | CACTCTGTGATGCTCTG | 39 | 4397 |
| 525637 | 26627 | 26643 | ACATGGTAAGTCCTGAT | 38 | 4398 |
| 525638 | 26628 | 26644 | GACATGGTAAGTCCTGA | 55 | 4399 |
| 525639 | 26629 | 26645 | TGACATGGTAAGTCCTG | 58 | 4400 |
| 525640 | 26630 | 26646 | CTGACATGGTAAGTCCT | 55 | 4401 |
| 525641 | 26631 | 26647 | ACTGACATGGTAAGTCC | 35 | 4402 |
| 525642 | 26632 | 26648 | CACTGACATGGTAAGTC | 48 | 4403 |
| 525643 | 26783 | 26799 | TCTGCCATTTAATGAGC | 19 | 4404 |
| 525644 | 26784 | 26800 | CTCTGCCATTTAATGAG | 22 | 4405 |
| 525645 | 26785 | 26801 | ACTCTGCCATTTAATGA | 12 | 4406 |
| 525646 | 26788 | 26804 | CCAACTCTGCCATTTAA | 43 | 4407 |
| 525647 | 26789 | 26805 | CCCAACTCTGCCATTTA | 47 | 4408 |

TABLE 62-continued

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525648 | 26790 | 26806 | TCCCAACTCTGCCATTT | 35 | 4409 |
| 525649 | 26926 | 26942 | AGGGTTCATGGATCCCC | 69 | 4410 |
| 525650 | 26927 | 26943 | AAGGGTTCATGGATCCC | 67 | 4411 |
| 525651 | 26928 | 26944 | TAAGGGTTCATGGATCC | 44 | 4412 |
| 525652 | 27251 | 27267 | CTGGAGTCCCTGGGTTC | 45 | 4413 |
| 525653 | 27252 | 27268 | GCTGGAGTCCCTGGGTT | 30 | 4414 |
| 525654 | 27253 | 27269 | GGCTGGAGTCCCTGGGT | 31 | 4415 |
| 525655 | 27352 | 27368 | AGCCAGGCCCAGACCCA | 32 | 4416 |
| 525656 | 27353 | 27369 | CAGCCAGGCCCAGACCC | 22 | 4417 |
| 525657 | 27354 | 27370 | CCAGCCAGGCCCAGACC | 11 | 4418 |
| 525658 | 27382 | 27398 | GGTGTTCTACAAGCTGC | 61 | 4419 |
| 525659 | 27383 | 27399 | TGGTGTTCTACAAGCTG | 50 | 4420 |
| 525660 | 27384 | 27400 | CTGGTGTTCTACAAGCT | 49 | 4421 |
| 525661 | 27387 | 27403 | GAGCTGGTGTTCTACAA | 34 | 4422 |
| 525662 | 27388 | 27404 | TGAGCTGGTGTTCTACA | 47 | 4423 |
| 525663 | 27389 | 27405 | GTGAGCTGGTGTTCTAC | 55 | 4424 |
| 525664 | 27437 | 27453 | GATCAATTATTAACCTA | 14 | 4425 |
| 525665 | 27438 | 27454 | TGATCAATTATTAACCT | 0 | 4426 |
| 525666 | 27439 | 27455 | CTGATCAATTATTAACC | 5 | 4427 |
| 525667 | 29678 | 29694 | GCAGGTACTCATGTTTG | 50 | 4428 |
| 525668 | 29679 | 29695 | AGCAGGTACTCATGTTT | 39 | 4429 |
| 525669 | 29680 | 29696 | CAGCAGGTACTCATGTT | 31 | 4430 |
| 525670 | 29782 | 29798 | CCAATATCATACTATCT | 5 | 4431 |
| 525671 | 29783 | 29799 | CCCAATATCATACTATC | 13 | 4432 |
| 525672 | 29784 | 29800 | CCCCAATATCATACTAT | 40 | 4433 |
| 525673 | 29828 | 29844 | AACCTTTAAGGCCTATC | 16 | 4434 |
| 525674 | 29829 | 29845 | CAACCTTTAAGGCCTAT | 23 | 4435 |
| 525675 | 29830 | 29846 | CCAACCTTTAAGGCCTA | 35 | 4436 |
| 525676 | 29831 | 29847 | CCCAACCTTTAAGGCCT | 40 | 4437 |
| 525677 | 29839 | 29855 | ATTTTTTACCCAACCTT | 30 | 4438 |
| 525678 | 29840 | 29856 | CATTTTTTACCCAACCT | 24 | 4439 |
| 525679 | 29841 | 29857 | CCATTTTTTACCCAACC | 50 | 4440 |
| 525680 | 29842 | 29858 | TCCATTTTTTACCCAAC | 40 | 4441 |
| 525681 | 29843 | 29859 | TTCCATTTTTTACCCAA | 24 | 4442 |
| 525682 | 30483 | 30499 | GCTTTAGAAATTCACCA | 45 | 4443 |
| 525683 | 30484 | 30500 | GGCTTTAGAAATTCACC | 68 | 4444 |

TABLE 62-continued

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525684 | 30485 | 30501 | AGGCTTTAGAAATTCAC | 39 | 4445 |
| 496041 | 31122 | 31138 | CACAGCGATGAGCCAGC | 58 | 1096 |
| 413433 | 32431 | 32450 | GCCTGGACAAGTCCTGCCCA | 76 | 425 |
| 525685 | 32431 | 32447 | TGGACAAGTCCTGCCCA | 47 | 4446 |
| 525686 | 32432 | 32448 | CTGGACAAGTCCTGCCC | 58 | 4447 |
| 525687 | 32433 | 32449 | CCTGGACAAGTCCTGCC | 60 | 4448 |

TABLE 63

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 496041 | 31122 | 31138 | CACAGCGATGAGCCAGC | 44 | 1096 |
| 413433 | 32431 | 32450 | GCCTGGACAAGTCCTGCCCA | 74 | 425 |
| 525688 | 32434 | 32450 | GCCTGGACAAGTCCTGC | 77 | 4449 |
| 525689 | 32435 | 32451 | AGCCTGGACAAGTCCTG | 50 | 4450 |
| 525690 | 32447 | 32463 | ACTAGACTATGCAGCCT | 62 | 4451 |
| 525691 | 32448 | 32464 | TACTAGACTATGCAGCC | 55 | 4452 |
| 525692 | 32449 | 32465 | ATACTAGACTATGCAGC | 37 | 4453 |
| 525693 | 32450 | 32466 | CATACTAGACTATGCAG | 17 | 4454 |
| 525694 | 32451 | 32467 | TCATACTAGACTATGCA | 20 | 4455 |
| 525695 | 32452 | 32468 | ATCATACTAGACTATGC | 20 | 4456 |
| 525696 | 32453 | 32469 | CATCATACTAGACTATG | 13 | 4457 |
| 525697 | 32454 | 32470 | CCATCATACTAGACTAT | 32 | 4458 |
| 525698 | 32455 | 32471 | GCCATCATACTAGACTA | 58 | 4459 |
| 525699 | 32456 | 32472 | TGCCATCATACTAGACT | 51 | 4460 |
| 525700 | 32457 | 32473 | TTGCCATCATACTAGAC | 40 | 4461 |
| 525701 | 32458 | 32474 | GTTGCCATCATACTAGA | 51 | 4462 |
| 525702 | 32460 | 32476 | ATGTTGCCATCATACTA | 52 | 4463 |
| 525703 | 32461 | 32477 | AATGTTGCCATCATACT | 28 | 4464 |
| 525704 | 32462 | 32478 | CAATGTTGCCATCATAC | 40 | 4465 |
| 525705 | 32463 | 32479 | GCAATGTTGCCATCATA | 73 | 4466 |
| 525706 | 32464 | 32480 | TGCAATGTTGCCATCAT | 62 | 4467 |
| 525707 | 32465 | 32481 | TTGCAATGTTGCCATCA | 61 | 4468 |
| 525708 | 32466 | 32482 | GTTGCAATGTTGCCATC | 79 | 4469 |
| 525709 | 32467 | 32483 | GGTTGCAATGTTGCCAT | 69 | 4470 |
| 525710 | 32468 | 32484 | TGGTTGCAATGTTGCCA | 66 | 4471 |

TABLE 63-continued

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525711 | 32469 | 32485 | GTGGTTGCAATGTTGCC | 73 | 4472 |
| 525712 | 32470 | 32486 | GGTGGTTGCAATGTTGC | 45 | 4473 |
| 525713 | 32476 | 32492 | CTGGATGGTGGTTGCAA | 20 | 4474 |
| 525714 | 32477 | 32493 | CCTGGATGGTGGTTGCA | 59 | 4475 |
| 525715 | 32478 | 32494 | GCCTGGATGGTGGTTGC | 58 | 4476 |
| 525716 | 32479 | 32495 | AGCCTGGATGGTGGTTG | 34 | 4477 |
| 525717 | 32619 | 32635 | GAGATCTCCAGCAGCAA | 52 | 4478 |
| 525718 | 32620 | 32636 | TGAGATCTCCAGCAGCA | 57 | 4479 |
| 525719 | 32621 | 32637 | CTGAGATCTCCAGCAGC | 51 | 4480 |
| 525720 | 32622 | 32638 | ACTGAGATCTCCAGCAG | 16 | 4481 |
| 525721 | 32645 | 32661 | GGAGTGACAGGGCAGGA | 42 | 4482 |
| 525722 | 32646 | 32662 | TGGAGTGACAGGGCAGG | 42 | 4483 |
| 525723 | 32647 | 32663 | ATGGAGTGACAGGGCAG | 35 | 4484 |
| 525724 | 32752 | 32768 | AAGTCTATCAGGATGCA | 43 | 4485 |
| 525725 | 32753 | 32769 | AAAGTCTATCAGGATGC | 37 | 4486 |
| 525726 | 32754 | 32770 | CAAAGTCTATCAGGATG | 20 | 4487 |
| 525727 | 32755 | 32771 | ACAAAGTCTATCAGGAT | 0 | 4488 |
| 525728 | 32757 | 32773 | TGACAAAGTCTATCAGG | 25 | 4489 |
| 525729 | 32758 | 32774 | GTGACAAAGTCTATCAG | 51 | 4490 |
| 525730 | 32759 | 32775 | AGTGACAAAGTCTATCA | 28 | 4491 |
| 525731 | 33180 | 33196 | CCTAGTGCCCCAGGGAG | 29 | 4492 |
| 525732 | 33181 | 33197 | TCCTAGTGCCCCAGGGA | 25 | 4493 |
| 525733 | 33182 | 33198 | GTCCTAGTGCCCCAGGG | 74 | 4494 |
| 525734 | 33183 | 33199 | TGTCCTAGTGCCCCAGG | 53 | 4495 |
| 525735 | 36248 | 36264 | GGTATTCTGCTCATAAA | 43 | 4496 |
| 525736 | 36249 | 36265 | GGGTATTCTGCTCATAA | 50 | 4497 |
| 525737 | 36250 | 36266 | AGGGTATTCTGCTCATA | 65 | 4498 |
| 525738 | 36251 | 36267 | AAGGGTATTCTGCTCAT | 55 | 4499 |
| 525739 | 36252 | 36268 | TAAGGGTATTCTGCTCA | 58 | 4500 |
| 525740 | 36253 | 36269 | GTAAGGGTATTCTGCTC | 64 | 4501 |
| 525741 | 36254 | 36270 | AGTAAGGGTATTCTGCT | 60 | 4502 |
| 525742 | 36263 | 36279 | GAGACAATGAGTAAGGG | 25 | 4503 |
| 525743 | 36264 | 36280 | AGAGACAATGAGTAAGG | 19 | 4504 |
| 525744 | 36265 | 36281 | GAGAGACAATGAGTAAG | 11 | 4505 |
| 525745 | 36522 | 36538 | AAGCGACAGCCCTGTGC | 17 | 4506 |
| 525746 | 36523 | 36539 | CAAGCGACAGCCCTGTG | 16 | 4507 |

TABLE 63-continued

Inhibition of DGAT2 mRNA by 3-10-4 MOE gapmers targeting SEQ ID NO: 2

| ISIS NO | SEQ ID NO: 2 Start Site | SEQ ID NO: 2 Stop Site | Sequence | % inhibition | SEQ ID NO |
|---|---|---|---|---|---|
| 525747 | 36524 | 36540 | ACAAGCGACAGCCCTGT | 28 | 4508 |
| 525748 | 36652 | 36668 | AATGAGACAGGCAGCCC | 40 | 4509 |
| 525749 | 36653 | 36669 | GAATGAGACAGGCAGCC | 35 | 4510 |
| 525750 | 36654 | 36670 | AGAATGAGACAGGCAGC | 37 | 4511 |
| 525751 | 36679 | 36695 | CTCTGTGGGCTCCTCCA | 25 | 4512 |
| 525752 | 36680 | 36696 | GCTCTGTGGGCTCCTCC | 57 | 4513 |
| 525753 | 36681 | 36697 | TGCTCTGTGGGCTCCTC | 46 | 4514 |
| 525754 | 36682 | 36698 | GTGCTCTGTGGGCTCCT | 76 | 4515 |
| 525755 | 36683 | 36699 | TGTGCTCTGTGGGCTCC | 59 | 4516 |
| 525756 | 36686 | 36702 | CCCTGTGCTCTGTGGGC | 30 | 4517 |
| 525757 | 36687 | 36703 | GCCCTGTGCTCTGTGGG | 32 | 4518 |
| 525758 | 36688 | 36704 | GGCCCTGTGCTCTGTGG | 40 | 4519 |
| 525759 | 36738 | 36754 | CCACTGTCAGTCTCTCC | 40 | 4520 |
| 525760 | 36739 | 36755 | CCCACTGTCAGTCTCTC | 46 | 4521 |
| 525761 | 36740 | 36756 | CCCCACTGTCAGTCTCT | 29 | 4522 |
| 525762 | 36758 | 36774 | CTTGGCTGCAAGCTCTG | 22 | 4523 |
| 525763 | 36759 | 36775 | CCTTGGCTGCAAGCTCT | 37 | 4524 |
| 525764 | 36760 | 36776 | GCCTTGGCTGCAAGCTC | 30 | 4525 |

Example 5: Antisense Inhibition of Human DGAT2 in HepG2 Cells by MOE Gapmers

Antisense oligonucleotides were designed targeting a diacylglycerol acyltransferase 2 (DGAT2) nucleic acid and were tested for their effects on DGAT2 mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 1,000 nM antisense oligonucleotide. After a treatment period of approximately 24 hours, RNA was isolated from the cells and DGAT2 mRNA levels were measured by quantitative real-time PCR. Human primer probe set RTS2988_MGB was used to measure mRNA levels. DGAT2 mRNA levels were adjusted according to total RNA content, as measured by RIBOGREEN® Results are presented as percent inhibition of DGAT2, relative to untreated control cells. ISIS 413433, which consistently demonstrated higher potency than any of the previously disclosed oligonucleotides in the studies above was included in this study as a benchmark oligonucleotide. Antisense oligonucleotides that demonstrated about the same or greater potency than ISIS 413433 were therefore considered for further experimentation.

The newly designed chimeric antisense oligonucleotides in the Tables below were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to the human DGAT2 genomic sequence, designated herein as SEQ ID NO: 2 (RefSeq No. NT_033927.5 truncated from nucleotides 5669186 to 5712008). 'n/a' indicates that the antisense oligonucleotide does not target that particular gene sequence with 100% complementarity. In case the sequence alignment for a target gene in a particular table is not shown, it is understood that none of the oligonucleotides presented in that table align with 100% complementarity with that target gene.

TABLE 64

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472445 | 1000 | 1019 | CTGCATTCTTGCCAGGCATG | 70 | 38153 | 38172 | 4527 |
| 472446 | 1001 | 1020 | ACTGCATTCTTGCCAGGCAT | 76 | 38154 | 38173 | 4528 |
| 472447 | 1003 | 1022 | TGACTGCATTCTTGCCAGGC | 82 | 38156 | 38175 | 4529 |
| 472448 | 1004 | 1023 | GTGACTGCATTCTTGCCAGG | 76 | 38157 | 38176 | 4530 |
| 472449 | 1006 | 1025 | GGGTGACTGCATTCTTGCCA | 42 | 38159 | 38178 | 4531 |
| 472450 | 1007 | 1026 | AGGGTGACTGCATTCTTGCC | 81 | 38160 | 38179 | 4532 |
| 472451 | 1008 | 1027 | CAGGGTGACTGCATTCTTGC | 71 | 38161 | 38180 | 4533 |
| 472452 | 1010 | 1029 | CGCAGGGTGACTGCATTCTT | 69 | 38163 | 38182 | 4534 |
| 472453 | 1011 | 1030 | CCGCAGGGTGACTGCATTCT | 78 | 38164 | 38183 | 4535 |
| 472454 | 1013 | 1032 | TTCCGCAGGGTGACTGCATT | 53 | 38166 | 38185 | 4536 |
| 472455 | 1014 | 1033 | GTTCCGCAGGGTGACTGCAT | 76 | 38167 | 38186 | 4537 |
| 472456 | 1015 | 1034 | GGTTCCGCAGGGTGACTGCA | 86 | 38168 | 38187 | 4538 |
| 472457 | 1017 | 1036 | GCGGTTCCGCAGGGTGACTG | 77 | 38170 | 38189 | 4539 |
| 472458 | 1018 | 1037 | TGCGGTTCCGCAGGGTGACT | 81 | 38171 | 38190 | 4540 |
| 472459 | 1020 | 1039 | CTTGCGGTTCCGCAGGGTGA | 60 | 38173 | 38192 | 4541 |
| 472460 | 1021 | 1040 | CCTTGCGGTTCCGCAGGGTG | 55 | 38174 | 38193 | 4542 |
| 472461 | 1023 | 1042 | GCCCTTGCGGTTCCGCAGGG | 23 | 38176 | 38195 | 4543 |
| 472462 | 1024 | 1043 | AGCCCTTGCGGTTCCGCAGG | 61 | 38177 | 38196 | 4544 |
| 472463 | 1026 | 1045 | AAAGCCCTTGCGGTTCCGCA | 76 | 38179 | 38198 | 4545 |
| 472464 | 1027 | 1046 | CAAAGCCCTTGCGGTTCCGC | 74 | 38180 | 38199 | 4546 |
| 472465 | 1029 | 1048 | CACAAAGCCCTTGCGGTTCC | 53 | 38182 | 38201 | 4547 |
| 472466 | 1030 | 1049 | TCACAAAGCCCTTGCGGTTC | 23 | 38183 | 38202 | 4548 |
| 472467 | 1032 | 1051 | TTTCACAAAGCCCTTGCGGT | 0 | 38185 | 38204 | 4549 |
| 472468 | 1033 | 1052 | GTTTCACAAAGCCCTTGCGG | 46 | 38186 | 38205 | 4550 |
| 472469 | 1035 | 1054 | CAGTTTCACAAAGCCCTTGC | 51 | 38188 | 38207 | 4551 |
| 472470 | 1036 | 1055 | CCAGTTTCACAAAGCCCTTG | 55 | 38189 | 38208 | 4552 |
| 472471 | 1038 | 1057 | GGCCAGTTTCACAAAGCCCT | 37 | 38191 | 38210 | 4553 |
| 472472 | 1039 | 1058 | GGGCCAGTTTCACAAAGCCC | 0 | 38192 | 38211 | 4554 |
| 472473 | 1041 | 1060 | CAGGGCCAGTTTCACAAAGC | 34 | 38194 | 38213 | 4555 |
| 472474 | 1042 | 1061 | GCAGGGCCAGTTTCACAAAG | 63 | 38195 | 38214 | 4556 |
| 472475 | 1089 | 1108 | TTCATTCTCTCCAAAGGAGT | 66 | 39136 | 39155 | 4557 |
| 472476 | 1090 | 1109 | CTTCATTCTCTCCAAAGGAG | 75 | 39137 | 39156 | 4558 |
| 472477 | 1092 | 1111 | CACTTCATTCTCTCCAAAGG | 78 | 39139 | 39158 | 4559 |
| 472478 | 1093 | 1112 | ACACTTCATTCTCTCCAAAG | 84 | 39140 | 39159 | 4560 |
| 472479 | 1094 | 1113 | TACACTTCATTCTCTCCAAA | 62 | 39141 | 39160 | 4561 |
| 472480 | 1096 | 1115 | TGTACACTTCATTCTCTCCA | 95 | 39143 | 39162 | 4562 |
| 472481 | 1097 | 1116 | TTGTACACTTCATTCTCTCC | 89 | 39144 | 39163 | 4563 |

TABLE 64-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472482 | 1099 | 1118 | GCTTGTACACTTCATTCTCT | 91 | 39146 | 39165 | 4564 |
| 472483 | 1100 | 1119 | TGCTTGTACACTTCATTCTC | 75 | 39147 | 39166 | 4565 |
| 472484 | 1102 | 1121 | CCTGCTTGTACACTTCATTC | 90 | 39149 | 39168 | 4566 |
| 472485 | 1103 | 1122 | ACCTGCTTGTACACTTCATT | 86 | 39150 | 39169 | 4567 |
| 472486 | 1104 | 1123 | CACCTGCTTGTACACTTCAT | 95 | 39151 | 39170 | 4568 |
| 472487 | 1106 | 1125 | ATCACCTGCTTGTACACTTC | 90 | 39153 | 39172 | 4569 |
| 472488 | 1107 | 1126 | GATCACCTGCTTGTACACTT | 86 | 39154 | 39173 | 4570 |
| 472489 | 1109 | 1128 | AAGATCACCTGCTTGTACAC | 69 | 39156 | 39175 | 4571 |
| 472490 | 1110 | 1129 | GAAGATCACCTGCTTGTACA | 63 | 39157 | 39176 | 4572 |
| 472491 | 1112 | 1131 | TCGAAGATCACCTGCTTGTA | 72 | 39159 | 39178 | 4573 |
| 472492 | 1113 | 1132 | CTCGAAGATCACCTGCTTGT | 51 | 39160 | 39179 | 4574 |
| 472493 | 1115 | 1134 | TCCTCGAAGATCACCTGCTT | 71 | 39162 | 39181 | 4575 |
| 472494 | 1116 | 1135 | CTCCTCGAAGATCACCTGCT | 70 | 39163 | 39182 | 4576 |
| 472495 | 1118 | 1137 | CCCTCCTCGAAGATCACCTG | 69 | 39165 | 39184 | 4577 |
| 472496 | 1119 | 1138 | GCCCTCCTCGAAGATCACCT | 87 | 39166 | 39185 | 4578 |
| 472497 | 1121 | 1140 | GAGCCCTCCTCGAAGATCAC | 54 | 39168 | 39187 | 4579 |
| 472498 | 1122 | 1141 | GGAGCCCTCCTCGAAGATCA | 77 | 39169 | 39188 | 4580 |
| 472499 | 1124 | 1143 | CAGGAGCCCTCCTCGAAGAT | 65 | 39171 | 39190 | 4581 |
| 472500 | 1125 | 1144 | CCAGGAGCCCTCCTCGAAGA | 72 | 39172 | 39191 | 4582 |
| 472501 | 1127 | 1146 | CCCCAGGAGCCCTCCTCGAA | 60 | 39174 | 39193 | 4583 |
| 472502 | 1128 | 1147 | GCCCCAGGAGCCCTCCTCGA | 48 | 39175 | 39194 | 4584 |
| 472503 | 1130 | 1149 | CGGCCCCAGGAGCCCTCCTC | 21 | 39177 | 39196 | 4585 |
| 472504 | 1131 | 1150 | TCGGCCCCAGGAGCCCTCCT | 26 | 39178 | 39197 | 4586 |
| 472505 | 1132 | 1151 | ATCGGCCCCAGGAGCCCTCC | 1 | 39179 | 39198 | 4587 |
| 472506 | 1134 | 1153 | CCATCGGCCCCAGGAGCCCT | 70 | 39181 | 39200 | 4588 |
| 472507 | 1135 | 1154 | CCCATCGGCCCCAGGAGCCC | 74 | 39182 | 39201 | 4589 |
| 472508 | 1137 | 1156 | GACCCATCGGCCCCAGGAGC | 44 | 39184 | 39203 | 4590 |
| 472509 | 1138 | 1157 | GGACCCATCGGCCCCAGGAG | 45 | 39185 | 39204 | 4591 |
| 472510 | 1158 | 1177 | GTATTTCTGGAACTTCTTCT | 71 | 39205 | 39224 | 4592 |
| 472511 | 1159 | 1178 | TGTATTTCTGGAACTTCTTC | 63 | 39206 | 39225 | 4593 |
| 472512 | 1161 | 1180 | AATGTATTTCTGGAACTTCT | 60 | 39208 | 39227 | 4594 |
| 472513 | 1162 | 1181 | CAATGTATTTCTGGAACTTC | 36 | 39209 | 39228 | 4595 |
| 472514 | 1164 | 1183 | ACCAATGTATTTCTGGAACT | 72 | 39211 | 39230 | 4596 |
| 472515 | 1165 | 1184 | AACCAATGTATTTCTGGAAC | 68 | 39212 | 39231 | 4597 |
| 472516 | 1166 | 1185 | AAACCAATGTATTTCTGGAA | 50 | 39213 | 39232 | 4598 |
| 472517 | 1167 | 1186 | GAAACCAATGTATTTCTGGA | 65 | 39214 | 39233 | 4599 |

TABLE 64-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472518 | 1169 | 1188 | GCGAAACCAATGTATTTCTG | 76 | 39216 | 39235 | 4600 |
| 472519 | 1170 | 1189 | GGCGAAACCAATGTATTTCT | 75 | 39217 | 39236 | 4601 |
| 472520 | 1209 | 1228 | GTCGGAGGAGAAGAGGCCTC | 43 | 39256 | 39275 | 4602 |
| 472444 | 998 | 1017 | GCATTCTTGCCAGGCATGGA | 89 | 38151 | 38170 | 4526 |
| 413433 | n/a | n/a | GCCTGGACAAGTCCTGCCCA | 87 | 32431 | 32450 | 425 |

TABLE 65

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472588 | 1558 | 1577 | TTCTTAAAAAAGACCTAACA | 22 | 41529 | 41548 | 4603 |
| 472589 | 1560 | 1579 | CCTTCTTAAAAAGACCTAA | 70 | 41531 | 41550 | 4604 |
| 472590 | 1561 | 1580 | TCCTTCTTAAAAAGACCTA | 65 | 41532 | 41551 | 4605 |
| 472591 | 1562 | 1581 | TTCCTTCTTAAAAAGACCT | 58 | 41533 | 41552 | 4606 |
| 472592 | 1564 | 1583 | TTTTCCTTCTTAAAAAGAC | 14 | 41535 | 41554 | 4607 |
| 472593 | 1565 | 1584 | TTTTTCCTTCTTAAAAAGA | 9 | 41536 | 41555 | 4608 |
| 472594 | 1566 | 1585 | CTTTTTCCTTCTTAAAAAG | 15 | 41537 | 41556 | 4609 |
| 472595 | 1568 | 1587 | GACTTTTTCCTTCTTAAAAA | 36 | 41539 | 41558 | 4610 |
| 472596 | 1569 | 1588 | TGACTTTTCCTTCTTAAAA | 36 | 41540 | 41559 | 4611 |
| 472597 | 1570 | 1589 | CTGACTTTTCCTTCTTAAA | 75 | 41541 | 41560 | 4612 |
| 472598 | 1571 | 1590 | ACTGACTTTTCCTTCTTAA | 77 | 41542 | 41561 | 4613 |
| 472599 | 1615 | 1634 | CACCACCTAGAACAGGGCAA | 70 | 41586 | 41605 | 4614 |
| 472600 | 1617 | 1636 | GCCACCACCTAGAACAGGGC | 44 | 41588 | 41607 | 4615 |
| 472601 | 1618 | 1637 | AGCCACCACCTAGAACAGGG | 70 | 41589 | 41608 | 4616 |
| 472602 | 1619 | 1638 | TAGCCACCACCTAGAACAGG | 46 | 41590 | 41609 | 4617 |
| 472603 | 1621 | 1640 | TTTAGCCACCACCTAGAACA | 51 | 41592 | 41611 | 4618 |
| 472604 | 1622 | 1641 | ATTTAGCCACCACCTAGAAC | 40 | 41593 | 41612 | 4619 |
| 472605 | 1623 | 1642 | GATTTAGCCACCACCTAGAA | 63 | 41594 | 41613 | 4620 |
| 472606 | 1624 | 1643 | AGATTTAGCCACCACCTAGA | 54 | 41595 | 41614 | 4621 |
| 472607 | 1626 | 1645 | CCAGATTTAGCCACCACCTA | 74 | 41597 | 41616 | 4622 |
| 472608 | 1627 | 1646 | CCCAGATTTAGCCACCACCT | 88 | 41598 | 41617 | 4623 |
| 472609 | 1628 | 1647 | GCCCAGATTTAGCCACCACC | 78 | 41599 | 41618 | 4624 |
| 472610 | 1629 | 1648 | GGCCCAGATTTAGCCACCAC | 83 | 41600 | 41619 | 4625 |
| 472611 | 1631 | 1650 | TAGGCCCAGATTTAGCCACC | 51 | 41602 | 41621 | 4626 |
| 472612 | 1632 | 1651 | TTAGGCCCAGATTTAGCCAC | 14 | 41603 | 41622 | 4627 |
| 472613 | 1633 | 1652 | ATTAGGCCCAGATTTAGCCA | 45 | 41604 | 41623 | 4628 |

TABLE 65-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472614 | 1634 | 1653 | GATTAGGCCCAGATTTAGCC | 44 | 41605 | 41624 | 4629 |
| 472615 | 1636 | 1655 | CAGATTAGGCCCAGATTTAG | 16 | 41607 | 41626 | 4630 |
| 472616 | 1637 | 1656 | CCAGATTAGGCCCAGATTTA | 40 | 41608 | 41627 | 4631 |
| 472617 | 1638 | 1657 | CCCAGATTAGGCCCAGATTT | 40 | 41609 | 41628 | 4632 |
| 472618 | 1639 | 1658 | ACCCAGATTAGGCCCAGATT | 50 | 41610 | 41629 | 4633 |
| 472619 | 1641 | 1660 | CCACCCAGATTAGGCCCAGA | 71 | 41612 | 41631 | 4634 |
| 472620 | 1642 | 1661 | GCCACCCAGATTAGGCCCAG | 73 | 41613 | 41632 | 4635 |
| 472621 | 1643 | 1662 | AGCCACCCAGATTAGGCCCA | 65 | 41614 | 41633 | 4636 |
| 472622 | 1644 | 1663 | GAGCCACCCAGATTAGGCCC | 26 | 41615 | 41634 | 4637 |
| 472623 | 1646 | 1665 | CTGAGCCACCCAGATTAGGC | 23 | 41617 | 41636 | 4638 |
| 472624 | 1647 | 1666 | GCTGAGCCACCCAGATTAGG | 24 | 41618 | 41637 | 4639 |
| 472625 | 1648 | 1667 | AGCTGAGCCACCCAGATTAG | 2 | 41619 | 41638 | 4640 |
| 472626 | 1649 | 1668 | TAGCTGAGCCACCCAGATTA | 31 | 41620 | 41639 | 4641 |
| 472627 | 1651 | 1670 | GTTAGCTGAGCCACCCAGAT | 48 | 41622 | 41641 | 4642 |
| 472628 | 1652 | 1671 | GGTTAGCTGAGCCACCCAGA | 57 | 41623 | 41642 | 4643 |
| 472629 | 1654 | 1673 | GAGGTTAGCTGAGCCACCCA | 66 | 41625 | 41644 | 4644 |
| 472630 | 1655 | 1674 | AGAGGTTAGCTGAGCCACCC | 51 | 41626 | 41645 | 4645 |
| 472631 | 1677 | 1696 | GTCACTTCAGGAAGGGAAGA | 54 | 41648 | 41667 | 4646 |
| 472632 | 1678 | 1697 | TGTCACTTCAGGAAGGGAAG | 58 | 41649 | 41668 | 4647 |
| 472633 | 1749 | 1768 | AAAAGTGAATCATCTAACTG | 23 | 41720 | 41739 | 4648 |
| 472634 | 1750 | 1769 | AAAAAGTGAATCATCTAACT | 0 | 41721 | 41740 | 4649 |
| 472635 | 1751 | 1770 | CAAAAAGTGAATCATCTAAC | 2 | 41722 | 41741 | 4650 |
| 472636 | 1752 | 1771 | GCAAAAAGTGAATCATCTAA | 55 | 41723 | 41742 | 4651 |
| 472637 | 1754 | 1773 | GGGCAAAAAGTGAATCATCT | 79 | 41725 | 41744 | 4652 |
| 472638 | 1790 | 1809 | CTTGTATGAGAAGTGGCTTT | 58 | 41761 | 41780 | 4653 |
| 472639 | 1791 | 1810 | GCTTGTATGAGAAGTGGCTT | 49 | 41762 | 41781 | 4654 |
| 472640 | 1793 | 1812 | GGGCTTGTATGAGAAGTGGC | 67 | 41764 | 41783 | 4655 |
| 472641 | 1838 | 1857 | CCTGCAGTTTCAGGACTAGA | 64 | 41809 | 41828 | 4656 |
| 472642 | 1839 | 1858 | TCCTGCAGTTTCAGGACTAG | 50 | 41810 | 41829 | 4657 |
| 472643 | 1841 | 1860 | GGTCCTGCAGTTTCAGGACT | 11 | 41812 | 41831 | 4658 |
| 472644 | 1842 | 1861 | TGGTCCTGCAGTTTCAGGAC | 20 | 41813 | 41832 | 4659 |
| 472645 | 1843 | 1862 | CTGGTCCTGCAGTTTCAGGA | 41 | 41814 | 41833 | 4660 |
| 472646 | 1845 | 1864 | AACTGGTCCTGCAGTTTCAG | 50 | 41816 | 41835 | 4661 |
| 472647 | 1846 | 1865 | AAACTGGTCCTGCAGTTTCA | 56 | 41817 | 41836 | 4662 |
| 472648 | 1848 | 1867 | AGAAACTGGTCCTGCAGTTT | 40 | 41819 | 41838 | 4663 |
| 472649 | 1849 | 1868 | GAGAAACTGGTCCTGCAGTT | 24 | 41820 | 41839 | 4664 |

TABLE 65-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472650 | 1850 | 1869 | AGAGAAACTGGTCCTGCAGT | 29 | 41821 | 41840 | 4665 |
| 472651 | 1851 | 1870 | CAGAGAAACTGGTCCTGCAG | 35 | 41822 | 41841 | 4666 |
| 472652 | 1853 | 1872 | GGCAGAGAAACTGGTCCTGC | 84 | 41824 | 41843 | 4667 |
| 472653 | 1854 | 1873 | TGGCAGAGAAACTGGTCCTG | 71 | 41825 | 41844 | 4668 |
| 472654 | 1855 | 1874 | TTGGCAGAGAAACTGGTCCT | 63 | 41826 | 41845 | 4669 |
| 472655 | 1856 | 1875 | CTTGGCAGAGAAACTGGTCC | 62 | 41827 | 41846 | 4670 |
| 472656 | 1858 | 1877 | CCCTTGGCAGAGAAACTGGT | 49 | 41829 | 41848 | 4671 |
| 472657 | 1859 | 1878 | CCCCTTGGCAGAGAAACTGG | 66 | 41830 | 41849 | 4672 |
| 472658 | 1861 | 1880 | CTCCCCTTGGCAGAGAAACT | 58 | 41832 | 41851 | 4673 |
| 472659 | 1862 | 1881 | CCTCCCCTTGGCAGAGAAAC | 54 | 41833 | 41852 | 4674 |
| 472660 | 1863 | 1882 | TCCTCCCCTTGGCAGAGAAA | 49 | 41834 | 41853 | 4675 |
| 472661 | 1865 | 1884 | ACTCCTCCCCTTGGCAGAGA | 47 | 41836 | 41855 | 4676 |
| 472662 | 1866 | 1885 | AACTCCTCCCCTTGGCAGAG | 39 | 41837 | 41856 | 4677 |
| 472663 | 1867 | 1886 | CAACTCCTCCCCTTGGCAGA | 0 | 41838 | 41857 | 4678 |
| 472664 | 1869 | 1888 | TCCAACTCCTCCCCTTGGCA | 29 | 41840 | 41859 | 4679 |
| 413433 | n/a | n/a | GCCTGGACAAGTCCTGCCCA | 85 | 32431 | 32450 | 425 |

TABLE 66

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472445 | 1000 | 1019 | CTGCATTCTTGCCAGGCATG | 53 | 38153 | 38172 | 4527 |
| 472446 | 1001 | 1020 | ACTGCATTCTTGCCAGGCAT | 60 | 38154 | 38173 | 4528 |
| 472447 | 1003 | 1022 | TGACTGCATTCTTGCCAGGC | 52 | 38156 | 38175 | 4529 |
| 472448 | 1004 | 1023 | GTGACTGCATTCTTGCCAGG | 60 | 38157 | 38176 | 4530 |
| 472449 | 1006 | 1025 | GGGTGACTGCATTCTTGCCA | 0 | 38159 | 38178 | 4531 |
| 472450 | 1007 | 1026 | AGGGTGACTGCATTCTTGCC | 62 | 38160 | 38179 | 4532 |
| 472451 | 1008 | 1027 | CAGGGTGACTGCATTCTTGC | 43 | 38161 | 38180 | 4533 |
| 472452 | 1010 | 1029 | CGCAGGGTGACTGCATTCTT | 25 | 38163 | 38182 | 4534 |
| 472453 | 1011 | 1030 | CCGCAGGGTGACTGCATTCT | 45 | 38164 | 38183 | 4535 |
| 472454 | 1013 | 1032 | TTCCGCAGGGTGACTGCATT | 16 | 38166 | 38185 | 4536 |
| 472455 | 1014 | 1033 | GTTCCGCAGGGTGACTGCAT | 29 | 38167 | 38186 | 4537 |
| 472456 | 1015 | 1034 | GGTTCCGCAGGGTGACTGCA | 62 | 38168 | 38187 | 4538 |
| 472457 | 1017 | 1036 | GCGGTTCCGCAGGGTGACTG | 33 | 38170 | 38189 | 4539 |
| 472458 | 1018 | 1037 | TGCGGTTCCGCAGGGTGACT | 57 | 38171 | 38190 | 4540 |
| 472459 | 1020 | 1039 | CTTGCGGTTCCGCAGGGTGA | 39 | 38173 | 38192 | 4541 |

TABLE 66-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472460 | 1021 | 1040 | CCTTGCGGTTCCGCAGGGTG | 25 | 38174 | 38193 | 4542 |
| 472461 | 1023 | 1042 | GCCCTTGCGGTTCCGCAGGG | 9 | 38176 | 38195 | 4543 |
| 472462 | 1024 | 1043 | AGCCCTTGCGGTTCCGCAGG | 32 | 38177 | 38196 | 4544 |
| 472463 | 1026 | 1045 | AAAGCCCTTGCGGTTCCGCA | 46 | 38179 | 38198 | 4545 |
| 472464 | 1027 | 1046 | CAAAGCCCTTGCGGTTCCGC | 48 | 38180 | 38199 | 4546 |
| 472465 | 1029 | 1048 | CACAAAGCCCTTGCGGTTCC | 8 | 38182 | 38201 | 4547 |
| 472466 | 1030 | 1049 | TCACAAAGCCCTTGCGGTTC | 0 | 38183 | 38202 | 4548 |
| 472467 | 1032 | 1051 | TTTCACAAAGCCCTTGCGGT | 0 | 38185 | 38204 | 4549 |
| 472468 | 1033 | 1052 | GTTTCACAAAGCCCTTGCGG | 18 | 38186 | 38205 | 4550 |
| 472469 | 1035 | 1054 | CAGTTTCACAAAGCCCTTGC | 0 | 38188 | 38207 | 4551 |
| 472470 | 1036 | 1055 | CCAGTTTCACAAAGCCCTTG | 23 | 38189 | 38208 | 4552 |
| 472471 | 1038 | 1057 | GGCCAGTTTCACAAAGCCCT | 2 | 38191 | 38210 | 4553 |
| 472472 | 1039 | 1058 | GGGCCAGTTTCACAAAGCCC | 0 | 38192 | 38211 | 4554 |
| 472473 | 1041 | 1060 | CAGGGCCAGTTTCACAAAGC | 0 | 38194 | 38213 | 4555 |
| 472474 | 1042 | 1061 | GCAGGGCCAGTTTCACAAAG | 10 | 38195 | 38214 | 4556 |
| 472475 | 1089 | 1108 | TTCATTCTCTCCAAAGGAGT | 47 | 39136 | 39155 | 4557 |
| 472476 | 1090 | 1109 | CTTCATTCTCTCCAAAGGAG | 65 | 39137 | 39156 | 4558 |
| 472477 | 1092 | 1111 | CACTTCATTCTCTCCAAAGG | 51 | 39139 | 39158 | 4559 |
| 472478 | 1093 | 1112 | ACACTTCATTCTCTCCAAAG | 68 | 39140 | 39159 | 4560 |
| 472479 | 1094 | 1113 | TACACTTCATTCTCTCCAAA | 41 | 39141 | 39160 | 4561 |
| 472480 | 1096 | 1115 | TGTACACTTCATTCTCTCCA | 85 | 39143 | 39162 | 4562 |
| 472481 | 1097 | 1116 | TTGTACACTTCATTCTCTCC | 72 | 39144 | 39163 | 4563 |
| 472482 | 1099 | 1118 | GCTTGTACACTTCATTCTCT | 80 | 39146 | 39165 | 4564 |
| 472483 | 1100 | 1119 | TGCTTGTACACTTCATTCTC | 64 | 39147 | 39166 | 4565 |
| 472484 | 1102 | 1121 | CCTGCTTGTACACTTCATTC | 75 | 39149 | 39168 | 4566 |
| 472485 | 1103 | 1122 | ACCTGCTTGTACACTTCATT | 67 | 39150 | 39169 | 4567 |
| 472486 | 1104 | 1123 | CACCTGCTTGTACACTTCAT | 88 | 39151 | 39170 | 4568 |
| 472487 | 1106 | 1125 | ATCACCTGCTTGTACACTTC | 59 | 39153 | 39172 | 4569 |
| 472488 | 1107 | 1126 | GATCACCTGCTTGTACACTT | 70 | 39154 | 39173 | 4570 |
| 472489 | 1109 | 1128 | AAGATCACCTGCTTGTACAC | 28 | 39156 | 39175 | 4571 |
| 472490 | 1110 | 1129 | GAAGATCACCTGCTTGTACA | 53 | 39157 | 39176 | 4572 |
| 472491 | 1112 | 1131 | TCGAAGATCACCTGCTTGTA | 52 | 39159 | 39178 | 4573 |
| 472492 | 1113 | 1132 | CTCGAAGATCACCTGCTTGT | 49 | 39160 | 39179 | 4574 |
| 472493 | 1115 | 1134 | TCCTCGAAGATCACCTGCTT | 46 | 39162 | 39181 | 4575 |
| 472494 | 1116 | 1135 | CTCCTCGAAGATCACCTGCT | 55 | 39163 | 39182 | 4576 |
| 472495 | 1118 | 1137 | CCCTCCTCGAAGATCACCTG | 54 | 39165 | 39184 | 4577 |

TABLE 66-continued

Inhibition of DGAT2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 472496 | 1119 | 1138 | GCCCTCCTCGAAGATCACCT | 74 | 39166 | 39185 | 4578 |
| 472497 | 1121 | 1140 | GAGCCCTCCTCGAAGATCAC | 54 | 39168 | 39187 | 4579 |
| 472498 | 1122 | 1141 | GGAGCCCTCCTCGAAGATCA | 68 | 39169 | 39188 | 4580 |
| 472499 | 1124 | 1143 | CAGGAGCCCTCCTCGAAGAT | 37 | 39171 | 39190 | 4581 |
| 472500 | 1125 | 1144 | CCAGGAGCCCTCCTCGAAGA | 41 | 39172 | 39191 | 4582 |
| 472501 | 1127 | 1146 | CCCCAGGAGCCCTCCTCGAA | 34 | 39174 | 39193 | 4583 |
| 472502 | 1128 | 1147 | GCCCCAGGAGCCCTCCTCGA | 17 | 39175 | 39194 | 4584 |
| 472503 | 1130 | 1149 | CGGCCCCAGGAGCCCTCCTC | 0 | 39177 | 39196 | 4585 |
| 472504 | 1131 | 1150 | TCGGCCCCAGGAGCCCTCCT | 16 | 39178 | 39197 | 4586 |
| 472505 | 1132 | 1151 | ATCGGCCCCAGGAGCCCTCC | 0 | 39179 | 39198 | 4587 |
| 472506 | 1134 | 1153 | CCATCGGCCCCAGGAGCCCT | 64 | 39181 | 39200 | 4588 |
| 472507 | 1135 | 1154 | CCCATCGGCCCCAGGAGCCC | 55 | 39182 | 39201 | 4589 |
| 472508 | 1137 | 1156 | GACCCATCGGCCCCAGGAGC | 34 | 39184 | 39203 | 4590 |
| 472509 | 1138 | 1157 | GGACCCATCGGCCCCAGGAG | 50 | 39185 | 39204 | 4591 |
| 472510 | 1158 | 1177 | GTATTTCTGGAACTTCTTCT | 64 | 39205 | 39224 | 4592 |
| 472511 | 1159 | 1178 | TGTATTTCTGGAACTTCTTC | 49 | 39206 | 39225 | 4593 |
| 472512 | 1161 | 1180 | AATGTATTTCTGGAACTTCT | 40 | 39208 | 39227 | 4594 |
| 472513 | 1162 | 1181 | CAATGTATTTCTGGAACTTC | 4 | 39209 | 39228 | 4595 |
| 472514 | 1164 | 1183 | ACCAATGTATTTCTGGAACT | 41 | 39211 | 39230 | 4596 |
| 472515 | 1165 | 1184 | AACCAATGTATTTCTGGAAC | 41 | 39212 | 39231 | 4597 |
| 472516 | 1166 | 1185 | AAACCAATGTATTTCTGGAA | 34 | 39213 | 39232 | 4598 |
| 472517 | 1167 | 1186 | GAAACCAATGTATTTCTGGA | 51 | 39214 | 39233 | 4599 |
| 472518 | 1169 | 1188 | GCGAAACCAATGTATTTCTG | 54 | 39216 | 39235 | 4600 |
| 472519 | 1170 | 1189 | GGCGAAACCAATGTATTTCT | 59 | 39217 | 39236 | 4601 |
| 472520 | 1209 | 1228 | GTCGGAGGAGAAGAGGCCTC | 17 | 39256 | 39275 | 4602 |
| 472444 | 998 | 1017 | GCATTCTTGCCAGGCATGGA | 77 | 38151 | 38170 | 4526 |
| 413433 | n/a | n/a | GCCTGGACAAGTCCTGCCCA | 76 | 32431 | 32450 | 425 |

Example 6: Dose-Dependent Antisense Inhibition of Human DGAT2 in HepG2 Cells by MOE Gapmers Gapmers from the studies described in the Examples above exhibiting significant in vitro inhibition of DGAT2 mRNA were selected and tested at various doses in HepG2 cells. The antisense oligonucleotides were tested in a series of experiments that had similar culture conditions. Previously disclosed oligonucleotides, ISIS 21316, ISIS 217317, ISIS 217328, ISIS 369185, ISIS 366714, ISIS 366730, ISIS 366746, and ISIS 369241 from earlier published application, WO 2005/019418, were included in the assay. The results for each experiment are presented in separate tables shown below. Cells were plated at a density of 10,000 cells per well and transfected using Lipofectin reagent with 6.25 nM, 12.5 nM, 25.0 nM, 50 nM, 100 nM, or 200.0 nM concentrations of antisense oligonucleotide, as specified in the Tables below. After a treatment period of approximately 16 hours, RNA was isolated from the cells and DGAT2 mRNA levels were measured by quantitative real-time PCR. Human primer probe set RTS2367 was used to measure mRNA levels. DGAT2 mRNA levels were adjusted according to total RNA content, as measured by RIBOGREEN®. Results are presented as percent inhibition of DGAT2, relative to untreated control cells. '0' indicates that the mRNA levels were not inhibited. 'n.d.' indicates that the inhibition levels were not recorded.

The half maximal inhibitory concentration ($IC_{50}$) of each oligonucleotide is also presented. DGAT2 mRNA levels were significantly reduced in a dose-dependent manner in antisense oligonucleotide treated cells. The results also demonstrate that several newly designed oligonucleotides had greater efficacy than the previously disclosed oligonucleotides.

TABLE 67

| ISIS No | 6.25 nM | 12.5 nM | 25.0 nM | 50.0 nM | 100.0 nM | 200.0 nM | IC$_{50}$ (nM) |
|---|---|---|---|---|---|---|---|
| 217316 | 7 | 7 | 27 | 47 | 68 | 63 | 55 |
| 217317 | 3 | 12 | 32 | 50 | 75 | 84 | 44 |
| 369185 | 17 | 12 | 34 | 63 | 78 | 81 | 42 |
| 381726 | 4 | 30 | 44 | 56 | 76 | 83 | 37 |
| 411874 | 15 | 31 | 27 | 54 | 66 | 66 | 40 |
| 411899 | 5 | 22 | 31 | 57 | 74 | 87 | 39 |
| 411901 | 0 | 6 | 24 | 46 | 66 | 65 | 58 |
| 411905 | 6 | 30 | 29 | 58 | 73 | 76 | 34 |
| 411912 | 8 | 24 | 31 | 56 | 79 | 89 | 35 |
| 411941 | 11 | 22 | 30 | 59 | 77 | 82 | 35 |

TABLE 68

| ISIS No | 6.25 nM | 12.5 nM | 25.0 nM | 50.0 nM | 100.0 nM | 200.0 nM | IC$_{50}$ (nM) |
|---|---|---|---|---|---|---|---|
| 366714 | 7 | 8 | 42 | 67 | 79 | 82 | 33 |
| 366730 | 0 | 18 | 33 | 72 | 84 | 91 | 43 |
| 411944 | 2 | 14 | 46 | 65 | 82 | 93 | 30 |
| 411945 | 14 | 21 | 51 | 68 | 86 | n.d. | 24 |
| 411950 | 6 | 5 | 28 | 66 | 84 | n.d. | 29 |
| 413176 | 7 | 16 | 24 | 58 | 78 | 88 | 38 |
| 413192 | 0 | 6 | 30 | 62 | 80 | 80 | 57 |
| 413200 | 2 | 18 | 20 | 60 | 78 | 77 | 36 |
| 413213 | 9 | 12 | 34 | 55 | 84 | 90 | 45 |
| 413226 | 3 | 22 | 13 | 36 | 72 | 87 | 41 |

TABLE 69

| ISIS No | 6.25 nM | 12.5 nM | 25.0 nM | 50.0 nM | 100.0 nM | 200.0 nM | IC$_{50}$ (nM) |
|---|---|---|---|---|---|---|---|
| 366746 | 5 | 7 | 21 | 32 | 62 | 77 | 66 |
| 369241 | 0 | 4 | 10 | 35 | 56 | 63 | 106 |
| 413198 | 10 | 16 | 24 | 53 | 72 | 73 | 51 |
| 413214 | 1 | 17 | 43 | 61 | 81 | 77 | 34 |
| 413232 | 8 | 23 | 33 | 60 | 78 | 82 | 35 |
| 413236 | 0 | 12 | 3 | 52 | 71 | 72 | 47 |
| 413253 | 6 | 7 | 27 | 59 | 72 | 75 | 64 |
| 413258 | 0 | 12 | 27 | 46 | 78 | 77 | 62 |
| 413266 | 0 | 0 | 21 | 48 | 76 | 75 | 52 |
| 413284 | 4 | 0 | 22 | 45 | 57 | 65 | 78 |

TABLE 70

| ISIS No | 6.25 nM | 12.5 nM | 25.0 nM | 50.0 nM | 100.0 nM | 200.0 nM | IC$_{50}$ (nM) |
|---|---|---|---|---|---|---|---|
| 217328 | 4 | 15 | 31 | 50 | 64 | 72 | 62 |
| 413243 | 0 | 10 | 28 | 50 | 69 | 77 | 66 |
| 413351 | 4 | 16 | 16 | 39 | 56 | 69 | 51 |
| 413356 | 16 | 12 | 23 | 51 | 63 | 69 | 34 |
| 413364 | 0 | 0 | 21 | 41 | 58 | 53 | 52 |
| 413399 | 0 | 3 | 23 | 35 | 60 | 58 | 78 |
| 413413 | 1 | 0 | 30 | 50 | 71 | 77 | 64 |
| 413422 | 0 | 0 | 8 | 41 | 63 | 70 | 62 |
| 413433 | 5 | 5 | 20 | 55 | 77 | 82 | 47 |
| 413441 | 2 | 5 | 26 | 50 | 70 | 79 | 106 |
| 413446 | 0 | 0 | 10 | 41 | 63 | 78 | 35 |

TABLE 71

| ISIS No | 6.25 nM | 12.5 nM | 25.0 nM | 50.0 nM | 100.0 nM | 200.0 nM | IC$_{50}$ (nM) |
|---|---|---|---|---|---|---|---|
| 217317 | 0 | 0 | 11 | 34 | 64 | 84 | 77 |
| 366730 | 0 | 15 | 33 | 61 | 87 | 91 | 45 |
| 381726 | 1 | 11 | 31 | 51 | 71 | 83 | 48 |
| 411899 | 6 | 0 | 25 | 39 | 70 | 89 | 55 |
| 411912 | 0 | 0 | 13 | 58 | 77 | 87 | 40 |
| 411944 | 7 | 21 | 32 | 67 | 76 | 87 | 42 |
| 413176 | 0 | 12 | 20 | 54 | 89 | 88 | 46 |
| 413232 | 16 | 10 | 30 | 60 | 79 | 90 | 31 |
| 413433 | 15 | 17 | 37 | 71 | 84 | 87 | 24 |
| 413446 | 0 | 0 | 44 | 73 | 77 | 86 | 47 |

Example 7: Dose-Dependent Antisense Inhibition of Human DGAT2 in HepG2 Cells by MOE Gapmers Gapmers from the studies described in the Examples above exhibiting significant in vitro inhibition of DGAT2 mRNA were selected and tested at various doses in HepG2 cells. The antisense oligonucleotides were tested in a series of experiments that had similar culture conditions. Previously disclosed oligonucleotides from earlier published application, WO 2005/019418, were included in the assay. The results for each experiment are presented in separate tables shown below.

Study 1

Cells were plated at a density of 10,000 cells per well and transfected using Lipofectin reagent with 18.75 nM, 37.5 nM, 75.0 nM, or 150.0 nM concentrations of antisense oligonucleotide, as specified in the Tables below. After a treatment period of approximately 16 hours, RNA was isolated from the cells and DGAT2 mRNA levels were measured by quantitative real-time PCR. Human primer probe set RTS2988_MGB was used to measure mRNA levels. DGAT2 mRNA levels were adjusted according to total RNA content, as measured by RIBOGREEN®. Results are presented as percent inhibition of DGAT2, relative to untreated control cells. '0' indicates that the mRNA levels were not inhibited.

The half maximal inhibitory concentration (IC$_{50}$) of each oligonucleotide is also presented. DGAT2 mRNA levels were significantly reduced in a dose-dependent manner in antisense oligonucleotide treated cells.

TABLE 72

| ISIS No | Motif | 18.75 nM | 37.5 nM | 75.0 nM | 150.0 nM | IC$_{50}$ (nM) |
|---|---|---|---|---|---|---|
| 217328 | 5-10-5 | 27 | 44 | 62 | 73 | 47 |
| 366730 | 5-10-5 | 27 | 36 | 61 | 77 | 48 |
| 411944 | 5-10-5 | 19 | 38 | 48 | 69 | 67 |
| 411945 | 5-10-5 | 14 | 26 | 45 | 61 | 93 |
| 413253 | 5-10-5 | 24 | 34 | 50 | 68 | 73 |
| 413433 | 5-10-5 | 28 | 39 | 56 | 68 | 58 |
| 423440 | 5-10-5 | 18 | 39 | 53 | 70 | 67 |
| 423441 | 5-10-5 | 23 | 36 | 54 | 66 | 63 |
| 423444 | 5-10-5 | 15 | 32 | 53 | 69 | 71 |
| 423447 | 5-10-5 | 24 | 36 | 55 | 71 | 60 |
| 423463 | 5-10-5 | 23 | 39 | 59 | 73 | 56 |
| 423489 | 3-14-3 | 21 | 32 | 55 | 73 | 60 |
| 423490 | 3-14-3 | 27 | 32 | 51 | 60 | 76 |
| 423498 | 3-14-3 | 19 | 38 | 56 | 77 | 59 |
| 423499 | 5-10-5 | 23 | 37 | 59 | 77 | 53 |
| 423523 | 3-14-3 | 25 | 41 | 60 | 73 | 56 |
| 423524 | 3-14-3 | 24 | 37 | 62 | 75 | 54 |
| 423601 | 2-13-5 | 28 | 38 | 58 | 75 | 51 |

TABLE 73

| ISIS No | Motif | 18.75 nM | 37.5 nM | 75.0 nM | 150.0 nM | IC$_{50}$ (nM) |
|---|---|---|---|---|---|---|
| 217317 | 5-10-5 | 4 | 23 | 39 | 61 | 104 |
| 217328 | 5-10-5 | 20 | 33 | 54 | 67 | 73 |
| 411899 | 5-10-5 | 11 | 34 | 51 | 66 | 74 |
| 413214 | 5-10-5 | 8 | 32 | 52 | 68 | 73 |
| 413232 | 5-10-5 | 17 | 26 | 50 | 70 | 71 |
| 423452 | 5-10-5 | 12 | 26 | 45 | 65 | 88 |
| 423453 | 5-10-5 | 15 | 33 | 46 | 67 | 76 |
| 423458 | 5-10-5 | 14 | 31 | 49 | 70 | 74 |
| 423459 | 5-10-5 | 17 | 29 | 61 | 73 | 64 |
| 423464 | 5-10-5 | 19 | 33 | 52 | 64 | 74 |
| 423507 | 3-14-3 | 15 | 32 | 52 | 68 | 73 |
| 423508 | 3-14-3 | 14 | 37 | 48 | 69 | 73 |
| 423526 | 3-14-3 | 13 | 23 | 41 | 58 | 109 |
| 423527 | 3-14-3 | 13 | 28 | 51 | 58 | 102 |
| 423565 | 2-13-5 | 17 | 27 | 48 | 69 | 80 |
| 423567 | 2-13-5 | 0 | 29 | 53 | 74 | 79 |
| 423585 | 2-13-5 | 12 | 25 | 42 | 64 | 94 |
| 423595 | 2-13-5 | 12 | 26 | 47 | 69 | 81 |
| 423606 | 2-13-5 | 13 | 27 | 55 | 71 | 68 |

The same gapmers were also tested at various doses in HepG2 cells using electroporation. Cells were plated at a density of 20,000 cells per well and transfected using electroporation with 2.5 µM, 5.0 µM, 10.0 µM, or 20.0 µM concentrations of antisense oligonucleotide, as specified in the Tables below. After a treatment period of approximately 16 hours, RNA was isolated from the cells and DGAT2 mRNA levels were measured by quantitative real-time PCR. Human primer probe set RTS2988_MGB was used to measure mRNA levels. DGAT2 mRNA levels were adjusted according to total RNA content, as measured by RIBOGREEN®. Results are presented as percent inhibition of DGAT2, relative to untreated control cells. '0' indicates that the mRNA levels were not inhibited.

The half maximal inhibitory concentration (IC$_{50}$) of each oligonucleotide is also presented. DGAT2 mRNA levels were significantly reduced in a dose-dependent manner in antisense oligonucleotide treated cells.

TABLE 74

| ISIS No | Motif | 2.5 µM | 5.0 µM | 10.0 µM | 20.0 µM | IC$_{50}$ (µM) |
|---|---|---|---|---|---|---|
| 217328 | 5-10-5 | 55 | 70 | 85 | 94 | 2 |
| 366730 | 5-10-5 | 38 | 51 | 78 | 89 | 5 |
| 411944 | 5-10-5 | 30 | 32 | 48 | 73 | 10 |
| 411945 | 5-10-5 | 31 | 26 | 48 | 69 | 11 |
| 413253 | 5-10-5 | 39 | 51 | 77 | 84 | 4 |
| 413433 | 5-10-5 | 72 | 81 | 82 | 85 | <2.5 |
| 423440 | 5-10-5 | 30 | 54 | 65 | 91 | 5 |
| 423441 | 5-10-5 | 41 | 47 | 60 | 90 | 6 |
| 423444 | 5-10-5 | 19 | 46 | 70 | 81 | 6 |
| 423447 | 5-10-5 | 25 | 49 | 76 | 79 | 5 |
| 423463 | 5-10-5 | 59 | 79 | 85 | 86 | 2 |
| 423489 | 3-14-3 | 33 | 56 | 72 | 92 | 5 |
| 423490 | 3-14-3 | 17 | 25 | 53 | 82 | 9 |
| 423498 | 3-14-3 | 30 | 41 | 59 | 88 | 7 |
| 423499 | 5-10-5 | 27 | 26 | 63 | 78 | 10 |
| 423523 | 3-14-3 | 45 | 48 | 81 | 89 | 5 |
| 423524 | 3-14-3 | 35 | 59 | 84 | 92 | 4 |
| 423601 | 2-13-5 | 44 | 55 | 87 | 90 | 4 |

TABLE 75

| ISIS No | Motif | 18.75 nM | 37.5 nM | 75.0 nM | 150.0 nM | IC$_{50}$ (nM) |
|---|---|---|---|---|---|---|
| 217317 | 5-10-5 | 16 | 33 | 63 | 65 | 7 |
| 217328 | 5-10-5 | 32 | 56 | 79 | 91 | 4 |
| 411899 | 5-10-5 | 28 | 38 | 74 | 87 | 5 |
| 413214 | 5-10-5 | 37 | 46 | 65 | 91 | 6 |
| 413232 | 5-10-5 | 18 | 20 | 43 | 78 | 11 |
| 423452 | 5-10-5 | 14 | 47 | 73 | 85 | 6 |
| 423453 | 5-10-5 | 52 | 70 | 83 | 93 | 2 |
| 423458 | 5-10-5 | 28 | 31 | 65 | 87 | 8 |
| 423459 | 5-10-5 | 24 | 33 | 57 | 88 | 8 |
| 423464 | 5-10-5 | 68 | 81 | 86 | 88 | 1 |
| 423507 | 3-14-3 | 29 | 42 | 71 | 89 | 5 |
| 423508 | 3-14-3 | 16 | 38 | 53 | 83 | 7 |
| 423526 | 3-14-3 | 48 | 73 | 81 | 90 | 3 |
| 423527 | 3-14-3 | 27 | 51 | 68 | 85 | 6 |
| 423565 | 2-13-5 | 13 | 35 | 66 | 84 | 7 |
| 423567 | 2-13-5 | 27 | 42 | 61 | 91 | 7 |
| 423585 | 2-13-5 | 24 | 28 | 67 | 91 | 7 |
| 423595 | 2-13-5 | 12 | 25 | 50 | 78 | 10 |
| 423606 | 2-13-5 | 42 | 59 | 74 | 85 | 3 |

Study 2

Cells were plated at a density of 35,000 cells per well and transfected using electroporation with 0.22 µM, 0.67 µM, 2.0 µM, 6.0 µM, or 18.0 µM concentrations of antisense oligonucleotide, as specified in the Tables below. After a treatment period of approximately 16 hours, RNA was isolated from the cells and DGAT2 mRNA levels were measured by quantitative real-time PCR. Human primer probe set RTS2977_MGB (forward sequence ACTGGGCGGGCTTCATATT, designated herein as SEQ ID NO: 10; reverse sequence CCCGGAGTAGGCGGCTAT, designated herein as SEQ ID NO: 11; probe sequence AGCCATGAAGACCC, designated herein as SEQ ID NO: 12) was used to measure mRNA levels. DGAT2 mRNA levels were adjusted according to total RNA content, as measured by RIBOGREEN®. Results are presented as percent inhibition of DGAT2, relative to untreated control cells. '0' indicates that the mRNA levels were not inhibited.

The half maximal inhibitory concentration (IC$_{50}$) of each oligonucleotide is also presented. DGAT2 mRNA levels were significantly reduced in a dose-dependent manner in antisense oligonucleotide treated cells.

TABLE 76

| ISIS No | Motif | 0.22 µM | 0.67 µM | 2.0 µM | 6.0 µM | 18.0 µM | IC$_{50}$ (µM) |
|---|---|---|---|---|---|---|---|
| 217328 | 5-10-5 | 0 | 17 | 52 | 83 | 96 | 2.1 |
| 366730 | 5-10-5 | 0 | 0 | 27 | 72 | 93 | 3.9 |
| 413433 | 5-10-5 | 0 | 10 | 58 | 84 | 93 | 2.2 |
| 423453 | 5-10-5 | 14 | 21 | 53 | 86 | 94 | 1.9 |
| 423459 | 5-10-5 | 0 | 18 | 36 | 68 | 92 | 3.0 |
| 423463 | 5-10-5 | 16 | 15 | 50 | 76 | 80 | 2.7 |
| 423464 | 5-10-5 | 0 | 29 | 56 | 86 | 92 | 1.6 |
| 423489 | 3-14-3 | 0 | 0 | 37 | 63 | 91 | 3.8 |
| 423498 | 3-14-3 | 0 | 0 | 21 | 56 | 82 | 5.3 |
| 423499 | 5-10-5 | 0 | 6 | 26 | 62 | 88 | 4.1 |
| 423523 | 3-14-3 | 0 | 0 | 34 | 69 | 95 | 4.2 |
| 423524 | 3-14-3 | 0 | 6 | 15 | 62 | 90 | 4.4 |
| 423526 | 3-14-3 | 5 | 7 | 45 | 87 | 94 | 2.6 |
| 423601 | 2-13-5 | 0 | 0 | 31 | 65 | 89 | 4.3 |
| 423606 | 2-13-5 | 58 | 19 | 43 | 72 | 94 | 2.6 |

Study 3

Cells were plated at a density of 10,000 cells per well and transfected using Lipofectin reagent with 12.5 nM, 25.0 nM, 50.0 nM, 100.0 nM, or 200.0 nM concentrations of antisense oligonucleotide, as specified in the Tables below. After a treatment period of approximately 16 hours, RNA was isolated from the cells and DGAT2 mRNA levels were measured by quantitative real-time PCR. Human primer probe set RTS2988_MGB was used to measure mRNA levels. DGAT2 mRNA levels were adjusted according to total RNA content, as measured by RIBOGREEN®. Results are presented as percent inhibition of DGAT2, relative to untreated control cells. '0' indicates that the mRNA levels were not inhibited.

The half maximal inhibitory concentration ($IC_{50}$) of each oligonucleotide is also presented. DGAT2 mRNA levels were significantly reduced in a dose-dependent manner in antisense oligonucleotide treated cells.

TABLE 77

| ISIS No | Motif | 0.22 µM | 0.67 µM | 2.0 µM | 6.0 µM | 18.0 µM | $IC_{50}$ (µM) |
| --- | --- | --- | --- | --- | --- | --- | --- |
| 217328 | 5-10-5 | 25 | 31 | 58 | 71 | 85 | 38 |
| 366730 | 5-10-5 | 21 | 34 | 53 | 74 | 90 | 44 |
| 413433 | 5-10-5 | 23 | 40 | 63 | 75 | 86 | 37 |
| 423453 | 5-10-5 | 0 | 2 | 33 | 61 | 72 | 90 |
| 423459 | 5-10-5 | 16 | 22 | 44 | 65 | 79 | 64 |
| 423463 | 5-10-5 | 6 | 24 | 46 | 63 | 82 | 62 |
| 423464 | 5-10-5 | 20 | 28 | 45 | 64 | 79 | 60 |
| 423489 | 3-14-3 | 15 | 28 | 57 | 75 | 84 | 42 |
| 423498 | 3-14-3 | 8 | 21 | 52 | 71 | 85 | 49 |
| 423499 | 3-14-3 | 13 | 23 | 43 | 65 | 84 | 62 |
| 423523 | 3-14-3 | 25 | 38 | 58 | 72 | 86 | 38 |
| 423524 | 3-14-3 | 16 | 32 | 56 | 66 | 83 | 52 |
| 423526 | 3-14-3 | 28 | 33 | 51 | 54 | 68 | 71 |
| 423601 | 2-13-5 | 13 | 30 | 54 | 71 | 84 | 49 |
| 423606 | 2-13-5 | 12 | 36 | 52 | 69 | 80 | 47 |

Study 4

Cells were plated at a density of 10,000 cells per well and transfected using Lipofectin reagent with 12.5 nM, 25.0 nM, 50.0 nM, 100.0 nM, or 200.0 nM concentrations of antisense oligonucleotide, as specified in the Tables below. After a treatment period of approximately 16 hours, RNA was isolated from the cells and DGAT2 mRNA levels were measured by quantitative real-time PCR. Human primer probe set RTS2988_MGB was used to measure mRNA levels. DGAT2 mRNA levels were adjusted according to total RNA content, as measured by RIBOGREEN®. Results are presented as percent inhibition of DGAT2, relative to untreated control cells. '0' indicates that the mRNA levels were not inhibited.

The half maximal inhibitory concentration ($IC_{50}$) of each oligonucleotide is also presented. DGAT2 mRNA levels were significantly reduced in a dose-dependent manner in antisense oligonucleotide treated cells.

TABLE 78

| ISIS No | Motif | 0.22 µM | 0.67 µM | 2.0 µM | 6.0 µM | 18.0 µM | $IC_{50}$ (µM) |
| --- | --- | --- | --- | --- | --- | --- | --- |
| 217328 | 5-10-5 | 42 | 54 | 60 | 88 | 95 | 2 |
| 366730 | 5-10-5 | 26 | 44 | 61 | 85 | 95 | 3 |
| 413433 | 5-10-5 | 55 | 69 | 76 | 83 | 87 | <1.25 |
| 423453 | 5-10-5 | 40 | 62 | 78 | 91 | 95 | 2 |
| 423459 | 5-10-5 | 19 | 25 | 47 | 79 | 92 | 5 |
| 423463 | 5-10-5 | 51 | 52 | 83 | 86 | 90 | <1.25 |
| 423464 | 5-10-5 | 42 | 67 | 82 | 90 | 89 | 2 |
| 423489 | 3-14-3 | 8 | 19 | 40 | 77 | 96 | 5 |
| 423498 | 3-14-3 | 5 | 1 | 20 | 51 | 89 | 9 |
| 423499 | 3-14-3 | 23 | 24 | 35 | 71 | 95 | 5 |
| 423523 | 3-14-3 | 19 | 42 | 67 | 87 | 93 | 3 |
| 423524 | 3-14-3 | 38 | 53 | 71 | 90 | 95 | 2 |
| 423526 | 3-14-3 | 33 | 59 | 78 | 91 | 93 | 2 |
| 423601 | 2-13-5 | 22 | 45 | 72 | 88 | 93 | 3 |
| 423606 | 2-13-5 | 30 | 46 | 64 | 83 | 86 | 3 |

Study 5

Cells were plated at a density of 20,000 cells per well and transfected using electroporation with 12.5 µM, 25.0 µM, 50.0 µM, 100.0 µM, or 200.0 µM concentrations of antisense oligonucleotide, as specified in the Tables below. After a treatment period of approximately 16 hours, RNA was isolated from the cells and DGAT2 mRNA levels were measured by quantitative real-time PCR. Human primer probe set RTS2988_MGB (forward sequence AACTGGCCCTGCGTCATG, designated herein as SEQ ID NO: 7; reverse sequence CTTGTACACTTCATTCTCTC-CAAAGG; designated herein as SEQ ID NO: 8; probe sequence CTGACCTGGTTCCC, designated herein as SEQ ID NO: 9) was used to measure mRNA levels. DGAT2 mRNA levels were adjusted according to total RNA content, as measured by RIBOGREEN®. Results are presented as percent inhibition of DGAT2, relative to untreated control cells. '0' indicates that the mRNA levels were not inhibited.

The half maximal inhibitory concentration ($IC_{50}$) of each oligonucleotide is also presented. DGAT2 mRNA levels were significantly reduced in a dose-dependent manner in antisense oligonucleotide treated cells.

TABLE 79

| ISIS No | Motif | 12.5 µM | 25 µM | 50 µM | 100 µM | 200 µM | $IC_{50}$ (µM) |
| --- | --- | --- | --- | --- | --- | --- | --- |
| 217316 | 5-10-5 | 0 | 0 | 17 | 43 | 76 | 10.9 |
| 217318 | 5-10-5 | 0 | 0 | 10 | 48 | 45 | 18.4 |
| 217328 | 5-10-5 | 12 | 22 | 40 | 69 | 82 | 6.0 |
| 217376 | 5-10-5 | 0 | 0 | 51 | 50 | 70 | 9.8 |
| 381728 | 5-10-5 | 0 | 3 | 17 | 37 | 58 | 15.8 |
| 411896 | 5-10-5 | 5 | 16 | 52 | 73 | 87 | 5.5 |
| 411899 | 5-10-5 | 0 | 0 | 15 | 42 | 54 | 15.7 |
| 411900 | 5-10-5 | 0 | 0 | 18 | 38 | 76 | 11.5 |
| 411950 | 5-10-5 | 5 | 13 | 21 | 49 | 70 | 10.7 |
| 411951 | 5-10-5 | 0 | 10 | 31 | 52 | 76 | 8.9 |
| 413433 | 5-10-5 | 0 | 37 | 58 | 75 | 82 | 5.6 |
| 423453 | 5-10-5 | 16 | 21 | 41 | 73 | 86 | 5.5 |
| 423463 | 5-10-5 | 26 | 33 | 62 | 81 | 85 | 3.5 |
| 423464 | 5-10-5 | 21 | 43 | 58 | 82 | 84 | 3.4 |
| 423606 | 2-13-5 | 30 | 43 | 53 | 76 | 80 | 3.6 |

Study 6

Cells were plated at a density of 20,000 cells per well and transfected using electroporation with 0.625 µM, 1.25 µM, 2.5 µM, 5.0 µM, 10 µM, or 20 µM, concentrations of antisense oligonucleotide, as specified in the Tables below. After a treatment period of approximately 16 hours, RNA was isolated from the cells and DGAT2 mRNA levels were measured by quantitative real-time PCR. Human primer probe set RTS2988_MGB was used to measure mRNA levels. DGAT2 mRNA levels were adjusted according to total RNA content, as measured by RIBOGREEN®. Results are presented as percent inhibition of DGAT2, relative to untreated control cells. '0' indicates that the mRNA levels were not inhibited.

The half maximal inhibitory concentration ($IC_{50}$) of each oligonucleotide is also presented. DGAT2 mRNA levels were significantly reduced in a dose-dependent manner in antisense oligonucleotide treated cells.

TABLE 80

| ISIS No | Motif | 0.625 µM | 1.25 µM | 2.5 µM | 5.0 µM | 10.0 µM | 20.0 µM | IC$_{50}$ (µM) |
|---|---|---|---|---|---|---|---|---|
| 217317 | 5-10-5 | 11 | 18 | 39 | 59 | 79 | 94 | 3.5 |
| 217328 | 5-10-5 | 13 | 45 | 58 | 87 | 84 | 95 | 1.9 |
| 217376 | 5-10-5 | 10 | 9 | 4 | 28 | 12 | 11 | >20 |
| 217376 | 5-10-5 | 18 | 15 | 12 | 23 | 9 | 0 | >20 |
| 366730 | 5-10-5 | 14 | 23 | 55 | 74 | 86 | 97 | 2.6 |
| 411897 | 5-10-5 | 30 | 28 | 28 | 57 | 73 | 94 | 3.3 |
| 411901 | 5-10-5 | 19 | 22 | 30 | 58 | 76 | 93 | 4.0 |
| 411902 | 5-10-5 | 11 | 6 | 19 | 42 | 72 | 83 | 5.6 |
| 411947 | 5-10-5 | 14 | 14 | 10 | 35 | 66 | 87 | 7.1 |
| 411948 | 5-10-5 | 25 | 21 | 34 | 50 | 57 | 80 | 5.4 |
| 411950 | 5-10-5 | 7 | 24 | 41 | 56 | 74 | 83 | 3.9 |
| 411950 | 5-10-5 | 13 | 14 | 34 | 46 | 79 | 88 | 4.6 |
| 411951 | 5-10-5 | 28 | 18 | 22 | 43 | 83 | 92 | 5.4 |
| 411955 | 5-10-5 | 11 | 26 | 52 | 71 | 96 | 97 | 2.5 |
| 411958 | 5-10-5 | 19 | 17 | 21 | 60 | 81 | 92 | 4.7 |
| 413433 | 5-10-5 | 39 | 62 | 82 | 87 | 88 | 89 | 0.9 |
| 423463 | 5-10-5 | 15 | 36 | 76 | 87 | 92 | 90 | 1.7 |
| 423463 | 5-10-5 | 31 | 64 | 85 | 90 | 91 | 89 | 1.0 |
| 423489 | 3-14-3 | 21 | 17 | 39 | 73 | 89 | 98 | 3.2 |
| 423606 | 2-13-5 | 18 | 36 | 50 | 85 | 87 | 92 | 2.2 |

Example 8: Dose-Dependent Antisense Inhibition of Human DGAT2 in HepG2 Cells by MOE Gapmers Gapmers from the studies described in the Examples above exhibiting significant in vitro inhibition of DGAT2 mRNA were selected and tested at various doses in HepG2 cells. The antisense oligonucleotides were tested in a series of experiments that had similar culture conditions. The results for each experiment are presented in separate tables shown below. Cells were plated at a density of 20,000 cells per well and transfected using electroporation with 0.625 µM, 1.25 µM, 2.50 µM, 5.00 µM, or 10.00 µM concentrations of antisense oligonucleotide, as specified in the Tables below. After a treatment period of approximately 16 hours, RNA was isolated from the cells and DGAT2 mRNA levels were measured by quantitative real-time PCR. Human primer probe set RTS2988_MGB was used to measure mRNA levels. DGAT2 mRNA levels were adjusted according to total RNA content, as measured by RIBOGREEN®. Results are presented as percent inhibition of DGAT2, relative to untreated control cells. '0' indicates that the mRNA levels were not inhibited.

The half maximal inhibitory concentration (IC$_{50}$) of each oligonucleotide is also presented. DGAT2 mRNA levels were significantly reduced in a dose-dependent manner in antisense oligonucleotide treated cells.

TABLE 81

| ISIS No | 0.625 µM | 1.25 µM | 2.50 µM | 5.00 µM | 10.00 µM | IC$_{50}$ (µM) |
|---|---|---|---|---|---|---|
| 483817 | 47 | 71 | 82 | 89 | 90 | <0.6 |
| 483825 | 40 | 56 | 78 | 85 | 85 | 0.8 |
| 483828 | 45 | 69 | 75 | 70 | 76 | <0.6 |
| 483832 | 42 | 59 | 67 | 78 | 72 | 0.8 |
| 483834 | 26 | 38 | 64 | 86 | 90 | 1.6 |
| 483852 | 47 | 60 | 69 | 81 | 85 | 0.7 |
| 483866 | 76 | 77 | 82 | 86 | 86 | <0.6 |
| 483869 | 39 | 69 | 74 | 72 | 80 | 0.6 |
| 483873 | 46 | 71 | 78 | 82 | 87 | <0.6 |

TABLE 82

| ISIS No | 0.625 µM | 1.25 µM | 2.50 µM | 5.00 µM | 10.00 µM | IC$_{50}$ (µM) |
|---|---|---|---|---|---|---|
| 483811 | 29 | 34 | 58 | 87 | 87 | 1.7 |
| 483816 | 21 | 14 | 34 | 71 | 87 | 3.0 |
| 483831 | 34 | 37 | 55 | 81 | 83 | 1.7 |
| 483835 | 28 | 47 | 56 | 82 | 89 | 1.6 |
| 483840 | 4 | 17 | 49 | 75 | 81 | 2.9 |
| 483870 | 13 | 31 | 52 | 84 | 88 | 2.2 |
| 483889 | 21 | 0 | 56 | 81 | 85 | 2.7 |
| 483895 | 43 | 21 | 74 | 88 | 92 | 2.0 |
| 483898 | 46 | 47 | 81 | 89 | 86 | 0.8 |
| 483908 | 29 | 16 | 73 | 84 | 88 | 1.9 |
| 483910 | 31 | 39 | 73 | 79 | 76 | 1.5 |
| 483923 | 24 | 0 | 62 | 81 | 89 | 3.4 |
| 483952 | 63 | 67 | 86 | 91 | 89 | <0.6 |

TABLE 83

| ISIS No | 0.625 µM | 1.25 µM | 2.50 µM | 5.00 µM | 10.00 µM | IC$_{50}$ (µM) |
|---|---|---|---|---|---|---|
| 483968 | 39 | 55 | 76 | 89 | 88 | 0.9 |
| 483969 | 29 | 57 | 70 | 82 | 89 | 1.2 |
| 483970 | 16 | 48 | 62 | 71 | 85 | 1.9 |
| 483972 | 17 | 52 | 69 | 78 | 78 | 1.7 |
| 483984 | 53 | 74 | 85 | 83 | 78 | <0.6 |
| 483986 | 15 | 37 | 59 | 71 | 83 | 2.2 |
| 483987 | 9 | 0 | 76 | 78 | 91 | 1.5 |
| 483993 | 42 | 58 | 69 | 69 | 78 | 0.8 |
| 483996 | 20 | 46 | 53 | 63 | 74 | 2.3 |
| 483997 | 20 | 61 | 72 | 82 | 82 | 1.3 |
| 484004 | 27 | 57 | 65 | 74 | 83 | 1.4 |
| 484006 | 22 | 47 | 65 | 72 | 86 | 1.7 |
| 484010 | 27 | 0 | 51 | 78 | 86 | 2.0 |
| 484017 | 28 | 51 | 66 | 79 | 88 | 1.4 |

TABLE 84

| ISIS No | 0.625 µM | 1.25 µM | 2.50 µM | 5.00 µM | 10.00 µM | IC$_{50}$ (µM) |
|---|---|---|---|---|---|---|
| 413433 | 11 | 53 | 74 | 85 | 83 | 1.6 |
| 484012 | 19 | 36 | 49 | 76 | 88 | 2.2 |
| 484020 | 26 | 49 | 66 | 70 | 78 | 1.6 |
| 484041 | 12 | 45 | 51 | 68 | 80 | 2.4 |
| 484049 | 35 | 62 | 68 | 82 | 81 | 0.9 |
| 484094 | 20 | 37 | 52 | 62 | 74 | 2.7 |
| 484099 | 32 | 44 | 77 | 84 | 89 | 1.3 |
| 484111 | 22 | 50 | 65 | 54 | 80 | 2.0 |
| 484114 | 29 | 47 | 69 | 68 | 72 | 1.6 |
| 484118 | 10 | 42 | 60 | 74 | 84 | 2.1 |
| 484182 | 0 | 57 | 59 | 79 | 74 | 2.3 |

TABLE 85

| ISIS No | 0.625 µM | 1.25 µM | 2.50 µM | 5.00 µM | 10.00 µM | IC$_{50}$ (µM) |
|---|---|---|---|---|---|---|
| 413433 | 33 | 46 | 65 | 81 | 87 | 1.4 |
| 484109 | 17 | 1 | 46 | 65 | 83 | 3.3 |
| 484138 | 9 | 15 | 17 | 28 | 53 | >10 |
| 484139 | 14 | 21 | 60 | 75 | 90 | 2.3 |
| 484152 | 25 | 46 | 75 | 89 | 91 | 1.4 |
| 484175 | 10 | 15 | 21 | 35 | 43 | >10 |
| 484183 | 3 | 15 | 20 | 34 | 55 | >10 |
| 484203 | 23 | 35 | 54 | 70 | 75 | 2.3 |
| 484209 | 21 | 36 | 50 | 74 | 88 | 2.2 |
| 484215 | 42 | 45 | 59 | 84 | 91 | 1.2 |
| 484217 | 23 | 36 | 56 | 82 | 93 | 1.9 |
| 484231 | 34 | 0 | 72 | 79 | 82 | 1 |
| 423463 | 35 | 53 | 73 | 86 | 87 | 1.1 |

TABLE 86

| ISIS No | 0.625 μM | 1.25 μM | 2.50 μM | 5.00 μM | 10.00 μM | IC$_{50}$ (μM) |
|---|---|---|---|---|---|---|
| 413433 | 37 | 55 | 72 | 84 | 88 | 1 |
| 423464 | 41 | 62 | 79 | 92 | 90 | 0.7 |
| 484268 | 34 | 57 | 73 | 81 | 84 | 1 |
| 484269 | 24 | 47 | 64 | 67 | 75 | 1.8 |
| 484270 | 29 | 50 | 65 | 88 | 91 | 1.3 |
| 484271 | 43 | 66 | 81 | 88 | 84 | 0.6 |
| 484273 | 42 | 62 | 73 | 79 | 78 | 0.7 |
| 484283 | 26 | 0 | 61 | 85 | 93 | 1.6 |
| 484284 | 27 | 38 | 54 | 76 | 81 | 1.9 |
| 484292 | 31 | 31 | 53 | 81 | 91 | 1.8 |
| 484293 | 26 | 36 | 61 | 78 | 87 | 1.8 |
| 484327 | 24 | 48 | 48 | 67 | 79 | 2.1 |
| 484342 | 21 | 34 | 48 | 67 | 88 | 2.4 |
| 484387 | 21 | 0 | 21 | 40 | 58 | 9.6 |
| 484396 | 15 | 13 | 18 | 24 | 44 | >10 |

TABLE 87

| ISIS No | 0.625 μM | 1.25 μM | 2.50 μM | 5.00 μM | 10.00 μM | IC$_{50}$ (μM) |
|---|---|---|---|---|---|---|
| 413433 | 30 | 57 | 80 | 81 | 86 | 1.1 |
| 484345 | 17 | 28 | 68 | 60 | 79 | 2.4 |
| 484354 | 20 | 28 | 75 | 60 | 79 | 2.2 |
| 484366 | 25 | 33 | 37 | 62 | 82 | 2.8 |
| 484368 | 16 | 39 | 57 | 73 | 89 | 2.1 |
| 484369 | 22 | 18 | 57 | 27 | 35 | >10 |
| 484372 | 3 | 28 | 37 | 69 | 76 | 3.3 |
| 484376 | 12 | 0 | 52 | 64 | 67 | 3.1 |
| 484379 | 0 | 19 | 21 | 37 | 75 | 5.6 |
| 484380 | 0 | 26 | 34 | 47 | 71 | 4.7 |
| 484395 | 7 | 41 | 61 | 29 | 46 | >10 |
| 484397 | 0 | 7 | 52 | 16 | 34 | >10 |
| 484406 | 17 | 6 | 53 | 39 | 53 | 7.5 |
| 484408 | 4 | 0 | 16 | 24 | 38 | >10 |
| 484409 | 0 | 6 | 0 | 41 | 59 | 9.0 |

TABLE 88

| ISIS No | 0.625 μM | 1.25 μM | 2.50 μM | 5.00 μM | 10.00 μM | IC$_{50}$ (μM) |
|---|---|---|---|---|---|---|
| 413433 | 22 | 51 | 68 | 72 | 88 | 1.6 |
| 472316 | 15 | 45 | 45 | 82 | 89 | 2.1 |
| 472317 | 34 | 30 | 43 | 77 | 91 | 2.0 |
| 472318 | 22 | 38 | 52 | 68 | 85 | 2.2 |
| 472444 | 22 | 27 | 41 | 39 | 74 | 4.4 |
| 472447 | 0 | 18 | 16 | 18 | 69 | 9.0 |
| 472456 | 10 | 10 | 48 | 51 | 68 | 4.3 |
| 472480 | 7 | 0 | 41 | 59 | 87 | 3.0 |
| 472481 | 29 | 29 | 37 | 62 | 84 | 2.7 |
| 472482 | 16 | 29 | 42 | 67 | 85 | 2.7 |
| 472484 | 23 | 19 | 51 | 72 | 87 | 2.4 |
| 472486 | 28 | 40 | 59 | 83 | 90 | 1.7 |
| 472488 | 27 | 31 | 36 | 53 | 64 | 4.4 |
| 472496 | 0 | 0 | 37 | 51 | 76 | 3.8 |
| 484410 | 0 | 40 | 19 | 24 | 39 | >10 |

TABLE 89

| ISIS No | 0.625 μM | 1.25 μM | 2.50 μM | 5.00 μM | 10.00 μM | IC$_{50}$ (μM) |
|---|---|---|---|---|---|---|
| 413433 | 37 | 51 | 70 | 84 | 88 | 1.1 |
| 472548 | 15 | 30 | 25 | 54 | 78 | 3.9 |
| 472552 | 15 | 28 | 33 | 51 | 66 | 4.7 |
| 472570 | 29 | 46 | 56 | 83 | 90 | 1.6 |
| 472571 | 29 | 34 | 53 | 70 | 86 | 2 |
| 411955 | 0 | 41 | 46 | 68 | 85 | 2.2 |
| 472608 | 28 | 26 | 56 | 59 | 72 | 2.7 |
| 472610 | 18 | 0 | 51 | 70 | 79 | 2.6 |
| 472637 | 24 | 37 | 39 | 53 | 72 | 3.4 |
| 472652 | 18 | 43 | 55 | 71 | 81 | 2.1 |
| 472725 | 35 | 46 | 61 | 77 | 86 | 1.4 |
| 472733 | 39 | 34 | 41 | 63 | 74 | 2.5 |
| 472738 | 38 | 53 | 65 | 81 | 85 | 1.1 |
| 472793 | 0 | 0 | 51 | 67 | 75 | 2 |
| 472811 | 0 | 44 | 65 | 78 | 77 | 1.4 |

TABLE 90

| ISIS No | 0.625 μM | 1.25 μM | 2.50 μM | 5.00 μM | 10.00 μM | IC$_{50}$ (μM) |
|---|---|---|---|---|---|---|
| 413433 | 0 | 47 | 72 | 84 | 88 | 2 |
| 472316 | 21 | 42 | 69 | 86 | 94 | 2 |
| 484152 | 20 | 57 | 79 | 90 | 93 | 1 |
| 484215 | 33 | 39 | 70 | 91 | 95 | 1 |
| 484217 | 19 | 18 | 49 | 89 | 94 | 2 |
| 484231 | 4 | 52 | 76 | 83 | 91 | 2 |
| 423463 | 33 | 54 | 79 | 91 | 91 | 1 |
| 423464 | 0 | 48 | 78 | 83 | 88 | 3 |
| 484268 | 0 | 3 | 0 | 13 | 50 | >10 |
| 484270 | 7 | 36 | 49 | 80 | 83 | 2 |
| 484271 | 16 | 59 | 76 | 86 | 91 | 1 |
| 484283 | 10 | 35 | 56 | 87 | 92 | 2 |
| 484369 | 25 | 1 | 0 | 5 | 33 | >10 |

TABLE 91

| ISIS No | 0.625 μM | 1.25 μM | 2.50 μM | 5.00 μM | 10.00 μM | IC$_{50}$ (μM) |
|---|---|---|---|---|---|---|
| 413433 | 28 | 60 | 69 | 84 | 92 | 1 |
| 483811 | 0 | 19 | 53 | 77 | 85 | 3 |
| 483823 | 47 | 69 | 85 | 88 | 94 | <0.6 |
| 483825 | 18 | 50 | 80 | 82 | 87 | 1 |
| 483834 | 16 | 37 | 72 | 89 | 87 | 2 |
| 483835 | 1 | 29 | 56 | 80 | 85 | 2 |
| 483866 | 55 | 79 | 88 | 83 | 90 | <0.6 |
| 483873 | 27 | 75 | 87 | 86 | 91 | 1 |
| 483898 | 49 | 72 | 82 | 89 | 89 | <0.6 |
| 483908 | 35 | 45 | 76 | 89 | 88 | 1 |
| 483913 | 0 | 42 | 76 | 86 | 89 | 2 |

TABLE 92

| ISIS No | 0.625 μM | 1.25 μM | 2.50 μM | 5.00 μM | 10.00 μM | IC$_{50}$ (μM) |
|---|---|---|---|---|---|---|
| 413433 | 47 | 68 | 84 | 90 | 88 | <0.6 |
| 423453 | 36 | 66 | 81 | 95 | 96 | 0.8 |
| 472158 | 56 | 51 | 75 | 91 | 96 | 0.6 |
| 472725 | 43 | 59 | 63 | 78 | 80 | 0.8 |
| 472738 | 38 | 58 | 65 | 77 | 81 | 1 |
| 483895 | 35 | 53 | 76 | 92 | 93 | 1.0 |
| 483923 | 26 | 46 | 76 | 88 | 92 | 1.3 |
| 483952 | 60 | 82 | 88 | 93 | 92 | <0.6 |
| 483968 | 46 | 70 | 82 | 91 | 93 | <0.6 |
| 483984 | 39 | 67 | 87 | 88 | 88 | 0.6 |
| 483987 | 40 | 60 | 75 | 90 | 95 | 0.9 |
| 483997 | 50 | 63 | 73 | 90 | 92 | 0.6 |
| 484099 | 56 | 75 | 88 | 93 | 95 | <0.6 |

TABLE 93

| ISIS No | 0.625 μM | 1.25 μM | 2.50 μM | 5.00 μM | 10.00 μM | IC$_{50}$ (μM) |
|---|---|---|---|---|---|---|
| 413433 | 26 | 53 | 75 | 86 | 91 | 1.3 |
| 495429 | 8 | 42 | 68 | 86 | 92 | 1.9 |
| 495449 | 19 | 53 | 74 | 87 | 86 | 1.4 |
| 495450 | 30 | 58 | 74 | 87 | 93 | 1.1 |
| 495470 | 0 | 36 | 59 | 82 | 92 | 2.2 |
| 495481 | 15 | 39 | 75 | 84 | 86 | 1.7 |
| 495484 | 19 | 50 | 73 | 87 | 87 | 1.5 |
| 495488 | 5 | 32 | 45 | 67 | 86 | 2.8 |
| 495489 | 13 | 36 | 54 | 81 | 91 | 2.1 |
| 495490 | 20 | 42 | 66 | 83 | 88 | 1.7 |
| 495492 | 5 | 38 | 64 | 81 | 90 | 2.1 |
| 495495 | 29 | 32 | 62 | 78 | 90 | 1.8 |
| 495496 | 21 | 44 | 62 | 79 | 92 | 1.7 |
| 495497 | 20 | 42 | 59 | 69 | 88 | 2.0 |
| 495498 | 21 | 54 | 68 | 81 | 90 | 1.5 |

TABLE 94

| ISIS No | 0.625 μM | 1.25 μM | 2.50 μM | 5.00 μM | 10.00 μM | IC$_{50}$ (μM) |
|---|---|---|---|---|---|---|
| 413433 | 35 | 42 | 73 | 86 | 90 | 1.3 |
| 495442 | 6 | 29 | 43 | 68 | 80 | 3.0 |
| 495451 | 21 | 31 | 51 | 76 | 87 | 2.2 |
| 495453 | 21 | 34 | 64 | 80 | 84 | 1.9 |
| 495454 | 23 | 33 | 53 | 80 | 86 | 2.1 |
| 495463 | 4 | 28 | 53 | 74 | 85 | 2.6 |
| 495464 | 21 | 41 | 65 | 84 | 84 | 1.7 |
| 495466 | 12 | 35 | 57 | 76 | 84 | 2.2 |
| 495467 | 17 | 28 | 44 | 69 | 89 | 2.6 |
| 495469 | 17 | 24 | 53 | 81 | 83 | 2.4 |
| 495471 | 29 | 43 | 58 | 83 | 84 | 1.6 |
| 495472 | 4 | 38 | 63 | 78 | 80 | 2.3 |
| 495482 | 7 | 32 | 52 | 76 | 91 | 2.4 |
| 495485 | 8 | 29 | 55 | 76 | 76 | 2.6 |
| 495491 | 25 | 42 | 64 | 85 | 92 | 1.6 |

TABLE 95

| ISIS No | 0.625 μM | 1.25 μM | 2.50 μM | 5.00 μM | 10.00 μM | IC$_{50}$ (μM) |
|---|---|---|---|---|---|---|
| 413433 | 40 | 48 | 75 | 86 | 86 | 1 |
| 495430 | 0 | 5 | 11 | 47 | 67 | 6.2 |
| 495441 | 17 | 17 | 55 | 77 | 87 | 2.5 |
| 495443 | 28 | 51 | 59 | 74 | 84 | 1.6 |
| 495448 | 13 | 28 | 32 | 61 | 79 | 3.4 |
| 495452 | 13 | 51 | 47 | 71 | 78 | 2.3 |
| 495462 | 46 | 47 | 51 | 76 | 84 | 1.2 |
| 495465 | 2 | 20 | 35 | 68 | 78 | 3.5 |
| 495468 | 22 | 20 | 46 | 56 | 84 | 3 |
| 495473 | 11 | 24 | 48 | 69 | 75 | 3 |
| 495479 | 19 | 29 | 54 | 76 | 85 | 2.2 |
| 495483 | 15 | 9 | 47 | 77 | 88 | 2.7 |
| 495516 | 49 | 76 | 89 | 90 | 93 | <0.6 |
| 495562 | 20 | 55 | 70 | 88 | 92 | 1.4 |
| 495576 | 51 | 69 | 88 | 93 | 94 | <0.6 |

TABLE 96

| ISIS No | 0.625 μM | 1.25 μM | 2.50 μM | 5.00 μM | 10.00 μM | IC$_{50}$ (μM) |
|---|---|---|---|---|---|---|
| 413433 | 34 | 51 | 71 | 86 | 89 | 1.1 |
| 495505 | 34 | 58 | 80 | 87 | 91 | 1.0 |
| 495517 | 19 | 55 | 78 | 85 | 91 | 1.3 |
| 495518 | 24 | 51 | 72 | 87 | 90 | 1.4 |
| 495519 | 33 | 46 | 70 | 86 | 90 | 1.3 |
| 495520 | 63 | 84 | 89 | 90 | 91 | <0.6 |
| 495522 | 45 | 32 | 54 | 82 | 89 | 1.5 |
| 495523 | 14 | 46 | 66 | 86 | 91 | 1.7 |
| 495524 | 12 | 39 | 60 | 84 | 93 | 1.9 |
| 495554 | 35 | 64 | 75 | 89 | 90 | 0.9 |
| 495555 | 42 | 49 | 72 | 87 | 91 | 1 |
| 495563 | 35 | 41 | 66 | 84 | 91 | 1.4 |
| 495571 | 21 | 41 | 67 | 87 | 93 | 1.6 |
| 495575 | 33 | 43 | 62 | 82 | 84 | 1.5 |
| 495577 | 33 | 56 | 71 | 85 | 91 | 1.1 |

TABLE 97

| ISIS No | 0.625 μM | 1.25 μM | 2.50 μM | 5.00 μM | 10.00 μM | IC$_{50}$ (μM) |
|---|---|---|---|---|---|---|
| 413433 | 39 | 52 | 66 | 81 | 87 | 1.1 |
| 495570 | 27 | 50 | 55 | 78 | 89 | 1.6 |
| 495650 | 0 | 38 | 58 | 65 | 85 | 2.7 |
| 495561 | 24 | 54 | 71 | 87 | 92 | 1.3 |
| 495618 | 0 | 35 | 50 | 79 | 87 | 2.5 |
| 495540 | 11 | 35 | 48 | 74 | 88 | 2.4 |
| 495649 | 0 | 24 | 43 | 76 | 82 | 3.1 |
| 495515 | 22 | 45 | 69 | 83 | 91 | 1.6 |
| 495599 | 25 | 23 | 42 | 73 | 86 | 2.5 |
| 495620 | 27 | 54 | 63 | 85 | 91 | 1.4 |
| 495606 | 16 | 27 | 56 | 80 | 90 | 2.2 |
| 495604 | 31 | 48 | 77 | 83 | 90 | 1.2 |
| 495609 | 52 | 66 | 80 | 84 | 90 | <0.6 |
| 495619 | 29 | 42 | 63 | 73 | 90 | 1.6 |
| 495621 | 0 | 28 | 31 | 69 | 84 | 3.3 |

TABLE 98

| ISIS No | 0.625 μM | 1.25 μM | 2.50 μM | 5.00 μM | 10.00 μM | IC$_{50}$ (μM) |
|---|---|---|---|---|---|---|
| 413433 | 19 | 24 | 66 | 81 | 88 | 2.1 |
| 495591 | 7 | 24 | 43 | 66 | 82 | 3.0 |
| 495744 | 25 | 41 | 51 | 73 | 84 | 2.0 |
| 495685 | 34 | 58 | 73 | 84 | 83 | 1.0 |
| 495738 | 26 | 41 | 61 | 81 | 83 | 1.7 |
| 495707 | 33 | 46 | 61 | 76 | 72 | 1.5 |
| 495837 | 30 | 33 | 67 | 90 | 94 | 1.6 |
| 495752 | 14 | 30 | 68 | 86 | 91 | 1.9 |
| 495839 | 15 | 67 | 83 | 90 | 91 | 1.2 |
| 495736 | 28 | 41 | 65 | 83 | 85 | 1.6 |
| 495840 | 39 | 59 | 78 | 92 | 93 | 0.8 |
| 495753 | 43 | 48 | 69 | 87 | 97 | 1.0 |
| 495878 | 34 | 62 | 78 | 92 | 96 | 0.9 |
| 495749 | 21 | 23 | 52 | 84 | 89 | 2.2 |
| 495756 | 24 | 29 | 58 | 80 | 89 | 2.0 |

TABLE 99

| ISIS No | 0.625 μM | 1.25 μM | 2.50 μM | 5.00 μM | 10.00 μM | IC$_{50}$ (μM) |
|---|---|---|---|---|---|---|
| 413433 | 28 | 60 | 70 | 83 | 84 | 1.1 |
| 495853 | 39 | 51 | 78 | 92 | 96 | 1 |
| 495857 | 41 | 49 | 67 | 87 | 91 | 1.1 |
| 495829 | 41 | 68 | 81 | 90 | 90 | 0.6 |
| 495818 | 12 | 38 | 57 | 77 | 93 | 2.1 |
| 495842 | 40 | 67 | 80 | 88 | 91 | 0.7 |
| 495849 | 37 | 53 | 66 | 79 | 82 | 1.1 |
| 495836 | 16 | 54 | 63 | 80 | 88 | 1.6 |
| 495875 | 22 | 58 | 63 | 80 | 93 | 1.4 |
| 495841 | 43 | 66 | 76 | 87 | 90 | 0.6 |
| 495819 | 13 | 38 | 54 | 74 | 90 | 2.2 |
| 495825 | 36 | 52 | 69 | 88 | 93 | 1.1 |
| 495832 | 20 | 50 | 65 | 78 | 85 | 1.6 |

TABLE 99-continued

| ISIS No | 0.625 µM | 1.25 µM | 2.50 µM | 5.00 µM | 10.00 µM | IC$_{50}$ (µM) |
|---|---|---|---|---|---|---|
| 495809 | 16 | 37 | 46 | 78 | 85 | 2.3 |
| 495876 | 19 | 39 | 65 | 86 | 95 | 1.7 |

TABLE 100

| ISIS No | 0.625 µM | 1.25 µM | 2.50 µM | 5.00 µM | 10.00 µM | IC$_{50}$ (µM) |
|---|---|---|---|---|---|---|
| 413433 | 46 | 61 | 82 | 86 | 86 | 0.6 |
| 496037 | 23 | 38 | 57 | 74 | 93 | 1.9 |
| 496038 | 10 | 31 | 42 | 67 | 93 | 2.6 |
| 496039 | 9 | 19 | 35 | 67 | 88 | 3.1 |
| 496040 | 4 | 38 | 45 | 70 | 88 | 2.6 |
| 496041 | 21 | 30 | 50 | 84 | 95 | 2.1 |
| 496043 | 2 | 26 | 58 | 80 | 87 | 2.4 |
| 495826 | 7 | 44 | 72 | 82 | 85 | 1.9 |
| 495868 | 27 | 38 | 75 | 83 | 85 | 1.5 |
| 495901 | 18 | 46 | 69 | 79 | 83 | 1.7 |
| 495902 | 20 | 48 | 66 | 82 | 85 | 1.6 |
| 495955 | 3 | 3 | 54 | 66 | 75 | 3.5 |
| 495992 | 26 | 43 | 74 | 86 | 92 | 1.4 |
| 496100 | 20 | 30 | 56 | 71 | 85 | 2.3 |
| 496104 | 37 | 35 | 48 | 72 | 81 | 1.9 |

TABLE 101

| ISIS No | 0.625 µM | 1.25 µM | 2.50 µM | 5.00 µM | 10.00 µM | IC$_{50}$ (µM) |
|---|---|---|---|---|---|---|
| 413433 | 33 | 49 | 70 | 75 | 90 | 1.3 |
| 501838 | 32 | 52 | 67 | 73 | 71 | 1.3 |
| 501849 | 39 | 63 | 76 | 85 | 93 | 0.8 |
| 501850 | 29 | 59 | 72 | 88 | 92 | 1.1 |
| 501852 | 43 | 63 | 75 | 80 | 87 | 0.7 |
| 501855 | 57 | 70 | 87 | 90 | 92 | <0.6 |
| 501861 | 39 | 63 | 80 | 90 | 93 | 0.8 |
| 501871 | 28 | 53 | 76 | 84 | 93 | 1.2 |
| 501883 | 33 | 45 | 62 | 73 | 82 | 1.5 |
| 501884 | 41 | 59 | 75 | 86 | 92 | 0.8 |
| 501886 | 42 | 63 | 71 | 78 | 84 | 0.7 |
| 501890 | 32 | 49 | 61 | 72 | 79 | 1.5 |
| 501932 | 38 | 49 | 68 | 80 | 85 | 1.1 |
| 501944 | 30 | 43 | 69 | 80 | 87 | 1.4 |
| 501950 | 32 | 49 | 70 | 72 | 91 | 1.3 |

TABLE 102

| ISIS No | 0.625 µM | 1.25 µM | 2.50 µM | 5.00 µM | 10.00 µM | IC$_{50}$ (µM) |
|---|---|---|---|---|---|---|
| 413433 | 35 | 53 | 69 | 86 | 91 | 1.1 |
| 501903 | 32 | 39 | 62 | 80 | 90 | 1.6 |
| 501916 | 29 | 42 | 61 | 78 | 88 | 1.6 |
| 501933 | 37 | 51 | 66 | 75 | 77 | 1.2 |
| 501934 | 26 | 41 | 52 | 69 | 82 | 2 |
| 501946 | 15 | 34 | 57 | 76 | 90 | 2.1 |
| 501947 | 35 | 54 | 74 | 87 | 93 | 1.1 |
| 501951 | 36 | 54 | 75 | 85 | 93 | 1 |
| 501957 | 27 | 41 | 67 | 76 | 86 | 1.7 |
| 501959 | 40 | 52 | 72 | 81 | 87 | 1 |
| 501960 | 35 | 52 | 67 | 82 | 90 | 1.2 |
| 501966 | 34 | 42 | 64 | 75 | 84 | 1.5 |
| 501968 | 29 | 49 | 73 | 84 | 91 | 1.3 |
| 501977 | 19 | 28 | 49 | 74 | 88 | 2.3 |
| 502040 | 24 | 38 | 54 | 73 | 88 | 2 |

TABLE 103

| ISIS No | 0.625 µM | 1.25 µM | 2.50 µM | 5.00 µM | 10.00 µM | IC$_{50}$ (µM) |
|---|---|---|---|---|---|---|
| 413433 | 37 | 53 | 72 | 83 | 39 | 1.1 |
| 501981 | 21 | 43 | 62 | 79 | 90 | 1.7 |
| 501982 | 28 | 53 | 64 | 70 | 82 | 1.5 |
| 501983 | 29 | 41 | 57 | 75 | 84 | 1.8 |
| 502013 | 24 | 42 | 60 | 74 | 80 | 1.9 |
| 502015 | 19 | 39 | 57 | 63 | 71 | 2.5 |
| 502025 | 22 | 48 | 59 | 78 | 89 | 1.7 |
| 502026 | 21 | 39 | 56 | 77 | 86 | 2 |
| 502037 | 15 | 13 | 38 | 56 | 87 | 3.4 |
| 502038 | 3 | 14 | 52 | 55 | 77 | 3.5 |
| 502045 | 45 | 47 | 63 | 75 | 85 | 1.1 |
| 502046 | 21 | 37 | 50 | 71 | 81 | 2.3 |
| 502056 | 44 | 67 | 82 | 86 | 41 | 0.6 |
| 502083 | 37 | 55 | 76 | 89 | 93 | 1 |
| 502119 | 37 | 60 | 77 | 88 | 92 | 0.9 |

TABLE 104

| ISIS No | 0.625 µM | 1.25 µM | 2.50 µM | 5.00 µM | 10.00 µM | IC$_{50}$ (µM) |
|---|---|---|---|---|---|---|
| 413433 | 40 | 58 | 77 | 88 | 91 | 0.8 |
| 502075 | 30 | 47 | 69 | 82 | 91 | 1.4 |
| 502098 | 37 | 59 | 74 | 88 | 94 | 0.9 |
| 502099 | 43 | 59 | 76 | 88 | 94 | 0.8 |
| 502154 | 64 | 72 | 84 | 88 | 90 | <0.6 |
| 502155 | 34 | 54 | 72 | 82 | 87 | 1.1 |
| 502156 | 17 | 38 | 57 | 83 | 87 | 2 |
| 502163 | 41 | 60 | 82 | 92 | 93 | 0.7 |
| 502164 | 41 | 73 | 78 | 89 | 90 | 0.6 |
| 502175 | 33 | 58 | 74 | 87 | 90 | 1 |
| 502179 | 61 | 74 | 81 | 87 | 87 | <0.6 |
| 502189 | 33 | 52 | 79 | 91 | 94 | 1.1 |
| 502191 | 53 | 67 | 84 | 92 | 92 | <0.6 |
| 502194 | 48 | 64 | 83 | 87 | 92 | <0.6 |
| 502228 | 34 | 47 | 67 | 80 | 89 | 1.3 |

TABLE 105

| ISIS No | 0.625 µM | 1.25 µM | 2.50 µM | 5.00 µM | 10.00 µM | IC$_{50}$ (µM) |
|---|---|---|---|---|---|---|
| 413433 | 24 | 28 | 51 | 68 | 83 | 2.4 |
| 495756 | 49 | 71 | 87 | 88 | 94 | <0.6 |
| 507692 | 48 | 70 | 83 | 88 | 93 | <0.6 |
| 507693 | 48 | 68 | 86 | 91 | 93 | <0.6 |
| 507694 | 41 | 61 | 81 | 88 | 93 | 0.7 |
| 507695 | 36 | 53 | 72 | 84 | 93 | 1.1 |
| 507696 | 51 | 74 | 83 | 89 | 94 | <0.6 |
| 507710 | 48 | 72 | 71 | 90 | 91 | <0.6 |
| 507716 | 42 | 54 | 83 | 91 | 95 | 0.8 |
| 507717 | 44 | 65 | 79 | 86 | 90 | 0.6 |
| 502314 | 25 | 38 | 61 | 79 | 93 | 1.7 |
| 502319 | 47 | 66 | 80 | 92 | 94 | 0.6 |
| 502322 | 45 | 69 | 81 | 89 | 86 | <0.6 |
| 502331 | 34 | 45 | 53 | 71 | 89 | 1.6 |
| 502334 | 52 | 68 | 77 | 89 | 93 | <0.6 |

TABLE 106

| ISIS No | 0.625 µM | 1.25 µM | 2.50 µM | 5.00 µM | 10.00 µM | IC$_{50}$ (µM) |
|---|---|---|---|---|---|---|
| 413433 | 30 | 49 | 73 | 87 | 90 | 1.2 |
| 522366 | 32 | 53 | 68 | 80 | 84 | 1.2 |
| 522373 | 39 | 62 | 81 | 87 | 91 | 0.8 |
| 522374 | 39 | 50 | 71 | 85 | 91 | 1.1 |
| 522375 | 23 | 49 | 73 | 87 | 91 | 1.4 |
| 522383 | 46 | 64 | 79 | 83 | 85 | <0.6 |
| 522435 | 39 | 62 | 76 | 86 | 88 | 0.8 |

TABLE 106-continued

| ISIS No | 0.625 μM | 1.25 μM | 2.50 μM | 5.00 μM | 10.00 μM | IC$_{50}$ (μM) |
|---|---|---|---|---|---|---|
| 522437 | 33 | 62 | 78 | 87 | 90 | 0.9 |
| 522444 | 37 | 69 | 81 | 88 | 92 | 0.7 |
| 522445 | 62 | 54 | 68 | 85 | 91 | <0.6 |
| 522450 | 29 | 46 | 69 | 86 | 86 | 1.4 |
| 522473 | 19 | 33 | 66 | 78 | 86 | 2 |
| 522484 | 63 | 72 | 81 | 80 | 81 | <0.6 |
| 522485 | 37 | 43 | 70 | 82 | 90 | 1.3 |
| 522501 | 38 | 66 | 79 | 84 | 86 | 0.7 |

TABLE 107

| ISIS No | 0.625 μM | 1.25 μM | 2.50 μM | 5.00 μM | 10.00 μM | IC$_{50}$ (μM) |
|---|---|---|---|---|---|---|
| 413433 | 20 | 48 | 75 | 84 | 89 | 1.5 |
| 522440 | 31 | 51 | 69 | 79 | 85 | 1.3 |
| 522465 | 26 | 45 | 68 | 81 | 89 | 1.5 |
| 522474 | 17 | 40 | 65 | 78 | 87 | 1.9 |
| 522495 | 15 | 28 | 69 | 82 | 85 | 2 |
| 522509 | 24 | 38 | 61 | 88 | 87 | 1.7 |
| 522529 | 21 | 38 | 68 | 58 | 87 | 2 |
| 522553 | 15 | 29 | 61 | 81 | 90 | 2.1 |
| 522579 | 23 | 43 | 58 | 83 | 89 | 1.7 |
| 522580 | 50 | 36 | 68 | 84 | 93 | 1.1 |
| 522581 | 16 | 21 | 59 | 82 | 92 | 2.2 |
| 522582 | 23 | 48 | 59 | 86 | 91 | 1.6 |
| 522587 | 21 | 52 | 69 | 90 | 95 | 1.4 |
| 522588 | 19 | 41 | 65 | 88 | 94 | 1.7 |
| 522589 | 38 | 57 | 80 | 96 | 92 | 0.9 |

TABLE 108

| ISIS No | 0.625 μM | 1.25 μM | 2.50 μM | 5.00 μM | 10.00 μM | IC$_{50}$ (μM) |
|---|---|---|---|---|---|---|
| 413433 | 34 | 49 | 77 | 79 | 91 | 1.2 |
| 522550 | 16 | 45 | 58 | 80 | 89 | 1.9 |
| 522554 | 26 | 39 | 60 | 71 | 87 | 1.9 |
| 522555 | 38 | 50 | 66 | 74 | 81 | 1.2 |
| 522556 | 33 | 39 | 59 | 76 | 85 | 1.7 |
| 522609 | 41 | 67 | 87 | 92 | 84 | 0.6 |
| 522610 | 21 | 41 | 65 | 71 | 93 | 1.8 |
| 522621 | 35 | 54 | 71 | 85 | 94 | 1.1 |
| 522627 | 18 | 9 | 57 | 81 | 95 | 2.3 |
| 522631 | 26 | 34 | 70 | 81 | 93 | 1.7 |
| 522632 | 40 | 55 | 82 | 91 | 95 | 0.8 |
| 522638 | 8 | 33 | 63 | 74 | 91 | 2.2 |
| 522643 | 64 | 53 | 69 | 82 | 93 | <0.6 |
| 522667 | 23 | 55 | 75 | 86 | 91 | 1.3 |
| 522688 | 45 | 57 | 80 | 88 | 94 | 0.7 |

TABLE 109

| ISIS No | 0.625 μM | 1.25 μM | 2.50 μM | 5.00 μM | 10.00 μM | IC$_{50}$ (μM) |
|---|---|---|---|---|---|---|
| 413433 | 33 | 51 | 73 | 80 | 86 | 1.2 |
| 522672 | 20 | 20 | 57 | 89 | 93 | 2.1 |
| 522675 | 20 | 29 | 63 | 78 | 94 | 2 |
| 522676 | 6 | 43 | 62 | 88 | 93 | 1.9 |
| 522677 | 6 | 39 | 63 | 83 | 96 | 2 |
| 522679 | 17 | 35 | 62 | 82 | 92 | 1.9 |
| 522682 | 61 | 57 | 69 | 86 | 90 | <0.6 |
| 522689 | 29 | 57 | 78 | 87 | 93 | 1.1 |
| 522694 | 28 | 33 | 57 | 76 | 92 | 1.8 |
| 522697 | 19 | 31 | 68 | 86 | 95 | 1.8 |
| 522698 | 20 | 54 | 72 | 85 | 93 | 1.4 |
| 522715 | 12 | 48 | 68 | 80 | 88 | 1.8 |
| 522716 | 25 | 35 | 67 | 84 | 90 | 1.7 |

TABLE 109-continued

| ISIS No | 0.625 μM | 1.25 μM | 2.50 μM | 5.00 μM | 10.00 μM | IC$_{50}$ (μM) |
|---|---|---|---|---|---|---|
| 522717 | 27 | 56 | 74 | 90 | 88 | 1.2 |
| 522745 | 42 | 62 | 85 | 90 | 92 | 0.7 |

TABLE 110

| ISIS No | 0.625 μM | 1.25 μM | 2.50 μM | 5.00 μM | 10.00 μM | IC$_{50}$ (μM) |
|---|---|---|---|---|---|---|
| 413433 | 34 | 52 | 78 | 84 | 91 | 1.1 |
| 522671 | 36 | 43 | 72 | 85 | 92 | 1.2 |
| 522678 | 35 | 43 | 65 | 83 | 92 | 1.3 |
| 522680 | 25 | 50 | 63 | 82 | 86 | 1.5 |
| 522681 | 26 | 57 | 69 | 86 | 90 | 1.3 |
| 522683 | 24 | 33 | 65 | 77 | 88 | 1.8 |
| 522687 | 36 | 41 | 68 | 82 | 93 | 1.3 |
| 522690 | 23 | 51 | 67 | 84 | 93 | 1.5 |
| 522692 | 33 | 38 | 59 | 77 | 92 | 1.6 |
| 522705 | 35 | 48 | 66 | 73 | 86 | 1.3 |
| 522719 | 29 | 38 | 62 | 80 | 92 | 1.7 |
| 522757 | 29 | 41 | 60 | 79 | 93 | 1.6 |
| 522770 | 33 | 47 | 78 | 91 | 94 | 1.1 |
| 522784 | 20 | 33 | 54 | 71 | 90 | 2.2 |
| 522807 | 20 | 35 | 61 | 78 | 92 | 1.9 |

TABLE 111

| ISIS No | 0.625 μM | 1.25 μM | 2.50 μM | 5.00 μM | 10.00 μM | IC$_{50}$ (μM) |
|---|---|---|---|---|---|---|
| 413433 | 32 | 54 | 75 | 84 | 89 | 1.1 |
| 522758 | 26 | 49 | 66 | 87 | 94 | 1.4 |
| 522783 | 32 | 33 | 59 | 77 | 89 | 1.8 |
| 522838 | 16 | 39 | 64 | 75 | 82 | 2.0 |
| 522865 | 16 | 34 | 58 | 80 | 92 | 2.0 |
| 522866 | 16 | 25 | 45 | 66 | 83 | 2.8 |
| 522870 | 18 | 38 | 46 | 79 | 95 | 2.1 |
| 522871 | 13 | 35 | 57 | 80 | 91 | 2.1 |
| 522888 | 27 | 52 | 71 | 85 | 89 | 1.3 |
| 522889 | 36 | 59 | 75 | 81 | 80 | 0.9 |
| 522894 | 31 | 42 | 54 | 80 | 92 | 1.6 |
| 522897 | 29 | 53 | 76 | 88 | 92 | 1.2 |
| 522898 | 18 | 34 | 63 | 77 | 87 | 2.0 |
| 522913 | 40 | 54 | 79 | 90 | 90 | 0.9 |
| 522942 | 27 | 57 | 77 | 85 | 88 | 1.1 |

TABLE 112

| ISIS No | 0.625 μM | 1.25 μM | 2.50 μM | 5.00 μM | 10.00 μM | IC$_{50}$ (μM) |
|---|---|---|---|---|---|---|
| 413433 | 20 | 46 | 71 | 82 | 89 | 1.6 |
| 334177 | 9 | 30 | 60 | 74 | 92 | 2.3 |
| 522905 | 9 | 24 | 50 | 76 | 94 | 2.5 |
| 522917 | 17 | 35 | 58 | 82 | 93 | 2.0 |
| 522924 | 7 | 36 | 59 | 79 | 95 | 2.1 |
| 522925 | 15 | 36 | 64 | 85 | 95 | 1.8 |
| 522932 | 9 | 29 | 53 | 80 | 92 | 2.3 |
| 522941 | 23 | 44 | 65 | 85 | 91 | 1.6 |
| 522943 | 13 | 44 | 75 | 81 | 88 | 1.7 |
| 522947 | 45 | 30 | 62 | 78 | 94 | 1.4 |
| 522964 | 27 | 48 | 71 | 85 | 95 | 1.4 |
| 495876 | 24 | 33 | 58 | 86 | 94 | 1.8 |
| 495877 | 16 | 25 | 52 | 77 | 87 | 2.4 |
| 495878 | 37 | 69 | 86 | 91 | 96 | 0.7 |
| 523002 | 34 | 54 | 80 | 89 | 93 | 1.0 |

Example 9: Dose-Dependent Antisense Inhibition of Human DGAT2 in HepG2 Cells by MOE Gapmers Gapmers from the studies described in the Examples above exhibiting significant in vitro inhibition of DGAT2 mRNA were selected and tested at various doses in HepG2 cells. The antisense oligonucleotides were tested in a series of experiments that had similar culture conditions. The results for each experiment are presented in separate tables shown below. Cells were plated at a density of 20,000 cells per well and transfected using electroporation with 0.3125 µM, 0.625 µM, 1.25 µM, 2.50 µM, 5.00 µM, or 10.00 µM concentrations of antisense oligonucleotide, as specified in the Tables below. After a treatment period of approximately 16 hours, RNA was isolated from the cells and DGAT2 mRNA levels were measured by quantitative real-time PCR. Human primer probe set RTS2988_MGB was used to measure mRNA levels. DGAT2 mRNA levels were adjusted according to total RNA content, as measured by RIBOGREEN®. Results are presented as percent inhibition of DGAT2, relative to untreated control cells. '0' indicates that the mRNA levels were not inhibited.

The half maximal inhibitory concentration ($IC_{50}$) of each oligonucleotide is also presented. DGAT2 mRNA levels were significantly reduced in a dose-dependent manner in antisense oligonucleotide treated cells.

TABLE 113

| ISIS No | 0.3125 µM | 0.625 µM | 1.25 µM | 2.50 µM | 5.00 µM | 10.00 µM | $IC_{50}$ (µM) |
|---|---|---|---|---|---|---|---|
| 413433 | 0 | 41 | 65 | 75 | 81 | 87 | 1.3 |
| 484157 | 24 | 52 | 78 | 87 | 95 | 94 | 0.6 |
| 484127 | 10 | 39 | 71 | 86 | 93 | 94 | 0.9 |
| 484181 | 49 | 57 | 76 | 79 | 89 | 90 | 0.3 |
| 484137 | 29 | 41 | 62 | 79 | 89 | 91 | 0.8 |
| 484148 | 0 | 30 | 72 | 77 | 91 | 93 | 1.2 |
| 484169 | 18 | 31 | 48 | 68 | 87 | 88 | 1.3 |
| 484170 | 0 | 51 | 58 | 75 | 94 | 90 | 1.3 |
| 484133 | 36 | 63 | 50 | 58 | 85 | 91 | 1.0 |
| 484140 | 31 | 60 | 65 | 73 | 87 | 92 | 0.6 |
| 484129 | 48 | 62 | 73 | 87 | 91 | 93 | 0.3 |
| 484141 | 40 | 33 | 55 | 64 | 85 | 96 | 0.9 |

TABLE 114

| ISIS No | 0.3125 µM | 0.625 µM | 1.25 µM | 2.50 µM | 5.00 µM | 10.00 µM | $IC_{50}$ (µM) |
|---|---|---|---|---|---|---|---|
| 413433 | 36 | 38 | 57 | 64 | 83 | 87 | 0.9 |
| 484158 | 8 | 6 | 39 | 61 | 86 | 91 | 1.9 |
| 484377 | 0 | 2 | 15 | 33 | 78 | 94 | 2.8 |
| 484130 | 18 | 41 | 51 | 79 | 91 | 96 | 1.0 |
| 484336 | 26 | 24 | 45 | 67 | 90 | 92 | 1.3 |
| 484167 | 0 | 0 | 33 | 72 | 89 | 96 | 2.3 |
| 484344 | 17 | 18 | 29 | 48 | 75 | 83 | 2.2 |
| 484156 | 0 | 5 | 29 | 47 | 76 | 81 | 2.9 |
| 484391 | 0 | 0 | 42 | 66 | 84 | 96 | 2.0 |
| 484353 | 0 | 16 | 48 | 72 | 91 | 99 | 1.6 |
| 484350 | 0 | 37 | 49 | 79 | 89 | 87 | 1.5 |
| 484357 | 15 | 23 | 39 | 69 | 91 | 94 | 1.5 |
| 484343 | 25 | 28 | 58 | 80 | 90 | 93 | 1.0 |

TABLE 115

| ISIS No | 0.3125 µM | 0.625 µM | 1.25 µM | 2.50 µM | 5.00 µM | 10.00 µM | $IC_{50}$ (µM) |
|---|---|---|---|---|---|---|---|
| 413433 | 34 | 34 | 65 | 83 | 86 | 85 | 0.8 |
| 472155 | 21 | 14 | 20 | 35 | 54 | 73 | 4.1 |
| 472156 | 11 | 23 | 41 | 42 | 66 | 84 | 2.3 |
| 472158 | 27 | 36 | 62 | 77 | 87 | 95 | 0.9 |
| 472175 | 4 | 25 | 30 | 60 | 69 | 89 | 2.1 |
| 472178 | 0 | 0 | 6 | 30 | 54 | 82 | 4.2 |
| 423453 | 32 | 31 | 57 | 77 | 90 | 94 | 0.9 |
| 380132 | 17 | 9 | 0 | 30 | 21 | 54 | >10 |
| 472433 | 0 | 0 | 0 | 0 | 18 | 62 | >10 |
| 217328 | 29 | 28 | 45 | 65 | 76 | 83 | 1.4 |

TABLE 116

| ISIS No | 0.3125 µM | 0.625 µM | 1.25 µM | 2.50 µM | 5.00 µM | 10.00 µM | $IC_{50}$ (µM) |
|---|---|---|---|---|---|---|---|
| 413433 | 36 | 55 | 70 | 81 | 92 | 93 | <0.6 |
| 501094 | 43 | 60 | 76 | 85 | 90 | 90 | <0.6 |
| 501097 | 23 | 39 | 56 | 74 | 81 | 82 | 1.1 |
| 501098 | 56 | 70 | 83 | 92 | 90 | 91 | <0.6 |
| 501100 | 51 | 62 | 82 | 91 | 92 | 90 | <0.6 |
| 501103 | 58 | 65 | 77 | 86 | 93 | 92 | <0.6 |
| 501118 | 26 | 50 | 54 | 72 | 85 | 88 | 0.9 |
| 501122 | 28 | 40 | 59 | 69 | 85 | 84 | 1.0 |
| 501127 | 38 | 61 | 75 | 81 | 89 | 88 | <0.6 |
| 501165 | 34 | 24 | 59 | 70 | 85 | 82 | 1.1 |
| 501171 | 38 | 57 | 64 | 80 | 88 | 89 | <0.6 |
| 501214 | 36 | 50 | 68 | 84 | 83 | 85 | <0.6 |

TABLE 117

| ISIS No | 0.3125 µM | 0.625 µM | 1.25 µM | 2.50 µM | 5.00 µM | 10.00 µM | $IC_{50}$ (µM) |
|---|---|---|---|---|---|---|---|
| 413433 | 17 | 38 | 61 | 84 | 88 | 91 | 1.0 |
| 500998 | 37 | 57 | 74 | 84 | 90 | 92 | 0.4 |
| 501020 | 29 | 53 | 73 | 83 | 89 | 92 | 0.6 |
| 501033 | 9 | 27 | 45 | 66 | 76 | 80 | 1.7 |
| 501034 | 14 | 42 | 56 | 75 | 83 | 90 | 1.1 |
| 501035 | 39 | 61 | 77 | 86 | 86 | 86 | 0.3 |
| 501040 | 17 | 25 | 40 | 71 | 86 | 91 | 1.4 |
| 501041 | 49 | 66 | 80 | 81 | 85 | 83 | <0.3 |
| 501062 | 24 | 29 | 50 | 66 | 81 | 88 | 1.3 |
| 501064 | 45 | 51 | 73 | 84 | 85 | 85 | 0.4 |
| 501093 | 12 | 34 | 55 | 72 | 76 | 78 | 1.4 |
| 501111 | 14 | 26 | 43 | 65 | 69 | 78 | 1.9 |

TABLE 118

| ISIS No | 0.3125 µM | 0.625 µM | 1.25 µM | 2.50 µM | 5.00 µM | 10.00 µM | $IC_{50}$ (µM) |
|---|---|---|---|---|---|---|---|
| 413433 | 41 | 47 | 65 | 81 | 91 | 94 | 0.6 |
| 500841 | 32 | 38 | 67 | 75 | 83 | 84 | 0.8 |
| 500844 | 35 | 51 | 77 | 74 | 77 | 63 | 0.4 |
| 500852 | 35 | 38 | 63 | 79 | 88 | 89 | 0.8 |
| 500859 | 58 | 39 | 52 | 85 | 91 | 96 | 0.5 |
| 500867 | 21 | 54 | 46 | 88 | 90 | 93 | 0.8 |
| 500913 | 42 | 65 | 58 | 89 | 91 | 90 | 0.4 |
| 500942 | 32 | 31 | 50 | 86 | 92 | 95 | 0.9 |
| 500966 | 53 | 75 | 78 | 84 | 88 | 89 | <0.3 |
| 500989 | 32 | 69 | 74 | 90 | 87 | 86 | 0.3 |
| 501018 | 13 | 58 | 72 | 86 | 87 | 82 | 0.7 |
| 501067 | 7 | 63 | 45 | 77 | 88 | 94 | 1.0 |

TABLE 119

| ISIS No | 0.3125 μM | 0.625 μM | 1.25 μM | 2.50 μM | 5.00 μM | 10.00 μM | IC$_{50}$ (μM) |
|---|---|---|---|---|---|---|---|
| 413433 | 0 | 39 | 44 | 70 | 77 | 92 | 1.7 |
| 501385 | 0 | 9 | 30 | 25 | 37 | 63 | 7.0 |
| 501387 | 0 | 0 | 0 | 14 | 27 | 75 | 6.8 |
| 501404 | 28 | 37 | 48 | 59 | 61 | 83 | 1.5 |
| 501412 | 0 | 23 | 24 | 16 | 51 | 75 | 4.6 |
| 501427 | 3 | 18 | 50 | 41 | 68 | 92 | 2.1 |
| 501430 | 21 | 7 | 47 | 53 | 74 | 90 | 1.9 |
| 501442 | 35 | 39 | 65 | 72 | 92 | 94 | 0.8 |
| 501443 | 36 | 50 | 34 | 48 | 62 | 75 | 1.6 |
| 501447 | 21 | 9 | 49 | 56 | 74 | 90 | 1.8 |
| 501448 | 23 | 25 | 48 | 60 | 69 | 88 | 1.6 |
| 501450 | 27 | 36 | 28 | 31 | 52 | 77 | 3.4 |

TABLE 120

| ISIS No | 0.3125 μM | 0.625 μM | 1.25 μM | 2.50 μM | 5.00 μM | 10.00 μM | IC$_{50}$ (μM) |
|---|---|---|---|---|---|---|---|
| 413433 | 0 | 13 | 31 | 51 | 80 | 86 | 2.1 |
| 501391 | 0 | 9 | 15 | 7 | 46 | 67 | 8.6 |
| 501393 | 0 | 0 | 0 | 50 | 64 | 81 | 3.1 |
| 501398 | 0 | 5 | 0 | 0 | 41 | 58 | >10 |
| 501405 | 0 | 31 | 33 | 57 | 73 | 80 | 2.0 |
| 501429 | 5 | 10 | 0 | 2 | 40 | 62 | >10 |
| 501435 | 20 | 15 | 34 | 50 | 79 | 89 | 1.9 |
| 501438 | 12 | 39 | 30 | 64 | 83 | 89 | 1.6 |
| 501440 | 42 | 21 | 41 | 57 | 81 | 92 | 1.3 |
| 501451 | 0 | 0 | 19 | 39 | 67 | 84 | 3.5 |
| 501452 | 0 | 7 | 14 | 38 | 54 | 85 | 3.6 |
| 501454 | 12 | 4 | 1 | 19 | 65 | 82 | 4.2 |

TABLE 121

| ISIS No | 0.3125 μM | 0.625 μM | 1.25 μM | 2.50 μM | 5.00 μM | 10.00 μM | IC$_{50}$ (μM) |
|---|---|---|---|---|---|---|---|
| 413433 | 0 | 26 | 56 | 75 | 82 | 92 | 1.2 |
| 501388 | 0 | 15 | 28 | 63 | 86 | 88 | 1.8 |
| 501389 | 0 | 0 | 0 | 58 | 69 | 84 | 2.1 |
| 501390 | 0 | 33 | 0 | 0 | 73 | 86 | 2.0 |
| 501392 | 0 | 19 | 57 | 60 | 75 | 81 | 2.2 |
| 501396 | 0 | 13 | 0 | 53 | 81 | 83 | 2.3 |
| 501411 | 0 | 0 | 0 | 31 | 45 | 78 | 5.5 |
| 501428 | 14 | 0 | 14 | 38 | 74 | 81 | 3.2 |
| 501436 | 0 | 0 | 41 | 61 | 80 | 78 | 2.2 |
| 501449 | 0 | 0 | 35 | 56 | 71 | 82 | 2.7 |
| 501455 | 0 | 0 | 19 | 30 | 61 | 75 | 4.1 |
| 501457 | 18 | 0 | 23 | 39 | 63 | 87 | 3.1 |

TABLE 122

| ISIS No | 0.3125 μM | 0.625 μM | 1.25 μM | 2.50 μM | 5.00 μM | 10.00 μM | IC$_{50}$ (μM) |
|---|---|---|---|---|---|---|---|
| 413433 | 19 | 33 | 46 | 69 | 80 | 91 | 1.3 |
| 501154 | 24 | 22 | 33 | 42 | 74 | 81 | 2.2 |
| 501183 | 18 | 42 | 54 | 71 | 71 | 80 | 1.2 |
| 501199 | 23 | 22 | 44 | 68 | 80 | 79 | 1.5 |
| 501200 | 8 | 13 | 40 | 65 | 78 | 87 | 1.9 |
| 501212 | 39 | 32 | 24 | 52 | 65 | 70 | 2.3 |
| 501213 | 12 | 34 | 40 | 69 | 75 | 79 | 1.6 |
| 501224 | 36 | 33 | 53 | 65 | 74 | 81 | 1.1 |
| 501270 | 12 | 9 | 42 | 59 | 67 | 76 | 2.3 |
| 501287 | 2 | 24 | 33 | 46 | 71 | 80 | 2.5 |
| 501322 | 8 | 9 | 6 | 31 | 54 | 77 | 4.4 |
| 501345 | 10 | 17 | 21 | 50 | 55 | 81 | 3.0 |

TABLE 123

| ISIS No | 0.3125 μM | 0.625 μM | 1.25 μM | 2.50 μM | 5.00 μM | 10.00 μM | IC$_{50}$ (μM) |
|---|---|---|---|---|---|---|---|
| 413433 | 0 | 11 | 17 | 33 | 60 | 69 | 4.2 |
| 525395 | 18 | 18 | 15 | 47 | 49 | 69 | 4.4 |
| 525401 | 10 | 28 | 33 | 58 | 68 | 68 | 2.5 |
| 525402 | 0 | 9 | 23 | 43 | 62 | 73 | 3.5 |
| 525414 | 2 | 11 | 29 | 36 | 56 | 56 | 5.2 |
| 525415 | 22 | 0 | 21 | 39 | 49 | 73 | 4.7 |
| 525431 | 6 | 19 | 36 | 49 | 67 | 66 | 2.9 |
| 525442 | 13 | 0 | 23 | 44 | 56 | 81 | 3.4 |
| 525443 | 4 | 6 | 24 | 61 | 65 | 78 | 2.7 |
| 525469 | 28 | 38 | 50 | 69 | 79 | 85 | 1.1 |
| 525470 | 3 | 17 | 23 | 41 | 70 | 82 | 2.8 |
| 525501 | 0 | 5 | 34 | 31 | 58 | 79 | 3.5 |

TABLE 124

| ISIS No | 0.3125 μM | 0.625 μM | 1.25 μM | 2.50 μM | 5.00 μM | 10.00 μM | IC$_{50}$ (μM) |
|---|---|---|---|---|---|---|---|
| 413433 | 22 | 35 | 48 | 62 | 76 | 86 | 1.4 |
| 525468 | 11 | 30 | 21 | 61 | 72 | 83 | 2.1 |
| 525471 | 29 | 47 | 62 | 70 | 77 | 84 | 0.8 |
| 525472 | 23 | 35 | 54 | 70 | 81 | 81 | 1.2 |
| 525474 | 22 | 38 | 54 | 69 | 79 | 78 | 1.2 |
| 525479 | 25 | 26 | 35 | 63 | 75 | 84 | 1.6 |
| 525480 | 0 | 21 | 29 | 50 | 75 | 75 | 2.7 |
| 525500 | 4 | 23 | 39 | 60 | 80 | 87 | 1.8 |
| 525513 | 32 | 21 | 45 | 55 | 77 | 86 | 1.6 |
| 525551 | 15 | 31 | 38 | 8 | 84 | 90 | 2.3 |
| 525552 | 11 | 29 | 49 | 56 | 78 | 87 | 1.6 |
| 525554 | 16 | 7 | 31 | 62 | 68 | 79 | 2.3 |

TABLE 125

| ISIS No | 0.3125 μM | 0.625 μM | 1.25 μM | 2.50 μM | 5.00 μM | 10.00 μM | IC$_{50}$ (μM) |
|---|---|---|---|---|---|---|---|
| 413433 | 28 | 21 | 44 | 50 | 68 | 79 | 1.9 |
| 525544 | 0 | 3 | 22 | 41 | 52 | 63 | 4.8 |
| 525612 | 26 | 36 | 56 | 72 | 76 | 79 | 1.1 |
| 525631 | 0 | 8 | 26 | 54 | 77 | 82 | 2.7 |
| 525649 | 0 | 0 | 10 | 46 | 64 | 76 | 3.7 |
| 496041 | 14 | 9 | 8 | 31 | 53 | 65 | 5.7 |
| 525688 | 5 | 25 | 43 | 68 | 82 | 89 | 1.6 |
| 525705 | 27 | 30 | 48 | 69 | 82 | 90 | 1.2 |
| 525708 | 5 | 26 | 54 | 69 | 84 | 89 | 1.5 |
| 525711 | 14 | 28 | 49 | 67 | 81 | 88 | 1.4 |
| 525733 | 21 | 42 | 60 | 76 | 82 | 93 | 1.0 |
| 525754 | 0 | 17 | 34 | 55 | 79 | 85 | 2.2 |

Example 10: Final Confirmation of Antisense Inhibition of Human DGAT2 in HepG2 Cells by MOE Gapmers Gapmers from the studies described in the Examples above exhibiting significant in vitro inhibition of DGAT2 mRNA were selected and tested at various doses in HepG2 cells. Cells were plated at a density of 20,000 cells per well and transfected using electroporation with 0.3125 μM, 0.625 μM, 1.25 μM, 2.50 μM, 5.00 μM, or 10.00 μM concentrations of antisense oligonucleotide, as specified in the Tables below. After a treatment period of approximately 16 hours, RNA was isolated from the cells and DGAT2 mRNA levels were measured by quantitative real-time PCR. Human primer probe set RTS2988_MGB was used to measure mRNA levels. DGAT2 mRNA levels were adjusted according to total RNA content, as measured by RIBOGREEN®. Results are presented as percent inhibition of DGAT2, relative to untreated control cells. '0' indicates that the mRNA levels were not inhibited.

The half maximal inhibitory concentration ($IC_{50}$) of each oligonucleotide is also presented. DGAT2 mRNA levels were significantly reduced in a dose-dependent manner in antisense oligonucleotide treated cells.

TABLE 126

| ISIS No | 0.3125 μM | 0.625 μM | 1.25 μM | 2.50 μM | 5.00 μM | 10.00 μM | $IC_{50}$ (μM) |
|---|---|---|---|---|---|---|---|
| 413433 | 19 | 26 | 52 | 72 | 86 | 92 | 1.3 |
| 483817 | 18 | 31 | 60 | 74 | 86 | 90 | 1.1 |
| 483898 | 40 | 41 | 68 | 77 | 89 | 90 | 0.6 |
| 483908 | 21 | 47 | 63 | 83 | 89 | 92 | 0.8 |
| 484152 | 18 | 25 | 47 | 63 | 84 | 91 | 1.4 |
| 484181 | 42 | 45 | 73 | 81 | 87 | 86 | 0.5 |
| 484215 | 27 | 37 | 47 | 69 | 80 | 93 | 1.1 |
| 484231 | 16 | 33 | 58 | 71 | 83 | 89 | 1.2 |
| 472316 | 0 | 5 | 40 | 50 | 84 | 92 | 2.3 |
| 423463 | 17 | 34 | 55 | 80 | 90 | 93 | 1.1 |
| 484271 | 26 | 29 | 62 | 83 | 89 | 92 | 1.0 |
| 484283 | 7 | 12 | 30 | 50 | 79 | 90 | 2.2 |

TABLE 127

| ISIS No | 0.3125 μM | 0.625 μM | 1.25 μM | 2.50 μM | 5.00 μM | 10.00 μM | $IC_{50}$ (μM) |
|---|---|---|---|---|---|---|---|
| 413433 | 3 | 25 | 51 | 69 | 89 | 92 | 1.5 |
| 472158 | 18 | 25 | 26 | 44 | 71 | 80 | 2.4 |
| 483874 | 30 | 42 | 62 | 82 | 90 | 93 | 0.8 |
| 483910 | 20 | 30 | 49 | 74 | 85 | 90 | 1.2 |
| 483952 | 36 | 62 | 80 | 88 | 92 | 93 | 0.4 |
| 483968 | 8 | 35 | 57 | 73 | 86 | 91 | 1.2 |
| 483984 | 32 | 34 | 62 | 78 | 88 | 91 | 0.9 |
| 483987 | 12 | 10 | 36 | 61 | 80 | 92 | 1.9 |
| 483997 | 0 | 7 | 33 | 57 | 77 | 89 | 2.4 |
| 484085 | 25 | 24 | 53 | 72 | 87 | 89 | 1.2 |
| 484099 | 29 | 44 | 67 | 82 | 91 | 94 | 0.7 |
| 423453 | 19 | 24 | 46 | 62 | 88 | 95 | 1.4 |

TABLE 128

| ISIS No | 0.3125 μM | 0.625 μM | 1.25 μM | 2.50 μM | 5.00 μM | 10.00 μM | $IC_{50}$ (μM) |
|---|---|---|---|---|---|---|---|
| 413433 | 22 | 19 | 46 | 61 | 83 | 90 | 1.5 |
| 484127 | 16 | 18 | 54 | 74 | 90 | 95 | 1.3 |
| 484129 | 33 | 39 | 64 | 79 | 90 | 89 | 0.8 |
| 484130 | 30 | 29 | 52 | 66 | 85 | 92 | 1.1 |
| 484140 | 0 | 16 | 37 | 63 | 86 | 87 | 1.9 |
| 484133 | 1 | 2 | 44 | 71 | 83 | 93 | 1.8 |
| 484137 | 0 | 27 | 64 | 81 | 92 | 92 | 1.3 |
| 484148 | 16 | 37 | 67 | 79 | 91 | 94 | 1.0 |
| 484157 | 0 | 31 | 70 | 86 | 92 | 93 | 0.9 |
| 484170 | 23 | 40 | 57 | 77 | 90 | 94 | 1.0 |
| 484181 | 9 | 18 | 63 | 83 | 76 | 88 | 1.4 |
| 484343 | 18 | 21 | 40 | 72 | 88 | 91 | 1.4 |

TABLE 129

| ISIS No | 0.3125 μM | 0.625 μM | 1.25 μM | 2.50 μM | 5.00 μM | 10.00 μM | $IC_{50}$ (μM) |
|---|---|---|---|---|---|---|---|
| 413433 | 0 | 23 | 30 | 57 | 71 | 83 | 2.4 |
| 501849 | 22 | 33 | 46 | 65 | 79 | 87 | 1.4 |
| 501850 | 12 | 19 | 40 | 52 | 76 | 83 | 2.0 |
| 501852 | 17 | 25 | 47 | 63 | 68 | 77 | 1.8 |
| 501855 | 24 | 37 | 59 | 78 | 82 | 84 | 1.0 |
| 501861 | 15 | 23 | 45 | 61 | 77 | 84 | 1.7 |
| 501871 | 14 | 19 | 39 | 57 | 71 | 85 | 2.0 |
| 501884 | 14 | 25 | 42 | 57 | 74 | 83 | 1.9 |

TABLE 129-continued

| ISIS No | 0.3125 μM | 0.625 μM | 1.25 μM | 2.50 μM | 5.00 μM | 10.00 μM | $IC_{50}$ (μM) |
|---|---|---|---|---|---|---|---|
| 501886 | 30 | 40 | 47 | 58 | 70 | 73 | 1.4 |
| 501932 | 8 | 24 | 28 | 55 | 68 | 78 | 2.4 |
| 501944 | 6 | 31 | 0 | 44 | 67 | 82 | 3.3 |
| 501950 | 0 | 14 | 19 | 55 | 79 | 85 | 2.4 |

TABLE 130

| ISIS No | 0.3125 μM | 0.625 μM | 1.25 μM | 2.50 μM | 5.00 μM | 10.00 μM | $IC_{50}$ (μM) |
|---|---|---|---|---|---|---|---|
| 413433 | 31 | 43 | 53 | 74 | 80 | 84 | 0.9 |
| 502154 | 29 | 46 | 68 | 81 | 86 | 91 | 0.7 |
| 502163 | 22 | 33 | 55 | 71 | 89 | 97 | 1.1 |
| 502164 | 20 | 32 | 71 | 72 | 85 | 91 | 1.0 |
| 502179 | 28 | 50 | 67 | 84 | 81 | 90 | 0.7 |
| 502191 | 29 | 47 | 64 | 74 | 94 | 97 | 0.7 |
| 502194 | 24 | 23 | 62 | 78 | 90 | 90 | 1.1 |
| 502314 | 25 | 14 | 21 | 44 | 66 | 85 | 2.6 |
| 502319 | 20 | 32 | 56 | 78 | 86 | 92 | 1.1 |
| 502322 | 17 | 35 | 49 | 68 | 79 | 83 | 1.4 |
| 502331 | 11 | 22 | 11 | 45 | 60 | 82 | 3.1 |
| 502334 | 35 | 40 | 59 | 69 | 82 | 92 | 0.8 |

TABLE 131

| ISIS No | 0.3125 μM | 0.625 μM | 1.25 μM | 2.50 μM | 5.00 μM | 10.00 μM | $IC_{50}$ (μM) |
|---|---|---|---|---|---|---|---|
| 413433 | 13 | 16 | 25 | 38 | 59 | 75 | 3.5 |
| 495702 | 29 | 37 | 49 | 65 | 78 | 80 | 1.2 |
| 495718 | 21 | 34 | 28 | 56 | 71 | 77 | 2.0 |
| 495756 | 23 | 40 | 56 | 76 | 87 | 95 | 1.0 |
| 507692 | 20 | 33 | 56 | 68 | 89 | 91 | 1.1 |
| 507693 | 28 | 38 | 56 | 79 | 89 | 94 | 0.9 |
| 507694 | 19 | 30 | 45 | 72 | 87 | 94 | 1.3 |
| 507695 | 28 | 32 | 44 | 70 | 84 | 92 | 1.2 |
| 507696 | 18 | 37 | 59 | 78 | 88 | 90 | 1.0 |
| 507710 | 27 | 39 | 52 | 73 | 91 | 92 | 1.0 |
| 507716 | 32 | 51 | 52 | 68 | 88 | 93 | 0.8 |
| 507717 | 31 | 49 | 44 | 66 | 84 | 90 | 1.0 |

TABLE 132

| ISIS No | 0.3125 μM | 0.625 μM | 1.25 μM | 2.50 μM | 5.00 μM | 10.00 μM | $IC_{50}$ (μM) |
|---|---|---|---|---|---|---|---|
| 413433 | 0 | 43 | 64 | 80 | 84 | 90 | 1.2 |
| 501947 | 7 | 23 | 42 | 65 | 79 | 89 | 1.7 |
| 501951 | 13 | 25 | 45 | 68 | 85 | 92 | 1.5 |
| 501959 | 8 | 29 | 38 | 66 | 74 | 90 | 1.7 |
| 501960 | 14 | 22 | 41 | 68 | 75 | 88 | 1.7 |
| 501968 | 17 | 33 | 44 | 59 | 88 | 87 | 1.4 |
| 502038 | 0 | 7 | 8 | 36 | 58 | 84 | 3.7 |
| 502045 | 13 | 38 | 53 | 67 | 81 | 88 | 1.3 |
| 502056 | 0 | 31 | 66 | 83 | 88 | 91 | 1.2 |
| 502098 | 9 | 35 | 48 | 72 | 86 | 93 | 1.3 |
| 502099 | 9 | 31 | 52 | 74 | 82 | 92 | 1.3 |
| 502119 | 1 | 45 | 61 | 79 | 89 | 95 | 1.1 |

TABLE 133

| ISIS No | 0.3125 μM | 0.625 μM | 1.25 μM | 2.50 μM | 5.00 μM | 10.00 μM | $IC_{50}$ (μM) |
|---|---|---|---|---|---|---|---|
| 413433 | 0 | 43 | 59 | 69 | 84 | 90 | 1.1 |
| 495697 | 15 | 32 | 50 | 66 | 78 | 79 | 1.5 |
| 495705 | 25 | 37 | 53 | 59 | 76 | 79 | 1.3 |
| 495719 | 21 | 30 | 44 | 64 | 76 | 84 | 1.5 |

TABLE 133-continued

| ISIS No | 0.3125 µM | 0.625 µM | 1.25 µM | 2.50 µM | 5.00 µM | 10.00 µM | IC$_{50}$ (µM) |
|---|---|---|---|---|---|---|---|
| 501388 | 13 | 34 | 44 | 62 | 71 | 87 | 1.6 |
| 501389 | 11 | 44 | 47 | 54 | 80 | 91 | 1.4 |
| 501392 | 0 | 25 | 42 | 51 | 75 | 87 | 1.9 |
| 501396 | 19 | 31 | 52 | 66 | 76 | 87 | 1.4 |
| 501428 | 0 | 0 | 33 | 46 | 63 | 85 | 2.8 |
| 501436 | 4 | 28 | 23 | 57 | 76 | 88 | 2.1 |
| 501449 | 19 | 21 | 42 | 59 | 75 | 92 | 1.7 |
| 501457 | 7 | 29 | 35 | 50 | 75 | 92 | 1.9 |

TABLE 134

| ISIS No | 0.3125 µM | 0.625 µM | 1.25 µM | 2.50 µM | 5.00 µM | 10.00 µM | IC$_{50}$ (µM) |
|---|---|---|---|---|---|---|---|
| 413433 | 13 | 35 | 53 | 73 | 83 | 87 | 1.3 |
| 522373 | 19 | 34 | 54 | 72 | 83 | 84 | 1.2 |
| 522374 | 13 | 31 | 54 | 65 | 79 | 85 | 1.4 |
| 522383 | 23 | 44 | 62 | 72 | 76 | 81 | 1.0 |
| 522435 | 25 | 39 | 55 | 73 | 81 | 80 | 1.1 |
| 522437 | 26 | 35 | 56 | 70 | 81 | 85 | 1.1 |
| 522440 | 14 | 33 | 50 | 67 | 77 | 82 | 1.5 |
| 522444 | 24 | 35 | 57 | 78 | 83 | 89 | 1.0 |
| 522445 | 25 | 45 | 57 | 69 | 83 | 86 | 1.0 |
| 522465 | 14 | 15 | 40 | 55 | 75 | 82 | 2.0 |
| 522484 | 37 | 0 | 72 | 75 | 76 | 74 | 1.3 |
| 522501 | 25 | 45 | 55 | 72 | 78 | 76 | 1.0 |

TABLE 135

| ISIS No | 0.3125 µM | 0.625 µM | 1.25 µM | 2.50 µM | 5.00 µM | 10.00 µM | IC$_{50}$ (µM) |
|---|---|---|---|---|---|---|---|
| 413433 | 25 | 36 | 50 | 79 | 83 | 87 | 1.1 |
| 522580 | 27 | 34 | 55 | 62 | 86 | 85 | 1.1 |
| 522587 | 35 | 40 | 56 | 73 | 88 | 92 | 0.8 |
| 522589 | 27 | 40 | 56 | 71 | 82 | 91 | 1.0 |
| 522609 | 37 | 48 | 70 | 82 | 94 | 93 | 0.5 |
| 522621 | 20 | 35 | 55 | 74 | 86 | 91 | 1.1 |
| 522632 | 31 | 52 | 66 | 80 | 90 | 93 | 0.6 |
| 522643 | 16 | 28 | 48 | 67 | 78 | 87 | 1.5 |
| 522688 | 16 | 38 | 57 | 75 | 76 | 89 | 1.2 |
| 522689 | 29 | 34 | 58 | 78 | 84 | 91 | 0.9 |
| 522717 | 18 | 24 | 50 | 72 | 82 | 88 | 1.4 |
| 522745 | 22 | 35 | 57 | 75 | 89 | 92 | 1.0 |

TABLE 136

| ISIS No | 0.3125 µM | 0.625 µM | 1.25 µM | 2.50 µM | 5.00 µM | 10.00 µM | IC$_{50}$ (µM) |
|---|---|---|---|---|---|---|---|
| 413433 | 23 | 32 | 45 | 74 | 78 | 88 | 1.3 |
| 522682 | 26 | 34 | 63 | 68 | 74 | 81 | 1.1 |
| 522770 | 8 | 26 | 50 | 65 | 83 | 91 | 1.5 |
| 522889 | 25 | 40 | 59 | 70 | 77 | 78 | 1.1 |
| 522897 | 14 | 22 | 45 | 69 | 83 | 89 | 1.5 |
| 522913 | 19 | 30 | 57 | 73 | 86 | 90 | 1.2 |
| 522941 | 8 | 18 | 41 | 56 | 73 | 82 | 2.1 |
| 522942 | 20 | 30 | 49 | 67 | 83 | 86 | 1.3 |
| 522947 | 14 | 0 | 40 | 58 | 80 | 91 | 2.0 |
| 522964 | 9 | 20 | 51 | 63 | 78 | 89 | 1.7 |
| 495878 | 16 | 36 | 62 | 80 | 90 | 93 | 1.0 |
| 523002 | 21 | 32 | 51 | 67 | 73 | 84 | 1.4 |

TABLE 137

| ISIS No | 0.3125 µM | 0.625 µM | 1.25 µM | 2.50 µM | 5.00 µM | 10.00 µM | IC$_{50}$ (µM) |
|---|---|---|---|---|---|---|---|
| 413433 | 40 | 35 | 66 | 81 | 87 | 89 | 0.7 |
| 525401 | 17 | 58 | 64 | 79 | 85 | 86 | 0.8 |
| 525402 | 30 | 41 | 49 | 74 | 87 | 90 | 0.9 |
| 525431 | 31 | 29 | 64 | 82 | 86 | 84 | 0.9 |
| 525442 | 35 | 39 | 59 | 76 | 90 | 87 | 0.8 |
| 525443 | 39 | 53 | 64 | 76 | 88 | 89 | 0.5 |
| 525469 | 32 | 68 | 85 | 93 | 92 | 93 | 0.3 |
| 525470 | 39 | 34 | 59 | 74 | 91 | 89 | 0.8 |
| 525471 | 27 | 34 | 59 | 84 | 86 | 0 | 0.9 |
| 525474 | 32 | 47 | 69 | 80 | 93 | 87 | 0.6 |
| 525479 | 25 | 33 | 51 | 60 | 75 | 75 | 1.5 |
| 525501 | 31 | 29 | 56 | 82 | 91 | 88 | 1.0 |

TABLE 138

| ISIS No | 0.3125 µM | 0.625 µM | 1.25 µM | 2.50 µM | 5.00 µM | 10.00 µM | IC$_{50}$ (µM) |
|---|---|---|---|---|---|---|---|
| 413433 | 22 | 41 | 54 | 69 | 81 | 88 | 1.1 |
| 525472 | 26 | 31 | 50 | 69 | 84 | 82 | 1.2 |
| 525500 | 11 | 33 | 52 | 68 | 83 | 83 | 1.4 |
| 525513 | 16 | 20 | 48 | 64 | 79 | 87 | 1.6 |
| 525552 | 27 | 30 | 57 | 70 | 83 | 90 | 1.1 |
| 525612 | 0 | 44 | 65 | 76 | 83 | 82 | 0.3 |
| 525688 | 11 | 40 | 60 | 75 | 88 | 97 | 1.1 |
| 525705 | 25 | 41 | 65 | 76 | 90 | 95 | 0.8 |
| 525708 | 36 | 38 | 64 | 75 | 93 | 96 | 0.7 |
| 525711 | 24 | 53 | 67 | 80 | 90 | 94 | 0.7 |
| 525733 | 27 | 70 | 73 | 86 | 91 | 95 | 0.4 |
| 525754 | 23 | 23 | 48 | 70 | 85 | 89 | 1.3 |

Example 11: Final Confirmation of Antisense Inhibition of Human DGAT2 in HepG2 Cells by MOE Gapmers Gapmers from the studies described in the Examples above exhibiting significant in vitro inhibition of DGAT2 mRNA were selected and tested at various doses in HepG2 cells. Cells were plated at a density of 20,000 cells per well and transfected using electroporation with 0.625 µM, 1.25 µM, 2.50 µM, 5.00 µM, or 10.00 µM concentrations of antisense oligonucleotide, as specified in the Tables below. After a treatment period of approximately 16 hours, RNA was isolated from the cells and DGAT2 mRNA levels were measured by quantitative real-time PCR. Human primer probe set RTS2988_MGB was used to measure mRNA levels. DGAT2 mRNA levels were adjusted according to total RNA content, as measured by RIBOGREEN®. Results are presented as percent inhibition of DGAT2, relative to untreated control cells. '0' indicates that the mRNA levels were not inhibited.

The half maximal inhibitory concentration (IC$_{50}$) of each oligonucleotide is also presented. DGAT2 mRNA levels were significantly reduced in a dose-dependent manner in antisense oligonucleotide treated cells.

TABLE 139

| ISIS No | 0.625 µM | 1.25 µM | 2.50 µM | 5.00 µM | 10.00 µM | IC$_{50}$ (µM) |
|---|---|---|---|---|---|---|
| 413433 | 48 | 60 | 77 | 85 | 86 | 0.6 |
| 495450 | 42 | 50 | 73 | 83 | 83 | 1.0 |
| 495516 | 64 | 78 | 87 | 84 | 84 | <0.6 |
| 495520 | 70 | 76 | 87 | 83 | 82 | <0.6 |
| 495554 | 26 | 61 | 75 | 76 | 85 | 1.1 |

TABLE 139-continued

| ISIS No | 0.625 µM | 1.25 µM | 2.50 µM | 5.00 µM | 10.00 µM | IC$_{50}$ (µM) |
|---|---|---|---|---|---|---|
| 495555 | 30 | 72 | 80 | 87 | 84 | 0.8 |
| 495576 | 61 | 73 | 86 | 88 | 88 | <0.6 |
| 495577 | 44 | 64 | 75 | 85 | 80 | 0.6 |
| 495609 | 64 | 69 | 83 | 86 | 89 | <0.6 |
| 495685 | 0 | 53 | 75 | 82 | 85 | 2.0 |
| 495707 | 9 | 41 | 72 | 75 | 66 | 2.2 |
| 495736 | 16 | 61 | 80 | 85 | 81 | 1.3 |
| 495749 | 16 | 33 | 76 | 90 | 93 | 1.7 |
| 495752 | 0 | 66 | 75 | 74 | 93 | 1.7 |
| 495753 | 0 | 59 | 79 | 91 | 92 | 1.8 |

TABLE 140

| ISIS No | 0.625 µM | 1.25 µM | 2.50 µM | 5.00 µM | 10.00 µM | IC$_{50}$ (µM) |
|---|---|---|---|---|---|---|
| 413433 | 54 | 70 | 87 | 91 | 93 | <0.6 |
| 495738 | 55 | 57 | 81 | 92 | 92 | <0.6 |
| 495744 | 37 | 59 | 78 | 88 | 90 | 0.9 |
| 495756 | 52 | 61 | 80 | 90 | 94 | <0.6 |
| 495825 | 34 | 69 | 89 | 94 | 97 | 0.7 |
| 495829 | 38 | 79 | 88 | 90 | 91 | <0.6 |
| 495837 | 52 | 67 | 93 | 93 | 96 | <0.6 |
| 495839 | 66 | 89 | 91 | 93 | 93 | <0.6 |
| 495840 | 64 | 84 | 94 | 96 | 94 | <0.6 |
| 495841 | 51 | 82 | 90 | 92 | 93 | <0.6 |
| 495842 | 54 | 73 | 88 | 90 | 92 | <0.6 |
| 495849 | 63 | 69 | 82 | 85 | 91 | <0.6 |
| 495853 | 72 | 77 | 91 | 96 | 94 | <0.6 |
| 495857 | 52 | 61 | 88 | 91 | 92 | <0.6 |
| 495878 | 54 | 77 | 93 | 97 | 96 | <0.6 |

TABLE 141

| ISIS No | 0.625 µM | 1.25 µM | 2.50 µM | 5.00 µM | 10.00 µM | IC$_{50}$ (µM) |
|---|---|---|---|---|---|---|
| 413433 | 38 | 63 | 73 | 85 | 88 | 0.8 |
| 501171 | 38 | 53 | 69 | 83 | 84 | 1.0 |
| 501183 | 51 | 70 | 79 | 87 | 89 | <0.6 |
| 501199 | 44 | 68 | 88 | 91 | 87 | <0.6 |
| 501213 | 25 | 57 | 82 | 93 | 96 | 1.1 |
| 501214 | 35 | 56 | 72 | 88 | 92 | 1.0 |
| 501224 | 48 | 68 | 83 | 90 | 90 | <0.6 |
| 501405 | 27 | 51 | 72 | 90 | 96 | 1.3 |
| 501430 | 10 | 26 | 65 | 90 | 94 | 2.0 |
| 501435 | 35 | 41 | 71 | 92 | 94 | 1.3 |
| 501438 | 27 | 71 | 83 | 92 | 92 | 0.9 |
| 501440 | 24 | 40 | 66 | 90 | 97 | 1.6 |
| 501442 | 58 | 79 | 91 | 96 | 94 | <0.6 |
| 501443 | 32 | 29 | 57 | 89 | 96 | 1.7 |
| 501448 | 27 | 46 | 72 | 91 | 93 | 1.4 |

TABLE 142

| ISIS No | 0.625 µM | 1.25 µM | 2.50 µM | 5.00 µM | 10.00 µM | IC$_{50}$ (µM) |
|---|---|---|---|---|---|---|
| 413433 | 43 | 58 | 82 | 91 | 94 | 0.8 |
| 501127 | 46 | 68 | 81 | 91 | 92 | <0.6 |
| 501103 | 34 | 70 | 85 | 93 | 91 | 0.7 |
| 501100 | 54 | 75 | 88 | 93 | 94 | <0.6 |
| 501098 | 55 | 81 | 91 | 91 | 89 | <0.6 |
| 501094 | 62 | 70 | 87 | 90 | 92 | <0.6 |
| 501064 | 52 | 67 | 81 | 88 | 89 | <0.6 |
| 501041 | 53 | 71 | 82 | 86 | 85 | <0.6 |
| 501035 | 57 | 77 | 87 | 88 | 90 | <0.6 |
| 501020 | 47 | 63 | 86 | 94 | 94 | 0.6 |
| 500998 | 47 | 61 | 86 | 91 | 95 | 0.6 |
| 500989 | 55 | 75 | 83 | 86 | 85 | <0.6 |

TABLE 142-continued

| ISIS No | 0.625 µM | 1.25 µM | 2.50 µM | 5.00 µM | 10.00 µM | IC$_{50}$ (µM) |
|---|---|---|---|---|---|---|
| 500966 | 71 | 82 | 85 | 87 | 87 | <0.6 |
| 500913 | 29 | 46 | 74 | 85 | 88 | 1.3 |
| 500859 | 6 | 44 | 75 | 87 | 90 | 1.8 |

Example 12: Tolerability of Antisense Oligonucleotides Targeting Human DGAT2 in CD1 Mice CD1® mice (Charles River, MA) are a multipurpose mice model, frequently utilized for safety and efficacy testing. The mice were treated with ISIS antisense oligonucleotides selected from studies described above and evaluated for changes in the levels of various plasma chemistry markers. Liver and kidney tissue from the treated mice were microscopically reviewed; no toxicity or tissue injury was seen in any treated animal.

Treatment

Groups of five male CD1 mice each were injected subcutaneously twice a week for 6 weeks with 100 mg/kg (200 mg/kg/week) of ISIS oligonucleotide. One group of ten male CD1 mice was injected subcutaneously twice a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, and BUN were measured on day 27 using an automated clinical chemistry analyzer (Hitachi Olympus AU400e, Melville, NY). The results are presented in the Table below. ISIS oligonucleotides that caused changes in the levels of any of the liver or kidney function markers outside the expected range for antisense oligonucleotides were excluded in further studies.

TABLE 143

Plasma chemistry markers in CD1 mice

| | ALT (IU/L) | AST (IU/L) | BUN (mg/dL) | Bilirubin (mg/dL) |
|---|---|---|---|---|
| PBS | 33 | 50 | 30 | 0.3 |
| ISIS 483984 | 193 | 177 | 30 | 0.3 |
| ISIS 484099 | 69 | 77 | 23 | 0.2 |
| ISIS 484129 | 43 | 46 | 24 | 0.2 |
| ISIS 484157 | 136 | 105 | 26 | 0.2 |
| ISIS 495576 | 36 | 53 | 30 | 0.3 |
| ISIS 495609 | 102 | 112 | 28 | 0.3 |
| ISIS 495753 | 68 | 76 | 28 | 0.2 |
| ISIS 495756 | 154 | 123 | 26 | 0.3 |
| ISIS 501849 | 45 | 58 | 26 | 0.2 |
| ISIS 501850 | 294 | 306 | 26 | 0.3 |
| ISIS 501855 | 62 | 56 | 28 | 0.2 |
| ISIS 501861 | 100 | 97 | 30 | 0.3 |
| ISIS 502322 | 42 | 46 | 28 | 0.2 |
| ISIS 507696 | 99 | 132 | 30 | 0.2 |
| ISIS 507710 | 50 | 68 | 27 | 0.3 |
| ISIS 507716 | 3112 | 3302 | 19 | 7.8 |

Body and Organ Weights

Body weights of the mice were measured on day 35 and are presented in the Table below. Liver, spleen and kidney weights were measured at the end of the study (day 41), and are also presented in the Table below. ISIS oligonucleotides that caused any changes in body or organ weights outside the expected range for antisense oligonucleotides were excluded from further studies. 'n/a' indicates that the particular endpoint was not measured in that group of mice.

TABLE 144

Body and organ weights of CD1 mice (g)

|  | Body weight | Kidney | Liver | Spleen |
|---|---|---|---|---|
| PBS | 41.2 | 0.7 | 2.0 | 0.1 |
| ISIS 483984 | 41.0 | n/a | n/a | n/a |
| ISIS 484129 | 41.0 | 0.6 | 2.1 | 0.2 |
| ISIS 484157 | 38.8 | n/a | n/a | n/a |
| ISIS 495576 | 41.4 | 0.6 | 2.1 | 0.2 |
| ISIS 495609 | 42.5 | 0.6 | 2.1 | 0.2 |
| ISIS 495753 | 40.0 | 0.5 | 2.2 | 0.2 |
| ISIS 495756 | 42.0 | 0.7 | 2.6 | 0.2 |
| ISIS 501849 | 42.3 | 0.6 | 2.4 | 0.2 |
| ISIS 501850 | 41.7 | 0.7 | 2.5 | 0.2 |
| ISIS 501855 | 39.9 | n/a | n/a | n/a |
| ISIS 501861 | 40.3 | 0.6 | 2.3 | 0.2 |
| ISIS 502322 | 41.1 | 0.7 | 2.2 | 0.2 |
| ISIS 507696 | 38.9 | 0.6 | 2.3 | 0.2 |
| ISIS 507710 | 42.7 | 0.6 | 2.5 | 0.2 |

Example 13: Tolerability of Antisense Oligonucleotides Targeting Human DGAT2 in CD1 Mice CD1 ® mice were treated with ISIS antisense oligonucleotides selected from studies described above and evaluated for changes in the levels of various plasma chemistry markers.

Treatment

Groups of five male CD1 mice each were injected subcutaneously twice a week for 6 weeks with 50 mg/kg of ISIS 483817, ISIS 483910, ISIS 484085, ISIS 484127, ISIS 484130, ISIS 484137, ISIS 484215, ISIS 484231, ISIS 484271, ISIS 501871, ISIS 502098, ISIS 502119, ISIS 502154, ISIS 502163, ISIS 502164, ISIS 502194, ISIS 525443, ISIS 525474, ISIS 525552, ISIS 525612, ISIS 525688, ISIS 525705, ISIS 525708, ISIS 525711, and ISIS 525733. One group often male CD1 mice was injected subcutaneously twice a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, and BUN were measured on day 26 using an automated clinical chemistry analyzer (Hitachi Olympus AU400e, Melville, NY). The results are presented in the Table below. ISIS oligonucleotides that caused changes in the levels of any of the liver or kidney function markers outside the expected range for antisense oligonucleotides were excluded in further studies.

TABLE 145

Plasma chemistry markers in CD1 mice

|  | ALT (IU/L) | AST (IU/L) | BUN (mg/dL) | Bilirubin (mg/dL) |
|---|---|---|---|---|
| PBS | 26 | 55 | 29 | 0.6 |
| ISIS 483817 | 40 | 54 | 27 | 0.3 |
| ISIS 483910 | 244 | 155 | 28 | 0.6 |
| ISIS 484085 | 46 | 58 | 27 | 0.4 |
| ISIS 484127 | 100 | 147 | 25 | 0.4 |

TABLE 145-continued

Plasma chemistry markers in CD1 mice

|  | ALT (IU/L) | AST (IU/L) | BUN (mg/dL) | Bilirubin (mg/dL) |
|---|---|---|---|---|
| ISIS 484130 | 151 | 91 | 29 | 0.3 |
| ISIS 484137 | 31 | 49 | 26 | 0.3 |
| ISIS 484215 | 42 | 49 | 25 | 0.2 |
| ISIS 484231 | 31 | 45 | 26 | 0.2 |
| ISIS 484271 | 2847 | 3267 | 26 | 2.9 |
| ISIS 501871 | 108 | 96 | 23 | 0.2 |
| ISIS 502098 | 60 | 62 | 24 | 0.3 |
| ISIS 502119 | 402 | 370 | 26 | 0.3 |
| ISIS 502154 | 293 | 294 | 28 | 0.3 |
| ISIS 502163 | 45 | 60 | 23 | 0.4 |
| ISIS 502164 | 81 | 75 | 25 | 0.4 |
| ISIS 502194 | 32 | 43 | 24 | 0.4 |
| ISIS 525443 | 93 | 101 | 24 | 0.3 |
| ISIS 525474 | 49 | 94 | 24 | 0.6 |
| ISIS 525552 | 1374 | 874 | 25 | 0.3 |
| ISIS 525612 | 78 | 54 | 27 | 0.4 |
| ISIS 525705 | 76 | 117 | 31 | 0.3 |
| ISIS 525708 | 59 | 79 | 29 | 0.3 |
| ISIS 525711 | 1670 | 787 | 26 | 0.3 |

Body and Organ Weights

Body weights of the mice were measured on day 36 and are presented in the Table below. Liver, spleen and kidney weights were measured at the end of the study, and are also presented in the Table below. ISIS oligonucleotides that caused any changes in body or organ weights outside the expected range for antisense oligonucleotides were excluded from further studies. 'n/a' indicates that the particular endpoint was not measured in that group of mice.

TABLE 146

Body and organ weights of CD1 mice (g)

|  | Body weight | Kidney | Liver | Spleen |
|---|---|---|---|---|
| PBS | 39.4 | 0.7 | 2.0 | 0.1 |
| ISIS 483817 | 38.8 | 0.6 | 2.3 | 0.2 |
| ISIS 483910 | 39.2 | 0.6 | 2.3 | 0.2 |
| ISIS 484085 | 37.9 | 0.6 | 2.3 | 0.1 |
| ISIS 484127 | 35.3 | n/a | n/a | n/a |
| ISIS 484130 | 41.5 | n/a | n/a | n/a |
| ISIS 484137 | 39.6 | 0.7 | 2.3 | 0.1 |
| ISIS 484215 | 38.5 | 0.6 | 2.4 | 0.2 |
| ISIS 484231 | 38.3 | 0.6 | 2.1 | 0.1 |
| ISIS 501871 | 38.7 | 0.6 | 2.3 | 0.2 |
| ISIS 502098 | 38.8 | 0.6 | 2.5 | 0.2 |
| ISIS 502163 | 39.1 | 0.6 | 2.0 | 0.2 |
| ISIS 502164 | 37.7 | 0.6 | 2.1 | 0.2 |
| ISIS 502194 | 40.5 | 0.6 | 1.9 | 0.1 |
| ISIS 525443 | 39.5 | 0.6 | 2.0 | 0.2 |
| ISIS 525474 | 37.0 | 0.6 | 1.8 | 0.1 |
| ISIS 525612 | 37.8 | 0.6 | 2.0 | 0.1 |
| ISIS 525705 | 36.5 | 0.7 | 2.0 | 0.4 |
| ISIS 525708 | 38.7 | 0.7 | 2.0 | 0.3 |

Example 14: Tolerability of Antisense Oligonucleotides Targeting Human DGAT2 in Sprague-Dawley Rats Sprague-Dawley rats are a multipurpose model used for safety and efficacy evaluations. The rats were treated with ISIS antisense oligonucleotides from the study described above and evaluated for changes in the levels of various plasma chemistry markers.

Treatment

Male Sprague-Dawley rats were maintained on a 12-hour light/dark cycle and fed ad libitum with Purina normal rat chow, diet 5001. Groups of 4 Sprague-Dawley rats each were injected subcutaneously twice a week for 8 weeks with 50 mg/kg of ISIS 484129, ISIS 495576, ISIS 495609, ISIS 495753, ISIS 495756, ISIS 501849, ISIS 501850, ISIS 501861, ISIS 502322, ISIS 507696, and ISIS 507710. Forty eight hours after the last dose, rats were euthanized and organs and plasma were harvested for further analysis.

Liver Function

To evaluate the effect of ISIS oligonucleotides on hepatic function, plasma levels of transaminases were measured on day 56 using an automated clinical chemistry analyzer (Hitachi Olympus AU400e, Melville, NY). Plasma levels of ALT and AST were measured and the results are presented in the Table below expressed in IU/L. Plasma levels of Bilirubin were also measured using the same clinical chemistry analyzer and the results are also presented in the Table below. ISIS oligonucleotides that caused changes in the levels of any markers of liver function outside the expected range for antisense oligonucleotides were excluded in further studies.

TABLE 147

Liver function markers in Sprague-Dawley rats

|  | ALT (IU/L) | AST (IU/L) | Bilirubin (mg/dL) |
|---|---|---|---|
| PBS | 49 | 70 | 0.16 |
| ISIS 484129 | 133 | 130 | 0.18 |
| ISIS 495576 | 99 | 148 | 0.17 |
| ISIS 495609 | 406 | 269 | 0.32 |
| ISIS 495753 | 968 | 1258 | 1.83 |
| ISIS 495756 | 165 | 206 | 0.24 |
| ISIS 501849 | 57 | 103 | 0.16 |
| ISIS 501850 | 1218 | 1916 | 6.55 |
| ISIS 501861 | 61 | 113 | 0.14 |
| ISIS 502322 | 79 | 84 | 0.14 |

Kidney Function

To evaluate the effect of ISIS oligonucleotides on kidney function, urine levels of creatinine and total protein were measured on day 56 using an automated clinical chemistry analyzer (Hitachi Olympus AU400e, Melville, NY). Results are presented in the Table below, expressed in mg/dL.

TABLE 148

Kidney function markers (mg/dL) in Sprague-Dawley rats

|  | Creatinine | Total protein |
|---|---|---|
| PBS | 146 | 114 |
| ISIS 495756 | 63 | 978 |
| ISIS 501849 | 82 | 445 |
| ISIS 501861 | 67 | 309 |
| ISIS 501850 | 52 | 268 |
| ISIS 502322 | 84 | 507 |
| ISIS 495576 | 108 | 587 |
| ISIS 495609 | 38 | 264 |
| ISIS 495753 | 73 | 411 |
| ISIS 484129 | 66 | 312 |

Body and Organ Weights

Body weights of the rat were measured on day 50 and are presented in the Table below. Liver, heart, spleen and kidney weights were measured at the end of the study, and are also presented in the Table below. ISIS oligonucleotides that caused any changes in body or organ weights outside the expected range for antisense oligonucleotides were excluded from further studies. 'n/a' indicates that the particular endpoint was not measured in that group of mice.

TABLE 149

Body and organ weights of Sprague-Dawley rats (g)

|  | Body weight | Heart | Kidney | Liver | Spleen |
|---|---|---|---|---|---|
| PBS | 486 | 1.7 | 3.5 | 14.2 | 0.7 |
| ISIS 495756 | 374 | 1.1 | 3.5 | 15.5 | 2.2 |
| ISIS 501849 | 404 | 1.2 | 3.3 | 13.7 | 1.9 |
| ISIS 501861 | 390 | 1.1 | 3.6 | 16.0 | 2.7 |
| ISIS 501850 | 329 | 1.3 | 4.1 | 16.3 | 4.5 |
| ISIS 502322 | 424 | 1.3 | 3.4 | 15.6 | 1.7 |
| ISIS 495576 | 461 | 1.3 | 3.5 | 17.3 | 2.1 |
| ISIS 495609 | 383 | 1.4 | 3.8 | 18.9 | 3.8 |
| ISIS 495753 | 384 | 1.2 | 3.4 | 16.3 | 3.6 |
| ISIS 484129 | 415 | 1.3 | 3.1 | 14.9 | 1.5 |

Example 15: Tolerability of Antisense Oligonucleotides Targeting Human DGAT2 in Sprague-Dawley Rats Sprague-Dawley rats were treated with ISIS antisense oligonucleotides from the studies described above and evaluated for changes in the levels of various plasma chemistry markers.

Treatment

Male Sprague-Dawley rats were maintained on a 12-hour light/dark cycle and fed ad libitum with Purina normal rat chow, diet 5001. Groups of 4 Sprague-Dawley rats each were injected subcutaneously twice a week for 8 weeks with 50 mg/kg of ISIS 483817, ISIS 483910, ISIS 484085, ISIS 484137, ISIS 484215, ISIS 484231, ISIS 501871, ISIS 502098, ISIS 502163, ISIS 502164, ISIS 502194, ISIS 525443, ISIS 525474, ISIS 525612, and ISIS 525708. Forty eight hours after the last dose, rats were euthanized and organs and plasma were harvested for further analysis.

Liver Function

To evaluate the effect of ISIS oligonucleotides on hepatic function, plasma levels of transaminases were measured on day 53 using an automated clinical chemistry analyzer (Hitachi Olympus AU400e, Melville, NY). Plasma levels of ALT and AST were measured and the results are presented in the Table below expressed in IU/L. Plasma levels of Bilirubin were also measured using the same clinical chemistry analyzer and the results are also presented in the Table below. ISIS oligonucleotides that caused changes in the levels of any markers of liver function outside the expected range for antisense oligonucleotides were excluded in further studies.

TABLE 150

Liver function markers in Sprague-Dawley rats

|  | ALT (IU/L) | AST (IU/L) | Bilirubin (mg/dL) |
|---|---|---|---|
| PBS | 53 | 83 | 0.21 |
| ISIS 483817 | 81 | 127 | 0.13 |
| ISIS 483910 | 283 | 428 | 3.38 |
| ISIS 484085 | 131 | 208 | 0.27 |
| ISIS 484137 | 63 | 98 | 0.16 |
| ISIS 484215 | 50 | 86 | 0.13 |
| ISIS 484231 | 75 | 106 | 0.17 |
| ISIS 501871 | 45 | 73 | 0.10 |
| ISIS 502098 | 57 | 156 | 0.12 |
| ISIS 502163 | 85 | 177 | 0.21 |
| ISIS 502164 | 67 | 94 | 0.15 |
| ISIS 502194 | 54 | 82 | 0.15 |
| ISIS 525443 | 50 | 82 | 0.13 |

TABLE 150-continued

Liver function markers in Sprague-Dawley rats

|  | ALT (IU/L) | AST (IU/L) | Bilirubin (mg/dL) |
|---|---|---|---|
| ISIS 525474 | 118 | 136 | 0.22 |
| ISIS 525612 | 313 | 314 | 0.18 |
| ISIS 525708 | 65 | 117 | 0.16 |

Kidney Function

To evaluate the effect of ISIS oligonucleotides on kidney function, plasma levels of creatinine and total protein were measured on day 53 using an automated clinical chemistry analyzer (Hitachi Olympus AU400e, Melville, NY). Results are presented in the Table below, expressed in mg/dL. Urine levels of creatinine and total protein were also measured on day 53 using the same automated clinical chemistry analyzer. Results are presented in the Table below, expressed in mg/dL.

TABLE 151

Kidney function markers in the plasma (mg/dL) in Sprague-Dawley rats

|  | BUN | Creatinine |
|---|---|---|
| PBS | 20 | 0.44 |
| ISIS 483817 | 22 | 0.40 |
| ISIS 483910 | 24 | 0.42 |
| ISIS 484085 | 19 | 0.37 |
| ISIS 484137 | 22 | 0.43 |
| ISIS 484215 | 19 | 0.36 |
| ISIS 484231 | 21 | 0.39 |
| ISIS 501871 | 23 | 0.31 |
| ISIS 502098 | 25 | 0.42 |
| ISIS 502163 | 21 | 0.37 |
| ISIS 502164 | 23 | 0.43 |
| ISIS 502194 | 21 | 0.44 |
| ISIS 525443 | 24 | 0.51 |
| ISIS 525474 | 22 | 0.39 |
| ISIS 525612 | 18 | 0.38 |
| ISIS 525708 | 31 | 0.53 |

TABLE 152

Kidney function markers in the urine (mg/dL) in Sprague-Dawley rats

|  | Creatinine | Total protein |
|---|---|---|
| PBS | 227 | 193 |
| ISIS 483817 | 95 | 2129 |
| ISIS 483910 | 60 | 1030 |
| ISIS 484085 | 87 | 868 |
| ISIS 484137 | 84 | 517 |
| ISIS 484215 | 146 | 1115 |
| ISIS 484231 | 89 | 652 |
| ISIS 501871 | 52 | 3426 |
| ISIS 502098 | 64 | 550 |
| ISIS 502163 | 73 | 522 |
| ISIS 502164 | 100 | 554 |
| ISIS 502194 | 95 | 410 |
| ISIS 525443 | 73 | 595 |
| ISIS 525474 | 79 | 1547 |
| ISIS 525612 | 94 | 453 |
| ISIS 525708 | 41 | 2043 |

Body and Organ Weights

Body weights of the rat were measured on day 49 and are presented in the Table below. Liver, heart, spleen and kidney weights were measured at the end of the study, and are also presented in the Table below. ISIS oligonucleotides that caused any changes in body or organ weights outside the expected range for antisense oligonucleotides were excluded from further studies. 'n/a' indicates that the particular endpoint was not measured in that group of mice.

TABLE 153

Body and organ weights of Sprague-Dawley rats (g)

|  | Body weight | Heart | Kidney | Liver | Spleen |
|---|---|---|---|---|---|
| PBS | 485 | 1.6 | 3.5 | 14.5 | 0.9 |
| ISIS 483817 | 362 | 1.2 | 4.2 | 17.0 | 2.3 |
| ISIS 483910 | 358 | 1.0 | 3.2 | 19.0 | 3.0 |
| ISIS 484085 | 348 | 1.1 | 2.9 | 15.3 | 1.6 |
| ISIS 484137 | 353 | 1.1 | 3.0 | 14.2 | 1.6 |
| ISIS 484215 | 391 | 1.2 | 3.7 | 16.6 | 2.0 |
| ISIS 484231 | 386 | 1.1 | 3.2 | 16.6 | 2.5 |
| ISIS 501871 | 322 | 1.1 | 3.5 | 17.4 | 1.8 |
| ISIS 502098 | 315 | 1.2 | 2.9 | 15.8 | 2.3 |
| ISIS 502163 | 326 | 1.0 | 3.5 | 14.5 | 3.4 |
| ISIS 502164 | 381 | 1.2 | 2.8 | 15.4 | 2.2 |
| ISIS 502194 | 439 | 1.3 | 3.4 | 18.6 | 2.0 |
| ISIS 525443 | 469 | 1.5 | 3.7 | 22.1 | 1.7 |
| ISIS 525474 | 445 | 1.7 | 3.8 | 19.2 | 2.2 |
| ISIS 525612 | 427 | 1.5 | 3.1 | 13.1 | 1.4 |
| ISIS 525708 | 338 | 1.0 | 3.6 | 15.9 | 2.3 |

Example 16: Effect of ISIS Antisense Oligonucleotides Targeting Human DGAT2 in Cynomolgus Monkeys Cynomolgus monkeys were treated with ISIS antisense oligonucleotides selected from studies described above. Antisense oligonucleotide efficacy and tolerability were evaluated.

At the time this study was undertaken, the cynomolgus monkey genomic sequence was not available in the National Center for Biotechnology Information (NCBI) database; therefore, cross-reactivity with the cynomolgus monkey gene sequence could not be confirmed. Instead, the sequences of the ISIS antisense oligonucleotides used in the cynomolgus monkeys was compared to a rhesus monkey sequence for homology. It is expected that ISIS oligonucleotides with homology to the rhesus monkey sequence are fully cross-reactive with the cynomolgus monkey sequence as well. The human antisense oligonucleotides tested are cross-reactive with the rhesus genomic sequence (RefSeq No. NW_001100387.1 truncated from nucleotides 1232000 to 1268000, designated herein as SEQ ID NO: 3). The greater the complementarity between the human oligonucleotide and the rhesus monkey sequence, the more likely the human oligonucleotide can cross-react with the rhesus monkey sequence. The start and stop sites of each oligonucleotide to SEQ ID NO: 3 is presented in the Table below. "Start site" indicates the 5'-most nucleotide to which the gapmer is targeted in the rhesus monkey gene sequence.

TABLE 154

Antisense oligonucleotides complementary to SEQ ID NO: 3

| ISIS No | Start Site | Stop Site | Sequence | Motif | SEQ ID NO |
|---|---|---|---|---|---|
| 484085 | 14986 | 15005 | GTCTGGGAACAGCAGCATCA | 5-10-5 | 1371 |
| 484129 | 18207 | 18226 | GCACTGACATGGTAAGTCCT | 5-10-5 | 1415 |
| 484137 | 18355 | 18374 | TGCCATTTAATGAGCTTCAC | 5-10-5 | 1423 |
| 495576 | 7054 | 7073 | CACCATAATCTGCACAGGTT | 5-10-5 | 1849 |
| 501861 | 19517 | 19536 | TCACAGAATTATCAGCAGTA | 5-10-5 | 2959 |
| 502194 | 27298 | 27317 | CCTCTTAGAAGTAATGCTTC | 5-10-5 | 3292 |
| 525443 | 2716 | 2732 | TCCATGTCAGAGAGGCT | 3-10-4 | 4198 |
| 525612 | 14990 | 15006 | GGTCTGGGAACAGCAGC | 3-10-4 | 4373 |

Treatment

Prior to the study, the monkeys were kept in quarantine for a 30-week period, during which the animals were observed daily for general health. The monkeys were 2-4 years old and weighed between 2 and 4 kg. Eight groups of 5 randomly assigned male cynomolgus monkeys each were injected subcutaneously with ISIS oligonucleotide or PBS using a stainless steel dosing needle and syringe of appropriate size into the intracapsular region and outer thigh of the monkeys. The monkeys were dosed 3 times a week for the first week (days 1, 3, and 5) as loading doses, and subsequently twice a week for weeks 2-13, with 20 mg/kg of ISIS oligonucleotide. A control group of 6 cynomolgus monkeys was injected with 0.9% sterile saline subcutaneously three times a week for the first week (days 1, 3, and 5), and subsequently once a week for weeks 2-13.

During the study period, the monkeys were observed for signs of mortality, clinical observations, and body weight, qualitative food consumption, ophthalmoscopic and electrocardiographic examination, clinical and anatomic pathology. Scheduled euthanasia of the animals was conducted on day 93 for animals assigned to terminal necroscopy and on Day 182 for animals assigned to the recovery necroscopy. A full panel of tissues were taken, processed to slides and examined microscopically for histopathology. The protocols described in the Example were approved by the Institutional Animal Care and Use Committee (IACUC).

Hepatic Target Reduction
Target Gene RNA Analysis

On day 93, RNA was extracted from liver tissue for real-time PCR analysis of DGAT2 using primer probe set mkDGAT2 (forward sequence CCGCAAGGGCTTTGT-GAA, designated herein as SEQ ID NO: 13, reverse sequence TTCTCTCCAAAGGAGTACATGGG, designated herein as SEQ ID NO: 14, probe sequence CCTGCGCCATGGAGCCGAC, designated herein as SEQ ID NO: 15). Results are presented as percent inhibition of DGAT2 mRNA, relative to PBS control, normalized to the house keeping gene CyclophilinA. Similar results were obtained on normalization with RIBOGREEN®. As shown in the Table below, treatment with ISIS antisense oligonucleotides resulted in significant reduction of DGAT2 mRNA in comparison to the sterile saline control. Specifically, treatment with ISIS 484137 and ISIS 501861 resulted in the significant reduction of DGAT2 mRNA expression.

Inhibition levels with select oligonucleotides were also measured with the human primer probe set RTS2977_MGB. As presented in the Table below, treatment with ISIS oligonucleotides significantly reduced DGAT2 levels. Specifically, treatment with ISIS 484137 and ISIS 501861 resulted in the significant reduction of DGAT2 mRNA expression.

TABLE 155

Percent Inhibition of DGAT2 mRNA in the cynomolgus monkey liver relative to the saline control (mkDGAT2 primer probe set)

| ISIS No | RIBOGREEN | CyclophilinA |
|---|---|---|
| 484085 | 20 | 21 |
| 484129 | 54 | 52 |
| 484137 | 71 | 69 |
| 495576 | 70 | 66 |
| 501861 | 89 | 88 |
| 502194 | 26 | 29 |
| 525443 | 49 | 48 |
| 525612 | 35 | 43 |

TABLE 156

Percent Inhibition of DGAT2 mRNA in the cynomolgus monkey liver relative to the saline control (RTS2977_MGB primer probe set)

| ISIS No | RIBOGREEN | CyclophilinA |
|---|---|---|
| 501861 | 82 | 79 |
| 484137 | 63 | 58 |
| 525443 | 22 | 17 |

Secondary Lipid Gene RNA Analysis

Gene expression analysis of secondary lipid genes, DGAT1, ACC1, ACC2, FAS, and SCD1 2 was also performed. The results are presented in the Table below, expressed as % expression of each gene compared to the PBS control. As presented in the Table below, treatment with ISIS oligonucleotides significantly reduced lipogenic gene levels. Specifically, treatment with ISIS 484137 resulted in the significant reduction of mRNA expression.

TABLE 157

% lipid gene expression

|  | DGAT1 | ACC1 | ACC2 | FAS | SCD-1 |
|---|---|---|---|---|---|
| sterile saline | 100 | 100 | 100 | 100 | 100 |
| ISIS 484129 | 85 | 95 | 95 | 122 | 64 |
| ISIS 495576 | 82 | 66 | 59 | 65 | 40 |
| ISIS 501861 | 140 | 69 | 67 | 51 | 22 |
| ISIS 484085 | 118 | 122 | 86 | 281 | 123 |
| ISIS 484137 | 81 | 99 | 77 | 115 | 51 |
| ISIS 502194 | 103 | 91 | 81 | 114 | 63 |
| ISIS 525443 | 118 | 87 | 75 | 57 | 25 |
| ISIS 525612 | 170 | 106 | 96 | 83 | 42 |

Tolerability Studies
Body Weight Measurements

To evaluate the effect of ISIS oligonucleotides on the overall health of the animals, body weights were measured at regularly and are presented in the Table below. The results indicate that effect of treatment with antisense oligonucleotides on body weights was within the expected range for antisense oligonucleotides. Specifically, treatment with ISIS 484137 was well tolerated in terms of the body weights of the monkeys.

TABLE 158

Body weights in the cynomolgus monkey

|  | Day 1 | Day 15 | Day 29 | Day 36 | Day 50 | Day 64 | Day 78 | Day 85 |
|---|---|---|---|---|---|---|---|---|
| sterile saline | 2734 | 2795 | 2775 | 2719 | 2743 | 2739 | 2807 | 2779 |
| ISIS 484085 | 2759 | 2785 | 2822 | 2762 | 2815 | 2812 | 2910 | 2911 |
| ISIS 484129 | 2780 | 2889 | 2906 | 2852 | 2918 | 2937 | 3043 | 3029 |
| ISIS 484137 | 2756 | 2793 | 2847 | 2763 | 2850 | 2823 | 2906 | 2900 |
| ISIS 495576 | 2748 | 2865 | 2905 | 2823 | 2869 | 2908 | 2996 | 2979 |
| ISIS 501861 | 2702 | 2775 | 2797 | 2750 | 2775 | 2828 | 2893 | 2860 |
| ISIS 502194 | 2817 | 2886 | 2902 | 2840 | 2926 | 2929 | 3038 | 3045 |
| ISIS 525443 | 2790 | 2835 | 2814 | 2767 | 2790 | 2772 | 2843 | 2859 |
| ISIS 525612 | 2921 | 2962 | 2995 | 2937 | 3006 | 3020 | 3093 | 3166 |

Liver Function

To evaluate the effect of ISIS oligonucleotides on hepatic function, blood samples were collected from all the study groups. The blood samples were collected via femoral venipuncture on day 93, 48 hrs post-dosing. The monkeys were fasted overnight prior to blood collection. Blood was collected in tubes without any anticoagulant, and kept at room temperature for a minimum of 30 min for serum separation. The tubes were then centrifuged to obtain serum. Levels of various liver function markers were measured using a Toshiba 200FR NEO chemistry analyzer (Toshiba Co., Japan). Serum levels of ALT and AST were measured and the results are presented in the Table below, expressed in IU/L. Bilirubin, a liver function marker, was similarly measured and is presented in the Table below, expressed in mg/dL. The results indicate that antisense oligonucleotides had no effect on liver function outside the expected range for antisense oligonucleotides. Specifically, treatment with ISIS 484137 was well tolerated in terms of the liver function in monkeys.

TABLE 159

Liver function markers in cynomolgus monkey serum

|  | ALT (IU/L) | AST (IU/L) | Bilirubin (mg/dL) |
|---|---|---|---|
| sterile saline | 40 | 42 | 0.20 |
| ISIS 484085 | 57 | 52 | 0.15 |
| ISIS 484129 | 43 | 43 | 0.16 |
| ISIS 484137 | 52 | 57 | 0.16 |
| ISIS 495576 | 56 | 45 | 0.15 |
| ISIS 501861 | 70 | 67 | 0.16 |
| ISIS 502194 | 88 | 54 | 0.16 |
| ISIS 525443 | 56 | 45 | 0.23 |
| ISIS 525612 | 38 | 37 | 0.23 |

Kidney Function

To evaluate the effect of ISIS oligonucleotides on kidney function, blood samples were collected from all the study groups. The blood samples were collected via femoral venipuncture on day 93, 48 hrs post-dosing. The monkeys were fasted overnight prior to blood collection. Blood was collected in tubes without any anticoagulant, and kept at room temperature for a minimum of 30 min for serum separation. The tubes were then centrifuged to obtain serum. Levels of BUN and creatinine were measured using a Toshiba 200FR NEO chemistry analyzer (Toshiba Co., Japan). Results are presented in the Table below, expressed in mg/dL.

The plasma chemistry data indicate that most of the ISIS oligonucleotides did not have any effect on the kidney function outside the expected range for antisense oligonucleotides. Specifically, treatment with ISIS 484137 was well tolerated in terms of the kidney function of the monkeys.

TABLE 160

BUN and creatinine levels (mg/dL) in cynomolgus monkeys

|  | BUN | Creatinine |
|---|---|---|
| sterile saline | 25 | 0.87 |
| ISIS 484085 | 26 | 0.94 |
| ISIS 484129 | 21 | 0.81 |
| ISIS 484137 | 24 | 0.94 |
| ISIS 495576 | 22 | 0.92 |
| ISIS 501861 | 25 | 0.90 |
| ISIS 502194 | 27 | 0.86 |
| ISIS 525443 | 26 | 1.08 |
| ISIS 525612 | 23 | 0.98 |

Example 17: Effect of ISIS 484137 Targeting Human DGAT2 in Cynomolgus Monkeys

Cynomolgus monkeys were treated with ISIS 484137 to evaluate the safety of this antisense oligonucleotide over a 13-week dosing period followed by a 13 week recovery period. The protocols described in the Example were approved by the Testing Facility's Institutional Animal Care and Use Committee (IACUC).

Treatment

The monkeys were 2-4 years old and weighed between 2.3 and 3.7 kg. Five groups of 6-10 randomly assigned cynomolgus monkeys each were injected subcutaneously with ISIS oligonucleotide or 0.9% sterile saline using a stainless steel dosing needle and syringe of appropriate size into one of four delineated sites on the backs of the monkeys. The monkeys were dosed on Days 1, 3, 5, and 7, and then once weekly thereafter for a total of 13 weeks at dose levels of 4 mg/kg, 8 mg/kg, 12 mg/kg, or 40 mg/kg of ISIS 484137. A control group of 10 cynomolgus monkeys was injected with 0.9% sterile saline subcutaneously using the same regimen. Toxicokinetics were assessed in a sixth group of 14 animals (7 of each sex) at the 8 mg/kg dose level. Recovery was assessed in the controls and at the 12 mg/kg and 40 mg/kg dose levels of ISIS 484137 (2 per sex).

During the study period, the monkeys were observed for signs of mortality, clinical observations, and body weight, qualitative food consumption, ophthalmoscopic and electro-cardiographic examination, clinical and anatomic pathology. Scheduled euthanasia of the animals was conducted on day 93 for animals assigned to terminal necroscopy and on Day 182 for animals assigned to the recovery necroscopy. A full panel of tissues were taken, processed to slides and examined microscopically for histopathology.

Body and Organ Weight Measurements

To evaluate the effect of ISIS 484137 on the overall health of the animals, body weights were measured at regularly and are presented in the Table below. Organ weights were measured after euthanasia. 'n.d.' indicates that there is no data for that timepoint. The results indicate that effect of treatment with ISIS 484137 on body and organ weights was within the expected range for antisense oligonucleotides. Specifically, treatment with ISIS 484137 was well tolerated in terms of the body and organ weights of the monkeys.

Plasma Homeostasis

To evaluate the potential for ISIS 484137 to produce complement activation, plasma samples were obtained once prior to treatment initiation on Day −7, then following the first dose on Day 1 at 4, 8 and 24 hours, and finally following the last dose on Day 91 predose and at 4 hours for determination of complement split product Bb using ELISA. Serum samples were also obtained for measurement of Complement C5 on Day −7, on Day 1 (at 24 hours post dose), on Day 91 (predose and at 24 hours post dose) and for recovery animals on Days 121 and 182 using an automated clinical chemistry analyzer. Additionally, blood for coagulation analyses was taken on Day 1 (4 hours post dose) and on Day 91 (predose, 1, 4, 8, and 24 hours post dose) and evaluated using an automated coagulation analyzer.

At the 40 mg/kg dose level, indications of alternative pathway activation were observed as acute, transient increases in Complement Bb (up to 7-fold over baseline) at 4 hours post dose on Days 1 and 91. Complement Bb then returned to baseline levels at 24 hours on Day 1 or to near baseline levels on Day 91. There were no significant changes in Complement C5 observed during the study. Mild, transient prolongations of APTT (up to 29%), relative to controls were observed at 4 to 8 hours post dose and then diminished by 24 or 48 hours post dose. The acute transient increases in Complement Bb and APTT observed following treatment with ISIS 484137 were typical of those commonly seen oligonucleotide-treated monkeys.

Liver Function

To evaluate the effect of ISIS 484137 on hepatic function, blood samples were collected from all the study groups on Days 44, 93, 121, and 182 for determination of liver transaminases and liver functions. Serum levels of ALT and AST were measured and the results are presented in the Table below, expressed in IU/L. Bilirubin, a liver function marker, was similarly measured and the results are presented in the Table below, expressed in mg/dL. ISIS 484137 had no adverse effect on liver function outside the expected range for antisense oligonucleotides. 'n.d.' indicates that there is no data for that timepoint. The results indicate that treatment with ISIS 484137 was well tolerated in terms of the liver function in monkeys.

TABLE 161

Body weights (g) of cynomolgus monkeys

|  | Dose (mg/kg) | Day 93 | Day 182 |
| --- | --- | --- | --- |
| sterile saline | — | 3035 | 3075 |
| ISIS 484137 | 4 | 2848 | n.d. |
|  | 8 | 2850 | n.d. |
|  | 12 | 3125 | 3325 |
|  | 40 | 3027 | 2875 |

TABLE 162

Organ weights (g) of cynomolgus monkeys on day 93

|  | Dose (mg/kg) | Brain | Adrenal gland | Heart | Kidney | Liver | Spleen | Thyroid |
| --- | --- | --- | --- | --- | --- | --- | --- | --- |
| sterile saline | — | 67 | 0.46 | 10.8 | 12.6 | 60.0 | 4.1 | 0.4 |
| ISIS 484137 | 4 | 67 | 0.52 | 9.7 | 13.2 | 60.8 | 3.9 | 0.3 |
|  | 8 | 67 | 0.51 | 10.9 | 14.2 | 73.7 | 3.6 | 0.4 |
|  | 12 | 69 | 0.56 | 10.1 | 14.0 | 65.1 | 3.2 | 0.3 |
|  | 40 | 69 | 0.59 | 10.2 | 15.8 | 79.2 | 6.2 | 0.4 |

TABLE 163

ALT levels (IU/L) in cynomolgus monkey serum

|  | Dose (mg/kg) | Day 44 | Day 93 | Day 182 |
| --- | --- | --- | --- | --- |
| sterile saline | — | 43 | 36 | 36 |
| ISIS 484137 | 4 | 31 | 38 | n.d. |
|  | 8 | 33 | 31 | n.d. |
|  | 12 | 32 | 40 | 27 |
|  | 40 | 41 | 62 | 42 |

TABLE 164

AST levels (IU/L) in cynomolgus monkey serum

|  | Dose (mg/kg) | Day 44 | Day 93 | Day 121 |
| --- | --- | --- | --- | --- |
| sterile saline | — | 54 | 65 | 41 |
| ISIS 484137 | 4 | 33 | 53 | n.d. |
|  | 8 | 50 | 53 | n.d. |
|  | 12 | 29 | 71 | 31 |
|  | 40 | 49 | 90 | 44 |

TABLE 165

Total bilirubin levels (mg/dL) in cynomolgus monkey serum

|  | Dose (mg/kg) | Day 44 | Day 93 | Day 121 | Day 182 |
|---|---|---|---|---|---|
| sterile saline | — | 0.20 | 0.25 | 0.23 | 0.20 |
| ISIS 484137 | 4 | 0.17 | 0.20 | n.d. | n.d. |
|  | 8 | 0.20 | 0.20 | n.d. | n.d. |
|  | 12 | 0.20 | 0.35 | 0.20 | 0.20 |
|  | 40 | 0.20 | 0.20 | 0.18 | 0.23 |

Kidney Function

To evaluate the effect of ISIS 484137 on kidney function, blood samples were collected from all the study groups on days 44, 93, 121, and 182. Results are presented in the Table below, expressed in mg/dL.

The serum chemistry data indicate that ISIS 484137 did not have any effect on the kidney function outside the expected range for antisense oligonucleotides. Similar results were found with urine samples of the monkeys. Treatment with ISIS 484137 was therefore well tolerated in terms of the kidney function of the monkeys.

TABLE 166

Albumin levels (g/dL) in cynomolgus monkey serum

|  | Dose (mg/kg) | Day 44 | Day 93 |
|---|---|---|---|
| sterile saline | — | 4.2 | 4.1 |
| ISIS 484137 | 4 | 4.2 | 4.1 |
|  | 8 | 4.3 | 3.9 |
|  | 12 | 3.8 | 4.0 |
|  | 40 | 3.8 | 3.8 |

TABLE 167

BUN levels (mg/dL) in cynomolgus monkey serum

|  | Dose (mg/kg) | Day 44 | Day 93 | Day 121 |
|---|---|---|---|---|
| sterile saline | — | 23.7 | 22.5 | 23.0 |
| ISIS 484137 | 4 | 18.0 | 17.7 | n.d. |
|  | 8 | 20.0 | 21.0 | n.d. |
|  | 12 | 22.0 | 22.0 | 21.0 |
|  | 40 | 21.3 | 20.0 | 24.0 |

TABLE 168

Creatinine levels (mg/dL) in cynomolgus monkey serum

|  | Dose (mg/kg) | Day 44 | Day 93 | Day 121 | Day 182 |
|---|---|---|---|---|---|
| sterile saline | — | 128 | 81 | 120 | 93 |
| ISIS 484137 | 4 | 129 | 138 | n.d. | n.d. |
|  | 8 | 69 | 79 | n.d. | n.d. |
|  | 12 | 183 | 153 | 79 | 84 |
|  | 40 | 129 | 85 | 74 | 72 |

Plasma Toxicokinetics

Following subcutaneous injection in monkeys, ISIS 484137 was quickly absorbed into the systemic circulation with a median $T_{max}$ (time to reach plasma $C_{max}$) ranging from 1 to 4 hours. Peak exposure ($C_{max}$) and total exposure ($AUC_{0-48hr}$) were dose-dependent on Day 1, Day 7, and Day 91. Similar AUC (area under the curve) values were observed between Day 1 (after a single dose) and Day 91 (after 16 doses). These results indicate a lack of plasma accumulation of ISIS 484137 following multiple doses. Mean clearance values ($CL/F_{0-48\,hr}$) following subcutaneous administration at all dose levels following single or multiple administrations ranged from 31.3 to 75.8 mL/hr/kg and appeared to decrease with increasing dose. The post-distribution plasma elimination half-life ($t_{1/2\lambda z}$) ranged from 9.42 days to 20.2 days following the 13 weeks of treatment. A review of ISIS 484137 plasma toxicokinetic parameters revealed no gender difference. The Table below presents the results. 'n.d.' means 'not determined'.

TABLE 169

Plasma toxicokinetic summary in monkeys for ISIS 484137

| Dose (mg/kg) | Day | Number of animals | $C_{max}$ (µg/mL) | $T_{max}$ (hr) | $AUC_{0-48hr}$ (hr * µg/mL) | $t_{1/2\lambda z}$ (days) |
|---|---|---|---|---|---|---|
| 4 | 1 | 6 | 15 | 1.5 | 59 | n.d. |
|  | 91 | 6 | 7 | 3.0 | 53 | n.d. |
| 8 | 1 | 6 | 30 | 1.5 | 138 | n.d. |
|  | 7 | 12 | 28 | 2.0 | 137 | 9.42 |
|  | 91 | 6 | 19 | 2.0 | 127 | n.d. |
| 12 | 1 | 10 | 43 | 1.0 | 263 | n.d. |
|  | 91 | 10 | 24 | 4.0 | 261 | 15.1 |
| 40 | 1 | 10 | 113 | 1.0 | 1030 | n.d. |
|  | 91 | 10 | 92 | 1.0 | 1300 | 20.2 |

Tissue Toxicokinetics

There was a dose-dependent increase in kidney cortex and liver concentrations over the 10-fold increase in dose of ISIS 484137. Based on the mean tissue ISIS 484137 concentrations at the end of treatment and after recovery, the estimated tissue half-lives were 16.4 to 21.3 days and 17.8 to 22.8 days in kidney and liver, respectively, similar to the tissue half-lives determined following 8 mg/kg ISIS 484137. These findings are also consistent with the estimated terminal elimination half-life values in plasma. The Table below presents the results. 'n.d.' means 'not determined'.

The tissue half-life (approximately 2-3 weeks) observed supports an infrequent clinical dosing regimen.

TABLE 170

Tissue toxicokinetic summary in monkeys for ISIS 484137

| | Intact ISIS 484137 (µg/g) | | | | | |
|---|---|---|---|---|---|---|
| | Day 3 (2 days after 1st dose) | | Day 93 (2 days after last dose) | | Day 182 (91 days after last dose) | |
| Dose (mg/kg) | Kidney | Liver | Kidney | Liver | Kidney | Liver |
| 4 | n.d. | n.d. | 610 | 221 | n.d. | n.d. |
| 8 | 594 | 84 | 889 | 406 | n.d. | n.d. |
| 12 | n.d. | n.d. | 1320 | 586 | 30 | 18 |
| 40 | n.d. | n.d. | 4220 | 993 | 233 | 66 |

Pro-Inflammatory Effects

None of the inflammatory marker levels were changed beyond the expected range for antisense oligonucleotides. Therefore, treatment with ISIS 484137 did not cause any adverse inflammation and was well tolerated in the monkeys.

In summary, 13 weeks treatment with ISIS 484137 was clinically well tolerated at doses up to 40 mg/kg/week. There was no mortality during the study and there were no treatment-related effects in clinical findings, body weights, food consumption/appetence, ophthalomoscopic and electrocardiographic examinations, hematology, urinalysis, or complement C3 levels during the study. Overall, the results of the study indicate that ISIS 484137 is the most potent and well tolerated compound of those tested for inhibiting DGAT2 and is an important candidate for the treatment of metabolic diseases, such as NAFLD and NASH.

Example 18: Double-Blind, Placebo-Controlled, Dose-Escalation Phase I Study

A double-blind, placebo-controlled, dose-escalation Phase I study to assess the safety, tolerability, pharmacokinetics and pharmacodynamics of single and multiple doses of ISIS 484137 administered subcutaneously to healthy overweight volunteers is conducted in a Study Center. Treatment Protocol Approximately 48 subjects are planned to be enrolled in the study: 16 subjects in the single-dose cohorts and 32 subjects in the multiple-dose cohorts. Subjects are healthy males or females aged 18-65, inclusive, who have given written consent and are able to comply with all the study requirements. BMI of the volunteers is 29.0-38.0 kg/m² inclusive. Any volunteers with clinically significant abnormalities in medical history are excluded from the study. ISIS 484137 solution or placebo (0.9% sterile saline) is prepared by an unblinded pharmacist or qualified delegate shortly before use, using aseptic technique. Study staff, who are blinded to the identity of the drug, administer the drug to the subjects.

There are 4 single-dose cohorts (Cohort A-D) with 4 subjects per cohort randomized 3:1 of ISIS 484137: placebo. The length of each subject's participation is approximately 8 weeks, which includes a 4-week screening period, a single dose, and a 4-week post-treatment evaluation period. Subjects receive a single dose of ISIS 484137 by subcutaneous administration. The dose of the antisense oligonucleotide to each cohort is presented in the Table below.

TABLE 171

Single-dose cohort dosing regimen of ISIS 484137

| Cohort | Total dose (mg) |
|---|---|
| A | 50 |
| B | 100 |
| C | 200 |
| D | 400 |

There are 4 multiple-dose cohorts (Cohort AA-DD) with 8 subjects per cohort randomized 3:1 of ISIS 484137: placebo. The length of each subject's participation is approximately 23 weeks, which includes a 4-week screening period, a 6-week treatment period, and a 13-week post-treatment evaluation period. Subjects receive 3 doses of ISIS 484137 by subcutaneous administration during the first week (Days 1, 3, and 5) and subsequently receive one subcutaneous dose once a week for the next 5 weeks (Days 8, 15, 22, 29, and 36) for a total of 8 doses. Subjects have follow-up visits at the Study Center on Days 37, 43, 50, 64, 78, 92, 106, and 127.

TABLE 172

Multiple-dose cohort dosing regimen of ISIS 484137

| Cohort | Dose per administration (mg) | Total dose (mg) |
|---|---|---|
| AA | 100 | 800 |
| BB | 200 | 1600 |
| CC | 300 | 2400 |
| DD | 400 | 3200 |

Blood and urine samples are collected regularly throughout the study for safety, pharmacokinetic, and pharmacodynamics analysis. The safety and tolerability of ISIS 484137 is assessed by determining the incidence, severity, and dose-relationship of adverse events, vital signs, physical examination, ECG findings, and clinical laboratory parameters. Safety results in subjects dosed with ISIS 484137 are compared with those in subjects dosed with placebo.

SEQUENCE LISTING

The patent contains a lengthy sequence listing. A copy of the sequence listing is available in electronic form from the USPTO web site (https://seqdata.uspto.gov/?pageRequest=docDetail&DocID=US12215321B2). An electronic copy of the sequence listing will also be available from the USPTO upon request and payment of the fee set forth in 37 CFR 1.19(b)(3).

What is claimed:
1. A method of treating, preventing, or ameliorating NAFLD, NASH, lipodystrophy, or partial lipodystrophy in an individual comprising administering to the individual a compound comprising or consisting of a modified oligonucleotide according to the following formula:
(SEQ ID NO: 1423)
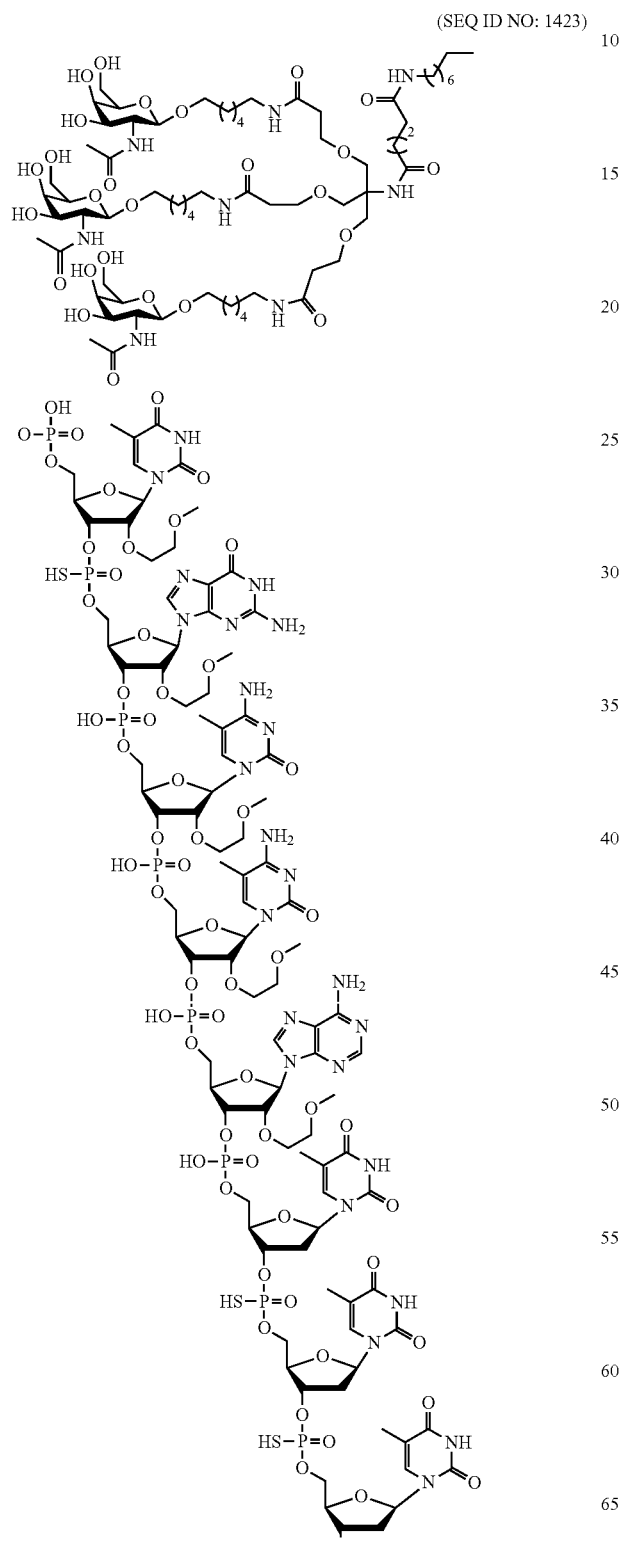
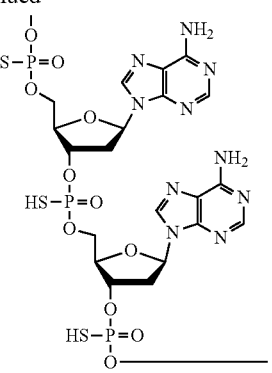
-continued
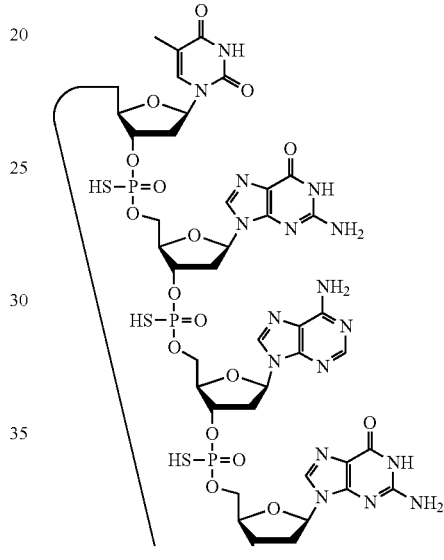
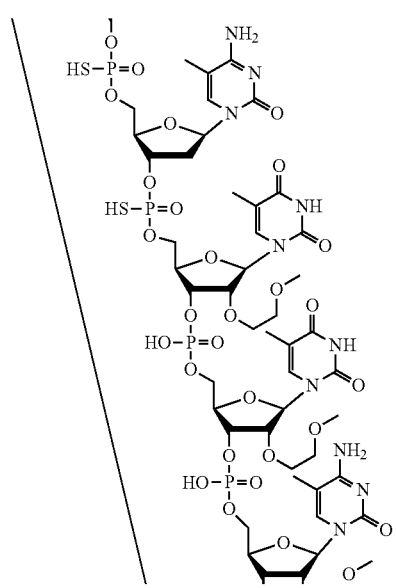

411

-continued

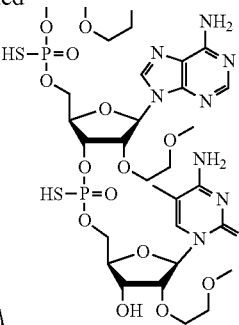

or a salt thereof;
  wherein administering the compound reduces or inhibits triglyceride synthesis, lipid synthesis and/or insulin resistance in the liver or white adipose tissue of the individual;
  thereby treating, preventing, or ameliorating NAFLD, NASH, lipodystrophy, or partial lipodystrophy.

2. The method of claim 1, wherein the pharmaceutically acceptable salt is a potassium salt or a sodium salt.

3. The method of claim 1, wherein the compound is administered as a pharmaceutical composition comprising the compound and a pharmaceutically acceptable diluent.

4. The method of claim 3, wherein the pharmaceutically acceptable diluent comprises water or saline or phosphate buffered saline (PBS).

5. The method of claim 1, wherein the individual has, or is at risk of having, NAFLD, NASH, lipodystrophy, or partial lipodystrophy.

6. The method of claim 1, wherein the compound or composition is administered to the individual parenterally.

7. The method of claim 6, wherein parenterally is subcutaneous administration or intravenous administration.

8. A method of treating, preventing, or ameliorating NAFLD, NASH, lipodystrophy, or partial lipodystrophy in an individual comprising administering to the individual a compound comprising or consisting of a modified oligonucleotide according to the following formula:

(SEQ ID NO: 1423)

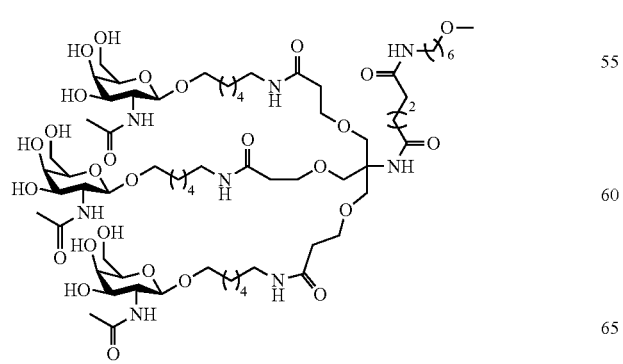

412

-continued

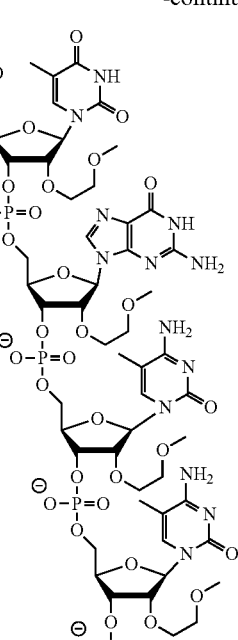

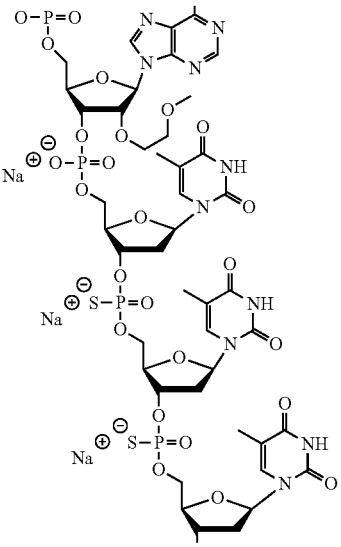

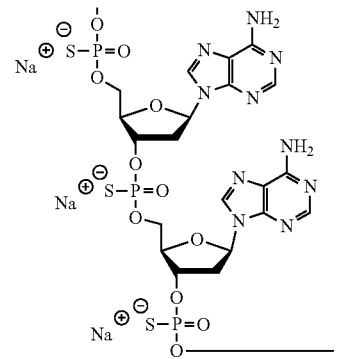

413
-continued

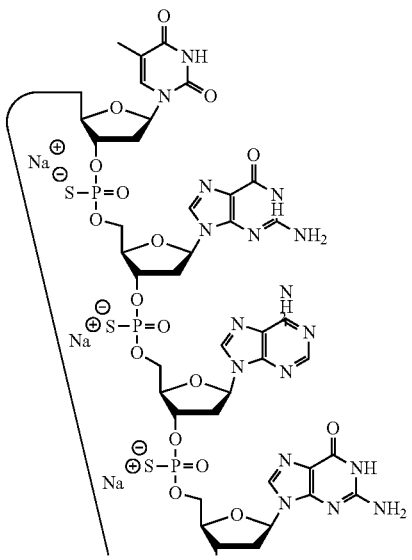

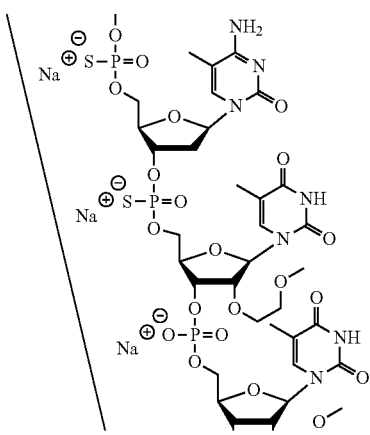

414
-continued

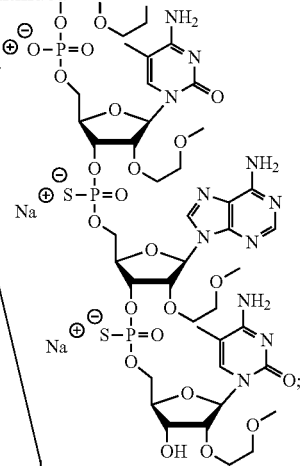

wherein administering the compound reduces or inhibits triglyceride synthesis, lipid synthesis, and/or insulin resistance, or improves insulin signaling, insulin sensitivity and/or cardiovascular risk profile in the individual;

thereby treating, preventing, or ameliorating NAFLD, NASH, lipodystrophy, or partial lipodystrophy.

9. The method of claim 8, wherein the compound is administered as a pharmaceutical composition comprising the compound and a pharmaceutically acceptable diluent.

10. The method of claim 9, wherein the pharmaceutically acceptable diluent comprises water or saline or phosphate buffered saline (PBS).

11. The method of claim 8, wherein the individual has, or is at risk of having, NAFLD, NASH, lipodystrophy, or partial lipodystrophy.

12. The method of claim 8, wherein the compound or composition is administered to the individual parenterally.

13. The method of claim 12, wherein parenterally is subcutaneous administration or intravenous administration.

* * * * *